US012471982B2

(12) United States Patent
Shelton, IV et al.

(10) Patent No.: US 12,471,982 B2
(45) Date of Patent: Nov. 18, 2025

(54) METHOD FOR TISSUE TREATMENT BY SURGICAL INSTRUMENT

(71) Applicant: Cilag GmbH International, Zug (CH)

(72) Inventors: Frederick E. Shelton, IV, Hillsboro, OH (US); Kevin M. Fiebig, Cincinnati, OH (US); Sarah A. Worthington, Cincinnati, OH (US); Nina Mastroianni, Cincinnati, OH (US); John E. Brady, Cincinnati, OH (US); Demetrius N. Harris, Cincinnati, OH (US); Ravi C. Patel, East Providence, RI (US); Joshua L. Liebowitz, Naples, FL (US)

(73) Assignee: Cilag GmbH International, Zug (CH)

( * ) Notice: Subject to any disclaimer, the term of this patent is extended or adjusted under 35 U.S.C. 154(b) by 685 days.

(21) Appl. No.: 17/109,589

(22) Filed: Dec. 2, 2020

(65) Prior Publication Data

US 2022/0168038 A1 Jun. 2, 2022

(51) Int. Cl.
*A61B 18/14* (2006.01)
*A61B 17/068* (2006.01)
(Continued)

(52) U.S. Cl.
CPC ...... *A61B 18/1445* (2013.01); *A61B 17/0682* (2013.01); *A61B 17/07207* (2013.01);
(Continued)

(58) Field of Classification Search
CPC ............ A61B 18/1442; A61B 18/1445; A61B 18/1447; A61B 2018/124;
(Continued)

(56) References Cited

U.S. PATENT DOCUMENTS

| | | | |
|---|---|---|---|
| 66,052 A | 6/1867 | Smith | |
| 662,587 A | 11/1900 | Blake | |

(Continued)

FOREIGN PATENT DOCUMENTS

| | | | |
|---|---|---|---|
| AU | 2012200594 A1 | 2/2012 | |
| AU | 2012203035 A1 | 6/2012 | |

(Continued)

OTHER PUBLICATIONS

ASTM procedure D2240-00, "Standard Test Method for Rubber Property-Durometer Hardness," (Published Aug. 2000).

(Continued)

*Primary Examiner* — Thomas A Giuliani
(74) *Attorney, Agent, or Firm* — Lempia Summerfield Katz LLC

(57) ABSTRACT

A method for treating tissue using a surgical instrument including at least one electrode and a staple cartridge is disclosed. The method includes causing the at least one electrode to deliver a therapeutic energy to the tissue in a first phase of a surgical treatment by the surgical instrument, deploying staples from the staple cartridge into the tissue in a second phase of the surgical treatment, monitoring a first tissue property in the first phase of the surgical treatment, switching from the first phase to the second phase if at least one of two conditions is met, setting a parameter of the second phase of the surgical treatment based on at least one measurement of the first tissue property determined in the first phase of the surgical treatment, and monitoring a second tissue property, different from the first tissue property, in the second phase of the surgical treatment.

12 Claims, 161 Drawing Sheets

(51) Int. Cl.

| | |
|---|---|
| ***A61B 17/072*** | (2006.01) |
| *A61B 17/00* | (2006.01) |
| *A61B 18/00* | (2006.01) |

(52) U.S. Cl.

CPC .............. *A61B 2017/00026* (2013.01); *A61B 2017/00039* (2013.01); *A61B 2017/00084* (2013.01); *A61B 2017/00225* (2013.01); *A61B 2017/0023* (2013.01); *A61B 2017/00367* (2013.01); *A61B 2017/00398* (2013.01); *A61B 2017/00402* (2013.01); *A61B 2017/00876* (2013.01); *A61B 2017/07257* (2013.01); *A61B 2017/07271* (2013.01); *A61B 2017/07278* (2013.01); *A61B 2017/07285* (2013.01); *A61B 2018/00101* (2013.01); *A61B 2018/0063* (2013.01); *A61B 2018/00702* (2013.01); *A61B 2018/00791* (2013.01); *A61B 2018/00875* (2013.01)

(58) Field of Classification Search

CPC ...... A61B 2018/147; A61B 2018/0063; A61B 2018/00702; A61B 2018/00791; A61B 2018/00875; A61B 2018/00666; A61B 2018/1455; A61B 17/0682; A61B 17/068; A61B 17/07207; A61B 2017/00017; A61B 2017/00026; A61B 2017/00039; A61B 2017/00084; A61B 2017/00398; A61B 2017/07257; A61B 2017/07271; A61B 2017/07278; A61B 2017/07285

USPC .... 606/41, 42, 49–52; 607/98, 99, 101, 102, 607/113, 115, 116

See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | Place |
| 2,366,274 | A | 1/1945 | Luth et al. |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,458,152 | A | 1/1949 | Eakins |
| 2,491,872 | A | 12/1949 | Neuman |
| 2,507,872 | A | 5/1950 | Unsinger |
| 2,510,693 | A | 6/1950 | Green |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,736,960 | A | 3/1956 | Armstrong |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,849,788 | A | 9/1958 | Creek |
| 2,853,074 | A | 9/1958 | Olson |
| 2,856,192 | A | 10/1958 | Schuster |
| 2,867,039 | A | 1/1959 | Zach |
| 2,887,004 | A | 5/1959 | Stewart |
| 2,957,353 | A | 10/1960 | Lewis |
| 2,959,974 | A | 11/1960 | Emrick |
| 3,015,961 | A | 1/1962 | Roney |
| 3,026,744 | A | 3/1962 | Rouse |
| 3,032,769 | A | 5/1962 | Palmer |
| 3,035,256 | A | 5/1962 | Egbert |
| 3,043,309 | A | 7/1962 | McCarthy |
| 3,060,972 | A | 10/1962 | Sheldon |
| 3,075,062 | A | 1/1963 | Laccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,166,971 | A | 1/1965 | Stoecker |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,358,676 | A | 12/1967 | Frei et al. |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,525,912 | A | 8/1970 | Wallin |
| 3,526,219 | A | 9/1970 | Balamuth |
| 3,551,987 | A | 1/1971 | Wilkinson |
| 3,568,675 | A | 3/1971 | Harvey |
| 3,572,159 | A | 3/1971 | Tschanz |
| 3,580,841 | A | 5/1971 | Cadotte et al. |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,614,484 | A | 10/1971 | Shoh |
| 3,616,278 | A | 10/1971 | Jansen |
| 3,618,842 | A | 11/1971 | Bryan |
| 3,635,394 | A | 1/1972 | Natelson |
| 3,636,943 | A | 1/1972 | Balamuth |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |

(56) References Cited

U.S. PATENT DOCUMENTS

| | | | |
|---|---|---|---|
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,703,651 | A | 11/1972 | Blowers |
| 3,709,221 | A | 1/1973 | Riely |
| 3,710,399 | A | 1/1973 | Hurst |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,776,238 | A | 12/1973 | Peyman et al. |
| 3,777,760 | A | 12/1973 | Essner |
| 3,797,494 | A | 3/1974 | Zaffaroni |
| 3,799,151 | A | 3/1974 | Fukaumi et al. |
| 3,805,787 | A | 4/1974 | Banko |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,825,007 | A | 7/1974 | Rand |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,862,630 | A | 1/1975 | Balamuth |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,900,823 | A | 8/1975 | Sokal et al. |
| 3,902,247 | A | 9/1975 | Fleer et al. |
| 3,906,217 | A | 9/1975 | Lackore |
| 3,918,442 | A | 11/1975 | Nikolaev et al. |
| 3,940,844 | A | 3/1976 | Colby et al. |
| 3,944,163 | A | 3/1976 | Hayashi et al. |
| 3,946,738 | A | 3/1976 | Newton et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,955,859 | A | 5/1976 | Stella et al. |
| 3,956,826 | A | 5/1976 | Perdreaux, Jr. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,988,535 | A | 10/1976 | Hickman et al. |
| 3,993,072 | A | 11/1976 | Zaffaroni |
| 3,999,110 | A | 12/1976 | Ramstrom et al. |
| 4,005,714 | A | 2/1977 | Hiltebrandt |
| 4,025,216 | A | 5/1977 | Hives |
| 4,027,746 | A | 6/1977 | Kine |
| 4,034,143 | A | 7/1977 | Sweet |
| 4,034,762 | A | 7/1977 | Cosens et al. |
| 4,038,987 | A | 8/1977 | Komiya |
| 4,047,136 | A | 9/1977 | Satto |
| 4,047,654 | A | 9/1977 | Alvarado |
| 4,054,108 | A | 10/1977 | Gill |
| 4,058,126 | A | 11/1977 | Leveen |
| 4,060,089 | A | 11/1977 | Noiles |
| 4,063,561 | A | 12/1977 | McKenna |
| 4,066,133 | A | 1/1978 | Voss |
| 4,085,337 | A | 4/1978 | Moeller |
| 4,099,192 | A | 7/1978 | Aizawa et al. |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,156,187 | A | 5/1979 | Murry et al. |
| 4,160,857 | A | 7/1979 | Nardella et al. |
| 4,169,476 | A | 10/1979 | Hiltebrandt |
| 4,169,990 | A | 10/1979 | Lerdman |
| 4,180,285 | A | 12/1979 | Reneau |
| 4,185,701 | A | 1/1980 | Boys |
| 4,188,927 | A | 2/1980 | Harris |
| 4,190,042 | A | 2/1980 | Sinnreich |
| 4,191,377 | A | 3/1980 | Burnside |
| 4,198,734 | A | 4/1980 | Brumlik |
| 4,198,982 | A | 4/1980 | Fortner et al. |
| 4,200,106 | A | 4/1980 | Douvas et al. |
| 4,203,430 | A | 5/1980 | Takahashi |
| 4,203,444 | A | 5/1980 | Bonnell et al. |
| 4,207,898 | A | 6/1980 | Becht |
| 4,213,562 | A | 7/1980 | Garrett et al. |
| 4,220,154 | A | 9/1980 | Semm |
| 4,226,242 | A | 10/1980 | Jarvik |
| 4,237,441 | A | 12/1980 | van Konynenburg et al. |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,077 | A | 7/1981 | Mizumoto |
| 4,278,091 | A | 7/1981 | Borzone |
| 4,281,785 | A | 8/1981 | Brooks |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,304,987 | A | 12/1981 | van Konynenburg |
| 4,305,539 | A | 12/1981 | Korolkov et al. |
| 4,312,363 | A | 1/1982 | Rothfuss et al. |
| 4,312,685 | A | 1/1982 | Riedl |
| 4,314,559 | A | 2/1982 | Allen |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |

(56) References Cited

U.S. PATENT DOCUMENTS 4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,384,584 A 5/1983 Chen
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,445,063 A 4/1984 Smith
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,463,759 A 8/1984 Garito et al.
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,491,132 A 1/1985 Aikins
4,492,231 A 1/1985 Auth
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,535,773 A 8/1985 Yoon
4,540,202 A 9/1985 Amphoux et al.
4,545,926 A 10/1985 Fouts, Jr. et al.
4,548,202 A 10/1985 Duncan
4,550,870 A 11/1985 Krumme et al.
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,582,236 A 4/1986 Hirose
4,585,153 A 4/1986 Failla et al.
4,585,282 A 4/1986 Bosley
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,390 A 7/1986 Mulhollan et al.
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,927 A 10/1986 Manes
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,634,420 A 1/1987 Spinosa et al.
4,635,638 A 1/1987 Weintraub et al.
4,640,279 A 2/1987 Beard
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,655,746 A 4/1987 Daniels et al.
4,662,555 A 5/1987 Thornton

(56) References Cited

U.S. PATENT DOCUMENTS 4,663,874 A 5/1987 Sano et al.
4,664,305 A 5/1987 Blake et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,287 A 6/1987 Fiddian-Green
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,127 A 11/1987 Abdelghani
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,735,603 A 4/1988 Goodson et al.
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,761,871 A 8/1988 O’Connor et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,777,951 A 10/1988 Cribier et al.
4,781,186 A 11/1988 Simpson et al.
4,784,137 A 11/1988 Kulik et al.
4,787,387 A 11/1988 Burbank et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,797,803 A 1/1989 Carroll
4,798,588 A 1/1989 Aillon
4,802,461 A 2/1989 Cho
4,803,506 A 2/1989 Diehl et al.
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,462 A 5/1989 Karny et al.
4,830,855 A 5/1989 Stewart
4,832,158 A 5/1989 Farrar et al.
4,832,683 A 5/1989 Idemoto et al.
4,833,937 A 5/1989 Nagano
4,834,096 A 5/1989 Oh et al.
4,834,720 A 5/1989 Blinkhorn
4,838,853 A 6/1989 Parisi
4,838,859 A 6/1989 Strassmann
4,844,068 A 7/1989 Arata et al.
4,848,637 A 7/1989 Pruitt
4,849,133 A 7/1989 Yoshida et al.
4,850,354 A 7/1989 McGurk-Burleson et al.
4,856,078 A 8/1989 Konopka
4,860,644 A 8/1989 Kohl et al.
4,860,745 A 8/1989 Farin et al.
4,862,891 A 9/1989 Smith
4,863,423 A 9/1989 Wallace
4,865,030 A 9/1989 Polyak
4,865,159 A 9/1989 Jamison
4,868,530 A 9/1989 Ahs
4,868,958 A 9/1989 Suzuki et al.
4,869,414 A 9/1989 Green et al.
4,869,415 A 9/1989 Fox
4,873,977 A 10/1989 Avant et al.
4,875,486 A 10/1989 Rapoport et al.
4,878,493 A 11/1989 Pasternak et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,009 A 1/1990 Pawlowski
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,910,389 A 3/1990 Sherman et al.
4,910,633 A 3/1990 Quinn
4,911,148 A 3/1990 Sosnowski et al.
4,915,100 A 4/1990 Green
4,919,039 A 4/1990 Nutter
4,919,129 A 4/1990 Weber, Jr. et al.
4,919,679 A 4/1990 Averill et al.
4,920,978 A 5/1990 Colvin
4,921,479 A 5/1990 Grayzel
4,922,902 A 5/1990 Wuchinich et al.
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
4,936,842 A 6/1990 D’Amelio et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,961,738 A 10/1990 Mackin
4,962,681 A 10/1990 Yang
4,962,877 A 10/1990 Hervas

(56) References Cited

U.S. PATENT DOCUMENTS

| | | | |
|---|---|---|---|
| 4,964,559 | A | 10/1990 | Deniega et al. |
| 4,964,863 | A | 10/1990 | Kanshin et al. |
| 4,965,709 | A | 10/1990 | Ngo |
| 4,967,670 | A | 11/1990 | Morishita et al. |
| 4,970,656 | A | 11/1990 | Lo et al. |
| 4,973,274 | A | 11/1990 | Hirukawa |
| 4,973,302 | A | 11/1990 | Armour et al. |
| 4,976,173 | A | 12/1990 | Yang |
| 4,978,049 | A | 12/1990 | Green |
| 4,978,333 | A | 12/1990 | Broadwin et al. |
| 4,979,952 | A | 12/1990 | Kubota et al. |
| 4,981,756 | A | 1/1991 | Rhandhawa |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,001,649 | A | 3/1991 | Lo et al. |
| 5,002,543 | A | 3/1991 | Bradshaw et al. |
| 5,002,553 | A | 3/1991 | Shiber |
| 5,005,754 | A | 4/1991 | Van Overloop |
| 5,007,919 | A | 4/1991 | Silva et al. |
| 5,009,222 | A | 4/1991 | Her |
| 5,009,661 | A | 4/1991 | Michelson |
| 5,012,411 | A | 4/1991 | Policastro et al. |
| 5,014,898 | A | 5/1991 | Heidrich |
| 5,014,899 | A | 5/1991 | Presty et al. |
| 5,015,227 | A | 5/1991 | Broadwin et al. |
| 5,018,515 | A | 5/1991 | Gilman |
| 5,018,657 | A | 5/1991 | Pedlick et al. |
| 5,019,075 | A | 5/1991 | Spears et al. |
| 5,019,077 | A | 5/1991 | De Bastiani et al. |
| 5,020,514 | A | 6/1991 | Heckele |
| 5,024,652 | A | 6/1991 | Dumenek et al. |
| 5,024,671 | A | 6/1991 | Tu et al. |
| 5,025,559 | A | 6/1991 | McCullough |
| 5,026,387 | A | 6/1991 | Thomas |
| 5,027,834 | A | 7/1991 | Pruitt |
| 5,030,226 | A | 7/1991 | Green et al. |
| 5,031,814 | A | 7/1991 | Tompkins et al. |
| 5,033,552 | A | 7/1991 | Hu |
| 5,035,040 | A | 7/1991 | Kerrigan et al. |
| 5,037,018 | A | 8/1991 | Matsuda et al. |
| 5,038,109 | A | 8/1991 | Goble et al. |
| 5,038,247 | A | 8/1991 | Kelley et al. |
| 5,040,715 | A | 8/1991 | Green et al. |
| 5,042,707 | A | 8/1991 | Taheri |
| 5,056,953 | A | 10/1991 | Marot et al. |
| 5,060,658 | A | 10/1991 | Dejter, Jr. et al. |
| 5,061,269 | A | 10/1991 | Muller |
| 5,062,491 | A | 11/1991 | Takeshima et al. |
| 5,062,563 | A | 11/1991 | Green et al. |
| 5,065,929 | A | 11/1991 | Schulze et al. |
| 5,071,052 | A | 12/1991 | Rodak et al. |
| 5,071,430 | A | 12/1991 | de Salis et al. |
| 5,074,454 | A | 12/1991 | Peters |
| 5,077,506 | A | 12/1991 | Krause |
| 5,079,006 | A | 1/1992 | Urquhart |
| 5,080,556 | A | 1/1992 | Carreno |
| 5,083,695 | A | 1/1992 | Foslien et al. |
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,093,754 | A | 3/1992 | Kawashima |
| 5,094,247 | A | 3/1992 | Hernandez et al. |
| 5,098,004 | A | 3/1992 | Kerrigan |
| 5,098,360 | A | 3/1992 | Hirota |
| 5,099,216 | A | 3/1992 | Pelrine |
| 5,099,840 | A | 3/1992 | Goble et al. |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,106,538 | A | 4/1992 | Barma et al. |
| 5,108,368 | A | 4/1992 | Hammerslag et al. |
| 5,108,383 | A | 4/1992 | White |
| 5,109,722 | A | 5/1992 | Hufnagle et al. |
| 5,111,987 | A | 5/1992 | Moeinzadeh et al. |
| 5,112,300 | A | 5/1992 | Ureche |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,123,903 | A | 6/1992 | Quaid et al. |
| 5,124,990 | A | 6/1992 | Williamson |
| 5,129,570 | A | 7/1992 | Schulze et al. |
| 5,135,483 | A | 8/1992 | Wagner et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,150,102 | A | 9/1992 | Takashima |
| 5,150,272 | A | 9/1992 | Danley et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,156,633 | A | 10/1992 | Smith |
| 5,158,222 | A | 10/1992 | Green et al. |
| 5,158,567 | A | 10/1992 | Green |
| D330,699 | S | 11/1992 | Gill |
| 5,160,334 | A | 11/1992 | Billings et al. |
| 5,162,044 | A | 11/1992 | Gahn et al. |
| 5,163,598 | A | 11/1992 | Peters et al. |
| 5,163,842 | A | 11/1992 | Nonomura |
| 5,164,652 | A | 11/1992 | Johnson et al. |
| 5,167,725 | A | 12/1992 | Clark et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| D332,660 | S | 1/1993 | Rawson et al. |
| 5,176,677 | A | 1/1993 | Wuchinich |
| 5,176,688 | A | 1/1993 | Narayan et al. |
| 5,176,695 | A | 1/1993 | Dulebohn |
| 5,180,375 | A | 1/1993 | Feibus |
| 5,181,514 | A | 1/1993 | Solomon et al. |
| 5,184,605 | A | 2/1993 | Grzeszykowski |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,541 | A | 3/1993 | Abele et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,196,007 | A | 3/1993 | Ellman et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,205,817 | A | 4/1993 | Idemoto et al. |
| 5,207,672 | A | 5/1993 | Roth et al. |
| 5,207,697 | A | 5/1993 | Carusillo et al. |
| 5,209,719 | A | 5/1993 | Baruch et al. |

(56) References Cited

U.S. PATENT DOCUMENTS 5,209,747 A 5/1993 Knoepfler
5,209,756 A 5/1993 Seedhom et al.
5,211,649 A 5/1993 Kohler et al.
5,211,655 A 5/1993 Hasson
5,213,569 A 5/1993 Davis
5,217,457 A 6/1993 Delahuerga et al.
5,217,460 A 6/1993 Knoepfler
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,221,282 A 6/1993 Wuchinich
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
5,226,910 A 7/1993 Kajiyama et al.
D338,729 S 8/1993 Sprecklemeier et al.
5,234,428 A 8/1993 Kaufman
5,234,447 A 8/1993 Kaster et al.
5,236,269 A 8/1993 Handy
5,236,424 A 8/1993 Imran
5,236,440 A 8/1993 Hlavacek
5,236,629 A 8/1993 Mahabadi et al.
5,239,981 A 8/1993 Anapliotis
5,240,163 A 8/1993 Stein et al.
5,241,236 A 8/1993 Sasaki et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,251,801 A 10/1993 Ruckdeschel et al.
5,253,647 A 10/1993 Takahashi et al.
5,253,793 A 10/1993 Green et al.
5,254,130 A 10/1993 Poncet et al.
5,257,988 A 11/1993 L'Esperance, Jr.
5,258,004 A 11/1993 Bales et al.
5,258,006 A 11/1993 Rydell et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,957 A 11/1993 Davison
5,263,973 A 11/1993 Cook
5,264,218 A 11/1993 Rogozinski
5,267,091 A 11/1993 Chen
5,268,622 A 12/1993 Philipp
5,269,794 A 12/1993 Rexroth
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,800 A 2/1994 Foshee et al.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,286 A 3/1994 Parins
5,290,310 A 3/1994 Makower et al.
5,291,133 A 3/1994 Gokhale et al.
5,292,053 A 3/1994 Bilotti et al.
5,293,024 A 3/1994 Sugahara et al.
5,293,863 A 3/1994 Zhu et al.
5,297,714 A 3/1994 Kramer
5,300,087 A 4/1994 Knoepfler
5,302,148 A 4/1994 Heinz
5,303,606 A 4/1994 Kokinda
5,304,115 A 4/1994 Pflueger et al.
5,304,204 A 4/1994 Bregen
D347,474 S 5/1994 Olson
5,307,976 A 5/1994 Olson et al.
5,308,353 A 5/1994 Beurrier
5,308,358 A 5/1994 Bond et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,306 A 5/1994 Kuban et al.
5,313,935 A 5/1994 Kortenbach et al.
5,313,967 A 5/1994 Lieber et al.
5,314,424 A 5/1994 Nicholas
5,314,445 A 5/1994 Heidmueller et al.
5,314,466 A 5/1994 Stern et al.
5,318,221 A 6/1994 Green et al.
5,318,563 A 6/1994 Malis et al.
5,318,564 A 6/1994 Eggers
5,318,565 A 6/1994 Kuriloff et al.
5,318,570 A 6/1994 Hood et al.
5,318,589 A 6/1994 Lichtman
5,320,627 A 6/1994 Sorensen et al.
5,322,055 A 6/1994 Davison et al.
5,324,260 A 6/1994 O'Neill et al.
5,324,299 A 6/1994 Davison et al.
D348,930 S 7/1994 Olson
5,326,013 A 7/1994 Green et al.
5,329,923 A 7/1994 Lundquist
5,330,471 A 7/1994 Eggers
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,624 A 8/1994 Tovey
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,723 A 8/1994 Huitema
5,339,799 A 8/1994 Kami et al.
5,341,724 A 8/1994 Vatel
5,341,807 A 8/1994 Nardella
5,341,810 A 8/1994 Dardel
5,342,359 A 8/1994 Rydell
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,420 A 9/1994 Hilal et al.
5,344,454 A 9/1994 Clarke et al.
5,346,502 A 9/1994 Estabrook et al.
5,346,504 A 9/1994 Ortiz et al.

(56) References Cited

U.S. PATENT DOCUMENTS

| | | | |
|---|---|---|---|
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Lacovelli |
| 5,350,400 | A | 9/1994 | Esposito et al. |
| 5,352,219 | A | 10/1994 | Reddy |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,992 | A | 11/1994 | Hori et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,583 | A | 11/1994 | Huitema |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,466 | A | 11/1994 | Christian et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,640 | A | 12/1994 | Kolff |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| D354,564 | S | 1/1995 | Medema |
| 5,379,933 | A | 1/1995 | Green et al. |
| 5,381,067 | A | 1/1995 | Greenstein et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,738 | A | 1/1995 | Herbermann |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |
| 5,383,888 | A | 1/1995 | Zvenyatsky et al. |
| 5,383,895 | A | 1/1995 | Holmes et al. |
| 5,387,207 | A | 2/1995 | Dyer et al. |
| 5,388,568 | A | 2/1995 | van der Heide |
| 5,388,748 | A | 2/1995 | Davignon et al. |
| 5,389,072 | A | 2/1995 | Imran |
| 5,389,098 | A | 2/1995 | Tsuruta et al. |
| 5,389,102 | A | 2/1995 | Green et al. |
| 5,389,104 | A | 2/1995 | Hahnen et al. |
| 5,391,180 | A | 2/1995 | Tovey et al. |
| 5,392,979 | A | 2/1995 | Green et al. |
| 5,395,030 | A | 3/1995 | Kuramoto et al. |
| 5,395,033 | A | 3/1995 | Byrne et al. |
| 5,395,034 | A | 3/1995 | Allen et al. |
| 5,395,312 | A | 3/1995 | Desai |
| 5,395,331 | A | 3/1995 | O'Neill et al. |
| 5,395,363 | A | 3/1995 | Billings et al. |
| 5,395,364 | A | 3/1995 | Anderhub et al. |
| 5,395,384 | A | 3/1995 | Duthoit et al. |
| 5,396,266 | A | 3/1995 | Brimhall |
| 5,396,900 | A | 3/1995 | Slater et al. |
| 5,397,046 | A | 3/1995 | Savage et al. |
| 5,397,324 | A | 3/1995 | Carroll et al. |
| 5,400,267 | A | 3/1995 | Denen et al. |
| 5,403,276 | A | 4/1995 | Schechter et al. |
| 5,403,312 | A | 4/1995 | Yates et al. |
| 5,404,106 | A | 4/1995 | Matsuda |
| 5,404,870 | A | 4/1995 | Brinkerhoff et al. |
| 5,404,960 | A | 4/1995 | Wada et al. |
| 5,405,072 | A | 4/1995 | Zlock et al. |
| 5,405,073 | A | 4/1995 | Porter |
| 5,405,344 | A | 4/1995 | Williamson et al. |
| 5,405,360 | A | 4/1995 | Tovey |
| 5,407,293 | A | 4/1995 | Crainich |
| 5,408,409 | A | 4/1995 | Glassman et al. |
| 5,409,483 | A | 4/1995 | Campbell et al. |
| 5,409,498 | A | 4/1995 | Braddock et al. |
| 5,409,703 | A | 4/1995 | McAnalley et al. |
| D357,981 | S | 5/1995 | Green et al. |
| D358,887 | S | 5/1995 | Feinberg |
| 5,411,481 | A | 5/1995 | Allen et al. |
| 5,411,508 | A | 5/1995 | Bessler et al. |
| 5,413,107 | A | 5/1995 | Oakley et al. |
| 5,413,267 | A | 5/1995 | Solyntjes et al. |
| 5,413,268 | A | 5/1995 | Green et al. |
| 5,413,272 | A | 5/1995 | Green et al. |
| 5,413,573 | A | 5/1995 | Koivukangas |
| 5,413,575 | A | 5/1995 | Haenggi |
| 5,415,334 | A | 5/1995 | Williamson et al. |
| 5,415,335 | A | 5/1995 | Knodell, Jr. |
| 5,417,203 | A | 5/1995 | Tovey et al. |
| 5,417,361 | A | 5/1995 | Williamson, IV |
| 5,417,709 | A | 5/1995 | Slater |
| 5,419,761 | A | 5/1995 | Narayanan et al. |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,423,835 | A | 6/1995 | Green et al. |
| 5,425,355 | A | 6/1995 | Kulick |
| 5,425,745 | A | 6/1995 | Green et al. |
| 5,427,298 | A | 6/1995 | Tegtmeier |
| 5,428,504 | A | 6/1995 | Bhatla |
| 5,429,131 | A | 7/1995 | Scheinman et al. |
| 5,431,322 | A | 7/1995 | Green et al. |
| 5,431,323 | A | 7/1995 | Smith et al. |
| 5,431,640 | A | 7/1995 | Gabriel |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,615 | A | 8/1995 | Yoon |
| 5,445,638 | A | 8/1995 | Rydell et al. |
| 5,445,644 | A | 8/1995 | Pietrafitta et al. |
| 5,446,646 | A | 8/1995 | Miyazaki |

(56) References Cited

U.S. PATENT DOCUMENTS 5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,451,227 A 9/1995 Michaelson
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,824 A 10/1995 Fontayne et al.
5,454,827 A 10/1995 Aust et al.
5,456,401 A 10/1995 Green et al.
5,456,684 A 10/1995 Schmidt et al.
5,456,917 A 10/1995 Wise et al.
5,458,279 A 10/1995 Plyley
5,458,579 A 10/1995 Chodorow et al.
5,458,598 A 10/1995 Feinberg et al.
5,462,215 A 10/1995 Viola et al.
5,462,604 A 10/1995 Shibano et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,472,443 A 12/1995 Cordis et al.
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,477,788 A 12/1995 Morishita
5,478,003 A 12/1995 Green et al.
5,478,308 A 12/1995 Cartmell et al.
5,478,354 A 12/1995 Tovey et al.
5,480,089 A 1/1996 Blewett
5,480,409 A 1/1996 Riza
5,482,197 A 1/1996 Green et al.
5,483,501 A 1/1996 Park et al.
5,483,952 A 1/1996 Aranyi
5,484,095 A 1/1996 Green et al.
5,484,398 A 1/1996 Stoddard
5,484,436 A 1/1996 Eggers et al.
5,484,451 A 1/1996 Akopov et al.
5,485,947 A 1/1996 Olson et al.
5,485,952 A 1/1996 Fontayne
5,486,162 A 1/1996 Brumbach
5,486,189 A 1/1996 Mudry et al.
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,500,216 A 3/1996 Julian et al.
5,501,654 A 3/1996 Failla et al.
5,503,320 A 4/1996 Webster et al.
5,503,635 A 4/1996 Sauer et al.
5,503,638 A 4/1996 Cooper et al.
5,504,650 A 4/1996 Katsui et al.
5,505,363 A 4/1996 Green et al.
5,505,693 A 4/1996 Mackool
5,507,425 A 4/1996 Ziglioli
5,507,426 A 4/1996 Young et al.
5,507,773 A 4/1996 Huitema et al.
5,508,080 A 4/1996 Sorimachi et al.
5,509,596 A 4/1996 Green et al.
5,509,916 A 4/1996 Taylor
5,509,918 A 4/1996 Romano
5,509,922 A 4/1996 Aranyi et al.
5,510,138 A 4/1996 Sanftleben et al.
5,511,556 A 4/1996 DeSantis
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,520,704 A 5/1996 Castro et al.
5,522,817 A 6/1996 Sander et al.
5,522,831 A 6/1996 Sleister et al.
5,522,839 A 6/1996 Pilling
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,648 A 7/1996 Yoon
5,540,681 A 7/1996 Strul et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,916 A 8/1996 Hirsch et al.
5,542,938 A 8/1996 Avellanet et al.
5,542,945 A 8/1996 Fritzsch
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis

(56) References Cited

U.S. PATENT DOCUMENTS

| | | | |
|---|---|---|---|
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,609 | A | 10/1996 | Brumbach |
| 5,562,610 | A | 10/1996 | Brumbach |
| 5,562,657 | A | 10/1996 | Griffin |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,179 | A | 10/1996 | Stone et al. |
| 5,563,481 | A | 10/1996 | Krause |
| 5,564,615 | A | 10/1996 | Bishop et al. |
| 5,569,161 | A | 10/1996 | Ebling et al. |
| 5,569,164 | A | 10/1996 | Lurz |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,121 | A | 11/1996 | Heifetz |
| 5,571,285 | A | 11/1996 | Chow et al. |
| 5,571,488 | A | 11/1996 | Beerstecher et al. |
| 5,573,169 | A | 11/1996 | Green et al. |
| 5,573,534 | A | 11/1996 | Stone |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,584,830 | A | 12/1996 | Ladd et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,601 | A | 2/1997 | Tal et al. |
| 5,601,604 | A | 2/1997 | Vincent |
| 5,602,449 | A | 2/1997 | Krause et al. |
| 5,603,443 | A | 2/1997 | Clark et al. |
| 5,604,531 | A | 2/1997 | Iddan et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,303 | A | 3/1997 | Nakamura |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,573 | A | 3/1997 | Sandock |
| 5,609,601 | A | 3/1997 | Kolesa et al. |
| 5,611,709 | A | 3/1997 | McAnulty |
| 5,611,813 | A | 3/1997 | Lichtman |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,618,492 | A | 4/1997 | Auten et al. |
| 5,619,992 | A | 4/1997 | Guthrie et al. |
| 5,620,289 | A | 4/1997 | Curry |
| 5,620,326 | A | 4/1997 | Younker |
| 5,620,415 | A | 4/1997 | Lucey et al. |
| 5,620,452 | A | 4/1997 | Yoon |
| 5,624,398 | A | 4/1997 | Smith et al. |
| 5,624,452 | A | 4/1997 | Yates |
| 5,626,578 | A | 5/1997 | Tihon |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,628,760 | A | 5/1997 | Knoepfler |
| 5,630,420 | A | 5/1997 | Vaitekunas |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |
| 5,633,374 | A | 5/1997 | Humphrey et al. |
| 5,634,584 | A | 6/1997 | Okorocha et al. |
| 5,636,779 | A | 6/1997 | Palmer |
| 5,636,780 | A | 6/1997 | Green et al. |
| 5,637,110 | A | 6/1997 | Pennybacker et al. |
| 5,638,582 | A | 6/1997 | Klatt et al. |
| 5,639,008 | A | 6/1997 | Gallagher et al. |
| D381,077 | S | 7/1997 | Hunt |
| 5,643,175 | A | 7/1997 | Adair |
| 5,643,291 | A | 7/1997 | Pier et al. |
| 5,643,293 | A | 7/1997 | Kogasaka et al. |
| 5,643,294 | A | 7/1997 | Tovey et al. |
| 5,643,319 | A | 7/1997 | Green et al. |
| 5,645,065 | A | 7/1997 | Shapiro et al. |
| 5,645,209 | A | 7/1997 | Green et al. |
| 5,647,526 | A | 7/1997 | Green et al. |
| 5,647,869 | A | 7/1997 | Goble et al. |
| 5,647,871 | A | 7/1997 | Levine et al. |
| 5,649,937 | A | 7/1997 | Bito et al. |
| 5,649,956 | A | 7/1997 | Jensen et al. |
| 5,651,491 | A | 7/1997 | Heaton et al. |
| 5,651,762 | A | 7/1997 | Bridges |
| 5,651,780 | A | 7/1997 | Jackson et al. |
| 5,651,821 | A | 7/1997 | Uchida |
| 5,653,373 | A | 8/1997 | Green et al. |
| 5,653,374 | A | 8/1997 | Young et al. |
| 5,653,677 | A | 8/1997 | Okada et al. |
| 5,653,713 | A | 8/1997 | Michelson |
| 5,653,721 | A | 8/1997 | Knodel et al. |
| 5,653,748 | A | 8/1997 | Strecker |
| 5,655,698 | A | 8/1997 | Yoon |
| 5,656,917 | A | 8/1997 | Theobald |
| 5,657,417 | A | 8/1997 | Di Troia |
| 5,657,429 | A | 8/1997 | Wang et al. |
| 5,657,697 | A | 8/1997 | Murai |
| 5,657,921 | A | 8/1997 | Young et al. |
| 5,658,238 | A | 8/1997 | Suzuki et al. |
| 5,658,281 | A | 8/1997 | Heard |
| 5,658,298 | A | 8/1997 | Vincent et al. |
| 5,658,300 | A | 8/1997 | Bito et al. |
| 5,658,307 | A | 8/1997 | Exconde |
| 5,662,258 | A | 9/1997 | Knodel et al. |
| 5,662,260 | A | 9/1997 | Yoon |

(56) References Cited

U.S. PATENT DOCUMENTS

| | | | |
|---|---|---|---|
| 5,662,662 | A | 9/1997 | Bishop et al. |
| 5,662,667 | A | 9/1997 | Knodel |
| 5,664,404 | A | 9/1997 | Ivanov et al. |
| 5,665,085 | A | 9/1997 | Nardella |
| 5,665,100 | A | 9/1997 | Yoon |
| 5,667,517 | A | 9/1997 | Hooven |
| 5,667,526 | A | 9/1997 | Levin |
| 5,667,527 | A | 9/1997 | Cook |
| 5,667,864 | A | 9/1997 | Landoll |
| 5,669,544 | A | 9/1997 | Schulze et al. |
| 5,669,904 | A | 9/1997 | Platt, Jr. et al. |
| 5,669,907 | A | 9/1997 | Platt, Jr. et al. |
| 5,669,918 | A | 9/1997 | Balazs et al. |
| 5,669,922 | A | 9/1997 | Hood |
| 5,672,945 | A | 9/1997 | Krause |
| 5,673,840 | A | 10/1997 | Schulze et al. |
| 5,673,841 | A | 10/1997 | Schulze et al. |
| 5,673,842 | A | 10/1997 | Bittner et al. |
| 5,674,184 | A | 10/1997 | Hassler, Jr. |
| 5,674,219 | A | 10/1997 | Monson et al. |
| 5,674,220 | A | 10/1997 | Fox et al. |
| 5,674,235 | A | 10/1997 | Parisi |
| 5,674,286 | A | 10/1997 | D'Alessio et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,681,260 | A | 10/1997 | Ueda et al. |
| 5,681,341 | A | 10/1997 | Lunsford et al. |
| 5,683,349 | A | 11/1997 | Makower et al. |
| 5,683,432 | A | 11/1997 | Goedeke et al. |
| 5,685,474 | A | 11/1997 | Seeber |
| 5,686,090 | A | 11/1997 | Schilder et al. |
| 5,688,270 | A | 11/1997 | Yates et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,693,020 | A | 12/1997 | Rauh |
| 5,693,042 | A | 12/1997 | Boiarski et al. |
| 5,693,051 | A | 12/1997 | Schulze et al. |
| 5,694,936 | A | 12/1997 | Fujimoto et al. |
| 5,695,494 | A | 12/1997 | Becker |
| 5,695,502 | A | 12/1997 | Pier et al. |
| 5,695,504 | A | 12/1997 | Gifford, III et al. |
| 5,695,524 | A | 12/1997 | Kelley et al. |
| 5,697,542 | A | 12/1997 | Knodel et al. |
| 5,697,543 | A | 12/1997 | Burdorff |
| 5,697,909 | A | 12/1997 | Eggers et al. |
| 5,697,943 | A | 12/1997 | Sauer et al. |
| 5,700,243 | A | 12/1997 | Narciso, Jr. |
| 5,700,261 | A | 12/1997 | Brinkerhoff |
| 5,700,265 | A | 12/1997 | Romano |
| 5,700,270 | A | 12/1997 | Peyser et al. |
| 5,700,276 | A | 12/1997 | Benecke |
| 5,702,387 | A | 12/1997 | Arts et al. |
| 5,702,408 | A | 12/1997 | Wales et al. |
| 5,702,409 | A | 12/1997 | Rayburn et al. |
| 5,704,087 | A | 1/1998 | Strub |
| 5,704,534 | A | 1/1998 | Huitema et al. |
| 5,704,792 | A | 1/1998 | Sobhani |
| 5,704,900 | A | 1/1998 | Dobrovolny et al. |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |
| 5,715,836 | A | 2/1998 | Kliegis et al. |
| 5,715,987 | A | 2/1998 | Kelley et al. |
| 5,715,988 | A | 2/1998 | Palmer |
| 5,716,352 | A | 2/1998 | Viola et al. |
| 5,716,366 | A | 2/1998 | Yates |
| 5,718,359 | A | 2/1998 | Palmer et al. |
| 5,718,360 | A | 2/1998 | Green et al. |
| 5,718,548 | A | 2/1998 | Cotellessa |
| 5,718,714 | A | 2/1998 | Livneh |
| 5,720,742 | A | 2/1998 | Zacharias |
| 5,720,744 | A | 2/1998 | Eggleston et al. |
| D393,067 | S | 3/1998 | Geary et al. |
| 5,722,326 | A | 3/1998 | Post |
| 5,722,426 | A | 3/1998 | Kolff |
| 5,724,025 | A | 3/1998 | Tavori |
| 5,725,536 | A | 3/1998 | Oberlin et al. |
| 5,725,554 | A | 3/1998 | Simon et al. |
| 5,728,110 | A | 3/1998 | Vidal et al. |
| 5,728,113 | A | 3/1998 | Sherts |
| 5,728,121 | A | 3/1998 | Bimbo et al. |
| 5,730,758 | A | 3/1998 | Allgeyer |
| 5,732,636 | A | 3/1998 | Wang et al. |
| 5,732,712 | A | 3/1998 | Adair |
| 5,732,821 | A | 3/1998 | Stone et al. |
| 5,732,871 | A | 3/1998 | Clark et al. |
| 5,732,872 | A | 3/1998 | Bolduc et al. |
| 5,733,074 | A | 3/1998 | Stock et al. |
| 5,733,308 | A | 3/1998 | Daugherty et al. |
| 5,735,445 | A | 4/1998 | Vidal et al. |
| 5,735,848 | A | 4/1998 | Yates et al. |
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,738,652 | A | 4/1998 | Boyd et al. |
| 5,741,226 | A | 4/1998 | Strukel et al. |
| 5,741,271 | A | 4/1998 | Nakao et al. |
| 5,741,305 | A | 4/1998 | Vincent et al. |
| 5,743,456 | A | 4/1998 | Jones et al. |
| 5,743,906 | A | 4/1998 | Parins et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,779,701 | A | 7/1998 | McBrayer et al. |

(56) References Cited

U.S. PATENT DOCUMENTS 5,782,396 A 7/1998 Mastri et al.
5,782,397 A 7/1998 Koukline
5,782,748 A 7/1998 Palmer et al.
5,782,749 A 7/1998 Riza
5,782,834 A 7/1998 Lucey et al.
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,138 A 8/1998 Shipp
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,798,752 A 8/1998 Buxton et al.
5,799,857 A 9/1998 Robertson et al.
5,800,379 A 9/1998 Edwards
5,800,423 A 9/1998 Jensen
5,800,432 A 9/1998 Swanson
5,800,449 A 9/1998 Wales
5,804,726 A 9/1998 Geib et al.
5,804,936 A 9/1998 Brodsky et al.
5,805,140 A 9/1998 Rosenberg et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,240 A 9/1998 Robertson
5,810,718 A 9/1998 Akiba et al.
5,810,721 A 9/1998 Mueller et al.
5,810,811 A 9/1998 Yates et al.
5,810,846 A 9/1998 Virnich et al.
5,810,855 A 9/1998 Rayburn et al.
5,810,859 A 9/1998 DiMatteo et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,033 A 10/1998 DeSantis et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,828,160 A 10/1998 Sugishita
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,867 A 11/1998 Speier et al.
5,836,909 A 11/1998 Cosmescu
5,836,943 A 11/1998 Miller, III
5,836,960 A 11/1998 Kolesa et al.
5,836,990 A 11/1998 Li
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,109 A 12/1998 Mehta et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,853,412 A 12/1998 Mayenberger
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,664 A 2/1999 Speier et al.
5,868,760 A 2/1999 McGuckin, Jr.
5,868,790 A 2/1999 Vincent et al.
5,871,135 A 2/1999 Williamson IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,879,364 A 3/1999 Bromfield et al.
5,880,668 A 3/1999 Hall
5,881,777 A 3/1999 Bassi et al.
5,881,943 A 3/1999 Heck et al.
5,883,454 A 3/1999 Hones et al.
5,887,018 A 3/1999 Bayazitoglu et al.
5,891,094 A 4/1999 Masterson et al.
5,891,142 A 4/1999 Eggers et al.
5,891,160 A 4/1999 Williamson, IV et al.
5,891,558 A 4/1999 Bell et al.
5,893,506 A 4/1999 Powell
5,893,835 A 4/1999 Witt et al.
5,893,855 A 4/1999 Jacobs
5,893,863 A 4/1999 Yoon
5,893,878 A 4/1999 Pierce
5,894,979 A 4/1999 Powell
5,897,552 A 4/1999 Edwards et al.
5,897,562 A 4/1999 Bolanos et al.
5,897,569 A 4/1999 Kellogg et al.
5,899,824 A 5/1999 Kurtz et al.
5,899,914 A 5/1999 Zirps et al.
5,901,895 A 5/1999 Heaton et al.
5,902,239 A 5/1999 Buurman
5,902,312 A 5/1999 Frater et al.
5,903,117 A 5/1999 Gregory
5,904,147 A 5/1999 Conlan et al.
5,904,647 A 5/1999 Ouchi
5,904,693 A 5/1999 Dicesare et al.
5,904,702 A 5/1999 Ek et al.
5,906,577 A 5/1999 Beane et al.
5,906,579 A 5/1999 Vander Salm et al.
5,906,625 A 5/1999 Bito et al.
5,907,211 A 5/1999 Hall et al.
5,907,664 A 5/1999 Wang et al.
5,908,149 A 6/1999 Welch et al.
5,908,402 A 6/1999 Blythe
5,908,427 A 6/1999 McKean et al.
5,909,062 A 6/1999 Krietzman
5,910,129 A 6/1999 Koblish et al.

(56) References Cited

U.S. PATENT DOCUMENTS 5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.
5,924,864 A 7/1999 Loge et al.
5,928,137 A 7/1999 Green
5,928,256 A 7/1999 Riza
5,929,846 A 7/1999 Rosenberg et al.
5,931,847 A 8/1999 Bittner et al.
5,931,853 A 8/1999 McEwen et al.
5,935,143 A 8/1999 Hood
5,935,144 A 8/1999 Estabrook
5,937,951 A 8/1999 Izuchukwu et al.
5,938,633 A 8/1999 Beaupre
5,938,667 A 8/1999 Peyser et al.
5,941,442 A 8/1999 Geiste et al.
5,941,890 A 8/1999 Voegele et al.
5,944,172 A 8/1999 Hannula
5,944,298 A 8/1999 Koike
5,944,715 A 8/1999 Goble et al.
5,944,718 A 8/1999 Austin et al.
5,944,737 A 8/1999 Tsonton et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,954,736 A 9/1999 Bishop et al.
5,954,746 A 9/1999 Holthaus et al.
5,957,831 A 9/1999 Adair
5,957,849 A 9/1999 Munro
5,957,882 A 9/1999 Nita et al.
5,957,943 A 9/1999 Vaitekunas
5,964,394 A 10/1999 Robertson
5,964,774 A 10/1999 McKean et al.
5,966,126 A 10/1999 Szabo
5,968,007 A 10/1999 Simon et al.
5,968,060 A 10/1999 Kellogg
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,980,569 A 11/1999 Scirica
5,984,938 A 11/1999 Yoon
5,984,949 A 11/1999 Levin
5,988,479 A 11/1999 Palmer
5,989,182 A 11/1999 Hori et al.
5,989,274 A 11/1999 Davison et al.
5,989,275 A 11/1999 Estabrook et al.
5,990,379 A 11/1999 Gregory
5,993,466 A 11/1999 Yoon
5,993,972 A 11/1999 Reich et al.
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,484 A 12/1999 Thompson
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,052 A 1/2000 Durman et al.
6,013,076 A 1/2000 Goble et al.
6,013,991 A 1/2000 Philipp
6,014,580 A 1/2000 Blume et al.
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,275 A 2/2000 Horvitz et al.
6,023,641 A 2/2000 Thompson
6,024,708 A 2/2000 Bales et al.
6,024,741 A 2/2000 Williamson, IV et al.
6,024,744 A 2/2000 Kese et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,031,148 A 2/2000 Hayes et al.
6,032,849 A 3/2000 Mastri et al.
6,033,105 A 3/2000 Barker et al.
6,033,375 A 3/2000 Brumbach
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,172 A 4/2000 Hovda et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,068,629 A 5/2000 Haissaguerre et al.
6,068,647 A 5/2000 Witt et al.
6,071,233 A 6/2000 Ishikawa et al.
6,072,299 A 6/2000 Kurle et al.
6,074,386 A 6/2000 Goble et al.
6,074,389 A 6/2000 Levine et al.
6,074,401 A 6/2000 Gardiner et al.

(56) References Cited

U.S. PATENT DOCUMENTS

| | | | |
|---|---|---|---|
| 6,075,441 | A | 6/2000 | Maloney |
| 6,077,280 | A | 6/2000 | Fossum |
| 6,077,285 | A | 6/2000 | Boukhny |
| 6,077,286 | A | 6/2000 | Cuschieri et al. |
| 6,077,290 | A | 6/2000 | Marini |
| 6,079,606 | A | 6/2000 | Milliman et al. |
| 6,080,152 | A | 6/2000 | Nardella et al. |
| 6,080,181 | A | 6/2000 | Jensen et al. |
| 6,082,577 | A | 7/2000 | Coates et al. |
| 6,083,151 | A | 7/2000 | Renner et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,584 | A | 7/2000 | Miller |
| 6,086,600 | A | 7/2000 | Kortenbach |
| 6,090,106 | A | 7/2000 | Goble et al. |
| 6,090,120 | A | 7/2000 | Wright et al. |
| 6,090,123 | A | 7/2000 | Culp et al. |
| 6,091,995 | A | 7/2000 | Ingle et al. |
| 6,093,186 | A | 7/2000 | Goble |
| 6,094,021 | A | 7/2000 | Noro et al. |
| D429,252 | S | 8/2000 | Haitani et al. |
| 6,099,483 | A | 8/2000 | Palmer et al. |
| 6,099,537 | A | 8/2000 | Sugai et al. |
| 6,099,550 | A | 8/2000 | Yoon |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,594 | A | 9/2000 | Savage |
| 6,113,598 | A | 9/2000 | Baker |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,466 | A | 9/2000 | Persson et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,127,757 | A | 10/2000 | Swinbanks |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,320 | A | 10/2000 | Hahn |
| 6,139,546 | A | 10/2000 | Koenig et al. |
| 6,142,149 | A | 11/2000 | Steen |
| 6,142,933 | A | 11/2000 | Longo et al. |
| 6,144,402 | A | 11/2000 | Norsworthy et al. |
| 6,147,135 | A | 11/2000 | Yuan et al. |
| 6,148,979 | A | 11/2000 | Roach et al. |
| 6,149,660 | A | 11/2000 | Laufer et al. |
| 6,151,323 | A | 11/2000 | O'Connell et al. |
| 6,152,902 | A | 11/2000 | Christian et al. |
| 6,152,923 | A | 11/2000 | Ryan |
| 6,152,935 | A | 11/2000 | Kammerer et al. |
| 6,154,198 | A | 11/2000 | Rosenberg |
| 6,155,083 | A | 12/2000 | Goeser et al. |
| 6,155,473 | A | 12/2000 | Tompkins et al. |
| 6,156,056 | A | 12/2000 | Kearns et al. |
| 6,157,169 | A | 12/2000 | Lee |
| 6,157,303 | A | 12/2000 | Bodie et al. |
| 6,159,146 | A | 12/2000 | El Gazayerli |
| 6,159,160 | A | 12/2000 | Hsei et al. |
| 6,159,175 | A | 12/2000 | Strukel et al. |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,173,199 | B1 | 1/2001 | Gabriel |
| 6,173,715 | B1 | 1/2001 | Sinanan et al. |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,176,857 | B1 | 1/2001 | Ashley |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,193,709 | B1 | 2/2001 | Miyawaki et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,844 | B1 | 3/2001 | Reichel et al. |
| 6,206,876 | B1 | 3/2001 | Levine et al. |
| 6,206,877 | B1 | 3/2001 | Kese et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,023 | B1 | 4/2001 | Whipple et al. |
| 6,214,028 | B1 | 4/2001 | Yoon et al. |
| 6,219,572 | B1 | 4/2001 | Young |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |
| 6,228,089 | B1 | 5/2001 | Wahrburg |
| 6,228,098 | B1 | 5/2001 | Kayan et al. |
| 6,231,565 | B1 | 5/2001 | Tovey et al. |
| 6,233,476 | B1 | 5/2001 | Strommer et al. |
| 6,234,178 | B1 | 5/2001 | Goble et al. |
| 6,235,036 | B1 | 5/2001 | Gardner et al. |
| 6,237,604 | B1 | 5/2001 | Burnside et al. |
| 6,238,366 | B1 | 5/2001 | Savage et al. |
| 6,238,384 | B1 | 5/2001 | Peer |
| 6,241,139 | B1 | 6/2001 | Milliman et al. |
| 6,241,140 | B1 | 6/2001 | Adams et al. |
| 6,241,723 | B1 | 6/2001 | Heim et al. |
| 6,241,724 | B1 | 6/2001 | Fleischman et al. |
| 6,245,084 | B1 | 6/2001 | Mark et al. |
| 6,248,074 | B1 | 6/2001 | Ohno et al. |
| 6,248,116 | B1 | 6/2001 | Chevillon et al. |
| 6,248,117 | B1 | 6/2001 | Blatter |

(56) References Cited

U.S. PATENT DOCUMENTS

| | | | |
|---|---|---|---|
| 6,249,076 | B1 | 6/2001 | Madden et al. |
| 6,249,105 | B1 | 6/2001 | Andrews et al. |
| 6,250,532 | B1 | 6/2001 | Green et al. |
| 6,251,485 | B1 | 6/2001 | Harris et al. |
| D444,365 | S | 7/2001 | Bass et al. |
| D445,745 | S | 7/2001 | Norman |
| 6,254,534 | B1 | 7/2001 | Butler et al. |
| 6,254,619 | B1 | 7/2001 | Garabet et al. |
| 6,254,623 | B1 | 7/2001 | Haibel, Jr. et al. |
| 6,254,642 | B1 | 7/2001 | Taylor |
| 6,258,034 | B1 | 7/2001 | Hanafy |
| 6,258,086 | B1 | 7/2001 | Ashley et al. |
| 6,258,107 | B1 | 7/2001 | Balazs et al. |
| 6,259,230 | B1 | 7/2001 | Chou |
| 6,261,246 | B1 | 7/2001 | Pantages et al. |
| 6,261,286 | B1 | 7/2001 | Goble et al. |
| 6,261,679 | B1 | 7/2001 | Chen et al. |
| 6,264,086 | B1 | 7/2001 | McGuckin, Jr. |
| 6,264,087 | B1 | 7/2001 | Whitman |
| 6,264,617 | B1 | 7/2001 | Bales et al. |
| 6,267,761 | B1 | 7/2001 | Ryan |
| 6,269,997 | B1 | 8/2001 | Balazs et al. |
| 6,270,508 | B1 | 8/2001 | Klieman et al. |
| 6,270,831 | B2 | 8/2001 | Kumar et al. |
| 6,270,916 | B1 | 8/2001 | Sink et al. |
| 6,273,252 | B1 | 8/2001 | Mitchell |
| 6,273,852 | B1 | 8/2001 | Lehe et al. |
| 6,273,876 | B1 | 8/2001 | Klima et al. |
| 6,273,887 | B1 | 8/2001 | Yamauchi et al. |
| 6,273,897 | B1 | 8/2001 | Dalessandro et al. |
| 6,274,963 | B1 | 8/2001 | Estabrook et al. |
| 6,277,114 | B1 | 8/2001 | Bullivant et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,292,700 | B1 | 9/2001 | Morrison et al. |
| 6,293,927 | B1 | 9/2001 | McGuckin, Jr. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,302,743 | B1 | 10/2001 | Chiu et al. |
| 6,305,891 | B1 | 10/2001 | Burlingame |
| 6,306,134 | B1 | 10/2001 | Goble et al. |
| 6,306,149 | B1 | 10/2001 | Meade |
| 6,306,424 | B1 | 10/2001 | Vyakarnam et al. |
| 6,309,397 | B1 | 10/2001 | Julian et al. |
| 6,309,400 | B2 | 10/2001 | Beaupre |
| 6,309,403 | B1 | 10/2001 | Minor et al. |
| 6,312,435 | B1 | 11/2001 | Wallace et al. |
| 6,315,184 | B1 | 11/2001 | Whitman |
| 6,315,789 | B1 | 11/2001 | Cragg |
| 6,317,616 | B1 | 11/2001 | Glossop |
| 6,319,221 | B1 | 11/2001 | Savage et al. |
| 6,319,510 | B1 | 11/2001 | Yates |
| 6,320,123 | B1 | 11/2001 | Reimers |
| 6,322,494 | B1 | 11/2001 | Bullivant et al. |
| 6,324,339 | B1 | 11/2001 | Hudson et al. |
| 6,325,799 | B1 | 12/2001 | Goble |
| 6,325,805 | B1 | 12/2001 | Ogilvie et al. |
| 6,325,810 | B1 | 12/2001 | Hamilton et al. |
| 6,325,811 | B1 | 12/2001 | Messerly |
| 6,328,498 | B1 | 12/2001 | Mersch |
| 6,328,751 | B1 | 12/2001 | Beaupre |
| 6,330,965 | B1 | 12/2001 | Milliman et al. |
| 6,331,181 | B1 | 12/2001 | Tierney et al. |
| 6,331,761 | B1 | 12/2001 | Kumar et al. |
| 6,333,029 | B1 | 12/2001 | Vyakarnam et al. |
| 6,334,860 | B1 | 1/2002 | Dorn |
| 6,334,861 | B1 | 1/2002 | Chandler et al. |
| 6,336,926 | B1 | 1/2002 | Goble |
| 6,338,737 | B1 | 1/2002 | Toledano |
| 6,338,738 | B1 | 1/2002 | Bellotti et al. |
| 6,340,878 | B1 | 1/2002 | Oglesbee |
| 6,343,731 | B1 | 2/2002 | Adams et al. |
| 6,346,077 | B1 | 2/2002 | Taylor et al. |
| 6,348,061 | B1 | 2/2002 | Whitman |
| 6,349,868 | B1 | 2/2002 | Mattingly et al. |
| D454,951 | S | 3/2002 | Bon |
| 6,352,503 | B1 | 3/2002 | Matsui et al. |
| 6,352,532 | B1 | 3/2002 | Kramer et al. |
| 6,355,699 | B1 | 3/2002 | Vyakarnam et al. |
| 6,356,072 | B1 | 3/2002 | Chass |
| 6,358,224 | B1 | 3/2002 | Tims et al. |
| 6,358,263 | B2 | 3/2002 | Mark et al. |
| 6,358,459 | B1 | 3/2002 | Ziegler et al. |
| 6,361,542 | B1 | 3/2002 | Dimitriu et al. |
| 6,364,828 | B1 | 4/2002 | Yeung et al. |
| 6,364,877 | B1 | 4/2002 | Goble et al. |
| 6,364,888 | B1 | 4/2002 | Niemeyer et al. |
| 6,366,441 | B1 | 4/2002 | Ozawa et al. |
| 6,370,981 | B2 | 4/2002 | Watarai |
| 6,371,114 | B1 | 4/2002 | Schmidt et al. |
| 6,371,952 | B1 | 4/2002 | Madhani et al. |
| 6,373,152 | B1 | 4/2002 | Wang et al. |
| 6,377,011 | B1 | 4/2002 | Ben-Ur |
| 6,379,320 | B1 | 4/2002 | Lafon et al. |
| 6,379,351 | B1 | 4/2002 | Thapliyal et al. |
| D457,958 | S | 5/2002 | Dycus et al. |
| 6,383,194 | B1 | 5/2002 | Pothula |
| 6,383,201 | B1 | 5/2002 | Dong |
| 6,387,092 | B1 | 5/2002 | Burnside et al. |
| 6,387,094 | B1 | 5/2002 | Eitenmuller |
| 6,387,109 | B1 | 5/2002 | Davison et al. |
| 6,387,113 | B1 | 5/2002 | Hawkins et al. |
| 6,387,114 | B2 | 5/2002 | Adams |
| 6,388,657 | B1 | 5/2002 | Natoli |
| 6,391,026 | B1 | 5/2002 | Hung et al. |
| 6,391,038 | B2 | 5/2002 | Vargas et al. |
| 6,391,042 | B1 | 5/2002 | Cimino |
| 6,392,854 | B1 | 5/2002 | O'Gorman |
| 6,394,998 | B1 | 5/2002 | Wallace et al. |
| 6,398,779 | B1 | 6/2002 | Buysse et al. |
| 6,398,781 | B1 | 6/2002 | Goble et al. |
| 6,398,797 | B2 | 6/2002 | Bombard et al. |
| 6,402,766 | B2 | 6/2002 | Bowman et al. |
| 6,402,780 | B2 | 6/2002 | Williamson, IV et al. |
| 6,406,440 | B1 | 6/2002 | Stefanchik |
| 6,406,472 | B1 | 6/2002 | Jensen |
| 6,409,722 | B1 | 6/2002 | Hoey et al. |
| 6,409,724 | B1 | 6/2002 | Penny et al. |
| H2037 | H | 7/2002 | Yates et al. |
| 6,412,639 | B1 | 7/2002 | Hickey |
| 6,413,274 | B1 | 7/2002 | Pedros |
| 6,415,542 | B1 | 7/2002 | Bates et al. |
| 6,416,469 | B1 | 7/2002 | Phung et al. |
| 6,416,486 | B1 | 7/2002 | Wampler |
| 6,416,509 | B1 | 7/2002 | Goble et al. |
| 6,419,675 | B1 | 7/2002 | Gallo, Sr. |
| 6,419,695 | B1 | 7/2002 | Gabbay |
| 6,423,073 | B2 | 7/2002 | Bowman |
| 6,423,079 | B1 | 7/2002 | Blake, III |
| 6,423,082 | B1 | 7/2002 | Houser et al. |
| 6,424,885 | B1 | 7/2002 | Niemeyer et al. |
| RE37,814 | E | 8/2002 | Allgeyer |
| 6,428,070 | B1 | 8/2002 | Takanashi et al. |
| 6,428,487 | B1 | 8/2002 | Burdorff et al. |
| 6,429,611 | B1 | 8/2002 | Li |
| 6,430,298 | B1 | 8/2002 | Kettl et al. |
| 6,430,446 | B1 | 8/2002 | Knowlton |
| 6,432,065 | B1 | 8/2002 | Burdorff et al. |
| 6,432,118 | B1 | 8/2002 | Messerly |
| 6,436,097 | B1 | 8/2002 | Nardella |
| 6,436,107 | B1 | 8/2002 | Wang et al. |
| 6,436,110 | B2 | 8/2002 | Bowman et al. |
| 6,436,114 | B1 | 8/2002 | Novak et al. |
| 6,436,115 | B1 | 8/2002 | Beaupre |
| 6,436,122 | B1 | 8/2002 | Frank et al. |
| 6,439,439 | B1 | 8/2002 | Rickard et al. |
| 6,439,446 | B1 | 8/2002 | Perry et al. |
| 6,440,146 | B2 | 8/2002 | Nicholas et al. |
| 6,441,577 | B2 | 8/2002 | Blumenkranz et al. |
| D462,758 | S | 9/2002 | Epstein et al. |

(56) References Cited

U.S. PATENT DOCUMENTS 6,443,968 B1 9/2002 Holthaus et al.
6,443,969 B1 9/2002 Novak et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,454,782 B1 9/2002 Schwemberger
6,457,338 B1 10/2002 Frenken
6,457,625 B1 10/2002 Tormala et al.
6,458,077 B1 10/2002 Boebel et al.
6,458,128 B1 10/2002 Schulze
6,458,130 B1 10/2002 Frazier et al.
6,458,142 B1 10/2002 Faller et al.
6,458,147 B1 10/2002 Cruise et al.
6,460,627 B1 10/2002 Below et al.
6,461,363 B1 10/2002 Gadberry et al.
6,463,824 B1 10/2002 Prell et al.
6,464,689 B1 10/2002 Qin et al.
6,464,702 B2 10/2002 Schulze et al.
6,464,703 B2 10/2002 Bartel
6,468,275 B1 10/2002 Wampler et al.
6,468,286 B2 10/2002 Mastri et al.
6,471,106 B1 10/2002 Reining
6,471,172 B1 10/2002 Lemke et al.
6,471,659 B2 10/2002 Eggers et al.
6,475,211 B2 11/2002 Chess et al.
6,475,216 B2 11/2002 Mulier et al.
6,478,210 B2 11/2002 Adams et al.
6,480,796 B2 11/2002 Wiener
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,691 B1 12/2002 Morley et al.
6,491,701 B2 12/2002 Tierney et al.
6,491,702 B2 12/2002 Heilbrun et al.
6,491,708 B2 12/2002 Madan et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,497,715 B2 12/2002 Satou
6,498,480 B1 12/2002 Manara
6,500,112 B1 12/2002 Khouri
6,500,176 B1 12/2002 Truckai et al.
6,500,188 B2 12/2002 Harper et al.
6,500,189 B1 12/2002 Lang et al.
6,500,194 B2 12/2002 Benderev et al.
D468,749 S 1/2003 Friedman
6,503,139 B2 1/2003 Coral
6,503,248 B1 1/2003 Levine
6,503,257 B2 1/2003 Grant et al.
6,503,259 B2 1/2003 Huxel et al.
6,505,768 B2 1/2003 Whitman
6,506,197 B1 1/2003 Rollero et al.
6,506,208 B2 1/2003 Hunt et al.
6,506,399 B2 1/2003 Donovan
6,510,854 B2 1/2003 Goble
6,511,468 B1 1/2003 Cragg et al.
6,511,480 B1 1/2003 Tetzlaff et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,960 B2 2/2003 Blocher et al.
6,520,971 B1 2/2003 Perry et al.
6,520,972 B2 2/2003 Peters
6,522,101 B2 2/2003 Malackowski
6,522,909 B1 2/2003 Garibaldi et al.
6,524,180 B1 2/2003 Simms et al.
6,524,316 B1 2/2003 Nicholson et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,531,846 B1 3/2003 Smith
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,537,196 B1 3/2003 Creighton, IV et al.
6,537,272 B2 3/2003 Christopherson et al.
6,537,291 B2 3/2003 Friedman et al.
6,539,297 B2 3/2003 Weiberle et al.
D473,239 S 4/2003 Cockerill
6,539,816 B2 4/2003 Kogiso et al.
6,540,693 B2 4/2003 Burbank et al.
6,540,737 B2 4/2003 Bacher et al.
6,543,456 B1 4/2003 Freeman
6,544,260 B1 4/2003 Markel et al.
6,545,384 B1 4/2003 Pelrine et al.
6,547,786 B1 4/2003 Goble
6,550,546 B2 4/2003 Thurler et al.
6,551,309 B1 4/2003 LePivert
6,551,333 B2 4/2003 Kuhns et al.
6,554,829 B2 4/2003 Schulze et al.
6,554,844 B2 4/2003 Lee et al.
6,554,861 B2 4/2003 Knox et al.
6,555,770 B2 4/2003 Kawase
6,558,376 B2 5/2003 Bishop
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,561,983 B2 5/2003 Cronin et al.
6,562,037 B2 5/2003 Paton et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,569,173 B1 5/2003 Blatter et al.
6,572,629 B2 6/2003 Kalloo et al.
6,572,632 B2 6/2003 Zisterer et al.
6,572,639 B1 6/2003 Ingle et al.
6,575,969 B1 6/2003 Rittman et al.
6,578,751 B2 6/2003 Hartwick
6,582,364 B2 6/2003 Butler et al.
6,582,427 B1 6/2003 Goble et al.
6,582,441 B1 6/2003 He et al.
6,582,451 B1 6/2003 Marucci et al.
6,583,533 B2 6/2003 Pelrine et al.
6,584,360 B2 6/2003 Francischelli et al.
6,585,144 B2 7/2003 Adams et al.
6,585,664 B2 7/2003 Burdorff et al.
6,585,735 B1 7/2003 Frazier et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,589,200 B1 7/2003 Schwemberger et al.
6,589,239 B2 7/2003 Khandkar et al.

(56) References Cited

U.S. PATENT DOCUMENTS

| | | | |
|---|---|---|---|
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,517 | B1 | 7/2003 | Nevo |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,321 | B2 | 7/2003 | Hyde, Jr. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,610,060 | B2 | 8/2003 | Mulier et al. |
| 6,611,793 | B1 | 8/2003 | Burnside et al. |
| 6,613,069 | B2 | 9/2003 | Boyd et al. |
| 6,616,450 | B2 | 9/2003 | Mossle et al. |
| 6,616,600 | B2 | 9/2003 | Pauker |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,129 | B2 | 9/2003 | Stecker et al. |
| 6,620,161 | B2 | 9/2003 | Schulze et al. |
| 6,620,166 | B1 | 9/2003 | Wenstrom, Jr. et al. |
| 6,622,731 | B2 | 9/2003 | Daniel et al. |
| 6,623,482 | B2 | 9/2003 | Pendekanti et al. |
| 6,623,501 | B2 | 9/2003 | Heller et al. |
| 6,625,517 | B1 | 9/2003 | Bogdanov et al. |
| 6,626,834 | B2 | 9/2003 | Dunne et al. |
| 6,626,901 | B1 | 9/2003 | Treat et al. |
| 6,626,926 | B2 | 9/2003 | Friedman et al. |
| 6,626,938 | B1 | 9/2003 | Butaric et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,633,234 | B2 | 10/2003 | Wiener et al. |
| 6,635,057 | B2 | 10/2003 | Harano et al. |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,817 | B2 | 11/2003 | Schara et al. |
| 6,648,901 | B2 | 11/2003 | Fleischman et al. |
| 6,651,669 | B1 | 11/2003 | Burnside |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,656,198 | B2 | 12/2003 | Tsonton et al. |
| 6,659,940 | B2 | 12/2003 | Adler |
| 6,660,008 | B1 | 12/2003 | Foerster et al. |
| 6,662,127 | B2 | 12/2003 | Wiener et al. |
| 6,663,623 | B1 | 12/2003 | Oyama et al. |
| 6,663,641 | B1 | 12/2003 | Kovac et al. |
| 6,663,941 | B2 | 12/2003 | Brown et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,669,690 | B1 | 12/2003 | Okada et al. |
| 6,670,806 | B2 | 12/2003 | Wendt et al. |
| 6,671,185 | B2 | 12/2003 | Duval |
| D484,977 | S | 1/2004 | Ryan et al. |
| 6,673,248 | B2 | 1/2004 | Chowdhury |
| 6,676,660 | B2 | 1/2004 | Wampler et al. |
| 6,677,687 | B2 | 1/2004 | Ho et al. |
| 6,678,621 | B2 | 1/2004 | Wiener et al. |
| 6,679,269 | B2 | 1/2004 | Swanson |
| 6,679,410 | B2 | 1/2004 | Wursch et al. |
| 6,679,882 | B1 | 1/2004 | Kornerup |
| 6,679,899 | B2 | 1/2004 | Wiener et al. |
| 6,681,978 | B2 | 1/2004 | Geiste et al. |
| 6,681,979 | B2 | 1/2004 | Whitman |
| 6,682,501 | B1 | 1/2004 | Nelson et al. |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,840 | B2 | 2/2004 | Schulze |
| 6,695,849 | B2 | 2/2004 | Michelson |
| 6,696,814 | B2 | 2/2004 | Henderson et al. |
| 6,696,844 | B2 | 2/2004 | Wong et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,215 | B1 | 4/2004 | David et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,719,684 | B2 | 4/2004 | Kim et al. |
| 6,719,765 | B2 | 4/2004 | Bonutti |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,723,094 | B1 | 4/2004 | Desinger |
| 6,723,106 | B1 | 4/2004 | Charles et al. |
| 6,723,109 | B2 | 4/2004 | Solingen |
| 6,726,651 | B1 | 4/2004 | Robinson et al. |
| 6,726,686 | B2 | 4/2004 | Buysse et al. |
| 6,726,697 | B2 | 4/2004 | Nicholas et al. |
| 6,726,705 | B2 | 4/2004 | Peterson et al. |
| 6,726,706 | B2 | 4/2004 | Dominguez |
| 6,729,119 | B2 | 5/2004 | Schnipke et al. |
| 6,731,047 | B2 | 5/2004 | Kauf et al. |
| 6,731,976 | B2 | 5/2004 | Penn et al. |
| 6,733,498 | B2 | 5/2004 | Paton et al. |
| 6,733,506 | B1 | 5/2004 | McDevitt et al. |
| 6,736,810 | B2 | 5/2004 | Hoey et al. |
| 6,736,813 | B2 | 5/2004 | Yamauchi et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,229 | B2 | 6/2004 | Buysse et al. |
| 6,743,230 | B2 | 6/2004 | Lutze et al. |
| 6,744,385 | B2 | 6/2004 | Kazuya et al. |
| 6,746,443 | B1 | 6/2004 | Morley et al. |
| 6,747,121 | B2 | 6/2004 | Gogolewski |
| 6,747,300 | B2 | 6/2004 | Nadd et al. |
| 6,749,560 | B1 | 6/2004 | Konstorum et al. |

(56) References Cited

U.S. PATENT DOCUMENTS

| | | | |
|---|---|---|---|
| 6,749,600 | B1 | 6/2004 | Levy |
| 6,752,768 | B2 | 6/2004 | Burdorff et al. |
| 6,752,815 | B2 | 6/2004 | Beaupre |
| 6,752,816 | B2 | 6/2004 | Culp et al. |
| 6,754,959 | B1 | 6/2004 | Guiette, III et al. |
| 6,755,195 | B1 | 6/2004 | Lemke et al. |
| 6,755,338 | B2 | 6/2004 | Hahnen et al. |
| 6,755,825 | B2 | 6/2004 | Shoenman et al. |
| 6,755,843 | B2 | 6/2004 | Chung et al. |
| 6,756,705 | B2 | 6/2004 | Pulford, Jr. |
| 6,758,846 | B2 | 7/2004 | Goble et al. |
| 6,761,685 | B2 | 7/2004 | Adams et al. |
| 6,762,339 | B1 | 7/2004 | Klun et al. |
| 6,762,535 | B2 | 7/2004 | Take et al. |
| 6,763,307 | B2 | 7/2004 | Berg et al. |
| 6,764,445 | B2 | 7/2004 | Ramans et al. |
| 6,766,202 | B2 | 7/2004 | Underwood et al. |
| 6,766,957 | B2 | 7/2004 | Matsuura et al. |
| 6,767,349 | B2 | 7/2004 | Ouchi |
| 6,767,352 | B2 | 7/2004 | Field et al. |
| 6,767,356 | B2 | 7/2004 | Kanner et al. |
| 6,769,590 | B2 | 8/2004 | Vresh et al. |
| 6,769,594 | B2 | 8/2004 | Orban, III |
| 6,770,027 | B2 | 8/2004 | Banik et al. |
| 6,770,070 | B1 | 8/2004 | Balbierz |
| 6,770,072 | B1 | 8/2004 | Truckai et al. |
| 6,770,078 | B2 | 8/2004 | Bonutti |
| 6,773,409 | B2 | 8/2004 | Truckai et al. |
| 6,773,434 | B2 | 8/2004 | Ciarrocca |
| 6,773,435 | B2 | 8/2004 | Schulze et al. |
| 6,773,437 | B2 | 8/2004 | Ogilvie et al. |
| 6,773,438 | B1 | 8/2004 | Knodel et al. |
| 6,773,444 | B2 | 8/2004 | Messerly |
| 6,773,458 | B1 | 8/2004 | Brauker et al. |
| 6,775,575 | B2 | 8/2004 | Bommannan et al. |
| 6,776,165 | B2 | 8/2004 | Jin |
| 6,777,838 | B2 | 8/2004 | Miekka et al. |
| 6,778,846 | B1 | 8/2004 | Martinez et al. |
| 6,780,151 | B2 | 8/2004 | Grabover et al. |
| 6,780,180 | B1 | 8/2004 | Goble et al. |
| 6,783,524 | B2 | 8/2004 | Anderson et al. |
| 6,784,775 | B2 | 8/2004 | Mandell et al. |
| 6,786,382 | B1 | 9/2004 | Hoffman |
| 6,786,383 | B2 | 9/2004 | Stegelmann |
| 6,786,864 | B2 | 9/2004 | Matsuura et al. |
| 6,786,896 | B1 | 9/2004 | Madhani et al. |
| 6,788,018 | B1 | 9/2004 | Blumenkranz |
| 6,789,939 | B2 | 9/2004 | Schrodinger et al. |
| 6,790,173 | B2 | 9/2004 | Saadat et al. |
| 6,790,216 | B1 | 9/2004 | Ishikawa |
| 6,793,652 | B1 | 9/2004 | Whitman et al. |
| 6,793,661 | B2 | 9/2004 | Hamilton et al. |
| 6,793,663 | B2 | 9/2004 | Kneifel et al. |
| 6,793,669 | B2 | 9/2004 | Nakamura et al. |
| 6,796,921 | B1 | 9/2004 | Buck et al. |
| 6,796,981 | B2 | 9/2004 | Wham et al. |
| D496,997 | S | 10/2004 | Dycus et al. |
| 6,799,669 | B2 | 10/2004 | Fukumura et al. |
| 6,800,085 | B2 | 10/2004 | Selmon et al. |
| 6,801,009 | B2 | 10/2004 | Makaran et al. |
| 6,802,822 | B1 | 10/2004 | Dodge |
| 6,802,843 | B2 | 10/2004 | Truckai et al. |
| 6,802,844 | B2 | 10/2004 | Ferree |
| 6,805,273 | B2 | 10/2004 | Bilotti et al. |
| 6,806,317 | B2 | 10/2004 | Morishita et al. |
| 6,806,808 | B1 | 10/2004 | Watters et al. |
| 6,806,867 | B1 | 10/2004 | Arruda et al. |
| 6,808,491 | B2 | 10/2004 | Kortenbach et al. |
| 6,808,525 | B2 | 10/2004 | Latterell et al. |
| 6,810,359 | B2 | 10/2004 | Sakaguchi |
| 6,811,842 | B1 | 11/2004 | Ehrnsperger et al. |
| 6,814,154 | B2 | 11/2004 | Chou |
| 6,814,731 | B2 | 11/2004 | Swanson |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,818,018 | B1 | 11/2004 | Sawhney |
| 6,820,791 | B2 | 11/2004 | Adams |
| 6,821,273 | B2 | 11/2004 | Mollenauer |
| 6,821,282 | B2 | 11/2004 | Perry et al. |
| 6,821,284 | B2 | 11/2004 | Sturtz et al. |
| 6,827,246 | B2 | 12/2004 | Sullivan et al. |
| 6,827,712 | B2 | 12/2004 | Tovey et al. |
| 6,827,725 | B2 | 12/2004 | Batchelor et al. |
| 6,828,712 | B2 | 12/2004 | Battaglin et al. |
| 6,828,902 | B2 | 12/2004 | Casden |
| 6,830,174 | B2 | 12/2004 | Hillstead et al. |
| 6,831,629 | B2 | 12/2004 | Nishino et al. |
| 6,832,998 | B2 | 12/2004 | Goble |
| 6,834,001 | B2 | 12/2004 | Myono |
| 6,835,173 | B2 | 12/2004 | Couvillon, Jr. |
| 6,835,199 | B2 | 12/2004 | McGuckin, Jr. et al. |
| 6,835,336 | B2 | 12/2004 | Watt |
| 6,836,611 | B2 | 12/2004 | Popovic et al. |
| 6,837,846 | B2 | 1/2005 | Jaffe et al. |
| 6,837,883 | B2 | 1/2005 | Moll et al. |
| 6,838,493 | B2 | 1/2005 | Williams et al. |
| 6,840,423 | B2 | 1/2005 | Adams et al. |
| 6,840,938 | B1 | 1/2005 | Morley et al. |
| 6,841,967 | B2 | 1/2005 | Kim et al. |
| 6,843,403 | B2 | 1/2005 | Whitman |
| 6,843,789 | B2 | 1/2005 | Goble |
| 6,843,793 | B2 | 1/2005 | Brock et al. |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,847,190 | B2 | 1/2005 | Schaefer et al. |
| 6,849,071 | B2 | 2/2005 | Whitman et al. |
| 6,850,817 | B1 | 2/2005 | Green |
| 6,852,122 | B2 | 2/2005 | Rush |
| 6,852,330 | B2 | 2/2005 | Bowman et al. |
| 6,853,879 | B2 | 2/2005 | Sunaoshi |
| 6,858,005 | B2 | 2/2005 | Ohline et al. |
| 6,859,882 | B2 | 2/2005 | Fung |
| RE38,708 | E | 3/2005 | Bolanos et al. |
| D502,994 | S | 3/2005 | Blake, III |
| 6,860,169 | B2 | 3/2005 | Shinozaki |
| 6,860,880 | B2 | 3/2005 | Treat et al. |
| 6,861,142 | B1 | 3/2005 | Wilkie et al. |
| 6,861,954 | B2 | 3/2005 | Levin |
| 6,863,668 | B2 | 3/2005 | Gillespie et al. |
| 6,863,694 | B1 | 3/2005 | Boyce et al. |
| 6,863,924 | B2 | 3/2005 | Ranganathan et al. |
| 6,866,178 | B2 | 3/2005 | Adams et al. |
| 6,866,668 | B2 | 3/2005 | Giannetti et al. |
| 6,866,671 | B2 | 3/2005 | Tierney et al. |
| 6,867,248 | B1 | 3/2005 | Martin et al. |
| 6,869,430 | B2 | 3/2005 | Balbierz et al. |
| 6,869,435 | B2 | 3/2005 | Blake, III |
| 6,869,439 | B2 | 3/2005 | White et al. |
| 6,872,214 | B2 | 3/2005 | Sonnenschein et al. |
| 6,874,669 | B2 | 4/2005 | Adams et al. |
| 6,875,220 | B2 | 4/2005 | Du et al. |
| 6,876,850 | B2 | 4/2005 | Maeshima et al. |
| 6,877,647 | B2 | 4/2005 | Green et al. |
| 6,878,106 | B1 | 4/2005 | Herrmann |
| 6,882,127 | B2 | 4/2005 | Konigbauer |
| 6,883,199 | B1 | 4/2005 | Lundell et al. |
| 6,884,392 | B2 | 4/2005 | Malkin et al. |
| 6,884,428 | B2 | 4/2005 | Binette et al. |
| 6,886,730 | B2 | 5/2005 | Fujisawa et al. |
| 6,887,244 | B1 | 5/2005 | Walker et al. |
| 6,887,710 | B2 | 5/2005 | Call et al. |
| 6,889,116 | B2 | 5/2005 | Jinno |
| 6,893,435 | B2 | 5/2005 | Goble |
| 6,894,140 | B2 | 5/2005 | Roby |
| 6,895,176 | B2 | 5/2005 | Archer et al. |
| 6,899,538 | B2 | 5/2005 | Matoba |
| 6,899,593 | B1 | 5/2005 | Moeller et al. |
| 6,899,705 | B2 | 5/2005 | Niemeyer |
| 6,899,915 | B2 | 5/2005 | Yelick et al. |
| 6,905,057 | B2 | 6/2005 | Swayze et al. |
| 6,905,497 | B2 | 6/2005 | Truckai et al. |

(56) References Cited

U.S. PATENT DOCUMENTS 6,905,498 B2 6/2005 Hooven
6,908,463 B2 6/2005 Treat et al.
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,622 B2 8/2005 Chian
6,929,632 B2 8/2005 Nita et al.
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,003 B2 8/2005 Iddan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,347 B2 9/2005 Thompson
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
6,958,070 B2 10/2005 Witt et al.
D511,145 S 11/2005 Donofrio et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,976,844 B2 12/2005 Hickok et al.
6,976,969 B2 12/2005 Messerly
6,977,495 B2 12/2005 Donofrio
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,220 B2 1/2006 Wuchinich
6,984,231 B2 1/2006 Goble et al.
6,986,451 B1 1/2006 Mastri et al.
6,986,738 B2 1/2006 Glukhovsky et al.
6,986,780 B2 1/2006 Rudnick et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,994,709 B2 2/2006 Iida
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,004,951 B2 2/2006 Gibbens, III
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,039,453 B2 5/2006 Mullick et al.
7,041,083 B2 5/2006 Chu et al.
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,044,937 B1 5/2006 Kirwan et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,496 B2 5/2006 Yamauchi
7,052,499 B2 5/2006 Steger et al.
7,055,730 B2 6/2006 Ehrenfels et al.

(56) References Cited

U.S. PATENT DOCUMENTS

| | | | |
|---|---|---|---|
| 7,055,731 | B2 | 6/2006 | Shelton, IV et al. |
| 7,056,123 | B2 | 6/2006 | Gregorio et al. |
| 7,056,284 | B2 | 6/2006 | Martone et al. |
| 7,056,330 | B2 | 6/2006 | Gayton |
| 7,059,331 | B2 | 6/2006 | Adams et al. |
| 7,059,508 | B2 | 6/2006 | Shelton, IV et al. |
| 7,063,671 | B2 | 6/2006 | Couvillon, Jr. |
| 7,063,699 | B2 | 6/2006 | Hess et al. |
| 7,063,712 | B2 | 6/2006 | Vargas et al. |
| 7,064,509 | B1 | 6/2006 | Fu et al. |
| 7,066,879 | B2 | 6/2006 | Fowler et al. |
| 7,066,936 | B2 | 6/2006 | Ryan |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,074,219 | B2 | 7/2006 | Levine et al. |
| 7,075,412 | B1 | 7/2006 | Reynolds et al. |
| 7,075,770 | B1 | 7/2006 | Smith |
| 7,077,039 | B2 | 7/2006 | Gass et al. |
| 7,077,853 | B2 | 7/2006 | Kramer et al. |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,579 | B2 | 8/2006 | Yokoi et al. |
| 7,083,615 | B2 | 8/2006 | Peterson et al. |
| 7,083,617 | B2 | 8/2006 | Kortenbach et al. |
| 7,083,618 | B2 | 8/2006 | Couture et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,235 | B2 | 8/2006 | Francischelli |
| 7,094,247 | B2 | 8/2006 | Monassevitch et al. |
| 7,094,916 | B2 | 8/2006 | DeLuca et al. |
| 7,096,560 | B2 | 8/2006 | Oddsen, Jr. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,363 | B2 | 9/2006 | Nishizawa et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,201 | B2 | 9/2006 | Truckai et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,564 | B2 | 10/2006 | Ritchie et al. |
| 7,118,570 | B2 | 10/2006 | Tetzlaff et al. |
| 7,118,582 | B1 | 10/2006 | Wang et al. |
| 7,119,534 | B2 | 10/2006 | Butzmann |
| 7,120,498 | B2 | 10/2006 | Imran et al. |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,124,932 | B2 | 10/2006 | Isaacson et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,131,970 | B2 | 11/2006 | Moses et al. |
| 7,131,971 | B2 | 11/2006 | Dycus et al. |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,018 | B2 | 11/2006 | Ryan et al. |
| 7,135,027 | B2 | 11/2006 | Delmotte |
| 7,135,030 | B2 | 11/2006 | Schwemberger et al. |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,638 | B2 | 12/2006 | Chapman et al. |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,153,315 | B2 | 12/2006 | Miller |
| 7,155,316 | B2 | 12/2006 | Sutherland et al. |
| 7,156,189 | B1 | 1/2007 | Bar-Cohen et al. |
| 7,156,846 | B2 | 1/2007 | Dycus et al. |
| 7,156,853 | B2 | 1/2007 | Muratsu |
| 7,156,863 | B2 | 1/2007 | Sonnenschein et al. |
| 7,157,058 | B2 | 1/2007 | Marhasin et al. |
| 7,159,750 | B2 | 1/2007 | Racenet et al. |
| 7,160,296 | B2 | 1/2007 | Pearson et al. |
| 7,160,298 | B2 | 1/2007 | Lawes et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,548 | B2 | 1/2007 | Stulen et al. |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,104 | B2 | 1/2007 | Ueda et al. |
| 7,169,146 | B2 | 1/2007 | Truckai et al. |
| 7,169,156 | B2 | 1/2007 | Hart |
| 7,170,823 | B2 | 1/2007 | Fabricius et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |

(56) References Cited

U.S. PATENT DOCUMENTS

| | | | |
|---|---|---|---|
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,179,271 | B2 | 2/2007 | Friedman et al. |
| 7,182,239 | B1 | 2/2007 | Myers |
| 7,182,763 | B2 | 2/2007 | Nardella |
| 7,183,737 | B2 | 2/2007 | Kitagawa |
| 7,186,253 | B2 | 3/2007 | Truckai et al. |
| 7,187,960 | B2 | 3/2007 | Abreu |
| 7,188,758 | B2 | 3/2007 | Viola et al. |
| 7,189,207 | B2 | 3/2007 | Viola |
| 7,189,233 | B2 | 3/2007 | Truckai et al. |
| 7,190,147 | B2 | 3/2007 | Gileff et al. |
| 7,193,199 | B2 | 3/2007 | Jang |
| 7,195,627 | B2 | 3/2007 | Amoah et al. |
| 7,195,631 | B2 | 3/2007 | Dumbauld |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,820 | B2 | 4/2007 | Akahoshi |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,094 | B2 | 5/2007 | Gannoe et al. |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,220,951 | B2 | 5/2007 | Truckai et al. |
| 7,223,229 | B2 | 5/2007 | Inman et al. |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,448 | B2 | 6/2007 | Bertolero et al. |
| 7,226,450 | B2 | 6/2007 | Athanasiou et al. |
| 7,226,467 | B2 | 6/2007 | Lucatero et al. |
| 7,228,505 | B2 | 6/2007 | Shimazu et al. |
| 7,229,408 | B2 | 6/2007 | Douglas et al. |
| 7,229,455 | B2 | 6/2007 | Sakurai et al. |
| 7,232,440 | B2 | 6/2007 | Dumbauld et al. |
| 7,234,624 | B2 | 6/2007 | Gresham et al. |
| 7,235,064 | B2 | 6/2007 | Hopper et al. |
| 7,235,072 | B2 | 6/2007 | Sartor et al. |
| 7,235,073 | B2 | 6/2007 | Levine et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,238,901 | B2 | 7/2007 | Kim et al. |
| 7,239,657 | B1 | 7/2007 | Gunnarsson |
| 7,241,288 | B2 | 7/2007 | Braun |
| 7,241,289 | B2 | 7/2007 | Braun |
| 7,241,290 | B2 | 7/2007 | Doyle et al. |
| 7,241,294 | B2 | 7/2007 | Reschke |
| 7,241,296 | B2 | 7/2007 | Buysse et al. |
| 7,246,734 | B2 | 7/2007 | Shelton, IV |
| 7,247,161 | B2 | 7/2007 | Johnston et al. |
| 7,249,267 | B2 | 7/2007 | Chapuis |
| 7,251,531 | B2 | 7/2007 | Mosher et al. |
| 7,252,641 | B2 | 8/2007 | Thompson et al. |
| 7,252,660 | B2 | 8/2007 | Kunz |
| 7,252,667 | B2 | 8/2007 | Moses et al. |
| 7,255,012 | B2 | 8/2007 | Hedtke |
| 7,255,696 | B2 | 8/2007 | Goble et al. |
| 7,255,697 | B2 | 8/2007 | Dycus et al. |
| 7,256,695 | B2 | 8/2007 | Hamel et al. |
| 7,258,262 | B2 | 8/2007 | Mastri et al. |
| 7,258,546 | B2 | 8/2007 | Beier et al. |
| 7,260,431 | B2 | 8/2007 | Libbus et al. |
| 7,265,374 | B2 | 9/2007 | Lee et al. |
| 7,267,677 | B2 | 9/2007 | Johnson et al. |
| 7,267,679 | B2 | 9/2007 | McGuckin, Jr. et al. |
| 7,267,685 | B2 | 9/2007 | Butaric et al. |
| 7,270,658 | B2 | 9/2007 | Woloszko et al. |
| 7,270,664 | B2 | 9/2007 | Johnson et al. |
| 7,272,002 | B2 | 9/2007 | Drapeau |
| 7,273,483 | B2 | 9/2007 | Wiener et al. |
| 7,273,488 | B2 | 9/2007 | Nakamura et al. |
| D552,623 | S | 10/2007 | Vong et al. |
| 7,275,674 | B2 | 10/2007 | Racenet et al. |
| 7,276,044 | B2 | 10/2007 | Ferry et al. |
| 7,276,065 | B2 | 10/2007 | Morley et al. |
| 7,276,068 | B2 | 10/2007 | Johnson et al. |
| 7,278,562 | B2 | 10/2007 | Mastri et al. |
| 7,278,563 | B1 | 10/2007 | Green |
| 7,278,949 | B2 | 10/2007 | Bader |
| 7,278,994 | B2 | 10/2007 | Goble |
| 7,282,048 | B2 | 10/2007 | Goble et al. |
| 7,282,773 | B2 | 10/2007 | Li et al. |
| 7,283,096 | B2 | 10/2007 | Geisheimer et al. |
| 7,286,850 | B2 | 10/2007 | Frielink et al. |
| 7,287,682 | B1 | 10/2007 | Ezzat et al. |
| 7,289,139 | B2 | 10/2007 | Amling et al. |
| 7,293,685 | B2 | 11/2007 | Ehrenfels et al. |
| 7,295,893 | B2 | 11/2007 | Sunaoshi |
| 7,295,907 | B2 | 11/2007 | Lu et al. |
| 7,296,722 | B2 | 11/2007 | Ivanko |
| 7,296,724 | B2 | 11/2007 | Green et al. |
| 7,297,145 | B2 | 11/2007 | Woloszko et al. |
| 7,297,149 | B2 | 11/2007 | Vitali et al. |
| 7,300,373 | B2 | 11/2007 | Jinno et al. |
| 7,300,431 | B2 | 11/2007 | Dubrovsky |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,502 | B2 | 12/2007 | Thompson |
| 7,303,556 | B2 | 12/2007 | Metzger |
| 7,303,557 | B2 | 12/2007 | Wham et al. |
| 7,306,597 | B2 | 12/2007 | Manzo |
| 7,307,313 | B2 | 12/2007 | Ohyanagi et al. |
| 7,308,998 | B2 | 12/2007 | Mastri et al. |
| 7,309,849 | B2 | 12/2007 | Truckai et al. |
| 7,311,238 | B2 | 12/2007 | Liu |
| 7,311,709 | B2 | 12/2007 | Truckai et al. |
| 7,313,430 | B2 | 12/2007 | Urquhart et al. |
| 7,314,473 | B2 | 1/2008 | Jinno et al. |
| 7,317,955 | B2 | 1/2008 | McGreevy |
| 7,320,704 | B2 | 1/2008 | Lashinski et al. |
| 7,322,859 | B2 | 1/2008 | Evans |
| 7,322,975 | B2 | 1/2008 | Goble et al. |
| 7,322,994 | B2 | 1/2008 | Nicholas et al. |
| 7,324,572 | B2 | 1/2008 | Chang |
| 7,326,203 | B2 | 2/2008 | Papineau et al. |
| 7,326,213 | B2 | 2/2008 | Benderev et al. |
| 7,326,236 | B2 | 2/2008 | Andreas et al. |
| 7,328,828 | B2 | 2/2008 | Ortiz et al. |
| 7,328,829 | B2 | 2/2008 | Arad et al. |
| 7,329,257 | B2 | 2/2008 | Kanehira et al. |
| 7,330,004 | B2 | 2/2008 | DeJonge et al. |
| 7,331,340 | B2 | 2/2008 | Barney |
| 7,331,343 | B2 | 2/2008 | Schmidt et al. |
| 7,331,403 | B2 | 2/2008 | Berry et al. |
| 7,331,406 | B2 | 2/2008 | Wottreng, Jr. et al. |

(56) References Cited

U.S. PATENT DOCUMENTS 7,331,410 B2 2/2008 Yong et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,353,068 B2 4/2008 Tanaka et al.
7,354,398 B2 4/2008 Kanazawa
7,354,440 B2 4/2008 Truckal et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,360,542 B2 4/2008 Nelson et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,364,577 B2 4/2008 Wham et al.
7,367,485 B2 5/2008 Shelton, IV et al.
7,367,973 B2 5/2008 Manzo et al.
7,367,976 B2 5/2008 Lawes et al.
7,368,124 B2 5/2008 Chun et al.
7,371,210 B2 5/2008 Brock et al.
7,371,227 B2 5/2008 Zeiner
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,381,209 B2 6/2008 Truckai et al.
7,384,403 B2 6/2008 Sherman
7,384,417 B2 6/2008 Cucin
7,384,420 B2 6/2008 Dycus et al.
7,386,365 B2 6/2008 Nixon
7,386,730 B2 6/2008 Uchikubo
7,388,217 B2 6/2008 Buschbeck et al.
7,388,484 B2 6/2008 Hsu
7,390,317 B2 6/2008 Taylor et al.
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,403,224 B2 7/2008 Fuller et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,288 B2 8/2008 Hara
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
D576,725 S 9/2008 Shumer et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,422,582 B2 9/2008 Malackowski et al.
7,422,586 B2 9/2008 Morris et al.
7,422,592 B2 9/2008 Morley et al.
7,424,965 B2 9/2008 Racenet et al.
7,427,607 B2 9/2008 Suzuki
7,429,259 B2 9/2008 Cadeddu et al.
D578,643 S 10/2008 Shumer et al.
D578,644 S 10/2008 Shumer et al.
D578,645 S 10/2008 Shumer et al.
7,430,772 B2 10/2008 Van Es
7,430,849 B1 10/2008 Coutts et al.
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,704 B2 10/2008 Babaev
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,435,582 B2 10/2008 Zimmermann et al.
7,438,209 B1 10/2008 Hess et al.
7,438,718 B2 10/2008 Milliman et al.
7,439,354 B2 10/2008 Lenges et al.
7,439,732 B2 10/2008 LaPlaca
7,441,684 B2 10/2008 Shelton, IV et al.
7,441,685 B1 10/2008 Boudreaux
7,442,193 B2 10/2008 Shields et al.
7,442,194 B2 10/2008 Dumbauld et al.
7,442,201 B2 10/2008 Pugsley et al.
7,443,547 B2 10/2008 Moreno et al.
D580,942 S 11/2008 Oshiro et al.
7,445,621 B2 11/2008 Dumbauld et al.
7,446,131 B1 11/2008 Liu et al.
7,448,525 B2 11/2008 Shelton, IV et al.
7,448,993 B2 11/2008 Yokoi et al.
7,449,004 B2 11/2008 Yamada et al.
7,450,010 B1 11/2008 Gravelle et al.
7,450,991 B2 11/2008 Smith et al.
7,450,998 B2 11/2008 Zilberman et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.

(56) References Cited

U.S. PATENT DOCUMENTS

| | | | |
|---|---|---|---|
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,148 | B2 | 1/2009 | Beaupre |
| 7,479,160 | B2 | 1/2009 | Branch et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,488,319 | B2 | 2/2009 | Yates |
| 7,489,055 | B2 | 2/2009 | Jeong et al. |
| 7,490,749 | B2 | 2/2009 | Schall et al. |
| 7,491,201 | B2 | 2/2009 | Shields et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,468 | B2 | 2/2009 | Rabiner et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,498,080 | B2 | 3/2009 | Tung et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,503,893 | B2 | 3/2009 | Kucklick |
| 7,505,812 | B1 | 3/2009 | Eggers et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,556 | B2 | 3/2009 | Nguyen et al. |
| 7,510,566 | B2 | 3/2009 | Jacobs et al. |
| 7,511,733 | B2 | 3/2009 | Takizawa et al. |
| 7,513,025 | B2 | 4/2009 | Fischer |
| 7,513,407 | B1 | 4/2009 | Chang |
| 7,513,408 | B2 | 4/2009 | Shelton, IV et al. |
| 7,517,349 | B2 | 4/2009 | Truckai et al. |
| 7,517,356 | B2 | 4/2009 | Heinrich |
| 7,520,877 | B2 | 4/2009 | Lee, Jr. et al. |
| 7,524,320 | B2 | 4/2009 | Tierney et al. |
| 7,527,632 | B2 | 5/2009 | Houghton et al. |
| 7,530,984 | B2 | 5/2009 | Sonnenschein et al. |
| 7,530,985 | B2 | 5/2009 | Takemoto et al. |
| 7,533,790 | B1 | 5/2009 | Knodel et al. |
| 7,533,906 | B2 | 5/2009 | Luettgen et al. |
| 7,534,243 | B1 | 5/2009 | Chin et al. |
| 7,534,259 | B2 | 5/2009 | Lashinski et al. |
| D594,983 | S | 6/2009 | Price et al. |
| 7,540,867 | B2 | 6/2009 | Jinno et al. |
| 7,540,872 | B2 | 6/2009 | Schechter et al. |
| 7,542,807 | B2 | 6/2009 | Bertolero et al. |
| 7,543,730 | B1 | 6/2009 | Marczyk |
| 7,544,197 | B2 | 6/2009 | Kelsch et al. |
| 7,544,200 | B2 | 6/2009 | Houser |
| 7,546,939 | B2 | 6/2009 | Adams et al. |
| 7,546,940 | B2 | 6/2009 | Milliman et al. |
| 7,547,287 | B2 | 6/2009 | Boecker et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,550,216 | B2 | 6/2009 | Ofer et al. |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,553,309 | B2 | 6/2009 | Buysse et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,566,318 | B2 | 7/2009 | Haefner |
| 7,567,012 | B2 | 7/2009 | Namikawa |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,572,298 | B2 | 8/2009 | Roller et al. |
| 7,575,144 | B2 | 8/2009 | Ortiz et al. |
| 7,578,825 | B2 | 8/2009 | Huebner |
| D600,712 | S | 9/2009 | LaManna et al. |
| 7,582,086 | B2 | 9/2009 | Privitera et al. |
| 7,582,087 | B2 | 9/2009 | Tetzlaff et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |
| 7,591,818 | B2 | 9/2009 | Bertolero et al. |
| 7,593,766 | B2 | 9/2009 | Faber et al. |
| 7,594,925 | B2 | 9/2009 | Danek et al. |
| 7,595,642 | B2 | 9/2009 | Doyle |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,599,743 | B2 | 10/2009 | Hassler, Jr. et al. |
| 7,600,663 | B2 | 10/2009 | Green |
| 7,601,119 | B2 | 10/2009 | Shahinian |
| 7,604,118 | B2 | 10/2009 | Lio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,083 | B2 | 10/2009 | Lee et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,611,512 | B2 | 11/2009 | Ein-Gal |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| 7,621,910 | B2 | 11/2009 | Sugi |
| 7,621,930 | B2 | 11/2009 | Houser |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |

(56) References Cited

U.S. PATENT DOCUMENTS 7,625,662 B2 12/2009 Vaisnys et al.
7,628,791 B2 12/2009 Garrison et al.
7,628,792 B2 12/2009 Guerra
7,630,841 B2 12/2009 Comisky et al.
7,631,793 B2 12/2009 Rethy et al.
7,631,794 B2 12/2009 Rethy et al.
7,632,267 B2 12/2009 Dahla
7,632,269 B2 12/2009 Truckai et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,640,447 B2 12/2009 Qiu
7,641,091 B2 1/2010 Olson et al.
7,641,092 B2 1/2010 Kruszynski et al.
7,641,093 B2 1/2010 Doll et al.
7,641,095 B2 1/2010 Viola
7,641,653 B2 1/2010 Dalla Betta et al.
7,641,671 B2 1/2010 Crainich
7,644,016 B2 1/2010 Nycz et al.
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,645,277 B2 1/2010 McClurken et al.
7,648,055 B2 1/2010 Marczyk
7,648,457 B2 1/2010 Stefanchik et al.
7,648,499 B2 1/2010 Orszulak et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,151 B2 2/2010 Crompton, Jr. et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,666,206 B2 2/2010 Taniguchi et al.
7,669,746 B2 3/2010 Shelton, IV
7,669,747 B2 3/2010 Weisenburgh et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,043 B2 3/2010 Gilad
7,678,069 B1 3/2010 Baker et al.
7,678,105 B2 3/2010 McGreevy et al.
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,095 B2 4/2010 Bednarek et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,459 B2 4/2010 Saadat et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,735 B2 5/2010 Chapman et al.
7,708,751 B2 5/2010 Hughes et al.
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,914 B2 5/2010 Kimura
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
D618,797 S 6/2010 Price et al.
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,356 B2 6/2010 Cooper et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,615 B2 6/2010 Couture
7,744,624 B2 6/2010 Bettuchi
7,744,627 B2 6/2010 Orban et al.
7,744,628 B2 6/2010 Viola
7,747,146 B2 6/2010 Milano et al.
7,748,587 B2 7/2010 Haramiishi et al.
7,748,632 B2 7/2010 Coleman et al.

(56) References Cited

U.S. PATENT DOCUMENTS

| | | | |
|---|---|---|---|
| 7,749,204 | B2 | 7/2010 | Dhanaraj et al. |
| 7,749,240 | B2 | 7/2010 | Takahashi et al. |
| 7,751,115 | B2 | 7/2010 | Song |
| 7,751,870 | B2 | 7/2010 | Whitman |
| 7,753,245 | B2 | 7/2010 | Boudreaux et al. |
| 7,753,246 | B2 | 7/2010 | Scirica |
| 7,753,904 | B2 | 7/2010 | Shelton, IV et al. |
| 7,753,908 | B2 | 7/2010 | Swanson |
| 7,753,909 | B2 | 7/2010 | Chapman et al. |
| 7,757,924 | B2 | 7/2010 | Gerbi et al. |
| 7,758,594 | B2 | 7/2010 | Lamson et al. |
| 7,758,612 | B2 | 7/2010 | Shipp |
| 7,758,613 | B2 | 7/2010 | Whitman |
| 7,762,445 | B2 | 7/2010 | Heinrich et al. |
| 7,762,462 | B2 | 7/2010 | Gelbman |
| 7,762,998 | B2 | 7/2010 | Birk et al. |
| D621,503 | S | 8/2010 | Otten et al. |
| D622,286 | S | 8/2010 | Umezawa |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,766,910 | B2 | 8/2010 | Hixson et al. |
| 7,770,658 | B2 | 8/2010 | Ito et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,772,725 | B2 | 8/2010 | Siman-Tov |
| 7,775,972 | B2 | 8/2010 | Brock et al. |
| 7,776,036 | B2 | 8/2010 | Schechter et al. |
| 7,776,037 | B2 | 8/2010 | Odom |
| 7,776,060 | B2 | 8/2010 | Mooradian et al. |
| 7,776,065 | B2 | 8/2010 | Griffiths et al. |
| 7,778,004 | B2 | 8/2010 | Nerheim et al. |
| 7,779,614 | B1 | 8/2010 | McGonagle et al. |
| 7,779,737 | B2 | 8/2010 | Newman, Jr. et al. |
| 7,780,054 | B2 | 8/2010 | Wales |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,659 | B2 | 8/2010 | Okada et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,283 | B2 | 9/2010 | Shah |
| 7,789,875 | B2 | 9/2010 | Brock et al. |
| 7,789,878 | B2 | 9/2010 | Dumbauld et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,793,814 | B2 | 9/2010 | Racenet et al. |
| 7,794,475 | B2 | 9/2010 | Hess et al. |
| 7,798,386 | B2 | 9/2010 | Schall et al. |
| 7,799,027 | B2 | 9/2010 | Hafner |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,803,156 | B2 | 9/2010 | Eder et al. |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,641 | B2 | 10/2010 | Dodde et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,872 | B2 | 10/2010 | Johnson et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| D627,066 | S | 11/2010 | Romero |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,835,823 | B2 | 11/2010 | Sillman et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,425 | B2 | 11/2010 | Saeki et al. |
| 7,837,685 | B2 | 11/2010 | Weinberg et al. |
| 7,837,687 | B2 | 11/2010 | Harp |
| 7,837,694 | B2 | 11/2010 | Tethrake et al. |
| 7,837,699 | B2 | 11/2010 | Yamada et al. |
| 7,838,789 | B2 | 11/2010 | Stoffers et al. |
| 7,839,109 | B2 | 11/2010 | Carmen, Jr. et al. |
| 7,840,253 | B2 | 11/2010 | Tremblay et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,843,158 | B2 | 11/2010 | Prisco |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,845,538 | B2 | 12/2010 | Whitman |
| 7,845,912 | B2 | 12/2010 | Sung et al. |
| 7,846,085 | B2 | 12/2010 | Silverman et al. |
| 7,846,149 | B2 | 12/2010 | Jankowski |
| 7,846,159 | B2 | 12/2010 | Morrison et al. |
| 7,846,160 | B2 | 12/2010 | Payne et al. |
| 7,846,161 | B2 | 12/2010 | Dumbauld et al. |
| 7,848,066 | B2 | 12/2010 | Yanagishima |
| 7,850,623 | B2 | 12/2010 | Griffin et al. |
| 7,850,642 | B2 | 12/2010 | Moll et al. |
| 7,850,688 | B2 | 12/2010 | Hafner |
| 7,850,982 | B2 | 12/2010 | Stopek et al. |
| 7,853,813 | B2 | 12/2010 | Lee |
| 7,854,735 | B2 | 12/2010 | Houser et al. |
| 7,854,736 | B2 | 12/2010 | Ryan |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter et al. |
| 7,857,813 | B2 | 12/2010 | Schmitz et al. |
| D631,155 | S | 1/2011 | Peine et al. |
| 7,861,906 | B2 | 1/2011 | Doll et al. |
| 7,862,502 | B2 | 1/2011 | Pool et al. |
| 7,862,546 | B2 | 1/2011 | Conlon et al. |
| 7,862,560 | B2 | 1/2011 | Marion |
| 7,862,579 | B2 | 1/2011 | Ortiz et al. |
| 7,866,525 | B2 | 1/2011 | Scirica |
| 7,866,527 | B2 | 1/2011 | Hall et al. |

(56) References Cited

U.S. PATENT DOCUMENTS 7,866,528 B2 1/2011 Olson et al.
7,867,228 B2 1/2011 Nobis et al.
7,870,989 B2 1/2011 Viola et al.
7,871,392 B2 1/2011 Sartor
7,871,418 B2 1/2011 Thompson et al.
7,871,423 B2 1/2011 Livneh
7,871,440 B2 1/2011 Schwartz et al.
7,875,055 B2 1/2011 Cichocki, Jr.
D631,965 S 2/2011 Price et al.
7,877,852 B2 2/2011 Unger et al.
7,877,853 B2 2/2011 Unger et al.
7,877,869 B2 2/2011 Mehdizadeh et al.
7,879,035 B2 2/2011 Garrison et al.
7,879,063 B2 2/2011 Khosravi
7,879,070 B2 2/2011 Ortiz et al.
7,879,367 B2 2/2011 Heublein et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,887,755 B2 2/2011 Mingerink et al.
7,891,531 B1 2/2011 Ward
7,891,532 B2 2/2011 Mastri et al.
7,892,200 B2 2/2011 Birk et al.
7,892,245 B2 2/2011 Liddicoat et al.
7,892,606 B2 2/2011 Thies et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,875 B2 3/2011 Heim et al.
7,896,877 B2 3/2011 Hall et al.
7,896,878 B2 3/2011 Johnson et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,901,400 B2 3/2011 Wham et al.
7,901,423 B2 3/2011 Stulen et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,919,184 B2 4/2011 Mohapatra et al.
7,922,061 B2 4/2011 Shelton, IV et al.
7,922,063 B2 4/2011 Zemlok et al.
7,922,651 B2 4/2011 Yamada et al.
7,922,743 B2 4/2011 Heinrich et al.
7,922,953 B2 4/2011 Guerra
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,649 B2 4/2011 Couture et al.
7,931,660 B2 4/2011 Aranyi et al.
7,931,695 B2 4/2011 Ringeisen
7,931,877 B2 4/2011 Steffens et al.
D637,288 S 5/2011 Houghton
D638,540 S 5/2011 Ijiri et al.
7,934,630 B2 5/2011 Shelton, IV et al.
7,934,631 B2 5/2011 Balbierz et al.
7,934,896 B2 5/2011 Schnier
7,935,114 B2 5/2011 Takashino et al.
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,868 B2 5/2011 Cooper
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,947,039 B2 5/2011 Sartor
7,948,381 B2 5/2011 Lindsay et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,165 B2 5/2011 Golden et al.
7,951,166 B2 5/2011 Orban, III et al.
7,952,464 B2 5/2011 Nikitin et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,331 B2 6/2011 Truckai et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,959,626 B2 6/2011 Hong et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,602 B2 6/2011 Lindquist
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag

(56) References Cited

U.S. PATENT DOCUMENTS 7,976,544 B2 7/2011 McClurken et al.
7,976,563 B2 7/2011 Summerer
7,979,137 B2 7/2011 Tracey et al.
7,980,443 B2 7/2011 Scheib et al.
7,981,025 B2 7/2011 Pool et al.
7,981,102 B2 7/2011 Patel et al.
7,981,113 B2 7/2011 Truckai et al.
7,981,132 B2 7/2011 Dubrul et al.
7,987,405 B2 7/2011 Turner et al.
7,988,015 B2 8/2011 Mason et al.
7,988,026 B2 8/2011 Knodel et al.
7,988,027 B2 8/2011 Olson et al.
7,988,028 B2 8/2011 Farascioni et al.
7,988,567 B2 8/2011 Kim et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,278 B2 8/2011 Utley et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.
8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,741 B2 9/2011 Cole et al.
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,835 B2 10/2011 Yasuda et al.
8,028,882 B2 10/2011 Viola
8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,173 B2 10/2011 Ehlert et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,612 B2 10/2011 Paz
8,038,686 B2 10/2011 Huitema et al.
8,038,693 B2 10/2011 Allen
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,070 B2 11/2011 O'Brien et al.
8,048,503 B2 11/2011 Farnsworth et al.
8,052,636 B2 11/2011 Moll et al.
8,052,672 B2 11/2011 Laufer et al.
8,052,697 B2 11/2011 Phillips
8,056,720 B2 11/2011 Hawkes
8,056,787 B2 11/2011 Boudreaux et al.
8,056,788 B2 11/2011 Mastri et al.
8,056,789 B1 11/2011 White et al.
8,057,498 B2 11/2011 Robertson
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,211 B2 11/2011 Duval et al.
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,036 B1 12/2011 Knodel
8,070,743 B2 12/2011 Kagan et al.
8,070,748 B2 12/2011 Hixson et al.
8,074,858 B2 12/2011 Marczyk
8,074,859 B2 12/2011 Kostrzewski
8,074,861 B2 12/2011 Ehrenfels et al.
8,075,476 B2 12/2011 Vargas
8,075,555 B2 12/2011 Truckai et al.
8,075,558 B2 12/2011 Truckai et al.
8,075,571 B2 12/2011 Vitali et al.
8,079,950 B2 12/2011 Stern et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,475 B2 1/2012 Cotter et al.
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,100,894 B2 1/2012 Mucko et al.
8,102,138 B2 1/2012 Sekine et al.
8,102,278 B2 1/2012 Deck et al.
8,105,320 B2 1/2012 Manzo
8,105,323 B2 1/2012 Buysse et al.
8,105,324 B2 1/2012 Palanker et al.
8,105,350 B2 1/2012 Lee et al.
8,107,925 B2 1/2012 Natsuno et al.

(56) References Cited

U.S. PATENT DOCUMENTS 8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,114,104 B2 2/2012 Young et al.
8,114,119 B2 2/2012 Spivey et al.
8,114,345 B2 2/2012 Dlugos, Jr. et al.
8,118,206 B2 2/2012 Zand et al.
8,118,207 B2 2/2012 Racenet et al.
8,120,301 B2 2/2012 Goldberg et al.
8,122,128 B2 2/2012 Burke et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,657 B2 3/2012 Shiono et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,218 B2 3/2012 Daw et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,147,488 B2 4/2012 Masuda
8,147,508 B2 4/2012 Madan et al.
8,152,041 B2 4/2012 Kostrzewski
8,152,756 B2 4/2012 Webster et al.
8,152,825 B2 4/2012 Madan et al.
8,154,239 B2 4/2012 Katsuki et al.
8,157,145 B2 4/2012 Shelton, IV et al.
8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,940 B2 4/2012 Johnson et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,784 B2 5/2012 Van Wyk et al.
8,177,794 B2 5/2012 Cabrera et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,182,502 B2 5/2012 Stulen et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,187,166 B2 5/2012 Kuth et al.
8,187,267 B2 5/2012 Pappone et al.
8,190,238 B2 5/2012 Moll et al.
8,191,752 B2 6/2012 Scirica
8,192,350 B2 6/2012 Ortiz et al.
8,192,433 B2 6/2012 Johnson et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,472 B2 6/2012 Lau et al.
8,197,479 B2 6/2012 Olson et al.
8,197,494 B2 6/2012 Jaggi et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,206,212 B2 6/2012 Iddings et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,415 B2 7/2012 Francischelli
8,221,416 B2 7/2012 Townsend
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,230,235 B2 7/2012 Goodman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.

(56) References Cited

U.S. PATENT DOCUMENTS 8,235,274 B2 8/2012 Cappola
8,236,010 B2 8/2012 Ortiz et al.
8,236,011 B2 8/2012 Harris et al.
8,236,019 B2 8/2012 Houser
8,236,020 B2 8/2012 Smith et al.
8,237,388 B2 8/2012 Jinno et al.
8,240,537 B2 8/2012 Marczyk
8,241,235 B2 8/2012 Kahler et al.
8,241,271 B2 8/2012 Millman et al.
8,241,283 B2 8/2012 Guerra et al.
8,241,284 B2 8/2012 Dycus et al.
8,241,308 B2 8/2012 Kortenbach et al.
8,241,312 B2 8/2012 Messerly
8,241,322 B2 8/2012 Whitman et al.
8,244,368 B2 8/2012 Sherman
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,615 B2 8/2012 Behnke
8,246,618 B2 8/2012 Bucciaglia et al.
8,246,637 B2 8/2012 Viola et al.
8,251,994 B2 8/2012 McKenna et al.
8,252,009 B2 8/2012 Weller et al.
8,252,012 B2 8/2012 Stulen
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,352 B2 9/2012 Lawes et al.
8,257,356 B2 9/2012 Bleich et al.
8,257,377 B2 9/2012 Wiener et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,563 B2 9/2012 Bakos et al.
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,854 B2 9/2012 Asada et al.
8,267,924 B2 9/2012 Zemlok et al.
8,267,935 B2 9/2012 Couture et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,085 B2 9/2012 Park et al.
8,273,404 B2 9/2012 Dave et al.
8,276,594 B2 10/2012 Shah
8,276,801 B2 10/2012 Zemlok et al.
8,276,802 B2 10/2012 Kostrzewski
8,277,446 B2 10/2012 Heard
8,277,447 B2 10/2012 Garrison et al.
8,277,471 B2 10/2012 Wiener et al.
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,581 B2 10/2012 Zhao et al.
8,282,654 B2 10/2012 Ferrari et al.
8,282,669 B2 10/2012 Gerber et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,528 B2 10/2012 Wham et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,886 B2 10/2012 Kerr et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,228 B2 10/2012 Buysse et al.
8,298,232 B2 10/2012 Unger
8,298,233 B2 10/2012 Mueller
8,298,677 B2 10/2012 Wiesner et al.
8,302,323 B2 11/2012 Fortier et al.
8,303,583 B2 11/2012 Hosier et al.
8,303,621 B2 11/2012 Miyamoto et al.
8,306,629 B2 11/2012 Mioduski et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
8,319,400 B2 11/2012 Houser et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,302 B2 12/2012 Robertson et al.
8,323,310 B2 12/2012 Kingsley
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,761 B2 12/2012 Widenhouse et al.
8,328,802 B2 12/2012 Deville et al.
8,328,823 B2 12/2012 Aranyi et al.
8,328,834 B2 12/2012 Isaacs et al.
8,333,313 B2 12/2012 Boudreaux et al.
8,333,691 B2 12/2012 Schaaf
8,333,764 B2 12/2012 Francischelli et al.
8,333,778 B2 12/2012 Smith et al.
8,333,779 B2 12/2012 Smith et al.
8,334,468 B2 12/2012 Palmer et al.
8,334,635 B2 12/2012 Voegele et al.
8,336,753 B2 12/2012 Olson et al.
8,336,754 B2 12/2012 Cappola et al.
8,338,726 B2 12/2012 Palmer et al.

(56) References Cited

U.S. PATENT DOCUMENTS

| | | | |
|---|---|---|---|
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,343,146 | B2 | 1/2013 | Godara et al. |
| 8,343,150 | B2 | 1/2013 | Artale |
| 8,344,596 | B2 | 1/2013 | Nield et al. |
| 8,347,978 | B2 | 1/2013 | Forster et al. |
| 8,348,118 | B2 | 1/2013 | Segura |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,348,837 | B2 | 1/2013 | Wenchell |
| 8,348,880 | B2 | 1/2013 | Messerly et al. |
| 8,348,947 | B2 | 1/2013 | Takashino et al. |
| 8,348,948 | B2 | 1/2013 | Bahney |
| 8,348,959 | B2 | 1/2013 | Wolford et al. |
| 8,348,967 | B2 | 1/2013 | Stulen |
| 8,348,972 | B2 | 1/2013 | Soltz et al. |
| 8,349,987 | B2 | 1/2013 | Kapiamba et al. |
| 8,352,004 | B2 | 1/2013 | Mannheimer et al. |
| 8,353,297 | B2 | 1/2013 | Dacquay et al. |
| 8,353,437 | B2 | 1/2013 | Boudreaux |
| 8,353,438 | B2 | 1/2013 | Baxter, III et al. |
| 8,353,439 | B2 | 1/2013 | Baxter, III et al. |
| 8,356,740 | B1 | 1/2013 | Knodel |
| 8,357,144 | B2 | 1/2013 | Whitman et al. |
| 8,357,158 | B2 | 1/2013 | McKenna et al. |
| 8,357,161 | B2 | 1/2013 | Mueller |
| 8,359,174 | B2 | 1/2013 | Nakashima et al. |
| 8,360,296 | B2 | 1/2013 | Zingman |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,361,501 | B2 | 1/2013 | DiTizio et al. |
| 8,361,569 | B2 | 1/2013 | Saito et al. |
| D676,866 | S | 2/2013 | Chaudhri |
| 8,365,972 | B2 | 2/2013 | Aranyi et al. |
| 8,365,973 | B1 | 2/2013 | White et al. |
| 8,365,975 | B1 | 2/2013 | Manoux et al. |
| 8,365,976 | B2 | 2/2013 | Hess et al. |
| 8,366,559 | B2 | 2/2013 | Papenfuss et al. |
| 8,366,719 | B2 | 2/2013 | Markey et al. |
| 8,366,787 | B2 | 2/2013 | Brown et al. |
| 8,368,327 | B2 | 2/2013 | Benning et al. |
| 8,369,056 | B2 | 2/2013 | Senriuchi et al. |
| 8,371,393 | B2 | 2/2013 | Higuchi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,371,494 | B2 | 2/2013 | Racenet et al. |
| 8,372,064 | B2 | 2/2013 | Douglass et al. |
| 8,372,094 | B2 | 2/2013 | Bettuchi et al. |
| 8,372,099 | B2 | 2/2013 | Deville et al. |
| 8,372,101 | B2 | 2/2013 | Smith et al. |
| 8,374,723 | B2 | 2/2013 | Zhao et al. |
| 8,376,865 | B2 | 2/2013 | Forster et al. |
| 8,377,029 | B2 | 2/2013 | Nagao et al. |
| 8,377,044 | B2 | 2/2013 | Coe et al. |
| 8,377,053 | B2 | 2/2013 | Orszulak |
| 8,377,059 | B2 | 2/2013 | Deville et al. |
| 8,377,085 | B2 | 2/2013 | Smith et al. |
| 8,381,828 | B2 | 2/2013 | Whitman et al. |
| 8,381,834 | B2 | 2/2013 | Barhitte et al. |
| 8,382,754 | B2 | 2/2013 | Odom et al. |
| 8,382,773 | B2 | 2/2013 | Whitfield et al. |
| 8,382,782 | B2 | 2/2013 | Robertson et al. |
| 8,382,790 | B2 | 2/2013 | Uenohara et al. |
| 8,382,792 | B2 | 2/2013 | Chojin |
| D677,273 | S | 3/2013 | Randall et al. |
| 8,387,848 | B2 | 3/2013 | Johnson et al. |
| 8,388,633 | B2 | 3/2013 | Rousseau et al. |
| 8,388,646 | B2 | 3/2013 | Chojin |
| 8,388,647 | B2 | 3/2013 | Nau, Jr. et al. |
| 8,389,588 | B2 | 3/2013 | Ringeisen et al. |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,394,094 | B2 | 3/2013 | Edwards et al. |
| 8,394,115 | B2 | 3/2013 | Houser et al. |
| 8,397,832 | B2 | 3/2013 | Blickle et al. |
| 8,397,971 | B2 | 3/2013 | Yates et al. |
| 8,397,972 | B2 | 3/2013 | Kostrzewski |
| 8,397,973 | B1 | 3/2013 | Hausen |
| 8,398,633 | B2 | 3/2013 | Mueller |
| 8,398,669 | B2 | 3/2013 | Kim |
| 8,398,673 | B2 | 3/2013 | Hinchliffe et al. |
| 8,398,674 | B2 | 3/2013 | Prestel |
| 8,400,108 | B2 | 3/2013 | Powell et al. |
| 8,400,851 | B2 | 3/2013 | Byun |
| 8,403,138 | B2 | 3/2013 | Weisshaupt et al. |
| 8,403,195 | B2 | 3/2013 | Beardsley et al. |
| 8,403,196 | B2 | 3/2013 | Beardsley et al. |
| 8,403,198 | B2 | 3/2013 | Sorrentino et al. |
| 8,403,832 | B2 | 3/2013 | Cunningham et al. |
| 8,403,926 | B2 | 3/2013 | Nobis et al. |
| 8,403,945 | B2 | 3/2013 | Whitfield et al. |
| 8,403,946 | B2 | 3/2013 | Whitfield et al. |
| 8,403,948 | B2 | 3/2013 | Deville et al. |
| 8,403,949 | B2 | 3/2013 | Palmer et al. |
| 8,403,950 | B2 | 3/2013 | Palmer et al. |
| D680,646 | S | 4/2013 | Hunt et al. |
| 8,408,439 | B2 | 4/2013 | Huang et al. |
| 8,408,442 | B2 | 4/2013 | Racenet et al. |
| 8,409,076 | B2 | 4/2013 | Pang et al. |
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,409,234 | B2 | 4/2013 | Stahler et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,349 | B2 | 4/2013 | Smith et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,419,757 | B2 | 4/2013 | Smith et al. |
| 8,419,758 | B2 | 4/2013 | Smith et al. |
| 8,419,759 | B2 | 4/2013 | Dietz |
| 8,423,182 | B2 | 4/2013 | Robinson et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,424,741 | B2 | 4/2013 | McGuckin, Jr. et al. |
| 8,424,742 | B2 | 4/2013 | Bettuchi |
| 8,425,410 | B2 | 4/2013 | Murray et al. |
| 8,425,545 | B2 | 4/2013 | Smith et al. |
| 8,425,600 | B2 | 4/2013 | Maxwell |
| 8,427,430 | B2 | 4/2013 | Lee et al. |
| 8,430,292 | B2 | 4/2013 | Patel et al. |
| 8,430,811 | B2 | 4/2013 | Hess et al. |
| 8,430,876 | B2 | 4/2013 | Kappus et al. |
| 8,430,892 | B2 | 4/2013 | Bindra et al. |
| 8,430,897 | B2 | 4/2013 | Novak et al. |

(56) References Cited

U.S. PATENT DOCUMENTS 8,430,898 B2 4/2013 Wiener et al.
8,435,257 B2 5/2013 Smith et al.
8,439,246 B1 5/2013 Knodel
8,439,830 B2 5/2013 McKinley et al.
8,439,911 B2 5/2013 Mueller
8,439,939 B2 5/2013 Deville et al.
8,444,036 B2 5/2013 Shelton, IV
8,444,037 B2 5/2013 Nicholas et al.
8,444,549 B2 5/2013 Viola et al.
8,444,662 B2 5/2013 Palmer et al.
8,444,664 B2 5/2013 Balanev et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,599 B2 6/2013 Inagaki et al.
8,454,628 B2 6/2013 Smith et al.
8,454,639 B2 6/2013 Du et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,460,288 B2 6/2013 Tamai et al.
8,460,292 B2 6/2013 Truckai et al.
8,461,744 B2 6/2013 Wiener et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,956 B2 6/2013 McKenna et al.
8,469,973 B2 6/2013 Meade et al.
8,469,981 B2 6/2013 Robertson et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,361 B2 7/2013 Barlow et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,484,833 B2 7/2013 Cunningham et al.
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,486,057 B2 7/2013 Behnke, II
8,486,096 B2 7/2013 Robertson et al.
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,491,624 B2 7/2013 Kerr et al.
8,491,625 B2 7/2013 Horner
8,496,153 B2 7/2013 Demmy et al.
8,496,154 B2 7/2013 Marczyk et al.
8,496,156 B2 7/2013 Sniffin et al.
8,496,682 B2 7/2013 Guerra et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,505,802 B2 8/2013 Viola et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,336 B2 8/2013 Couture
8,512,359 B2 8/2013 Whitman et al.
8,512,364 B2 8/2013 Kowalski et al.
8,512,365 B2 8/2013 Wiener et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,889 B2 9/2013 Stulen et al.
8,523,900 B2 9/2013 Jinno et al.
8,529,437 B2 9/2013 Taylor et al.
8,529,565 B2 9/2013 Masuda et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,064 B2 9/2013 Robertson et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,311 B2 9/2013 Schal
8,535,340 B2 9/2013 Allen
8,535,341 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,542,501 B2 9/2013 Kyono
8,550,984 B2 10/2013 Takemoto
8,551,076 B2 10/2013 Duval et al.
8,553,430 B2 10/2013 Melanson et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,516 B2 10/2013 Saadat et al.
8,562,592 B2 10/2013 Conlon et al.
8,562,598 B2 10/2013 Falkenstein et al.

(56) References Cited

U.S. PATENT DOCUMENTS 8,562,604 B2 10/2013 Nishimura
8,567,656 B2 10/2013 Shelton, IV et al.
8,568,390 B2 10/2013 Mueller
8,568,412 B2 10/2013 Brandt et al.
8,568,416 B2 10/2013 Schmitz et al.
8,568,425 B2 10/2013 Ross et al.
8,569,997 B2 10/2013 Lee
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,187 B2 11/2013 Marion
8,574,199 B2 11/2013 von Bulow et al.
8,574,231 B2 11/2013 Boudreaux et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,928 B2 11/2013 Robertson et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
8,591,459 B2 11/2013 Clymer et al.
8,591,506 B2 11/2013 Wham et al.
D695,407 S 12/2013 Price et al.
8,596,513 B2 12/2013 Olson et al.
8,596,515 B2 12/2013 Okoniewski
8,597,182 B2 12/2013 Stein et al.
8,597,297 B2 12/2013 Couture et al.
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,623,011 B2 1/2014 Spivey
8,623,016 B2 1/2014 Fischer
8,623,027 B2 1/2014 Price et al.
8,623,044 B2 1/2014 Timm et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,529 B2 1/2014 Aldridge et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,461 B2 1/2014 Glossop
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,648 B2 1/2014 Gazdzinski
8,636,736 B2 1/2014 Yates et al.
8,636,761 B2 1/2014 Cunningham et al.
8,636,766 B2 1/2014 Milliman et al.
8,638,428 B2 1/2014 Brown
8,639,936 B2 1/2014 Hu et al.
8,640,788 B2 2/2014 Dachs et al.
8,641,712 B2 2/2014 Couture
8,646,674 B2 2/2014 Schulte et al.
8,647,258 B2 2/2014 Aranyi et al.
8,647,350 B2 2/2014 Mohan et al.
8,650,728 B2 2/2014 Wan et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,220 B2 3/2014 Wiener et al.
8,663,222 B2 3/2014 Anderson et al.
8,663,223 B2 3/2014 Masuda et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,668,691 B2 3/2014 Heard
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,114 B2 3/2014 Chapman et al.
8,679,137 B2 3/2014 Bauman et al.
8,679,154 B2 3/2014 Smith et al.
8,679,156 B2 3/2014 Smith et al.
8,679,454 B2 3/2014 Guire et al.
RE44,834 E 4/2014 Dumbauld et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,685,056 B2 4/2014 Evans et al.
8,690,893 B2 4/2014 Deitch et al.

(56) References Cited

U.S. PATENT DOCUMENTS 8,695,866 B2 4/2014 Leimbach et al.
8,696,662 B2 4/2014 Eder et al.
8,696,665 B2 4/2014 Hunt et al.
8,701,958 B2 4/2014 Shelton, IV et al.
8,701,959 B2 4/2014 Shah
8,702,609 B2 4/2014 Hadjicostis
8,702,704 B2 4/2014 Shelton, IV et al.
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,709,035 B2 4/2014 Johnson et al.
8,712,549 B2 4/2014 Zdeblick et al.
8,714,352 B2 5/2014 Farascioni et al.
8,714,429 B2 5/2014 Demmy
8,714,430 B2 5/2014 Natarajan et al.
8,715,256 B2 5/2014 Greener
8,715,270 B2 5/2014 Weitzner et al.
8,715,277 B2 5/2014 Weizman
8,715,302 B2 5/2014 Ibrahim et al.
8,720,766 B2 5/2014 Hess et al.
8,721,630 B2 5/2014 Ortiz et al.
8,721,640 B2 5/2014 Taylor et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,443 B2 5/2014 Hixson et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,351 B2 6/2014 Schultz
8,747,404 B2 6/2014 Boudreaux et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,338 B2 6/2014 Widenhouse et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,342 B2 6/2014 Bales et al.
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,764,747 B2 7/2014 Cummings et al.
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,784,418 B2 7/2014 Romero
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,342 B2 7/2014 Stulen et al.
8,790,658 B2 7/2014 Cigarini et al.
8,790,684 B2 7/2014 Dave et al.
D711,905 S 8/2014 Morrison et al.
8,794,098 B2 8/2014 Long
8,794,496 B2 8/2014 Scirica
8,794,497 B2 8/2014 Zingman
8,795,159 B2 8/2014 Moriyama
8,795,274 B2 8/2014 Hanna
8,795,276 B2 8/2014 Dietz et al.
8,795,308 B2 8/2014 Valin
8,795,324 B2 8/2014 Kawai et al.
8,795,327 B2 8/2014 Dietz et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,319 B2 8/2014 Houser et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,814,856 B2 8/2014 Elmouelhi et al.
8,814,865 B2 8/2014 Reschke
8,814,870 B2 8/2014 Paraschiv et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.

(56) References Cited

U.S. PATENT DOCUMENTS 8,827,992 B2 9/2014 Koss et al.
8,827,995 B2 9/2014 Schaller et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,466 B2 9/2014 Cummings et al.
8,834,488 B2 9/2014 Farritor et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,845,630 B2 9/2014 Mehta et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,184 B2 10/2014 Kucklick
8,852,185 B2 10/2014 Twomey
8,852,199 B2 10/2014 Deslauriers et al.
8,852,218 B2 10/2014 Hughett, Sr. et al.
8,855,822 B2 10/2014 Bartol et al.
8,857,692 B2 10/2014 Shima et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,864,757 B2 10/2014 Klimovitch et al.
8,864,761 B2 10/2014 Johnson et al.
8,869,912 B2 10/2014 Roßkamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,766 B2 11/2014 Couture et al.
8,882,791 B2 11/2014 Stulen
8,882,792 B2 11/2014 Dietz et al.
8,884,560 B2 11/2014 Ito
8,887,373 B2 11/2014 Brandt et al.
8,887,979 B2 11/2014 Mastri et al.
8,888,688 B2 11/2014 Julian et al.
8,888,695 B2 11/2014 Piskun et al.
8,888,776 B2 11/2014 Dietz et al.
8,888,783 B2 11/2014 Young
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,906,012 B2 12/2014 Conley et al.
8,906,016 B2 12/2014 Boudreaux et al.
8,906,017 B2 12/2014 Rioux et al.
8,910,846 B2 12/2014 Viola
8,910,847 B2 12/2014 Nalagatla et al.
8,911,426 B2 12/2014 Coppeta et al.
8,911,438 B2 12/2014 Swoyer et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,915,842 B2 12/2014 Weisenburgh, II et al.
8,920,368 B2 12/2014 Sandhu et al.
8,920,414 B2 12/2014 Stone et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,926,607 B2 1/2015 Norvell et al.
8,926,608 B2 1/2015 Bacher et al.
8,929,888 B2 1/2015 Rao et al.
8,931,576 B2 1/2015 Iwata
8,931,679 B2 1/2015 Kostrzewski
8,931,680 B2 1/2015 Milliman
8,931,682 B2 1/2015 Timm et al.
8,931,692 B2 1/2015 Sancak
8,936,614 B2 1/2015 Allen, IV
8,937,408 B2 1/2015 Ganem et al.
8,939,287 B2 1/2015 Markovitch
8,939,343 B2 1/2015 Milliman et al.
8,939,344 B2 1/2015 Olson et al.
8,939,898 B2 1/2015 Omoto
8,939,974 B2 1/2015 Boudreaux et al.
8,939,975 B2 1/2015 Twomey et al.
8,944,069 B2 2/2015 Miller et al.
8,944,997 B2 2/2015 Fernandez et al.
8,945,095 B2 2/2015 Blumenkranz et al.
8,945,098 B2 2/2015 Seibold et al.
8,945,125 B2 2/2015 Schechter et al.
8,945,163 B2 2/2015 Voegele et al.
8,951,248 B2 2/2015 Messerly et al.
8,951,272 B2 2/2015 Robertson et al.
8,955,732 B2 2/2015 Zemlok et al.
8,956,342 B1 2/2015 Russo et al.
8,956,349 B2 2/2015 Aldridge et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,961,515 B2 2/2015 Twomey et al.
8,961,542 B2 2/2015 Whitfield et al.
8,961,547 B2 2/2015 Dietz et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.

(56) References Cited

U.S. PATENT DOCUMENTS

| | | | |
|---|---|---|---|
| 8,968,332 | B2 | 3/2015 | Farritor et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,453 | B2 | 3/2015 | Wang |
| 8,974,542 | B2 | 3/2015 | Fujimoto et al. |
| 8,974,932 | B2 | 3/2015 | McGahan et al. |
| 8,978,845 | B2 | 3/2015 | Kim |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,838 | B2 | 3/2015 | Woloszko et al. |
| 8,979,843 | B2 | 3/2015 | Timm et al. |
| 8,979,844 | B2 | 3/2015 | White et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,855 | B2 | 3/2015 | Murphy et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,520 | B2 | 3/2015 | Van Wyk et al. |
| 8,992,526 | B2 | 3/2015 | Brodbeck et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,199 | B2 | 4/2015 | Beckman et al. |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,326 | B2 | 4/2015 | DiNardo et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,372 | B2 | 4/2015 | Artale et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,035 | B2 | 5/2015 | Allen, IV et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,031,667 | B2 | 5/2015 | Williams |
| 9,033,203 | B2 | 5/2015 | Woodard, Jr. et al. |
| 9,033,204 | B2 | 5/2015 | Shelton, IV et al. |
| 9,033,983 | B2 | 5/2015 | Takashino et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,695 | B2 | 5/2015 | Giordano et al. |
| 9,039,705 | B2 | 5/2015 | Takashino |
| 9,039,720 | B2 | 5/2015 | Madan |
| 9,039,731 | B2 | 5/2015 | Joseph |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,243 | B2 | 6/2015 | Johnson et al. |
| 9,044,245 | B2 | 6/2015 | Condie et al. |
| 9,044,256 | B2 | 6/2015 | Cadeddu et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,093 | B2 | 6/2015 | Aldridge et al. |
| 9,050,098 | B2 | 6/2015 | Deville et al. |
| 9,050,100 | B2 | 6/2015 | Yates et al. |
| 9,050,113 | B2 | 6/2015 | Bloom et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |
| 9,055,941 | B2 | 6/2015 | Schmid et al. |
| 9,055,942 | B2 | 6/2015 | Balbierz et al. |
| 9,055,943 | B2 | 6/2015 | Zemlok et al. |
| 9,055,944 | B2 | 6/2015 | Hodgkinson et al. |
| 9,055,961 | B2 | 6/2015 | Manzo et al. |
| 9,060,770 | B2 | 6/2015 | Shelton, IV et al. |
| 9,060,775 | B2 | 6/2015 | Wiener et al. |
| 9,060,776 | B2 | 6/2015 | Yates et al. |
| 9,060,794 | B2 | 6/2015 | Kang et al. |
| 9,060,894 | B2 | 6/2015 | Wubbeling |
| 9,061,392 | B2 | 6/2015 | Forgues et al. |
| 9,066,723 | B2 | 6/2015 | Beller et al. |
| 9,070,068 | B2 | 6/2015 | Coveley et al. |
| 9,072,515 | B2 | 7/2015 | Hall et al. |
| 9,072,523 | B2 | 7/2015 | Houser et al. |
| 9,072,535 | B2 | 7/2015 | Shelton, IV et al. |
| 9,072,536 | B2 | 7/2015 | Shelton, IV et al. |
| 9,078,653 | B2 | 7/2015 | Leimbach et al. |
| 9,078,654 | B2 | 7/2015 | Whitman et al. |
| 9,078,664 | B2 | 7/2015 | Palmer et al. |
| 9,084,586 | B2 | 7/2015 | Hafner et al. |
| 9,084,601 | B2 | 7/2015 | Moore et al. |
| 9,084,602 | B2 | 7/2015 | Gleiman |
| 9,086,875 | B2 | 7/2015 | Harrat et al. |
| 9,089,326 | B2 | 7/2015 | Krumanaker et al. |
| 9,089,327 | B2 | 7/2015 | Worrell et al. |
| 9,089,330 | B2 | 7/2015 | Widenhouse et al. |
| 9,089,338 | B2 | 7/2015 | Smith et al. |
| 9,089,352 | B2 | 7/2015 | Jeong |
| 9,089,360 | B2 | 7/2015 | Messerly et al. |

(56) References Cited

U.S. PATENT DOCUMENTS 9,091,588 B2 7/2015 Lefler
9,094,006 B2 7/2015 Gravati et al.
D736,792 S 8/2015 Brinda et al.
9,095,339 B2 8/2015 Moore et al.
9,095,346 B2 8/2015 Houser et al.
9,095,362 B2 8/2015 Dachs et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,672 B2 8/2015 Tetzlaff et al.
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke et al.
9,113,889 B2 8/2015 Reschke
9,113,900 B2 8/2015 Buysse et al.
9,119,615 B2 9/2015 Felder et al.
9,119,630 B2 9/2015 Townsend et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,125,667 B2 9/2015 Stone et al.
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,138,289 B2 9/2015 Conley et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,155,585 B2 10/2015 Bales, Jr. et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,082 B2 10/2015 Evans et al.
9,168,085 B2 10/2015 Juzkiw et al.
9,168,089 B2 10/2015 Buysse et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,204 B2 11/2015 Nishimura et al.
9,186,221 B2 11/2015 Burbank
9,187,758 B2 11/2015 Cai et al.
9,192,376 B2 11/2015 Almodovar
9,192,380 B2 11/2015 Racenet et al.
9,192,384 B2 11/2015 Bettuchi
9,192,421 B2 11/2015 Garrison
9,192,430 B2 11/2015 Rachlin et al.
9,192,431 B2 11/2015 Woodruff et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,198,714 B2 12/2015 Worrell et al.
9,198,715 B2 12/2015 Livneh
9,198,716 B2 12/2015 Masuda et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,919 B2 12/2015 Brandt et al.
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,050 B2 12/2015 Condie et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.
9,232,945 B2 1/2016 Zingman
9,232,979 B2 1/2016 Parihar et al.

(56) References Cited

U.S. PATENT DOCUMENTS 9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,165 B2 2/2016 Aronow et al.
9,254,170 B2 2/2016 Parihar et al.
9,259,234 B2 2/2016 Robertson et al.
9,259,265 B2 2/2016 Harris et al.
9,259,268 B2 2/2016 Behnke et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,567 B2 2/2016 Orban, III et al.
9,265,571 B2 2/2016 Twomey et al.
9,265,585 B2 2/2016 Wingardner et al.
9,265,926 B2 2/2016 Strobl et al.
9,271,718 B2 3/2016 Milad et al.
9,271,727 B2 3/2016 McGuckin, Jr. et al.
9,271,753 B2 3/2016 Butler et al.
9,271,784 B2 3/2016 Evans et al.
9,271,799 B2 3/2016 Shelton, IV et al.
9,272,406 B2 3/2016 Aronhalt et al.
9,274,095 B2 3/2016 Humayun et al.
9,274,988 B2 3/2016 Hsu et al.
9,277,919 B2 3/2016 Timmer et al.
9,277,922 B2 3/2016 Carter et al.
9,277,962 B2 3/2016 Koss et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,027 B2 3/2016 Monson et al.
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,014 B2 4/2016 Fischer
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,292 B2 4/2016 Trees et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,025 B2 5/2016 Monson et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,323 B2 5/2016 Eder et al.
9,339,326 B2 5/2016 McCullagh et al.
9,339,342 B2 5/2016 Prisco et al.
9,344,042 B2 5/2016 Mao
9,345,477 B2 5/2016 Anim et al.
9,345,479 B2 5/2016 Racenet et al.
9,345,480 B2 5/2016 Hessler et al.
9,345,481 B2 5/2016 Hall et al.
9,345,503 B2 5/2016 Ishida et al.
9,345,900 B2 5/2016 Wu et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,351,754 B2 5/2016 Vakharia et al.
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,061 B2 6/2016 Plascencia, Jr. et al.
9,358,065 B2 6/2016 Ladtkow et al.

(56) References Cited

U.S. PATENT DOCUMENTS

| | | | |
|---|---|---|---|
| 9,364,217 | B2 | 6/2016 | Kostrzewski et al. |
| 9,364,219 | B2 | 6/2016 | Olson et al. |
| 9,364,220 | B2 | 6/2016 | Williams |
| 9,364,223 | B2 | 6/2016 | Scirica |
| 9,364,225 | B2 | 6/2016 | Sniffin et al. |
| 9,364,226 | B2 | 6/2016 | Zemlok et al. |
| 9,364,228 | B2 | 6/2016 | Straehnz et al. |
| 9,364,229 | B2 | 6/2016 | D'Agostino et al. |
| 9,364,230 | B2 | 6/2016 | Shelton, IV et al. |
| 9,364,231 | B2 | 6/2016 | Wenchell |
| 9,364,233 | B2 | 6/2016 | Alexander et al. |
| 9,364,279 | B2 | 6/2016 | Houser et al. |
| 9,368,991 | B2 | 6/2016 | Qahouq |
| 9,370,341 | B2 | 6/2016 | Ceniccola et al. |
| 9,370,358 | B2 | 6/2016 | Shelton, IV et al. |
| 9,370,361 | B2 | 6/2016 | Viola et al. |
| 9,370,362 | B2 | 6/2016 | Petty et al. |
| 9,370,364 | B2 | 6/2016 | Smith et al. |
| 9,370,400 | B2 | 6/2016 | Parihar |
| 9,375,206 | B2 | 6/2016 | Vidal et al. |
| 9,375,218 | B2 | 6/2016 | Wheeler et al. |
| 9,375,230 | B2 | 6/2016 | Ross et al. |
| 9,375,232 | B2 | 6/2016 | Hunt et al. |
| 9,375,255 | B2 | 6/2016 | Houser et al. |
| 9,375,256 | B2 | 6/2016 | Cunningham et al. |
| 9,375,267 | B2 | 6/2016 | Kerr et al. |
| D761,309 | S | 7/2016 | Lee et al. |
| 9,381,058 | B2 | 7/2016 | Houser et al. |
| 9,381,060 | B2 | 7/2016 | Artale et al. |
| 9,383,881 | B2 | 7/2016 | Day et al. |
| 9,385,640 | B2 | 7/2016 | Sun et al. |
| 9,386,983 | B2 | 7/2016 | Swensgard et al. |
| 9,386,984 | B2 | 7/2016 | Aronhalt et al. |
| 9,386,985 | B2 | 7/2016 | Koch, Jr. et al. |
| 9,386,988 | B2 | 7/2016 | Baxter, III et al. |
| 9,387,003 | B2 | 7/2016 | Kaercher et al. |
| 9,392,885 | B2 | 7/2016 | Vogler et al. |
| 9,393,015 | B2 | 7/2016 | Laurent et al. |
| 9,393,017 | B2 | 7/2016 | Flanagan et al. |
| 9,393,018 | B2 | 7/2016 | Wang et al. |
| 9,393,037 | B2 | 7/2016 | Olson et al. |
| 9,393,354 | B2 | 7/2016 | Freedman et al. |
| 9,396,369 | B1 | 7/2016 | Whitehurst et al. |
| 9,396,669 | B2 | 7/2016 | Karkanias et al. |
| 9,398,905 | B2 | 7/2016 | Martin |
| 9,398,911 | B2 | 7/2016 | Auld |
| D763,277 | S | 8/2016 | Ahmed et al. |
| D764,498 | S | 8/2016 | Capela et al. |
| 9,402,604 | B2 | 8/2016 | Williams et al. |
| 9,402,625 | B2 | 8/2016 | Coleman et al. |
| 9,402,626 | B2 | 8/2016 | Ortiz et al. |
| 9,402,627 | B2 | 8/2016 | Stevenson et al. |
| 9,402,629 | B2 | 8/2016 | Ehrenfels et al. |
| 9,402,679 | B2 | 8/2016 | Ginnebaugh et al. |
| 9,402,682 | B2 | 8/2016 | Worrell et al. |
| 9,402,688 | B2 | 8/2016 | Min et al. |
| 9,408,604 | B2 | 8/2016 | Shelton, IV et al. |
| 9,408,605 | B1 | 8/2016 | Knodel et al. |
| 9,408,606 | B2 | 8/2016 | Shelton, IV |
| 9,408,622 | B2 | 8/2016 | Stulen et al. |
| 9,408,660 | B2 | 8/2016 | Strobl et al. |
| 9,411,370 | B2 | 8/2016 | Benni et al. |
| 9,413,128 | B2 | 8/2016 | Tien et al. |
| 9,414,838 | B2 | 8/2016 | Shelton, IV et al. |
| 9,414,849 | B2 | 8/2016 | Nagashimada |
| 9,414,880 | B2 | 8/2016 | Monson et al. |
| 9,420,967 | B2 | 8/2016 | Zand et al. |
| 9,421,003 | B2 | 8/2016 | Williams et al. |
| 9,421,014 | B2 | 8/2016 | Ingmanson et al. |
| 9,421,030 | B2 | 8/2016 | Cole et al. |
| 9,421,060 | B2 | 8/2016 | Monson et al. |
| 9,421,062 | B2 | 8/2016 | Houser et al. |
| 9,421,682 | B2 | 8/2016 | McClaskey et al. |
| 9,427,223 | B2 | 8/2016 | Park et al. |
| 9,427,231 | B2 | 8/2016 | Racenet et al. |
| 9,429,204 | B2 | 8/2016 | Stefan et al. |
| D767,624 | S | 9/2016 | Lee et al. |
| 9,433,411 | B2 | 9/2016 | Racenet et al. |
| 9,433,414 | B2 | 9/2016 | Chen et al. |
| 9,433,419 | B2 | 9/2016 | Gonzalez et al. |
| 9,433,420 | B2 | 9/2016 | Hodgkinson |
| 9,439,649 | B2 | 9/2016 | Shelton, IV et al. |
| 9,439,650 | B2 | 9/2016 | McGuckin, Jr. et al. |
| 9,439,651 | B2 | 9/2016 | Smith et al. |
| 9,439,668 | B2 | 9/2016 | Timm et al. |
| 9,445,808 | B2 | 9/2016 | Woodard, Jr. et al. |
| 9,445,813 | B2 | 9/2016 | Shelton, IV et al. |
| 9,445,816 | B2 | 9/2016 | Swayze et al. |
| 9,445,817 | B2 | 9/2016 | Bettuchi |
| 9,446,226 | B2 | 9/2016 | Zilberman |
| 9,451,938 | B2 | 9/2016 | Overes et al. |
| 9,451,958 | B2 | 9/2016 | Shelton, IV et al. |
| 9,452,020 | B2 | 9/2016 | Griffiths et al. |
| D768,152 | S | 10/2016 | Gutierrez et al. |
| D768,156 | S | 10/2016 | Frincke |
| D768,167 | S | 10/2016 | Jones et al. |
| D769,315 | S | 10/2016 | Scotti |
| D769,930 | S | 10/2016 | Agrawal |
| 9,456,863 | B2 | 10/2016 | Moua |
| 9,456,864 | B2 | 10/2016 | Witt et al. |
| 9,456,876 | B2 | 10/2016 | Hagn |
| 9,461,340 | B2 | 10/2016 | Li et al. |
| 9,463,012 | B2 | 10/2016 | Bonutti et al. |
| 9,463,040 | B2 | 10/2016 | Jeong et al. |
| 9,463,260 | B2 | 10/2016 | Stopek |
| 9,468,438 | B2 | 10/2016 | Baber et al. |
| 9,468,447 | B2 | 10/2016 | Aman et al. |
| 9,468,490 | B2 | 10/2016 | Twomey et al. |
| 9,470,297 | B2 | 10/2016 | Aranyi et al. |
| 9,471,969 | B2 | 10/2016 | Zeng et al. |
| 9,474,506 | B2 | 10/2016 | Magnin et al. |
| 9,474,513 | B2 | 10/2016 | Ishida et al. |
| 9,474,523 | B2 | 10/2016 | Meade et al. |
| 9,474,528 | B2 | 10/2016 | Marczyk |
| 9,474,540 | B2 | 10/2016 | Stokes et al. |
| 9,475,180 | B2 | 10/2016 | Eshleman et al. |
| 9,477,649 | B1 | 10/2016 | Davidson et al. |
| D770,476 | S | 11/2016 | Jitkoff et al. |
| D770,515 | S | 11/2016 | Cho et al. |
| D771,116 | S | 11/2016 | Dellinger et al. |
| D772,905 | S | 11/2016 | Ingenlath |
| 9,480,476 | B2 | 11/2016 | Aldridge et al. |
| 9,480,492 | B2 | 11/2016 | Aranyi et al. |
| 9,483,095 | B2 | 11/2016 | Tran et al. |
| 9,486,186 | B2 | 11/2016 | Fiebig et al. |
| 9,486,213 | B2 | 11/2016 | Altman et al. |
| 9,486,214 | B2 | 11/2016 | Shelton, IV |
| 9,486,215 | B2 | 11/2016 | Olson et al. |
| 9,486,302 | B2 | 11/2016 | Boey et al. |
| 9,488,197 | B2 | 11/2016 | Wi |
| 9,492,146 | B2 | 11/2016 | Kostrzewski et al. |
| 9,492,167 | B2 | 11/2016 | Shelton, IV et al. |
| 9,492,170 | B2 | 11/2016 | Bear et al. |
| 9,492,172 | B2 | 11/2016 | Weisshaupt et al. |
| 9,492,189 | B2 | 11/2016 | Williams et al. |
| 9,492,192 | B2 | 11/2016 | To et al. |
| 9,492,224 | B2 | 11/2016 | Boudreaux et al. |
| 9,492,237 | B2 | 11/2016 | Kang et al. |
| 9,498,213 | B2 | 11/2016 | Marczyk et al. |
| 9,498,219 | B2 | 11/2016 | Moore et al. |
| 9,498,231 | B2 | 11/2016 | Haider et al. |
| 9,504,455 | B2 | 11/2016 | Whitman et al. |
| 9,504,483 | B2 | 11/2016 | Houser et al. |
| 9,504,520 | B2 | 11/2016 | Worrell et al. |
| 9,504,521 | B2 | 11/2016 | Deutmeyer et al. |
| 9,504,524 | B2 | 11/2016 | Behnke, II |
| 9,504,528 | B2 | 11/2016 | Ivinson et al. |
| 9,507,399 | B2 | 11/2016 | Chien |
| D774,547 | S | 12/2016 | Capela et al. |
| D775,336 | S | 12/2016 | Shelton, IV et al. |
| 9,510,827 | B2 | 12/2016 | Kostrzewski |
| 9,510,828 | B2 | 12/2016 | Yates et al. |
| 9,510,830 | B2 | 12/2016 | Shelton, IV et al. |
| 9,510,846 | B2 | 12/2016 | Sholev et al. |

(56) References Cited

U.S. PATENT DOCUMENTS 9,510,895 B2 12/2016 Houser et al.
9,510,906 B2 12/2016 Boudreaux et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,565 B2 12/2016 Strobl
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,663 B2 1/2017 Larkin
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,554,845 B2 1/2017 Arts
9,554,846 B2 1/2017 Boudreaux
9,554,854 B2 1/2017 Yates et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,561,072 B2 2/2017 Ko
9,561,082 B2 2/2017 Yen et al.
9,566,061 B2 2/2017 Aronhalt et al.
9,566,062 B2 2/2017 Boudreaux
9,566,064 B2 2/2017 Williams et al.
9,566,065 B2 2/2017 Knodel
9,566,067 B2 2/2017 Milliman et al.
9,572,552 B1 2/2017 Bodor et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,585,709 B2 3/2017 Krapohl
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.
9,610,091 B2 4/2017 Johnson et al.
9,610,114 B2 4/2017 Baxter, III et al.
9,610,412 B2 4/2017 Zemlok et al.
9,614,258 B2 4/2017 Takahashi et al.
9,615,826 B2 4/2017 Shelton, IV et al.
9,615,877 B2 4/2017 Tyrrell et al.
9,622,745 B2 4/2017 Ingmanson et al.
9,622,746 B2 4/2017 Simms et al.
9,622,810 B2 4/2017 Hart et al.
9,627,120 B2 4/2017 Scott et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek et al.
9,641,122 B2 5/2017 Romanowich et al.
9,642,620 B2 5/2017 Baxter, III et al.
9,642,642 B2 5/2017 Lim
9,642,669 B2 5/2017 Takashino et al.
9,649,096 B2 5/2017 Sholev
9,649,110 B2 5/2017 Parihar et al.
9,649,111 B2 5/2017 Shelton, IV et al.
9,649,144 B2 5/2017 Aluru et al.
9,649,151 B2 5/2017 Goodman et al.
9,649,190 B2 5/2017 Mathies
9,651,032 B2 5/2017 Weaver et al.
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,111 B2 5/2017 Holsten et al.
9,662,116 B2 5/2017 Smith et al.
9,662,130 B2 5/2017 Bartels et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.

(56) References Cited

U.S. PATENT DOCUMENTS 9,668,735 B2 6/2017 Beetel
9,668,806 B2 6/2017 Unger et al.
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,873 B2 6/2017 Smith et al.
9,681,884 B2 6/2017 Clem et al.
9,687,230 B2 6/2017 Leimbach et al.
9,687,231 B2 6/2017 Baxter et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,687,295 B2 6/2017 Joseph
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,700,339 B2 7/2017 Nield
9,700,381 B2 7/2017 Amat Girbau
9,702,823 B2 7/2017 Maher et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,027 B2 7/2017 Ruddenklau et al.
9,707,030 B2 7/2017 Davison et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
9,713,489 B2 7/2017 Woloszko et al.
9,713,491 B2 7/2017 Roy et al.
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,152 B2 8/2017 Horlle et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,355 B2 8/2017 Yates et al.
9,737,358 B2 8/2017 Beckman et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,757,142 B2 9/2017 Shimizu
9,757,186 B2 9/2017 Boudreaux et al.
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,665 B2 10/2017 Ellman
9,775,669 B2 10/2017 Marczyk et al.
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,782,220 B2 10/2017 Mark et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,891 B2 10/2017 Christian et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,795,436 B2 10/2017 Yates et al.
9,797,486 B2 10/2017 Zergiebel et al.
9,801,626 B2 10/2017 Parihar et al.

(56) References Cited

U.S. PATENT DOCUMENTS 9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,808,308 B2 11/2017 Faller et al.
9,814,460 B2 11/2017 Kimsey et al.
9,814,462 B2 11/2017 Woodard, Jr. et al.
9,814,463 B2 11/2017 Williams et al.
9,814,514 B2 11/2017 Shelton, IV et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,820,771 B2 11/2017 Norton et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,313 B2 12/2017 DiCarlo et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,848,937 B2 12/2017 Trees et al.
9,848,939 B2 12/2017 Mayer et al.
9,850,499 B2 12/2017 Baylink et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,428 B2 1/2018 Trees et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,872,725 B2 1/2018 Worrell et al.
9,877,720 B2 1/2018 Worrell et al.
9,877,721 B2 1/2018 Schellin et al.
9,877,722 B2 1/2018 Schellin et al.
9,877,723 B2 1/2018 Hall et al.
9,877,776 B2 1/2018 Boudreaux
9,877,782 B2 1/2018 Voegele et al.
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,888,954 B2 2/2018 Van Wyk et al.
9,888,958 B2 2/2018 Evans et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,390 B2 2/2018 Allen, IV et al.
9,901,406 B2 2/2018 State et al.
9,901,412 B2 2/2018 Lathrop et al.
9,901,754 B2 2/2018 Yamada
D813,899 S 3/2018 Erant et al.
9,907,456 B2 3/2018 Miyoshi
9,907,552 B2 3/2018 Measamer et al.
9,907,553 B2 3/2018 Cole et al.
9,907,563 B2 3/2018 Germain et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,680 B2 3/2018 Voegele et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,918,773 B2 3/2018 Ishikawa et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.

(56) References Cited

U.S. PATENT DOCUMENTS 9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,931,157 B2 4/2018 Strobl et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,001 B2 4/2018 Nakamura
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,943,357 B2 4/2018 Cunningham et al.
9,949,620 B2 4/2018 Duval et al.
9,949,754 B2 4/2018 Newhauser et al.
9,949,785 B2 4/2018 Price et al.
9,949,788 B2 4/2018 Boudreaux
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,993,289 B2 6/2018 Sobajima et al.
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
10,010,322 B2 7/2018 Shelton, IV et al.
10,010,324 B2 7/2018 Huitema et al.
10,010,339 B2 7/2018 Witt et al.
10,010,395 B2 7/2018 Puckett et al.
10,013,049 B2 7/2018 Leimbach et al.
10,016,199 B2 7/2018 Baber et al.
10,016,207 B2 7/2018 Suzuki et al.
10,016,656 B2 7/2018 Devor et al.
10,022,120 B2 7/2018 Martin et al.
10,022,123 B2 7/2018 Williams et al.
10,022,125 B2 7/2018 Stopek et al.
10,022,142 B2 7/2018 Aranyi et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
10,034,707 B2 7/2018 Papaioannou et al.
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,376 B2 8/2018 Horner et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,070,916 B2 9/2018 Artale
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
10,080,606 B2 9/2018 Kappus et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.

(56) References Cited

U.S. PATENT DOCUMENTS

| | | | |
|---|---|---|---|
| 10,092,292 | B2 | 10/2018 | Boudreaux et al. |
| 10,092,310 | B2 | 10/2018 | Boudreaux et al. |
| 10,092,348 | B2 | 10/2018 | Boudreaux |
| 10,092,350 | B2 | 10/2018 | Rothweiler et al. |
| 10,098,635 | B2 | 10/2018 | Burbank |
| 10,098,636 | B2 | 10/2018 | Shelton, IV et al. |
| 10,098,640 | B2 | 10/2018 | Bertolero et al. |
| 10,098,642 | B2 | 10/2018 | Baxter, III et al. |
| 10,099,303 | B2 | 10/2018 | Yoshida et al. |
| 10,101,861 | B2 | 10/2018 | Kiyoto |
| 10,105,126 | B2 | 10/2018 | Sauer |
| 10,105,128 | B2 | 10/2018 | Cooper et al. |
| 10,105,136 | B2 | 10/2018 | Yates et al. |
| 10,105,139 | B2 | 10/2018 | Yates et al. |
| 10,105,140 | B2 | 10/2018 | Malinouskas et al. |
| 10,105,142 | B2 | 10/2018 | Baxter, III et al. |
| 10,105,149 | B2 | 10/2018 | Haider et al. |
| 10,105,174 | B2 | 10/2018 | Krapohl |
| 10,106,932 | B2 | 10/2018 | Anderson et al. |
| 10,111,657 | B2 | 10/2018 | McCuen |
| 10,111,658 | B2 | 10/2018 | Chowaniec et al. |
| 10,111,660 | B2 | 10/2018 | Hemmann |
| 10,111,665 | B2 | 10/2018 | Aranyi et al. |
| 10,111,679 | B2 | 10/2018 | Baber et al. |
| 10,111,698 | B2 | 10/2018 | Scheib et al. |
| 10,111,699 | B2 | 10/2018 | Boudreaux |
| 10,111,702 | B2 | 10/2018 | Kostrzewski |
| D833,608 | S | 11/2018 | Miller et al. |
| 10,117,649 | B2 | 11/2018 | Baxter, III et al. |
| 10,117,650 | B2 | 11/2018 | Nicholas et al. |
| 10,117,652 | B2 | 11/2018 | Schmid et al. |
| 10,117,653 | B2 | 11/2018 | Leimbach et al. |
| 10,117,654 | B2 | 11/2018 | Ingmanson et al. |
| 10,117,702 | B2 | 11/2018 | Danziger et al. |
| 10,123,798 | B2 | 11/2018 | Baxter et al. |
| 10,123,845 | B2 | 11/2018 | Yeung |
| 10,124,493 | B2 | 11/2018 | Rothfuss et al. |
| 10,130,352 | B2 | 11/2018 | Widenhouse et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,363 | B2 | 11/2018 | Huitema et al. |
| 10,130,366 | B2 | 11/2018 | Shelton, IV et al. |
| 10,130,367 | B2 | 11/2018 | Cappola et al. |
| 10,130,382 | B2 | 11/2018 | Gladstone |
| 10,130,410 | B2 | 11/2018 | Strobl et al. |
| 10,130,414 | B2 | 11/2018 | Weiler et al. |
| 10,130,738 | B2 | 11/2018 | Shelton, IV et al. |
| 10,130,830 | B2 | 11/2018 | Miret Carceller et al. |
| 10,133,248 | B2 | 11/2018 | Fitzsimmons et al. |
| 10,135,242 | B2 | 11/2018 | Baber et al. |
| 10,136,879 | B2 | 11/2018 | Ross et al. |
| 10,136,887 | B2 | 11/2018 | Shelton, IV et al. |
| 10,136,889 | B2 | 11/2018 | Shelton, IV et al. |
| 10,136,890 | B2 | 11/2018 | Shelton, IV et al. |
| 10,136,891 | B2 | 11/2018 | Shelton, IV et al. |
| 10,136,949 | B2 | 11/2018 | Felder et al. |
| D835,659 | S | 12/2018 | Anzures et al. |
| D836,124 | S | 12/2018 | Fan |
| 10,143,474 | B2 | 12/2018 | Bucciaglia et al. |
| 10,146,423 | B1 | 12/2018 | Reed et al. |
| 10,149,679 | B2 | 12/2018 | Shelton, IV et al. |
| 10,149,680 | B2 | 12/2018 | Parihar et al. |
| 10,149,682 | B2 | 12/2018 | Shelton, IV et al. |
| 10,149,683 | B2 | 12/2018 | Smith et al. |
| 10,149,712 | B2 | 12/2018 | Manwaring et al. |
| 10,152,789 | B2 | 12/2018 | Carnes et al. |
| 10,154,841 | B2 | 12/2018 | Weaner et al. |
| 10,159,481 | B2 | 12/2018 | Whitman et al. |
| 10,159,482 | B2 | 12/2018 | Swayze et al. |
| 10,159,483 | B2 | 12/2018 | Beckman et al. |
| 10,159,506 | B2 | 12/2018 | Boudreaux et al. |
| 10,159,524 | B2 | 12/2018 | Yates et al. |
| 10,161,816 | B2 | 12/2018 | Jackson et al. |
| 10,163,065 | B1 | 12/2018 | Koski et al. |
| 10,163,589 | B2 | 12/2018 | Zergiebel et al. |
| 10,164,466 | B2 | 12/2018 | Calderoni |
| D837,244 | S | 1/2019 | Kuo et al. |
| D837,245 | S | 1/2019 | Kuo et al. |
| 10,166,023 | B2 | 1/2019 | Vendely et al. |
| 10,166,025 | B2 | 1/2019 | Leimbach et al. |
| 10,166,026 | B2 | 1/2019 | Shelton, IV et al. |
| 10,166,060 | B2 | 1/2019 | Johnson et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,618 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,172,669 | B2 | 1/2019 | Felder et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,182,819 | B2 | 1/2019 | Shelton, IV |
| 10,182,868 | B2 | 1/2019 | Meier et al. |
| 10,188,385 | B2 | 1/2019 | Kerr et al. |
| 10,188,389 | B2 | 1/2019 | Vendely et al. |
| 10,188,393 | B2 | 1/2019 | Smith et al. |
| 10,188,394 | B2 | 1/2019 | Shelton, IV et al. |
| 10,190,888 | B2 | 1/2019 | Hryb et al. |
| D839,900 | S | 2/2019 | Gan |
| D841,667 | S | 2/2019 | Coren |
| 10,194,801 | B2 | 2/2019 | Elhawary et al. |
| 10,194,904 | B2 | 2/2019 | Viola et al. |
| 10,194,907 | B2 | 2/2019 | Marczyk et al. |
| 10,194,908 | B2 | 2/2019 | Duque et al. |
| 10,194,910 | B2 | 2/2019 | Shelton, IV et al. |
| 10,194,911 | B2 | 2/2019 | Miller et al. |
| 10,194,912 | B2 | 2/2019 | Scheib et al. |
| 10,194,913 | B2 | 2/2019 | Nalagatla et al. |
| 10,194,972 | B2 | 2/2019 | Yates et al. |
| 10,194,976 | B2 | 2/2019 | Boudreaux |
| 10,194,977 | B2 | 2/2019 | Yang |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,204 | B2 | 2/2019 | Aranyi et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,776 | B2 | 3/2019 | Artale et al. |
| 10,231,794 | B2 | 3/2019 | Shelton, IV et al. |
| 10,238,385 | B2 | 3/2019 | Yates et al. |

(56) References Cited

U.S. PATENT DOCUMENTS

| | | | |
|---|---|---|---|
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,038 | B2 | 4/2019 | Hopkins et al. |
| 10,245,058 | B2 | 4/2019 | Omori et al. |
| 10,245,095 | B2 | 4/2019 | Boudreaux |
| 10,251,645 | B2 | 4/2019 | Kostrzewski |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,363 | B2 | 4/2019 | Worrell et al. |
| 10,258,404 | B2 | 4/2019 | Wang |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,265,118 | B2 | 4/2019 | Gerhardt |
| 10,271,840 | B2 | 4/2019 | Sapre |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,847 | B2 | 4/2019 | Racenet et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,721 | B2 | 5/2019 | Dietz et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,307,203 | B2 | 6/2019 | Wyatt |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,314,638 | B2 | 6/2019 | Gee et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,321,950 | B2 | 6/2019 | Yates et al. |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,602 | B2 | 7/2019 | Strobl et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |

(56) References Cited

U.S. PATENT DOCUMENTS

| | | | |
|---|---|---|---|
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,352 | B2 | 9/2019 | Thomas et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| 10,420,601 | B2 | 9/2019 | Marion et al. |
| 10,420,607 | B2 | 9/2019 | Woloszko et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,426,873 | B2 | 10/2019 | Schultz |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter et al. |
| 10,433,846 | B2 | 10/2019 | Vendely et al. |
| 10,433,849 | B2 | 10/2019 | Shelton, IV et al. |
| 10,433,900 | B2 | 10/2019 | Harris et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,463,421 | B2 | 11/2019 | Boudreaux et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,478,243 | B2 | 11/2019 | Couture et al. |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| 10,485,607 | B2 | 11/2019 | Strobl et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,004 | B2 | 12/2019 | Hanuschik et al. |
| 10,500,309 | B2 | 12/2019 | Shah et al. |
| 10,507,034 | B2 | 12/2019 | Timm |

(56) References Cited

U.S. PATENT DOCUMENTS

| | | | |
|---|---|---|---|
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,524,852 | B1 | 1/2020 | Cagle et al. |
| 10,524,854 | B2 | 1/2020 | Woodruff et al. |
| 10,524,870 | B2 | 1/2020 | Saraliev et al. |
| 10,531,874 | B2 | 1/2020 | Morgan et al. |
| 10,531,887 | B2 | 1/2020 | Shelton, IV et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |
| 10,561,412 | B2 | 2/2020 | Bookbinder et al. |
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,568,682 | B2 | 2/2020 | Dycus et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |
| 10,582,928 | B2 | 3/2020 | Hunter et al. |
| 10,588,231 | B2 | 3/2020 | Sgroi, Jr. et al. |
| 10,588,623 | B2 | 3/2020 | Schmid et al. |
| 10,588,625 | B2 | 3/2020 | Weaner et al. |
| 10,588,626 | B2 | 3/2020 | Overmyer et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,589,410 | B2 | 3/2020 | Aho |
| 10,595,835 | B2 | 3/2020 | Kerr et al. |
| 10,595,862 | B2 | 3/2020 | Shelton, IV et al. |
| 10,595,882 | B2 | 3/2020 | Parfett et al. |
| 10,595,887 | B2 | 3/2020 | Shelton, IV et al. |
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,103 | B2 | 3/2020 | Thomas et al. |
| 10,603,117 | B2 | 3/2020 | Schings et al. |
| 10,603,128 | B2 | 3/2020 | Zergiebel et al. |
| D882,783 | S | 4/2020 | Shelton, IV et al. |
| 10,610,224 | B2 | 4/2020 | Shelton, IV et al. |
| 10,610,225 | B2 | 4/2020 | Reed et al. |
| 10,610,236 | B2 | 4/2020 | Baril |
| 10,610,313 | B2 | 4/2020 | Bailey et al. |
| 10,610,346 | B2 | 4/2020 | Schwartz |
| 10,614,184 | B2 | 4/2020 | Solki |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,617,438 | B2 | 4/2020 | O'Keefe et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,089 | B2 | 5/2020 | Manwaring et al. |
| 10,639,092 | B2 | 5/2020 | Corbett et al. |
| 10,639,115 | B2 | 5/2020 | Shelton, IV et al. |
| 10,642,633 | B1 | 5/2020 | Chopra et al. |
| 10,645,905 | B2 | 5/2020 | Gandola et al. |
| 10,646,220 | B2 | 5/2020 | Shelton, IV et al. |
| 10,646,269 | B2 | 5/2020 | Worrell et al. |
| 10,646,292 | B2 | 5/2020 | Solomon et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |
| 10,667,408 | B2 | 5/2020 | Sgroi, Jr. et al. |
| D888,953 | S | 6/2020 | Baxter, III et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,818 | B2 | 6/2020 | McLain et al. |
| 10,674,895 | B2 | 6/2020 | Yeung et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,675,080 | B2 | 6/2020 | Woloszko et al. |
| 10,675,082 | B2 | 6/2020 | Shelton, IV et al. |
| 10,675,102 | B2 | 6/2020 | Forgione et al. |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,137 | B2 | 6/2020 | Stokes et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |

(56) References Cited

U.S. PATENT DOCUMENTS 10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,702,329 B2 7/2020 Strobl et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,495 B2 7/2020 Broderick et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
D893,717 S 8/2020 Messerly et al.
10,729,432 B2 8/2020 Shelton, IV et al.
10,729,434 B2 8/2020 Harris et al.
10,729,435 B2 8/2020 Richard
10,729,436 B2 8/2020 Shelton, IV et al.
10,729,443 B2 8/2020 Cabrera et al.
10,729,458 B2 8/2020 Stoddard et al.
10,729,501 B2 8/2020 Leimbach et al.
10,729,509 B2 8/2020 Shelton, IV et al.
10,736,616 B2 8/2020 Scheib et al.
10,736,628 B2 8/2020 Yates et al.
10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,636 B2 8/2020 Baxter, III et al.
10,736,644 B2 8/2020 Windolf et al.
10,736,702 B2 8/2020 Harris et al.
10,737,398 B2 8/2020 Remirez et al.
10,743,849 B2 8/2020 Shelton, IV et al.
10,743,850 B2 8/2020 Hibner et al.
10,743,851 B2 8/2020 Swayze et al.
10,743,868 B2 8/2020 Shelton, IV et al.
10,743,870 B2 8/2020 Hall et al.
10,743,872 B2 8/2020 Leimbach et al.
10,743,873 B2 8/2020 Overmyer et al.
10,743,874 B2 8/2020 Shelton, IV et al.
10,743,875 B2 8/2020 Shelton, IV et al.
10,743,877 B2 8/2020 Shelton, IV et al.
10,743,930 B2 8/2020 Nagtegaal
10,751,048 B2 8/2020 Whitman et al.
10,751,053 B2 8/2020 Harris et al.
10,751,076 B2 8/2020 Laurent et al.
10,751,109 B2 8/2020 Yates et al.
10,751,110 B2 8/2020 Ding
10,751,117 B2 8/2020 Witt et al.
10,751,138 B2 8/2020 Giordano et al.
10,758,226 B2 9/2020 Weir et al.
10,758,229 B2 9/2020 Shelton, IV et al.
10,758,230 B2 9/2020 Shelton, IV et al.
10,758,232 B2 9/2020 Shelton, IV et al.
10,758,233 B2 9/2020 Scheib et al.
10,758,259 B2 9/2020 Demmy et al.
10,758,294 B2 9/2020 Jones
10,765,425 B2 9/2020 Yates et al.
10,765,427 B2 9/2020 Shelton, IV et al.
10,765,429 B2 9/2020 Leimbach et al.
10,765,430 B2 9/2020 Wixey
10,765,432 B2 9/2020 Moore et al.
10,765,442 B2 9/2020 Strobl
10,772,625 B2 9/2020 Shelton, IV et al.
10,772,628 B2 9/2020 Chen et al.
10,772,629 B2 9/2020 Shelton, IV et al.
10,772,630 B2 9/2020 Wixey
10,772,631 B2 9/2020 Zergiebel et al.
10,772,632 B2 9/2020 Kostrzewski
10,772,651 B2 9/2020 Shelton, IV et al.
10,779,818 B2 9/2020 Zemlok et al.
10,779,820 B2 9/2020 Harris et al.
10,779,821 B2 9/2020 Harris et al.
10,779,822 B2 9/2020 Yates et al.
10,779,823 B2 9/2020 Shelton, IV et al.
10,779,824 B2 9/2020 Shelton, IV et al.
10,779,825 B2 9/2020 Shelton, IV et al.
10,779,826 B2 9/2020 Shelton, IV et al.
10,779,876 B2 9/2020 Monson et al.
10,779,903 B2 9/2020 Wise et al.
10,780,539 B2 9/2020 Shelton, IV et al.
10,786,248 B2 9/2020 Rousseau et al.
10,786,253 B2 9/2020 Shelton, IV et al.
10,786,255 B2 9/2020 Hodgkinson et al.
10,792,038 B2 10/2020 Becerra et al.
10,796,471 B2 10/2020 Leimbach et al.
10,799,240 B2 10/2020 Shelton, IV et al.
10,799,284 B2 10/2020 Renner et al.
10,799,306 B2 10/2020 Robinson et al.
10,806,448 B2 10/2020 Shelton, IV et al.
10,806,449 B2 10/2020 Shelton, IV et al.
10,806,450 B2 10/2020 Yates et al.
10,806,451 B2 10/2020 Harris et al.
10,806,453 B2 10/2020 Chen et al.
10,806,479 B2 10/2020 Shelton, IV et al.
10,813,638 B2 10/2020 Shelton, IV et al.
10,813,639 B2 10/2020 Shelton, IV et al.
10,813,640 B2 10/2020 Adams et al.
10,813,641 B2 10/2020 Setser et al.
10,813,683 B2 10/2020 Baxter, III et al.
10,813,705 B2 10/2020 Hares et al.
10,813,710 B2 10/2020 Grubbs
10,820,938 B2 11/2020 Fischer et al.
10,820,939 B2 11/2020 Sartor
10,828,028 B2 11/2020 Harris et al.
10,828,030 B2 11/2020 Weir et al.
10,828,032 B2 11/2020 Leimbach et al.
10,828,033 B2 11/2020 Shelton, IV et al.
10,828,089 B2 11/2020 Clark et al.
10,835,245 B2 11/2020 Swayze et al.
10,835,246 B2 11/2020 Shelton, IV et al.
10,835,247 B2 11/2020 Shelton, IV et al.
10,835,249 B2 11/2020 Schellin et al.
10,835,251 B2 11/2020 Shelton, IV et al.
10,835,330 B2 11/2020 Shelton, IV et al.
10,842,357 B2 11/2020 Moskowitz et al.
10,842,473 B2 11/2020 Scheib et al.
10,842,488 B2 11/2020 Swayze et al.
10,842,489 B2 11/2020 Shelton, IV
10,842,490 B2 11/2020 DiNardo et al.
10,842,491 B2 11/2020 Shelton, IV et al.
10,842,492 B2 11/2020 Shelton, IV et al.
10,842,523 B2 11/2020 Shelton, IV et al.
D904,612 S 12/2020 Wynn et al.
D904,613 S 12/2020 Wynn et al.
D906,355 S 12/2020 Messerly et al.
10,849,621 B2 12/2020 Whitfield et al.
10,849,623 B2 12/2020 Dunki-Jacobs et al.

(56) References Cited

U.S. PATENT DOCUMENTS

| | | | |
|---|---|---|---|
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,856,934 | B2 | 12/2020 | Trees et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,339 | B2 | 1/2021 | Peyser et al. |
| 10,881,395 | B2 | 1/2021 | Merchant et al. |
| 10,881,396 | B2 | 1/2021 | Shelton, IV et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,881,449 | B2 | 1/2021 | Boudreaux et al. |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Biasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,912,600 | B2 | 2/2021 | Kitagawa et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,771 | B2 | 3/2021 | Boudreaux et al. |
| 10,959,797 | B2 | 3/2021 | Licht et al. |
| 10,959,806 | B2 | 3/2021 | Hibner et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,779 | B2 | 4/2021 | Hart et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,156 | B2 | 4/2021 | Trees et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,005,291 | B2 | 5/2021 | Calderoni |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,020,172 | B2 | 6/2021 | Garrison |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |

(56) References Cited

U.S. PATENT DOCUMENTS 11,026,712 B2 6/2021 Shelton, IV et al.
11,026,713 B2 6/2021 Stokes et al.
11,026,751 B2 6/2021 Shelton, IV et al.
11,033,267 B2 6/2021 Shelton, IV et al.
11,033,323 B2 6/2021 Witt et al.
11,033,325 B2 6/2021 Yates et al.
11,039,834 B2 6/2021 Harris et al.
11,039,836 B2 6/2021 Shelton, IV et al.
11,039,837 B2 6/2021 Shelton, IV et al.
11,039,849 B2 6/2021 Bucciaglia et al.
11,045,189 B2 6/2021 Yates et al.
11,045,191 B2 6/2021 Shelton, IV et al.
11,045,192 B2 6/2021 Harris et al.
11,045,196 B2 6/2021 Olson et al.
11,045,197 B2 6/2021 Shelton, IV et al.
11,045,199 B2 6/2021 Mozdzierz et al.
11,045,270 B2 6/2021 Shelton, IV et al.
11,051,807 B2 7/2021 Shelton, IV et al.
11,051,810 B2 7/2021 Harris et al.
11,051,811 B2 7/2021 Shelton, IV et al.
11,051,813 B2 7/2021 Shelton, IV et al.
11,051,836 B2 7/2021 Shelton, IV et al.
11,051,840 B2 7/2021 Shelton, IV et al.
11,051,873 B2 7/2021 Wiener et al.
11,058,418 B2 7/2021 Shelton, IV et al.
11,058,420 B2 7/2021 Shelton, IV et al.
11,058,422 B2 7/2021 Harris et al.
11,058,423 B2 7/2021 Shelton, IV et al.
11,058,424 B2 7/2021 Shelton, IV et al.
11,058,425 B2 7/2021 Widenhouse et al.
11,058,426 B2 7/2021 Nalagatla et al.
11,058,498 B2 7/2021 Shelton, IV et al.
11,064,997 B2 7/2021 Shelton, IV et al.
11,064,998 B2 7/2021 Shelton, IV
11,065,000 B2 7/2021 Shankarsetty et al.
11,065,048 B2 7/2021 Messerly et al.
11,069,012 B2 7/2021 Shelton, IV et al.
11,071,542 B2 7/2021 Chen et al.
11,071,543 B2 7/2021 Shelton, IV et al.
11,071,545 B2 7/2021 Baber et al.
11,071,554 B2 7/2021 Parfett et al.
11,071,560 B2 7/2021 Deck et al.
11,076,853 B2 8/2021 Parfett et al.
11,076,854 B2 8/2021 Baber et al.
11,076,921 B2 8/2021 Shelton, IV et al.
11,076,929 B2 8/2021 Shelton, IV et al.
11,083,452 B2 8/2021 Schmid et al.
11,083,453 B2 8/2021 Shelton, IV et al.
11,083,454 B2 8/2021 Harris et al.
11,083,455 B2 8/2021 Shelton, IV et al.
11,083,456 B2 8/2021 Shelton, IV et al.
11,083,457 B2 8/2021 Shelton, IV et al.
11,083,458 B2 8/2021 Harris et al.
11,090,045 B2 8/2021 Shelton, IV
11,090,046 B2 8/2021 Shelton, IV et al.
11,090,047 B2 8/2021 Shelton, IV et al.
11,090,048 B2 8/2021 Fanelli et al.
11,090,049 B2 8/2021 Bakos et al.
11,090,075 B2 8/2021 Hunter et al.
11,090,103 B2 8/2021 Ruddenklau et al.
11,096,688 B2 8/2021 Shelton, IV et al.
11,096,689 B2 8/2021 Overmyer et al.
11,100,631 B2 8/2021 Yates et al.
11,103,241 B2 8/2021 Yates et al.
11,103,248 B2 8/2021 Shelton, IV et al.
11,103,268 B2 8/2021 Shelton, IV et al.
11,103,269 B2 8/2021 Shelton, IV et al.
11,103,301 B2 8/2021 Messerly et al.
11,109,858 B2 9/2021 Shelton, IV et al.
11,109,859 B2 9/2021 Overmyer et al.
11,109,860 B2 9/2021 Shelton, IV et al.
11,109,866 B2 9/2021 Shelton, IV et al.
11,109,878 B2 9/2021 Shelton, IV et al.
11,109,925 B2 9/2021 Cooper et al.
11,116,485 B2 9/2021 Scheib et al.
11,116,502 B2 9/2021 Shelton, IV et al.
11,116,594 B2 9/2021 Beardsley
11,123,069 B2 9/2021 Baxter, III et al.
11,123,070 B2 9/2021 Shelton, IV et al.
11,129,611 B2 9/2021 Shelton, IV et al.
11,129,613 B2 9/2021 Harris et al.
11,129,615 B2 9/2021 Scheib et al.
11,129,616 B2 9/2021 Shelton, IV et al.
11,129,634 B2 9/2021 Scheib et al.
11,129,636 B2 9/2021 Shelton, IV et al.
11,129,666 B2 9/2021 Messerly et al.
11,129,680 B2 9/2021 Shelton, IV et al.
11,132,462 B2 9/2021 Shelton, IV et al.
11,133,106 B2 9/2021 Shelton, IV et al.
11,134,938 B2 10/2021 Timm et al.
11,134,940 B2 10/2021 Shelton, IV et al.
11,134,942 B2 10/2021 Harris et al.
11,134,943 B2 10/2021 Giordano et al.
11,134,944 B2 10/2021 Wise et al.
11,134,947 B2 10/2021 Shelton, IV et al.
11,135,352 B2 10/2021 Shelton, IV et al.
11,141,153 B2 10/2021 Shelton, IV et al.
11,141,154 B2 10/2021 Shelton, IV et al.
11,141,155 B2 10/2021 Shelton, IV
11,141,156 B2 10/2021 Shelton, IV
11,141,159 B2 10/2021 Scheib et al.
11,141,160 B2 10/2021 Shelton, IV et al.
11,147,547 B2 10/2021 Shelton, IV et al.
11,147,549 B2 10/2021 Timm et al.
11,147,551 B2 10/2021 Shelton, IV
11,147,553 B2 10/2021 Shelton, IV
11,147,554 B2 10/2021 Aronhalt et al.
11,154,296 B2 10/2021 Aronhalt et al.
11,154,297 B2 10/2021 Swayze et al.
11,154,298 B2 10/2021 Timm et al.
11,154,299 B2 10/2021 Shelton, IV et al.
11,154,300 B2 10/2021 Nalagatla et al.
11,154,301 B2 10/2021 Beckman et al.
11,160,551 B2 11/2021 Shelton, IV et al.
11,160,553 B2 11/2021 Simms et al.
11,160,601 B2 11/2021 Worrell et al.
11,166,716 B2 11/2021 Shelton, IV et al.
11,166,717 B2 11/2021 Shelton, IV et al.
11,166,720 B2 11/2021 Giordano et al.
11,166,772 B2 11/2021 Shelton, IV et al.
11,166,773 B2 11/2021 Ragosta et al.
11,172,580 B2 11/2021 Gaertner, II
11,172,927 B2 11/2021 Shelton, IV
11,172,929 B2 11/2021 Shelton, IV
11,179,150 B2 11/2021 Yates et al.
11,179,151 B2 11/2021 Shelton, IV et al.
11,179,152 B2 11/2021 Morgan et al.
11,179,153 B2 11/2021 Shelton, IV
11,179,155 B2 11/2021 Shelton, IV et al.
11,179,208 B2 11/2021 Yates et al.
11,185,325 B2 11/2021 Shelton, IV et al.
11,185,330 B2 11/2021 Huitema et al.
11,191,539 B2 12/2021 Overmyer et al.
11,191,540 B2 12/2021 Aronhalt et al.
11,191,543 B2 12/2021 Overmyer et al.
11,191,545 B2 12/2021 Vendely et al.
11,197,668 B2 12/2021 Shelton, IV et al.
11,197,670 B2 12/2021 Shelton, IV et al.
11,197,671 B2 12/2021 Shelton, IV et al.
11,197,672 B2 12/2021 Dunki-Jacobs et al.
11,202,570 B2 12/2021 Shelton, IV et al.
11,202,631 B2 12/2021 Shelton, IV et al.
11,202,633 B2 12/2021 Harris et al.
11,207,064 B2 12/2021 Shelton, IV et al.
11,207,065 B2 12/2021 Harris et al.
11,207,067 B2 12/2021 Shelton, IV et al.
11,207,089 B2 12/2021 Kostrzewski et al.
11,207,090 B2 12/2021 Shelton, IV et al.
11,207,146 B2 12/2021 Shelton, IV et al.
11,213,293 B2 1/2022 Worthington et al.
11,213,294 B2 1/2022 Shelton, IV et al.
11,213,302 B2 1/2022 Parfett et al.
11,213,359 B2 1/2022 Shelton, IV et al.
11,219,453 B2 1/2022 Shelton, IV et al.

(56) References Cited

U.S. PATENT DOCUMENTS

| | | | |
|---|---|---|---|
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,443 | B2 | 4/2022 | Viola et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,697 | B2 | 4/2022 | Fanelli et al. |
| 11,304,699 | B2 | 4/2022 | Shelton, IV et al. |
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| 11,350,843 | B2 | 6/2022 | Shelton, IV et al. |
| 11,350,916 | B2 | 6/2022 | Shelton, IV et al. |
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,364,027 | B2 | 6/2022 | Harris et al. |
| 11,364,046 | B2 | 6/2022 | Shelton, IV et al. |
| 11,369,366 | B2 | 6/2022 | Scheib et al. |
| 11,369,368 | B2 | 6/2022 | Shelton, IV et al. |
| 11,369,376 | B2 | 6/2022 | Simms et al. |
| 11,369,377 | B2 | 6/2022 | Boudreaux et al. |
| 11,373,755 | B2 | 6/2022 | Shelton, IV et al. |
| 11,376,001 | B2 | 7/2022 | Shelton, IV et al. |
| 11,376,002 | B2 | 7/2022 | Shelton, IV et al. |
| 11,376,082 | B2 | 7/2022 | Shelton, IV et al. |
| 11,376,098 | B2 | 7/2022 | Shelton, IV et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,628 | B2 | 7/2022 | Baxter, III et al. |
| 11,382,638 | B2 | 7/2022 | Harris et al. |
| 11,382,697 | B2 | 7/2022 | Shelton, IV et al. |
| 11,382,704 | B2 | 7/2022 | Overmyer et al. |
| 11,389,160 | B2 | 7/2022 | Shelton, IV et al. |
| 11,389,161 | B2 | 7/2022 | Shelton, IV et al. |
| 11,389,162 | B2 | 7/2022 | Baber et al. |
| 11,389,164 | B2 | 7/2022 | Yates et al. |
| 11,395,651 | B2 | 7/2022 | Shelton, IV et al. |
| 11,395,652 | B2 | 7/2022 | Parihar et al. |
| 11,399,828 | B2 | 8/2022 | Swayze et al. |
| 11,399,829 | B2 | 8/2022 | Leimbach et al. |
| 11,399,831 | B2 | 8/2022 | Overmyer et al. |
| 11,399,837 | B2 | 8/2022 | Shelton, IV et al. |
| 11,406,377 | B2 | 8/2022 | Schmid et al. |
| 11,406,378 | B2 | 8/2022 | Baxter, III et al. |
| 11,406,380 | B2 | 8/2022 | Yates et al. |
| 11,406,381 | B2 | 8/2022 | Parihar et al. |
| 11,406,382 | B2 | 8/2022 | Shelton, IV et al. |
| 11,406,386 | B2 | 8/2022 | Baber et al. |
| 11,406,390 | B2 | 8/2022 | Shelton, IV et al. |
| 11,406,442 | B2 | 8/2022 | Davison et al. |
| 11,410,259 | B2 | 8/2022 | Harris et al. |
| 11,413,041 | B2 | 8/2022 | Viola et al. |
| 11,413,042 | B2 | 8/2022 | Shelton, IV et al. |
| 11,413,102 | B2 | 8/2022 | Shelton, IV et al. |
| 11,419,606 | B2 | 8/2022 | Overmyer et al. |
| 11,419,630 | B2 | 8/2022 | Yates et al. |
| 11,424,027 | B2 | 8/2022 | Shelton, IV |
| 11,426,160 | B2 | 8/2022 | Shelton, IV et al. |
| 11,426,167 | B2 | 8/2022 | Shelton, IV et al. |
| 11,426,251 | B2 | 8/2022 | Kimball et al. |
| D964,564 | S | 9/2022 | Boudreaux |
| 11,432,816 | B2 | 9/2022 | Leimbach et al. |
| 11,432,885 | B2 | 9/2022 | Shelton, IV et al. |
| 11,439,391 | B2 | 9/2022 | Bruns et al. |
| 11,439,470 | B2 | 9/2022 | Spivey et al. |
| 11,446,029 | B2 | 9/2022 | Shelton, IV et al. |
| 11,446,034 | B2 | 9/2022 | Shelton, IV et al. |
| 11,452,526 | B2 | 9/2022 | Ross et al. |
| 11,452,528 | B2 | 9/2022 | Leimbach et al. |

(56) References Cited

U.S. PATENT DOCUMENTS

| | | | |
|---|---|---|---|
| D966,512 | S | 10/2022 | Shelton, IV et al. |
| D967,421 | S | 10/2022 | Shelton, IV et al. |
| 11,457,918 | B2 | 10/2022 | Shelton, IV et al. |
| 11,464,511 | B2 | 10/2022 | Timm et al. |
| 11,464,512 | B2 | 10/2022 | Shelton, IV et al. |
| 11,464,513 | B2 | 10/2022 | Shelton, IV et al. |
| 11,464,514 | B2 | 10/2022 | Yates et al. |
| 11,464,601 | B2 | 10/2022 | Shelton, IV et al. |
| 11,471,155 | B2 | 10/2022 | Shelton, IV et al. |
| 11,471,156 | B2 | 10/2022 | Shelton, IV et al. |
| 11,471,157 | B2 | 10/2022 | Baxter, III et al. |
| 11,478,241 | B2 | 10/2022 | Shelton, IV et al. |
| 11,478,242 | B2 | 10/2022 | Shelton, IV et al. |
| 11,478,244 | B2 | 10/2022 | DiNardo et al. |
| D971,232 | S | 11/2022 | Siebel et al. |
| 11,484,307 | B2 | 11/2022 | Hall et al. |
| 11,484,309 | B2 | 11/2022 | Harris et al. |
| 11,484,310 | B2 | 11/2022 | Shelton, IV et al. |
| 11,484,311 | B2 | 11/2022 | Shelton, IV et al. |
| 11,484,312 | B2 | 11/2022 | Shelton, IV et al. |
| 11,490,889 | B2 | 11/2022 | Overmyer et al. |
| 11,497,488 | B2 | 11/2022 | Leimbach et al. |
| 11,497,489 | B2 | 11/2022 | Baxter et al. |
| 11,497,492 | B2 | 11/2022 | Shelton, IV |
| 11,497,499 | B2 | 11/2022 | Shelton, IV et al. |
| 11,504,116 | B2 | 11/2022 | Schmid et al. |
| 11,504,119 | B2 | 11/2022 | Shelton, IV et al. |
| 11,504,122 | B2 | 11/2022 | Shelton, IV et al. |
| 11,504,192 | B2 | 11/2022 | Shelton, IV et al. |
| 11,510,671 | B2 | 11/2022 | Shelton, IV et al. |
| 11,510,673 | B1 | 11/2022 | Chen et al. |
| 11,510,741 | B2 | 11/2022 | Shelton, IV et al. |
| 11,517,304 | B2 | 12/2022 | Yates et al. |
| 11,517,306 | B2 | 12/2022 | Miller et al. |
| 11,517,309 | B2 | 12/2022 | Bakos et al. |
| 11,517,311 | B2 | 12/2022 | Lytle, IV et al. |
| 11,517,315 | B2 | 12/2022 | Huitema et al. |
| 11,517,325 | B2 | 12/2022 | Shelton, IV et al. |
| 11,517,390 | B2 | 12/2022 | Baxter, III |
| 11,523,821 | B2 | 12/2022 | Harris et al. |
| 11,523,822 | B2 | 12/2022 | Shelton, IV et al. |
| 11,523,823 | B2 | 12/2022 | Hunter et al. |
| 11,523,824 | B2 | 12/2022 | Williams |
| 11,523,859 | B2 | 12/2022 | Shelton, IV et al. |
| 11,529,137 | B2 | 12/2022 | Shelton, IV et al. |
| 11,529,138 | B2 | 12/2022 | Jaworek et al. |
| 11,529,139 | B2 | 12/2022 | Shelton, IV et al. |
| 11,529,140 | B2 | 12/2022 | Shelton, IV et al. |
| 11,529,142 | B2 | 12/2022 | Leimbach et al. |
| 11,534,162 | B2 | 12/2022 | Shelton, IV |
| 11,534,259 | B2 | 12/2022 | Leimbach et al. |
| D974,560 | S | 1/2023 | Shelton, IV et al. |
| D975,278 | S | 1/2023 | Shelton, IV et al. |
| D975,850 | S | 1/2023 | Shelton, IV et al. |
| D975,851 | S | 1/2023 | Shelton, IV et al. |
| D976,401 | S | 1/2023 | Shelton, IV et al. |
| 11,540,824 | B2 | 1/2023 | Shelton, IV et al. |
| 11,540,829 | B2 | 1/2023 | Shelton, IV et al. |
| 11,547,403 | B2 | 1/2023 | Shelton, IV et al. |
| 11,547,404 | B2 | 1/2023 | Shelton, IV et al. |
| 11,553,911 | B2 | 1/2023 | Shelton, IV et al. |
| 11,553,916 | B2 | 1/2023 | Vendely et al. |
| 11,553,919 | B2 | 1/2023 | Shelton, IV et al. |
| 11,553,971 | B2 | 1/2023 | Shelton, IV et al. |
| 11,559,302 | B2 | 1/2023 | Timm et al. |
| 11,559,303 | B2 | 1/2023 | Shelton, IV et al. |
| 11,559,304 | B2 | 1/2023 | Boudreaux et al. |
| 11,559,307 | B2 | 1/2023 | Shelton, IV et al. |
| 11,559,308 | B2 | 1/2023 | Yates et al. |
| 11,559,496 | B2 | 1/2023 | Widenhouse et al. |
| 11,564,679 | B2 | 1/2023 | Parihar et al. |
| 11,564,682 | B2 | 1/2023 | Timm et al. |
| 11,564,686 | B2 | 1/2023 | Yates et al. |
| 11,564,688 | B2 | 1/2023 | Swayze et al. |
| 11,564,703 | B2 | 1/2023 | Shelton, IV et al. |
| 11,564,756 | B2 | 1/2023 | Shelton, IV et al. |
| 11,571,207 | B2 | 2/2023 | Shelton, IV et al. |
| 11,571,210 | B2 | 2/2023 | Shelton, IV et al. |
| 11,571,212 | B2 | 2/2023 | Yates et al. |
| 11,571,215 | B2 | 2/2023 | Shelton, IV et al. |
| 11,571,231 | B2 | 2/2023 | Hess et al. |
| 11,576,668 | B2 | 2/2023 | Shelton, IV et al. |
| 11,576,672 | B2 | 2/2023 | Shelton, IV et al. |
| 11,576,673 | B2 | 2/2023 | Shelton, IV |
| 11,576,677 | B2 | 2/2023 | Shelton, IV et al. |
| 11,583,274 | B2 | 2/2023 | Widenhouse et al. |
| 11,583,277 | B2 | 2/2023 | Shelton, IV et al. |
| 11,583,278 | B2 | 2/2023 | Shelton, IV et al. |
| 11,583,279 | B2 | 2/2023 | Smith et al. |
| 11,589,865 | B2 | 2/2023 | Shelton, IV et al. |
| 11,589,888 | B2 | 2/2023 | Shelton, IV et al. |
| D980,425 | S | 3/2023 | Baxter, III |
| 11,596,406 | B2 | 3/2023 | Huitema et al. |
| 11,602,340 | B2 | 3/2023 | Schmid et al. |
| 11,602,346 | B2 | 3/2023 | Shelton, IV |
| 11,602,366 | B2 | 3/2023 | Shelton, IV et al. |
| 11,607,219 | B2 | 3/2023 | Shelton, IV et al. |
| 11,607,239 | B2 | 3/2023 | Swensgard et al. |
| 11,607,278 | B2 | 3/2023 | Shelton, IV et al. |
| 11,612,393 | B2 | 3/2023 | Morgan et al. |
| 11,612,394 | B2 | 3/2023 | Morgan et al. |
| 11,612,395 | B2 | 3/2023 | Yates et al. |
| 11,617,575 | B2 | 4/2023 | Yates et al. |
| 11,617,576 | B2 | 4/2023 | Yates et al. |
| 11,617,577 | B2 | 4/2023 | Huang |
| 11,622,763 | B2 | 4/2023 | Parihar et al. |
| 11,622,766 | B2 | 4/2023 | Shelton, IV |
| 11,622,785 | B2 | 4/2023 | Hess et al. |
| 11,627,959 | B2 | 4/2023 | Shelton, IV et al. |
| 11,627,960 | B2 | 4/2023 | Shelton, IV et al. |
| 11,628,006 | B2 | 4/2023 | Henderson et al. |
| 11,633,183 | B2 | 4/2023 | Parihar et al. |
| 11,638,581 | B2 | 5/2023 | Parihar et al. |
| 11,638,582 | B2 | 5/2023 | Bakos et al. |
| 11,638,583 | B2 | 5/2023 | Yates et al. |
| 11,638,587 | B2 | 5/2023 | Shelton, IV et al. |
| 11,642,125 | B2 | 5/2023 | Harris et al. |
| 11,642,128 | B2 | 5/2023 | Shelton, IV et al. |
| 11,648,005 | B2 | 5/2023 | Yates et al. |
| 11,648,006 | B2 | 5/2023 | Timm et al. |
| 11,648,008 | B2 | 5/2023 | Shelton, IV et al. |
| 11,648,009 | B2 | 5/2023 | Jenkins |
| 11,648,022 | B2 | 5/2023 | Shelton, IV |
| 11,648,024 | B2 | 5/2023 | Shelton, IV et al. |
| 11,653,914 | B2 | 5/2023 | Shelton, IV et al. |
| 11,653,915 | B2 | 5/2023 | Shelton, IV et al. |
| 11,653,917 | B2 | 5/2023 | Scott et al. |
| 11,653,918 | B2 | 5/2023 | Swayze et al. |
| 11,653,920 | B2 | 5/2023 | Shelton, IV et al. |
| 11,659,023 | B2 | 5/2023 | Shelton, IV et al. |
| 11,660,090 | B2 | 5/2023 | Bakos et al. |
| 11,660,110 | B2 | 5/2023 | Shelton, IV et al. |
| 11,660,163 | B2 | 5/2023 | Shelton, IV et al. |
| 11,666,332 | B2 | 6/2023 | Giordano et al. |
| 11,672,531 | B2 | 6/2023 | Timm et al. |
| 11,672,532 | B2 | 6/2023 | Shelton, IV et al. |
| 11,672,536 | B2 | 6/2023 | Shelton, IV et al. |
| 11,672,605 | B2 | 6/2023 | Messerly et al. |
| 11,678,877 | B2 | 6/2023 | Shelton, IV et al. |
| 11,678,880 | B2 | 6/2023 | Shelton, IV et al. |
| 11,678,881 | B2 | 6/2023 | Yates et al. |
| 11,678,882 | B2 | 6/2023 | Shelton, IV et al. |
| 11,684,360 | B2 | 6/2023 | Shelton, IV et al. |
| 11,684,361 | B2 | 6/2023 | Yates et al. |
| 11,684,365 | B2 | 6/2023 | Shelton, IV et al. |
| 11,684,369 | B2 | 6/2023 | Shelton, IV et al. |
| 11,684,434 | B2 | 6/2023 | Shelton, IV |
| 11,690,615 | B2 | 7/2023 | Parihar et al. |
| 11,690,623 | B2 | 7/2023 | Shelton, IV et al. |
| 11,696,757 | B2 | 7/2023 | Shelton, IV et al. |
| 11,696,759 | B2 | 7/2023 | Shelton, IV et al. |
| 11,696,761 | B2 | 7/2023 | Shelton, IV |
| 11,696,778 | B2 | 7/2023 | Shelton, IV et al. |
| 11,701,110 | B2 | 7/2023 | Yates et al. |

(56) References Cited

U.S. PATENT DOCUMENTS 11,701,111 B2 7/2023 Shelton, IV et al.
11,701,113 B2 7/2023 Shelton, IV et al.
11,701,114 B2 7/2023 Shelton, IV et al.
2001/0000531 A1 4/2001 Casscells et al.
2001/0025183 A1 9/2001 Shahidi
2001/0025184 A1 9/2001 Messerly
2001/0030219 A1 10/2001 Green et al.
2001/0031950 A1 10/2001 Ryan
2001/0034530 A1 10/2001 Malackowski et al.
2001/0039419 A1 11/2001 Francischelli et al.
2001/0045442 A1 11/2001 Whitman
2002/0002377 A1 1/2002 Cimino
2002/0014510 A1 2/2002 Richter et al.
2002/0019649 A1 2/2002 Sikora et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0045905 A1 4/2002 Gerbi et al.
2002/0049551 A1 4/2002 Friedman et al.
2002/0054158 A1 5/2002 Asami
2002/0065535 A1 5/2002 Kneifel et al.
2002/0066764 A1 6/2002 Perry et al.
2002/0077550 A1 6/2002 Rabiner et al.
2002/0077660 A1 6/2002 Kayan et al.
2002/0082612 A1 6/2002 Moll et al.
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0099374 A1 7/2002 Pendekanti et al.
2002/0103494 A1 8/2002 Pacey
2002/0107517 A1 8/2002 Witt et al.
2002/0111621 A1 8/2002 Wallace et al.
2002/0111624 A1 8/2002 Witt et al.
2002/0116063 A1 8/2002 Giannetti et al.
2002/0117533 A1 8/2002 Milliman et al.
2002/0117534 A1 8/2002 Green et al.
2002/0127265 A1 9/2002 Bowman et al.
2002/0128633 A1 9/2002 Brock et al.
2002/0133149 A1 9/2002 Bessette
2002/0133236 A1 9/2002 Rousseau
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0156493 A1 10/2002 Houser et al.
2002/0156497 A1 10/2002 Nagase et al.
2002/0158593 A1 10/2002 Henderson et al.
2002/0161277 A1 10/2002 Boone et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0004610 A1 1/2003 Niemeyer et al.
2003/0009193 A1 1/2003 Corsaro
2003/0011245 A1 1/2003 Fiebig
2003/0012805 A1 1/2003 Chen et al.
2003/0014053 A1 1/2003 Nguyen et al.
2003/0018323 A1 1/2003 Wallace et al.
2003/0028236 A1 2/2003 Gillick et al.
2003/0040670 A1 2/2003 Govari
2003/0045835 A1 3/2003 Anderson et al.
2003/0047230 A1 3/2003 Kim
2003/0047582 A1 3/2003 Sonnenschein et al.
2003/0050628 A1 3/2003 Whitman et al.
2003/0050654 A1 3/2003 Whitman et al.
2003/0055443 A1 3/2003 Spotnitz
2003/0066858 A1 4/2003 Holgersson
2003/0066938 A1 4/2003 Zimmerman
2003/0078647 A1 4/2003 Vallana et al.
2003/0083648 A1 5/2003 Wang et al.
2003/0084983 A1 5/2003 Rangachari et al.
2003/0093103 A1 5/2003 Malackowski et al.
2003/0093160 A1 5/2003 Maksimovic et al.
2003/0094356 A1 5/2003 Waldron
2003/0096158 A1 5/2003 Takano et al.
2003/0105475 A1 6/2003 Sancoff et al.
2003/0109875 A1 6/2003 Tetzlaff et al.
2003/0114731 A1 6/2003 Cadeddu et al.
2003/0114851 A1 6/2003 Truckai et al.
2003/0121586 A1 7/2003 Mitra et al.
2003/0130693 A1 7/2003 Levin et al.
2003/0135204 A1 7/2003 Lee et al.
2003/0135388 A1 7/2003 Martucci et al.
2003/0139741 A1 7/2003 Goble et al.
2003/0144660 A1 7/2003 Mollenauer
2003/0149406 A1 8/2003 Martineau et al.
2003/0153908 A1 8/2003 Goble et al.
2003/0153968 A1 8/2003 Geis et al.
2003/0158463 A1 8/2003 Julian et al.
2003/0158548 A1 8/2003 Phan et al.
2003/0163029 A1 8/2003 Sonnenschein et al.
2003/0163085 A1 8/2003 Tanner et al.
2003/0164172 A1 9/2003 Chumas et al.
2003/0171747 A1 9/2003 Kanehira et al.
2003/0181800 A1 9/2003 Bonutti
2003/0181900 A1 9/2003 Long
2003/0181910 A1 9/2003 Dycus et al.
2003/0190584 A1 10/2003 Heasley
2003/0195387 A1 10/2003 Kortenbach et al.
2003/0204199 A1 10/2003 Novak et al.
2003/0205029 A1 11/2003 Chapolini et al.
2003/0212005 A1 11/2003 Petito et al.
2003/0212332 A1 11/2003 Fenton et al.
2003/0216619 A1 11/2003 Scirica et al.
2003/0216732 A1 11/2003 Truckai et al.
2003/0220541 A1 11/2003 Salisbury et al.
2003/0229344 A1 12/2003 Dycus et al.
2003/0236505 A1 12/2003 Bonadio et al.
2004/0006335 A1 1/2004 Garrison
2004/0006340 A1 1/2004 Latterell et al.
2004/0007608 A1 1/2004 Ehrenfels et al.
2004/0024457 A1 2/2004 Boyce et al.
2004/0028502 A1 2/2004 Cummins
2004/0030254 A1 2/2004 Babaev
2004/0030333 A1 2/2004 Goble
2004/0034287 A1 2/2004 Hickle
2004/0034357 A1 2/2004 Beane et al.
2004/0044295 A1 3/2004 Reinert et al.
2004/0044364 A1 3/2004 DeVries et al.
2004/0047485 A1 3/2004 Sherrit et al.
2004/0049121 A1 3/2004 Yaron
2004/0049172 A1 3/2004 Root et al.
2004/0054364 A1 3/2004 Aranyi et al.
2004/0059362 A1 3/2004 Knodel et al.
2004/0068161 A1 4/2004 Couvillon
2004/0068224 A1 4/2004 Couvillon et al.
2004/0068307 A1 4/2004 Goble
2004/0070369 A1 4/2004 Sakakibara
2004/0073222 A1 4/2004 Koseki
2004/0078037 A1 4/2004 Batchelor et al.
2004/0082952 A1 4/2004 Dycus et al.
2004/0085180 A1 5/2004 Juang
2004/0092921 A1 5/2004 Kadziauskas et al.
2004/0092967 A1 5/2004 Sancoff et al.
2004/0092992 A1 5/2004 Adams et al.
2004/0093020 A1 5/2004 Sinton
2004/0093024 A1 5/2004 Lousararian et al.
2004/0093039 A1 5/2004 Schumert
2004/0097919 A1 5/2004 Wellman et al.
2004/0097996 A1 5/2004 Rabiner et al.
2004/0098040 A1 5/2004 Taniguchi et al.
2004/0101822 A1 5/2004 Wiesner et al.
2004/0102783 A1 5/2004 Sutterlin et al.
2004/0102804 A1 5/2004 Chin
2004/0108357 A1 6/2004 Milliman et al.
2004/0110439 A1 6/2004 Chaikof et al.
2004/0115022 A1 6/2004 Albertson et al.
2004/0116952 A1 6/2004 Sakurai et al.

(56) References Cited

U.S. PATENT DOCUMENTS

2004/0119185 A1 6/2004 Chen
2004/0122419 A1 6/2004 Neuberger
2004/0122423 A1 6/2004 Dycus et al.
2004/0133089 A1 7/2004 Kilcoyne et al.
2004/0133095 A1 7/2004 Dunki-Jacobs et al.
2004/0133189 A1 7/2004 Sakurai
2004/0138621 A1 7/2004 Jahns et al.
2004/0143297 A1 7/2004 Ramsey
2004/0147909 A1 7/2004 Johnston et al.
2004/0153100 A1 8/2004 Ahlberg et al.
2004/0158261 A1 8/2004 Vu
2004/0164123 A1 8/2004 Racenet et al.
2004/0166169 A1 8/2004 Malaviya et al.
2004/0167508 A1 8/2004 Wham et al.
2004/0167572 A1 8/2004 Roth et al.
2004/0181219 A1 9/2004 Goble et al.
2004/0193150 A1 9/2004 Sharkey et al.
2004/0193189 A1 9/2004 Kortenbach et al.
2004/0197367 A1 10/2004 Rezania et al.
2004/0199181 A1 10/2004 Knodel et al.
2004/0199193 A1 10/2004 Hayashi et al.
2004/0204735 A1 10/2004 Shiroff et al.
2004/0218451 A1 11/2004 Said et al.
2004/0222268 A1 11/2004 Bilotti et al.
2004/0225186 A1 11/2004 Horne et al.
2004/0231870 A1 11/2004 McCormick et al.
2004/0232194 A1 11/2004 Pedicini et al.
2004/0232197 A1 11/2004 Shelton, IV et al.
2004/0232201 A1 11/2004 Wenchell et al.
2004/0236352 A1 11/2004 Wang et al.
2004/0239582 A1 12/2004 Seymour
2004/0243147 A1 12/2004 Lipow
2004/0243151 A1 12/2004 Demmy et al.
2004/0243163 A1 12/2004 Casiano et al.
2004/0247415 A1 12/2004 Mangone
2004/0249366 A1 12/2004 Kunz
2004/0249367 A1 12/2004 Saadat et al.
2004/0249374 A1 12/2004 Tetzlaff et al.
2004/0254455 A1 12/2004 Iddan
2004/0254566 A1 12/2004 Plicchi et al.
2004/0254590 A1 12/2004 Hoffman et al.
2004/0254680 A1 12/2004 Sunaoshi
2004/0260273 A1 12/2004 Wan
2004/0260300 A1 12/2004 Gorensek et al.
2004/0260315 A1 12/2004 Dell et al.
2004/0267310 A1 12/2004 Racenet et al.
2005/0010158 A1 1/2005 Brugger et al.
2005/0010213 A1 1/2005 Stad et al.
2005/0015125 A1 1/2005 Mioduski et al.
2005/0021078 A1 1/2005 Vleugels et al.
2005/0023325 A1 2/2005 Gresham et al.
2005/0032511 A1 2/2005 Malone et al.
2005/0033278 A1 2/2005 McClurken et al.
2005/0033337 A1 2/2005 Muir et al.
2005/0033352 A1 2/2005 Zepf et al.
2005/0044489 A1 2/2005 Yamagami et al.
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0067548 A1 3/2005 Inoue
2005/0070925 A1 3/2005 Shelton et al.
2005/0070929 A1 3/2005 Dalessandro et al.
2005/0072827 A1* 4/2005 Mollenauer .......... A61B 18/085
227/180.1
2005/0074593 A1 4/2005 Day et al.
2005/0075561 A1 4/2005 Golden
2005/0079088 A1 4/2005 Wirth et al.
2005/0080342 A1 4/2005 Gilreath et al.
2005/0085693 A1 4/2005 Belson et al.
2005/0085838 A1 4/2005 Thompson et al.
2005/0090709 A1 4/2005 Okada et al.
2005/0090817 A1 4/2005 Phan
2005/0096502 A1 5/2005 Khalili
2005/0096683 A1 5/2005 Ellins et al.
2005/0116673 A1 6/2005 Carl et al.
2005/0119524 A1 6/2005 Sekine et al.
2005/0119640 A1 6/2005 Sverduk et al.
2005/0120836 A1 6/2005 Anderson
2005/0124855 A1 6/2005 Jaffe et al.
2005/0125028 A1 6/2005 Looper et al.
2005/0125897 A1 6/2005 Wyslucha et al.
2005/0129730 A1 6/2005 Pang et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131457 A1 6/2005 Douglas et al.
2005/0137454 A1 6/2005 Saadat et al.
2005/0137455 A1 6/2005 Ewers et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145672 A1 7/2005 Schwemberger et al.
2005/0149108 A1 7/2005 Cox
2005/0150928 A1 7/2005 Kameyama et al.
2005/0154258 A1 7/2005 Tartaglia et al.
2005/0154406 A1 7/2005 Bombard et al.
2005/0159778 A1 7/2005 Heinrich et al.
2005/0165419 A1 7/2005 Sauer et al.
2005/0165429 A1 7/2005 Douglas et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177184 A1 8/2005 Easley
2005/0177249 A1 8/2005 Kladakis et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0191936 A1 9/2005 Marine et al.
2005/0192610 A1 9/2005 Houser et al.
2005/0197859 A1 9/2005 Wilson et al.
2005/0203550 A1 9/2005 Laufer et al.
2005/0209614 A1 9/2005 Fenter et al.
2005/0215858 A1 9/2005 Vail
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0251110 A1 11/2005 Nixon
2005/0256405 A1 11/2005 Makin et al.
2005/0256452 A1 11/2005 DeMarchi et al.
2005/0256546 A1 11/2005 Vaisnys et al.
2005/0258963 A1 11/2005 Rodriguez et al.
2005/0261588 A1 11/2005 Makin et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0272972 A1 12/2005 Iddan
2005/0273139 A1 12/2005 Krauss et al.
2005/0274034 A1 12/2005 Hayashida et al.
2005/0283188 A1 12/2005 Loshakove et al.
2005/0283226 A1 12/2005 Haverkost
2005/0288555 A1 12/2005 Binmoeller
2005/0288659 A1 12/2005 Kimura et al.
2006/0000867 A1 1/2006 Shelton et al.

(56) References Cited

U.S. PATENT DOCUMENTS

2006/0008787 A1 1/2006 Hayman et al.
2006/0011698 A1 1/2006 Okada et al.
2006/0015009 A1 1/2006 Jaffe et al.
2006/0019056 A1 1/2006 Turner et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0030797 A1 2/2006 Zhou et al.
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0053951 A1 3/2006 Revelis et al.
2006/0058825 A1 3/2006 Ogura et al.
2006/0063130 A1 3/2006 Hayman et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0159731 A1 7/2006 Shoshan
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0189440 A1 8/2006 Gravagne
2006/0190034 A1 8/2006 Nishizawa et al.
2006/0199999 A1 9/2006 Ikeda et al.
2006/0201989 A1 9/2006 Ojeda
2006/0206100 A1 9/2006 Eskridge et al.
2006/0211943 A1 9/2006 Beaupre
2006/0217729 A1 9/2006 Eskridge et al.
2006/0226196 A1 10/2006 Hueil et al.
2006/0226957 A1 10/2006 Miller et al.
2006/0235368 A1 10/2006 Oz
2006/0241666 A1 10/2006 Briggs et al.
2006/0241691 A1 10/2006 Wilk
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0253050 A1 11/2006 Yoshimine et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0270916 A1 11/2006 Skwarek et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2006/0293656 A1 12/2006 Shadduck et al.
2007/0005045 A1 1/2007 Mintz et al.
2007/0008744 A1 1/2007 Heo et al.
2007/0009570 A1 1/2007 Kim et al.
2007/0010702 A1 1/2007 Wang et al.
2007/0010709 A1 1/2007 Reinschke
2007/0010838 A1 1/2007 Shelton et al.
2007/0016235 A1 1/2007 Tanaka et al.
2007/0016236 A1 1/2007 Beaupre
2007/0016272 A1 1/2007 Thompson et al.
2007/0018958 A1 1/2007 Tavakoli et al.
2007/0020065 A1 1/2007 Kirby
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0032701 A1 2/2007 Fowler et al.
2007/0032704 A1 2/2007 Gandini et al.
2007/0032785 A1 2/2007 Diederich et al.
2007/0034669 A1 2/2007 de la Torre et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0051766 A1 3/2007 Spencer
2007/0055228 A1 3/2007 Berg et al.
2007/0055305 A1 3/2007 Schnyder et al.
2007/0063618 A1 3/2007 Bromfield
2007/0069851 A1 3/2007 Sung et al.
2007/0073185 A1 3/2007 Nakao
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0123748 A1 5/2007 Meglan
2007/0130771 A1 6/2007 Ehlert et al.
2007/0134251 A1 6/2007 Ashkenazi et al.
2007/0135686 A1 6/2007 Pruitt et al.
2007/0135803 A1 6/2007 Belson
2007/0149881 A1 6/2007 Rabin
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173803 A1 7/2007 Wham et al.
2007/0173811 A1* 7/2007 Couture ............ A61B 18/1445
606/45
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0182842 A1 8/2007 Sonnenschein et al.
2007/0185474 A1 8/2007 Nahen
2007/0185545 A1 8/2007 Duke
2007/0187857 A1 8/2007 Riley et al.
2007/0190110 A1 8/2007 Pameijer et al.

(56) References Cited

U.S. PATENT DOCUMENTS

| | | | |
|---|---|---|---|
| 2007/0191713 | A1 | 8/2007 | Eichmann et al. |
| 2007/0191868 | A1 | 8/2007 | Theroux et al. |
| 2007/0191915 | A1 | 8/2007 | Strother et al. |
| 2007/0194079 | A1 | 8/2007 | Hueil et al. |
| 2007/0194081 | A1 | 8/2007 | Hueil et al. |
| 2007/0194082 | A1 | 8/2007 | Morgan et al. |
| 2007/0197954 | A1 | 8/2007 | Keenan |
| 2007/0198039 | A1 | 8/2007 | Jones et al. |
| 2007/0203483 | A1 | 8/2007 | Kim et al. |
| 2007/0203510 | A1 | 8/2007 | Bettuchi |
| 2007/0207010 | A1 | 9/2007 | Caspi |
| 2007/0208340 | A1 | 9/2007 | Ganz et al. |
| 2007/0208359 | A1 | 9/2007 | Hoffman |
| 2007/0208375 | A1 | 9/2007 | Nishizawa et al. |
| 2007/0213750 | A1 | 9/2007 | Weadock |
| 2007/0219481 | A1 | 9/2007 | Babaev |
| 2007/0221701 | A1 | 9/2007 | Ortiz et al. |
| 2007/0225562 | A1 | 9/2007 | Spivey et al. |
| 2007/0232926 | A1 | 10/2007 | Stulen et al. |
| 2007/0232928 | A1 | 10/2007 | Wiener et al. |
| 2007/0233163 | A1 | 10/2007 | Bombard et al. |
| 2007/0236213 | A1 | 10/2007 | Paden et al. |
| 2007/0243227 | A1 | 10/2007 | Gertner |
| 2007/0244471 | A1 | 10/2007 | Malackowski |
| 2007/0244496 | A1 | 10/2007 | Hellenkamp |
| 2007/0246505 | A1 | 10/2007 | Pace-Floridia et al. |
| 2007/0249941 | A1 | 10/2007 | Salehi et al. |
| 2007/0250093 | A1 | 10/2007 | Makower et al. |
| 2007/0260132 | A1 | 11/2007 | Sterling |
| 2007/0260242 | A1 | 11/2007 | Dycus et al. |
| 2007/0262592 | A1 | 11/2007 | Hwang et al. |
| 2007/0265560 | A1 | 11/2007 | Soltani et al. |
| 2007/0265613 | A1 | 11/2007 | Edelstein et al. |
| 2007/0265616 | A1 | 11/2007 | Couture et al. |
| 2007/0270651 | A1 | 11/2007 | Gilad et al. |
| 2007/0270660 | A1 | 11/2007 | Caylor et al. |
| 2007/0270790 | A1 | 11/2007 | Smith et al. |
| 2007/0275035 | A1 | 11/2007 | Herman et al. |
| 2007/0275348 | A1 | 11/2007 | Lemon |
| 2007/0276409 | A1 | 11/2007 | Ortiz et al. |
| 2007/0276424 | A1 | 11/2007 | Mikkaichi et al. |
| 2007/0279011 | A1 | 12/2007 | Jones et al. |
| 2007/0286892 | A1 | 12/2007 | Herzberg et al. |
| 2007/0287933 | A1 | 12/2007 | Phan et al. |
| 2007/0290027 | A1 | 12/2007 | Maatta et al. |
| 2007/0296286 | A1 | 12/2007 | Avenell |
| 2008/0000941 | A1 | 1/2008 | Sonnenschein et al. |
| 2008/0003196 | A1 | 1/2008 | Jonn et al. |
| 2008/0007237 | A1 | 1/2008 | Nagashima et al. |
| 2008/0015413 | A1 | 1/2008 | Barlow et al. |
| 2008/0015575 | A1 | 1/2008 | Odom et al. |
| 2008/0015598 | A1 | 1/2008 | Prommersberger |
| 2008/0021486 | A1 | 1/2008 | Oyola et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0030170 | A1 | 2/2008 | Dacquay et al. |
| 2008/0039746 | A1 | 2/2008 | Hissong et al. |
| 2008/0042861 | A1 | 2/2008 | Dacquay et al. |
| 2008/0046000 | A1 | 2/2008 | Lee et al. |
| 2008/0051833 | A1 | 2/2008 | Gramuglia et al. |
| 2008/0058775 | A1 | 3/2008 | Darian et al. |
| 2008/0058845 | A1 | 3/2008 | Shimizu et al. |
| 2008/0064920 | A1 | 3/2008 | Bakos et al. |
| 2008/0064921 | A1 | 3/2008 | Larkin et al. |
| 2008/0065153 | A1 | 3/2008 | Allard et al. |
| 2008/0069736 | A1 | 3/2008 | Mingerink et al. |
| 2008/0071269 | A1 | 3/2008 | Hilario et al. |
| 2008/0071328 | A1 | 3/2008 | Haubrich et al. |
| 2008/0077158 | A1 | 3/2008 | Haider et al. |
| 2008/0078802 | A1 | 4/2008 | Hess et al. |
| 2008/0081948 | A1 | 4/2008 | Weisenburgh et al. |
| 2008/0082039 | A1 | 4/2008 | Babaev |
| 2008/0082098 | A1 | 4/2008 | Tanaka et al. |
| 2008/0082114 | A1 | 4/2008 | McKenna et al. |
| 2008/0082125 | A1 | 4/2008 | Murray et al. |
| 2008/0082126 | A1 | 4/2008 | Murray et al. |
| 2008/0083807 | A1 | 4/2008 | Beardsley et al. |
| 2008/0083811 | A1 | 4/2008 | Marczyk |
| 2008/0085296 | A1 | 4/2008 | Powell et al. |
| 2008/0086078 | A1 | 4/2008 | Powell et al. |
| 2008/0091072 | A1 | 4/2008 | Omori et al. |
| 2008/0094228 | A1 | 4/2008 | Welch et al. |
| 2008/0103495 | A1 | 5/2008 | Mihori et al. |
| 2008/0108443 | A1 | 5/2008 | Jinno et al. |
| 2008/0114250 | A1 | 5/2008 | Urbano et al. |
| 2008/0114355 | A1 | 5/2008 | Whayne et al. |
| 2008/0125634 | A1 | 5/2008 | Ryan et al. |
| 2008/0125749 | A1 | 5/2008 | Olson |
| 2008/0126984 | A1 | 5/2008 | Fleishman et al. |
| 2008/0128469 | A1 | 6/2008 | Dalessandro et al. |
| 2008/0129253 | A1 | 6/2008 | Shiue et al. |
| 2008/0135600 | A1 | 6/2008 | Hiranuma et al. |
| 2008/0140088 | A1 | 6/2008 | Orban, III |
| 2008/0140115 | A1 | 6/2008 | Stopek |
| 2008/0140159 | A1 | 6/2008 | Bornhoft et al. |
| 2008/0147058 | A1 | 6/2008 | Horrell et al. |
| 2008/0147062 | A1 | 6/2008 | Truckai et al. |
| 2008/0149682 | A1 | 6/2008 | Uhm |
| 2008/0154299 | A1 | 6/2008 | Livneh |
| 2008/0154335 | A1 | 6/2008 | Thrope et al. |
| 2008/0169328 | A1 | 7/2008 | Shelton |
| 2008/0169332 | A1 | 7/2008 | Shelton et al. |
| 2008/0169333 | A1 | 7/2008 | Shelton et al. |
| 2008/0171938 | A1 | 7/2008 | Masuda et al. |
| 2008/0172087 | A1 | 7/2008 | Fuchs et al. |
| 2008/0177268 | A1 | 7/2008 | Daum et al. |
| 2008/0177392 | A1 | 7/2008 | Williams et al. |
| 2008/0188755 | A1 | 8/2008 | Hart |
| 2008/0190989 | A1 | 8/2008 | Crews et al. |
| 2008/0196253 | A1 | 8/2008 | Ezra et al. |
| 2008/0196419 | A1 | 8/2008 | Dube |
| 2008/0197167 | A1 | 8/2008 | Viola et al. |
| 2008/0200755 | A1 | 8/2008 | Bakos |
| 2008/0200762 | A1 | 8/2008 | Stokes et al. |
| 2008/0200835 | A1 | 8/2008 | Monson et al. |
| 2008/0200911 | A1 | 8/2008 | Long |
| 2008/0200933 | A1 | 8/2008 | Bakos et al. |
| 2008/0200934 | A1 | 8/2008 | Fox |
| 2008/0200940 | A1 | 8/2008 | Eichmann et al. |
| 2008/0206186 | A1 | 8/2008 | Butler et al. |
| 2008/0208058 | A1 | 8/2008 | Sabata et al. |
| 2008/0208231 | A1 | 8/2008 | Ota et al. |
| 2008/0214967 | A1 | 9/2008 | Aranyi et al. |
| 2008/0216704 | A1 | 9/2008 | Eisenbeis et al. |
| 2008/0217376 | A1 | 9/2008 | Clauson et al. |
| 2008/0228179 | A1 | 9/2008 | Eder et al. |
| 2008/0234709 | A1 | 9/2008 | Houser |
| 2008/0234866 | A1 | 9/2008 | Kishi et al. |
| 2008/0242939 | A1 | 10/2008 | Johnston |
| 2008/0243088 | A1 | 10/2008 | Evans |
| 2008/0243143 | A1 | 10/2008 | Kuhns et al. |
| 2008/0249536 | A1 | 10/2008 | Stahler et al. |
| 2008/0249608 | A1 | 10/2008 | Dave |
| 2008/0255413 | A1 | 10/2008 | Zemlok et al. |
| 2008/0255420 | A1 | 10/2008 | Lee et al. |
| 2008/0255421 | A1 | 10/2008 | Hegeman et al. |
| 2008/0255663 | A1 | 10/2008 | Akpek et al. |
| 2008/0262654 | A1 | 10/2008 | Omori et al. |
| 2008/0269596 | A1 | 10/2008 | Revie et al. |
| 2008/0281171 | A1 | 11/2008 | Fennell et al. |
| 2008/0281200 | A1 | 11/2008 | Voic et al. |
| 2008/0281315 | A1 | 11/2008 | Gines |
| 2008/0281332 | A1 | 11/2008 | Taylor |
| 2008/0287944 | A1 | 11/2008 | Pearson et al. |
| 2008/0287948 | A1 | 11/2008 | Newton et al. |
| 2008/0293910 | A1 | 11/2008 | Kapiamba et al. |
| 2008/0294179 | A1 | 11/2008 | Balbierz et al. |
| 2008/0296346 | A1 | 12/2008 | Shelton, IV et al. |
| 2008/0296347 | A1 | 12/2008 | Shelton, IV et al. |
| 2008/0297287 | A1 | 12/2008 | Shachar et al. |
| 2008/0298784 | A1 | 12/2008 | Kastner |
| 2008/0300588 | A1 | 12/2008 | Groth et al. |

(56) References Cited

U.S. PATENT DOCUMENTS

| | | | |
|---|---|---|---|
| 2008/0308504 | A1 | 12/2008 | Hallan et al. |
| 2008/0308602 | A1 | 12/2008 | Timm et al. |
| 2008/0308603 | A1 | 12/2008 | Shelton et al. |
| 2008/0308607 | A1 | 12/2008 | Timm et al. |
| 2008/0308807 | A1 | 12/2008 | Yamazaki et al. |
| 2008/0312502 | A1 | 12/2008 | Swain et al. |
| 2008/0312686 | A1 | 12/2008 | Ellingwood |
| 2008/0312687 | A1 | 12/2008 | Blier |
| 2008/0315829 | A1 | 12/2008 | Jones et al. |
| 2009/0001121 | A1 | 1/2009 | Hess et al. |
| 2009/0001130 | A1 | 1/2009 | Hess et al. |
| 2009/0004455 | A1 | 1/2009 | Gravagna et al. |
| 2009/0005809 | A1 | 1/2009 | Hess et al. |
| 2009/0007014 | A1 | 1/2009 | Coomer et al. |
| 2009/0012516 | A1 | 1/2009 | Curtis et al. |
| 2009/0012534 | A1 | 1/2009 | Madhani et al. |
| 2009/0015195 | A1 | 1/2009 | Loth-Krausser |
| 2009/0020958 | A1 | 1/2009 | Soul |
| 2009/0030437 | A1 | 1/2009 | Houser et al. |
| 2009/0043253 | A1 | 2/2009 | Podaima |
| 2009/0048583 | A1 | 2/2009 | Williams et al. |
| 2009/0048589 | A1 | 2/2009 | Takashino et al. |
| 2009/0053288 | A1 | 2/2009 | Eskridge, Jr. et al. |
| 2009/0057369 | A1 | 3/2009 | Smith et al. |
| 2009/0069806 | A1 | 3/2009 | De La Mora Levy et al. |
| 2009/0076506 | A1 | 3/2009 | Baker |
| 2009/0076510 | A1 | 3/2009 | Bell et al. |
| 2009/0078736 | A1 | 3/2009 | Van Lue |
| 2009/0081313 | A1 | 3/2009 | Aghion et al. |
| 2009/0082716 | A1 | 3/2009 | Akahoshi |
| 2009/0082766 | A1 | 3/2009 | Unger et al. |
| 2009/0088659 | A1 | 4/2009 | Graham et al. |
| 2009/0090763 | A1 | 4/2009 | Zemlok et al. |
| 2009/0099579 | A1 | 4/2009 | Nentwick et al. |
| 2009/0099876 | A1 | 4/2009 | Whitman |
| 2009/0110533 | A1 | 4/2009 | Jinno |
| 2009/0112234 | A1 | 4/2009 | Crainich et al. |
| 2009/0114701 | A1 | 5/2009 | Zemlok et al. |
| 2009/0118762 | A1 | 5/2009 | Crainch et al. |
| 2009/0119011 | A1 | 5/2009 | Kondo et al. |
| 2009/0120994 | A1 | 5/2009 | Murray et al. |
| 2009/0131819 | A1 | 5/2009 | Ritchie et al. |
| 2009/0132400 | A1 | 5/2009 | Conway |
| 2009/0135280 | A1 | 5/2009 | Johnston et al. |
| 2009/0138003 | A1 | 5/2009 | Deville et al. |
| 2009/0143678 | A1 | 6/2009 | Keast et al. |
| 2009/0143797 | A1 | 6/2009 | Smith et al. |
| 2009/0143855 | A1 | 6/2009 | Weber et al. |
| 2009/0149871 | A9 | 6/2009 | Kagan et al. |
| 2009/0167548 | A1 | 7/2009 | Sugahara |
| 2009/0171147 | A1 | 7/2009 | Lee et al. |
| 2009/0177218 | A1 | 7/2009 | Young et al. |
| 2009/0177226 | A1 | 7/2009 | Reinprecht et al. |
| 2009/0181290 | A1 | 7/2009 | Baldwin et al. |
| 2009/0182322 | A1 | 7/2009 | D'Amelio et al. |
| 2009/0182331 | A1 | 7/2009 | D'Amelio et al. |
| 2009/0182332 | A1 | 7/2009 | Long et al. |
| 2009/0188964 | A1 | 7/2009 | Orlov |
| 2009/0192534 | A1 | 7/2009 | Ortiz et al. |
| 2009/0196903 | A1 | 8/2009 | Kliman |
| 2009/0198272 | A1 | 8/2009 | Kerver et al. |
| 2009/0204108 | A1 | 8/2009 | Steffen |
| 2009/0204109 | A1 | 8/2009 | Grove et al. |
| 2009/0204126 | A1 | 8/2009 | Le |
| 2009/0204925 | A1 | 8/2009 | Bhat et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh, II et al. |
| 2009/0206133 | A1 | 8/2009 | Morgan et al. |
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0221993 | A1 | 9/2009 | Sohi et al. |
| 2009/0227834 | A1 | 9/2009 | Nakamoto et al. |
| 2009/0234273 | A1 | 9/2009 | Intoccia et al. |
| 2009/0236401 | A1 | 9/2009 | Cole et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248021 | A1 | 10/2009 | McKenna |
| 2009/0248100 | A1 | 10/2009 | Vaisnys et al. |
| 2009/0253959 | A1 | 10/2009 | Yoshie et al. |
| 2009/0254080 | A1 | 10/2009 | Honda |
| 2009/0255974 | A1 | 10/2009 | Viola |
| 2009/0261141 | A1 | 10/2009 | Stratton et al. |
| 2009/0262078 | A1 | 10/2009 | Pizzi |
| 2009/0264879 | A1 | 10/2009 | Mcclurken et al. |
| 2009/0264940 | A1 | 10/2009 | Beale et al. |
| 2009/0270771 | A1 | 10/2009 | Takahashi |
| 2009/0270853 | A1 | 10/2009 | Yachi et al. |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0287205 | A1 | 11/2009 | Ingle |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0318936 | A1 | 12/2009 | Harris et al. |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0022824 | A1 | 1/2010 | Cybulski et al. |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076433 | A1 | 3/2010 | Taylor et al. |
| 2010/0076483 | A1 | 3/2010 | Imuta |
| 2010/0076489 | A1 | 3/2010 | Stopek et al. |
| 2010/0081863 | A1 | 4/2010 | Hess et al. |
| 2010/0081864 | A1 | 4/2010 | Hess et al. |
| 2010/0081883 | A1 | 4/2010 | Murray et al. |
| 2010/0094312 | A1 | 4/2010 | Ruiz Morales et al. |
| 2010/0094323 | A1 | 4/2010 | Isaacs et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0106167 | A1 | 4/2010 | Boulnois et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0158307 | A1 | 6/2010 | Kubota et al. |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0187283 | A1 | 7/2010 | Crainich et al. |
| 2010/0187285 | A1 | 7/2010 | Harris et al. |
| 2010/0191255 | A1 | 7/2010 | Crainich et al. |

(56) References Cited

U.S. PATENT DOCUMENTS

2010/0191262 A1 7/2010 Harris et al.
2010/0191292 A1 7/2010 DeMeo et al.
2010/0193566 A1 8/2010 Scheib et al.
2010/0194541 A1 8/2010 Stevenson et al.
2010/0198159 A1 8/2010 Voss et al.
2010/0204717 A1 8/2010 Knodel
2010/0204721 A1 8/2010 Young et al.
2010/0204802 A1 8/2010 Wilson et al.
2010/0217281 A1 8/2010 Matsuoka et al.
2010/0218019 A1 8/2010 Eckhard
2010/0222752 A1 9/2010 Collins, Jr. et al.
2010/0222901 A1 9/2010 Swayze et al.
2010/0228250 A1 9/2010 Brogna
2010/0234687 A1 9/2010 Azarbarzin et al.
2010/0241115 A1 9/2010 Benamou et al.
2010/0241137 A1 9/2010 Doyle et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267525 A1 10/2010 Tanner
2010/0267662 A1 10/2010 Fielder et al.
2010/0274160 A1 10/2010 Yachi et al.
2010/0274278 A1 10/2010 Fleenor et al.
2010/0280368 A1 11/2010 Can et al.
2010/0291184 A1 11/2010 Clark et al.
2010/0292540 A1 11/2010 Hess et al.
2010/0298636 A1 11/2010 Castro et al.
2010/0298743 A1 11/2010 Nield et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0325568 A1 12/2010 Pedersen et al.
2010/0327041 A1 12/2010 Milliman et al.
2010/0331856 A1 12/2010 Carlson et al.
2011/0006101 A1 1/2011 Hall et al.
2011/0009694 A1 1/2011 Schultz et al.
2011/0009857 A1 1/2011 Subramaniam et al.
2011/0009863 A1 1/2011 Marczyk et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0028964 A1 2/2011 Edwards
2011/0028991 A1 2/2011 Ikeda et al.
2011/0029003 A1 2/2011 Lavigne et al.
2011/0029270 A1 2/2011 Mueglitz
2011/0036891 A1 2/2011 Zemlok et al.
2011/0046667 A1 2/2011 Culligan et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0066243 A1 3/2011 Rivin et al.
2011/0071473 A1 3/2011 Rogers et al.
2011/0082538 A1 4/2011 Dahlgren et al.
2011/0087224 A1 4/2011 Cadeddu et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0095067 A1 4/2011 Ohdaira
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0118601 A1 5/2011 Barnes et al.
2011/0118708 A1 5/2011 Burbank et al.
2011/0118754 A1 5/2011 Dachs, II et al.
2011/0125149 A1 5/2011 El-Galley et al.
2011/0125151 A1 5/2011 Strauss et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0189957 A1 8/2011 Hocke
2011/0192882 A1 8/2011 Hess et al.
2011/0198381 A1 8/2011 McCardle et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0257680 A1 10/2011 Reschke et al.
2011/0270245 A1 11/2011 Horner et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1* 11/2011 Knodel ............ A61B 17/07207 227/176.1
2011/0279268 A1 11/2011 Konishi et al.
2011/0284014 A1 11/2011 Cadeddu et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0306967 A1 12/2011 Payne et al.
2011/0313415 A1 12/2011 Fernandez et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0010615 A1 1/2012 Cummings et al.
2012/0016239 A1 1/2012 Barthe et al.
2012/0016413 A1 1/2012 Timm et al.
2012/0016467 A1 1/2012 Chen et al.
2012/0022519 A1 1/2012 Huang et al.
2012/0022526 A1 1/2012 Aldridge et al.
2012/0029272 A1 2/2012 Shelton, IV et al.
2012/0029550 A1 2/2012 Forsell
2012/0033360 A1 2/2012 Hsu
2012/0041358 A1 2/2012 Mann et al.
2012/0043100 A1 2/2012 Isobe et al.
2012/0059286 A1 3/2012 Hastings et al.
2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080334 A1 4/2012 Shelton, IV et al.
2012/0080336 A1 4/2012 Shelton, IV et al.
2012/0080344 A1 4/2012 Shelton, IV
2012/0080478 A1 4/2012 Morgan et al.
2012/0080491 A1 4/2012 Shelton, IV et al.
2012/0080498 A1 4/2012 Shelton, IV et al.
2012/0083836 A1 4/2012 Shelton, IV et al.
2012/0085358 A1 4/2012 Cadeddu et al.
2012/0086276 A1 4/2012 Sawyers
2012/0095458 A1 4/2012 Cybulski et al.
2012/0101488 A1 4/2012 Aldridge et al.
2012/0109186 A1 5/2012 Parrott et al.
2012/0116222 A1 5/2012 Sawada et al.

(56) References Cited

U.S. PATENT DOCUMENTS

2012/0116261 A1 5/2012 Mumaw et al.
2012/0116262 A1 5/2012 Houser et al.
2012/0116263 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0132663 A1 5/2012 Kasvikis et al.
2012/0143173 A1 6/2012 Steege et al.
2012/0143175 A1 6/2012 Hermann et al.
2012/0171539 A1 7/2012 Rejman et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0233298 A1 9/2012 Verbandt et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0265241 A1 10/2012 Hart et al.
2012/0271327 A1 10/2012 West et al.
2012/0283707 A1 11/2012 Giordano et al.
2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0296371 A1 11/2012 Kappus et al.
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0023915 A1 1/2013 Mueller
2013/0023925 A1 1/2013 Mueller
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0056522 A1 3/2013 Swensgard
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh et al.
2013/0087597 A1 4/2013 Shelton, IV et al.
2013/0090534 A1 4/2013 Burns et al.
2013/0096568 A1 4/2013 Justis
2013/0098968 A1 4/2013 Aranyi et al.
2013/0098970 A1 4/2013 Racenet et al.
2013/0106352 A1 5/2013 Nagamine
2013/0112729 A1 5/2013 Beardsley et al.
2013/0116669 A1 5/2013 Shelton, IV et al.
2013/0123776 A1 5/2013 Monson et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0158659 A1 6/2013 Bergs et al.
2013/0158660 A1 6/2013 Bergs et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman
2013/0172878 A1 7/2013 Smith
2013/0175315 A1 7/2013 Milliman
2013/0175317 A1 7/2013 Yates et al.
2013/0183769 A1 7/2013 Tajima
2013/0186936 A1 7/2013 Shelton, IV
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253256 A1 9/2013 Griffith et al.
2013/0253480 A1 9/2013 Kimball et al.
2013/0253499 A1 9/2013 Kimball et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0296843 A1 11/2013 Boudreaux et al.
2013/0303845 A1 11/2013 Skula et al.
2013/0304084 A1 11/2013 Beira et al.
2013/0306704 A1 11/2013 Balbierz et al.
2013/0310849 A1 11/2013 Malkowski
2013/0327552 A1 12/2013 Lovelass et al.
2013/0331826 A1 12/2013 Steege
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005705 A1 1/2014 Weir et al.
2014/0005718 A1 1/2014 Shelton, IV et al.
2014/0008289 A1 1/2014 Williams et al.
2014/0014544 A1 1/2014 Bugnard et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039493 A1 2/2014 Conley et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100554 A1 4/2014 Williams

(56) References Cited

U.S. PATENT DOCUMENTS

2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1* 5/2014 Taylor ................ A61B 18/1445 606/49
2014/0151433 A1 6/2014 Shelton, IV et al.
2014/0155916 A1 6/2014 Hodgkinson et al.
2014/0158747 A1 6/2014 Measamer et al.
2014/0166718 A1 6/2014 Swayze et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0194864 A1 7/2014 Martin et al.
2014/0194874 A1 7/2014 Dietz et al.
2014/0194875 A1 7/2014 Reschke et al.
2014/0207124 A1 7/2014 Aldridge et al.
2014/0207135 A1 7/2014 Winter
2014/0209658 A1 7/2014 Skalla et al.
2014/0215242 A1 7/2014 Jung
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0262408 A1 9/2014 Woodard
2014/0263535 A1 9/2014 Rajani et al.
2014/0263541 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2014/0379000 A1 12/2014 Romo et al.
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0032150 A1 1/2015 Ishida et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080876 A1 3/2015 Worrell et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0133957 A1 5/2015 Kostrzewski
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0202013 A1 7/2015 Teichtmann et al.
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.
2015/0257819 A1 9/2015 Dycus et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272606 A1 10/2015 Nobis
2015/0272659 A1 10/2015 Boudreaux et al.
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297824 A1 10/2015 Cabiri et al.
2015/0303417 A1 10/2015 Koeder et al.
2015/0305743 A1 10/2015 Casasanta et al.
2015/0313594 A1 11/2015 Shelton, IV et al.
2015/0324317 A1 11/2015 Collins et al.
2015/0327918 A1 11/2015 Sobajima et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.

(56) References Cited

U.S. PATENT DOCUMENTS

| | | | |
|---|---|---|---|
| 2016/0045248 | A1 | 2/2016 | Unger et al. |
| 2016/0047423 | A1 | 2/2016 | Bodtker |
| 2016/0051316 | A1 | 2/2016 | Boudreaux |
| 2016/0066913 | A1 | 3/2016 | Swayze et al. |
| 2016/0066980 | A1 | 3/2016 | Schall et al. |
| 2016/0069449 | A1 | 3/2016 | Kanai et al. |
| 2016/0074035 | A1 | 3/2016 | Whitman et al. |
| 2016/0074040 | A1 | 3/2016 | Widenhouse et al. |
| 2016/0081678 | A1 | 3/2016 | Kappel et al. |
| 2016/0082161 | A1 | 3/2016 | Zilberman et al. |
| 2016/0089175 | A1 | 3/2016 | Hibner et al. |
| 2016/0099601 | A1 | 4/2016 | Leabman et al. |
| 2016/0100747 | A1 | 4/2016 | Nitsan et al. |
| 2016/0100838 | A1 | 4/2016 | Beaupré et al. |
| 2016/0118201 | A1 | 4/2016 | Nicholas et al. |
| 2016/0132026 | A1 | 5/2016 | Wingardner et al. |
| 2016/0135835 | A1 | 5/2016 | Onuma |
| 2016/0135895 | A1 | 5/2016 | Faasse et al. |
| 2016/0139666 | A1 | 5/2016 | Rubin et al. |
| 2016/0174969 | A1 | 6/2016 | Kerr et al. |
| 2016/0174983 | A1 | 6/2016 | Shelton, IV et al. |
| 2016/0175021 | A1 | 6/2016 | Hassler, Jr. |
| 2016/0175029 | A1 | 6/2016 | Witt et al. |
| 2016/0183939 | A1 | 6/2016 | Shelton, IV et al. |
| 2016/0183944 | A1 | 6/2016 | Swensgard et al. |
| 2016/0192927 | A1 | 7/2016 | Kostrzewski |
| 2016/0192960 | A1 | 7/2016 | Bueno et al. |
| 2016/0199063 | A1 | 7/2016 | Mandakolathur Vasudevan et al. |
| 2016/0199956 | A1 | 7/2016 | Shelton, IV et al. |
| 2016/0220150 | A1 | 8/2016 | Sharonov |
| 2016/0235494 | A1 | 8/2016 | Shelton, IV et al. |
| 2016/0242783 | A1 | 8/2016 | Shelton, IV et al. |
| 2016/0242855 | A1 | 8/2016 | Fichtinger et al. |
| 2016/0249910 | A1 | 9/2016 | Shelton, IV et al. |
| 2016/0249922 | A1 | 9/2016 | Morgan et al. |
| 2016/0249929 | A1 | 9/2016 | Cappola et al. |
| 2016/0256159 | A1 | 9/2016 | Pinjala et al. |
| 2016/0256184 | A1 | 9/2016 | Shelton, IV et al. |
| 2016/0256221 | A1 | 9/2016 | Smith |
| 2016/0256229 | A1 | 9/2016 | Morgan et al. |
| 2016/0262745 | A1 | 9/2016 | Morgan et al. |
| 2016/0262921 | A1 | 9/2016 | Balbierz et al. |
| 2016/0270781 | A1 | 9/2016 | Scirica |
| 2016/0270842 | A1 | 9/2016 | Strobl et al. |
| 2016/0287265 | A1 | 10/2016 | Macdonald et al. |
| 2016/0287279 | A1 | 10/2016 | Bovay et al. |
| 2016/0296270 | A1 | 10/2016 | Strobl et al. |
| 2016/0302820 | A1 | 10/2016 | Hibner et al. |
| 2016/0310143 | A1 | 10/2016 | Bettuchi |
| 2016/0314716 | A1 | 10/2016 | Grubbs |
| 2016/0314717 | A1 | 10/2016 | Grubbs |
| 2016/0345972 | A1 | 12/2016 | Beardsley et al. |
| 2016/0367122 | A1 | 12/2016 | Ichimura et al. |
| 2016/0374669 | A1 | 12/2016 | Overmyer et al. |
| 2016/0374716 | A1 | 12/2016 | Kessler |
| 2017/0000549 | A1 | 1/2017 | Gilbert et al. |
| 2017/0007234 | A1 | 1/2017 | Chin et al. |
| 2017/0007244 | A1 | 1/2017 | Shelton, IV et al. |
| 2017/0007245 | A1 | 1/2017 | Shelton, IV et al. |
| 2017/0007347 | A1 | 1/2017 | Jaworek et al. |
| 2017/0020616 | A1 | 1/2017 | Vale et al. |
| 2017/0035419 | A1 | 2/2017 | Decker et al. |
| 2017/0055819 | A1 | 3/2017 | Hansen et al. |
| 2017/0055980 | A1 | 3/2017 | Vendely et al. |
| 2017/0056008 | A1 | 3/2017 | Shelton, IV et al. |
| 2017/0056016 | A1 | 3/2017 | Barton et al. |
| 2017/0056018 | A1 | 3/2017 | Zeiner et al. |
| 2017/0066054 | A1 | 3/2017 | Birky |
| 2017/0079642 | A1 | 3/2017 | Overmyer et al. |
| 2017/0086829 | A1 | 3/2017 | Vendely et al. |
| 2017/0086830 | A1 | 3/2017 | Yates et al. |
| 2017/0086930 | A1 | 3/2017 | Thompson et al. |
| 2017/0086932 | A1 | 3/2017 | Auld et al. |
| 2017/0095252 | A1 | 4/2017 | Smith et al. |
| 2017/0095922 | A1 | 4/2017 | Licht et al. |
| 2017/0105727 | A1 | 4/2017 | Scheib et al. |
| 2017/0105733 | A1 | 4/2017 | Scheib et al. |
| 2017/0105786 | A1 | 4/2017 | Scheib et al. |
| 2017/0105787 | A1 | 4/2017 | Witt et al. |
| 2017/0106302 | A1 | 4/2017 | Cummings et al. |
| 2017/0135711 | A1 | 5/2017 | Overmyer et al. |
| 2017/0135717 | A1 | 5/2017 | Boudreaux et al. |
| 2017/0135747 | A1 | 5/2017 | Broderick et al. |
| 2017/0135751 | A1 | 5/2017 | Rothweiler et al. |
| 2017/0143336 | A1 | 5/2017 | Shah et al. |
| 2017/0164972 | A1 | 6/2017 | Johnson et al. |
| 2017/0168187 | A1 | 6/2017 | Calderoni et al. |
| 2017/0172382 | A1 | 6/2017 | Nir et al. |
| 2017/0172549 | A1 | 6/2017 | Smaby et al. |
| 2017/0172662 | A1 | 6/2017 | Panescu et al. |
| 2017/0181803 | A1 | 6/2017 | Mayer-Ullmann et al. |
| 2017/0182195 | A1 | 6/2017 | Wagner |
| 2017/0182211 | A1 | 6/2017 | Raxworthy et al. |
| 2017/0196558 | A1 | 7/2017 | Morgan et al. |
| 2017/0196649 | A1 | 7/2017 | Yates et al. |
| 2017/0202605 | A1 | 7/2017 | Shelton, IV et al. |
| 2017/0202607 | A1 | 7/2017 | Shelton, IV et al. |
| 2017/0202770 | A1 | 7/2017 | Friedrich et al. |
| 2017/0224332 | A1 | 8/2017 | Hunter et al. |
| 2017/0231628 | A1 | 8/2017 | Shelton, IV et al. |
| 2017/0231629 | A1 | 8/2017 | Stopek et al. |
| 2017/0238962 | A1 | 8/2017 | Hansen et al. |
| 2017/0238991 | A1 | 8/2017 | Worrell et al. |
| 2017/0242455 | A1 | 8/2017 | Dickens |
| 2017/0245880 | A1 | 8/2017 | Honda et al. |
| 2017/0245949 | A1 | 8/2017 | Randle |
| 2017/0249431 | A1 | 8/2017 | Shelton, IV et al. |
| 2017/0252060 | A1 | 9/2017 | Ellingson et al. |
| 2017/0255799 | A1 | 9/2017 | Zhao et al. |
| 2017/0258471 | A1 | 9/2017 | DiNardo et al. |
| 2017/0262110 | A1 | 9/2017 | Polishchuk et al. |
| 2017/0265774 | A1 | 9/2017 | Johnson et al. |
| 2017/0281186 | A1 | 10/2017 | Shelton, IV et al. |
| 2017/0296173 | A1 | 10/2017 | Shelton, IV et al. |
| 2017/0296185 | A1 | 10/2017 | Swensgard et al. |
| 2017/0303984 | A1 | 10/2017 | Malackowski |
| 2017/0308665 | A1 | 10/2017 | Heck et al. |
| 2017/0312018 | A1 | 11/2017 | Trees et al. |
| 2017/0312042 | A1 | 11/2017 | Giordano et al. |
| 2017/0319047 | A1 | 11/2017 | Poulsen et al. |
| 2017/0319201 | A1 | 11/2017 | Morgan et al. |
| 2017/0325878 | A1 | 11/2017 | Messerly et al. |
| 2017/0325886 | A1 | 11/2017 | Graham et al. |
| 2017/0333034 | A1 | 11/2017 | Morgan et al. |
| 2017/0333035 | A1 | 11/2017 | Morgan et al. |
| 2017/0348010 | A1 | 12/2017 | Chiang |
| 2017/0348042 | A1 | 12/2017 | Drochner et al. |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |
| 2018/0008265 | A1 | 1/2018 | Hatanaka et al. |
| 2018/0036024 | A1 | 2/2018 | Allen, IV |
| 2018/0036025 | A1 | 2/2018 | Drochner et al. |
| 2018/0042610 | A1 | 2/2018 | Sgroi, Jr. |
| 2018/0042689 | A1 | 2/2018 | Mozdzierz et al. |
| 2018/0049738 | A1 | 2/2018 | Meloul et al. |
| 2018/0049794 | A1 | 2/2018 | Swayze et al. |
| 2018/0051780 | A1 | 2/2018 | Shelton, IV et al. |
| 2018/0055501 | A1 | 3/2018 | Zemlok et al. |
| 2018/0067004 | A1 | 3/2018 | Sgroi, Jr. |
| 2018/0085117 | A1 | 3/2018 | Shelton, IV et al. |
| 2018/0085120 | A1 | 3/2018 | Viola |
| 2018/0092710 | A1 | 4/2018 | Bosisio et al. |
| 2018/0114591 | A1 | 4/2018 | Pribanic et al. |
| 2018/0116658 | A1 | 5/2018 | Aronhalt, IV et al. |
| 2018/0125481 | A1 | 5/2018 | Yates et al. |
| 2018/0125487 | A1 | 5/2018 | Beardsley |
| 2018/0125488 | A1 | 5/2018 | Morgan et al. |
| 2018/0125571 | A1 | 5/2018 | Witt et al. |
| 2018/0125594 | A1 | 5/2018 | Beardsley |
| 2018/0132849 | A1 | 5/2018 | Miller et al. |
| 2018/0132850 | A1 | 5/2018 | Leimbach et al. |
| 2018/0132926 | A1 | 5/2018 | Asher et al. |

(56) References Cited

U.S. PATENT DOCUMENTS

2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168622 A1* 6/2018 Shelton, IV ..... A61B 17/07207
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271526 A1 9/2018 Zammataro
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280026 A1 10/2018 Zhang et al.
2018/0280073 A1 10/2018 Sanai et al.
2018/0280075 A1 10/2018 Nott et al.
2018/0289371 A1 10/2018 Wang et al.
2018/0296216 A1 10/2018 Shelton, IV et al.
2018/0296290 A1 10/2018 Namiki et al.
2018/0310995 A1 11/2018 Gliner et al.
2018/0317905 A1 11/2018 Olson et al.
2018/0317915 A1 11/2018 Mcdonald, II
2018/0325514 A1 11/2018 Harris et al.
2018/0333169 A1 11/2018 Leimbach et al.
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000470 A1 1/2019 Yates et al.
2019/0000481 A1 1/2019 Harris et al.
2019/0000535 A1 1/2019 Messerly et al.
2019/0000536 A1 1/2019 Yates et al.
2019/0000565 A1* 1/2019 Shelton, IV ........... A61B 34/30
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0038281 A1 2/2019 Shelton, IV et al.
2019/0038283 A1 2/2019 Shelton, IV et al.
2019/0038285 A1 2/2019 Mozdzierz
2019/0059980 A1 2/2019 Shelton, IV et al.
2019/0059984 A1 2/2019 Otrembiak et al.
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0099209 A1 4/2019 Witt et al.
2019/0099212 A1 4/2019 Davison et al.
2019/0099217 A1 4/2019 Witt et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117220 A1 4/2019 Nativ et al.
2019/0117224 A1 4/2019 Setser et al.
2019/0117287 A1 4/2019 Nativ et al.
2019/0122840 A1 4/2019 Zergiebel et al.
2019/0125320 A1 5/2019 Shelton, IV et al.
2019/0125336 A1 5/2019 Deck et al.
2019/0125338 A1 5/2019 Shelton, IV et al.
2019/0125342 A1 5/2019 Beardsley et al.
2019/0125344 A1 5/2019 DiNardo et al.
2019/0125361 A1 5/2019 Shelton, IV et al.
2019/0125378 A1 5/2019 Shelton, IV et al.
2019/0125388 A1 5/2019 Shelton, IV et al.
2019/0125432 A1 5/2019 Shelton, IV et al.
2019/0125454 A1 5/2019 Stokes et al.
2019/0125476 A1 5/2019 Shelton, IV et al.
2019/0133422 A1 5/2019 Nakamura
2019/0133577 A1 5/2019 Weadock et al.
2019/0138770 A1 5/2019 Compaijen et al.
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183502 A1 6/2019 Shelton, IV et al.
2019/0192147 A1 6/2019 Shelton, IV et al.
2019/0192148 A1 6/2019 Shelton, IV et al.
2019/0192151 A1 6/2019 Shelton, IV et al.
2019/0192153 A1 6/2019 Shelton, IV et al.
2019/0192155 A1 6/2019 Shelton, IV et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.
2019/0201034 A1 7/2019 Shelton, IV et al.
2019/0201045 A1 7/2019 Yates et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201158 A1 7/2019 Shelton, IV et al.
2019/0201594 A1 7/2019 Shelton, IV et al.

(56) References Cited

U.S. PATENT DOCUMENTS

2019/0205567 A1 7/2019 Shelton, IV et al.
2019/0206555 A1 7/2019 Morgan et al.
2019/0206561 A1 7/2019 Shelton, IV et al.
2019/0206564 A1 7/2019 Shelton, IV et al.
2019/0206569 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0239873 A1 8/2019 Laurent et al.
2019/0247048 A1 8/2019 Gasparovich et al.
2019/0261982 A1 8/2019 Holsten
2019/0261983 A1 8/2019 Granger et al.
2019/0261984 A1 8/2019 Nelson et al.
2019/0261987 A1 8/2019 Viola et al.
2019/0262153 A1 8/2019 Tassoni et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0274716 A1 9/2019 Nott et al.
2019/0282233 A1 9/2019 Burbank et al.
2019/0290264 A1 9/2019 Morgan et al.
2019/0290266 A1 9/2019 Scheib et al.
2019/0290267 A1 9/2019 Baxter, III et al.
2019/0290297 A1 9/2019 Haider et al.
2019/0298353 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0314015 A1 10/2019 Shelton, IV et al.
2019/0321062 A1 10/2019 Williams
2019/0328387 A1 10/2019 Overmyer et al.
2019/0388091 A1 12/2019 Eschbach et al.
2020/0000531 A1 1/2020 Giordano et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015836 A1 1/2020 Nicholas et al.
2020/0015915 A1 1/2020 Swayze et al.
2020/0030020 A1 1/2020 Wang et al.
2020/0037939 A1 2/2020 Castagna et al.
2020/0038016 A1 2/2020 Shelton, IV et al.
2020/0038018 A1 2/2020 Shelton, IV et al.
2020/0038021 A1 2/2020 Contini et al.
2020/0046355 A1 2/2020 Harris et al.
2020/0046356 A1 2/2020 Baxter et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060713 A1 2/2020 Leimbach et al.
2020/0061385 A1 2/2020 Schwarz et al.
2020/0085435 A1 3/2020 Shelton, IV et al.
2020/0085518 A1 3/2020 Giordano et al.
2020/0093484 A1 3/2020 Shelton, IV et al.
2020/0093506 A1 3/2020 Leimbach et al.
2020/0093550 A1 3/2020 Spivey et al.
2020/0100783 A1 4/2020 Yates et al.
2020/0107829 A1 4/2020 Shelton, IV et al.
2020/0113563 A1 4/2020 Gupta et al.
2020/0114505 A1 4/2020 Kikuchi
2020/0138507 A1 5/2020 Davison et al.
2020/0138534 A1 5/2020 Garcia Kilroy et al.
2020/0146166 A1 5/2020 Sgroi, Jr.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0229814 A1 7/2020 Amariglio et al.
2020/0237371 A1 7/2020 Huitema et al.
2020/0261086 A1 8/2020 Zeiner et al.
2020/0268377 A1 8/2020 Schmid et al.
2020/0268381 A1 8/2020 Roberts et al.
2020/0275927 A1 9/2020 Shelton, IV et al.
2020/0275930 A1 9/2020 Harris et al.
2020/0280219 A1 9/2020 Laughery et al.
2020/0289112 A1 9/2020 Whitfield et al.
2020/0289119 A1 9/2020 Viola et al.
2020/0305863 A1 10/2020 Yates et al.
2020/0305864 A1 10/2020 Yates et al.
2020/0305872 A1 10/2020 Weidner et al.
2020/0305874 A1 10/2020 Huitema et al.
2020/0315623 A1 10/2020 Eisinger et al.
2020/0323526 A1 10/2020 Huang et al.
2020/0330181 A1 10/2020 Junger et al.
2020/0337706 A1 10/2020 Truckai et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0367886 A1 11/2020 Shelton, IV et al.
2020/0375585 A1 12/2020 Swayze et al.
2020/0375597 A1 12/2020 Shelton, IV et al.
2020/0375651 A1 12/2020 Witt et al.
2020/0390444 A1 12/2020 Harris et al.
2020/0397430 A1 12/2020 Patel et al.
2020/0397439 A1 12/2020 Eisinger
2020/0405292 A1 12/2020 Shelton, IV et al.
2020/0405296 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405375 A1 12/2020 Shelton, IV et al.
2020/0405403 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0007742 A1 1/2021 Rector et al.
2021/0015480 A1 1/2021 Shelton, IV et al.
2021/0030416 A1 2/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068829 A1 3/2021 Miller et al.
2021/0068835 A1 3/2021 Shelton, IV et al.
2021/0077099 A1 3/2021 Shelton, IV et al.
2021/0077109 A1 3/2021 Harris et al.
2021/0084700 A1 3/2021 Daniels
2021/0085313 A1 3/2021 Morgan et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.

(56) References Cited

U.S. PATENT DOCUMENTS

2021/0093321 A1 4/2021 Auld et al.
2021/0093323 A1 4/2021 Scirica et al.
2021/0100541 A1 4/2021 Shelton, IV et al.
2021/0100605 A1 4/2021 Renner et al.
2021/0100982 A1 4/2021 Laby et al.
2021/0107031 A1 4/2021 Bales, Jr. et al.
2021/0121175 A1 4/2021 Yates et al.
2021/0128153 A1 5/2021 Sgroi
2021/0137522 A1 5/2021 Shelton, IV et al.
2021/0153866 A1 5/2021 Knapp et al.
2021/0177401 A1 6/2021 Abramek et al.
2021/0177411 A1 6/2021 Williams
2021/0177528 A1 6/2021 Cappelleri et al.
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0196265 A1 7/2021 Shelton, IV et al.
2021/0196269 A1 7/2021 Shelton, IV et al.
2021/0196270 A1 7/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212691 A1 7/2021 Smith et al.
2021/0212776 A1 7/2021 Schmitt et al.
2021/0228209 A1 7/2021 Shelton, IV et al.
2021/0236124 A1 8/2021 Shelton, IV et al.
2021/0244406 A1 8/2021 Kerr et al.
2021/0244407 A1 8/2021 Shelton, IV et al.
2021/0244410 A1 8/2021 Swayze et al.
2021/0244411 A1 8/2021 Smith et al.
2021/0244412 A1 8/2021 Vendely et al.
2021/0251720 A1 8/2021 Jhaveri et al.
2021/0259681 A1 8/2021 Shelton, IV et al.
2021/0259687 A1 8/2021 Gonzalez et al.
2021/0259790 A1 8/2021 Kaiser
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0313975 A1 10/2021 Shan et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0338309 A1 11/2021 Witt et al.
2021/0346082 A1 11/2021 Adams et al.
2021/0353284 A1 11/2021 Yang et al.
2021/0369271 A1 12/2021 Schings et al.
2021/0378669 A1 12/2021 Shelton, IV et al.
2021/0393261 A1 12/2021 Harris et al.
2021/0393262 A1 12/2021 Shelton, IV et al.
2021/0393366 A1 12/2021 Shelton, IV et al.
2021/0401487 A1 12/2021 Apostolopoulos et al.
2021/0401513 A1 12/2021 Apostolopoulos et al.
2022/0000478 A1 1/2022 Shelton, IV et al.
2022/0000479 A1 1/2022 Shelton, IV et al.
2022/0015760 A1 1/2022 Beardsley et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061642 A1 3/2022 Park et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0104695 A1 4/2022 Russell
2022/0104814 A1 4/2022 Shelton, IV et al.
2022/0104816 A1 4/2022 Fernandes et al.
2022/0104820 A1 4/2022 Shelton, IV et al.
2022/0110673 A1 4/2022 Boronyak et al.
2022/0117602 A1 4/2022 Wise et al.
2022/0125472 A1 4/2022 Beckman et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133312 A1 5/2022 Huang
2022/0133318 A1 5/2022 Hudson et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160355 A1 5/2022 Harris et al.
2022/0160358 A1 5/2022 Wixey
2022/0167968 A1 6/2022 Worthington et al.
2022/0167970 A1 6/2022 Aronhalt et al.
2022/0167972 A1 6/2022 Shelton, IV et al.
2022/0167973 A1 6/2022 Shelton, IV et al.
2022/0167975 A1 6/2022 Shelton, IV et al.
2022/0167977 A1 6/2022 Shelton, IV et al.
2022/0167979 A1 6/2022 Yates et al.
2022/0167981 A1 6/2022 Shelton, IV et al.
2022/0167982 A1 6/2022 Shelton, IV et al.
2022/0167983 A1 6/2022 Shelton, IV et al.
2022/0167995 A1 6/2022 Parfett et al.
2022/0175370 A1 6/2022 Shelton, IV et al.
2022/0175371 A1 6/2022 Hess et al.
2022/0175372 A1 6/2022 Shelton, IV et al.

(56) References Cited

U.S. PATENT DOCUMENTS

| | | | |
|---|---|---|---|
| 2022/0175375 | A1 | 6/2022 | Harris et al. |
| 2022/0175378 | A1 | 6/2022 | Leimbach et al. |
| 2022/0175381 | A1 | 6/2022 | Scheib et al. |
| 2022/0183685 | A1 | 6/2022 | Shelton, IV et al. |
| 2022/0202487 | A1 | 6/2022 | Shelton, IV et al. |
| 2022/0211367 | A1 | 7/2022 | Schmid et al. |
| 2022/0218332 | A1 | 7/2022 | Shelton, IV et al. |
| 2022/0218336 | A1 | 7/2022 | Timm et al. |
| 2022/0218338 | A1 | 7/2022 | Shelton, IV et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218347 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225986 | A1 | 7/2022 | Shelton, IV et al. |
| 2022/0225993 | A1 | 7/2022 | Huitema et al. |
| 2022/0225994 | A1 | 7/2022 | Setser et al. |
| 2022/0226013 | A1 | 7/2022 | Hall et al. |
| 2022/0233186 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0249095 | A1 | 8/2022 | Shelton, IV et al. |
| 2022/0265272 | A1 | 8/2022 | Li et al. |
| 2022/0273291 | A1 | 9/2022 | Shelton, IV et al. |
| 2022/0273292 | A1 | 9/2022 | Shelton, IV et al. |
| 2022/0273293 | A1 | 9/2022 | Shelton, IV et al. |
| 2022/0273294 | A1 | 9/2022 | Creamer et al. |
| 2022/0273299 | A1 | 9/2022 | Shelton, IV et al. |
| 2022/0273300 | A1 | 9/2022 | Shelton, IV et al. |
| 2022/0273301 | A1 | 9/2022 | Creamer et al. |
| 2022/0273303 | A1 | 9/2022 | Creamer et al. |
| 2022/0273304 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0278438 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296235 | A1 | 9/2022 | Morgan et al. |
| 2022/0296236 | A1 | 9/2022 | Bakos et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0346776 | A1 | 11/2022 | Aronhalt et al. |
| 2022/0346781 | A1 | 11/2022 | Shelton, IV et al. |
| 2022/0346783 | A1 | 11/2022 | Shelton, IV et al. |
| 2022/0346785 | A1 | 11/2022 | Aronhalt et al. |
| 2022/0354492 | A1 | 11/2022 | Baril |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378420 | A1 | 12/2022 | Leimbach et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |
| 2023/0016171 | A1 | 1/2023 | Yates et al. |
| 2023/0018950 | A1 | 1/2023 | Shelton, IV et al. |
| 2023/0057935 | A1 | 2/2023 | Baber et al. |
| 2023/0088531 | A1 | 3/2023 | Hall et al. |
| 2023/0094712 | A1 | 3/2023 | Shelton, IV et al. |
| 2023/0120983 | A1 | 4/2023 | Stokes et al. |
| 2023/0121131 | A1 | 4/2023 | Swayze et al. |
| 2023/0121658 | A1 | 4/2023 | Stokes et al. |
| 2023/0133811 | A1 | 5/2023 | Huang |
| 2023/0134883 | A1 | 5/2023 | Leimbach |
| 2023/0135070 | A1 | 5/2023 | Shelton, IV et al. |
| 2023/0135282 | A1 | 5/2023 | Schings et al. |
| 2023/0135811 | A1 | 5/2023 | Guest |
| 2023/0138314 | A1 | 5/2023 | Jenkins |
| 2023/0138743 | A1 | 5/2023 | Ross et al. |
| 2023/0165582 | A1 | 6/2023 | Harris et al. |
| 2023/0165584 | A1 | 6/2023 | Leimbach et al. |
| 2023/0172607 | A1 | 6/2023 | DiNardo et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 1922563 | A | 2/2007 |
| CN | 2868212 | Y | 2/2007 |
| CN | 2868227 | Y | 2/2007 |

(56) References Cited

FOREIGN PATENT DOCUMENTS

| | | | |
|---|---|---|---|
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101401736 | A | 4/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 4300307 | A1 | 7/1994 |
| DE | 19534043 | A1 | 3/1997 |
| DE | 29623113 | U1 | 10/1997 |
| DE | 19851291 | A1 | 1/2000 |
| DE | 20004812 | U1 | 9/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 10201569 | A1 | 7/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 102005032371 | A1 | 1/2007 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0171967 | A2 | 2/1986 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |

(56) References Cited

FOREIGN PATENT DOCUMENTS

| | | | |
|---|---|---|---|
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1862133 | A1 | 12/2007 |
| EP | 1330201 | B1 | 6/2008 |
| EP | 2039302 | A2 | 3/2009 |
| EP | 2060238 | A1 | 5/2009 |
| EP | 1719461 | B1 | 6/2009 |
| EP | 1747761 | B1 | 10/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 1767164 | B1 | 1/2013 |
| EP | 2578172 | A2 | 4/2013 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| ES | 2419159 | A2 | 8/2013 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2032221 | A | 4/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S537994 | A | 1/1978 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002186627 | A | 7/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |

(56) References Cited

FOREIGN PATENT DOCUMENTS

| | | | |
|---|---|---|---|
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009213878 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010057926 | A | 3/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | A1 | 5/1993 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| WO | WO-8103272 | A1 | 11/1981 |
| WO | WO-9308754 | A1 | 5/1993 |
| WO | WO-9314708 | A1 | 8/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9800069 | A1 | 1/1998 |
| WO | WO-9827870 | A1 | 7/1998 |
| WO | WO-9903407 | A1 | 1/1999 |
| WO | WO-9903409 | A1 | 1/1999 |
| WO | WO-9923960 | A1 | 5/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0128444 | A1 | 4/2001 |
| WO | WO-0154594 | A1 | 8/2001 |

(56) References Cited

FOREIGN PATENT DOCUMENTS

| | | | |
|---|---|---|---|
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-02080794 | A1 | 10/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2008130793 | A1 | 10/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010104755 | A1 | 9/2010 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2011144911 | A1 | 11/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061638 | A1 | 5/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013131823 | A1 | 9/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016088017 | A1 | 6/2016 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |
| WO | WO-2022249091 | A1 | 12/2022 |
| WO | WO-2022249094 | A1 | 12/2022 |

OTHER PUBLICATIONS

ASTM procedure D2240-05, “Standard Test Method for Rubber Property-Durometer Hardness,” (Published Apr. 2010).
Van Meer et al., “A Disposable Plastic Compact Wrist for Smart Minimally Invasive Surgical Tools,” LAAS/CNRS (Aug. 2005).
Breedveld et al., “A New, Easily Miniaturized Sterrable Endoscope,” IEEE Engineering in Medicine and Biology Magazine (Nov./Dec. 2005).
Disclosed Anonymously, “Motor-Driven Surgical Stapler Improvements,” Research Disclosure Database No. 526041, Published: Feb. 2008.
B.R. Coolman, DVM, MS et al., “Comparison of Skin Staples With Sutures for Anastomosis of the Small Intestine in Dogs,” Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., “Get The Lowdown On Ultracapacitors,” Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., “Poly-Lactic-Acid for Coating of Endovascular Stents: Preliminary Results in Canine Experimental Av-Fistulae,” Mat.-wiss. u. Werkstofftech., 32, pp. 193-199 (2001).
Miyata et al., “Biomolecule-Sensitive Hydrogels,” Advanced Drug Delivery Reviews, 54 (2002) pp. 79-98.
Jeong et al., “Thermosensitive Sol-Gel Reversible Hydrogels,” Advanced Drug Delivery Reviews, 54 (2002) pp. 37-51.
Covidien Brochure, “Endo GIA™ Ultra Universal Stapler,” (2010), 2 pages.
Qiu et al., “Environment-Sensitive Hydrogels for Drug Delivery,” Advanced Drug Delivery Reviews, 53 (2001) pp. 321-339.
Hoffman, “Hydrogels for Biomedical Applications,” Advanced Drug Delivery Reviews, 43 (2002) pp. 3-12.
Hoffman, “Hydrogels for Biomedical Applications,” Advanced Drug Delivery Reviews, 54 (2002) pp. 3-12.
Peppas, “Physiologically Responsive Hydrogels,” Journal of Bioactive and Compatible Polymers, vol. 6 (Jul. 1991) pp. 241-246.
Peppas, Editor “Hydrogels in Medicine and Pharmacy,” vol. I, Fundamentals, CRC Press, 1986.
Young, “Microcellular foams via phase separation,” Journal of Vacuum Science & Technology A 4(3), (May/Jun. 1986).
Ebara, “Carbohydrate-Derived Hydrogels and Microgels,” Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Solorio et al., “Gelatin Microspheres Crosslinked with Genipin for Local Delivery of Growth Factors,” J. Tissue Eng. Regen. Med. (2010), 4(7): pp. 514-523.
Covidien Brochure, “Endo GIA™ Reloads with Tri-Staple™ Technology,” (2010), 1 page.
Covidien Brochure, “Endo GIA™ Reloads with Tri-Staple™ Technology and Endo GIA™ Ultra Universal Staplers,” (2010), 2 pages.
Covidien Brochure, “Endo GIA™ Curved Tip Reload with Tri-Staple™ Technology,” (2012), 2 pages.
Covidien Brochure, “Endo GIA™ Reloads with Tri-Staple™ Technology,” (2010), 2 pages.
Pitt et al., “Attachment of Hyaluronan to Metallic Surfaces,” J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: “RFID for Dummies”, Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.

(56) References Cited

OTHER PUBLICATIONS

Byrne et al., "Molecular Imprinting Within Hydrogels," Advanced Drug Delivery Reviews, 54 (2002) pp. 149-161.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

Chen et al., "Elastomeric Biomaterials for Tissue Engineering," Progress in Polymer Science 38 (2013), pp. 584-671.

Matsuda, "Thermodynamics of Formation of Porous Polymeric Membrane from Solutions," Polymer Journal, vol. 23, No. 5, pp. 435-444 (1991).

Covidien Brochure, "Endo GIA™ Black Reload with Tri-Staple™ Technology," (2012), 2 pages.

Biomedical Coatings, Fort Wayne Metals, Research Products Corporation, obtained online at www.fwmetals.com on Jun. 21, 2010 (1 page).

The Sodem Aseptic Battery Transfer Kit, Sodem Systems, 2000, 3 pages.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.

Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.

Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].

Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.

Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.

Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).

Yan et al., Comparison of the effects of Mg—6Zn and Ti-3Al-2.5V alloys on TGF-β/TNF-α/VEGF/b-FGF in the healing of the intestinal track in vivo, Biomed. Mater. 9 (2014), 11 pages.

Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.

Anonymous, Analog Devices Wiki, Chapter 11: The Current Mirror, Aug. 20, 2017, 22 pages. https://wiki.analog.com/university/courses/electronics/text/chapter-11?rev=1503222341.

Yan et al., "Comparison of the effects of Mg—6Zn and titanium on intestinal tract in vivo," J Mater Sci: Mater Med (2013), 11 pages.

Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.

Texas Instruments: "Current Recirculation and Decay Modes," Application Report SLVA321 —Mar. 2009; Retrieved from the Internet: URL:http://www.ti.com/lit/an/slva321/slva321 [retrieved on Apr. 25, 2017], 7 pages.

Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.

Gao et al., "Mechanical Signature Enhancement of Response Vibrations in the Time Lag Domain," Fifth International Congress on Sound and Vibration, Dec. 15-18, 1997, pp. 1-8.

Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.

Youtube.com; video by Fibran (retrieved from URL https://www.youtube.com/watch?v=vN2Qjt51gFQ); (Year: 2018).

Foot and Ankle: Core Knowledge in Orthopaedics; by DiGiovanni MD, Elsevier; (p. 27, left column heading "Materials for Soft Orthoses", 7th bullet point); (Year: 2007).

Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.

Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.

Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).

Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).

Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).

Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).

Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).

Tutorial overview of inductively coupled RFID Systems, UPM, May 2003, pp. 1-7, UPM Rafsec,<http://cdn.mobiusconsulting.com/papers/rfidsystems.pdf>.

Schroeter, John, "*Demystifying UHF Gen 2 RFID, HF RFID*," Online Article, Jun. 2, 2008, pp. 1-3, <https://www.edn.com/design/industrial-control/4019123/Demystifying-UHF-Gen-2-RFID-HF-RFID>.

Adeeb, et al., "*An Inductive Link-Based Wireless Power Transfer System for Biomedical Applications*," Research Article, Nov. 14, 2011, pp. 1-12, vol. 2012, Article ID 879294, Hindawi Publishing Corporation.

Pushing Pixels (GIF), published on dribble.com, 2013.

Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.

NF Monographs: Sodium Stearate, U.S. Pharmacopeia, http://www.pharmacopeia.cn/v29240/usp29nf24s0_m77360.html, accessed May 23, 2016.

Fischer, Martin H, "Colloid-Chemical Studies on Soaps", The Chemical Engineer, pp. 184-193, Aug. 1919.

V.K. Ahluwalia and Madhuri Goyal, A Textbook of Organic Chemistry, Section 19.11.3, p. 356, 2000.

A.V. Kasture and S.G. Wadodkar, Pharmaceutical Chemistry-II: Second Year Diploma in Pharmacy, Nirali Prakashan, p. 339, 2007.

Forum discussion regarding "Speed is Faster", published on Oct. 1, 2014 and retrieved on Nov. 8, 2019 from URL https://english.

(56) References Cited

OTHER PUBLICATIONS stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Kurt Gieck & Reiner Gieck, *Engineering Formulas* § Z.7 (7th ed. 1997).
Leonard I. Malis, M.D., "The Value of Irrigation During Bipolar Coagulation," 1989.
Covidien Brochure, The LigaSure Precise™ Instrument, dated Mar. 2011 (2 pages).
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas ™ Hand Switching Instruments, dated Dec. 2008 (2 pages).
Covidien Brochure, The LigaSure™ 5 mm Blunt Tip Sealer/Divider Family, dated Apr. 2013 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.

(56) References Cited

OTHER PUBLICATIONS

Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser- Irradiated Tissue, A. J. Welch and M. J. C. van Gemert, eds., Plenum, New York (1995).
Campbell et al., "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Allegro MicroSystems, LLC, Automotive Full Bridge MOSFET Driver, A3941-DS, Rev. 5, 21 pages, http://www.allegromicor.com/~/media/Files/Datasheets/A3941-Datasheet.ashx?la=en, 2008-2013.
Covidien "iDrive™ Ultra Powered Stapling System, A Guide for Surgeons," (6 pages) 2012.
Covidien "iDrive™ Ultra Powered Stapling System, Cleaning and Sterilization Guide," (2 pages) 2012.
Covidien Brochure "iDrive™ Ultra Powered Stapling System," (6 pages), 2012.
Covidien iDrive™ Ultra in Service Reference Card, "iDrive™ Ultra Powered Stapling Device," (4 pages), 2018.
Covidien iDrive™ Ultra Powered Stapling System Brochure, "The Power of iDrive™ Ultra Powered Stapling System and Tri-Staple™ Technology," (23 pages), 2014.
Seils et al., Covidien Summary: Clinical Study "UCONN Biodynamics: Final Report on Results," (2 pages), 2012.

* cited by examiner

METHOD FOR TISSUE TREATMENT BY SURGICAL INSTRUMENT

BACKGROUND

The present disclosure relates to various forms of surgical instruments for treating tissue.

SUMMARY

In various embodiments, a method for treating tissue using a surgical instrument including at least one electrode and a staple cartridge is disclosed. The method includes causing the at least one electrode to deliver a therapeutic energy to the tissue in a first phase of a surgical treatment by the surgical instrument, deploying staples from the staple cartridge into the tissue in a second phase of the surgical treatment, monitoring a first tissue property in the first phase of the surgical treatment, switching from the first phase of the surgical treatment to the second phase of the surgical treatment if at least one of two conditions is met, setting a parameter of the second phase of the surgical treatment based on at least one measurement of the first tissue property determined in the first phase of the surgical treatment, and monitoring a second tissue property, different from the first tissue property, in the second phase of the surgical treatment. A first of the two conditions is triggered by reaching or exceeding a predetermined threshold of the first tissue property. A second of the two conditions is triggered by reaching or exceeding a predetermined threshold time of the first phase.

In various embodiments, a method for treating tissue using a surgical instrument including at least one electrode and a staple cartridge is disclosed. The method includes causing the at least one electrode to deliver a therapeutic energy to the tissue in a first phase of a surgical treatment, deploying staples from the staple cartridge into the tissue in a second phase of the surgical treatment, monitoring a tissue property in the first phase of the surgical treatment, switching from the first phase of the surgical treatment to the second phase of the surgical treatment based on at least one of a predetermined threshold of the tissue property and a predetermined threshold time of the first phase, and setting a parameter of the second phase of the surgical treatment based on at least one measurement of the tissue property determined in the first phase of the surgical treatment.

In various embodiments, a method for treating tissue using a surgical instrument including at least one electrode and a staple cartridge is disclosed. The method includes delivering a therapeutic energy to the tissue in consecutive treatment zones, deploying staples from the staple cartridge into the tissue, detecting a parameter indicative of a progress of the staple deployment from the staple cartridge in the consecutive treatment zones, and sequentially deactivating electrodes to sequentially seize the delivery of the therapeutic energy to the tissue in the consecutive treatment zones based on the progress of staple deployment from the staple cartridge.

BRIEF DESCRIPTION OF THE DRAWINGS

Various features of the embodiments described herein, together with advantages thereof, may be understood in accordance with the following description taken in conjunction with the accompanying drawings as follows:

FIG. 132 illustrates a suture grabber, according to at least one aspect of the present disclosure.

FIG. 133 illustrates an embodiment for securing a buttress to an anvil, according to at least one aspect of the present disclosure.

FIG. 134 illustrates a cross-section view of FIG. 133, according to at least one aspect of the present disclosure.

FIG. 135 illustrates a buttress applier cartridge, according to at least one aspect of the present disclosure.

FIG. 136 illustrates the buttress applier cartridge of FIG. 135 before and after interfacing with an end effector, according to at least one aspect of the present disclosure.

FIG. 137 illustrates a buttress applier cartridge, according to at least one aspect of the present disclosure.

FIG. 138 illustrates a buttress applier cartridge, according to at least one aspect of the present disclosure.

FIG. 139 illustrates a buttress applier cartridge, according to at least one aspect of the present disclosure.

FIG. 140 illustrates the buttress applier cartridge of FIG. 139 when interfacing with an anvil, according to at least one aspect of the present disclosure.

FIG. 141 illustrates a buttress assembly, according to at least one aspect of the present disclosure.

FIG. 142 illustrates the buttress assembly of FIG. 137 being removed from an anvil after a surgical stapling procedure, according to at least one aspect of the present disclosure.

FIG. 143 illustrates a buttress assembly interfacing with an anvil, according to at least one aspect of the present disclosure.

Figure 143:
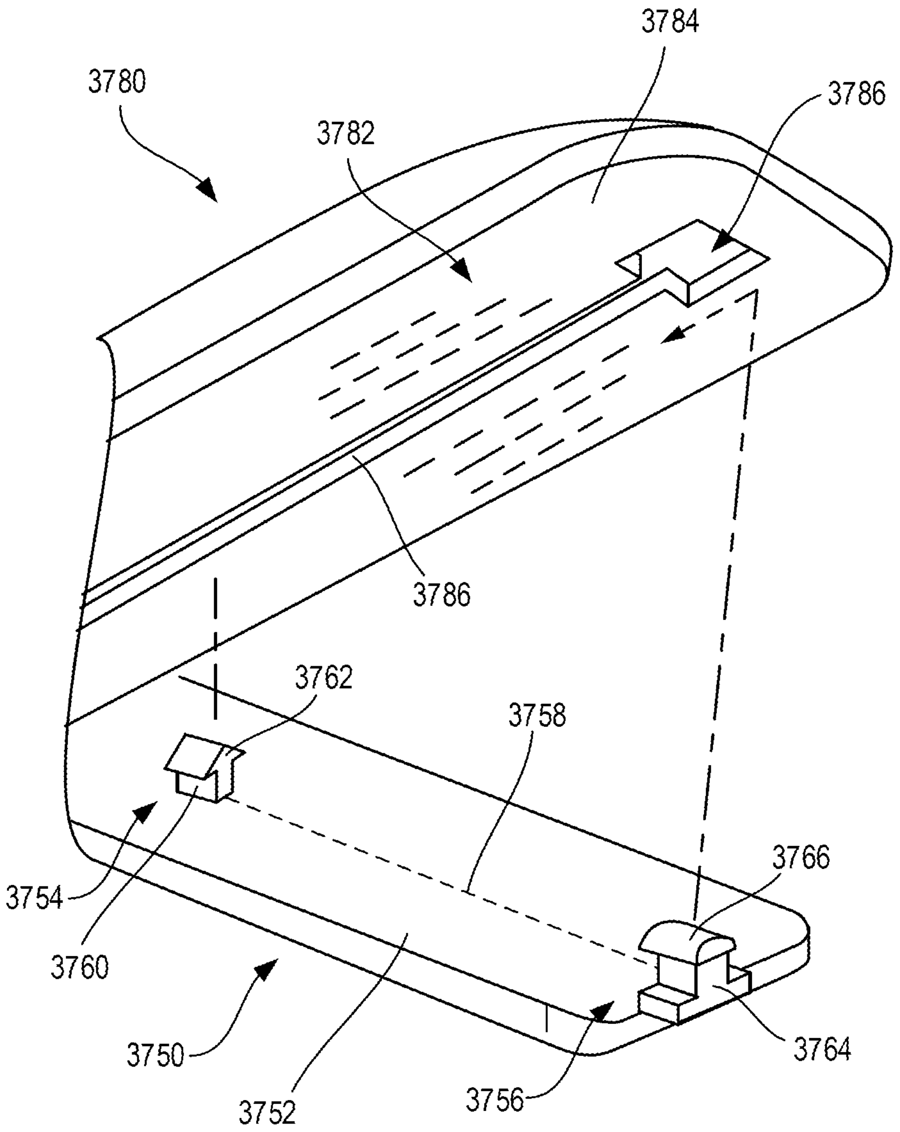
Figure 144:
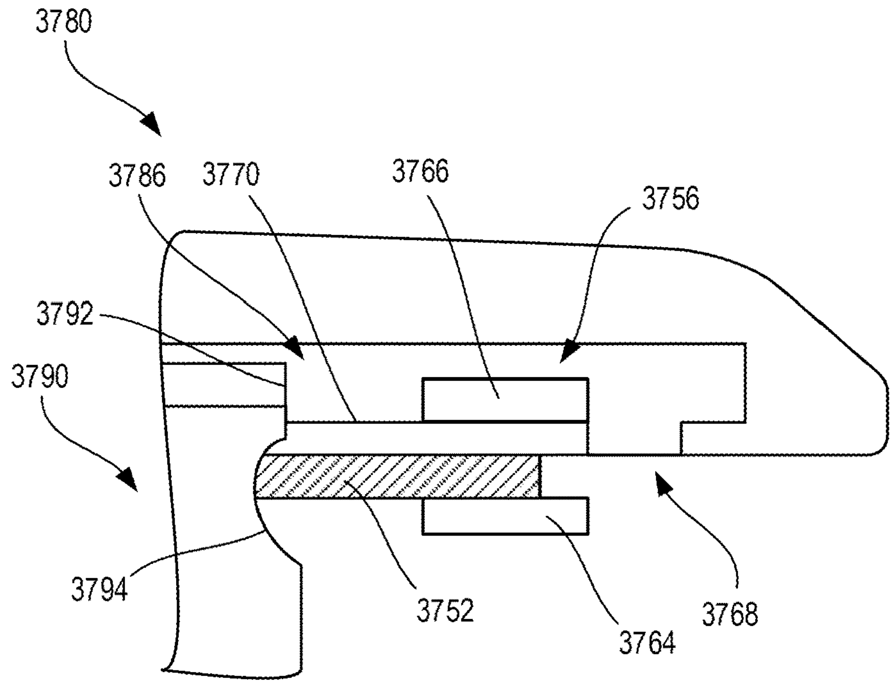

FIG. 144 illustrates a portion of the buttress assembly of FIG. 143 coupled to an anvil, according to at least one aspect of the present disclosure.

Figure 145:
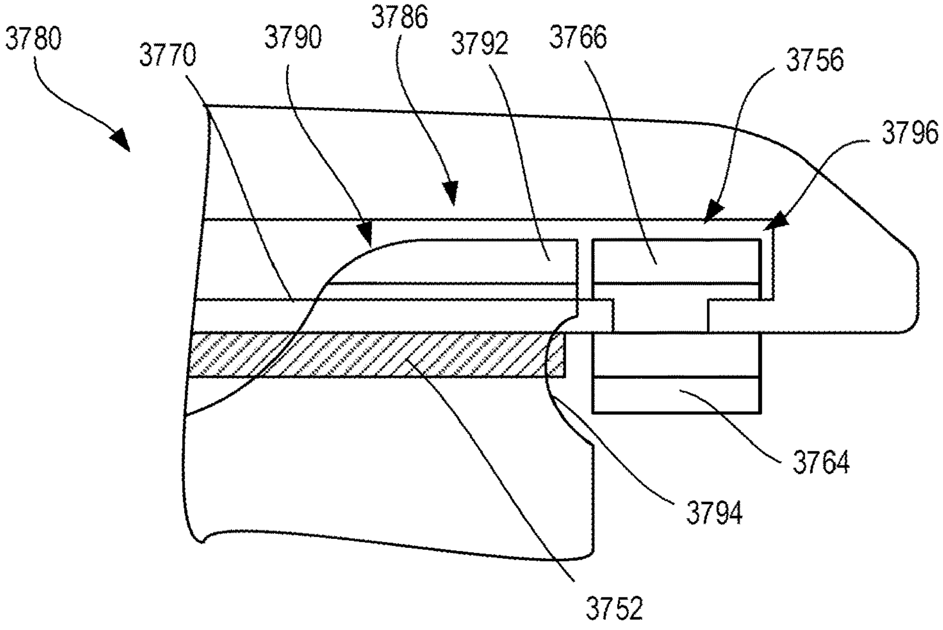

FIG. 145 illustrates a portion of the buttress assembly of FIG. 143 interfacing with a knife member, according to at least one aspect of the present disclosure.

Figure 146:
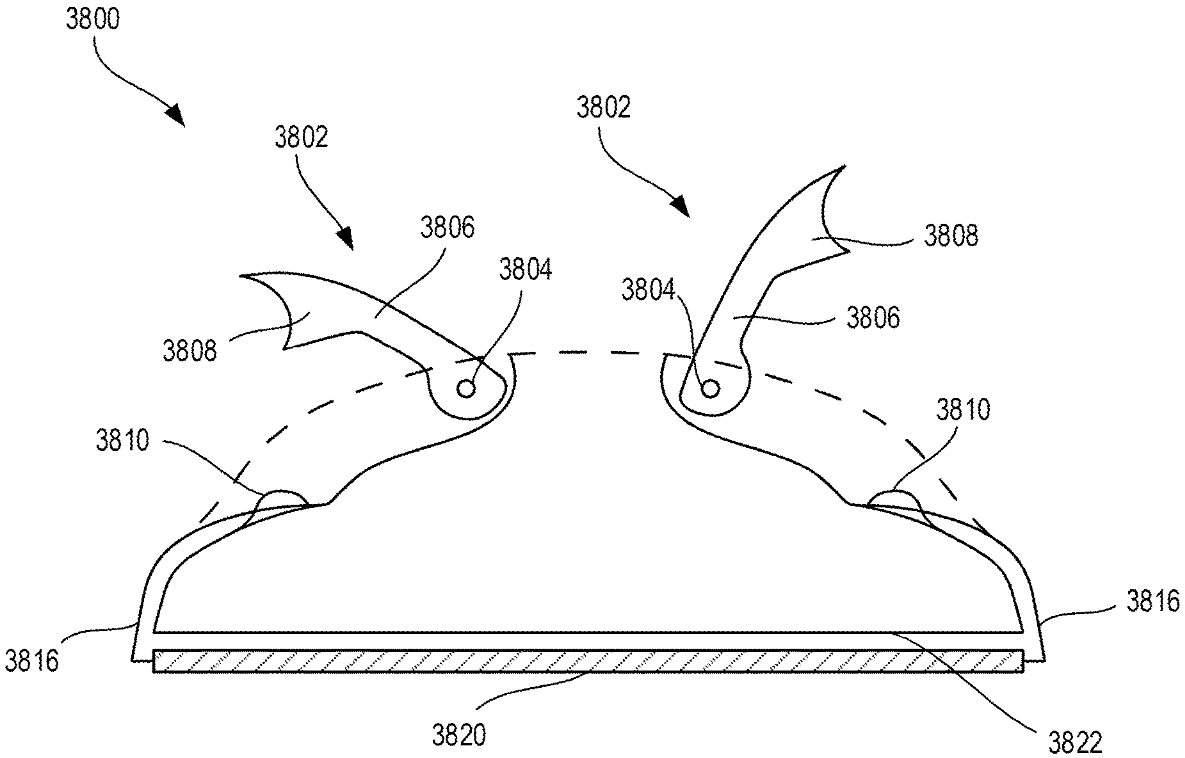
Figure 147:
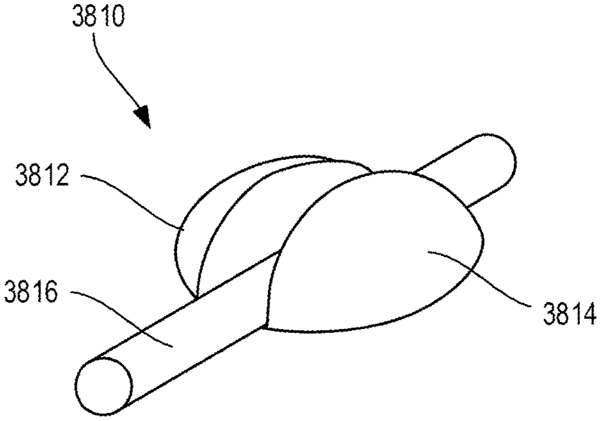

FIG. 146 illustrates an anvil interfacing with a buttress layer, according to at least aspect of the present disclose FIG. 147 illustrates a suture receiver, according to at least one aspect of the present disclosure.

Figure 148:
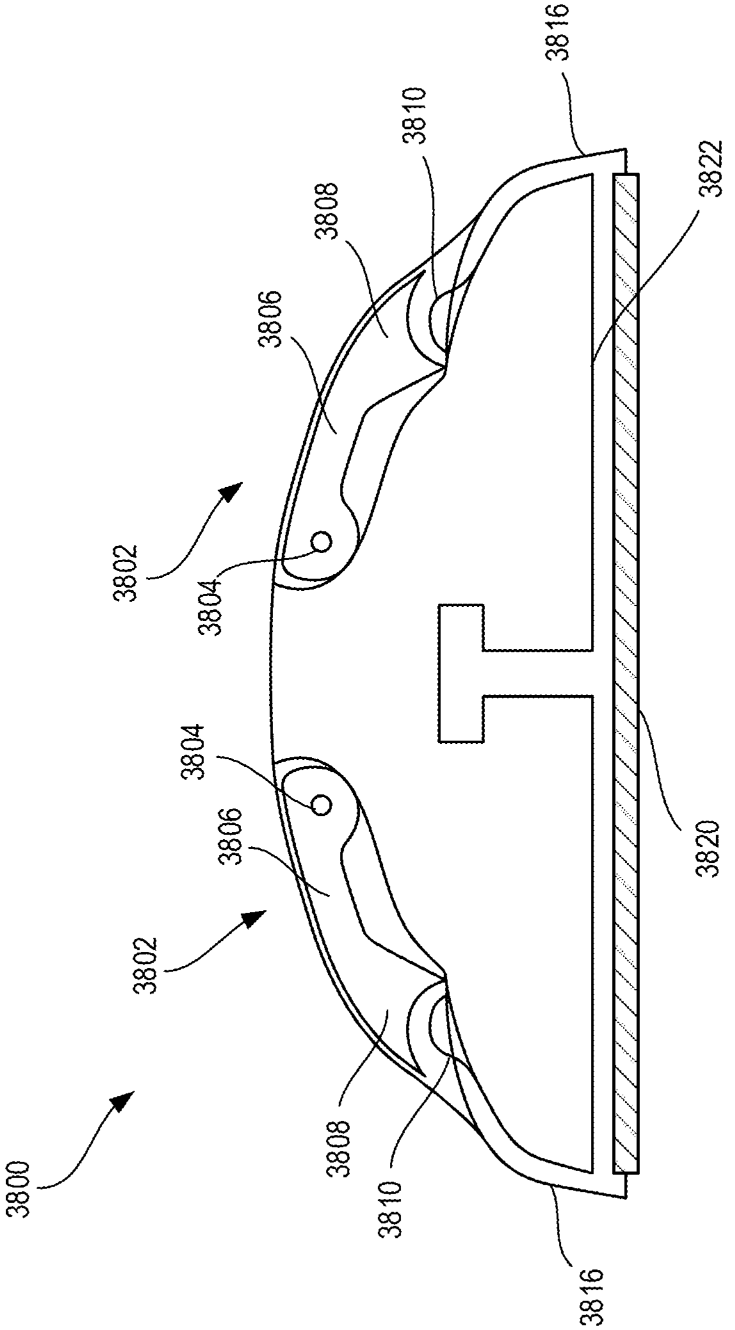

FIG. 148 illustrates the anvil and buttress layer of FIG. 146 coupled together, according to at least one aspect of the present disclosure.

Figure 149:
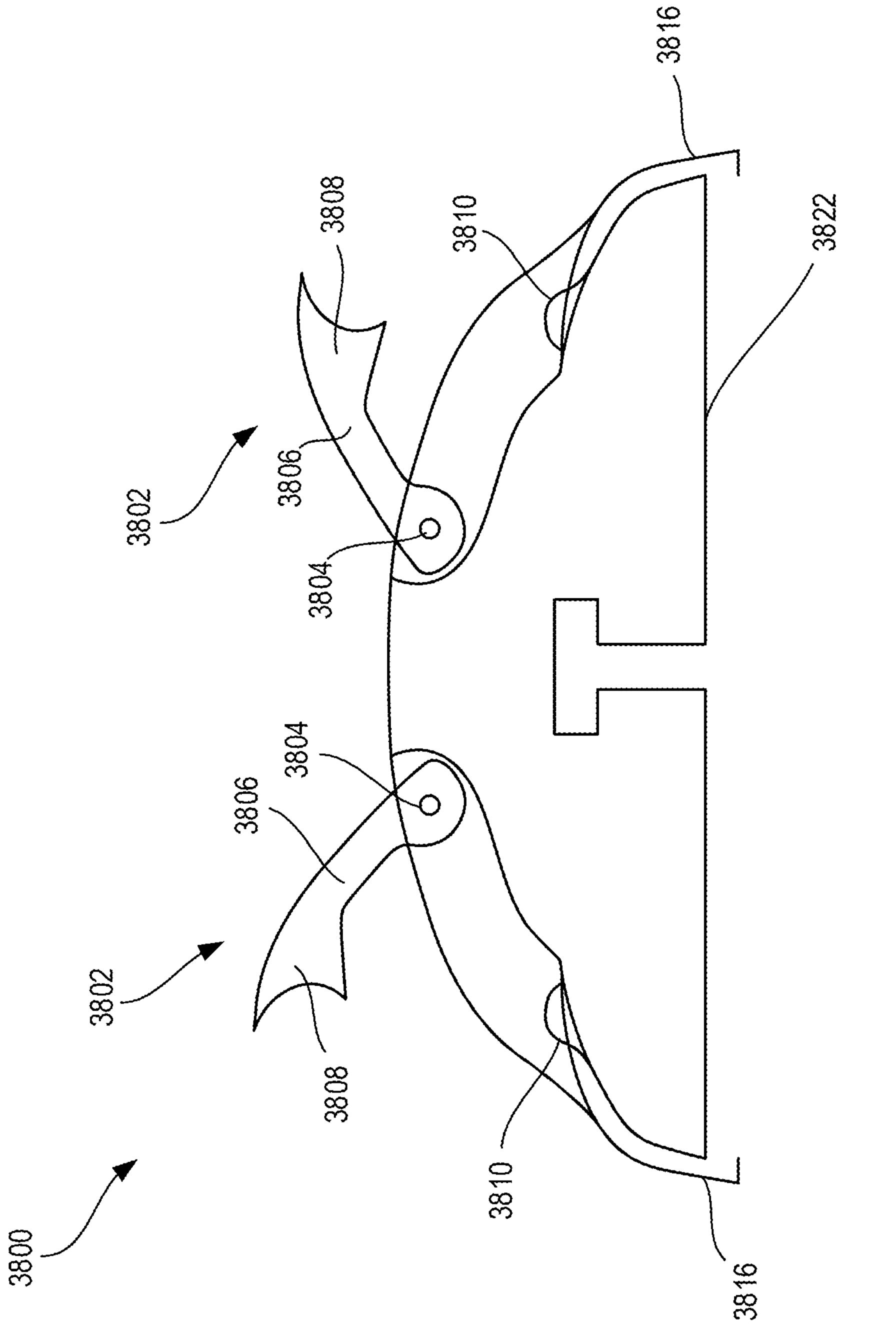

FIG. 149 illustrates the anvil of FIG. 146 decoupled from the buttress layer, according to at least one aspect of the present disclosure.

Figure 150:
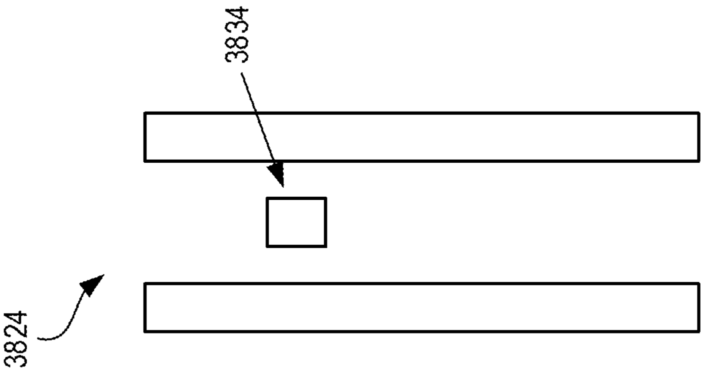

FIG. 150 illustrates a side view of a lockout mechanism, according to at least one aspect of the present disclosure.

Figure 151:
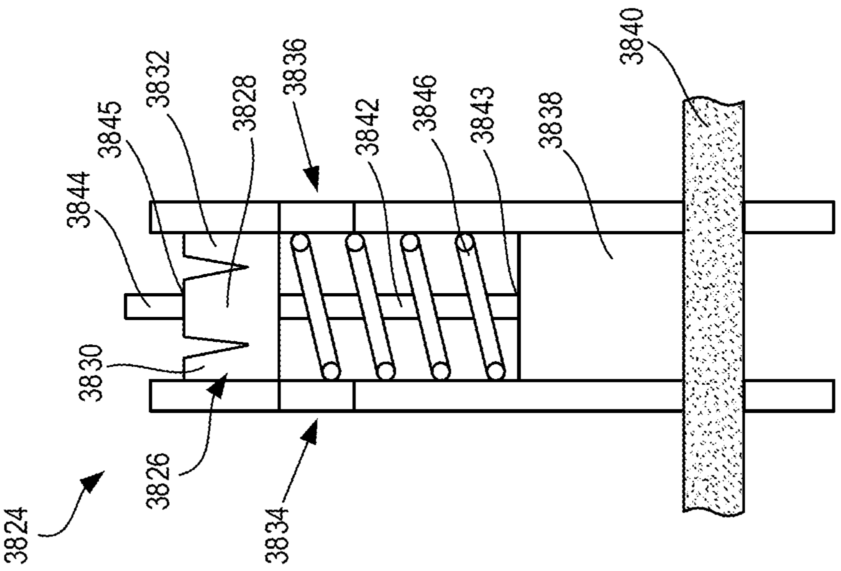

FIG. 151 illustrates a lockout mechanism in an unlocked state, according to at least one aspect of the present disclosure.

Figure 152:
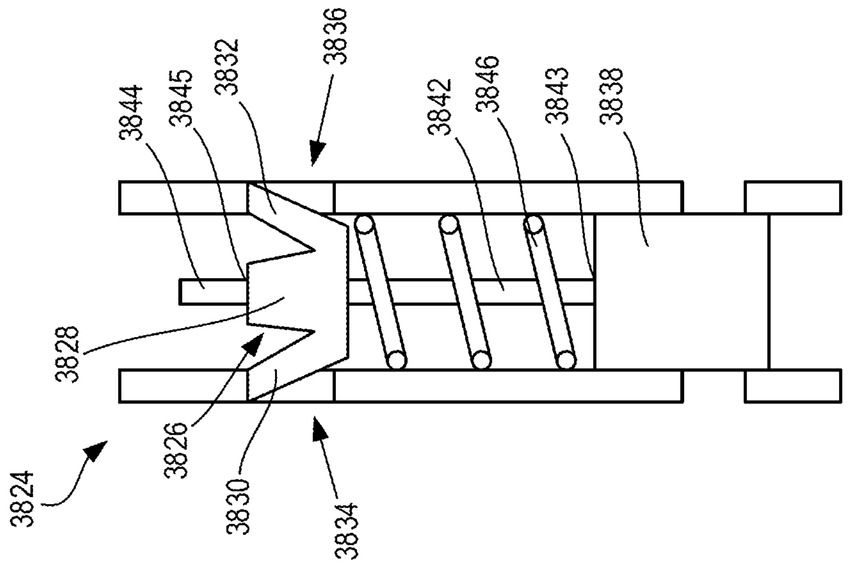

FIG. 152 illustrates a lockout mechanism in a lockout state, according to at least one aspect of the present disclosure.

Figure 153:
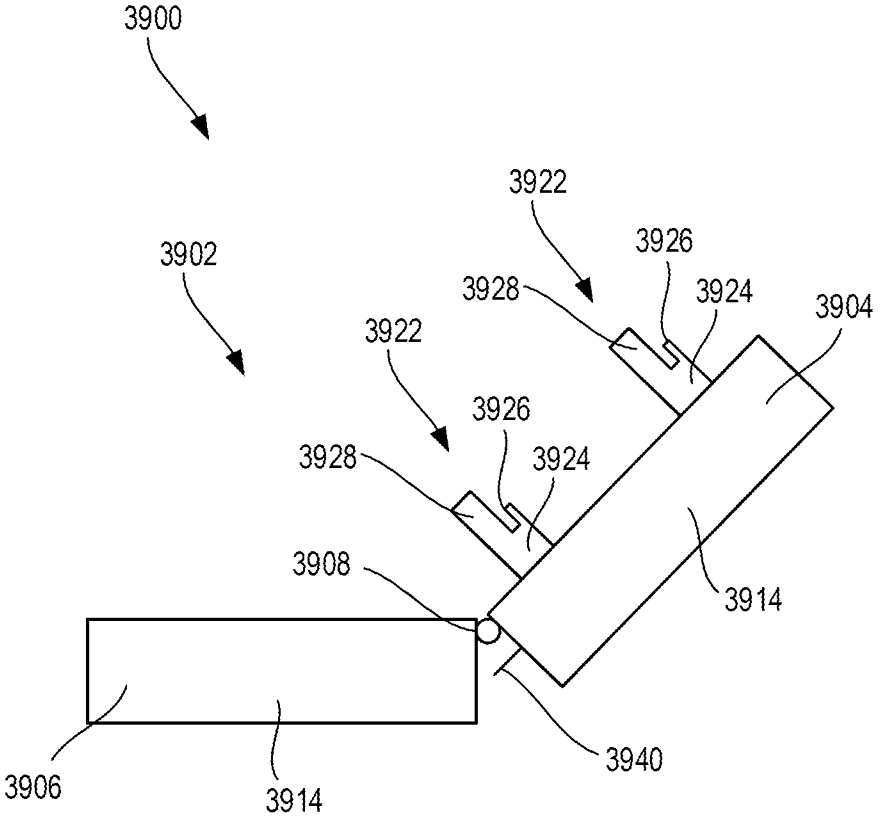

FIG. 153 illustrates a suture applier, according to at least one aspect of the present disclosure.

Figure 154:
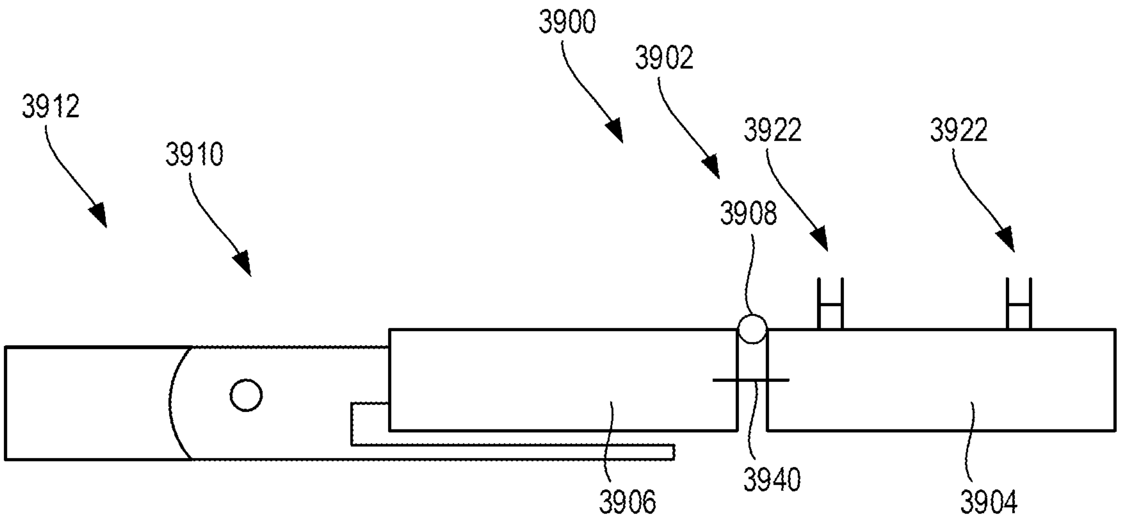

FIG. 154 illustrates the suture applier of FIG. 153 in an open position interfacing with an end effector, according to at least one aspect of the present disclosure.

Figure 155:
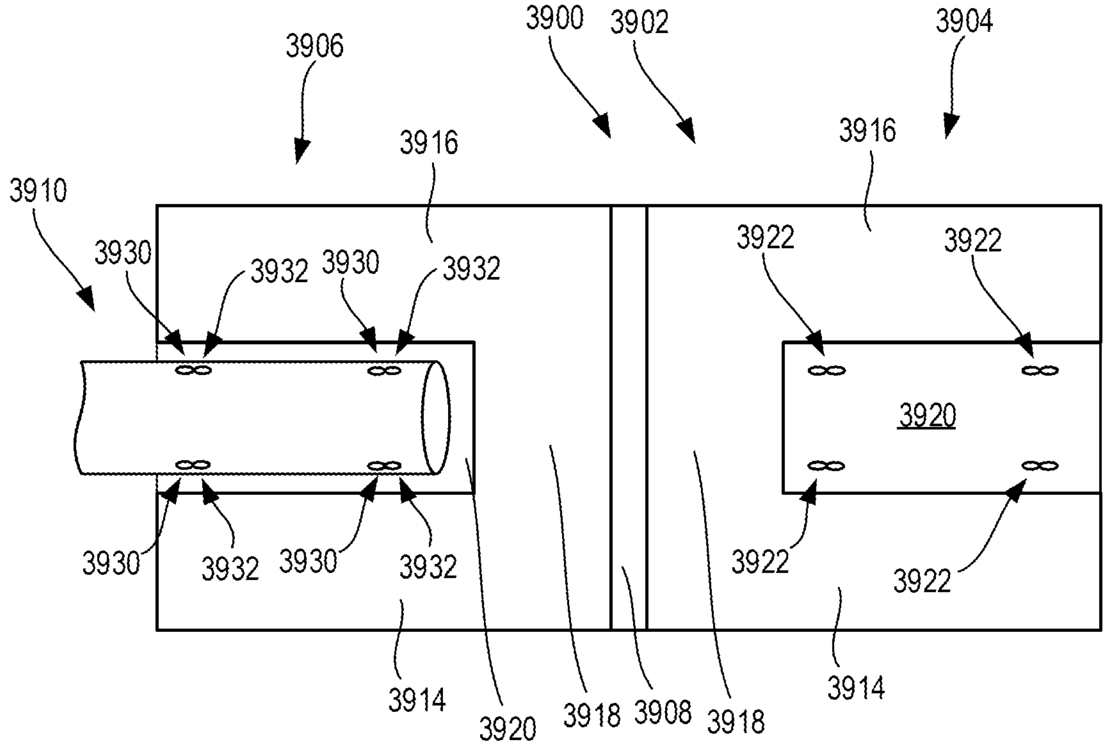

FIG. 155 illustrates a top view of FIG. 154, according to at least one aspect of the present disclosure.

Figure 156:
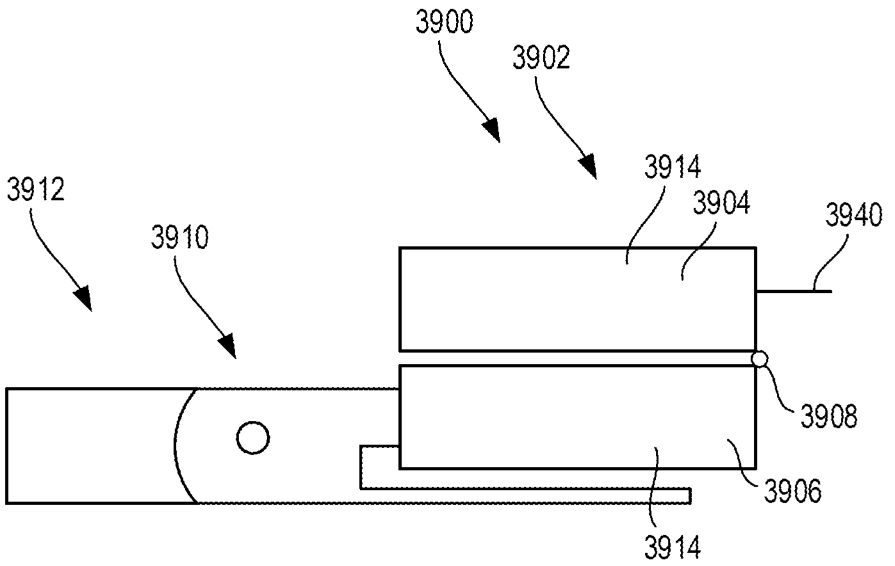

FIG. 156 illustrates the suture applier of FIG. 153 in a closed position interfacing with an end effector, according to at least one aspect of the present disclosure.

Figure 157:
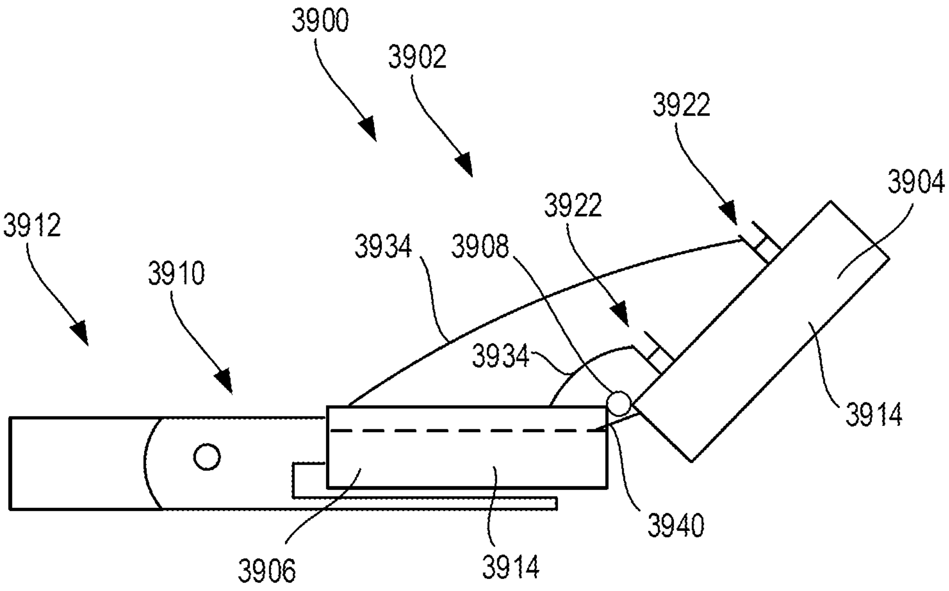

FIG. 157 illustrates the suture applier of FIG. 153 moving to the open position after closing onto the end effector, according to at least one aspect of the present disclosure.

Figure 158:
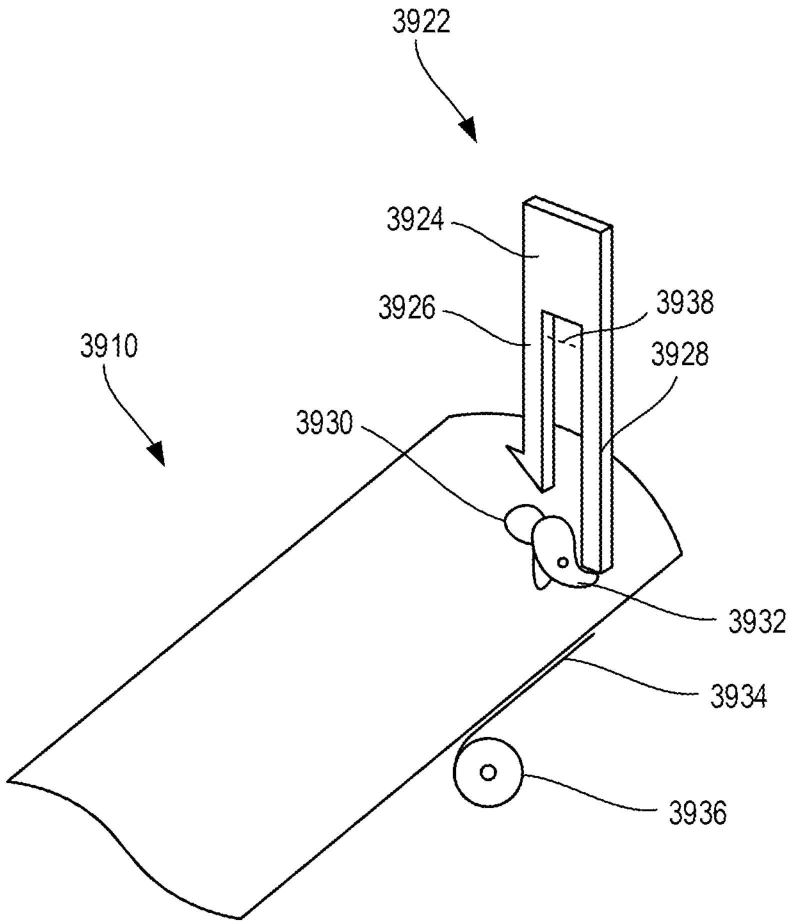

FIG. 158 illustrates a plunger assembly of the suture applier of FIG. 153, according to at least one aspect of the present disclosure.

Figure 159:
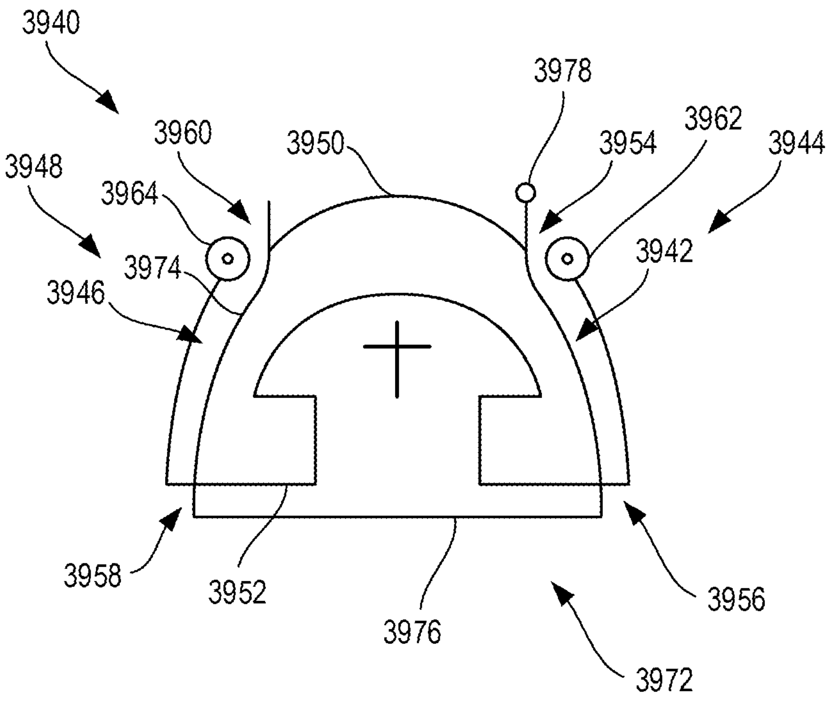

FIG. 159 illustrates an anvil, according to at least one aspect of the present disclosure.

Figure 160:
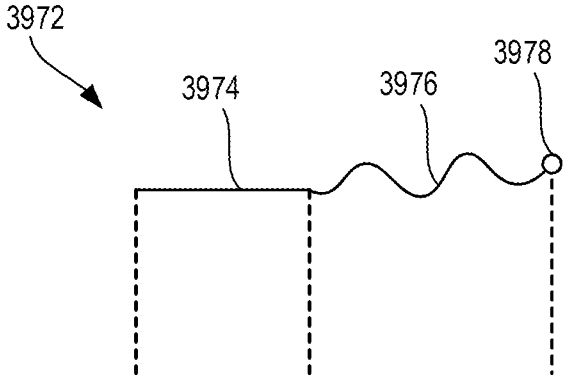

FIG. 160 illustrates a suture assembly, according to at least one aspect of the present disclosure.

Figure 161:
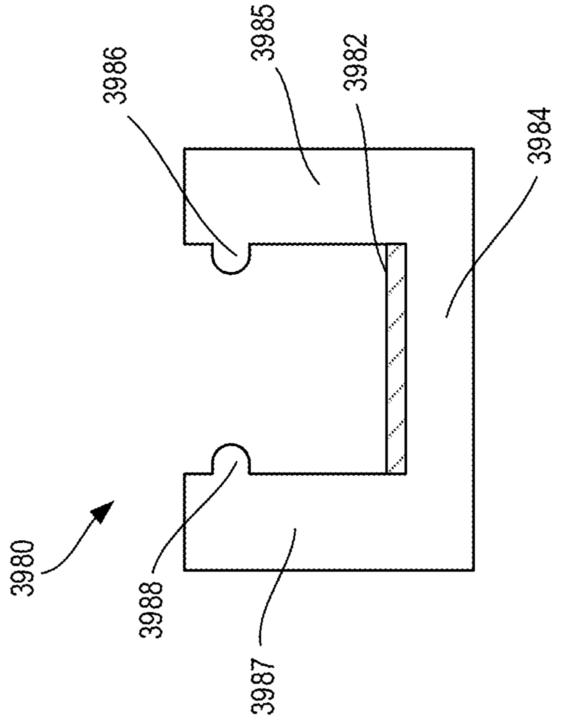

FIG. 161 illustrates a buttress cartridge usable with the anvil of FIG. 159, according to at least one aspect of the present disclosure.

Figures 42, 43, 44:
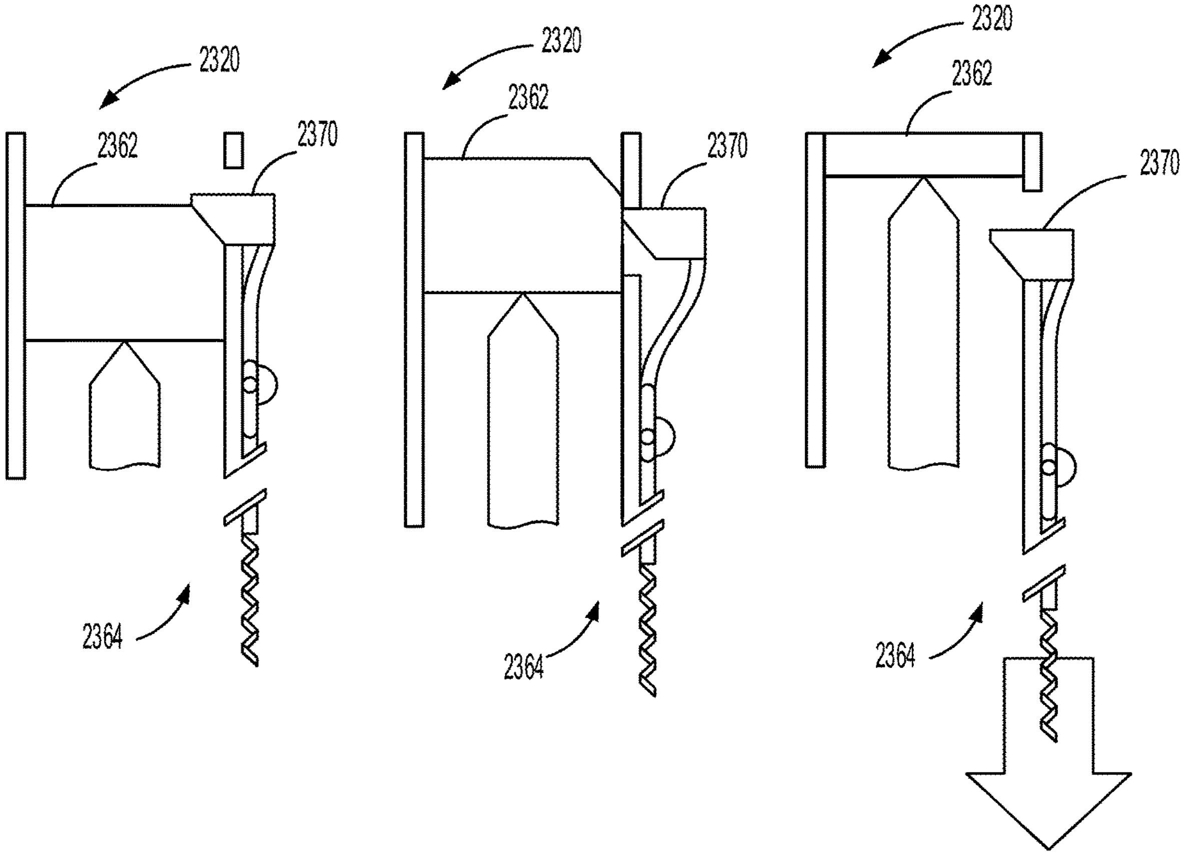
FIGS. 42-44 illustrate three positions of a sled over staple cartridge with respect to a retaining feature, in accordance with at least one aspect of the present disclosure.
Figure 162:
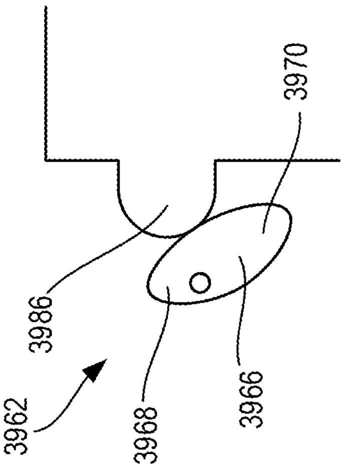

FIG. 162 illustrates an arm of the buttress cartridge of FIG. 161 contacting a cam lock of the anvil of FIG. 43, according to at least one aspect of the present disclosure.

Figure 163:
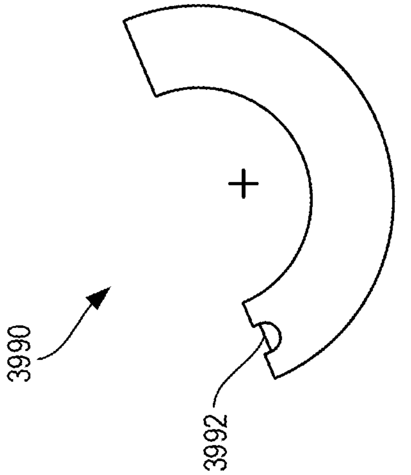

FIG. 163 illustrates a hooked shaped needle, according to at least one aspect of the present disclosure.

Figure 164:
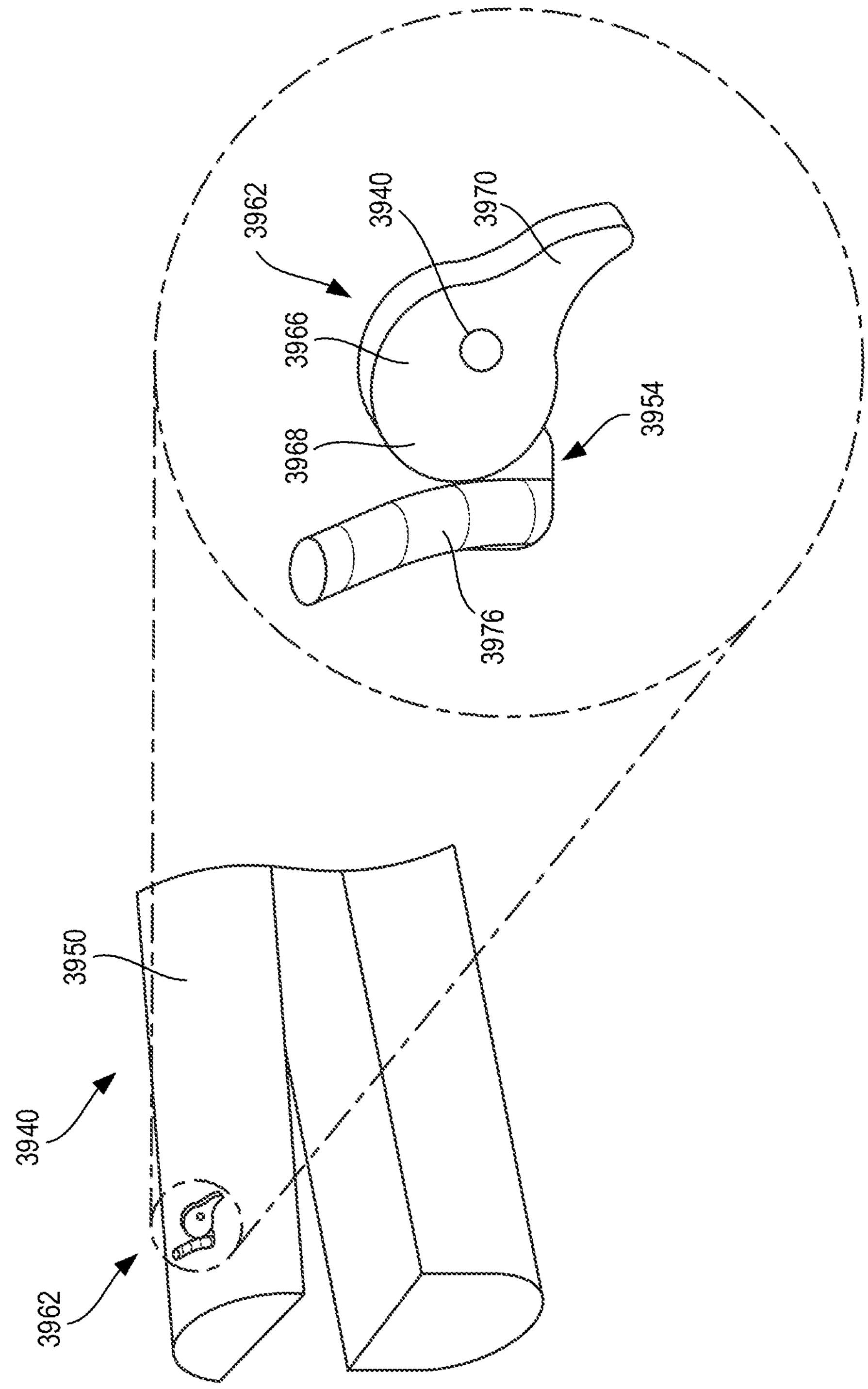

FIG. 164 illustrates a detailed view of a cam lock, according to at least one aspect of the present disclosure.

Figure 165:
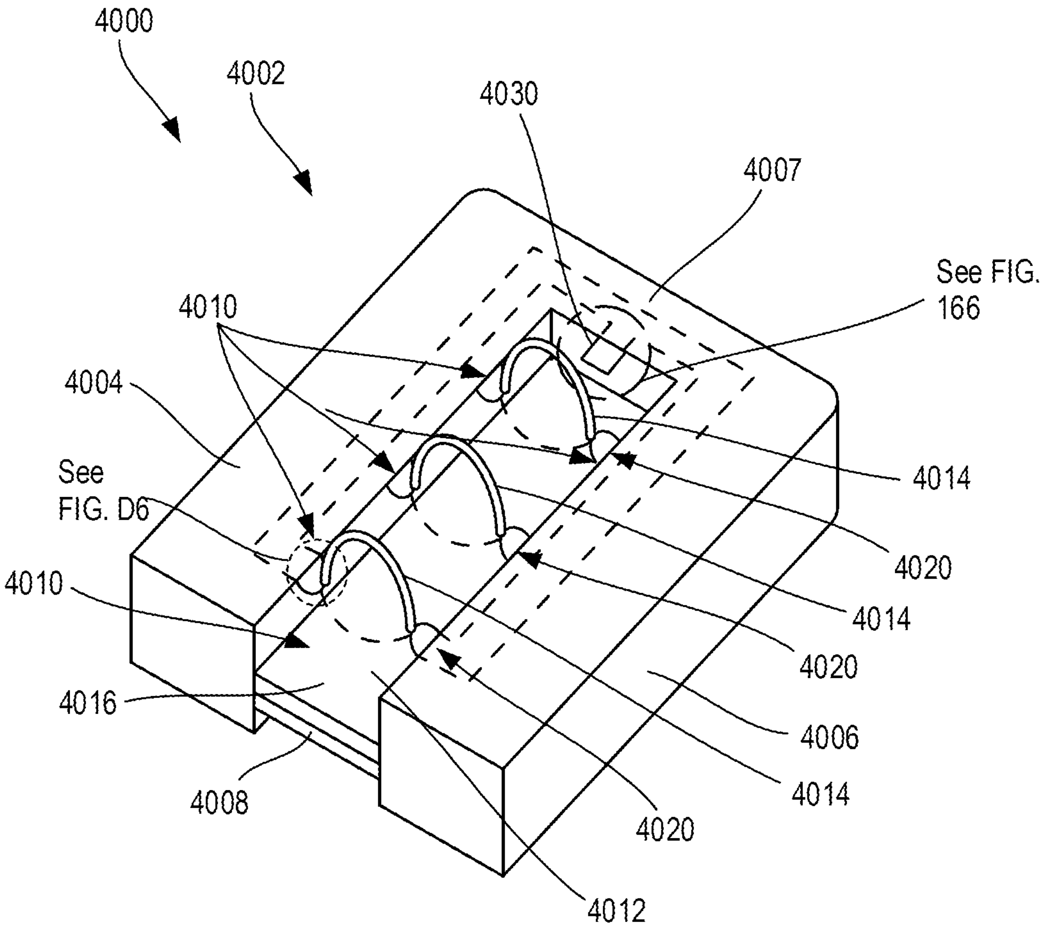

FIG. 165 illustrates a buttress applier cartridge, according to at least one aspect of the present disclosure.

Figure 166:
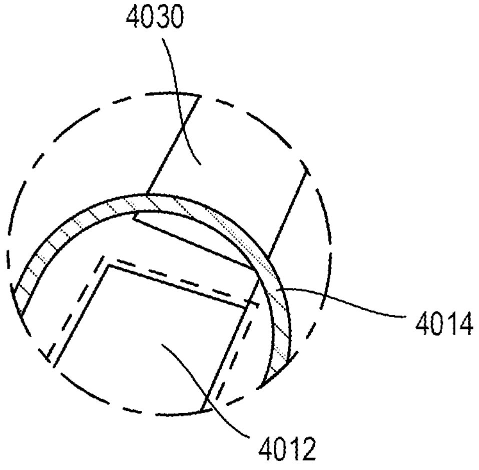

FIG. 166 illustrates a zoomed view of the buttress applier cartridge of FIG. 165, according to at least one aspect of the present disclosure.

Figure 167:
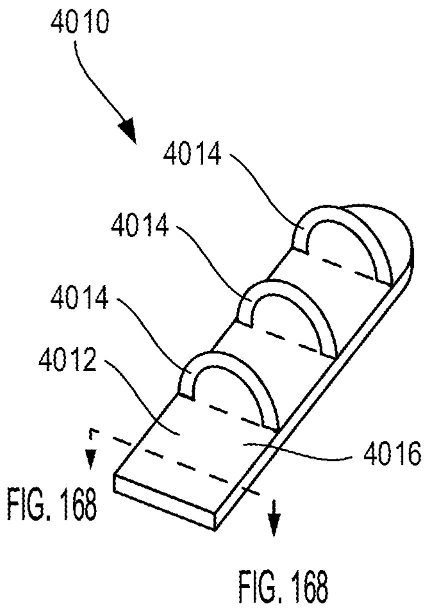

FIG. 167 illustrates a buttress assembly, according to at least one aspect of the present disclosure.

Figure 168:
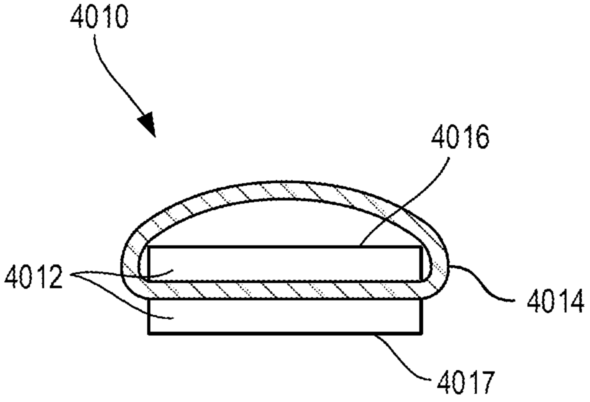

FIG. 168 illustrates a cross-sectional view of the buttress assembly of FIG. 167, according to at least one aspect of the present disclosure.

Figure 169:
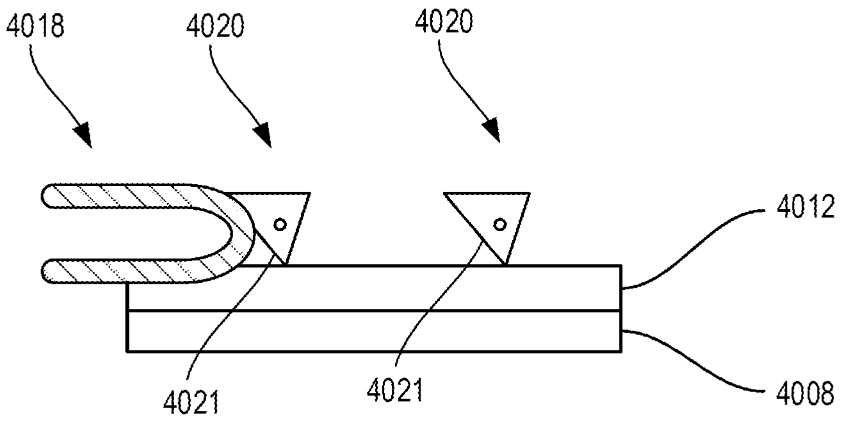

FIG. 169 illustrates an anvil interfacing with a proximal-most suture clamp of a buttress applier cartridge, according to at least one aspect of the present disclosure.

Figure 170:
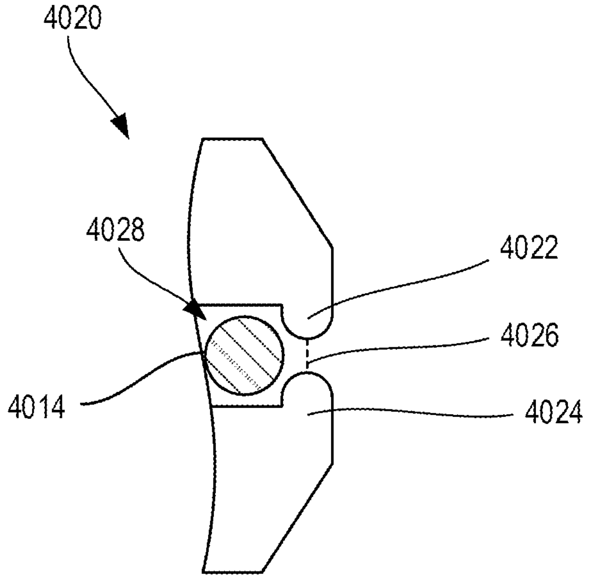

FIG. 170 illustrates a detailed, top view of a suture clamp, according to at least one aspect of the present disclosure.

Figure 171:
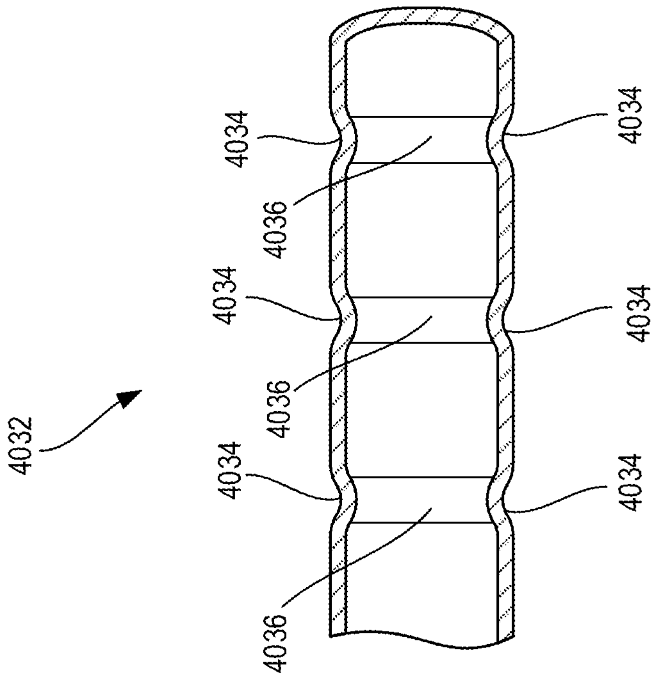

FIG. 171 illustrates an anvil, according to at least one aspect of the present disclosure.

Figure 172:
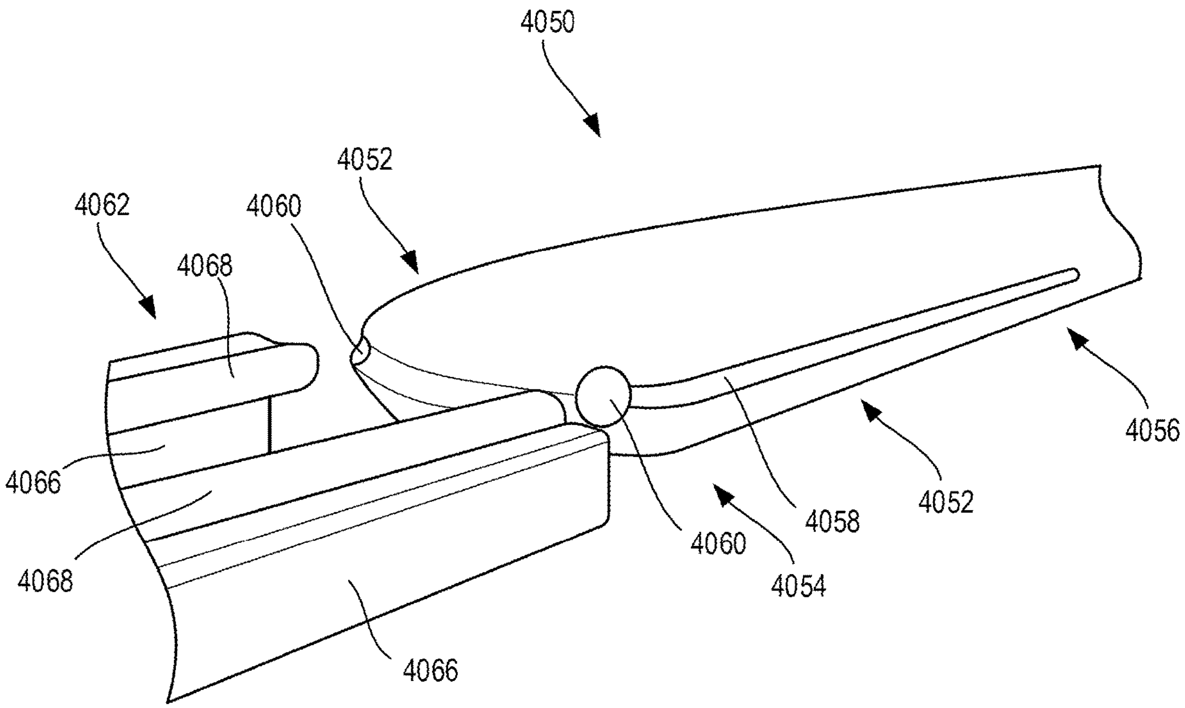

FIG. 172 illustrates an anvil interfacing with a buttress assembly, according to at least one aspect of the present disclosure.

Figure 173:
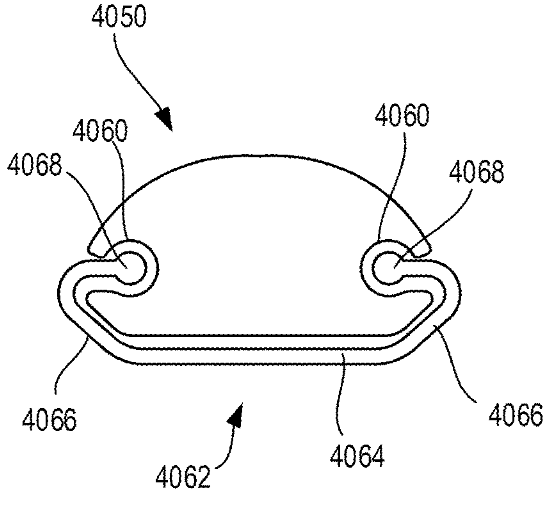

FIG. 173 illustrates a cross-sectional view of the buttress assembly of FIG. 172 positioned within the anvil of FIG. 172, according to at least one aspect of the present disclosure.

Figure 174:
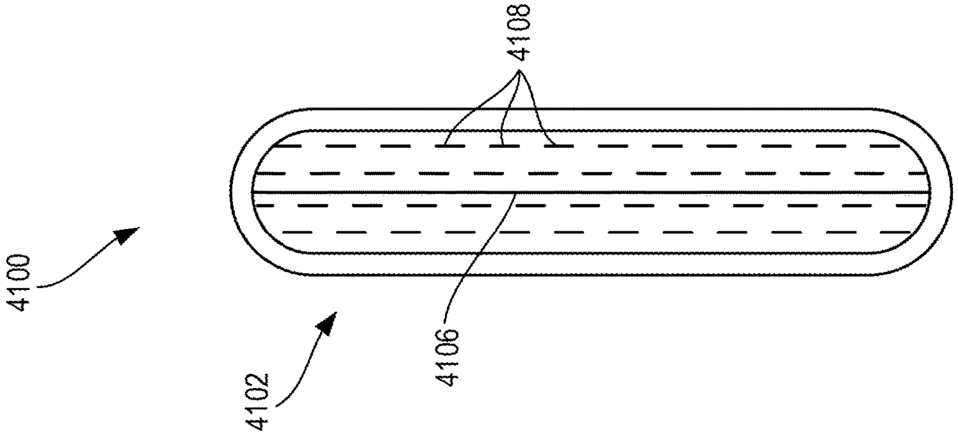

FIG. 174 illustrates a tissue contacting surface of an anvil, according to at least one aspect of the present disclosure.

Figure 175:
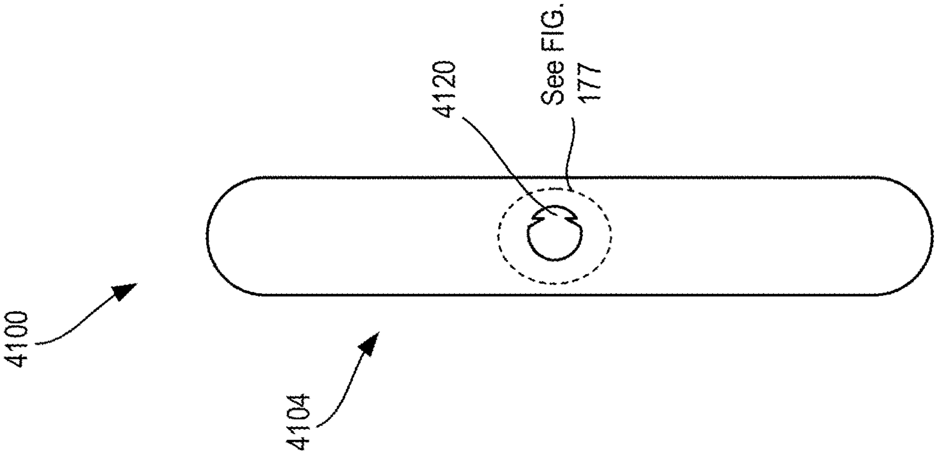

FIG. 175 illustrates an outer surface of the anvil of FIG. 174, according to at least one aspect of the present disclosure.

Figure 176:
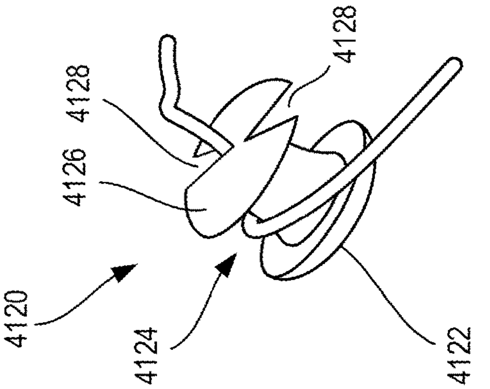

FIG. 176 illustrates an isometric view of a suture lock, according to at least one aspect of the present disclosure.

Figure 177:
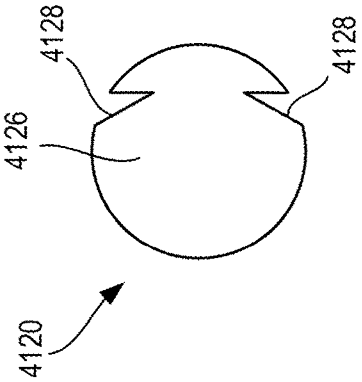

FIG. 177 illustrates a zoomed view of the suture lock of FIG. 175, according to at least one aspect of the present disclosure.

Figure 178:
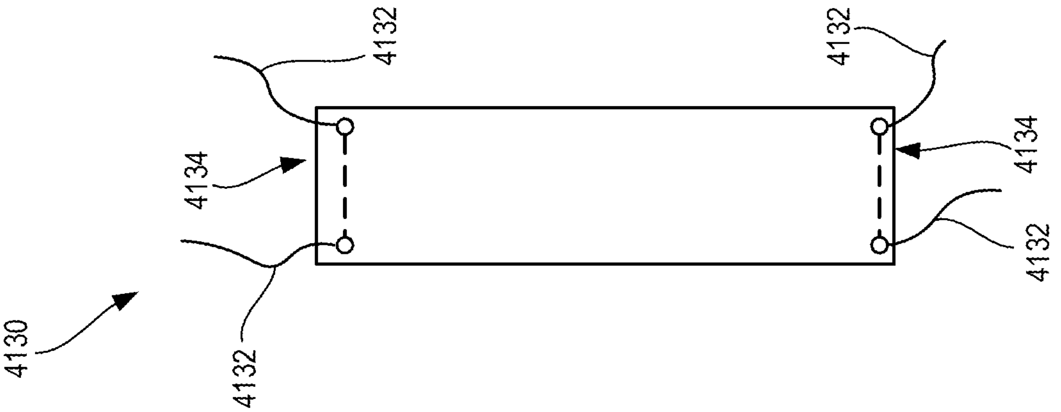

FIG. 178 illustrates a buttress layer, according to at least one aspect of the present disclosure.

Figure 179:
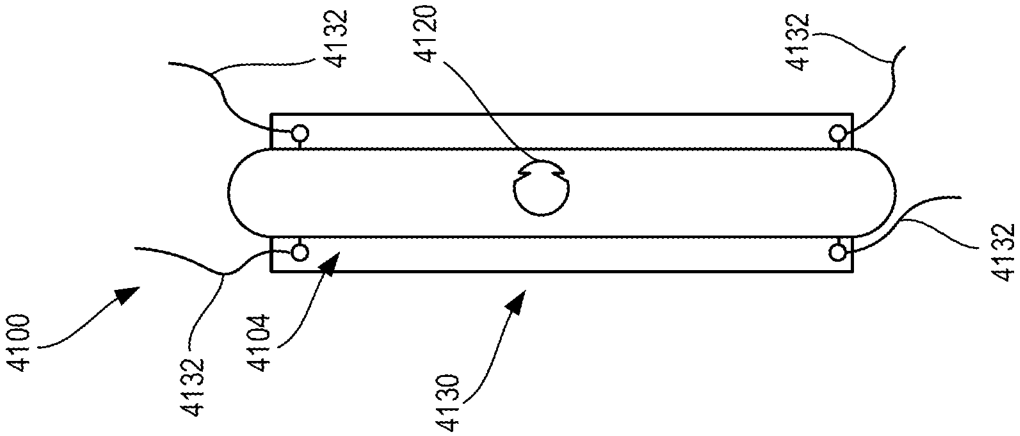

FIG. 179 illustrates the buttress layer of FIG. 178 interfacing with the anvil of FIG. 175, according to at least one aspect of the present disclosure.

Figure 180:
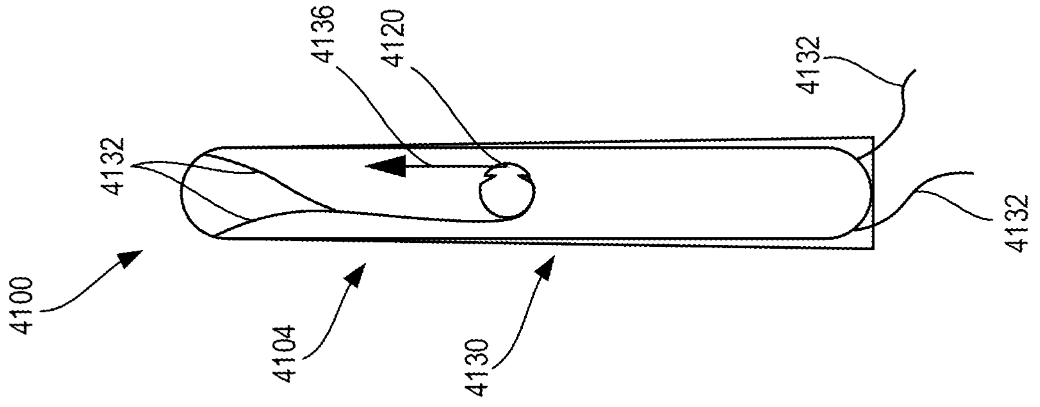

FIG. 180 illustrates distal-most suture legs of the buttress layer wrapping around the suture lock, according to at least one aspect of the present disclosure.

Figure 181:
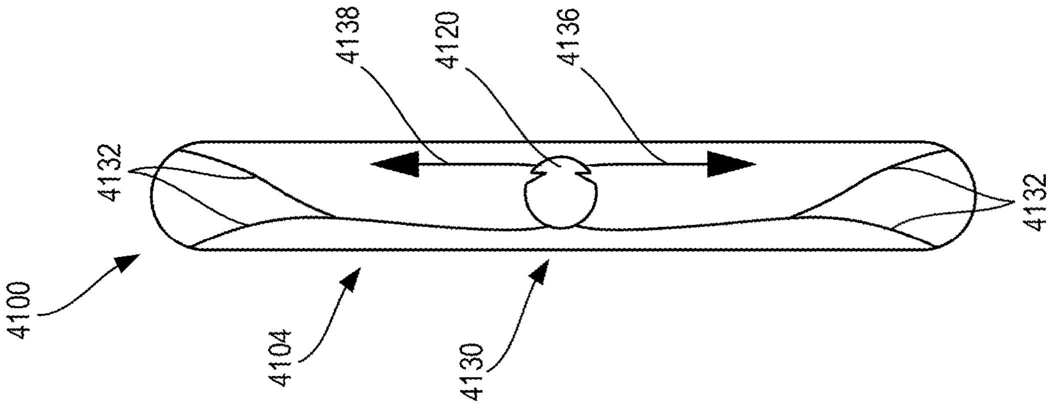

FIG. 181 illustrates proximal-most suture legs of the buttress layer wrapping around the suture lock, according to at least one aspect of the present disclosure.

Figure 182:
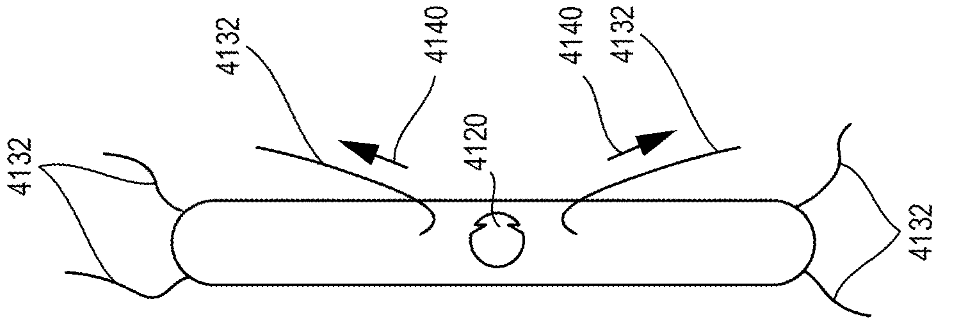

FIG. 182 illustrates the buttress layer being released from the anvil, according to at least one aspect of the present disclosure.

Figure 183:
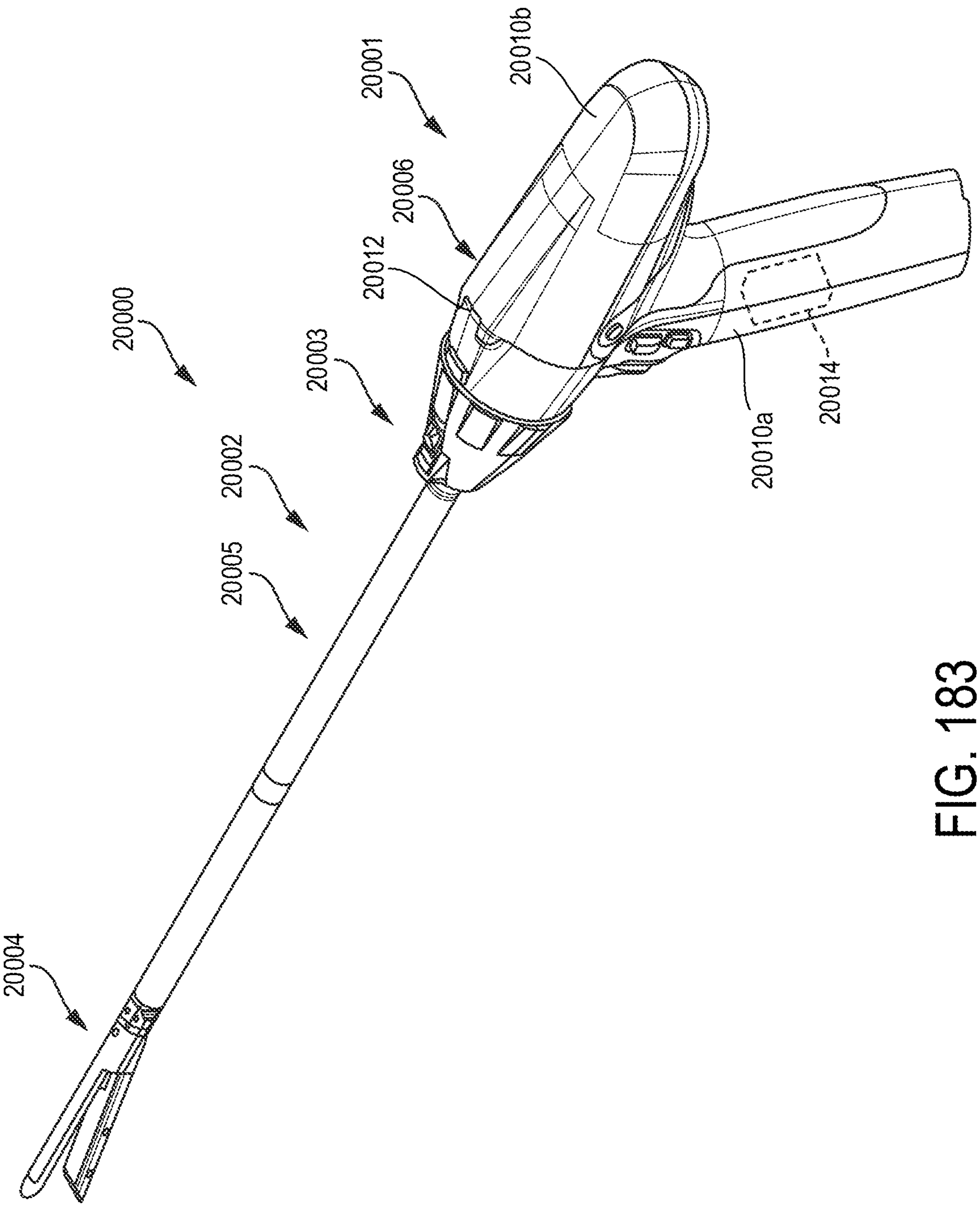

FIG. 183 illustrates an exemplary surgical device, according to at least one aspect of the present disclosure.

Figure 184:
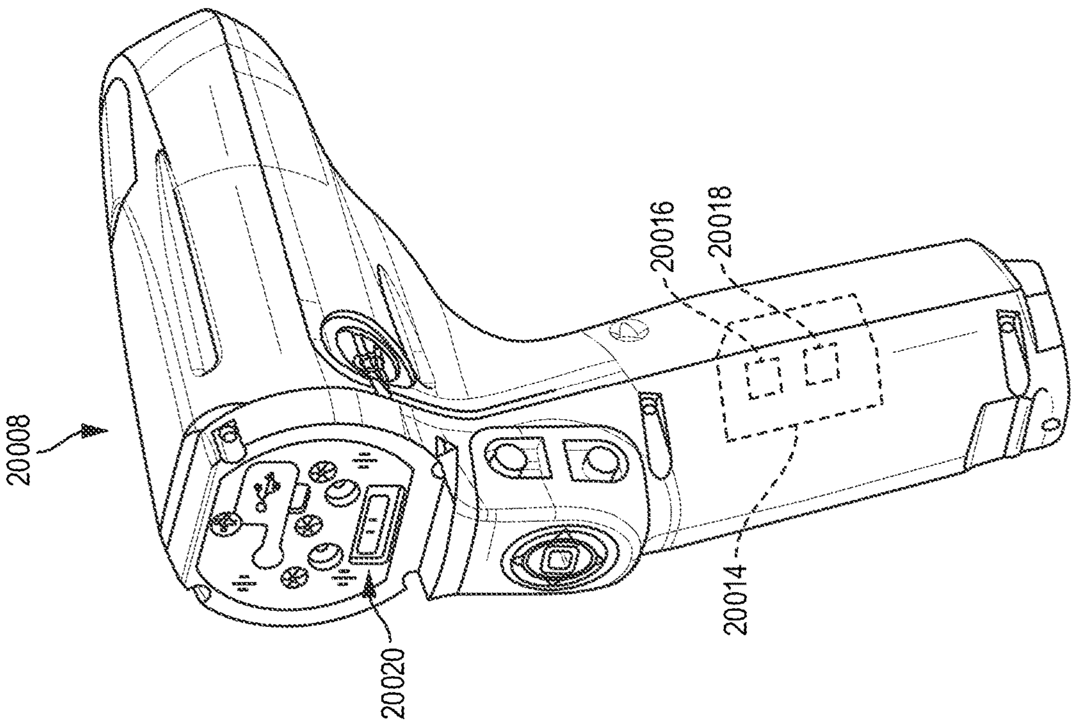

FIG. 184 illustrates a power-pack useable with the surgical device of FIG. 183, according to at least one aspect of the present disclosure.

Figure 185:
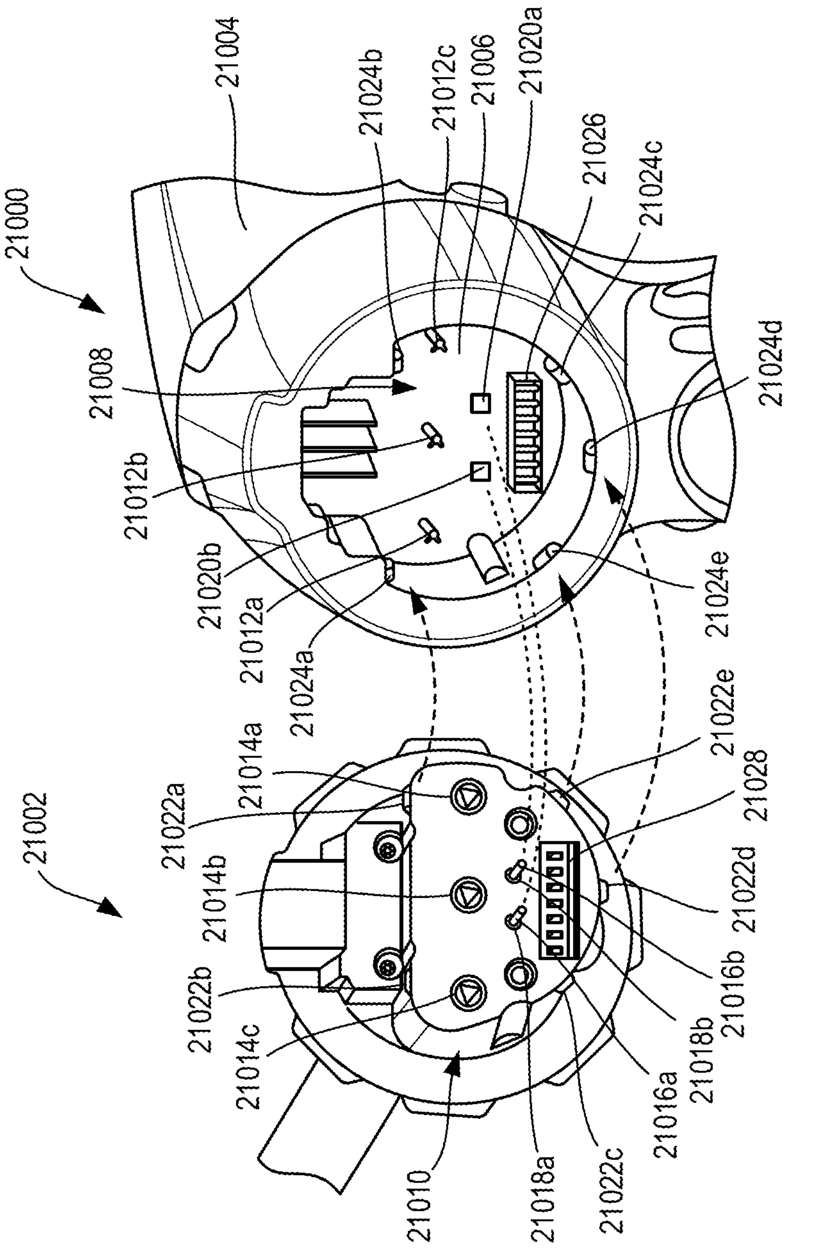

FIG. 185 illustrates a housing and an adapter selectively coupleable with the housing, according to at least one aspect of the present disclosure.

Figure 186:
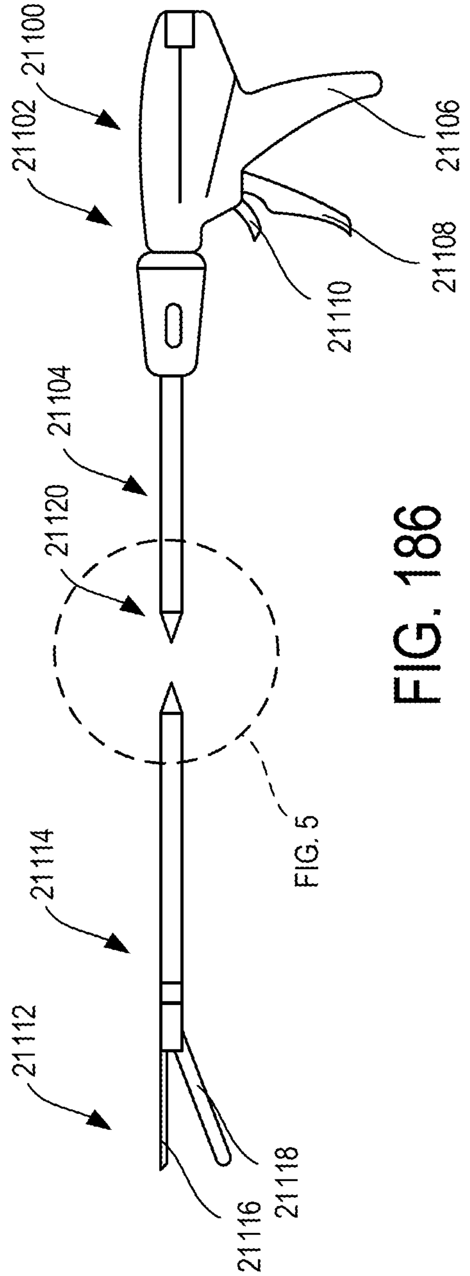

FIG. 186 illustrates a handle assembly and a loading unit, according to at least one aspect of the present disclosure.

Figure 187:
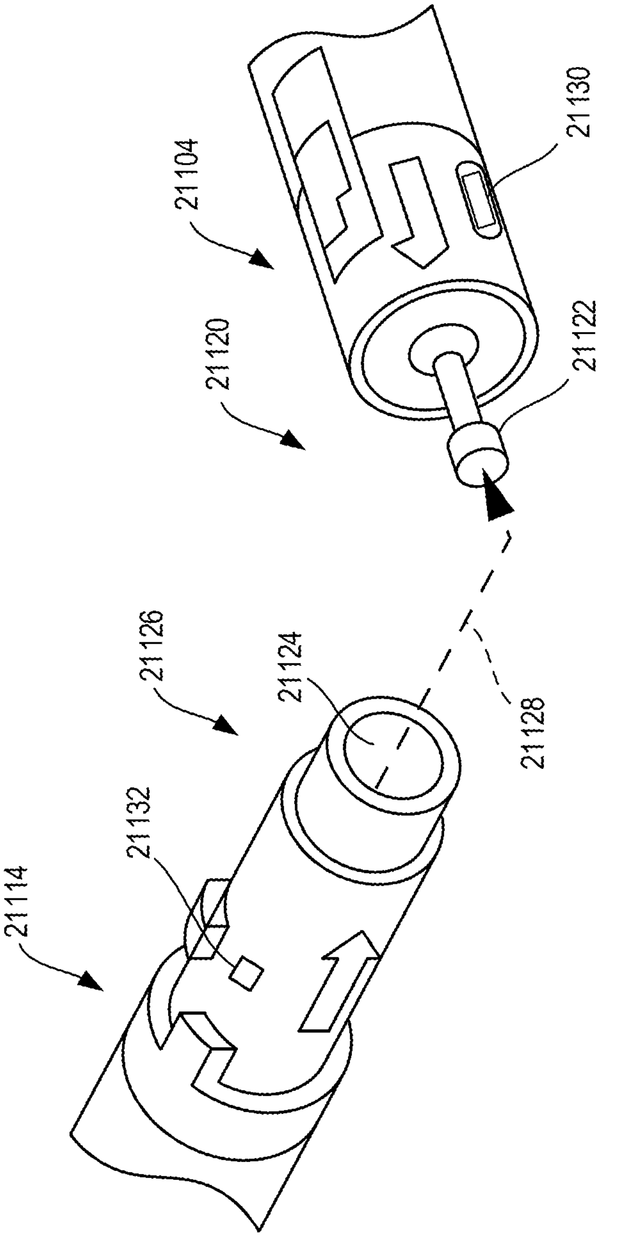

FIG. 187 illustrates a detailed view of the connection between the shaft assembly and the loading unit of FIG. 186, according to at least one aspect of the present disclosure.

Figure 188:
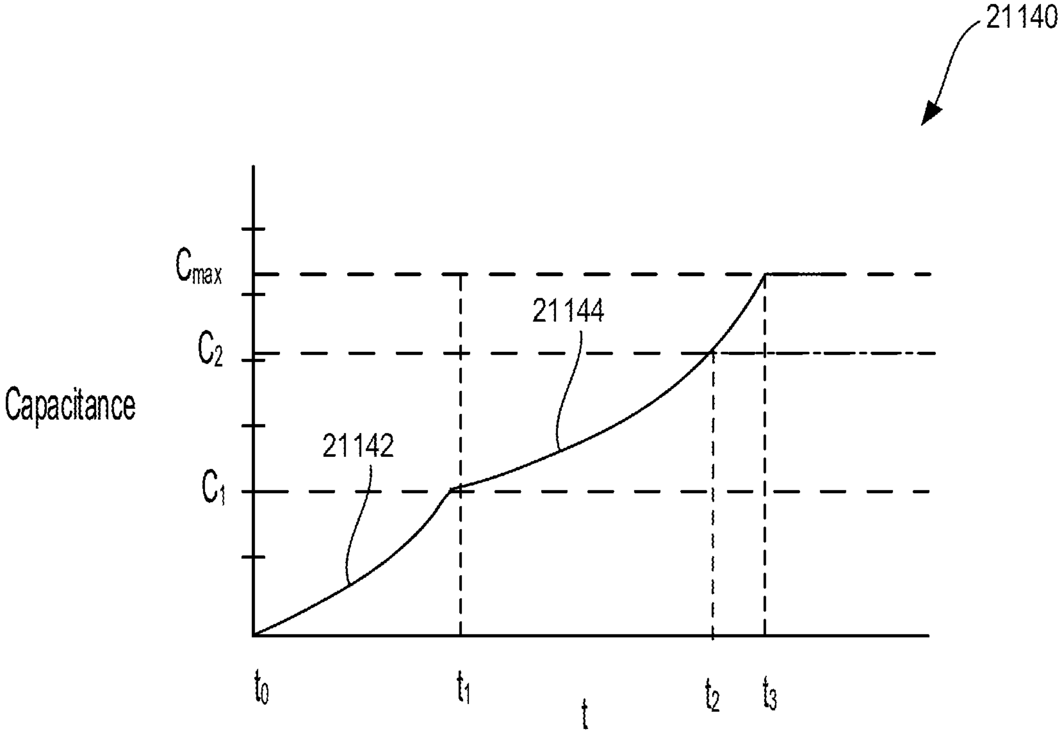

FIG. 188 illustrates a graphical representation of capacitance detected by a control circuit over time, according to at least one aspect of the present disclosure.

Figure 189:
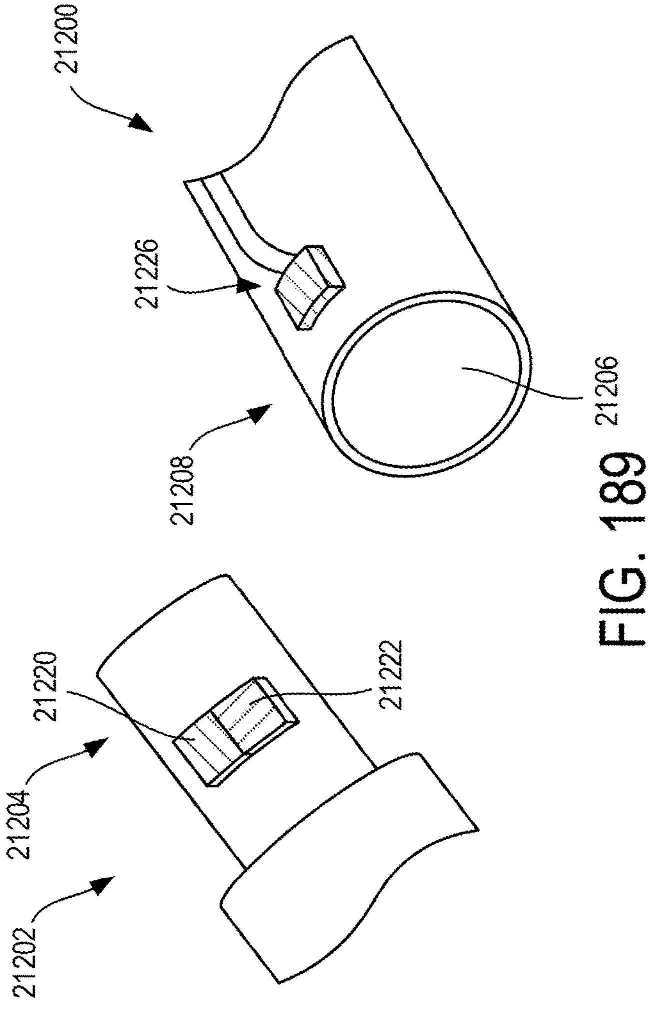

FIG. 189 illustrates a distal end of a shaft assembly and a proximal end of a loading unit, according to at least one aspect of the present disclosure.

Figure 190:
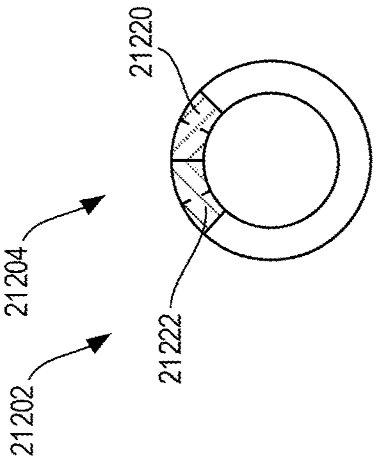

FIG. 190 illustrates a cross-sectional view of a loading unit, according to at least one aspect of the present disclosure.

Figure 191:
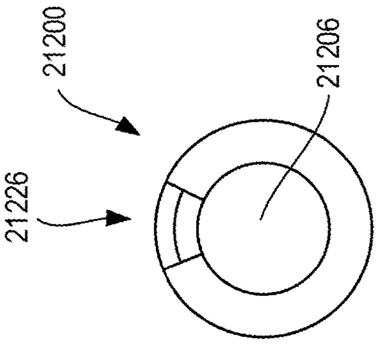

FIG. 191 illustrates a cross-sectional view of a shaft assembly, according to at least one aspect of the present disclosure.

Figure 192:
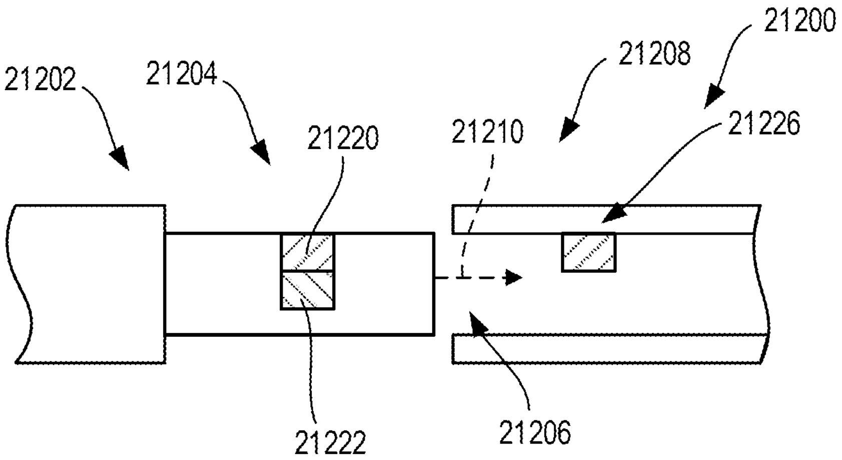

FIG. 192 illustrates the loading unit of FIG. 189 moving toward an aperture of the shaft assembly of FIG. 189 in an installation direction, according to at least one aspect of the present disclosure.

Figure 7:
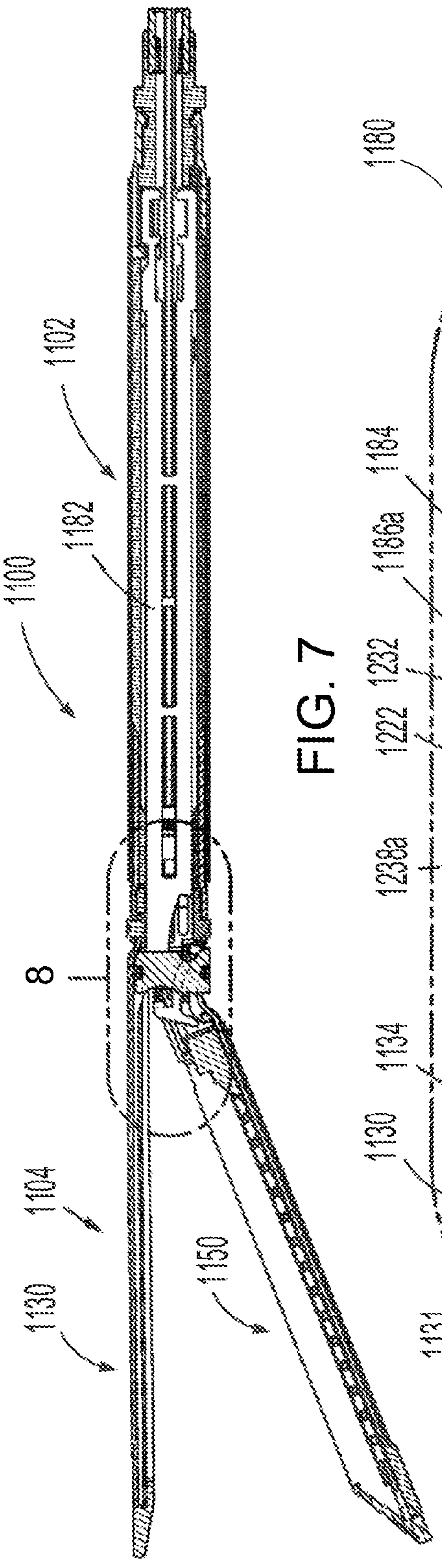
FIG. 7 is a cross-sectional view of a loading unit, in accordance with at least one aspect of the present disclosure.
Figure 193:
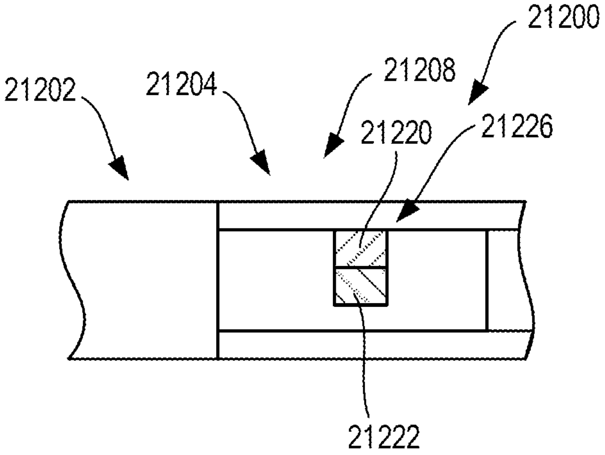

FIG. 193 illustrates the loading unit of FIG. 189 in an unlocked position with the shaft assembly of FIG. 7, according to at least one aspect of the present disclosure.

Figure 194:
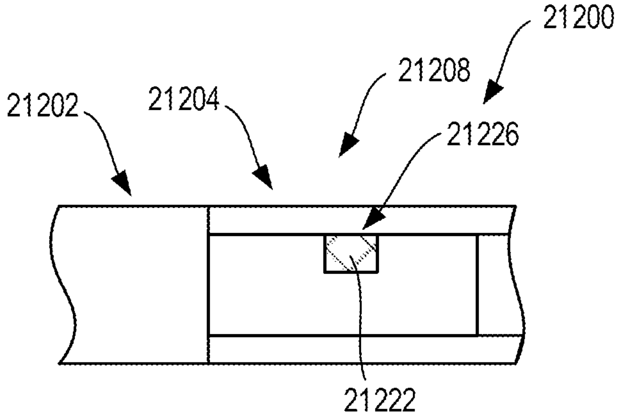

FIG. 194 illustrates the loading unit of FIG. 189 in a locked position with the shaft assembly of FIG. 7 according to at least one aspect of the present disclosure.

Figure 195:
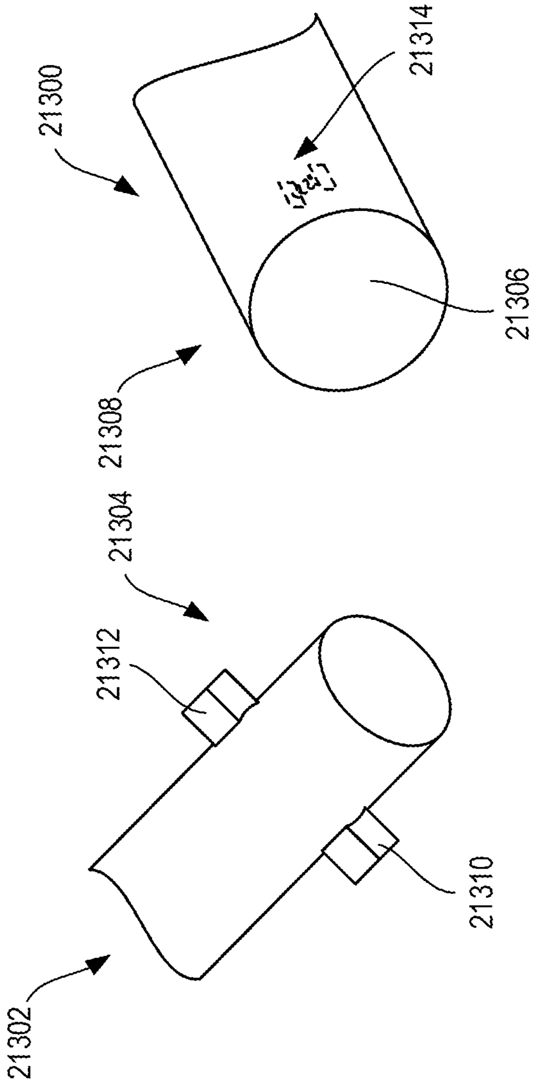

FIG. 195 illustrates a distal end of a shaft assembly and a proximal end of a loading unit, according to at least one aspect of the present disclosure.

Figure 196:
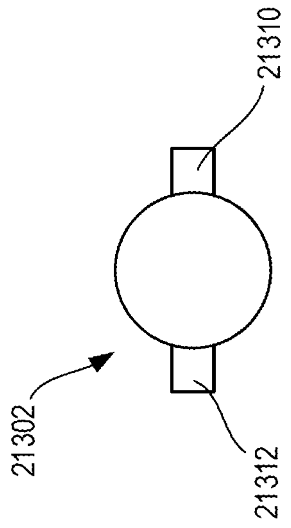

FIG. 196 illustrates a cross-sectional view of the loading unit of FIG. 195, according to at least one aspect of the present disclosure.

Figure 197:
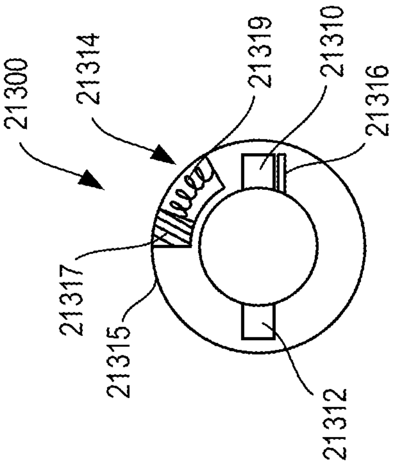

FIG. 197 illustrates a cross-sectional view of the loading unit of FIG. 195 in an unlocked position with the shaft assembly of FIG. 195, according to at least one aspect of the present disclosure.

Figure 198:
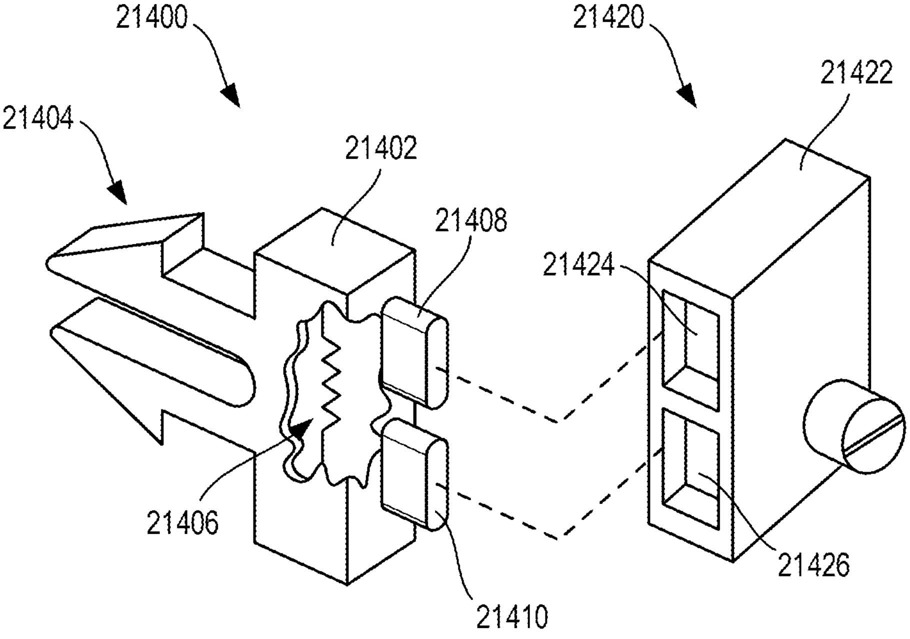

FIG. 198 illustrates a receptacle assembly and a resistor assembly, according to at least one aspect of the present disclosure.

Figure 199:
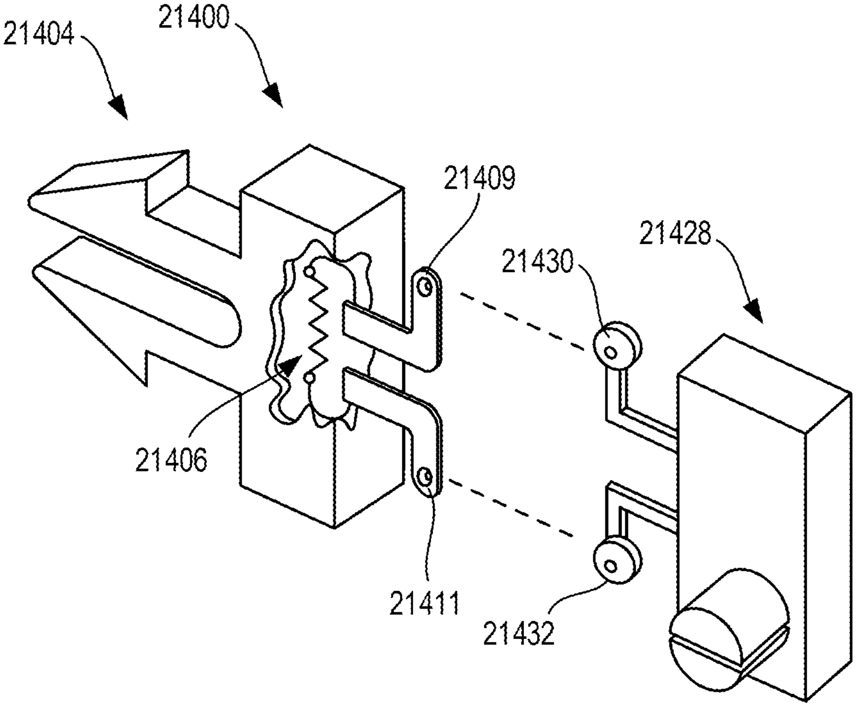

FIG. 199 illustrates a circuit and a resistor assembly, according to at least one aspect of the present disclosure.

Figure 200:
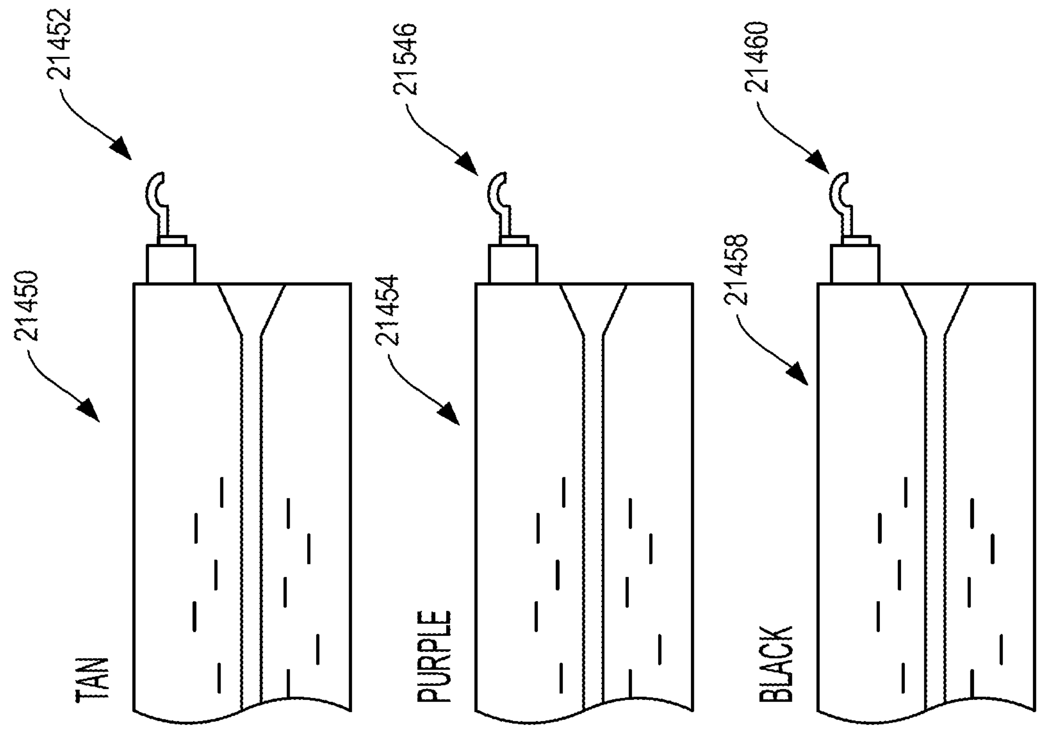

FIG. 200 illustrates a plurality of staple cartridges including resistor assemblies coupled thereto, according to at least one aspect of the present disclosure.

Figure 201:
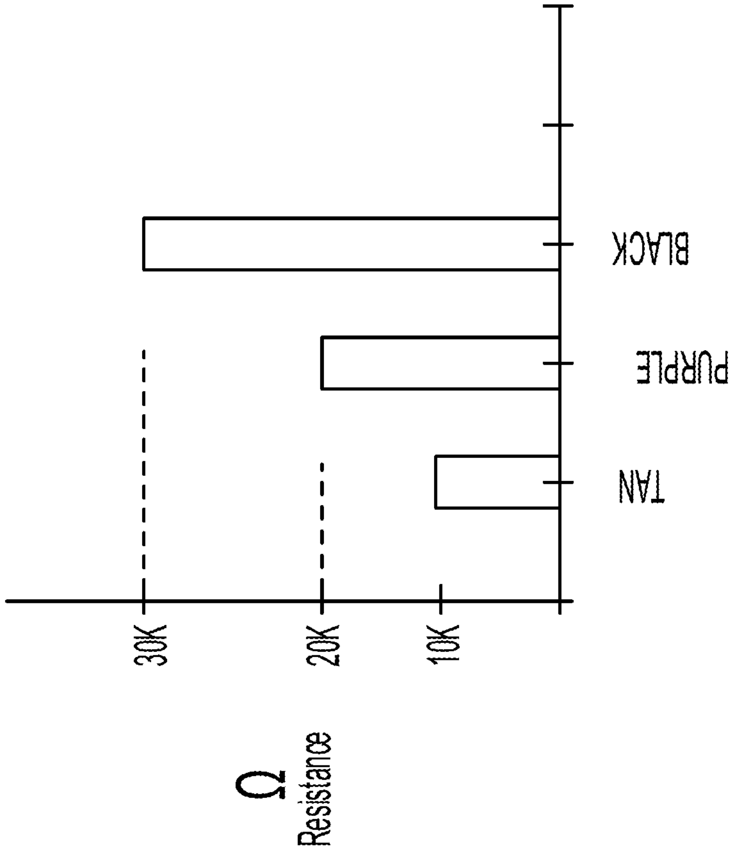

FIG. 201 illustrates a graphical representation of resistances determined by a control circuit of the resistor assemblies of FIG. 200, according to at least one aspect of the present disclosure.

Figure 202:
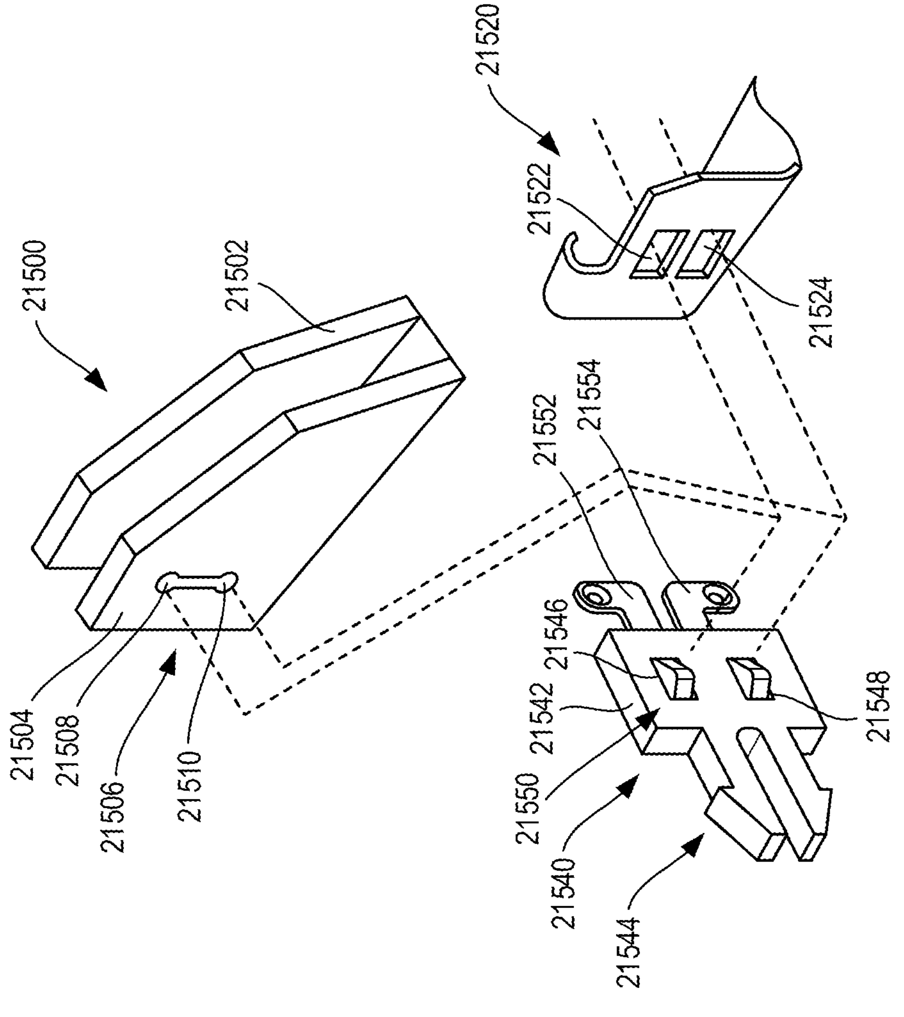

FIG. 202 illustrates an exploded view of a mechanism for determining if a staple cartridge is properly seated in a cartridge channel, according to at least one aspect of the present disclosure.

Figure 203:
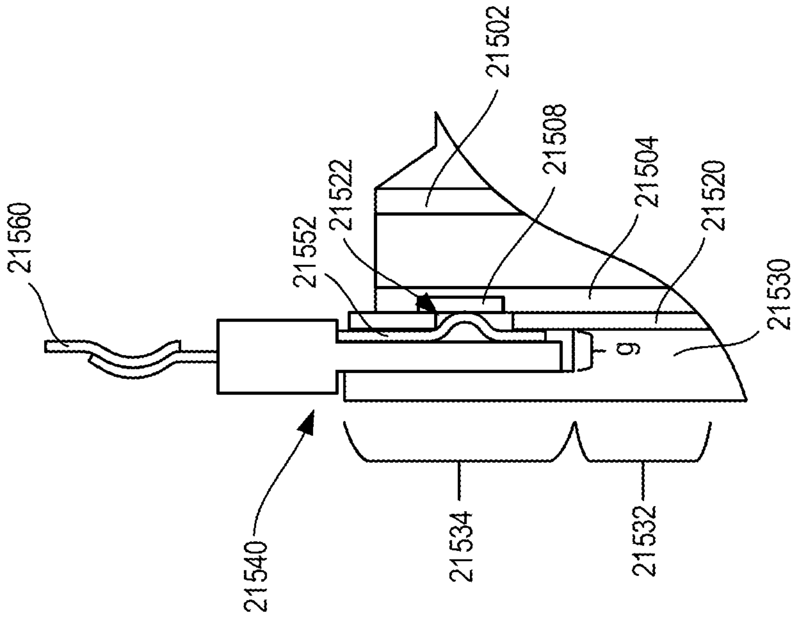

FIG. 203 illustrates an unexploded view of the mechanism of FIG. 202, according to at least one aspect of the present disclosure.

Figure 204:
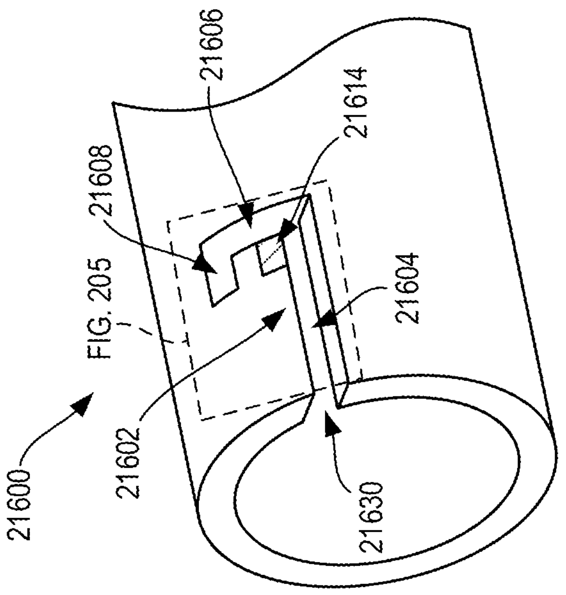

FIG. 204 illustrates a shaft assembly including a J-shaped passage defined therein and a closed-end tunnel including a magnet therein, according to at least one aspect of the present disclosure.

Figure 205:
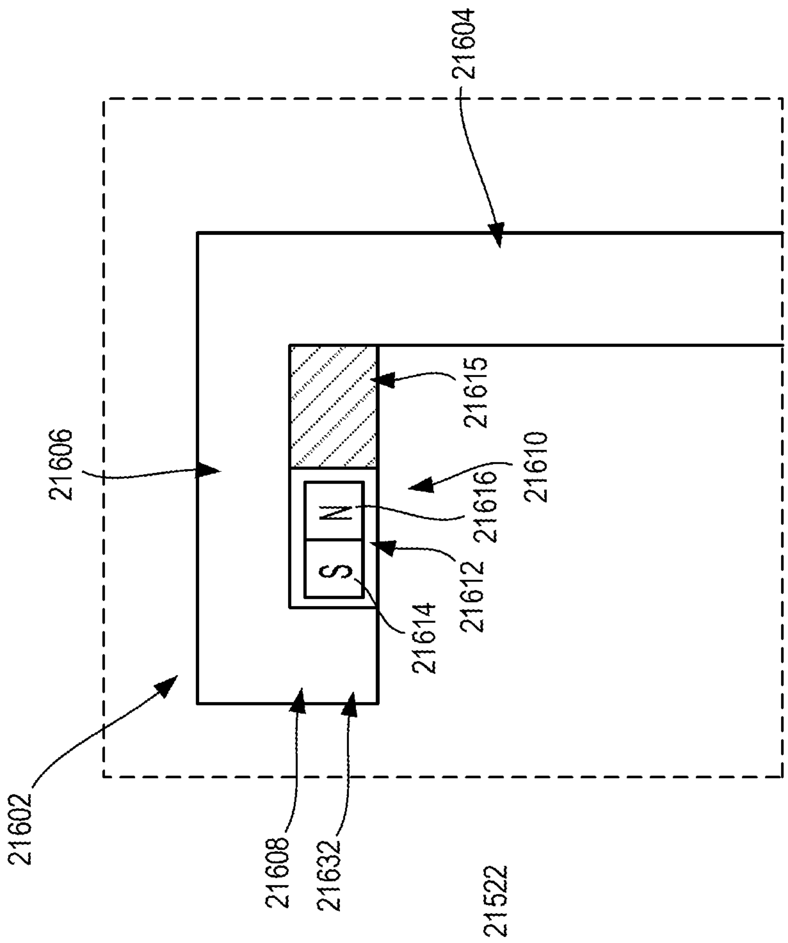

FIG. 205 illustrates a detailed view of the J-shaped passage and the closed-end tunnel of FIG. 205, according to at least one aspect of the present disclosure.

Figure 206:
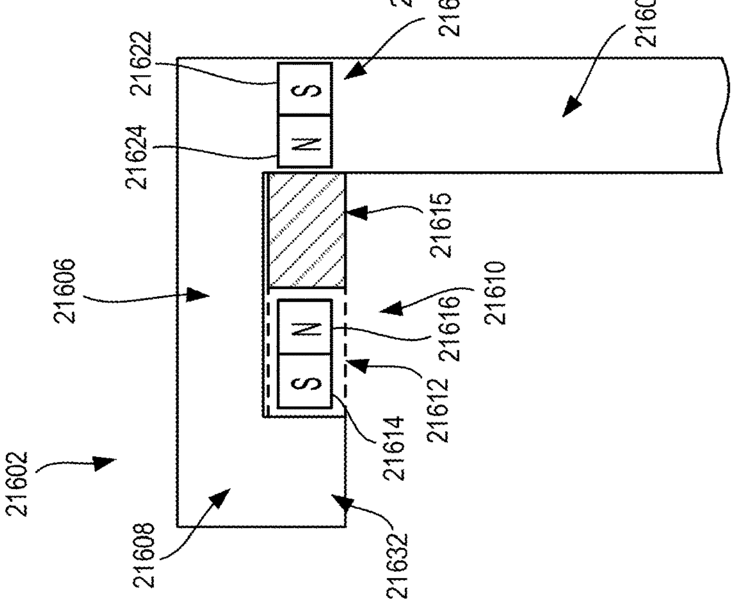

FIG. 206 illustrates a magnet of an adapter positioned in a first passage portion of the J-shaped passage of FIG. 204, according to at least one aspect of the present disclosure.

Figure 207:
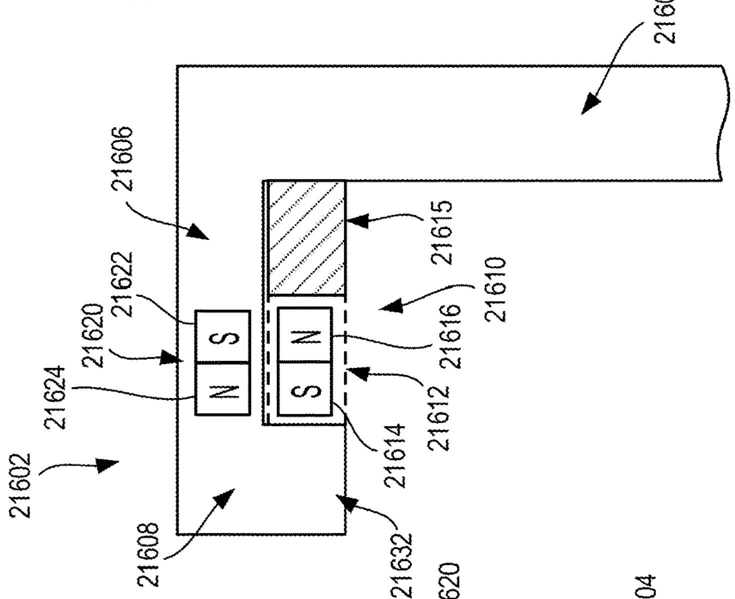

FIG. 207 illustrates the magnet of FIG. 206 moved to a second passage portion of the J-shaped passage, according to at least one aspect of the present disclosure.

Figure 208:
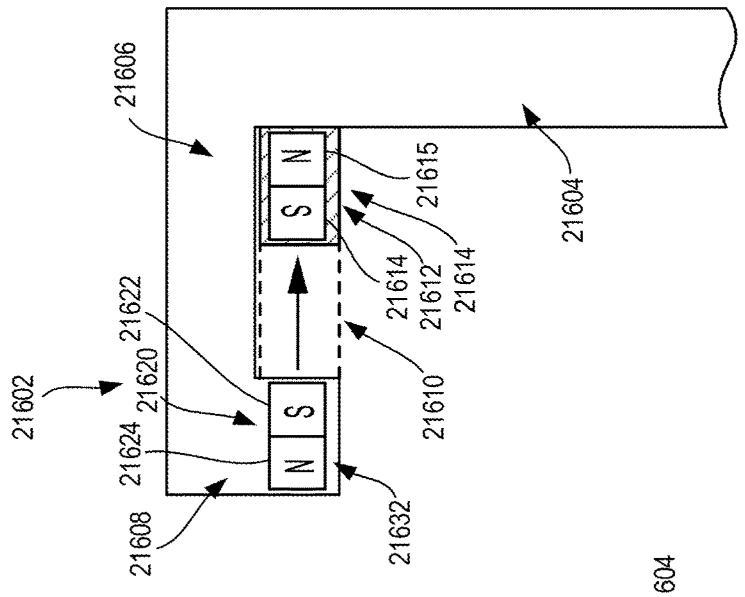

FIG. 208 illustrates the magnet of FIG. 206 moved to a third passage portion of the J-shaped passage, according to at least one aspect of the present disclosure.

Figure 209:
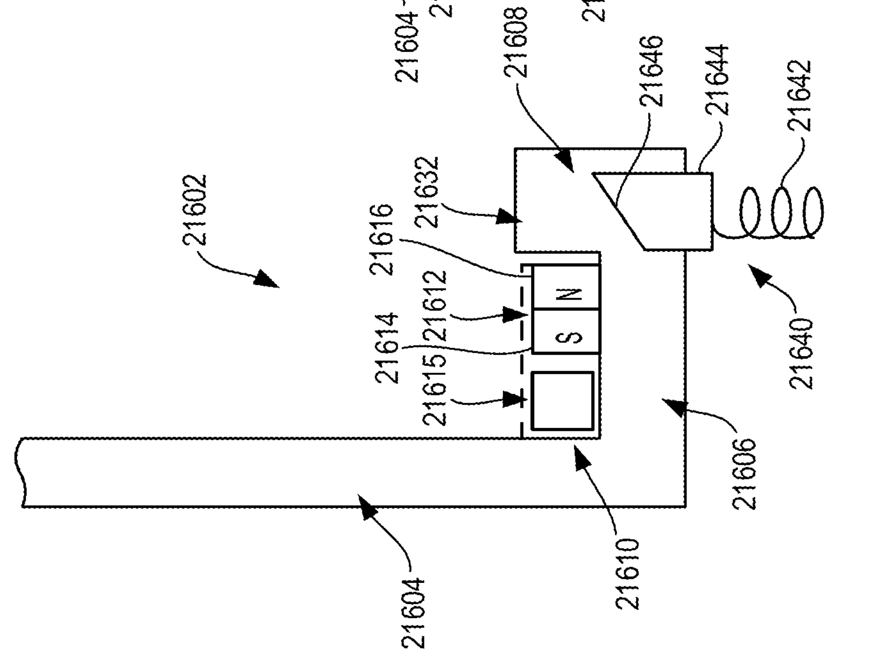

FIG. 209 illustrates a J-shaped passage including a spring assembly positioned at a transition between the second passage portion and the third passage portion, according to at least one aspect of the present disclosure.

Figure 210:
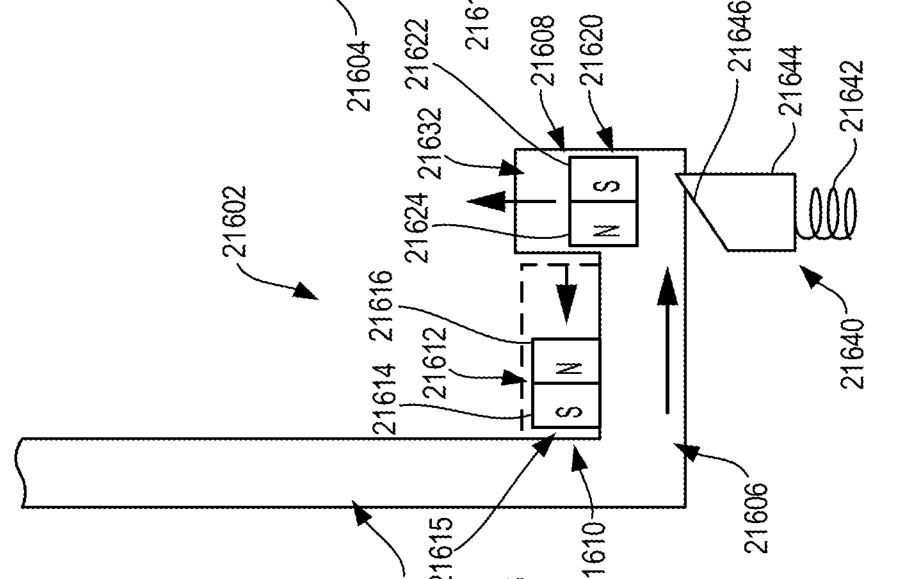

FIG. 210 illustrates the spring assembly of FIG. 209 in the compressed position and moving toward the expanded position to move a magnet of an adapter through the third passage portion, according to at least one aspect of the present disclosure.

Figure 211:
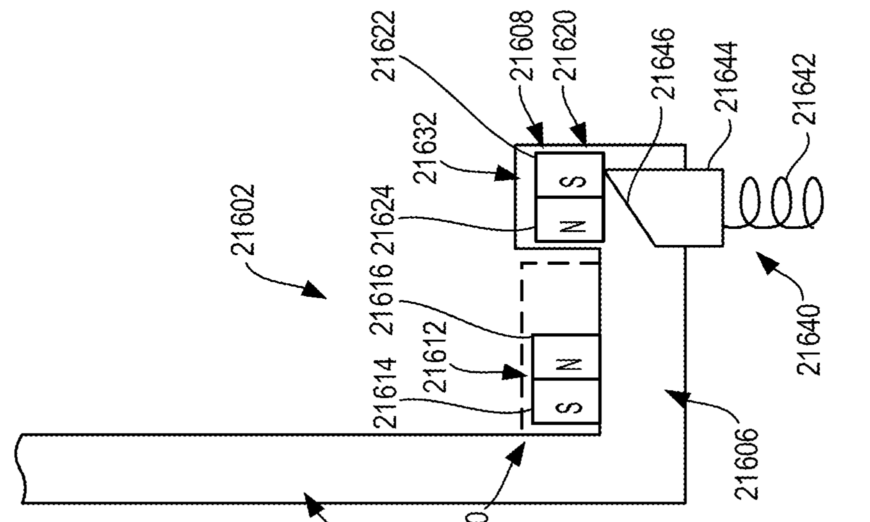

FIG. 211 illustrates the spring assembly of FIG. 209 holding the magnet in the third passage portion, according to at least one aspect of the present disclosure.

Figure 212:
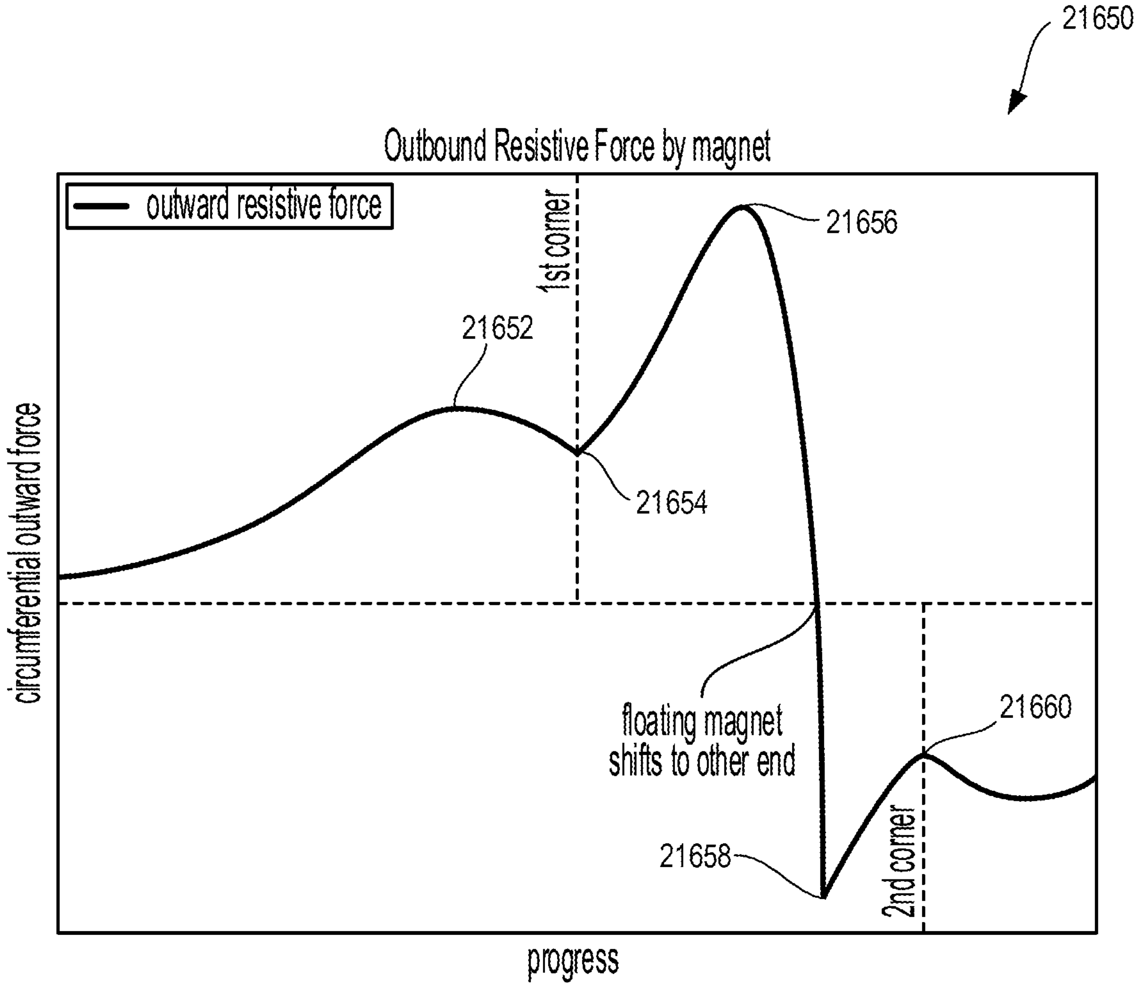

FIG. 212 illustrates a graphical representation of outward resistive force by a magnet as a magnet moves through a J-shaped passage, according to at least one aspect of the present disclosure.

Figure 213:
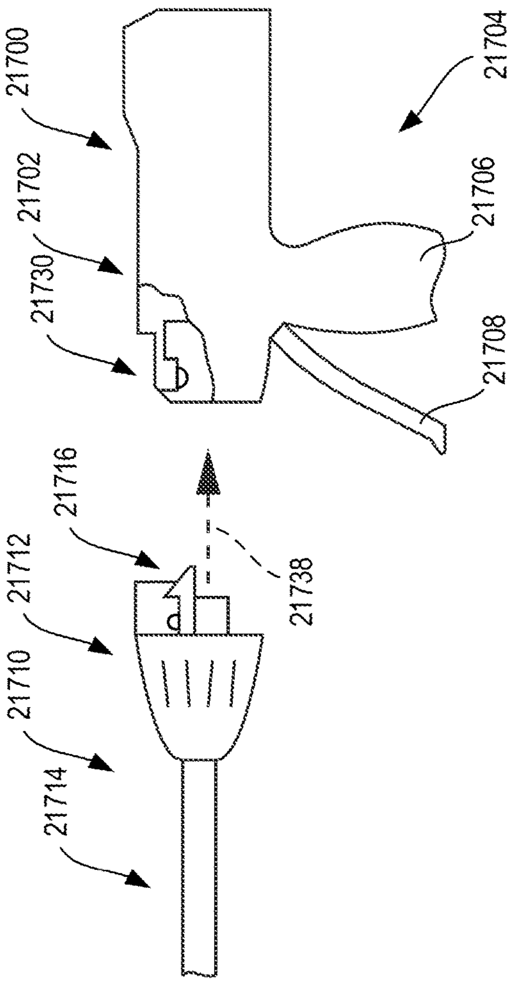

FIG. 213 illustrates a nozzle assembly and a handle assembly, according to at least one aspect of the present disclosure.

Figure 214:
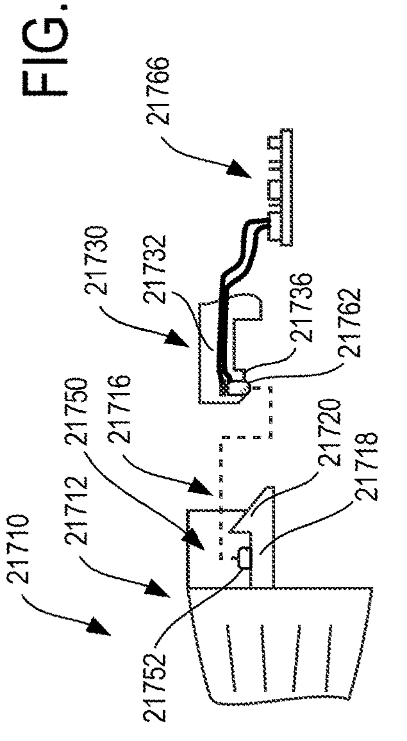

FIG. 214 illustrates a detailed view of a proximal end of the nozzle assembly of FIG. 213 and a distal end of the handle assembly of FIG. 213, according to at least one aspect of the present disclosure.

Figure 215:
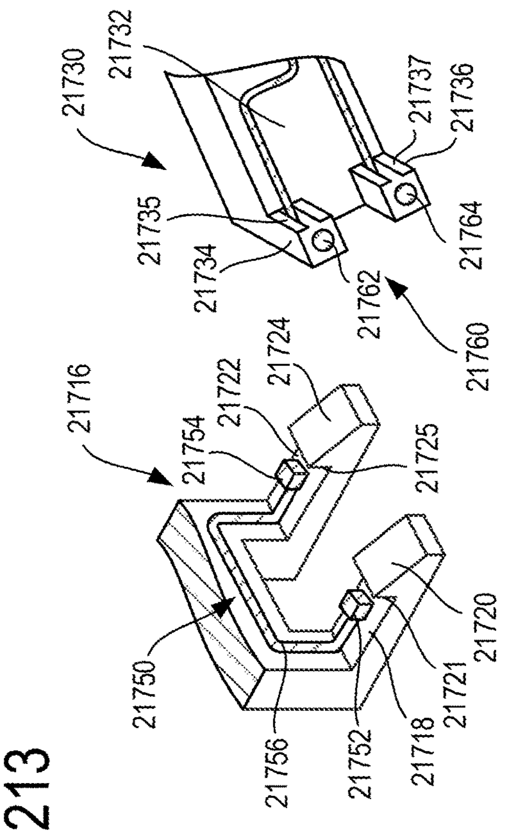

FIG. 215 illustrates a detailed view of the latch and contact arrangements of the nozzle assembly and handle assembly of FIG. 213, according to at least one aspect of the present disclosure.

Figure 216:
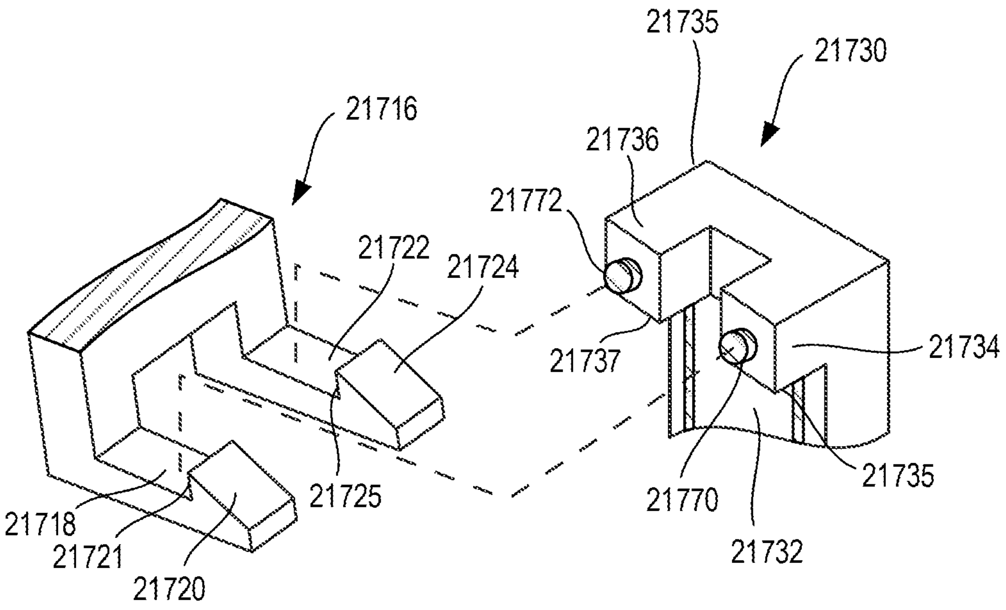

FIG. 216 illustrates an alternative latch and switch arrangement of the nozzle assembly and handle assembly of FIG. 213, according to at least one aspect of the present disclosure.

Figure 217:
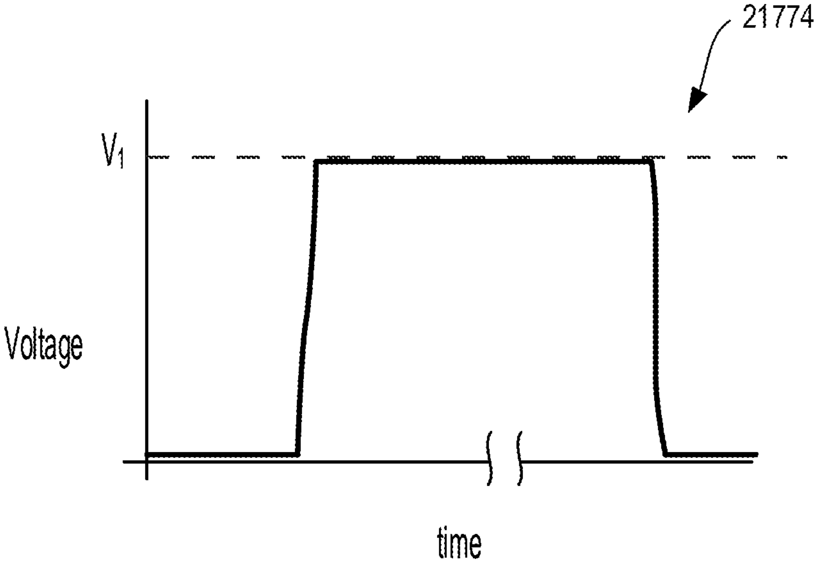

FIG. 217 illustrates a graphical representation of a voltage detected by a control circuit of the latch and switch arrangement of FIG. 216 over time, according to at least one aspect of the present disclosure.

Figure 218:
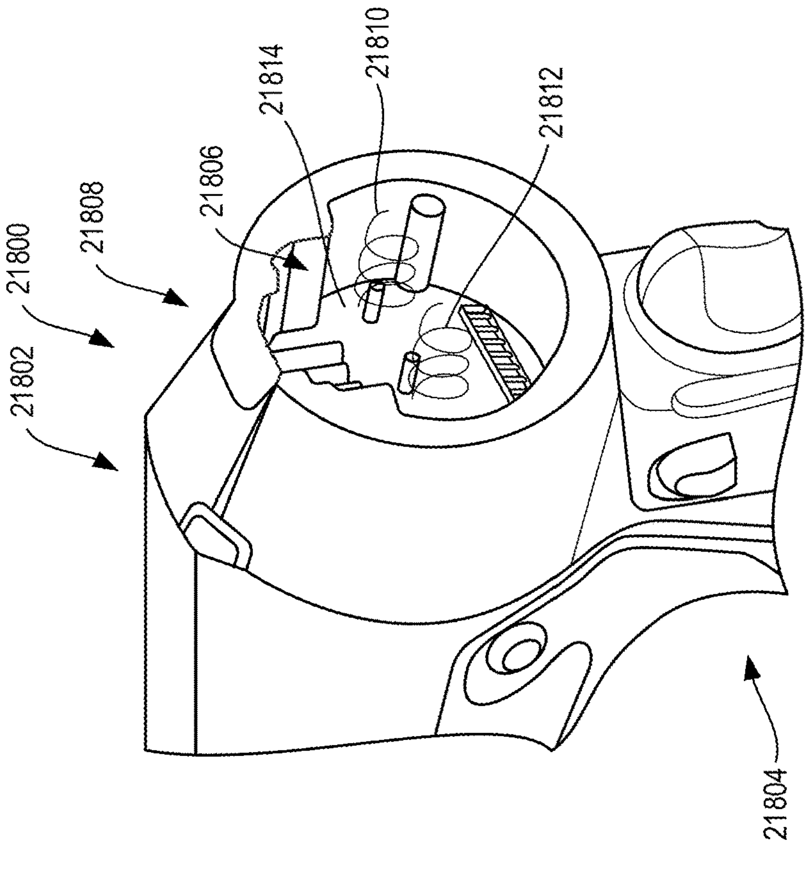

FIG. 218 illustrates a handle assembly, according to at least one aspect of the present disclosure.

Figure 219:
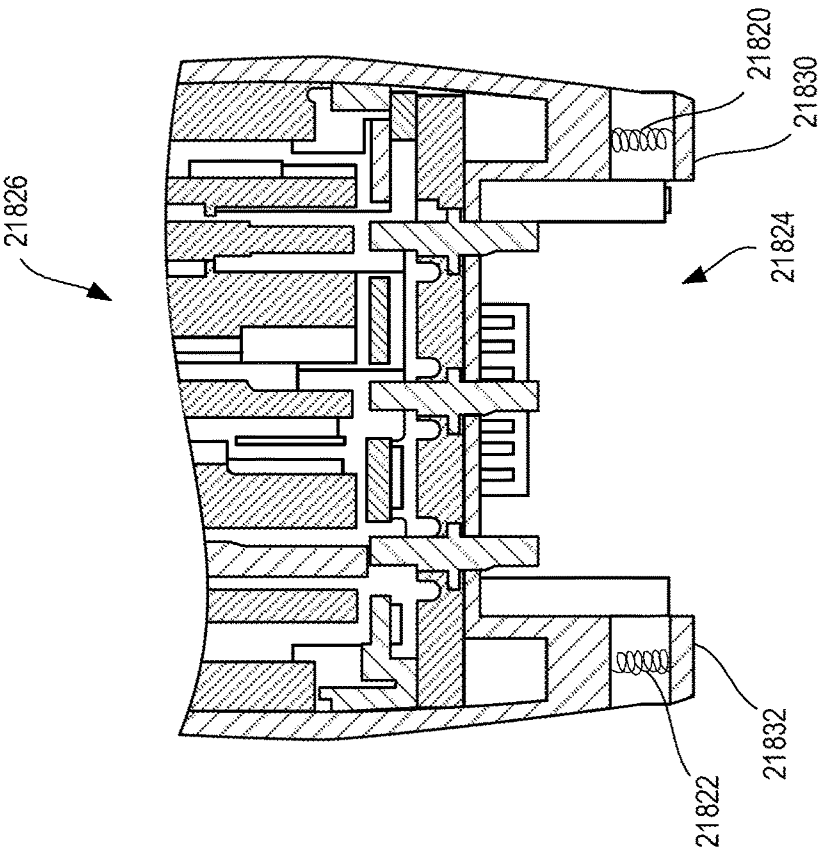

FIG. 219 illustrates a top-down view of a handle assembly, according to at least one aspect of the present disclosure.

Figure 220:
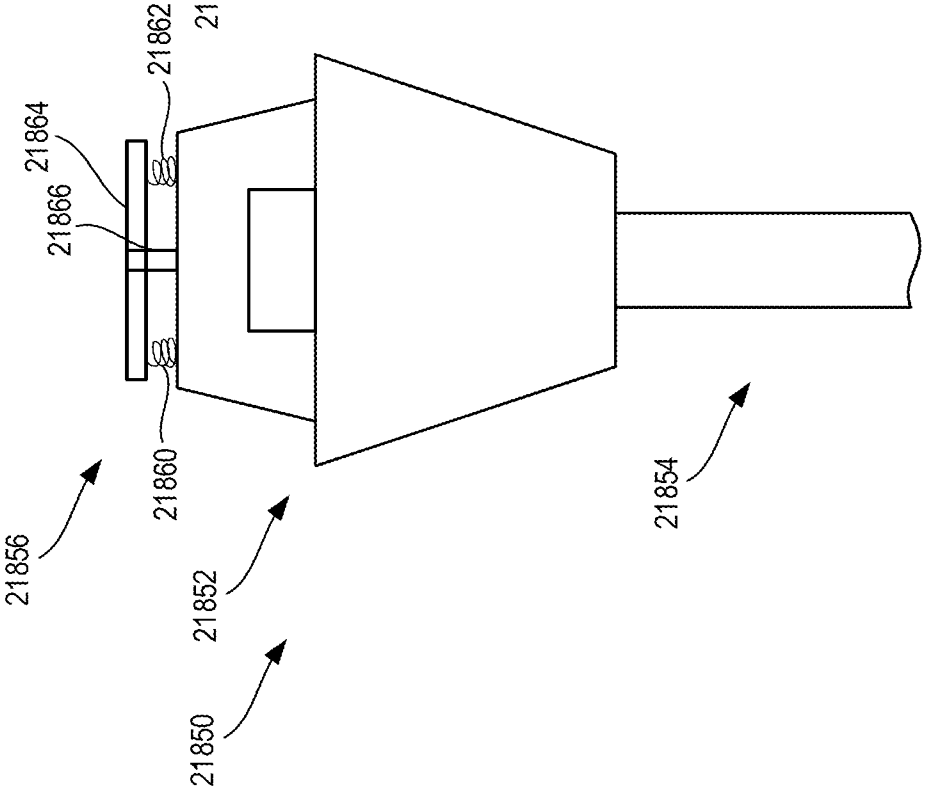

FIG. 220 illustrates a shaft assembly including a spring arrangement in an extended position, according to at least one aspect of the present disclosure.

Figure 221:
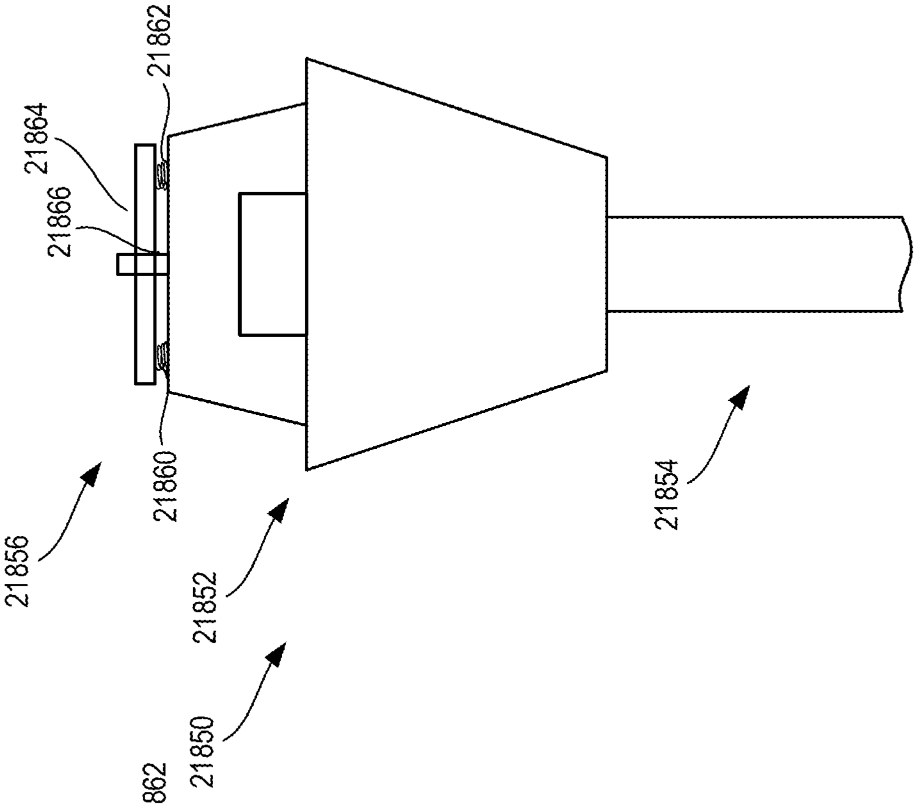

FIG. 221 illustrates a shaft assembly including a spring arrangement in a compressed position according to at least one aspect of the present disclosure.

Figure 222:
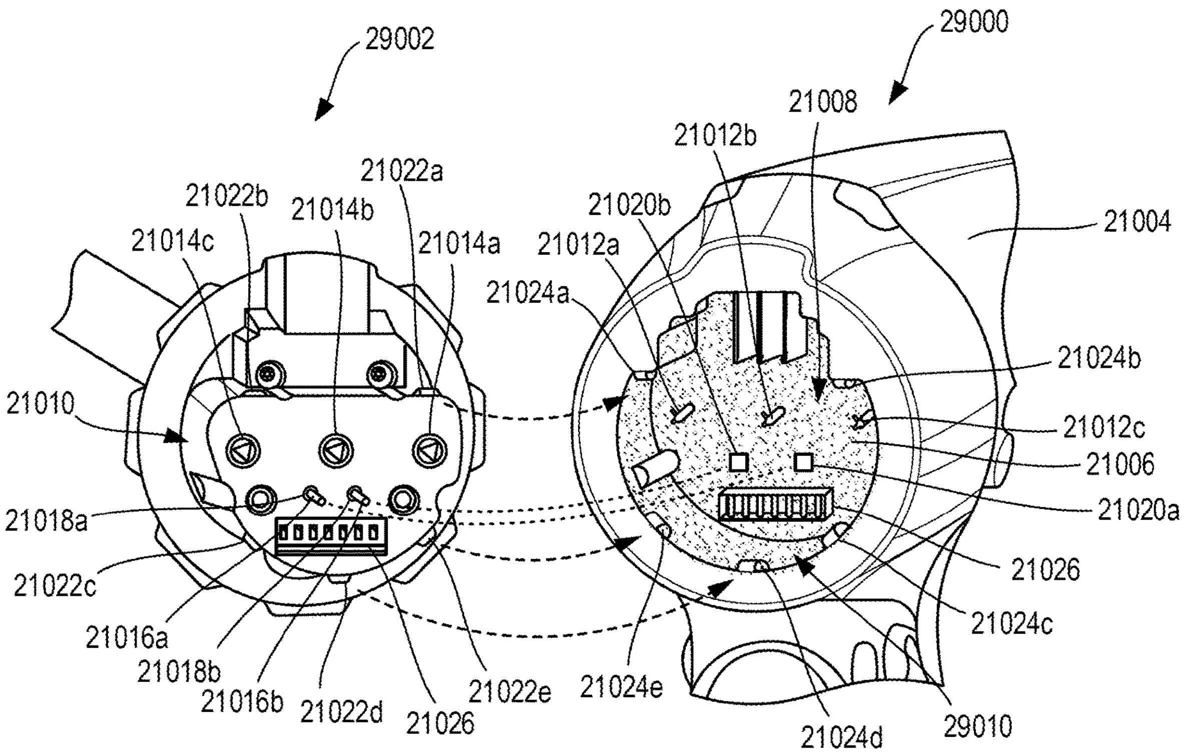

FIG. 222 illustrates a housing including a compressible material and an adapter selectively coupleable with the housing, according to at least one aspect of the present disclosure.

Figure 223:
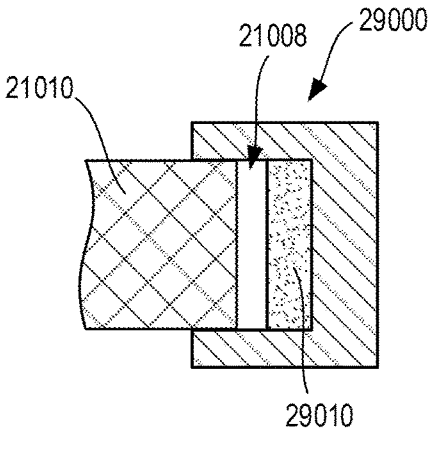

FIG. 223 illustrates a drive coupling assembly of an adapter and a compressible material in an uncompressed configuration, according to at least one aspect of the present disclosure.

Figure 224:
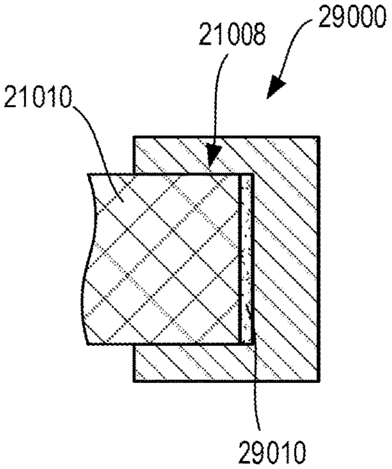

FIG. 224 illustrates a drive coupling assembly of an adapter compressing a compressible material to a compressed configuration, according to at least one aspect of the present disclosure.

Figure 225:
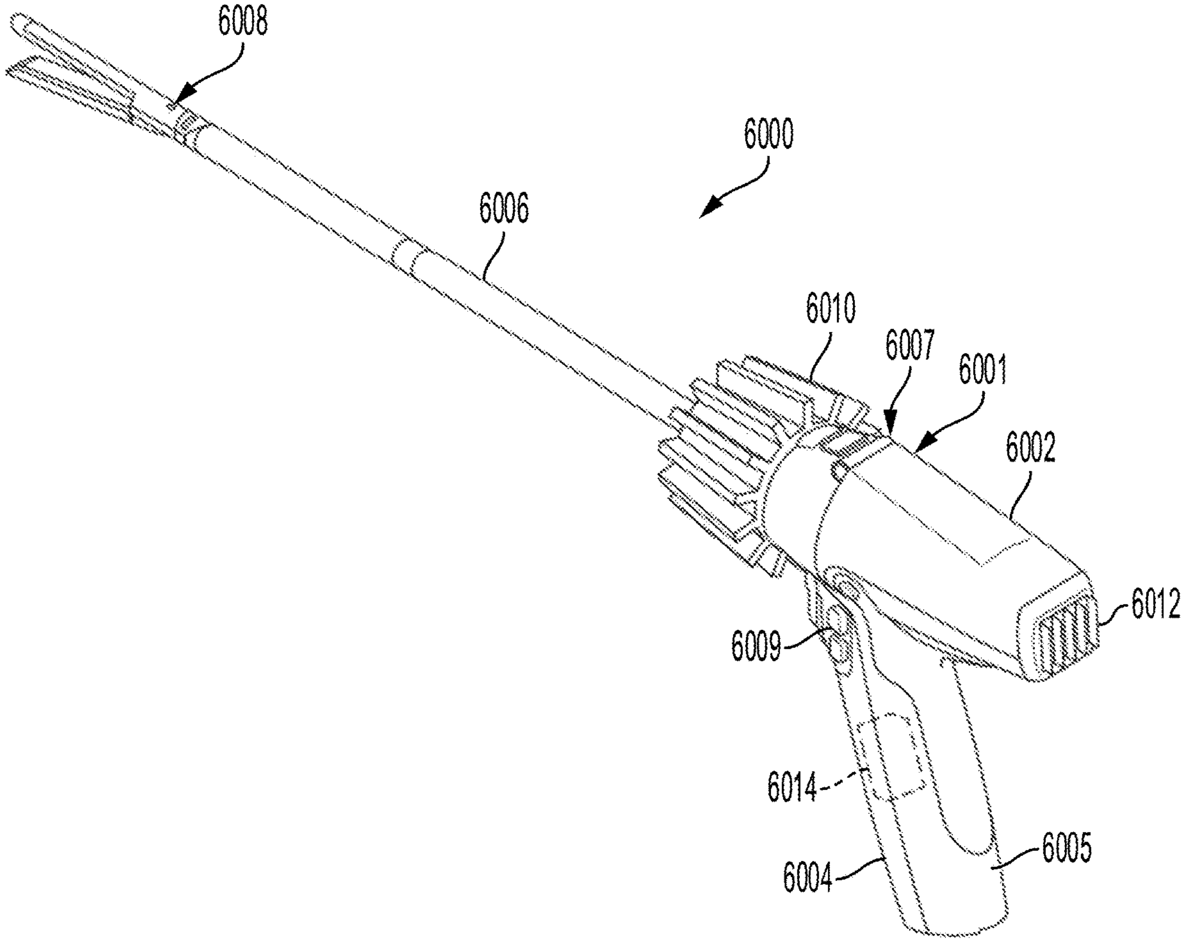

FIG. 225 illustrates a perspective view of a surgical instrument that includes an adapter assembly configured to create a sterile barrier around a handheld surgical device and energy management components, in accordance with at least one non-limiting aspect of the present disclosure.

Figure 226:
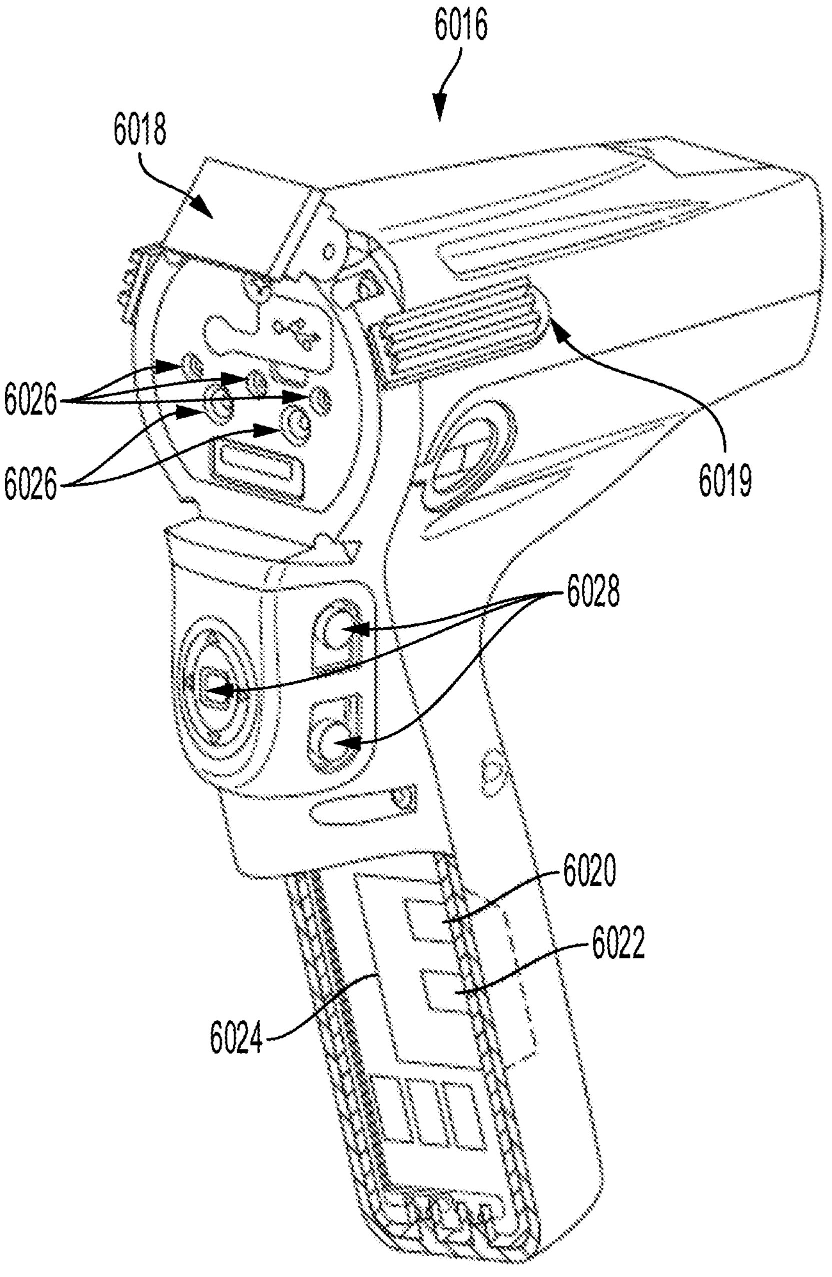

FIG. 226 illustrates a sectioned perspective view of a handheld assembly configured to be encased within the adapter assembly of the surgical instrument of FIG. 225.

Figure 227:
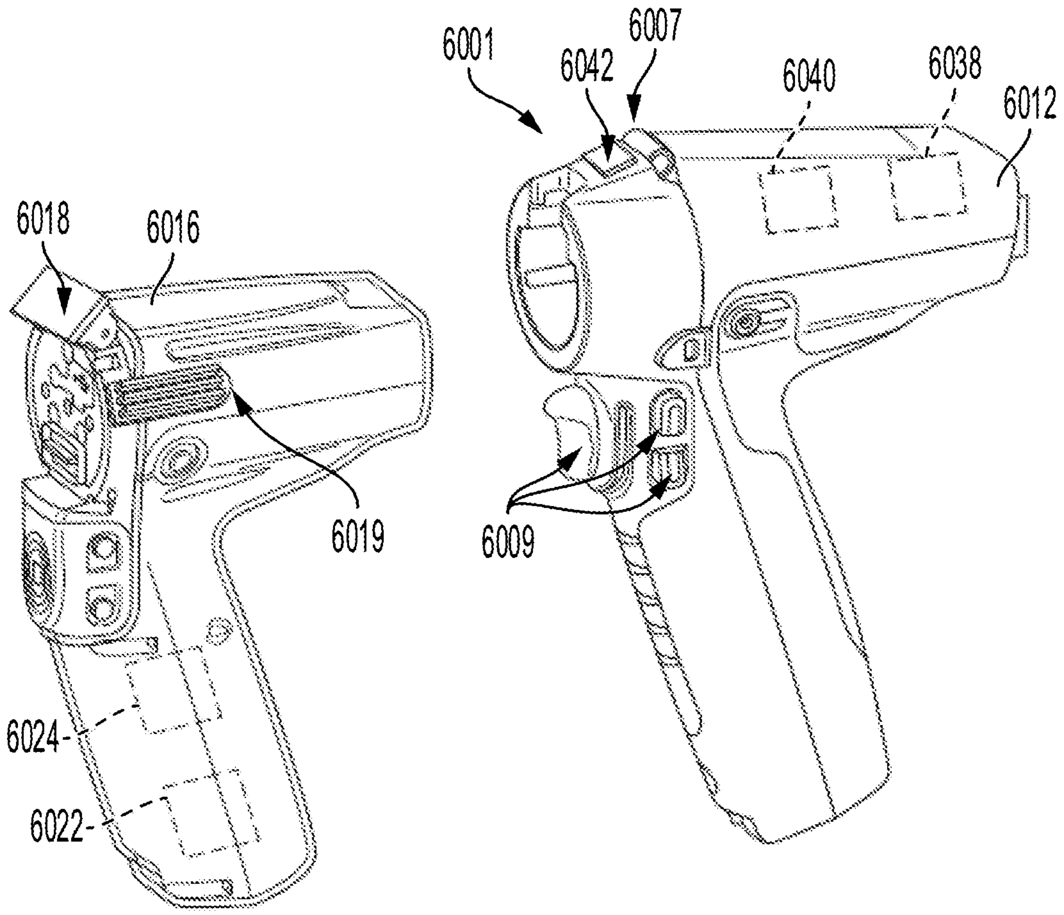

FIG. 227 illustrates a perspective view of the adapter assembly and handheld device of the surgical instrument of FIG. 225.

Figure 228:
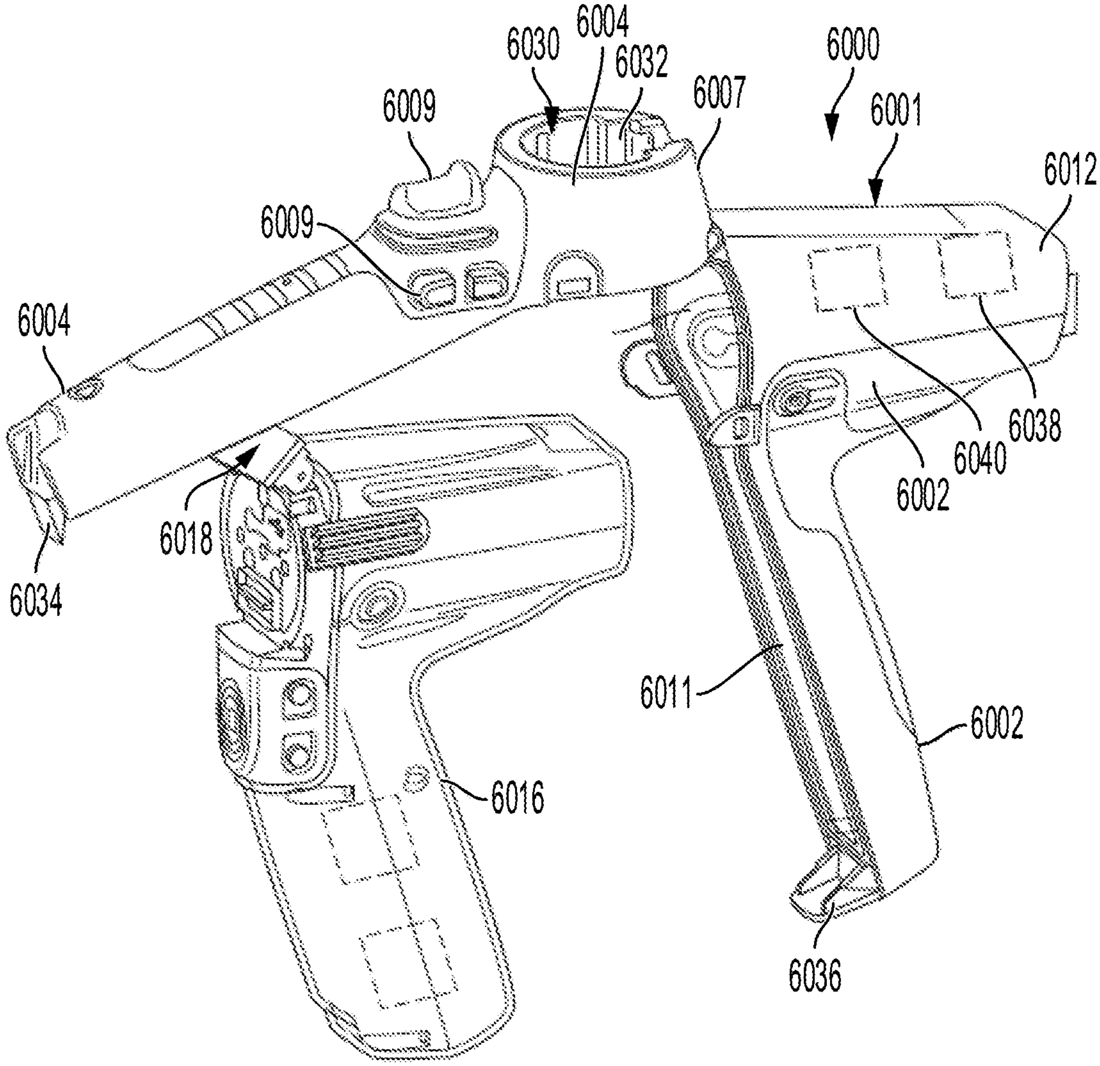

FIG. 228 illustrates a perspective view of the adapter assembly and handheld device of the surgical instrument of FIG. 225.

Figure 229:
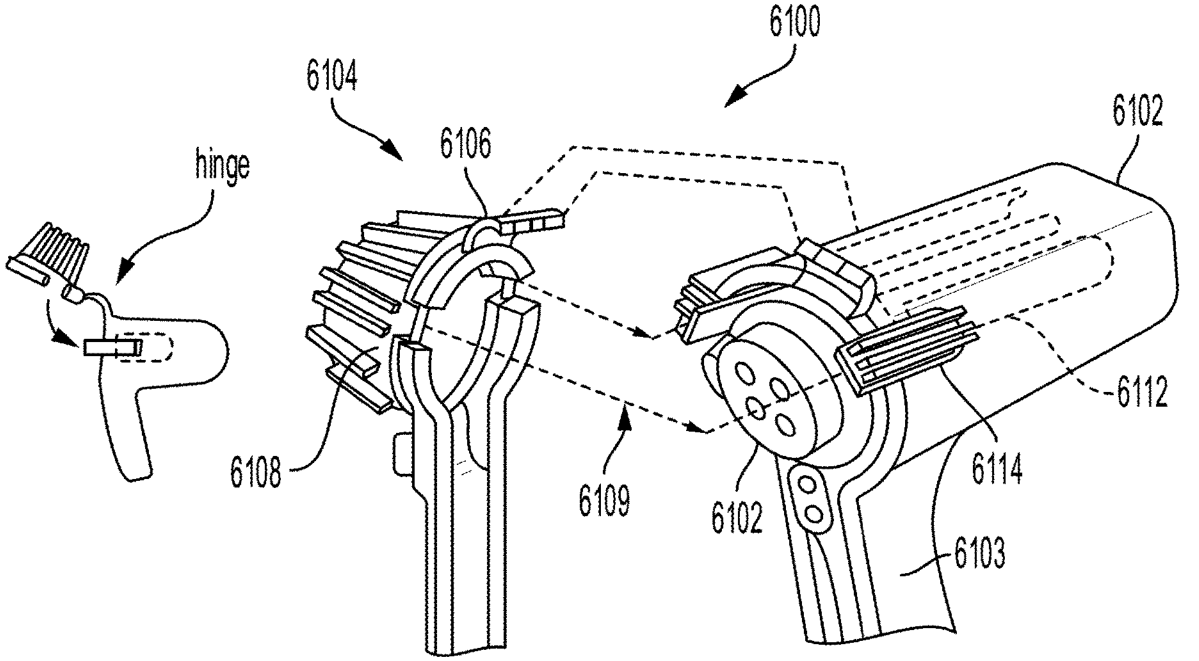

FIG. 229 illustrates a perspective assembly view of an adapter assembly that includes energy management components, in accordance with at least one non-limiting aspect of the present disclosure.

Figure 230:
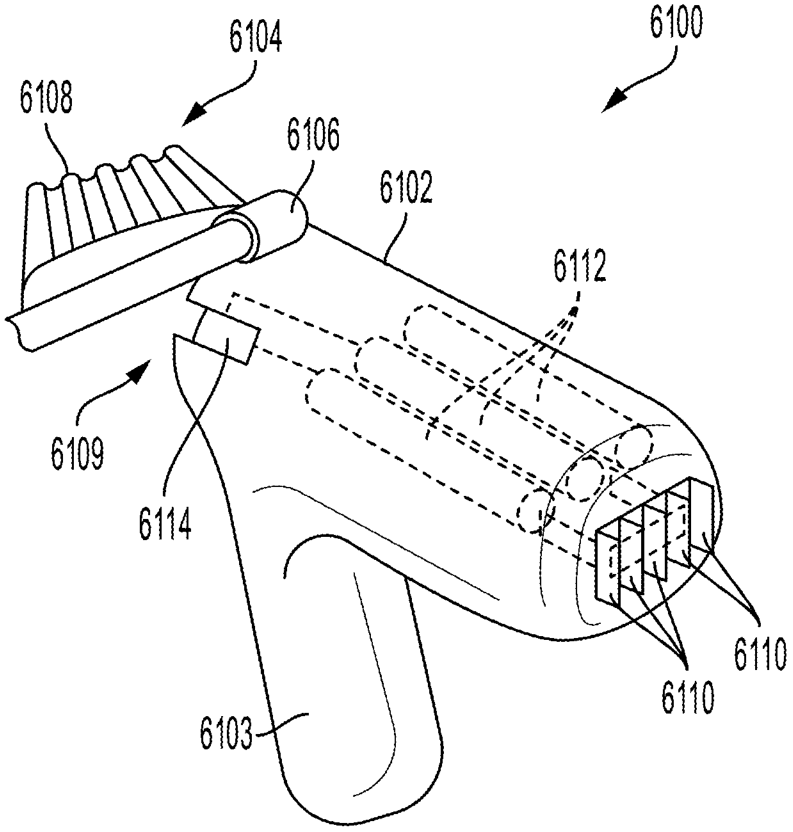

FIG. 230 illustrates a perspective back view of the adapter assembly of FIG. 229.

Figure 231B:
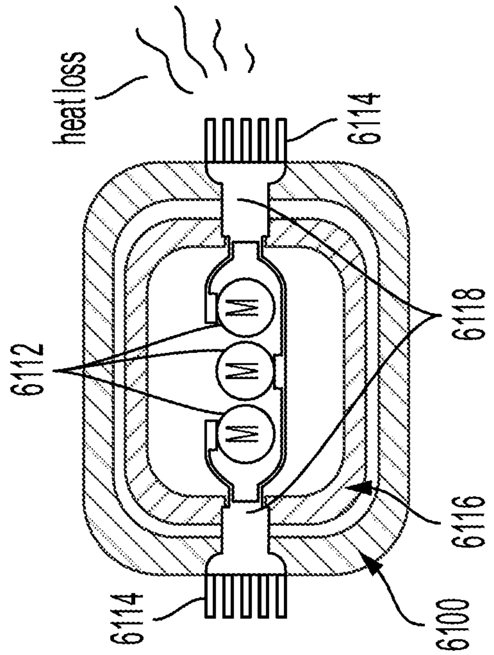
Figure 231A:
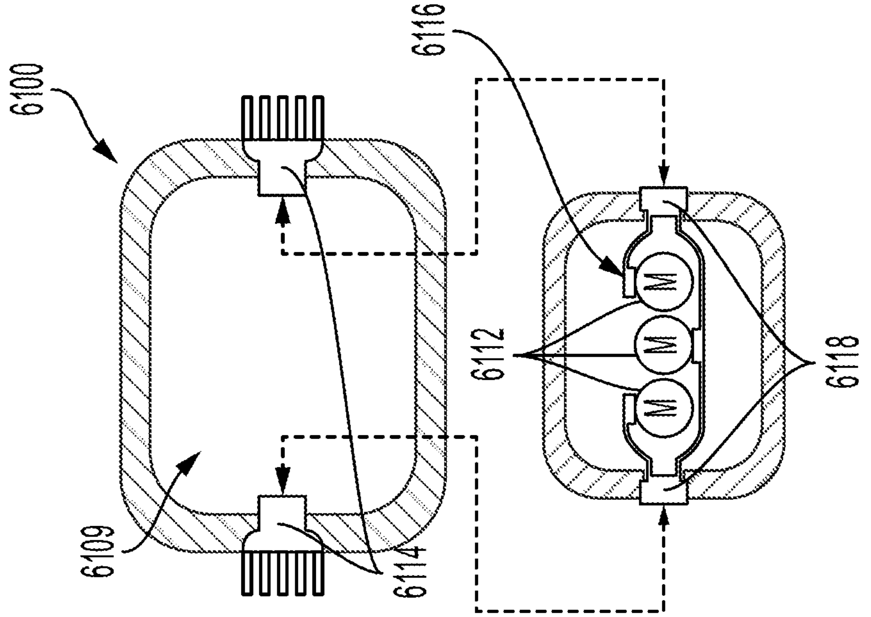

FIGS. 231A and 231B illustrate sectioned front views of a handheld surgical device being installed into the adapter assembly of FIGS. 229 and 230.

Figure 232:
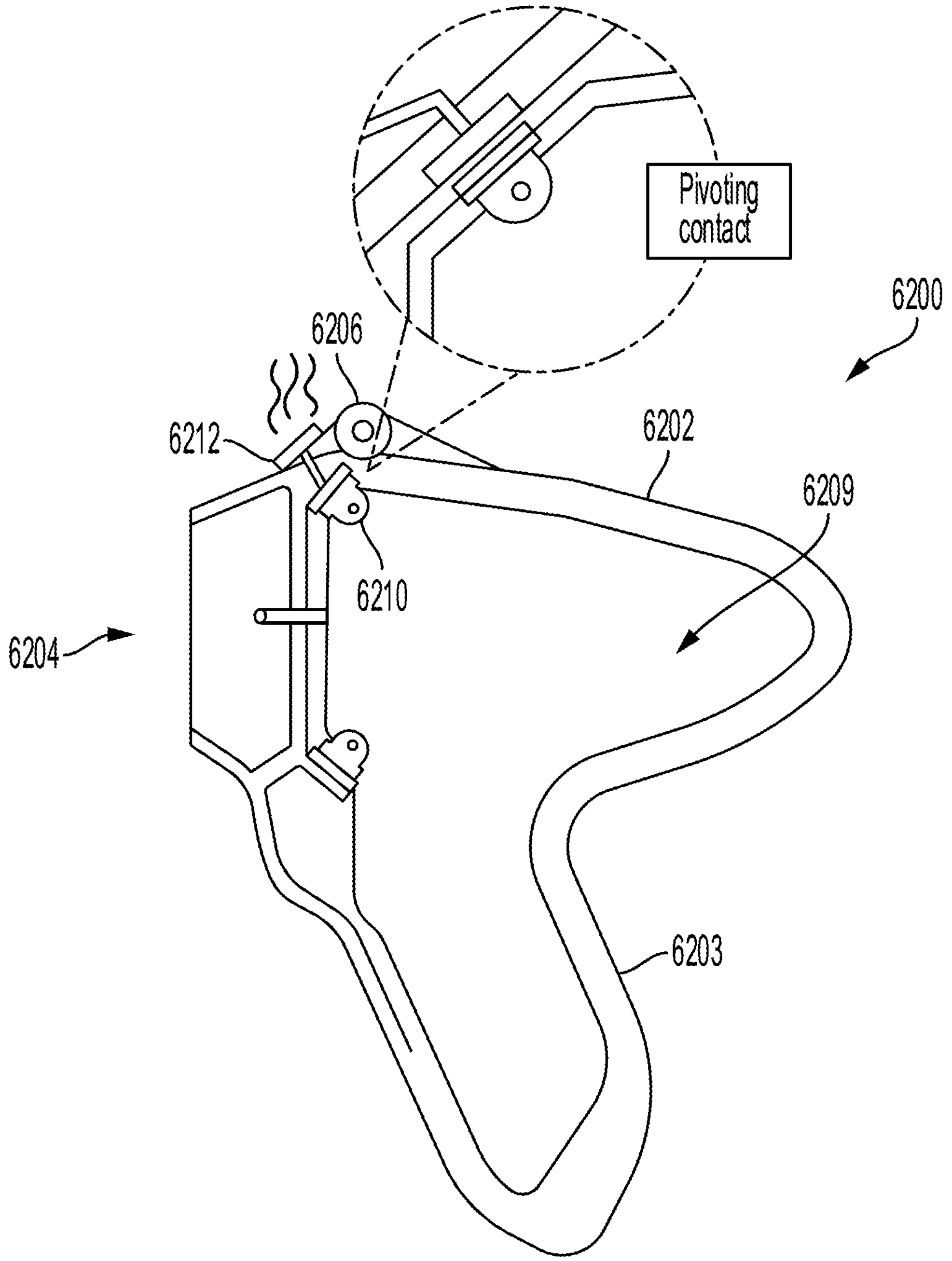

FIG. 232 illustrates a sectioned side view of an adapter assembly that includes energy management components, in accordance with at least one non-limiting aspect of the present disclosure.

Figure 233:
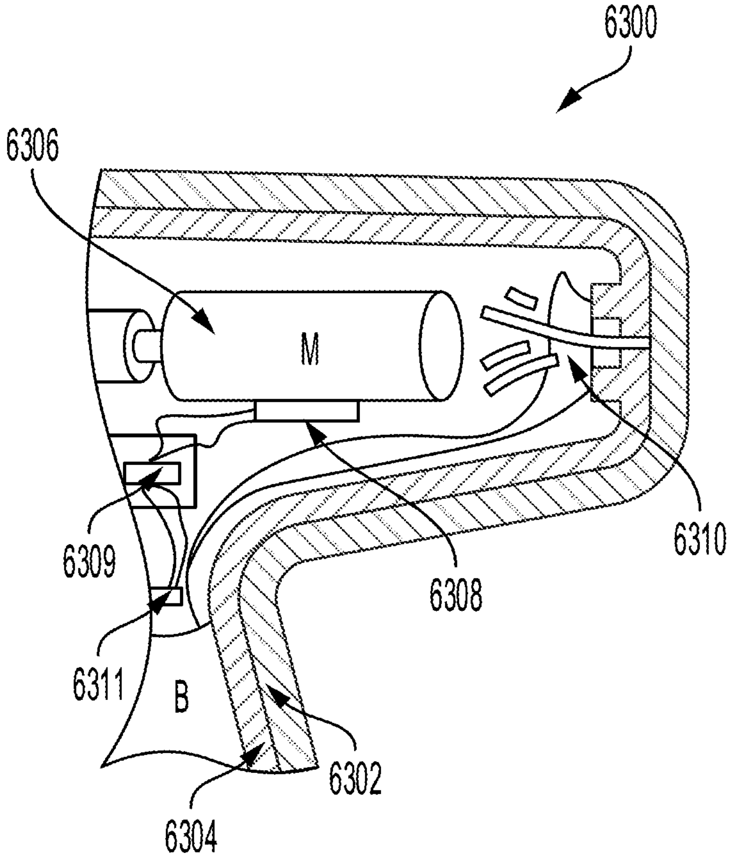

FIG. 233 illustrates a sectioned side view of a surgical instrument that includes energy management components, in accordance with at least one non-limiting aspect of the present disclosure.

Figure 234A:
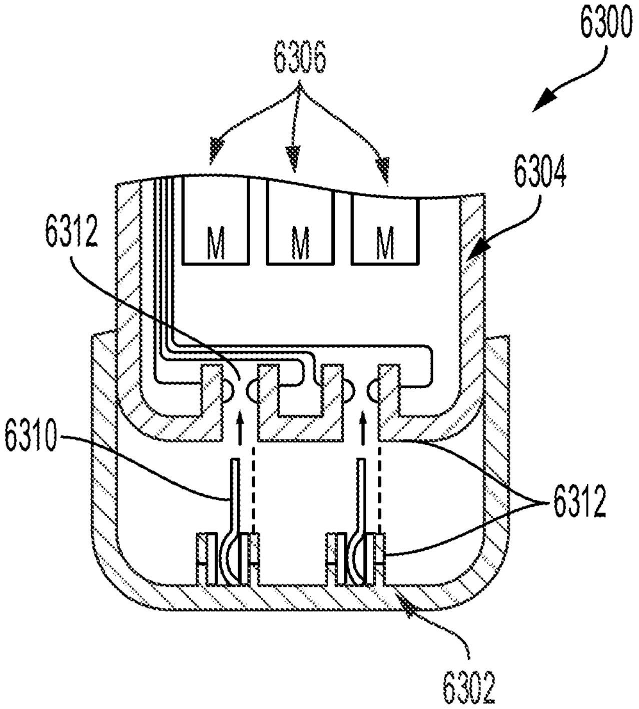
Figure 234B:
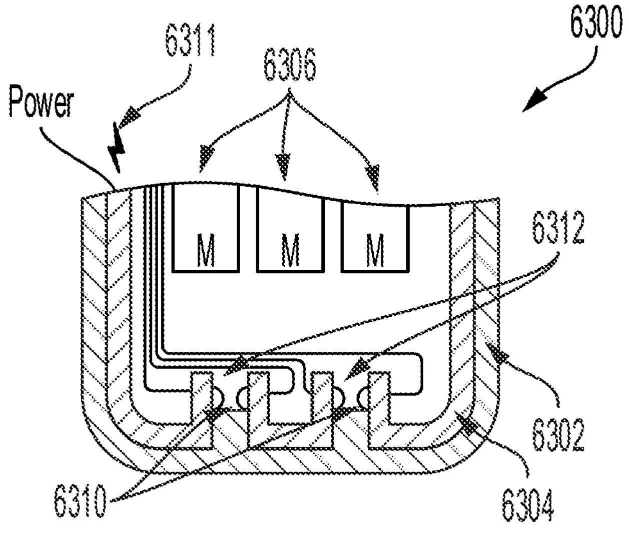

FIGS. 234A and 234B illustrate sectioned top views of the surgical instrument of FIG. 233.

Figure 235A:
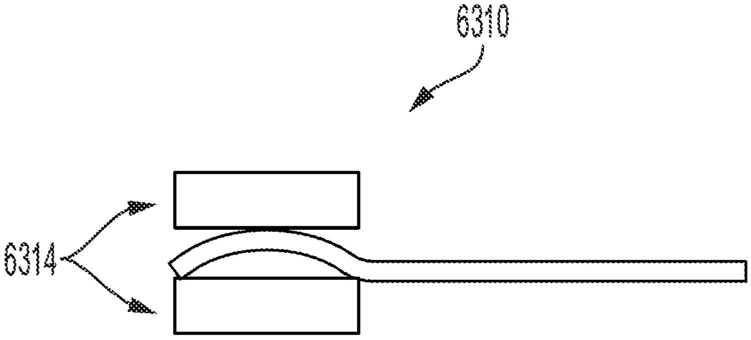
Figure 235B:
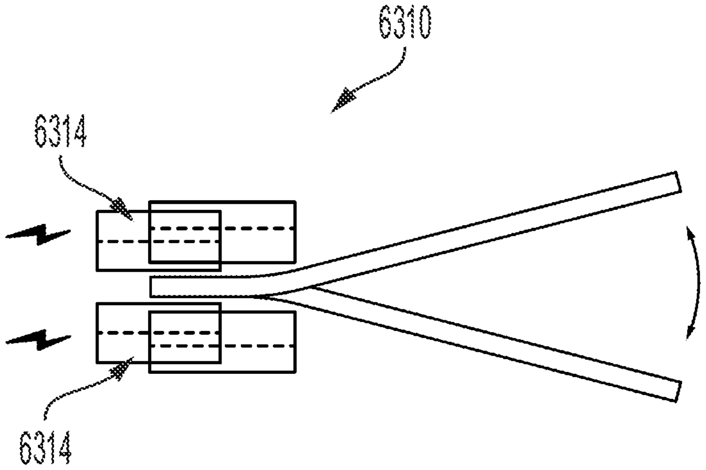

FIGS. 235A and 235B illustrate top views of an energy management component of the adapter assembly of FIG. 233.

Figure 236:
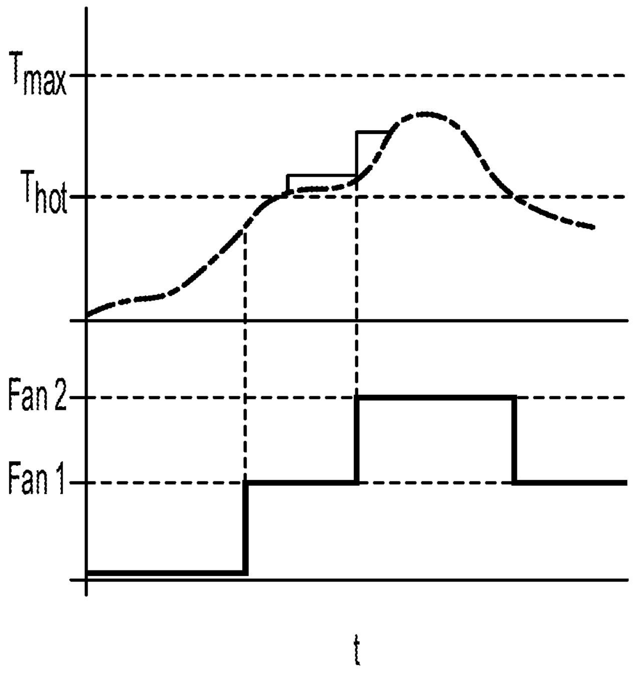

FIG. 236 illustrates a chart depicting a variable rate of energy management implemented by the surgical instrument of FIG. 233.

Figure 237:
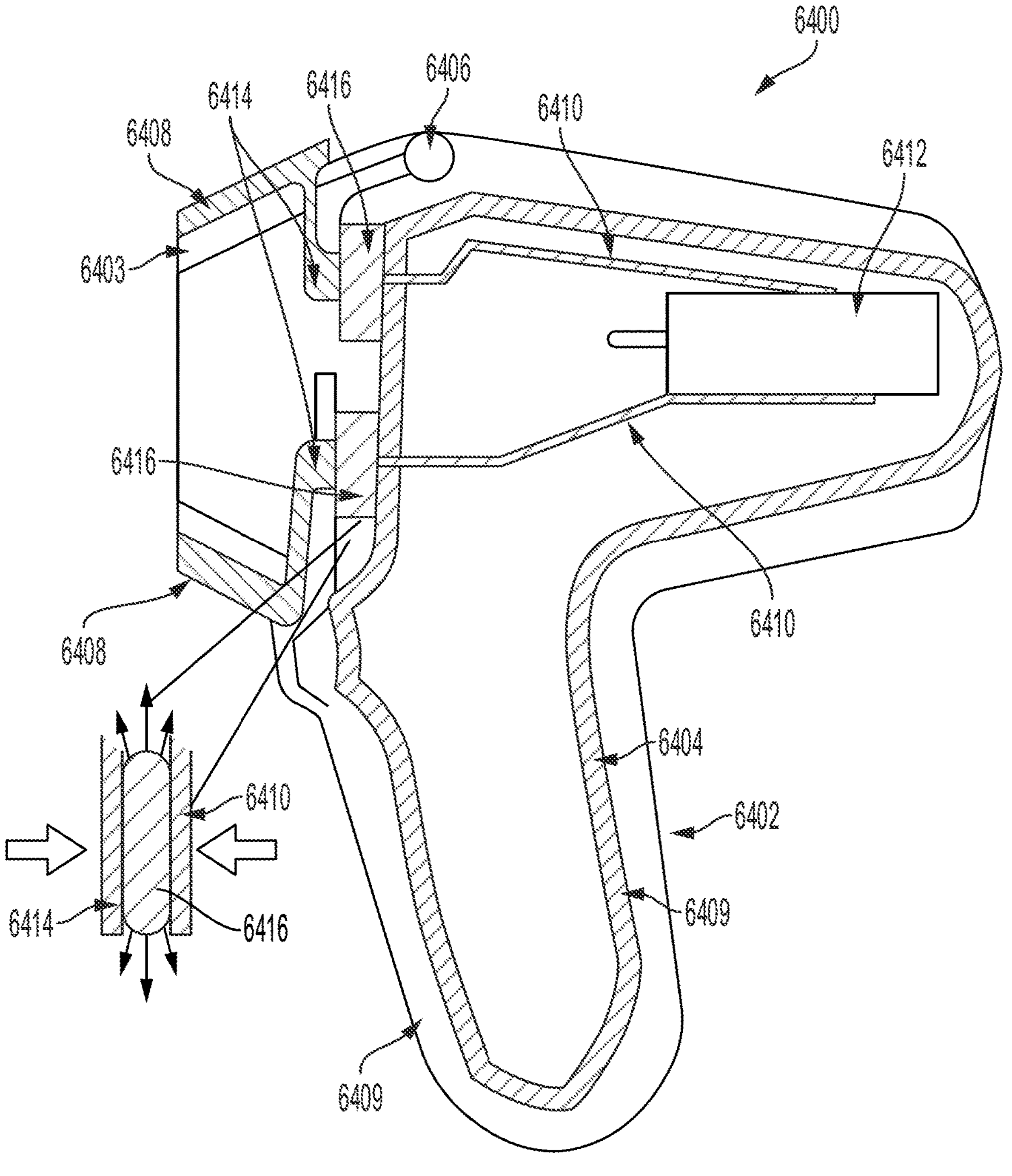

FIG. 237 illustrates a sectioned side view of a surgical instrument including a handheld surgical device and an adapter assembly that includes energy management components, in accordance with at least one non-limiting aspect of the present disclosure.

Figure 238:
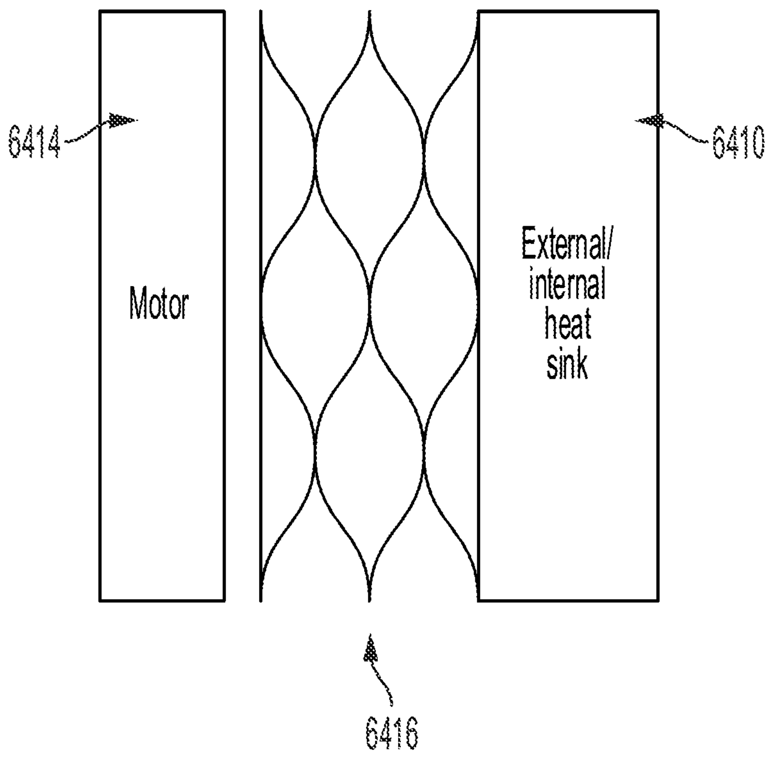

FIG. 238 illustrates a side view of an energy management component of the surgical instrument of FIG. 237.

Figure 239:
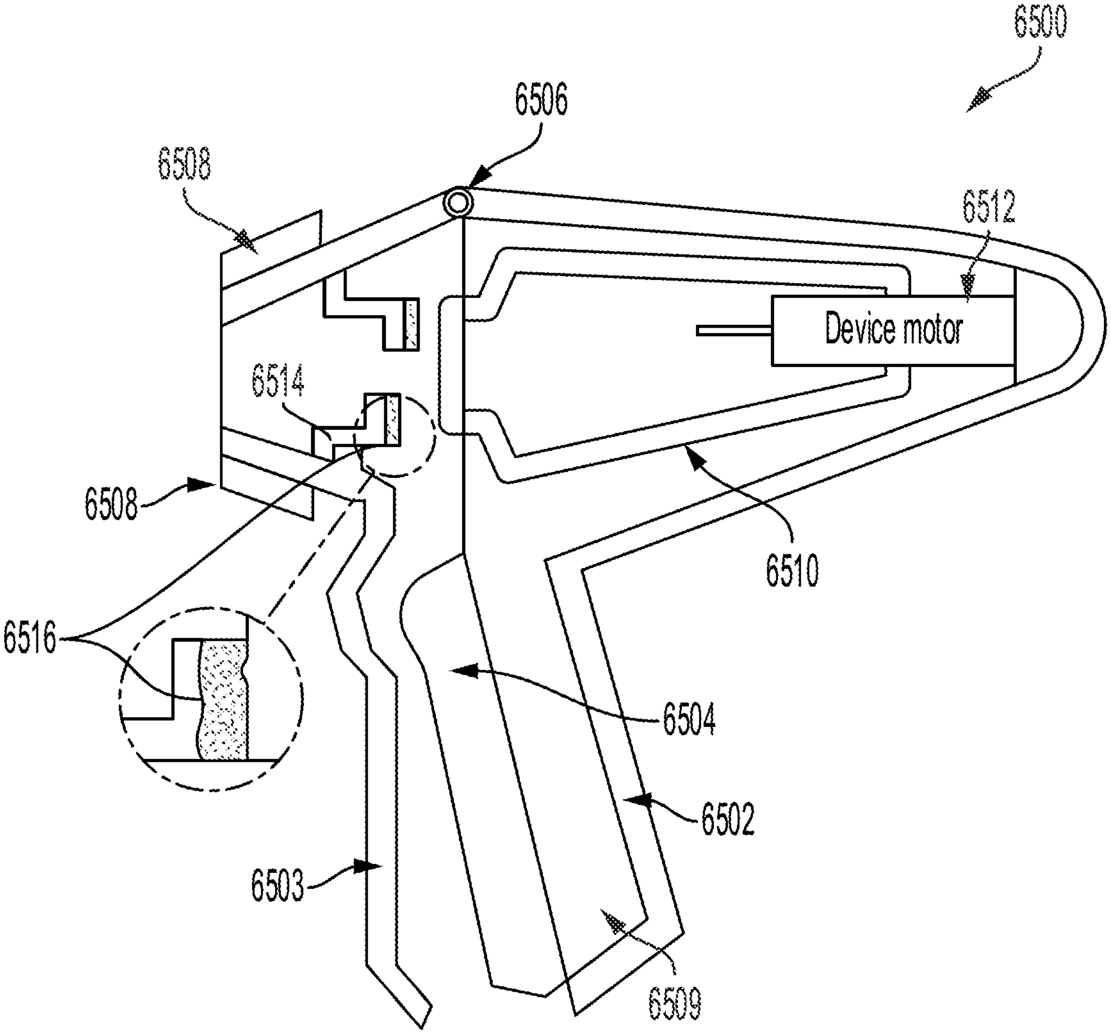

FIG. 239 illustrates a sectioned side view of a surgical instrument including a handheld surgical device and an adapter assembly with energy management components, in accordance with at least one non-limiting aspect of the present disclosure.

Figure 240:
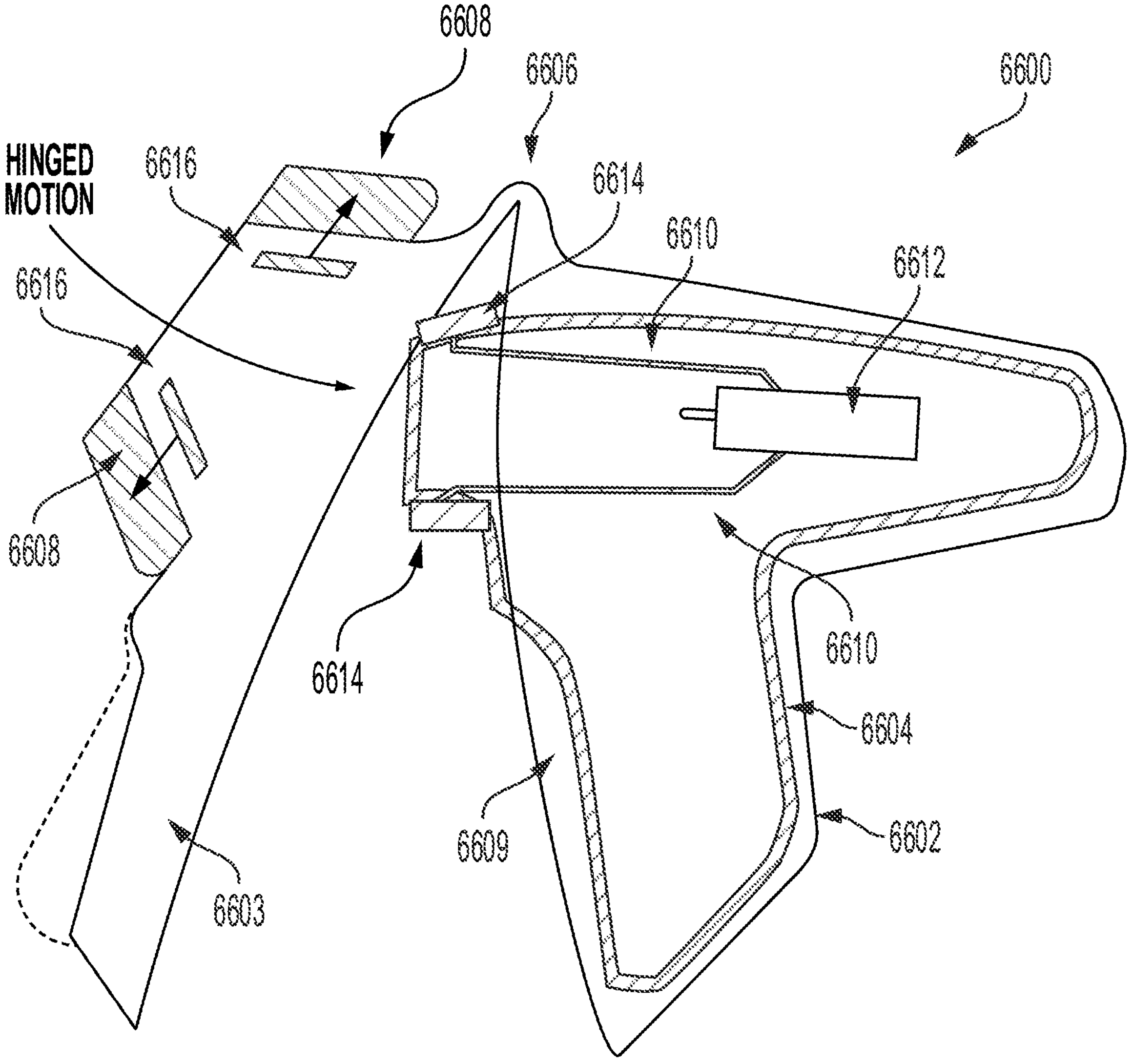

FIG. 240 illustrates a sectioned side view of a surgical instrument including a handheld surgical device and an adapter assembly that includes and energy management system, in accordance with at least one non-limiting aspect of the present disclosure.

Figure 241:
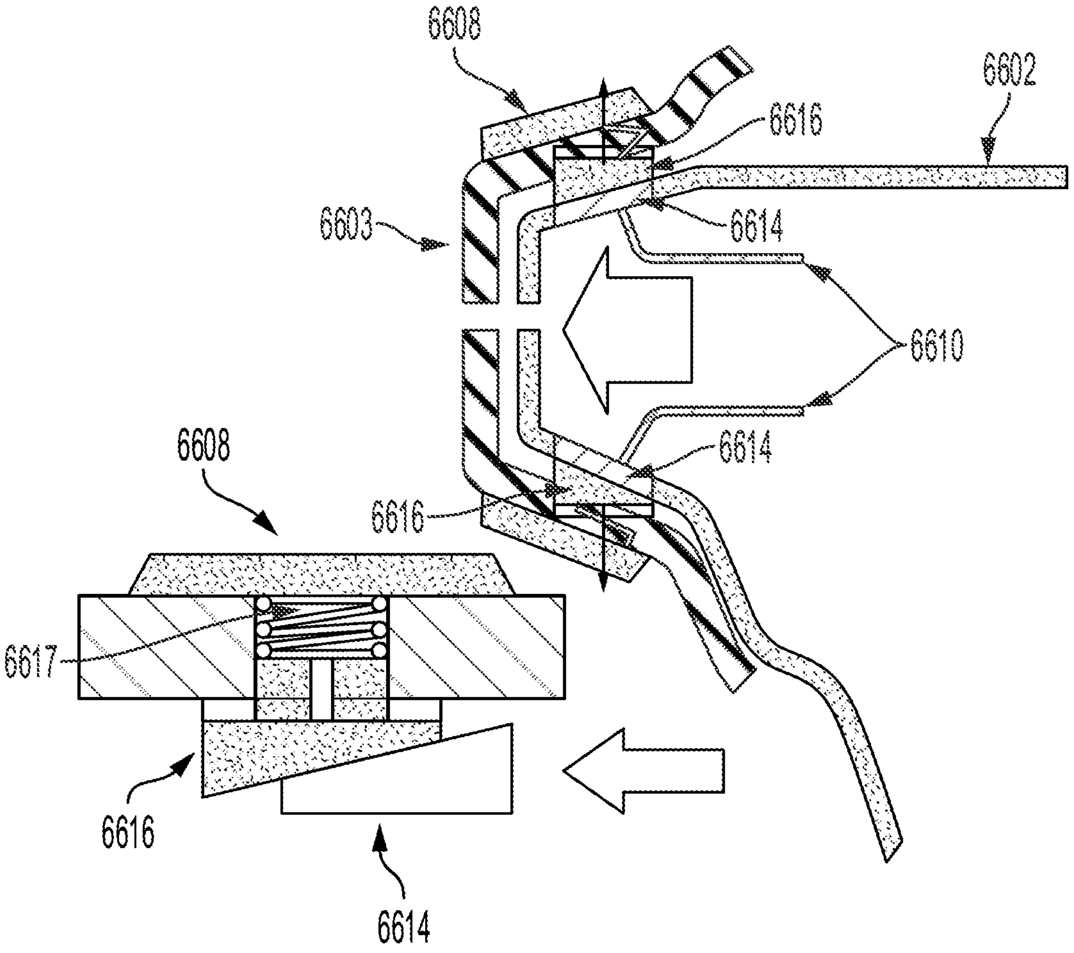

FIG. 241 illustrates a sectioned side view of the energy management system of the handheld device and adapter assembly of FIG. 240.

Figure 242:
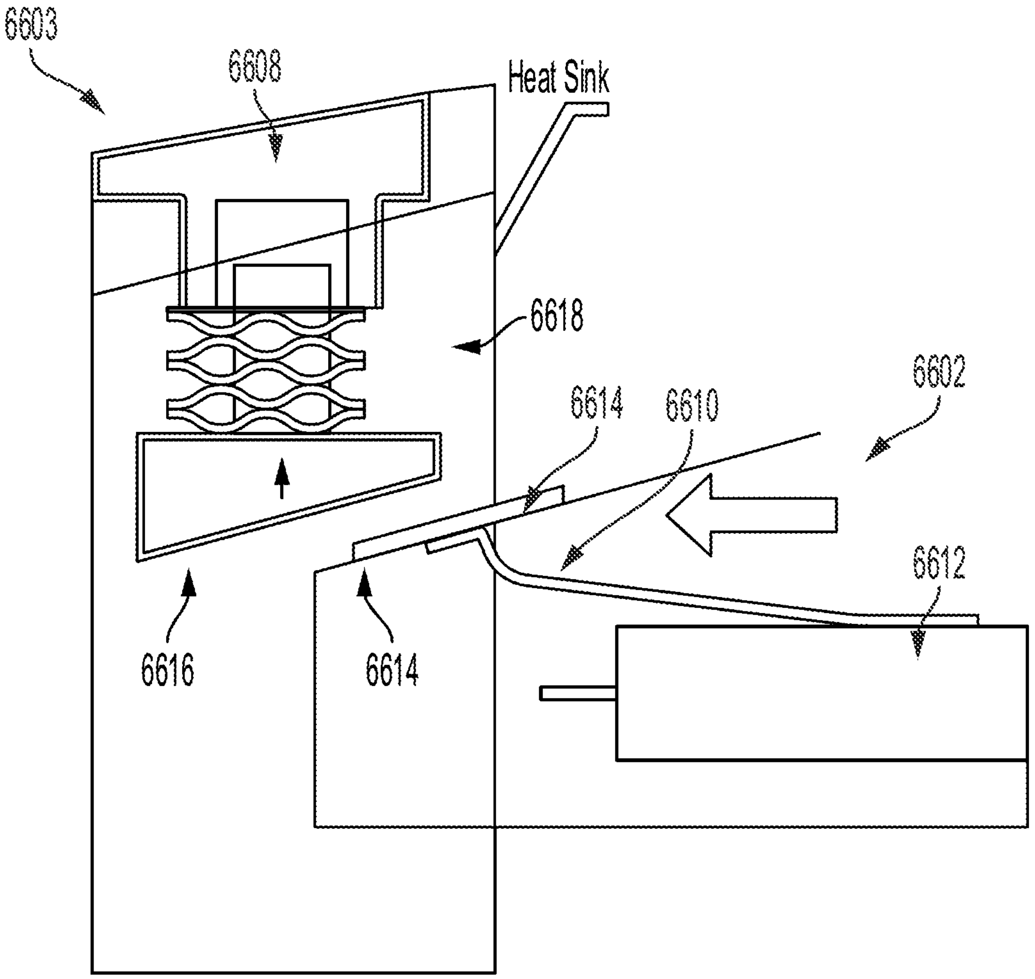

FIG. 242 illustrates a sectioned side view of an energy management component of the energy management system of FIG. 241.

Figure 243:
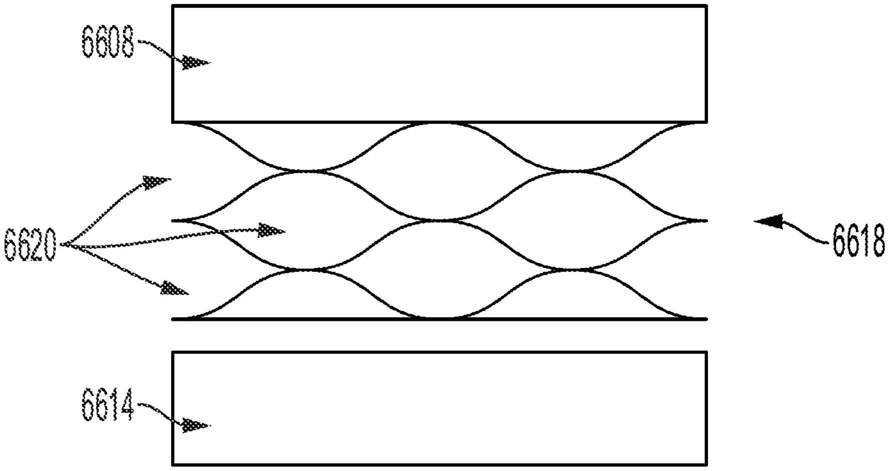

FIG. 243 illustrates a side view of another energy management component of the energy management system of FIG. 240.

Figure 244:
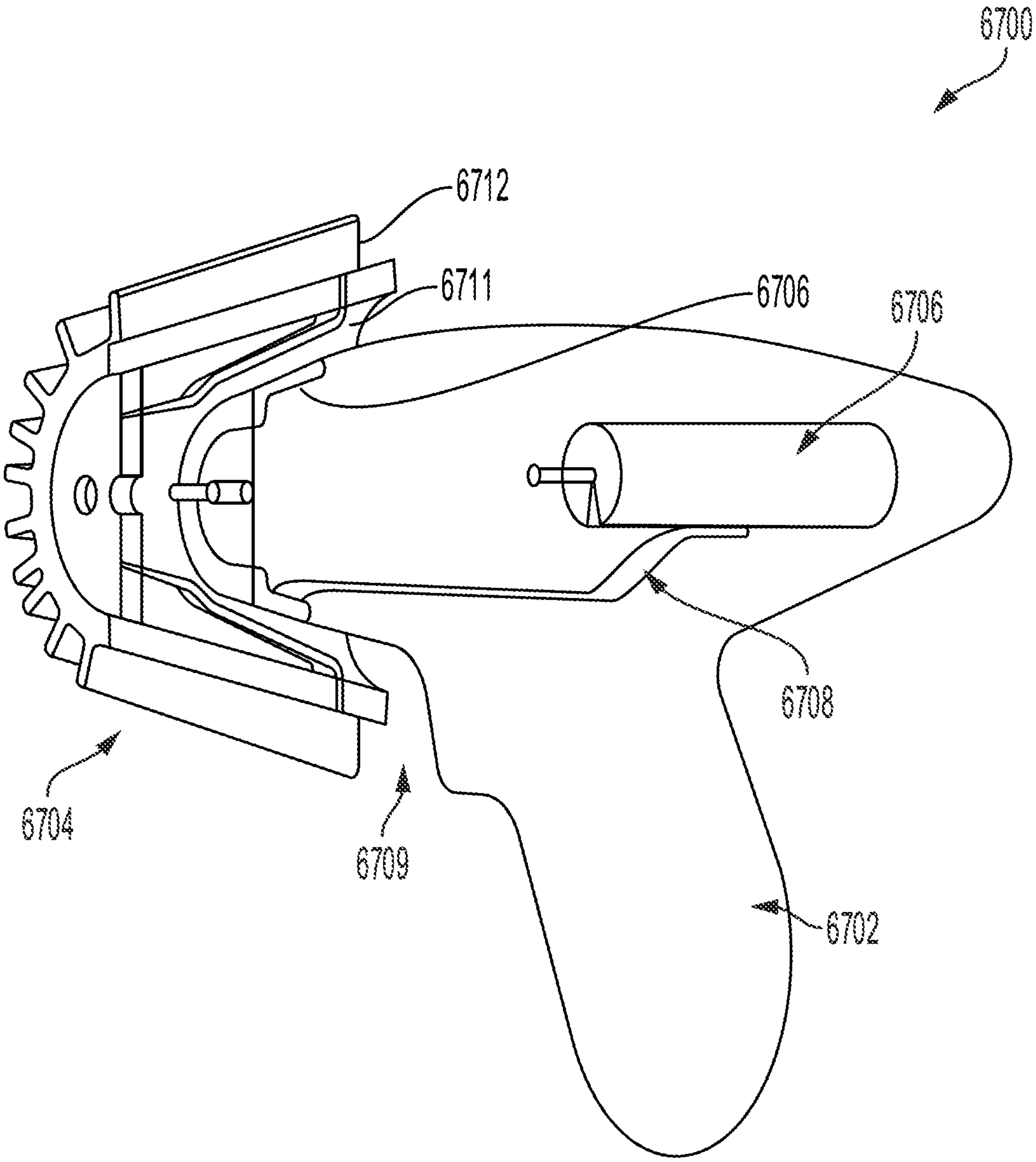

FIG. 244 illustrates a sectioned perspective view of a surgical instrument including a handheld surgical device and a distal portion of an adapter assembly with energy management components, in accordance with at least one non-limiting aspect of the present disclosure.

Figure 245:
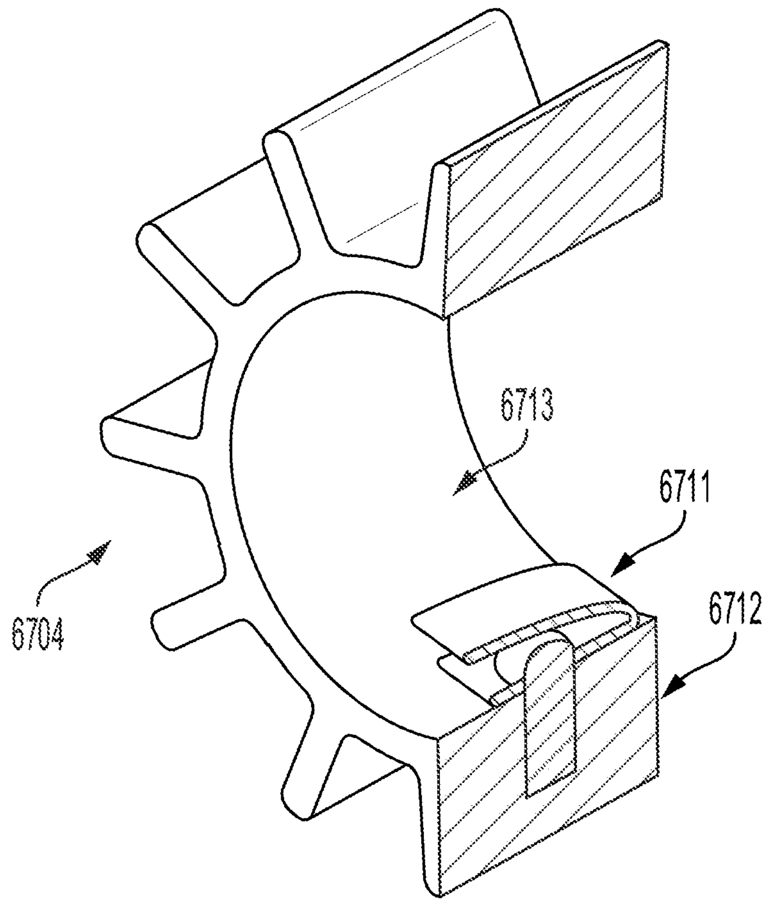

FIG. 245 illustrates a sectioned perspective view of an energy management component of the adapter assembly of FIG. 244.

Figure 246:
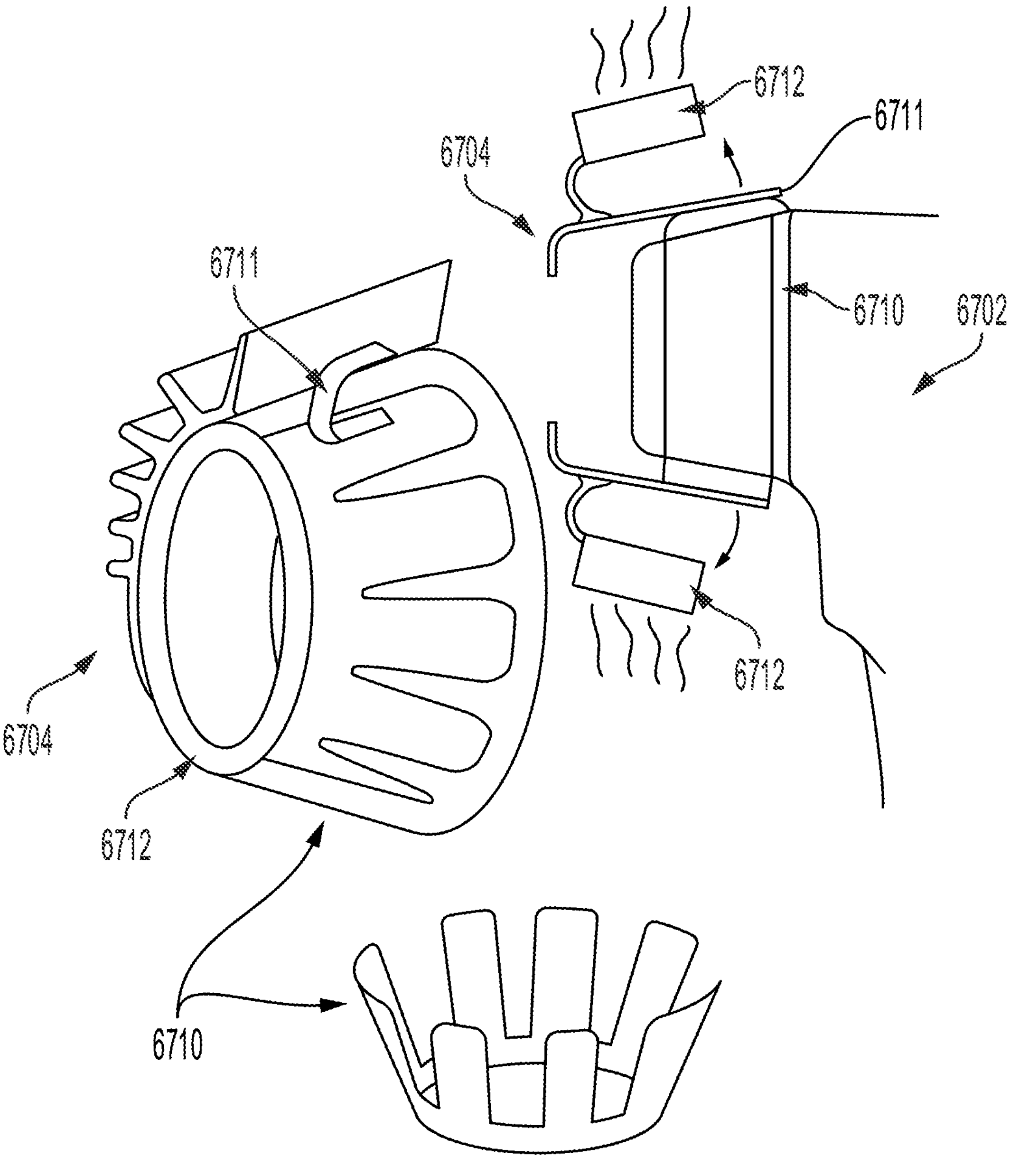

FIG. 246 illustrates a perspective view of another energy management component of the adapter assembly of FIG. 244.

Figure 247:
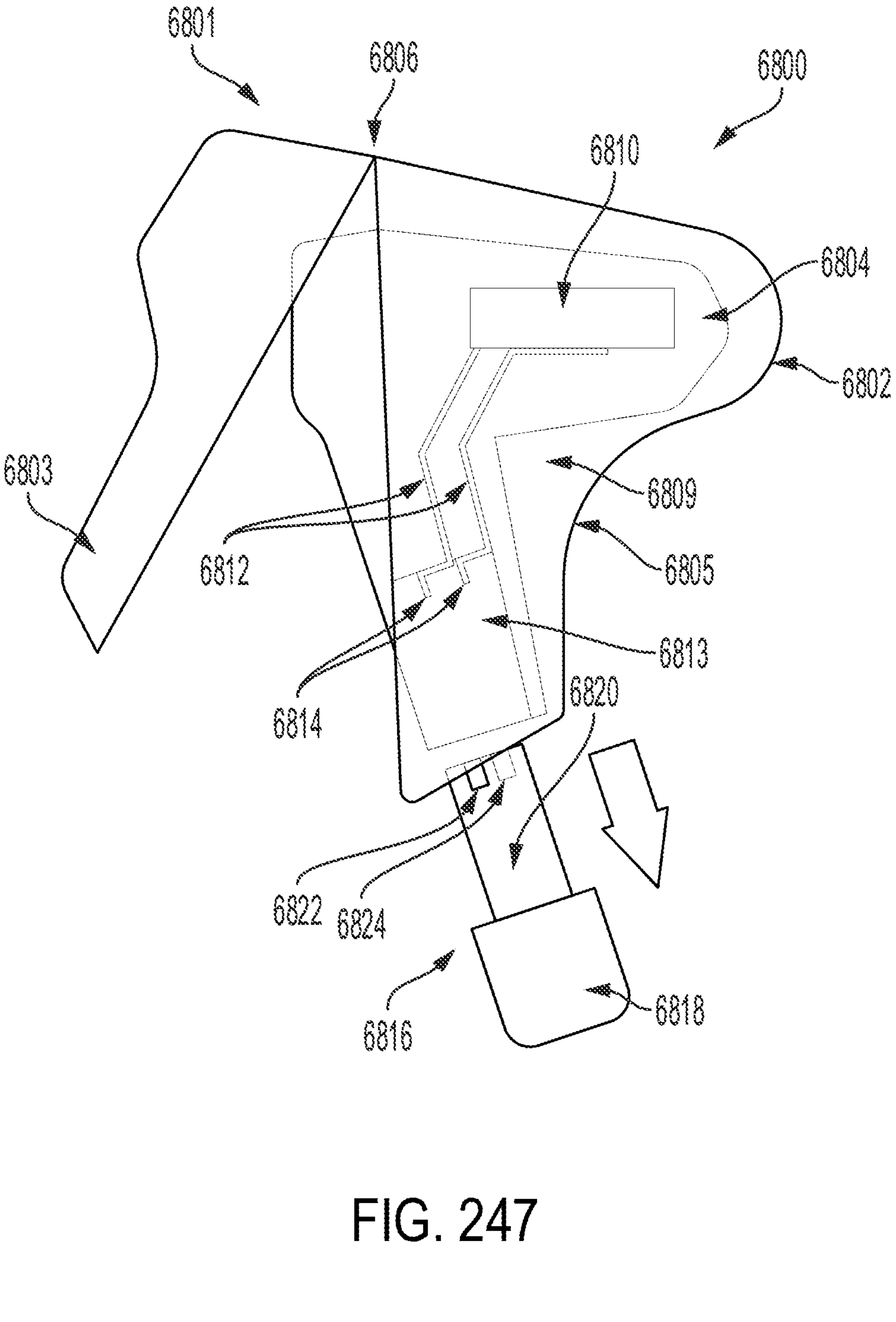

FIG. 247 illustrates a sectioned side view of a surgical instrument including a handheld surgical device and an adapter assembly that includes an energy management system, in accordance with at least one non-limiting aspect of the present disclosure.

Figure 248:
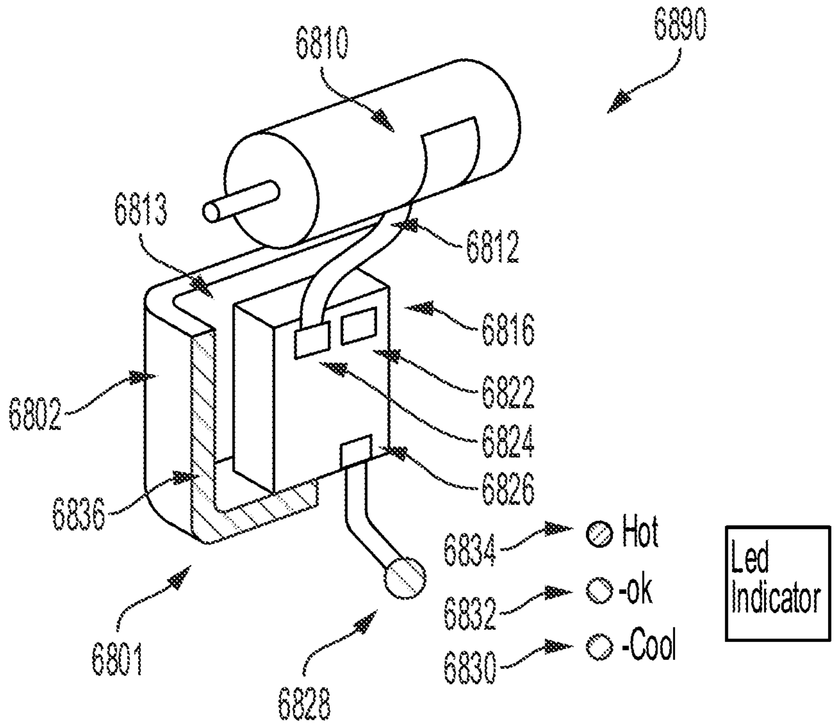

FIG. 248 illustrates a sectioned perspective view of the energy management component of the surgical instrument of FIG. 247.

Figure 249:
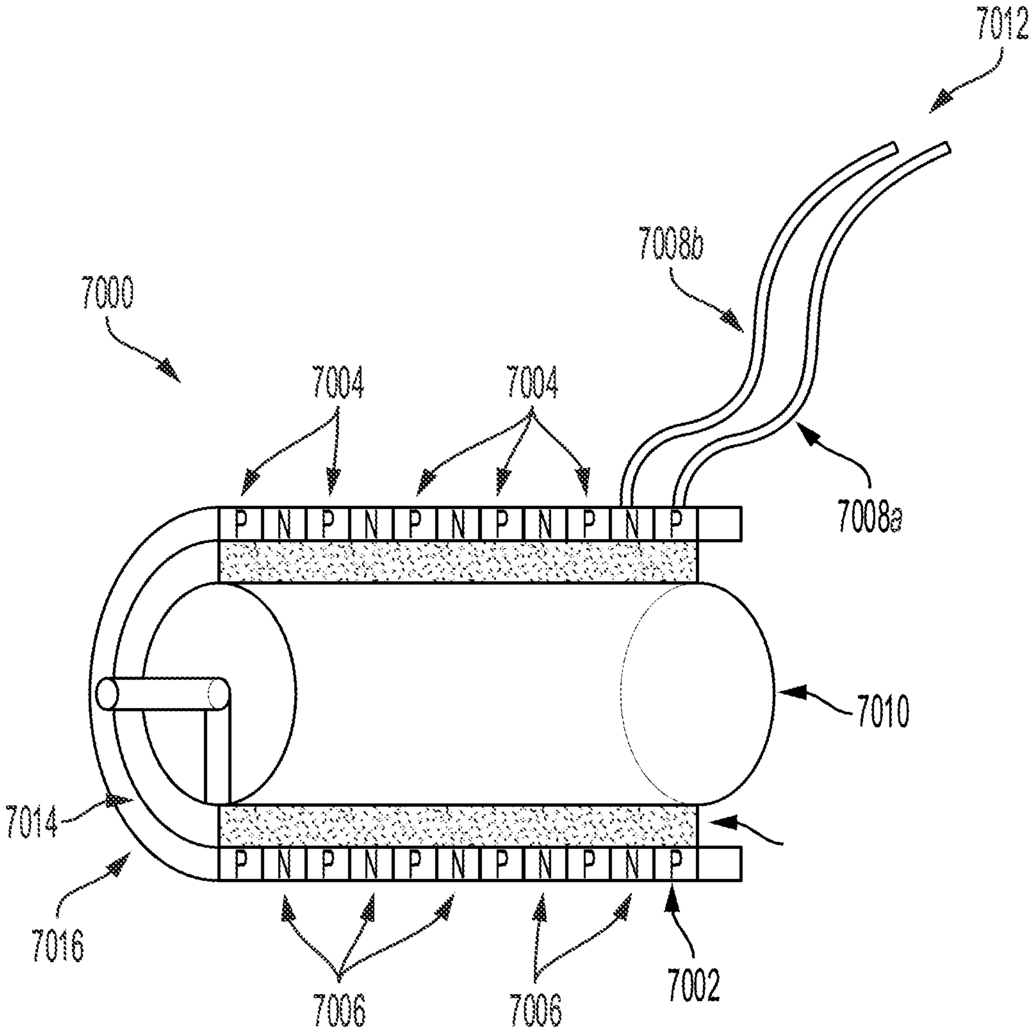

FIG. 249 illustrates a sectioned perspective view of another energy management component of an energy management system of a surgical instrument, in accordance with at least one non-limiting aspect of the present disclosure.

Figure 250:
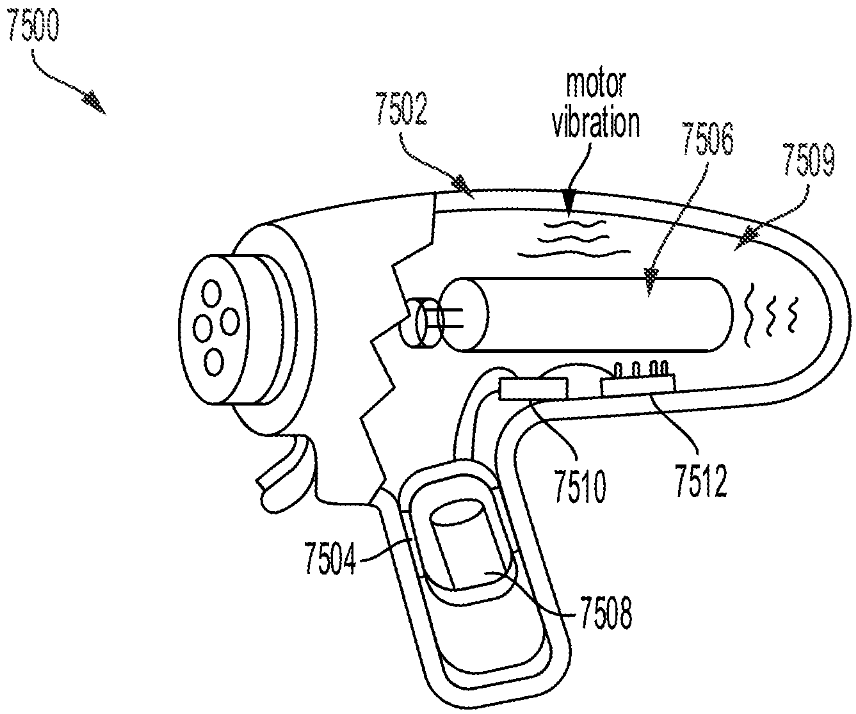

FIG. 250 illustrates a sectioned perspective view of a surgical instrument including an energy management system, in accordance with at least one non-limiting aspect of the present disclosure.

Figure 251:
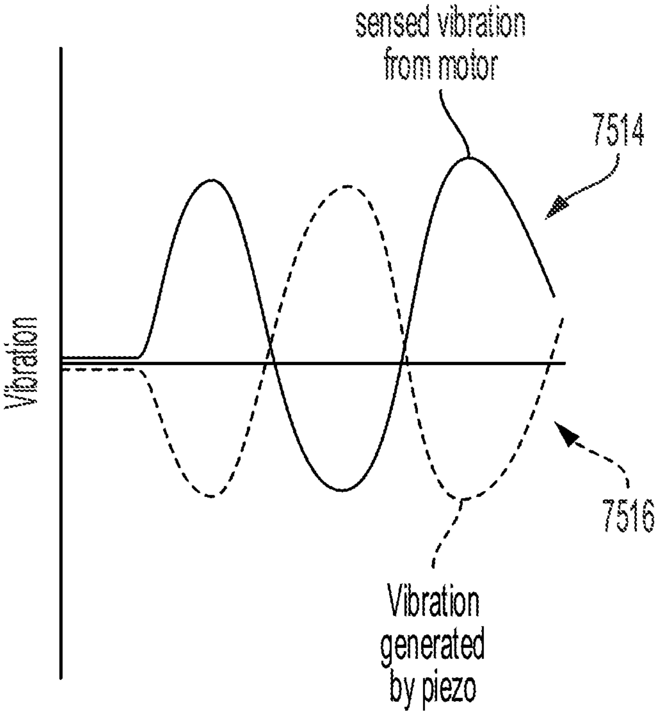

FIG. 251 illustrates a chart depicting an energy response of the energy management system of FIG. 250.

Figure 252:
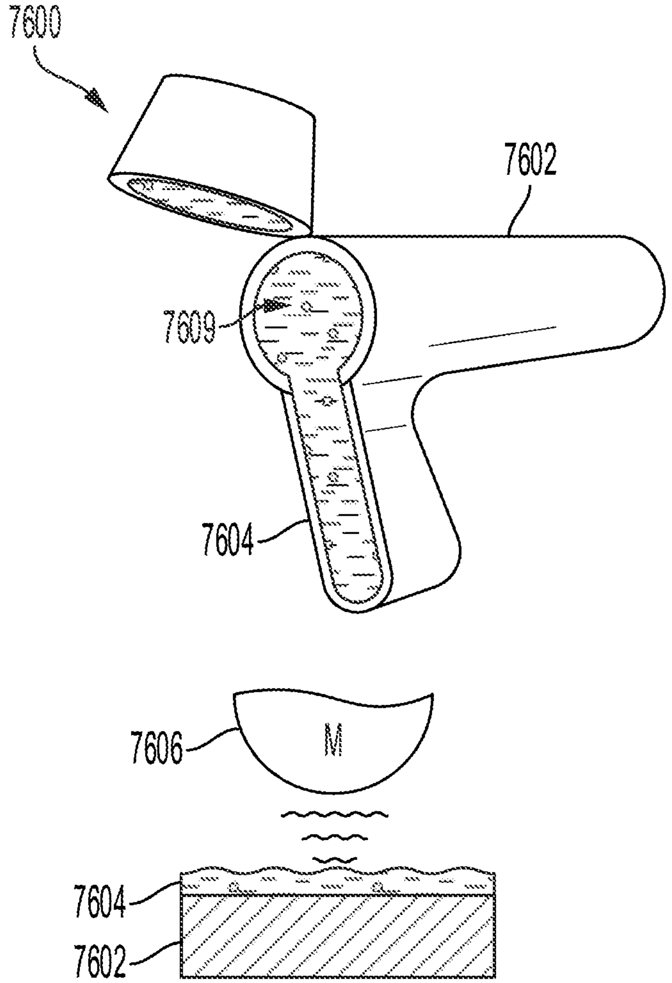

FIG. 252 illustrates a sectioned perspective view of an adapter assembly of a surgical instrument that includes an energy management component, in accordance with at least one non-limiting aspect of the present disclosure.

Figure 253A:
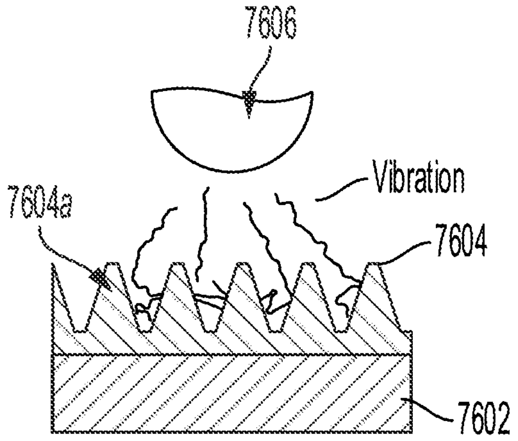
Figure 253B:
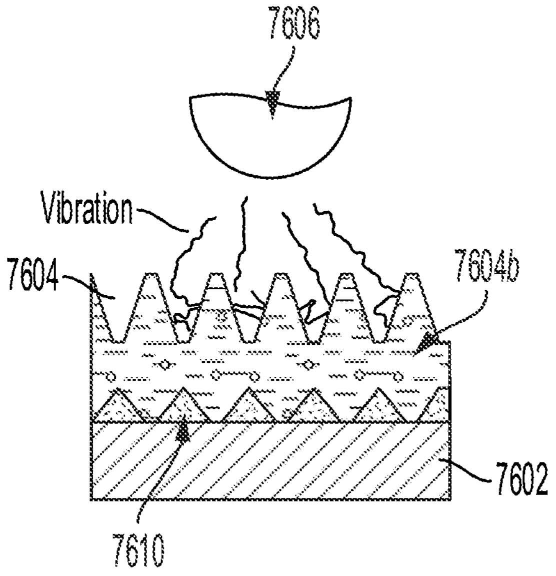

FIGS. 253A and 253B illustrate sectioned profile views of energy management components of the adapter assembly of FIG. 252.

Figure 254A:
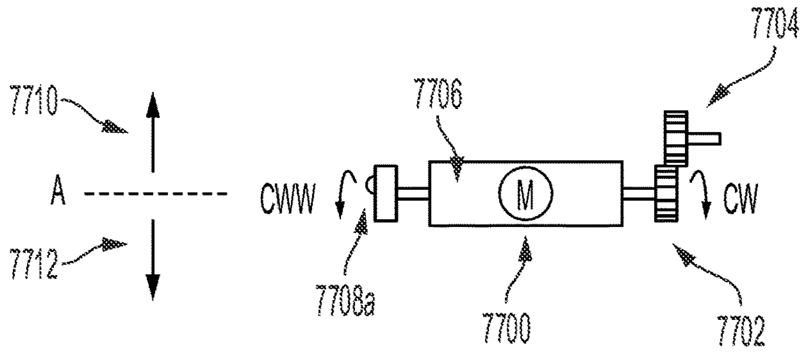
Figure 254B:
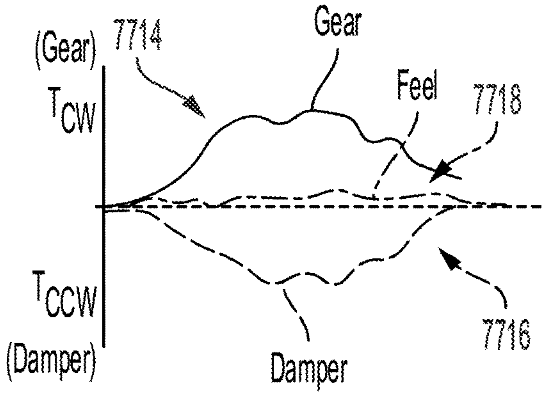
Figure 254C:
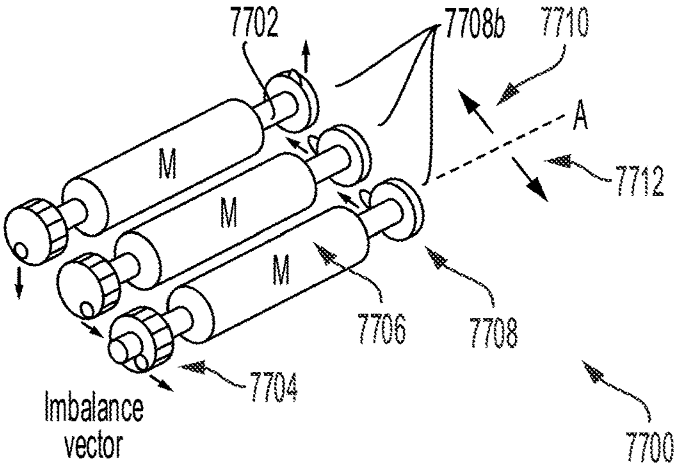

FIG. 254A-254C collectively illustrate various views of energy management systems and a chart depicting an energy response of the illustrated energy management systems, in accordance with at least one non-limiting aspect of the present disclosure.

Figure 255:
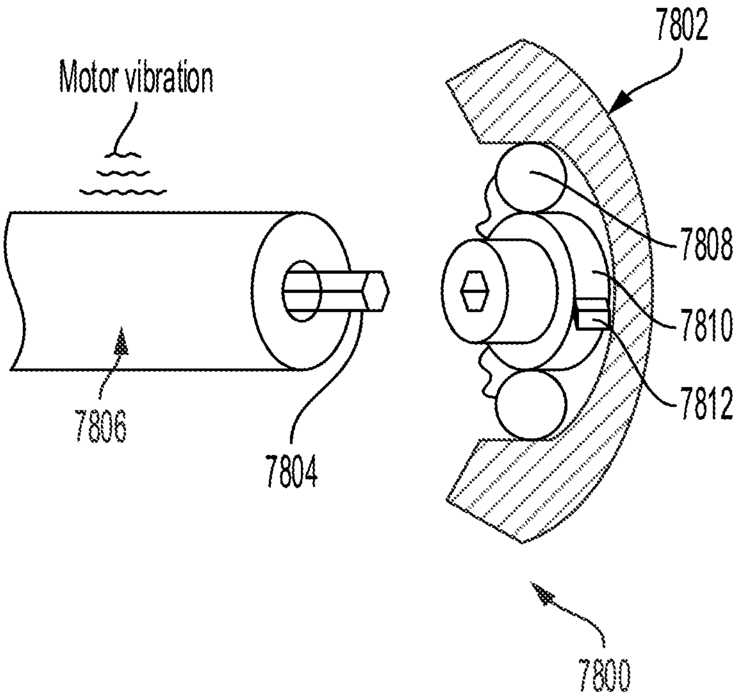

FIG. 255 illustrates a perspective view of an energy management system of a surgical instrument, in accordance with at least one non-limiting aspect of the present disclosure.

Figure 256:
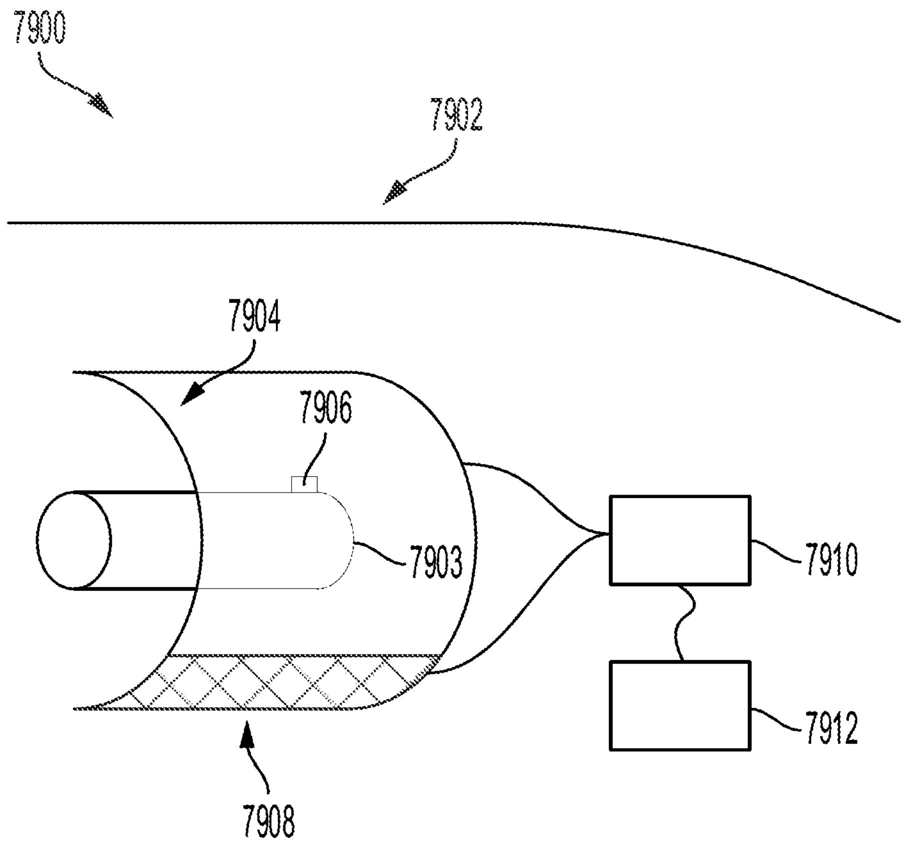

FIG. 256 illustrates a sectioned perspective view of an energy management system of a surgical instrument, in accordance with at least one non-limiting aspect of the present disclosure.

Figure 257:
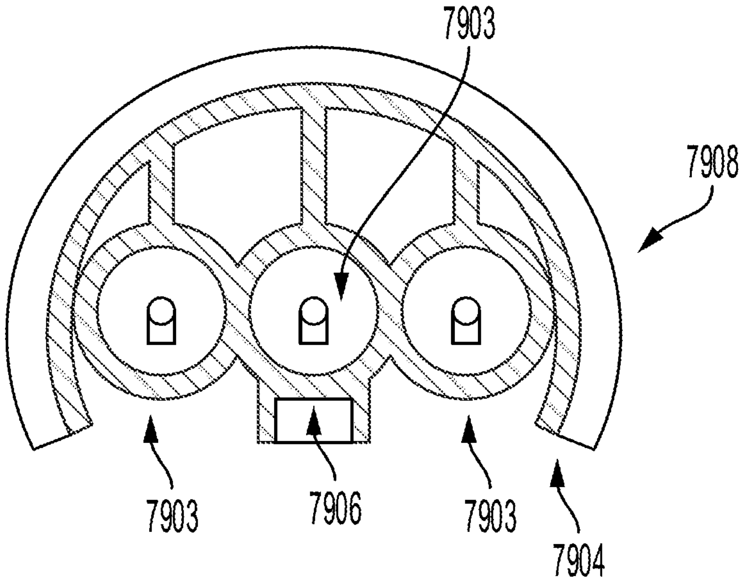

FIG. 257 illustrates a sectioned front view of the energy management system of FIG. 256.

Figure 258:
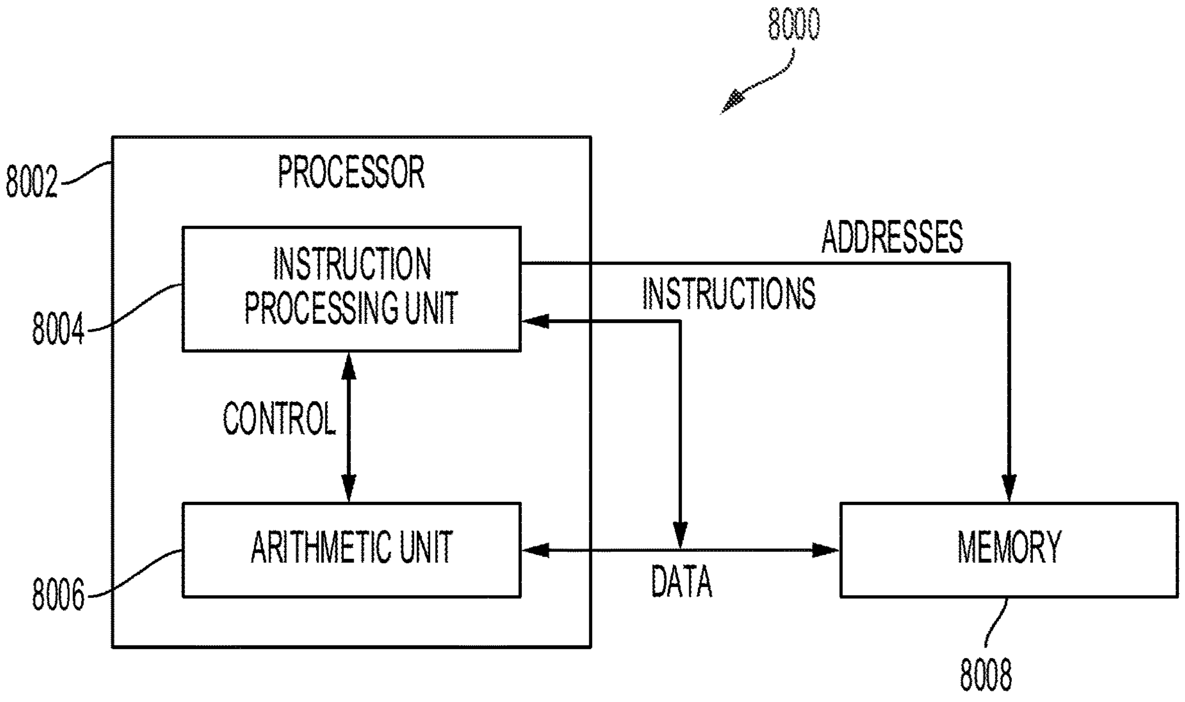

FIG. 258 illustrates a schematic of a control circuit configured to manage energy dissipated by a surgical instrument, in accordance with at least one non-limiting aspect of the present disclosure.

Figure 259:
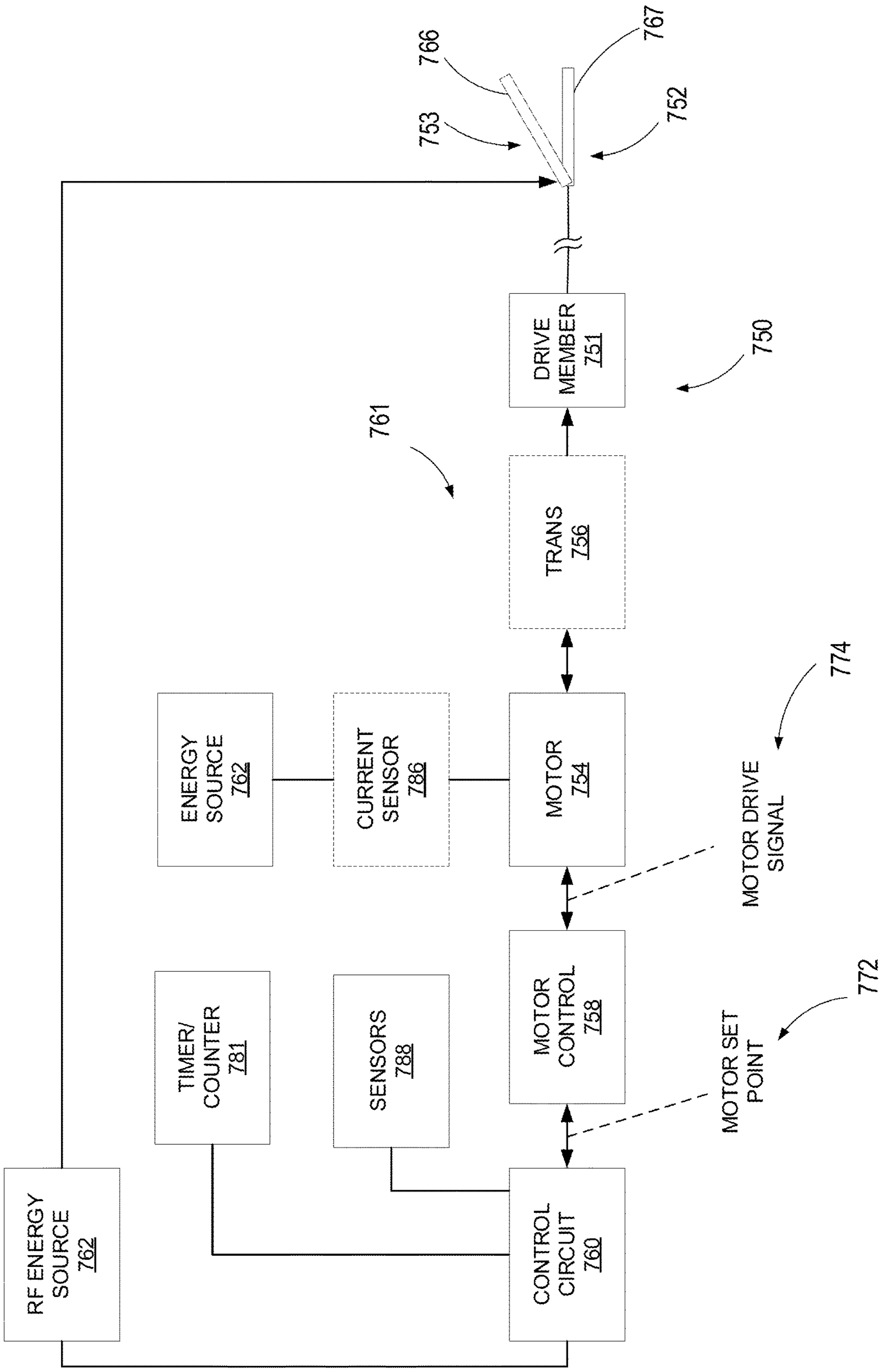

FIG. 259 is a schematic diagram of a surgical instrument, in accordance with at least one aspect of the present disclosure.

Figure 260:
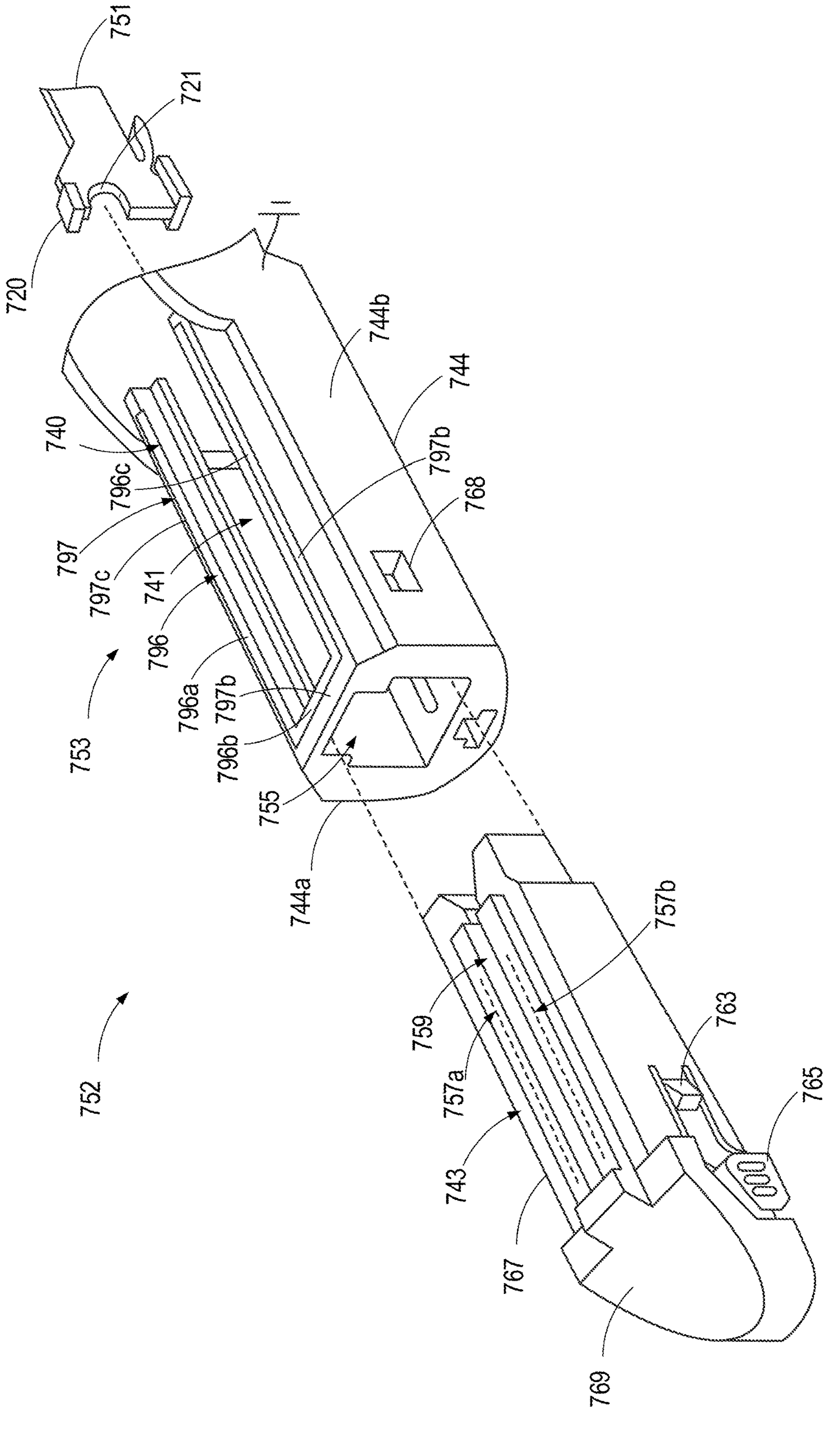

FIG. 260 is a partial perspective view of a jaw of an end effector of the surgical instrument of FIG. 259 and a staple cartridge for assembly therewith.

Figure 261:
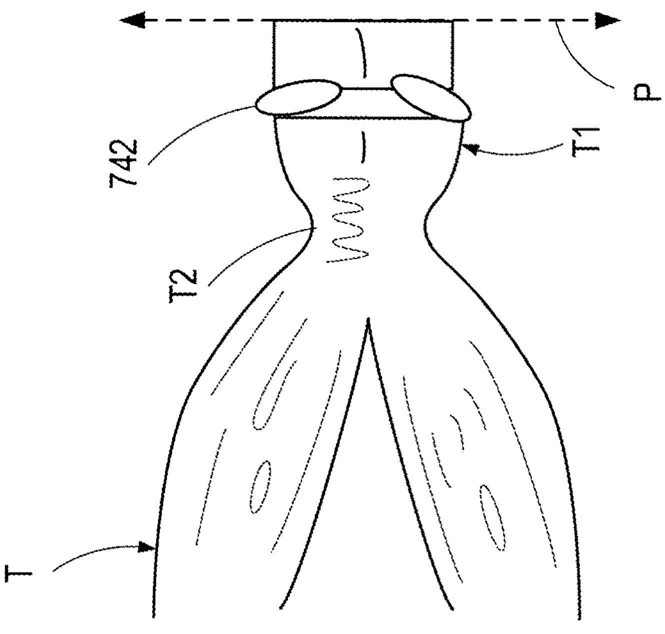

FIG. 261 is a cross-sectional view of the end effector of the surgical instrument of FIG. 259.

Figure 262:
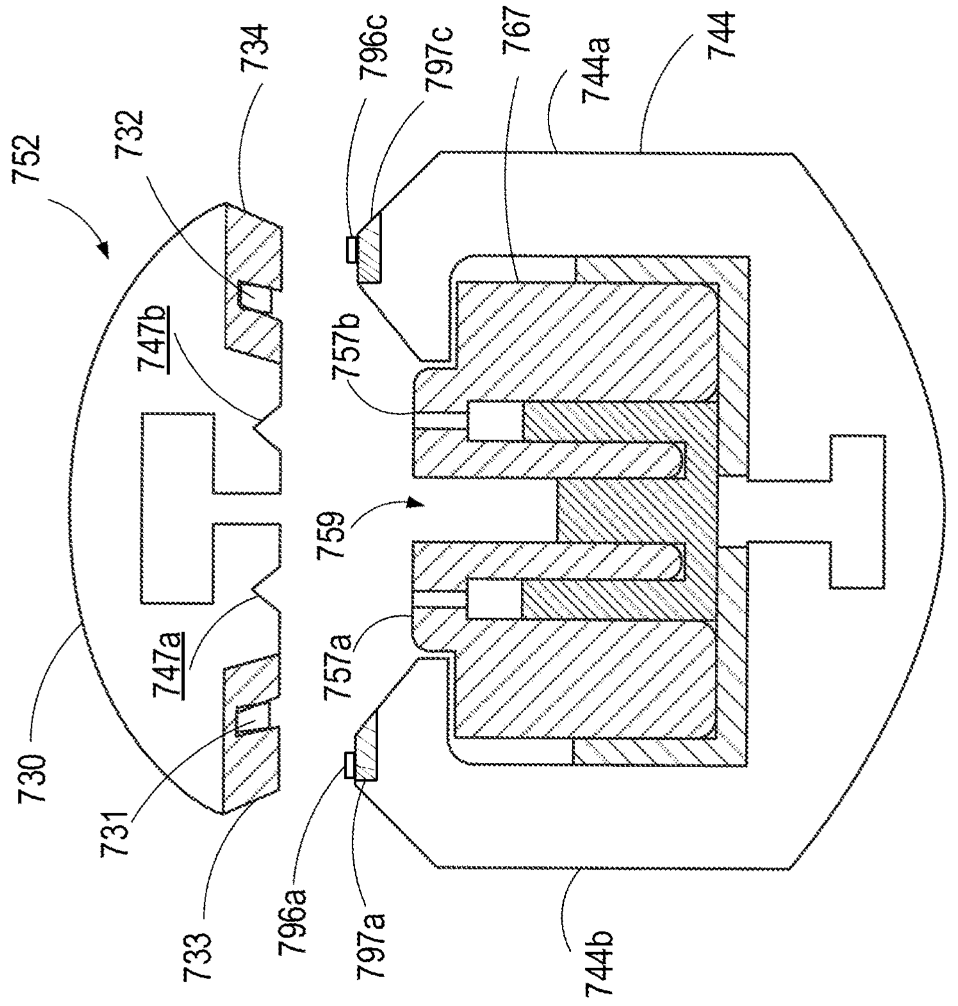

FIG. 262 is cross-sectional view of a tissue that received a surgical treatment from the surgical instrument of FIG. 259.

Figure 263:
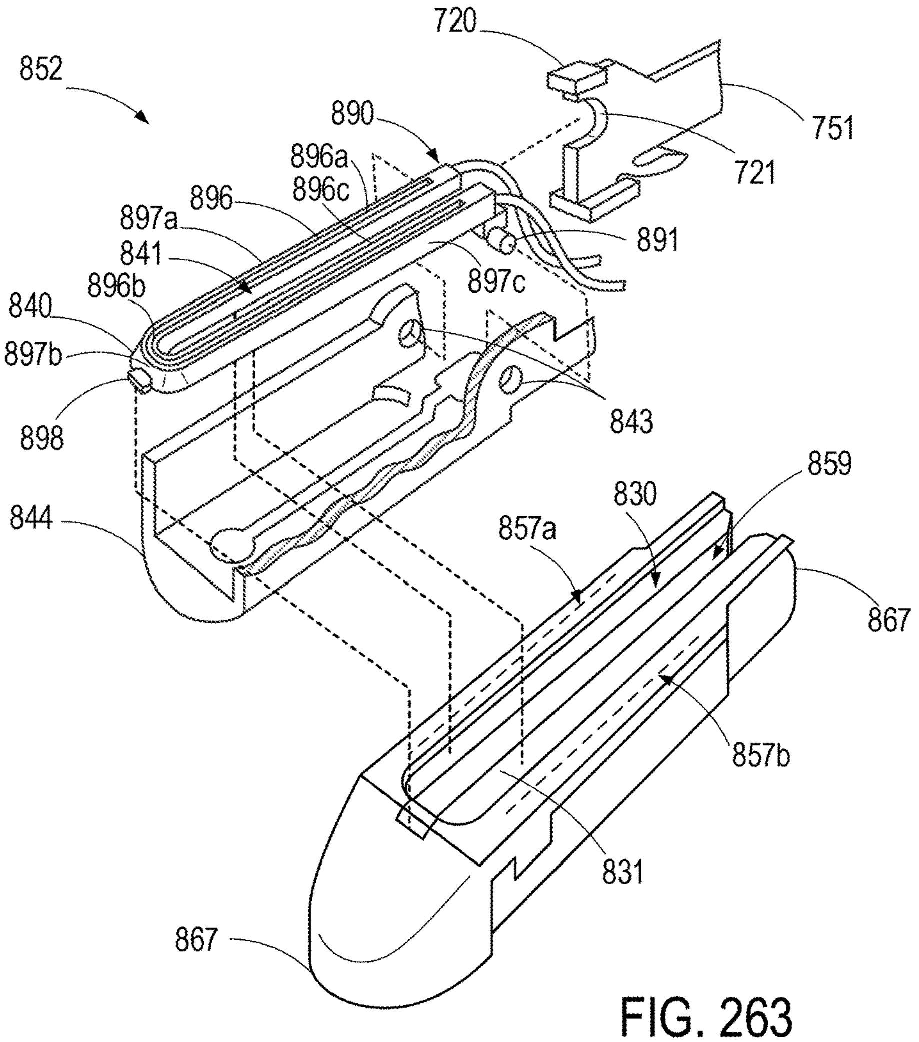

FIG. 263 is a partial exploded view of an end effector for use with the surgical instrument of FIG. 259, in accordance with at least one aspect of the present disclosure.

Figure 264:
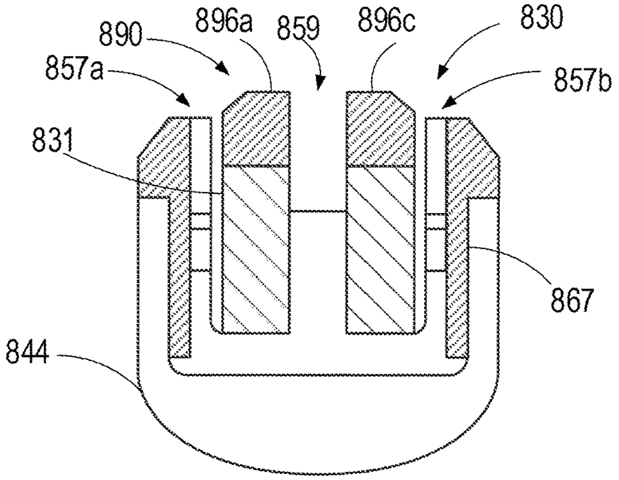

FIG. 264 is a partial cross-sectional view of the end effector of FIG. 263 illustrating a channel assembled with a staple cartridge and an radio frequency (RF) overlay, in accordance with at least one aspect of the present disclosure.

Figure 265:
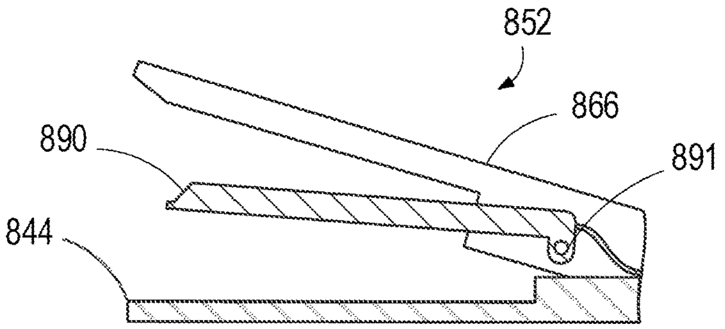
Figure 266:
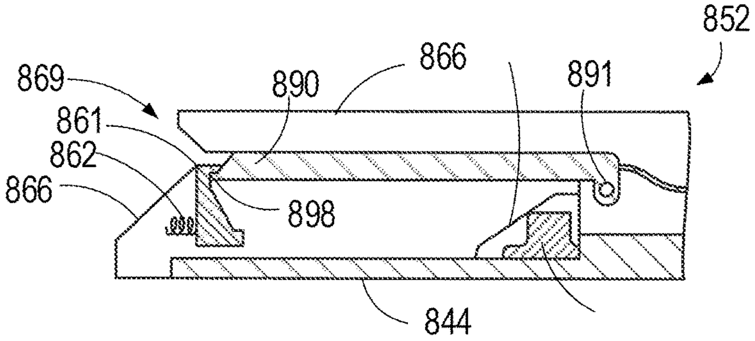
Figure 267:
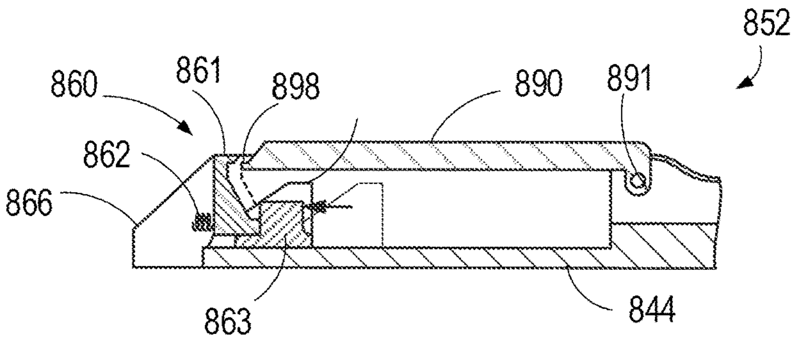

FIGS. 265-267 illustrate a process and mechanisms for assembly of the end effector of FIG. 263.

Figure 268:
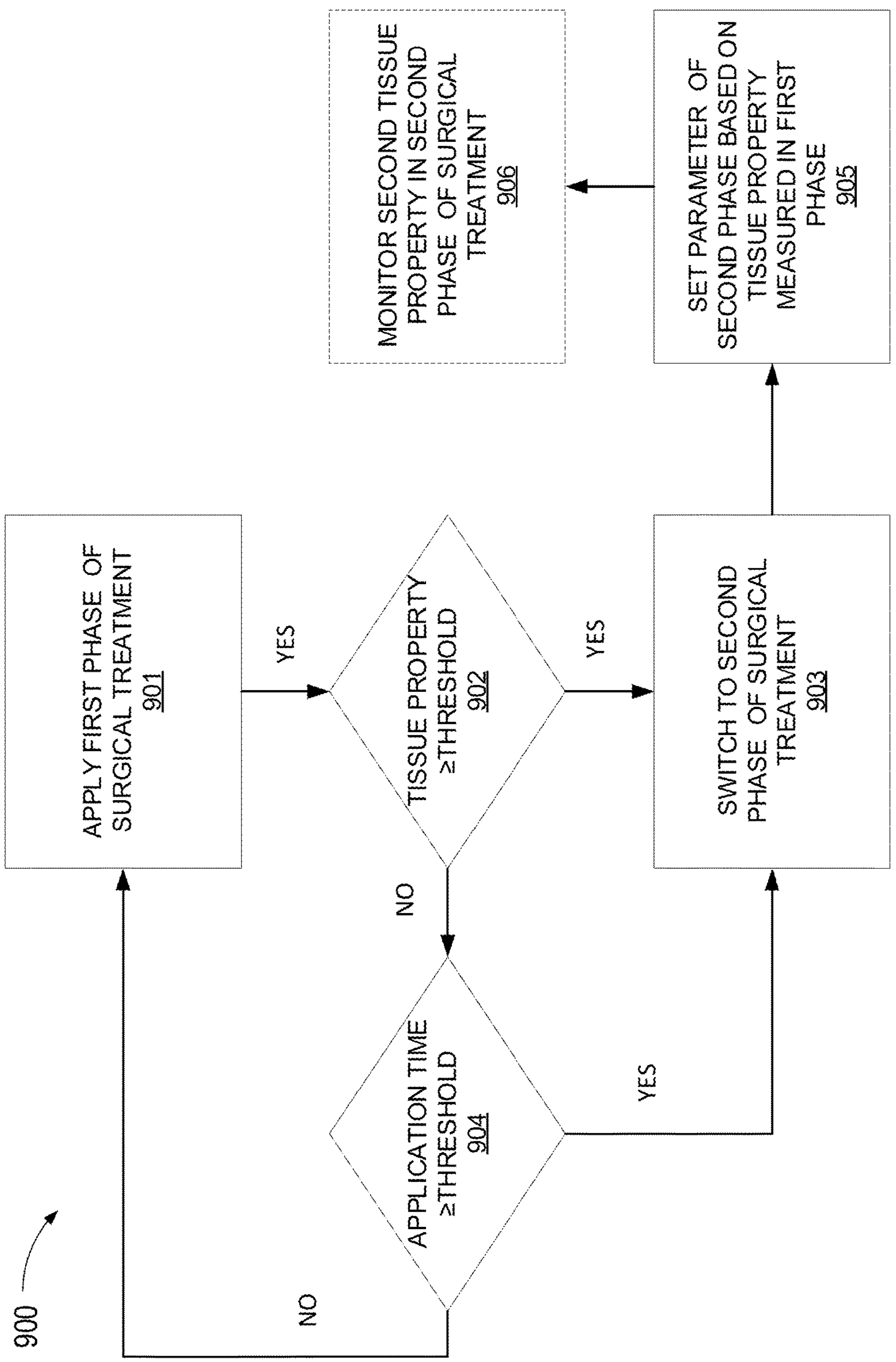

FIG. 268 is a logic flow diagram of a process depicting a control program or a logic configuration for effecting a surgical treatment of a tissue, in accordance with at least one aspect of the present disclosure.

Figure 269:
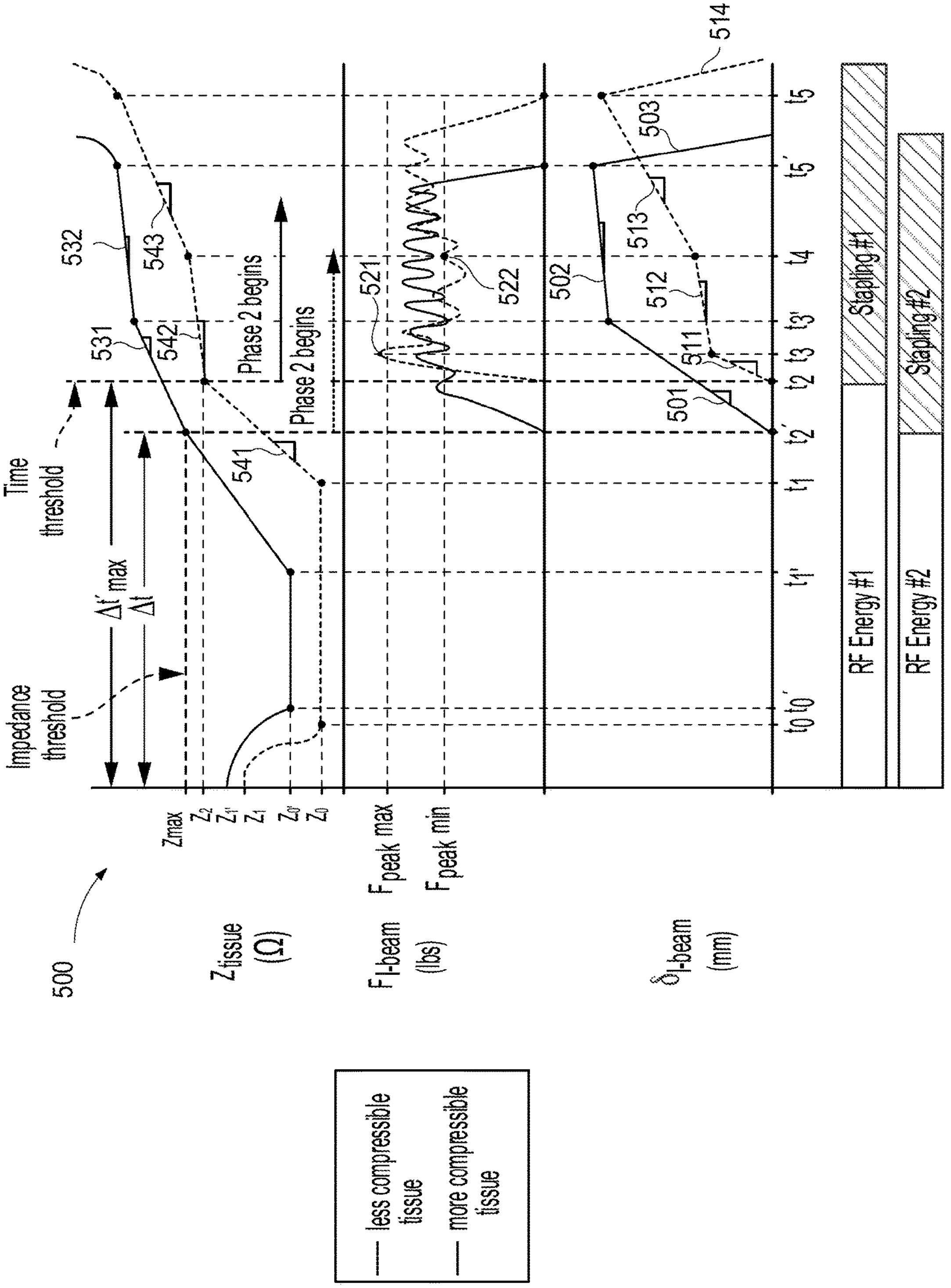

FIG. 269 a graph representing an example implementation of the surgical treatment of the process of FIG. 268 to two tissues with different tissue compressibility.

Figure 270:
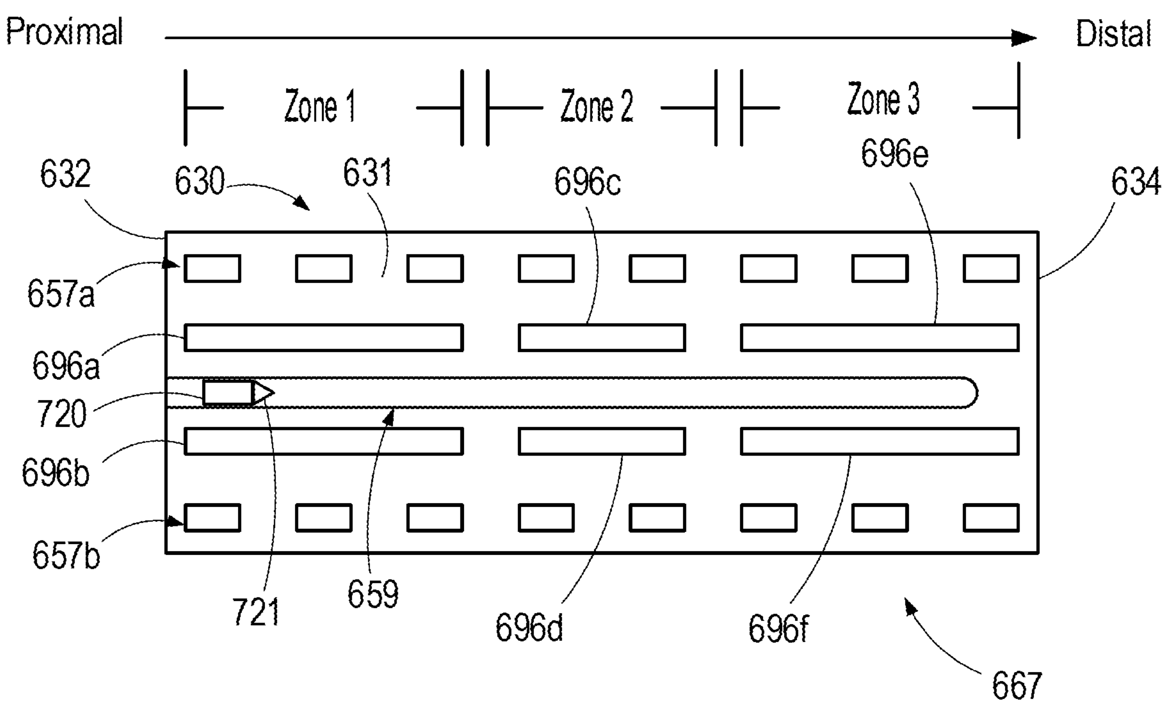

FIG. 270 is a partial top view a cartridge deck of a cartridge assembled with an end effector of the surgical instrument of FIG. 259.

Figure 271:
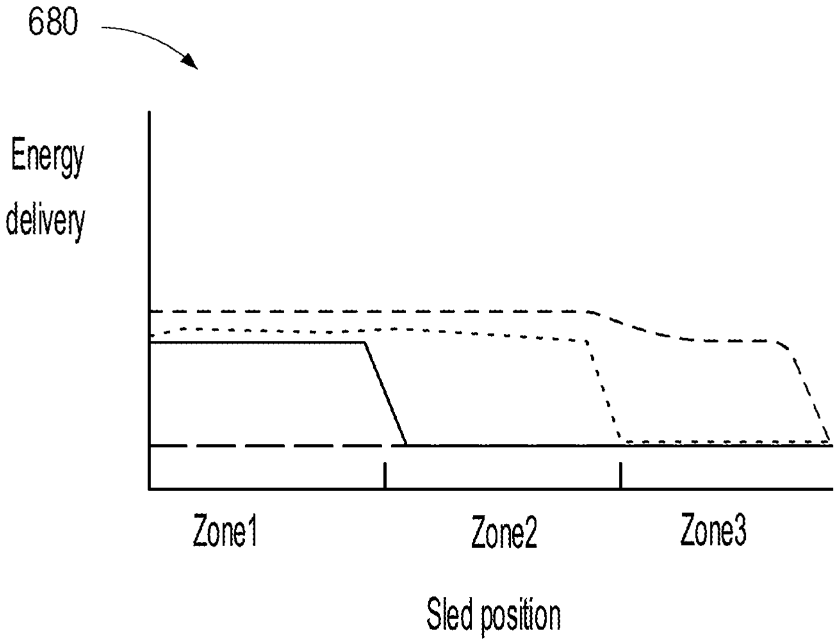

FIG. 271 is a logic flow diagram of a process depicting a control program or a logic configuration for effecting a surgical treatment of a tissue, in accordance with at least one aspect of the present disclosure.

Figure 272:
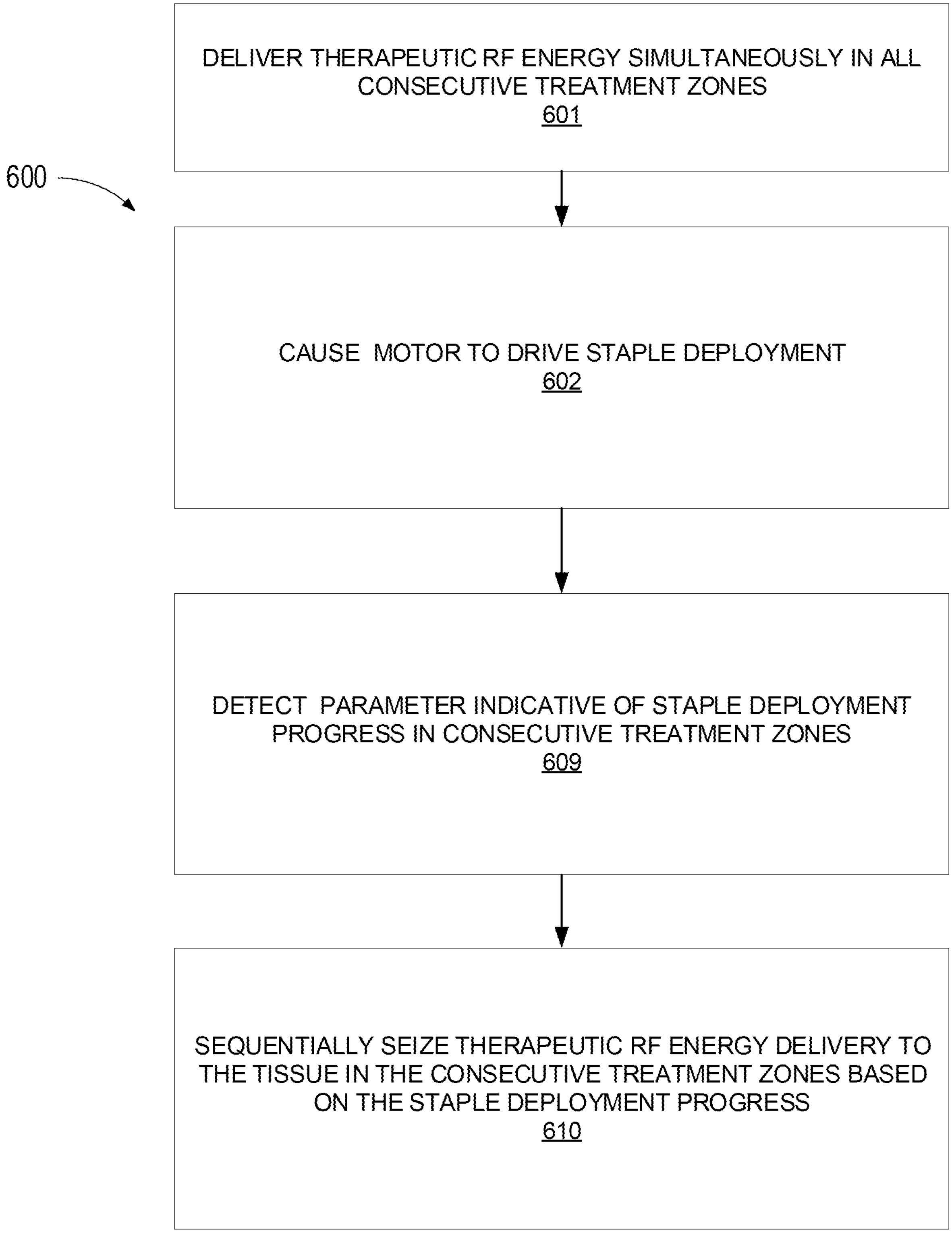

FIG. 272 is a graph illustrating a sequence for deactivating electrode segments of the end effector of FIG. 259, in accordance with at least one aspect of the present disclosure.

Figure 273:
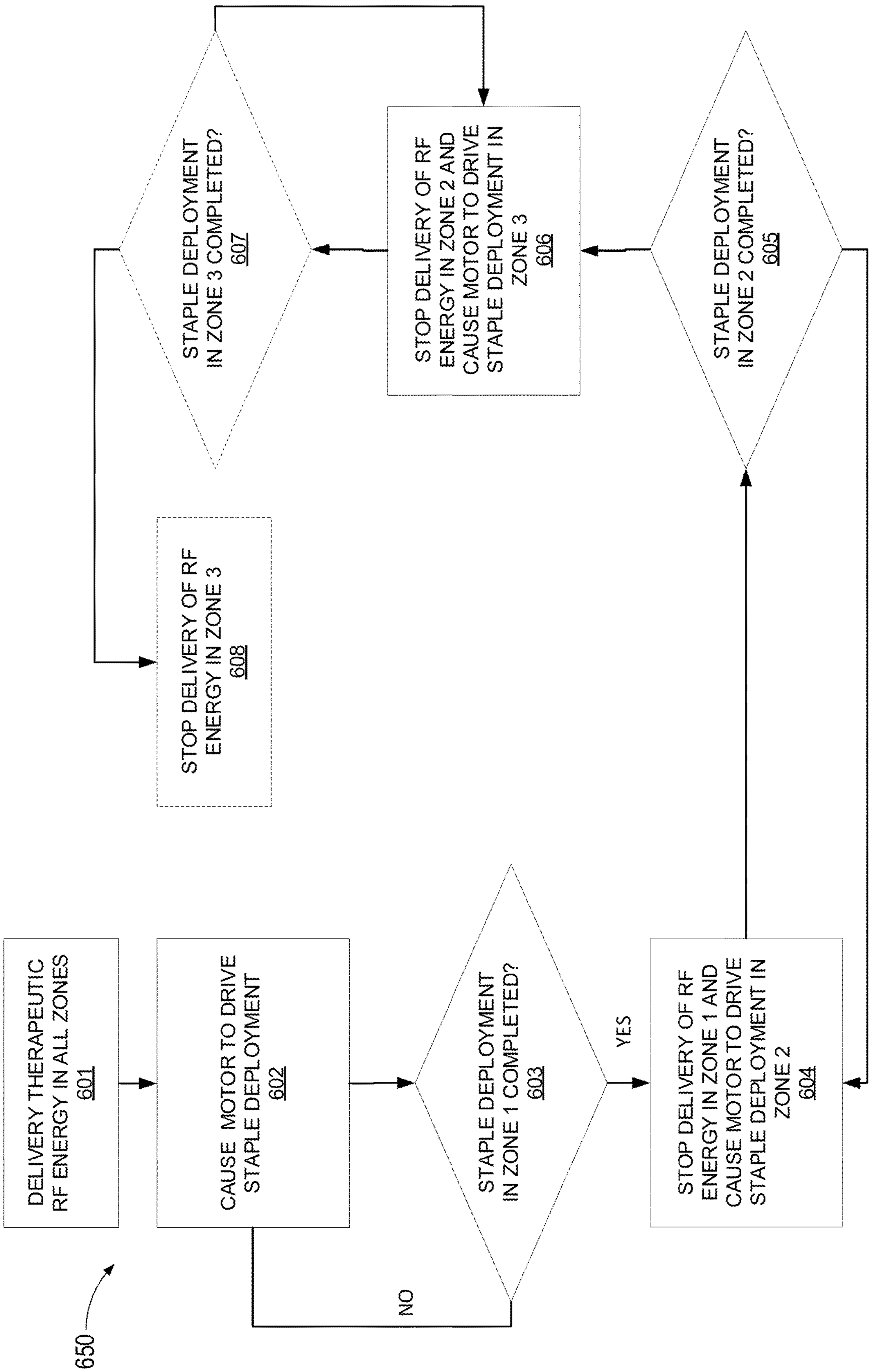

FIG. 273 is a logic flow diagram of a process depicting a control program or a logic configuration for effecting a surgical treatment of a tissue, in accordance with at least one aspect of the present disclosure.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Applicant of the present application also owns the following U.S. Patent Applications that were filed on Dec. 2, 2020 and which are each herein incorporated by reference in their respective entireties:

- U.S. patent application Ser. No. 17/109,595, entitled SURGICAL INSTRUMENTS WITH INTERACTIVE FEATURES TO REMEDY INCIDENTAL SLED MOVEMENTS, now U.S. Patent Application Publication No. 2022/0167980;
- U.S. patent application Ser. No. 17/109,598, entitled SURGICAL INSTRUMENTS WITH SLED LOCATION DETECTION AND ADJUSTMENT FEATURES, now U.S. Patent Application Publication No. 2022/0167971;
- U.S. patent application Ser. No. 17/109,615, entitled SURGICAL INSTRUMENT WITH CARTRIDGE RELEASE MECHANISMS, now U.S. Patent Application Publication No. 2022/0167972;
- U.S. patent application Ser. No. 17/109,627, entitled DUAL-SIDED REINFORCED RELOAD FOR SURGICAL INSTRUMENTS, now U.S. Patent Application Publication No. 2022/0167981;
- U.S. patent application Ser. No. 17/109,636, entitled SURGICAL SYSTEMS WITH DETACHABLE SHAFT RELOAD DETECTION, now U.S. Patent Application Publication No. 2022/0167973;
- U.S. patent application Ser. No. 17/109,645, entitled SURGICAL INSTRUMENTS WITH ELECTRICAL CONNECTORS FOR POWER TRANSMISSION ACROSS STERILE BARRIER, now U.S. Patent Application Publication No. 2022/0167982;
- U.S. patent application Ser. No. 17/109,648, entitled DEVICES AND METHODS OF MANAGING ENERGY DISSIPATED WITHIN STERILE BARRIERS OF SURGICAL INSTRUMENT HOUSINGS, now U.S. Patent Application Publication No. 2022/0167983;
- U.S. patent application Ser. No. 17/109,651, entitled POWERED SURGICAL INSTRUMENTS WITH EXTERNAL CONNECTORS, now U.S. Patent Application Publication No. 2022/0167977;
- U.S. patent application Ser. No. 17/109,656, entitled POWERED SURGICAL INSTRUMENTS WITH SMART RELOAD WITH SEPARATELY ATTACHABLE EXTERIORLY MOUNTED WIRING CONNECTIONS, now U.S. Patent Application Publication No. 2022/0167974;
- U.S. patent application Ser. No. 17/109,667, entitled POWERED SURGICAL INSTRUMENTS WITH COMMUNICATION INTERFACES THROUGH STERILE BARRIER, now U.S. Patent Application Publication No. 2022/0167984;
- U.S. patent application Ser. No. 17/109,669, entitled POWERED SURGICAL INSTRUMENTS WITH MULTI-PHASE TISSUE TREATMENT, now U.S. Patent Application Publication No. 2022/0167975.

Applicant of the present application owns the following U.S. patent applications, filed on Dec. 4, 2018, the disclosure of each of which is herein incorporated by reference in its entirety:

- U.S. patent application Ser. No. 16/209,385, entitled METHOD OF HUB COMMUNICATION, PROCESSING, STORAGE AND DISPLAY;
- U.S. patent application Ser. No. 16/209,395, entitled METHOD OF HUB COMMUNICATION;
- U.S. patent application Ser. No. 16/209,403, entitled METHOD OF CLOUD BASED DATA ANALYTICS FOR USE WITH THE HUB;
- U.S. patent application Ser. No. 16/209,407, entitled METHOD OF ROBOTIC HUB COMMUNICATION, DETECTION, AND CONTROL;

U.S. patent application Ser. No. 16/209,416, entitled METHOD OF HUB COMMUNICATION, PROCESSING, DISPLAY, AND CLOUD ANALYTICS;

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, entitled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, entitled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, entitled METHOD FOR SMOKE EVACUATION FOR SURGICAL HUB;

U.S. patent application Ser. No. 16/209,453, entitled METHOD FOR CONTROLLING SMART ENERGY DEVICES;

U.S. patent application Ser. No. 16/209,458, entitled METHOD FOR SMART ENERGY DEVICE INFRASTRUCTURE;

U.S. patent application Ser. No. 16/209,465, entitled METHOD FOR ADAPTIVE CONTROL SCHEMES FOR SURGICAL NETWORK CONTROL AND INTERACTION;

U.S. patent application Ser. No. 16/209,478, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, entitled METHOD FOR FACILITY DATA COLLECTION AND INTERPRETATION; and U.S. patent application Ser. No. 16/209,491, entitled METHOD FOR CIRCULAR STAPLER CONTROL ALGORITHM ADJUSTMENT BASED ON SITUATIONAL AWARENESS.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

With reference to FIGS. 1-4, a surgical instrument system is provided, such as, for example, an electromechanical surgical instrument system 10. System 10 includes a handle assembly 100, a plurality of types of adapter or shaft assemblies such as, for example, adapter assembly 200*a*, and a plurality of types of end effectors such as, for example, end effector 300*a*. Handle assembly 100 is configured for selective attachment thereto with any one of a number of adapter assemblies, for example, adapter assembly 200*a*, and, in turn, each unique adapter assembly 200*a* is configured for selective connection with any number of surgical loading units or end effectors, such as, for example, end effector 300*a*. End effector 300*a* and adapter assembly 200*a* are configured for actuation and manipulation by handle assembly 100. Upon connecting one adapter assembly 200*a*, for example, to handle assembly 100 and one type of end effector such as, for example, end effector 300*a* to the selected adapter assembly 200*a*, a powered, hand-held, electromechanical surgical instrument is formed.

For a detailed description of the construction and operation of an exemplary electromechanical, hand-held, powered surgical instrument, reference may be made to International Publication No. WO 2009/039506 and U.S. Patent Application Publication No. 2011/0121049, the entire contents of all of which are incorporated herein by reference.

Figure 1:
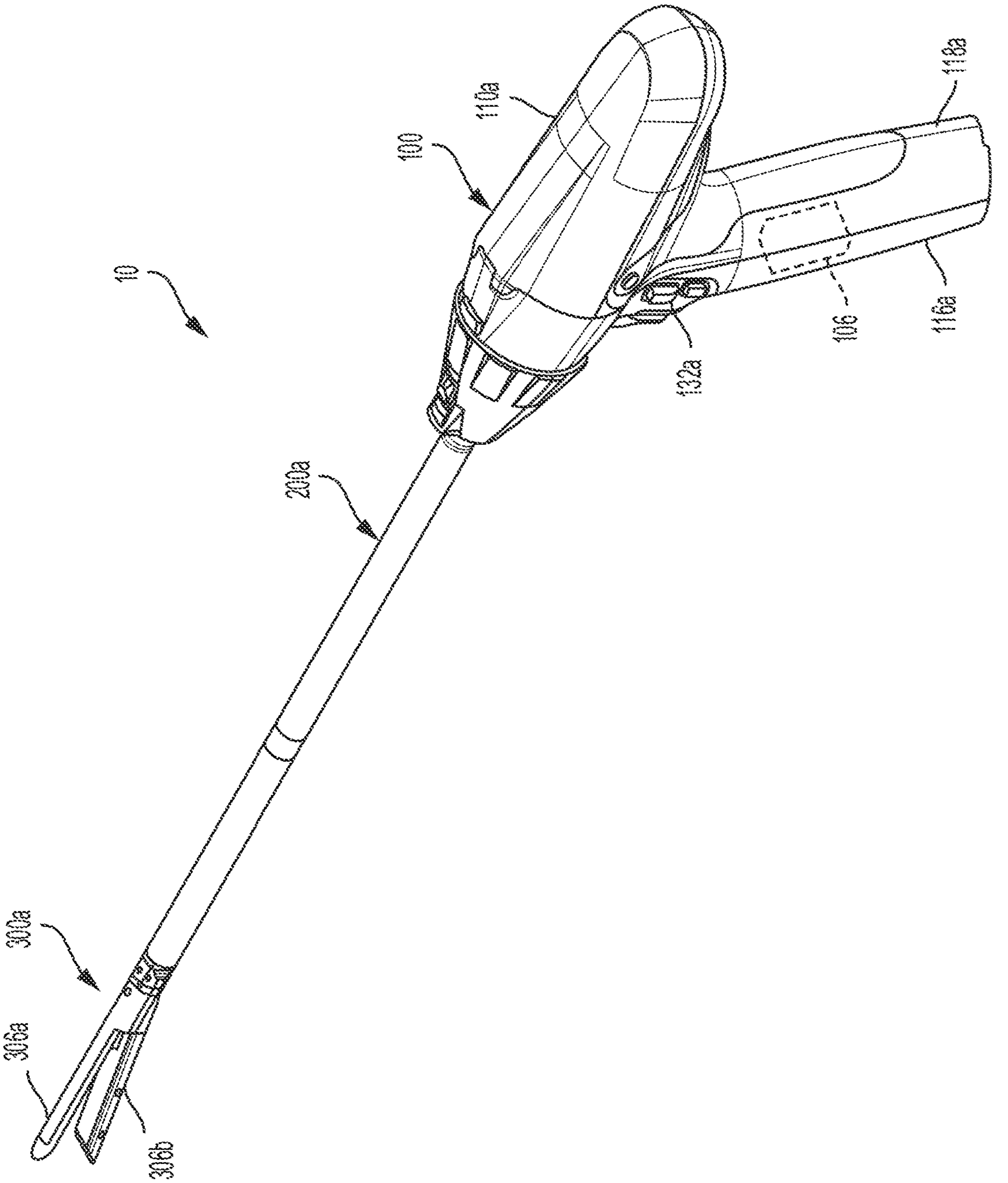
FIG. 1 is a perspective view of a surgical instrument, in accordance with at least one aspect of the present disclosure.
Figure 2:
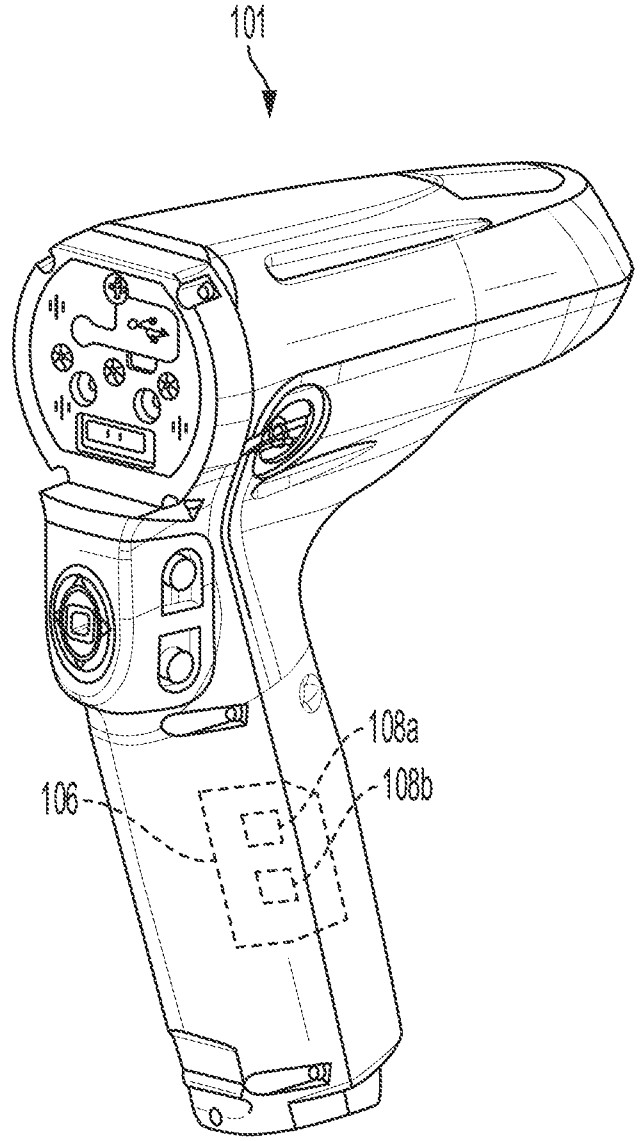
FIG. 2 is a perspective view of a motor operable, inner core, in accordance with at least one aspect of the present disclosure.

With reference to FIGS. 1 and 2, handle assembly 100 includes an inner core 101 and a housing or shell 110*a* configured to selectively receive and encase inner core 101. Inner core 101 is motor operable and configured to drive an operation of a plurality of types of end effectors. Inner core 101 has a plurality of sets of operating parameters (e.g., speed of operation of motors of inner core 101, an amount of power to be delivered by motors of inner core 101 to an adapter assembly, selection of motors of inner core 101 to be actuated, functions of an end effector to be performed by inner core 101, or the like). Each set of operating parameters of inner core 101 is designed to drive the actuation of a specific set of functions unique to respective types of end effectors when an end effector is coupled to inner core 101. For example, inner core 101 may vary its power output, deactivate or activate certain buttons thereof, and/or actuate different motors thereof depending on the type of end effector that is coupled to inner core 101.

With specific reference to FIG. 2, inner core 101 defines an inner housing cavity therein in which a power-pack 106 is situated. Power-pack 106 is configured to control the various operations of inner core 101. Power-pack 106 includes a plurality of motors 108*a*, 108*b* operatively engaged thereto. The rotation of motors 108*a*, 108*b* function to drive shafts and/or gear components of adapter assembly 200*a*, for example, in order to drive the various operations of end effectors attached thereto, for example, end effector 300*a*. Although two motors are depicted in the example illustrated in FIG. 2, in other examples, a handle assembly can include more or less than two motors.

In various examples, the handle assembly 100 is replaced with a robotic arm of a robotic system. In such examples, the adapter assembly 200*a* may also be effectively employed with a tool drive assembly of a robotically controlled or automated surgical system. For example, the adapter assemblies disclosed herein may be employed with various robotic systems, instruments, components, and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

When end effector 300*a* is coupled to inner core 101, motors of power-pack 106 are configured to drive shafts and/or gear components of adapter assembly 200*a* in order to selectively move end effector 300*a* relative to a proximal body portion 302*a* of end effector 300*a*, to rotate end effector 300*a* about a longitudinal axis “X”, to move a cartridge assembly 308*a* and an anvil assembly 306*a* of end effector 300*a* relative to one another, and/or to fire staples from within cartridge assembly 308*a* of end effector 300*a*.

Figure 3:
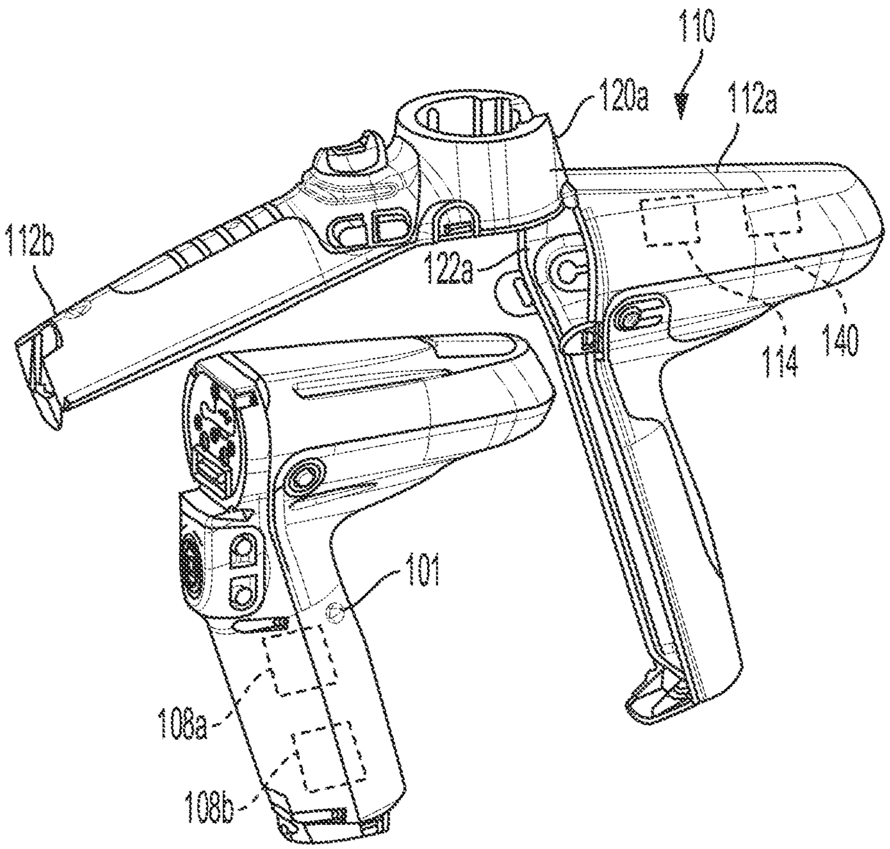
FIG. 3 is a perspective view of an embodiment of a housing in an open configuration and the inner core shown in FIG. 2.
Figure 4:
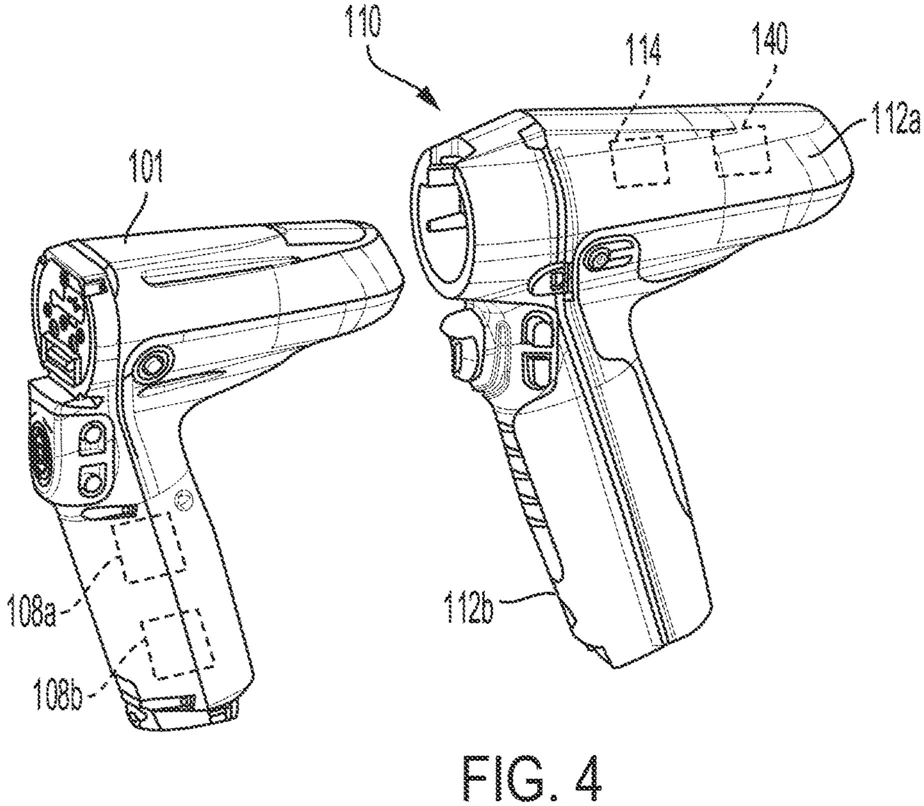
FIG. 4 is a perspective view of the housing of FIG. 3 having a different color associated therewith and being in a closed configuration, and the inner core shown in FIG. 2.

With reference to FIGS. 3 and 4, surgical instrument system 10 further includes a disposable outer housing 110. The housing 110 is configured to encase inner core 101 thereby inhibiting surgical debris from penetrating and contaminating inner core 101 during a surgical procedure. The housing 110 selectively encases inner core 101 prior to use and may then be detached from inner core 101 following use in order to be disposed of, or, in some instances, sterilized for re-use.

With reference to FIG. 3, the housing 110 includes a housing portion 112*a*. The housing 110 further includes a housing portion 112*b* movably coupled to the housing portion 112*b* by a hinge 120*a* located along an upper edge of housing portion 112*b*. Housing portions 112*a*, 112*b* are pivotable relative to one another between a closed, fully coupled configuration, as shown in FIG. 4, and an open, partially detached configuration, as shown in FIG. 3. When joined, housing portions 112*a*, 112*b* define a cavity 122*a* therein in which inner core 101, memory 114, and a microprocessor 140 may be selectively situated. In certain instances, the housing portions 112*a* 112*b* may be fabricated from any suitable material, such as, for example, a polycarbonate. In certain instances, the memory 114 and the microprocessor 140 are incorporated into the inner core 101, for example.

It is contemplated that the memory 114 may be non-volatile memories, such as, for example, electrically erasable programmable read-only memories. Memory 114 have stored therein discrete operating parameters of inner core 101 that correspond to the operation of one type of end effector, for example, end effectors such as, for example end effector 300*a* and/or one type of adapter assembly such as, for example, adapter assembly 200*a*. The operating parameter(s) stored in memory 114 can be at least one of: a speed of operation of motors 108*a*, 108*b* of inner core 101; an amount of power to be delivered by motors 108*a*, 108*b* of inner core 101 during operation thereof; which motors 108*a*, 108*b* of inner core 101 are to be actuated upon operating inner core 101; types of functions of end effectors to be performed by inner core 101; or the like.

Figure 5:
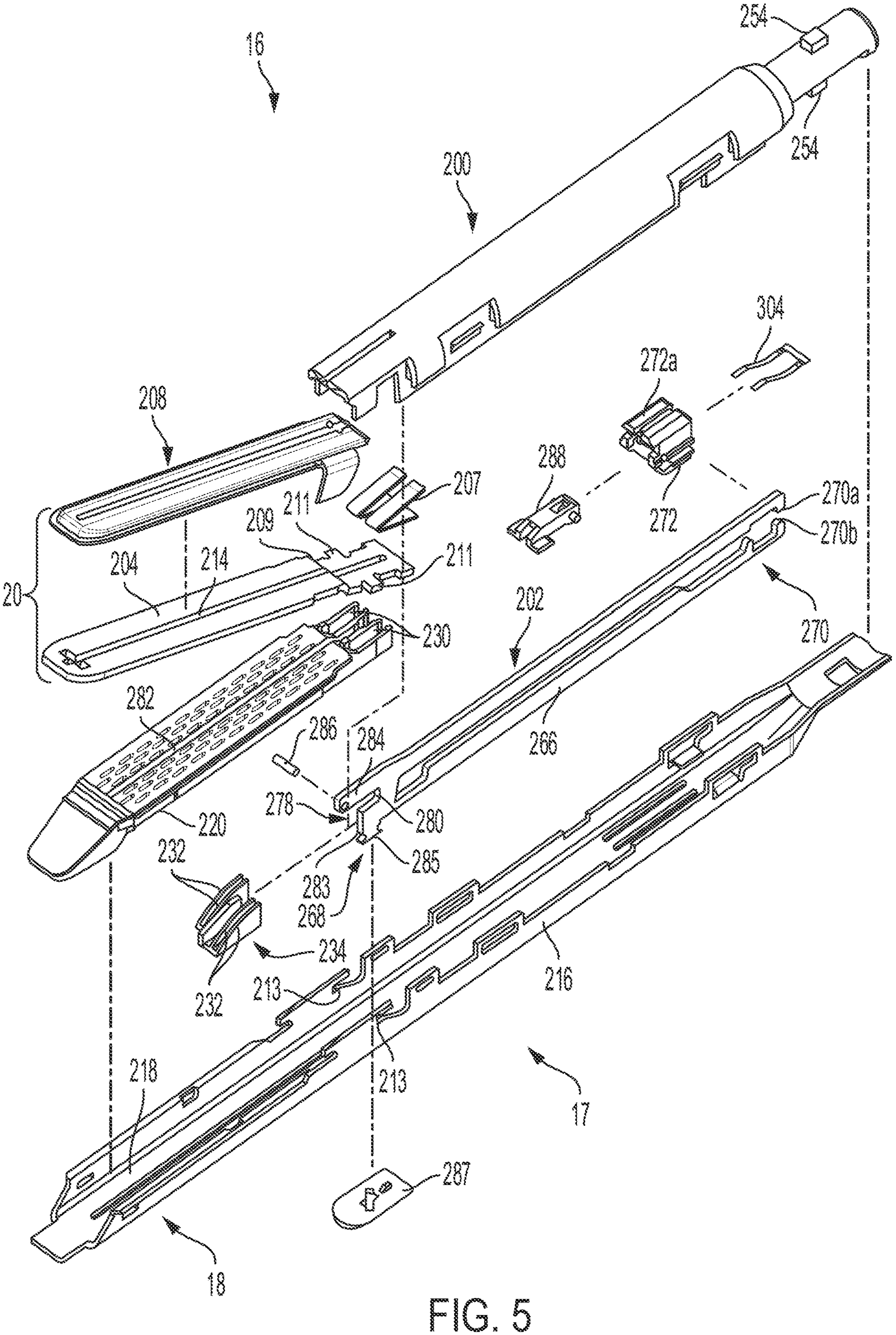
FIG. 5 is an exploded assembly view of a non-articulatable loading unit, in accordance with at least one aspect of the present disclosure.

FIG. 5 depicts an example of a loading unit 16 that may be used in connection with the surgical instrument system 10 in a manner discussed in U.S. Pat. No. 5,865,361, the disclosure of which is herein incorporated by reference in its entirety.

As can be seen in FIG. 5, the loading unit 16 may generally comprise a tool assembly 17 for performing surgical procedures such as cutting tissue and applying staples on each side of the cut. In particular, the tool assembly includes a cartridge assembly 18 that houses a plurality of surgical staples therein. The tool assembly 17 also includes a staple-forming anvil assembly 20 that has an anvil portion 204 that has a plurality of staple deforming concavities formed in the undersurface thereof. A cover plate 208 is commonly secured to a top surface of anvil portion 204 to define an anvil cavity therebetween. The anvil cavity is dimensioned to receive a distal end of an axial drive assembly 212. A longitudinal slot 214 extends through anvil portion 204 to facilitate passage of retention flange 284 of axial drive assembly 212 into the anvil cavity. A camming surface 209 is formed on a proximal end of anvil portion 204 and is positioned to engage axial drive assembly 212 to facilitate closing of the anvil assembly 20.

Cartridge assembly 18 generally includes a carrier 216 which defines an elongated support channel 218. Elongated support channel 218 is dimensioned and configured to receive a staple cartridge 220 therein. Such staple cartridge 220 supports a plurality of fasteners and pushers as is known in the art. A plurality of spaced-apart longitudinal slots 230 extend through staple cartridge 220 to accommodate upstanding cam wedges 232 of an actuation sled 234. A central longitudinal slot 282 extends along the length of staple cartridge 220 to facilitate passage of a knife blade 280 formed on the axial drive assembly 212. During operation of the loading unit 16, actuation sled 234 translates through longitudinal slots 230 of staple cartridge 220 to advance cam wedges 232 into sequential contact with the pushers that are operably supported in the cartridge 220 to cause the pushers to translate vertically within the cartridge 220 and urge the fasteners (staples) associated with the pushers into the staple deforming cavities of the anvil assembly 20. A pair of pivot members 211 are formed on the proximal end of the anvil portion 204 and are configured to be received in slots 213 that are formed in carrier 216 to enable the anvil portion 204 to pivot between the open and tissue-clamping positions.

As can also be seen in FIG. 5, the loading unit 16 also has a housing portion 200 that is adapted to snap onto or otherwise be attached to the carrier 216. The axial drive assembly 212 includes an elongated drive beam 266 that has a distal working head 268 and a proximal engagement section 270. As is known, the drive beam 266 may be constructed from a single sheet of material or, preferably, from multiple stacked sheets. Engagement section 270 includes a pair of engagement fingers **270*a* and 270*b* that are dimensioned and configured to mountingly engage a pair of corresponding retention slots 272*a* formed in a drive member 272. Drive member 272** may include a proximal aperture that is configured to receive the distal end of a control rod as discussed in U.S. Pat. No. 5,865,361.

The distal end of drive beam 266 includes a vertical support strut 278 which supports the knife blade 280, and an abutment surface 283 which engages the central portion of actuation sled 234 during a stapling procedure. Surface 285 is located at the base of surface 283 and is configured to receive a support member 287 that is slidably positioned along the bottom of the carrier 216. Knife blade 280 is generally positioned to translate slightly behind actuation sled 234 through a central longitudinal slot 282 in staple cartridge 220 to form an incision between rows of stapled body tissue.

A retention flange 284 projects distally from vertical strut 278 and supports a camming pin 286 at its distal end. Camming pin 286 is dimensioned and configured to engage camming surface 209 on anvil portion 204 to clamp anvil portion 204 against body tissue. In addition, a leaf spring 207 may be provided between the proximal end of the anvil portion 204 and the distal end portion of the housing 200 to bias the anvil assembly 20 to a normally open position. The loading unit 16 may further include a lockout device 288 and spring 304 arrangement as described in U.S. Pat. No. 5,865,361.

Figure 6:
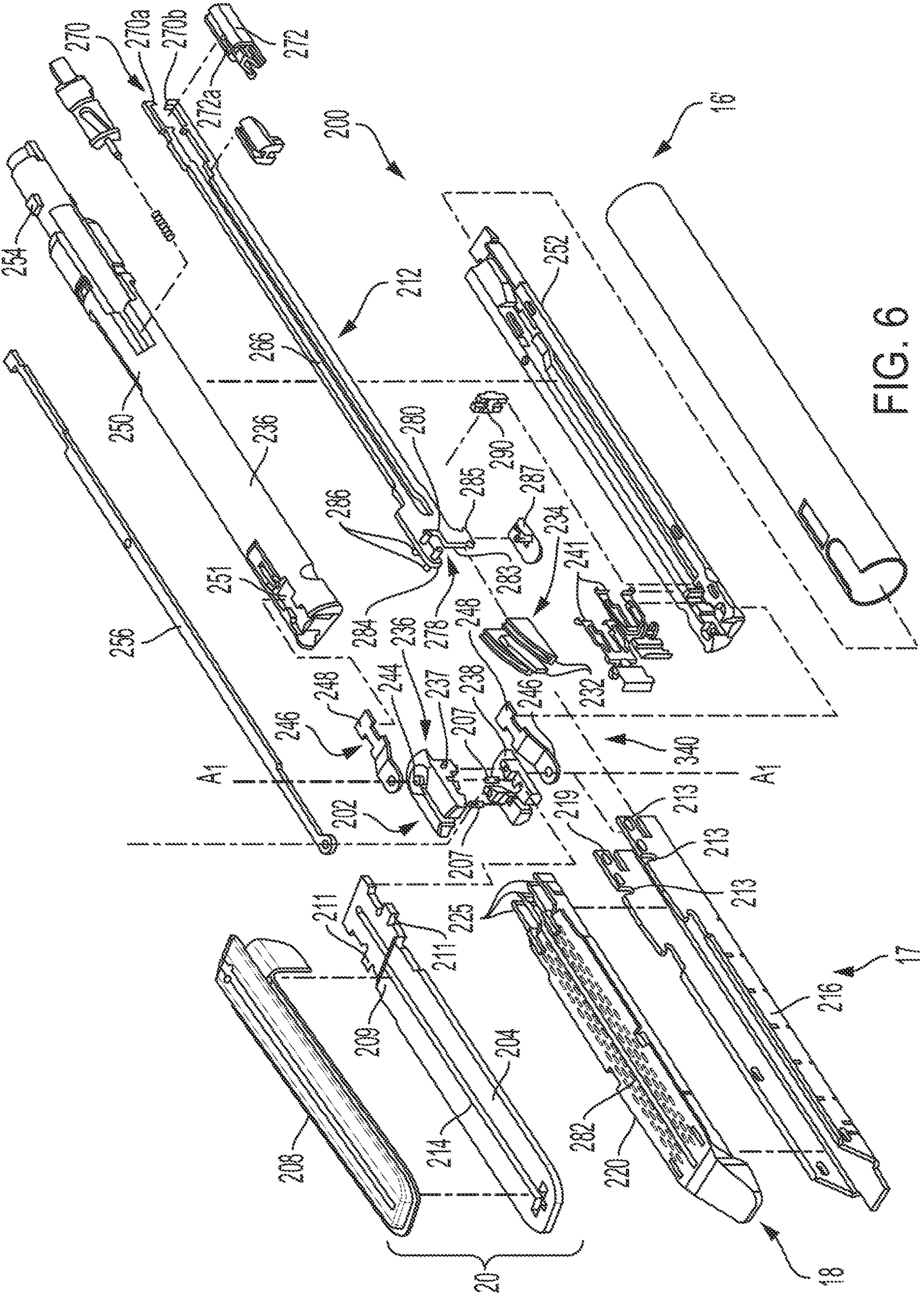
FIG. 6 is an exploded assembly view of an articulatable loading unit, in accordance with at least one aspect of the present disclosure.

FIG. 6 illustrates an articulatable loading unit 16' that includes a tool assembly 17 that has an anvil assembly 20 and cartridge assembly 18. Anvil assembly 20 includes an anvil portion 204 that has a plurality of staple deforming concavities formed in the undersurface thereof. A cover plate 208 is secured to a top surface of anvil portion 204 to define an anvil cavity therebetween. The anvil cavity is dimensioned to receive a distal end of an axial drive assembly 212. A longitudinal slot 214 extends through anvil portion 204 to facilitate passage of retention flange 284 of axial drive assembly 212 into the anvil cavity. A camming surface 209 formed on anvil portion 204 may be positioned to engage axial drive assembly 212 to facilitate clamping of tissue between the anvil assembly 20 and the cartridge assembly 18.

The cartridge assembly 18 includes a carrier 216 that supports a staple cartridge 220 therein. Staple cartridge 220 includes retention slots 225 for receiving a plurality of fasteners (staples) and pushers. A plurality of spaced apart longitudinal slots 230 extend through staple cartridge 220 to accommodate upstanding cam wedges 232 of an actuation sled 234. A central longitudinal slot 282 extends along the length of staple cartridge 220 to facilitate passage of a knife blade 280. During operation of the loading unit 16', actuation sled 234 translates through longitudinal slots 230 of staple cartridge 220 to advance cam wedges 232 into sequential contact with the pushers that are operably supported in the cartridge 220 to cause the pushers to urge the fasteners into the staple deforming cavities of the anvil assembly 20. A pair of pivot members 211 are formed on anvil portion 204 and are positioned within slots 213 formed in the carrier 216 to guide the anvil portion 204 between the open and tissue-clamping positions.

The articulatable loading unit 16' further includes a housing portion 200 that comprises an upper housing half 250 and a lower housing half 252. The proximal end of housing half 250 may include engagement nubs 254 for releasably engaging elongated body 14. Nubs 254 form a bayonet type coupling with the distal end of body 14 as described in U.S. Pat. No. 5,865,361. As can also be seen in FIG. 6, the axial drive assembly 212 includes an elongated drive beam 266 that has a distal working head and a proximal engagement section 270. Drive beam 266 may be constructed from a single sheet of material or, preferably, from multiple stacked sheets. Engagement section 270 includes a pair of engagement fingers **270*a* and 270*b* that are dimensioned and configured to mountingly engage a pair of corresponding retention slots 272 a formed in a drive member 272. Drive member 272 includes a proximal port-aperture configured to receive the distal end of control rod when the proximal end of loading unit 16' is engaged with elongated body 14** of a surgical stapling apparatus as disclosed in U.S. Pat. No. 5,865,361.

The distal end of drive beam 266 is defined by a vertical support strut 278 which supports a knife blade 280, and an abutment surface 283 which engages the central portion of actuation sled 234 during a stapling procedure. Surface 285 at the base of surface 283 may be configured to receive a support member 287 that is slidably positioned along the bottom of the carrier 216. Knife blade 280 is generally positioned to translate slightly behind actuation sled 234 through a central longitudinal slot 282 in staple cartridge 220 to form an incision between rows of stapled body tissue. To provide support to the drive beam 266 within the housing portion 200 as the drive beam 266 is advanced axially, a blade stabilizing member 290 is mounted within the housing portion 200. A retention flange 284 projects distally from vertical strut 278 and supports a pair of cylindrical cam rollers 286 at its distal end. Cam rollers 286 are dimensioned and configured to engage camming surface 209 on anvil portion 204 to clamp anvil portion 204 against body tissue.

The articulatable reload unit 16' includes an articulation joint 340 that includes a mounting assembly 202 that comprises an upper mounting portion 236 and a lower mounting portion 238. A pivot pin 244 is formed on each of the mounting portions 236, 238 and serve to define a pivot axis "A1-A1" which may be substantially perpendicular to the longitudinal axis "L-L" of the articulatable loading unit 16'. The mounting assembly 202 is pivotally coupled to the distal end of the housing portion 200 by a pair of coupling members 246. Each of coupling members 246 has an aperture 247 therethrough for receiving a corresponding pin 244 therethrough. The proximal end 248 of each coupling member 246 is configured to be interlockingly received in a corresponding groove 251 formed in the distal end of the upper housing half 250 and the distal end of the lower housing half 252. A pair of springs 207 are provided between the proximal end of the anvil portion 204 and the upper mounting portion 236 to bias the anvil assembly 20 to a normally open position. An articulation link 256 may be provided to articulate the tool assembly 17 about the articulation axis "A1-A1" relative to the housing portion 200 as is taught in U.S. Pat. No. 5,865,361.

Figure 8:
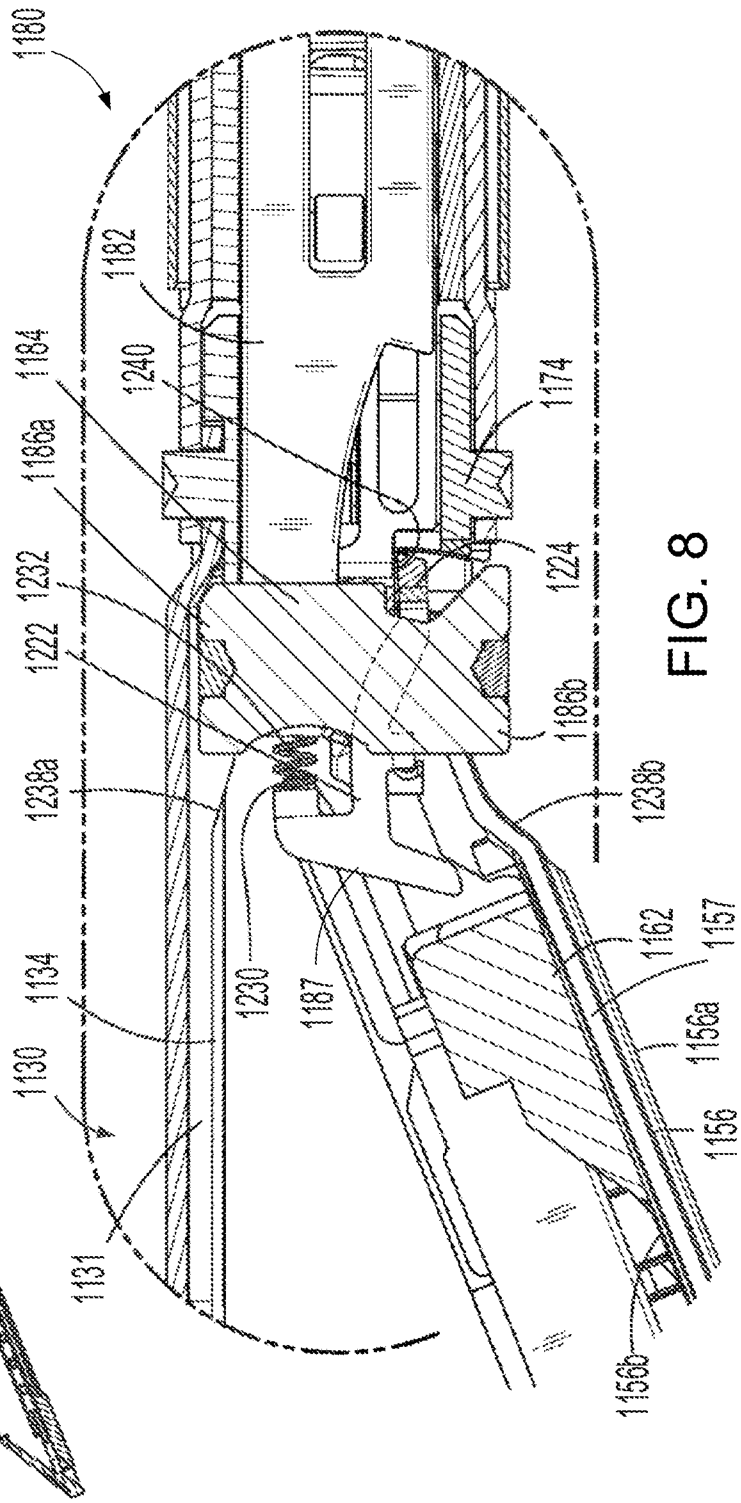
FIG. 8 is an expanded view of a portion of the loading unit of FIG. 7.

FIGS. 7 and 8 illustrate an example of a loading unit 1100 for use with the surgical instrument system 10. The loading unit 1100 is substantially as described in U.S. Patent Application Publication No. 2013/0098965 and U.S. Patent Application Publication No. 2016/0249921, which are incorporated by reference herein in their entireties. The loading unit 1100 includes a proximal body portion 1102 and a tool assembly 1104.

The loading unit 1100 further includes a drive assembly 1180 that includes a drive member 1182 having a body and a working end 1184. The working end 1184 includes an upper flange **1186*a*, a lower flange 1186*b*, a vertical strut interconnecting the upper flange 1186*a* and the lower flange 1186*b*, and a knife 1187 supported on or formed into the vertical strut. The upper flange 1186*a* is positioned to be slidably received within the channel 1131 of the anvil assembly 1130 and the lower flange 1186*b* is positioned to be slidably positioned along an outer surface 1156*a* of the jaw member 1156. In use, distal movement of the drive member 1182 initially advances the upper flange 1186*a* into a cam surface formed on the anvil plate 134 and advances the lower flange 1186*b* into engagement with a cam surface 1156*b* formed on the jaw member 1156 to pivot the cartridge assembly 1150 towards the anvil assembly 1130 to the approximated or closed position. Continued advancement of the drive member 1182 progressively maintains a minimum tissue gap between the anvil assembly 1130 and the cartridge assembly 1150 adjacent the working end 184 of the drive assembly 1180 as the working end 1184 moves through the tool assembly 1104**.

Actuation sled 1162 is disposed within cartridge assembly 1150 at a position distal of the working end 1184. When the working end 1184 is in its proximal-most position and the tool assembly 1104 is in the open or unapproximated position, the sled 1162 and the working end 1184 are in their initial position. The sled 1162 includes a plurality of cam surfaces which are positioned to engage and lift the pushers within the staple retention slots the cartridge body of cartridge assembly 1150. The pushers are positioned within the cartridge assembly 1150 to eject the staples from the cartridge body when the sled 1162 is advanced through the tool assembly 1104.

Figure 10:
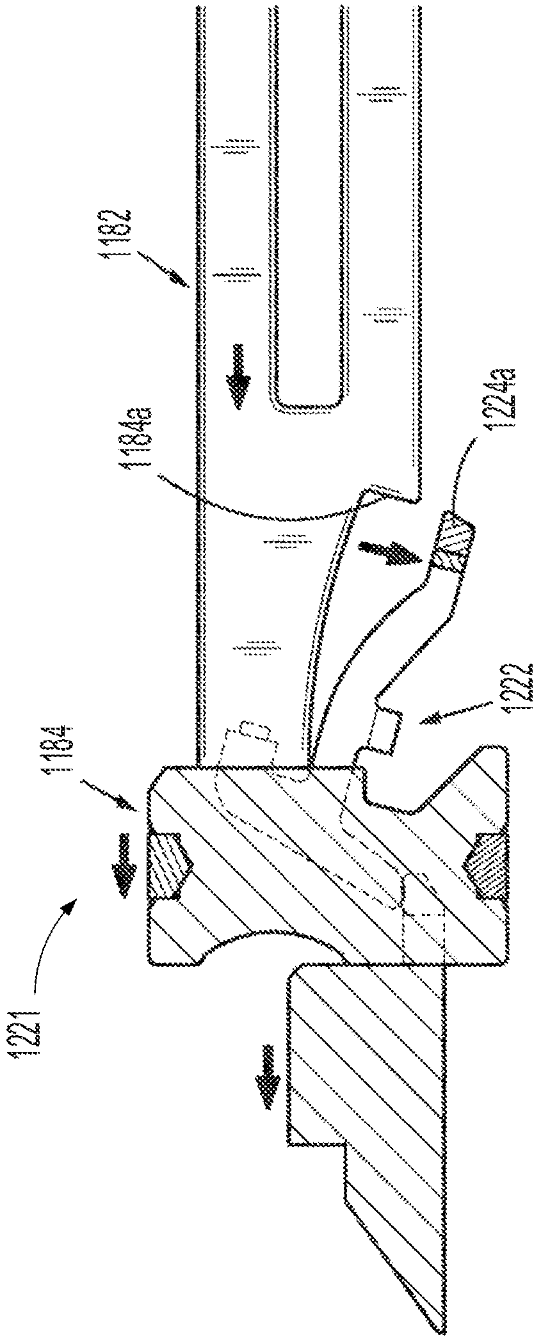
FIG. 10 is a partial cross-sectional side view of the distal end of the drive assembly of FIG. 9 showing the latch member in a second or locked configuration.

Referring to FIGS. 7-10, the loading unit 1100 includes a firing lockout assembly 1221 that includes a latch member 1222 which is pivotally supported on a distal end of a lower mounting portion 1174. The latch member 1222 includes a U-shaped body having a proximal base member 224 and two spaced distally extending legs. The base member 1224 is provided with a blocking member which defines a blocking surface and is welded or secured to the base member 1224 to provide additional support to the base member 1224. Alternatively, the base member 1224 and the blocking member are integrally or monolithically formed. The latch member 1222 is pivotal from a first position (FIG. 9) to a second position (FIG. 10). In the first position shown in FIG. 9, the blocking member **1224*a* of the latch member 1222 is aligned with the stop surface 1184*a* of the drive member 1182 to prevent advancement of the drive member 1182 within the tool assembly 1104. In the second position shown in FIG. 10, the blocking member 1224*a* is misaligned with the stop surface 1184*a* of the drive member 1182 to permit advancement of the drive member 1182 within the tool assembly 1104**.

Further to the above, insertion of an unfired cartridge assembly 1150 into an elongated channel 1157 of the jaw member 1156 pivots the latch member 1222 to the second position thereby permitting advancement of the drive member 1182 within the tool assembly 1104. A proximal portion of the sled 1162 holds the latch member 1222 in the second position against the biasing force of a biasing member 1230. During firing, when the sled 1162 is advanced distally through the cartridge assembly 1150, the sled 1162 disengages from the latch member 1222, and the biasing member 230 causes the latch member 1222 to return to the first position where the latch member 1222 re-enters a locking engagement with the drive member 182.

Notably, an incidental bumping or shaking of the unfired cartridge assembly 1150 may cause a slight movement of the sled 1162 within the unfired cartridge assembly 1150. Such movement can be problematic as a misaligned sled 1162 cannot deactivate the firing lockout assembly 1221 by causing the latch member 1222 to transition to the second position upon insertion of the unfired cartridge assembly 1150. Consequently, advancement of the drive member 1182 remains hindered even though a new unfired cartridge assembly 1150 is ready for firing.

Further to the above, a properly installed unfired cartridge assembly 1150 can suffer the same fate due to incidental bumping or shaking of the loading unit 1100. The slight movement of the sled 1162 may cause the latch member 1222 to be disengaged from the sled 1162, thereby allowing the latch member 1222 to be returned to the first position by the biasing force of the biasing member 1230. Consequently, the firing lockout assembly 1221 is prematurely reactivated by the incidental bumping or shaking of the loading unit 1100 before an actual firing commences.

In either event, the misalignment of the sled 1162 can be frustrating to a user expecting an apparently properly-installed unfired cartridge assembly 1150 to be fired to deploy staples into a tissue grasped between the anvil assembly 1130 and the cartridge assembly 1500. When the firing inevitably fails, the user is left with no recourse but to release the tissue sacrificing all the time spent to identifying the most suitable tissue bite and aligning the loading unit 1100 therewith for grasping. Moreover, confident in that the cartridge assembly is new and unfired, the user may attempt to replace the loading unit 1100 and/or the surgical instrument system 10, which is costly and will not be a successful remedy if the user installs the cartridge assembly 1150 was the misaligned sled 1162 into the new loading unit 1100.

The present disclosure provides various solutions that maintain a sled 1162 in a proper position for an unfired cartridge assembly 1150. Additionally, or alternatively, the present disclosure provides various mechanisms for detecting an incidental movement of the sled 1162 from its proper position. The present disclosure further provides various mechanisms actively returning the sled 1162 to its proper position.

Figure 11:
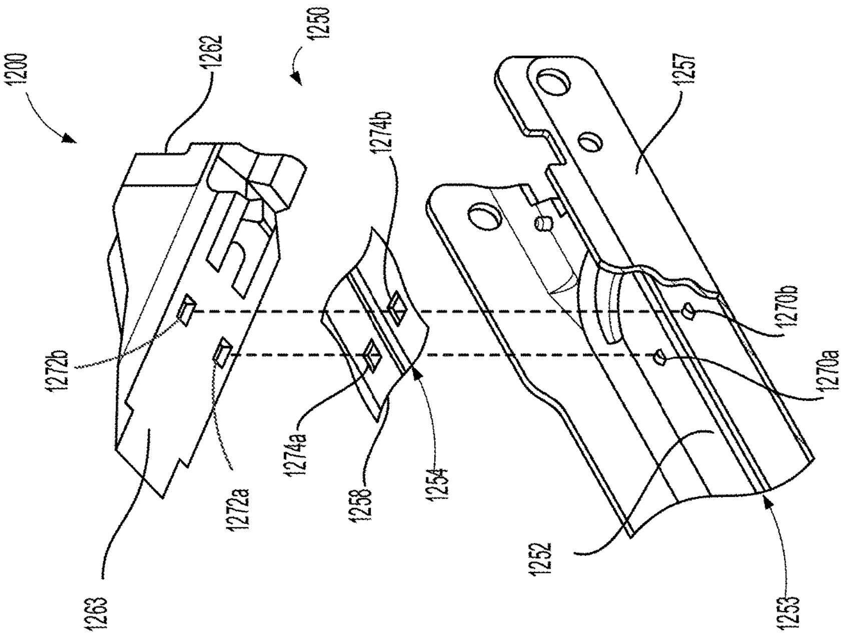
FIG. 11 is a partial exploded view of a staple cartridge assembly of a load unit, in accordance with at least one aspect of the present disclosure.
Figure 12:
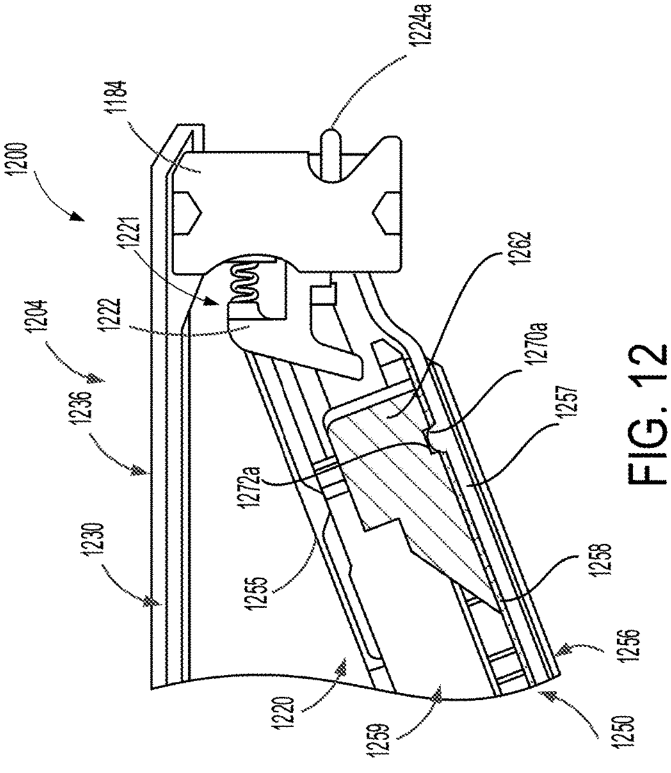
FIG. 12 is a partial cross-sectional view of the loading unit of FIG. 11.
Figure 13:
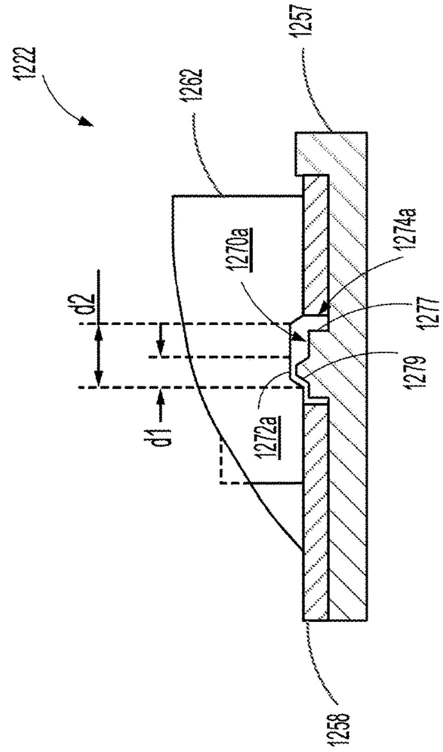
FIG. 13 is a partial cross-sectional view of the staple cartridge assembly of FIG. 11.

Referring to FIGS. 11-13, a loading unit 1200 is similar in many respects to the loading unit 1100. For example, the loading unit 1200 includes the proximal body portion 1102 (FIG. 8) and a tool assembly 1204 that includes an end effector with a jaw 1236 including an anvil assembly 1230 and a jaw 1256 including a staple cartridge assembly 1250. At least one of the jaws 1236, 1256 is movable relative to the other to grasp tissue between the anvil assembly 1230 and the staple cartridge assembly 1250.

Furthermore, the staple cartridge assembly 1250 includes an elongated channel 1257 dimensioned and designed to receive and releasably retain a staple cartridge 1220 similar in many respects to other staple cartridges described elsewhere herein such as, for example, the staple cartridge 220. Staples are deployed from the staple cartridge 1220 through a cartridge deck 1255 into the tissue via staple drivers motivated by the sled 1262 in a similar manner to that described in connection loading units 16, 16', 1100 of FIGS. 1-8. The staples and the staple drivers are stored in a cartridge body 1259 of the staple cartridge 1220.

A cartridge pan 1258 is attached to the bottom of the cartridge body 1259 to prevent the staple drivers from falling out of the cartridge body 1259. The cartridge pan 1258 includes a pan slot 1254 that is aligned with a cartridge slot defined in the cartridge deck 1255. The pan slot 1254 is also aligned with a channel slot 1253 defined in a base portion 1252 of the elongated channel 1257. During firing, the working end 1184 of the drive member 1182 (FIG. 9) slidably moves through the cartridge slot, the pan slot 1254, and the channel slot 1253 distally advancing the sled 1262 from a first position toward a second position within the cartridge body to cause the staple drivers to deploy the staples through the cartridge deck 1255.

Furthermore, the loading unit 1200 includes the firing lockout assembly 1221 configured to prevent advancement of the drive member 1182 in the absence of an unfired staple cartridge 1220 with a properly positioned sled 1262. To resist a movement of the sled 1262 due to an incidental bumping or shaking of the staple cartridge 1220, the base portion 1252 includes one or more retaining features (e.g., retaining features 1270*a*, 1270*b*) configured to matingly engage the sled 1262 and resist a movement of the sled 1262 up to a predetermined force.

In certain instances, as illustrated in FIG. 13, the sled 1262 includes one or more apertures, bores, grooves, or detents (e.g., detents 1272*a*, 1272*b*) defined in a sled base 1263. The detents 1272*a*, 1272*b* are aligned with and configured to receive the retaining features 1270*a*, 1270*b* when the sled 1262 is located at the first position. In the example illustrated in FIGS. 11-13, the retaining features 1270*a*, 1270*b* extend through corresponding apertures or cutouts 1274*a*, 1274*b* in the cartridge pan 1258 when the staple cartridge 1220 is properly seated in the elongated channel 1257.

In the illustrated example, when the sled 1262 is at the first position, the retaining feature 1270*a*, the detent 1272*a*, and the cutout 1274*a* reside on a first side of a plane longitudinally bisecting the staple cartridge 1220 and extending longitudinally along the cartridge slot, the pan slot 1254, and the channel slot 1253. The retaining feature 1270*b*, the detent 1272*b*, and the cutout 1274*b* reside on a second side of a plane opposite the first side.

In various examples, the retaining features 1270*a*, 1270*b* are in the form of bumps or protrusions extending upwardly from the base portion 1252. The retaining features 1270*a*, 1270*b* may define ramps and/or curved profiles comprise with radii of curvatures dimensioned to resist advancement of the sled 1262 when a driving force applied by the drive member 1182 to the sled 1262 is less than or equal to a predetermined force.

In various aspects, a retaining feature may comprise a triangular prism shape, a partial ellipsoid shape, a partial spherical shape, a partial cylindrical shape, or a truncated pyramid shape. Other shapes are also contemplated by the present disclosure. In various aspects, a retaining feature height may be less than, or equal to, than a depth a corresponding detent of a sled to ensure that the sled is not lifted by the retaining feature when assembled therewith. In various aspects, the number of retaining features can be more or less than two. In one example, a single retaining feature can be employed with corresponding detent and cutout. In another example, three or more retaining features can be employed with corresponding detents and cutouts. In certain examples, dedicated cutouts are replaced with a single cutout that accommodates the passing of multiple retaining features therethrough.

When the driving force applied by the drive member 1182 exceeds the predetermined force, the sled 1262 moves out of alignment with the retaining features 1270*a*, 1270*b* toward the second position. After the sled 1262 reaches the second position, the drive member 1182 is retracted to a starting position where the firing lockout assembly 1221 is reactivated to prevent re-advancement of the drive member 1182 until an unfired staple cartridge 1220 is assembled with the elongated channel such that a sled 1262 is properly located at the first position. A proximal portion of the sled 1262 engages the latch member 1222 deactivating the firing lockout assembly 1221.

FIG. 13 illustrates an example of a retaining feature 1270*a* of the unfired staple cartridge 1220 properly seated in the elongated channel 1257. The detent 1272*a* of the sled 1262 of the unfired staple cartridge 1220 is properly aligned to receive the retaining feature 1270*a* through the cutout 1274*a* at a first position, which yields an unlocked configuration of the firing lockout assembly 1221. The retaining feature 1270*a* includes a base portion 1277 protruding from the elongated channel 1257 and extending into the cutout 1274*a*, and a head portion 1279 protruding from the based portion and extending into the detent 1272*a* of the sled 1262. The head portion 1279, but not the base portion 1277, extend through the cutout 1274*a* beyond the cartridge pan 1258 and into the detent 1272*a*.

The base portion 1277 ensures proper alignment of the staple cartridge 1220 with the elongated channel 1257, and the head portion 1279 ensures that the sled 1262 remains at the first position until a driving force greater than a predetermined driving force is applied thereto. In the illustrated example, the base portion 1277 has a rectangular, or at least substantially rectangular, cross-section. In certain instances, the head portion 1279 has a curved profile that defines a ramp resists advancement of the sled 1262 at or below a predetermined force defined by a radius of curvature of the head portion 1279.

Furthermore, the head portion 1277 is slightly smaller in size than the detent 1272*a* to permit slight movements of the sled relative to the head portion 1279 without an unintended transition in the firing lockout assembly from the unlocked configuration to the locked configuration. In the illustrated example, the detent 1272*a* has a length $d_2$ greater than a length $d_1$ of the head portion 1279 by a distance $\Delta d$ (difference between $d_1$ and $d_2$). As such, the sled is slidably movable relative to the cartridge pan 1258 a distance $\Delta d$ without compromising the mating engagement between the head portion 1279 and the detent 1272*a*.

Figure 9:
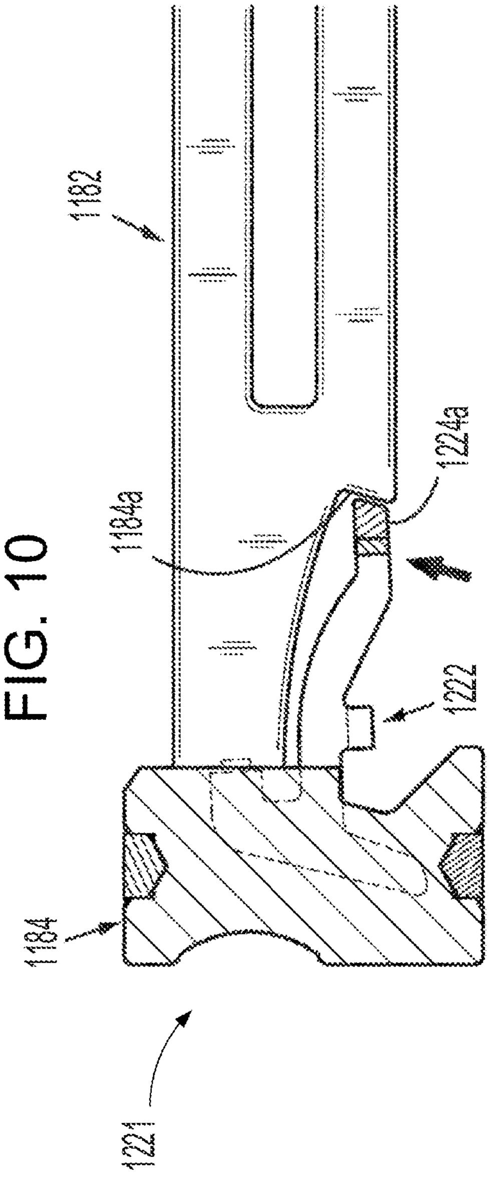
FIG. 9 is a partial cross-sectional side view of the distal end of a drive assembly showing a latch member of a firing lockout assembly in a first or unlocked configuration.
Figure 14:
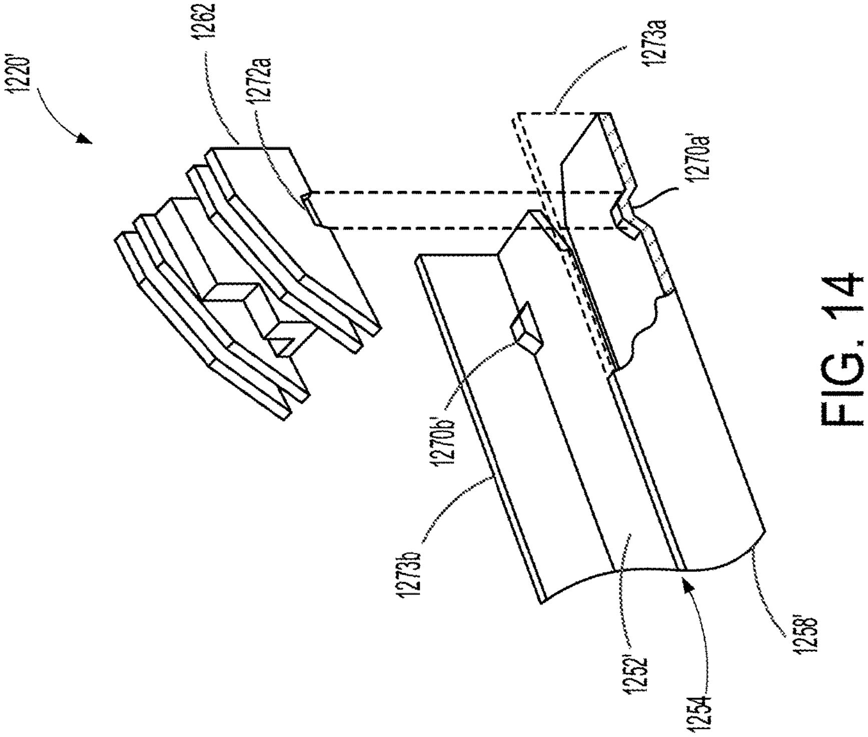
FIG. 14 is a partial exploded view of a staple cartridge, in accordance with at least one aspect of the present disclosure.
Figure 15:
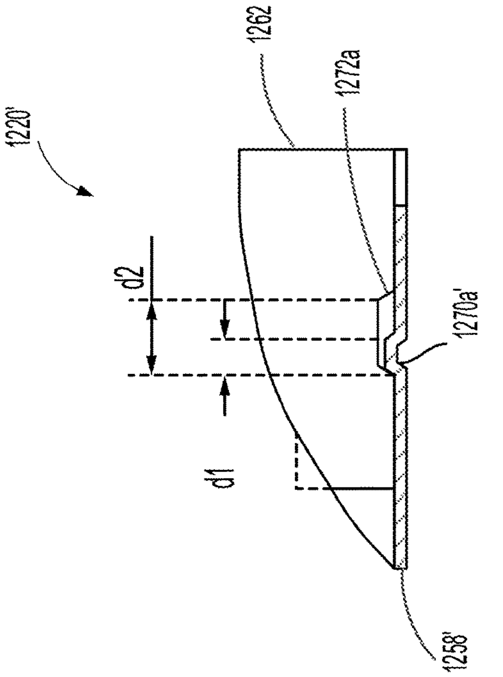
FIG. 15 is a partial cross-sectional view of the staple cartridge of FIG. 14.

FIGS. 14 and 15 illustrate a staple cartridge 1220' similar in many respects to the staple cartridges 220, 1220. For example, the staple cartridge 1220' includes the sled 1262 with the detents 1272*a*. However, unlike the staple cartridge 1220, a cartridge pan 1258' of the staple cartridge 1220' does not include cutouts to accommodate retaining features of an elongated channel. Instead, the cartridge pan 1258' includes retaining features 1270*a*' and 1270*b*' protruding from the cartridge pan 1258'. The retaining features 1270*a*' and 1270*b*' are similar in many respects to the retaining features 1270*a*, 1270*b*. For example, the retaining features 1270*a*' and 1270*b*' are configured to matingly engage the detents 1272*a*, 1272*b* of the sled 1262 to maintain the sled 1262 at the first position corresponding to an unlocked configuration of the firing lockout assembly 1221 (FIG. 9).

In the example illustrated in FIGS. 14 and 15, the retaining features 1270*a*', 1270*b*' are on opposite sides of the pan slot 1254. The retaining features 1270*a*' 1270*b*' are defined in a base portion of the cartridge pan 1258' adjacent side walls 1273*a*, 1273*b*. In the illustrated examples, the retaining features 1270*a*' 1270*b*' are aligned across the pan slot 1254. In other examples, the retaining features 1270*a*' 1270*b*' can be offset.

Figure 16:
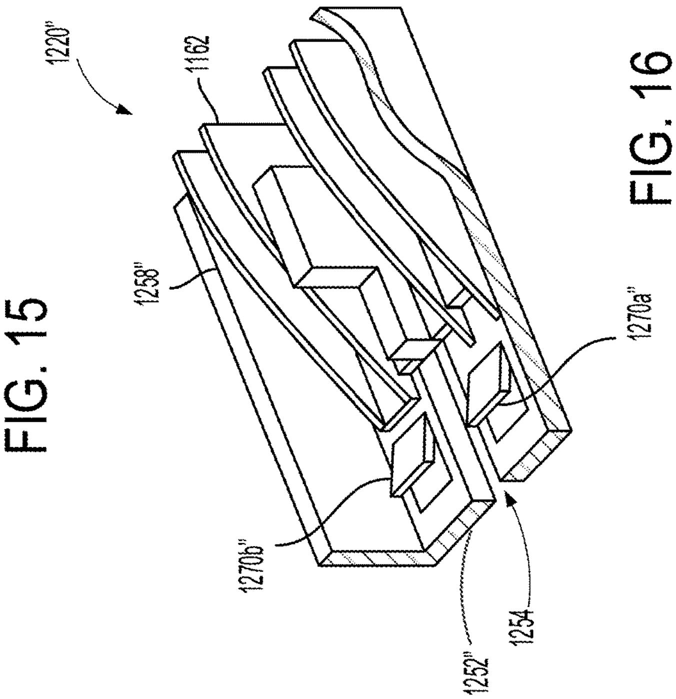
FIG. 16 is a partial perspective view of a staple cartridge, in accordance with at least one aspect of the present disclosure.

FIG. 16 illustrates an alternative staple cartridge 1220" similar in many respects to other staple cartridges described elsewhere herein such as, for example, the staple cartridges 220. 1220. 1220'. Staples are deployed from the staple cartridge 1220" through a cartridge deck into tissue via staple drivers motivated by a sled 1162 in a similar manner to that described in connection loading units 16, 16', 1100 of FIGS. 1-8. The drive member 1182 is configured to deploy the staples from a cartridge body through the cartridge deck by slidably advancing the sled 1162 distally from a first position toward the second position relative to the cartridge pan 1258". The staple cartridge 1220" includes retaining features 1270*a*", 1270*b*" defined in a base portion 1252" of a cartridge pan 1258" on opposite sides of a pan slot 1254.

The staple cartridge 1220" differs from the staple cartridge 1220' in that the retaining features 1270*a*", 1270*b*" are in the form of tabs that are bent away from the base portion 1252". The retaining features 1270*a*", 1270*b*" define collapsible ramps that are configured to resist a movement of the sled 1162 beyond the first position thereby maintaining the firing lockout assembly 1221 (FIG. 9) in the unlocked configuration while the sled 1162 is at the first position.

In the illustrated example, the sled 1162 can be slidably moved slightly from the first position before engaging the retaining features 1270*a*", 1270*b*". The permissible movement is insufficient to disengage the sled 1162 from the latch member 1222 and, accordingly, is insufficient to prematurely transition the firing lockout assembly 1221 to the locked configuration. As a distal portion of the sled 1162 engages the retaining features 1270*a*", 1270*b*", an additional advancement of the sled 1162 is resisted by the retaining features 1270*a*", 1270*b*".

When a drive force exerted by the drive member 1182 on the sled 1162 exceeds the predetermined driving force, the sled 1162 is advanced over the retaining features 1270*a*", 1270*b*". In certain instances, the retaining features 1270*a*", 1270*b*" are collapsed under the sled 1162 when the drive force exerted by the drive member 1182 on the sled 1162 exceeds the predetermined driving force.

Figure 17:
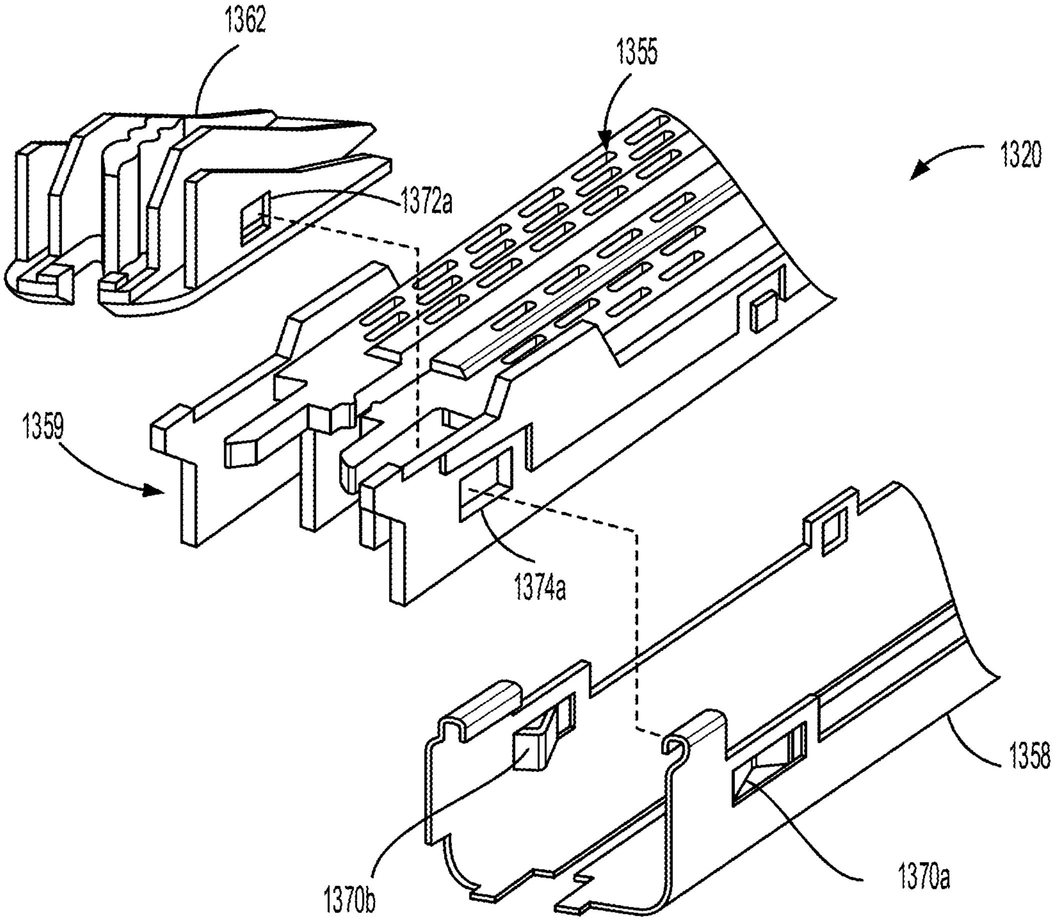
FIG. 17 is a partial exploded view of a staple cartridge, in accordance with at least one aspect of the present disclosure.
Figure 18:
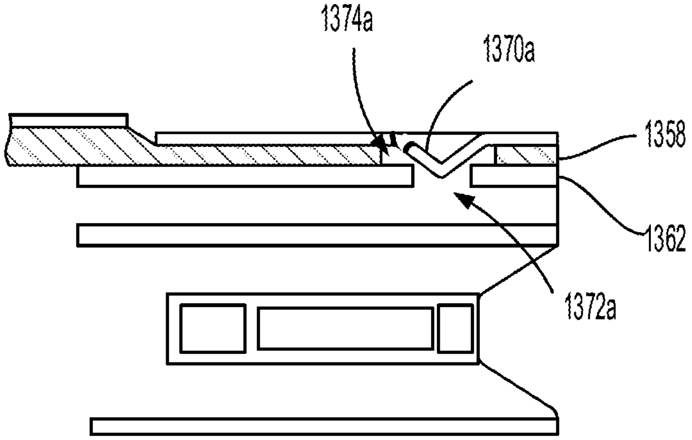
FIG. 18 is a partial cross-sectional view of the staple cartridge of FIG. 17.

FIGS. 17 and 18 illustrate a staple cartridge 1320 similar in many respects to other staple cartridges described elsewhere herein such as, for example, the staple cartridges 220. 1220. 1220'. Staples are deployed from the staple cartridge 1320 through a cartridge deck 1355 into the tissue via staple drivers motivated by a sled 1362 in a similar manner to that described in connection loading units 16, 16', 1100 of FIGS. 1-8. The staples and the staple drivers are stored in a cartridge body 1359 of the staple cartridge 1320.

Further to the above, the sled 1362 of an unfired staple cartridge 1320 is maintained at a default first position using retaining features 1370*a*, 1370*b* defined in proximal portions of sidewalls of the cartridge pan 1358. In the example illustrated in FIG. 17, retaining features 1370*a*, 1370*b* are in the form of leaf springs projecting inward. The leaf springs can be stamped or formed in the sidewalls of the cartridge pan 1358. The retaining feature 1370*a* includes a base attached to, and protruding from, a sidewall of the cartridge pan 1358. An apex portion extends from the base, and is dimensioned to pass through cutouts (e.g., cutout 1374*a*) defined in the cartridge body 1359, and into the detents defined in sidewalls of the sled 1362 (e.g., detent 1372*a*). The retaining feature 1370*a* defines a ramp that resists a distal advancement of the sled 1362 up to a predetermined driving force.

Figure 19:
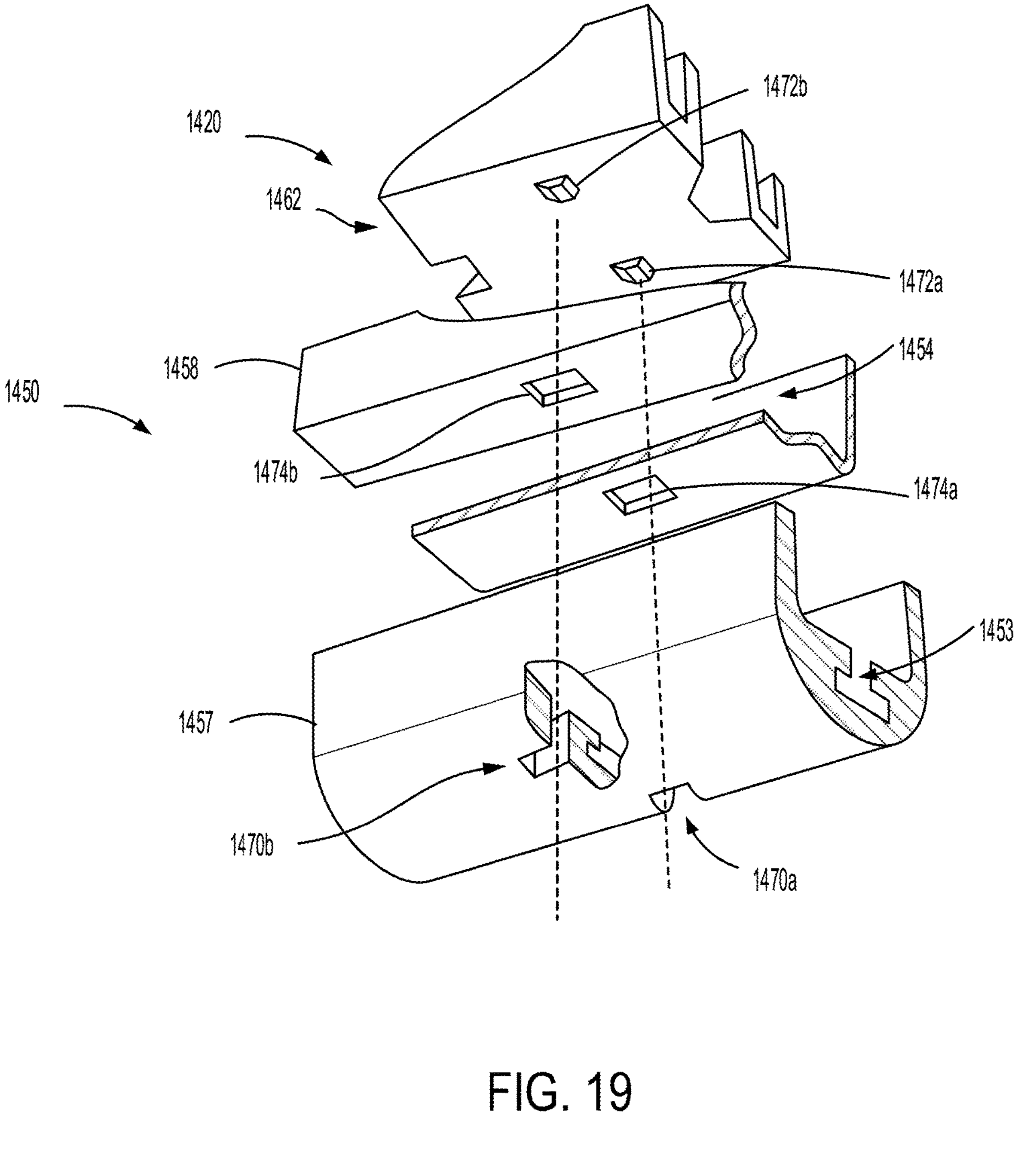
FIG. 19 is a partial exploded view of a staple cartridge assembly, in accordance with at least one aspect of the present disclosure.

FIG. 19 illustrates an alternative staple cartridge assembly 1450 similar in many respects to the cartridge assembly 1250. For example, like the staple cartridge assembly 1250, the staple cartridge assembly 1450 includes a staple cartridge 1420 that includes a sled 1462 configured to deploy staples from a cartridge body through a cartridge deck by slidably advancing the sled 1462 distally from a first position toward the second position relative to the cartridge pan 1458. When an unfired staple cartridge 1420 is properly assembled with an elongated channel 1457 of a loading unit, a firing lockout assembly 1221 is transitioned into an unlocked configuration to permit advancement of a drive member 1182 distally to motivate the sled 1462 to deploy the staples.

The staple cartridge assembly 1450 differs from the staple cartridge assembly 1250 in that the elongated channel 1457 includes retaining features 1470*a*, 1470*b* in the form of grooves, bores, apertures, or detents. The retaining features 1470*a*, 1470*b* are configured to receive sled protrusions 1472*a*, 1472*b* through cutouts 1474*a*, 1474*b* defined in the base portion of the cartridge pan 1458. The retaining features 1470*a*, 1470*b* are configured to resist a movement of the sled 1462 up to a predetermined force. When the driving force of the drive member 1182 is greater than the predetermined force, the sled 1462 is advanced distally beyond the first position causing the sled protrusions 1472*a*, 1472*b* to exit the retaining features 1470*a*, 1470*b*.

Figure 20:
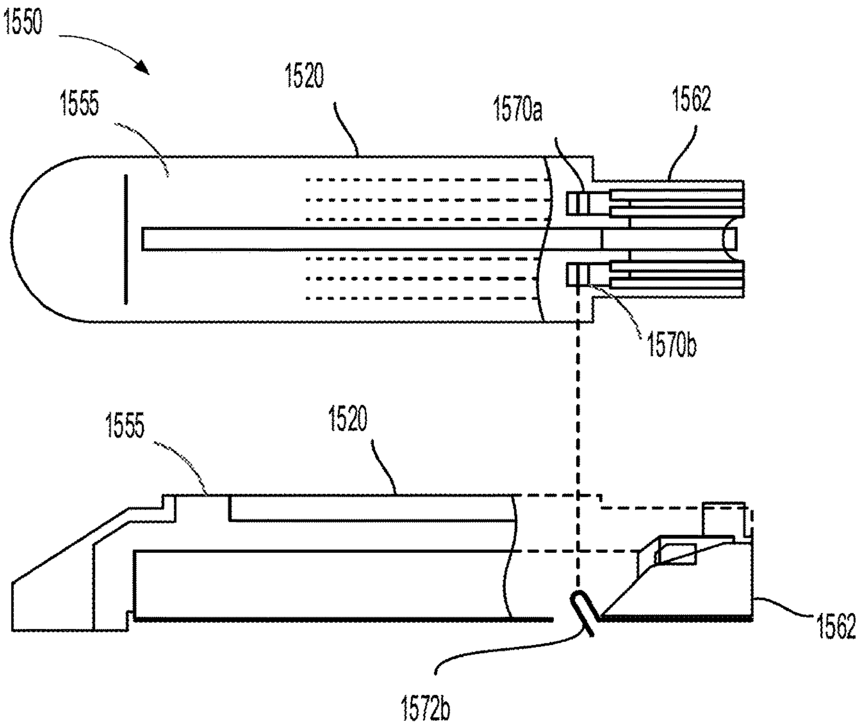
FIG. 20 is a top view and a cross-sectional view of a staple cartridge, in accordance with at least one aspect of the present disclosure.
Figure 21:
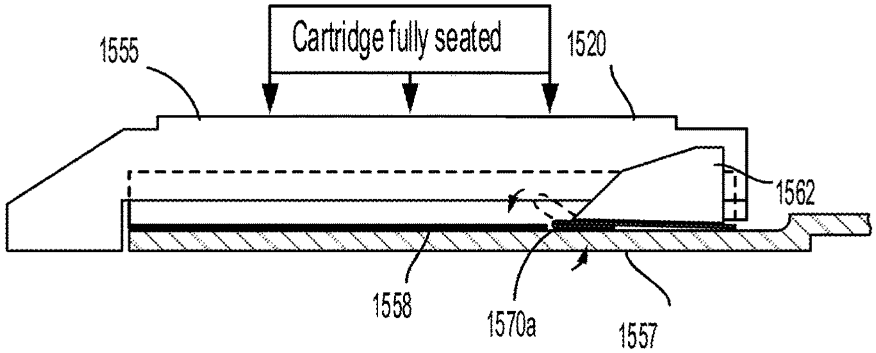
FIG. 21 is a cross-sectional view of a staple cartridge assembly including the staple cartridge of FIG. 20.

FIGS. 20-21 illustrate an alternative staple cartridge assembly 1550 similar in many respects to the cartridge assemblies 1250, 1450. The staple cartridge assembly 1550 includes a staple cartridge 1520 similar in many respects to other staple cartridges described elsewhere herein such as, for example, the staple cartridges 220, 1220, 1220', 1220", 1420. Staples are deployed from the staple cartridge 1520 through a cartridge deck 1555 into tissue via staple drivers motivated by a sled 1562 in a similar manner to that described in connection loading units 16, 16', 1100 of FIGS. 1-8. The drive member 1182 is configured to deploy the staples from a cartridge body through the cartridge deck 1555 by slidably advancing the sled 1562 distally from a first position toward the second position relative to a cartridge pan 1558.

The staple cartridge 1520 includes one or more retaining features (e.g., retaining features 1570*a*, 1570*b*) that are configured to resist a distal advancement of the sled 1562 until the staple cartridge 1520 is fully seated, or assembled, with an elongated channel 1557 of a loading unit. In the illustrated example, a retaining feature 1570*b* is in the form of a collapsible leaf spring defined in a cartridge pan 1558 by bending an existing pan sheet metal. In the illustrated example, the retaining feature 1570*b* comprises a first portion bent towards the cartridge deck 1555 and a second portion bent away from the cartridge deck 1555. A curved portion extends between, and connects, the first portion and the second portion. In the illustrated example, the second portion is slightly longer than the first portion.

Insertion of the staple cartridge 1520 into the elongated channel 1557, as illustrated in FIG. 21, causes the retaining features 1570*a*, 1570*b* to be collapsed, or flattened, against the elongated channel 1557, which allows the sled 1562 to be moved distally by the drive member 1182. The retaining features 1570*a*, 1570*b* resist an advancement of the sled 1562 until their collapse by the insertion of the staple cartridge 1520 into the elongated channel 1557. In other words, the retaining features 1570*a*, 1570*b* are configured to maintain the sled 1562 at the first position until the staple cartridge 1520 is inserted into the elongated channel 1557. In doing so, the retaining features 1570*a*, 1570*b* ensure that the sled 1562 transitions the firing lockout assembly 1221 to the unlocked configuration to allow advancement of the drive member 1182.

Figure 22:
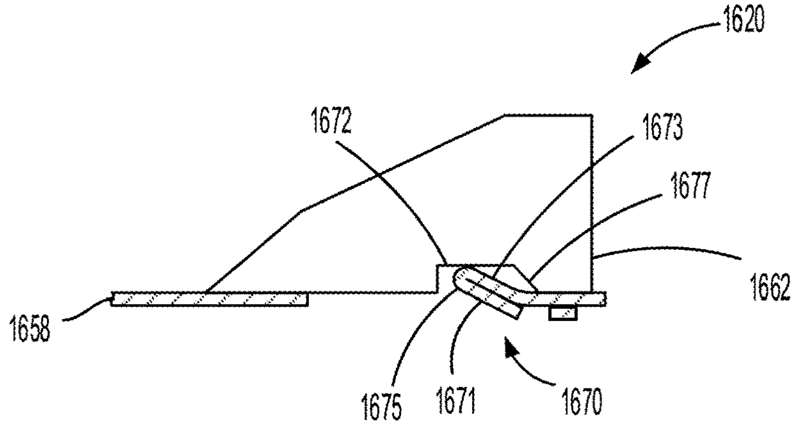
FIG. 22 is a partial cross-sectional view of a staple cartridge including a sled and a retaining feature, in accordance with at least one aspect of the present disclosure.
Figure 23:
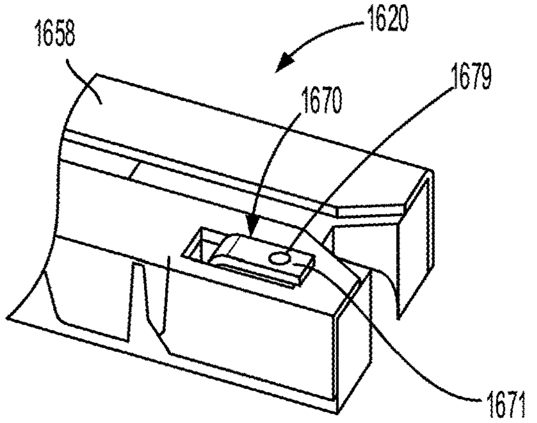
FIG. 23 is a partial upside down perspective view of the staple cartridge of FIG. 22.
Figure 24:
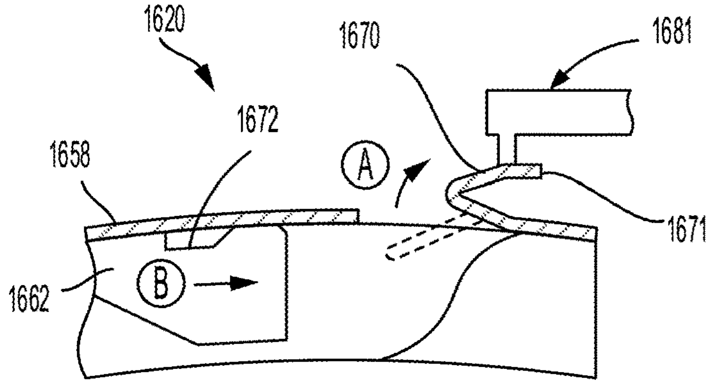
FIG. 24 illustrates a method of assembling the sled of the staple cartridge of FIG. 22 with the retaining feature.
Figure 25:
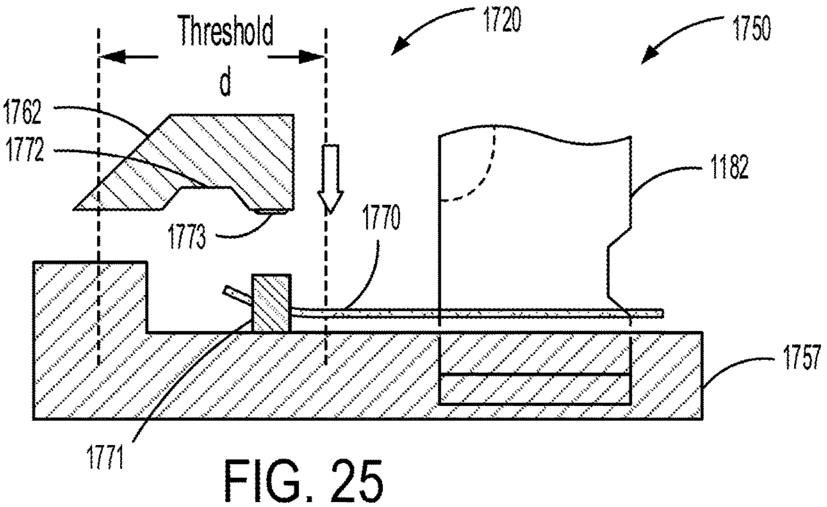
FIG. 25 partially illustrates a staple cartridge assembly including a staple cartridge and an elongated channel, and a drive member of a loading unit, in accordance with at least one aspect of the present disclosure.
Figure 26:
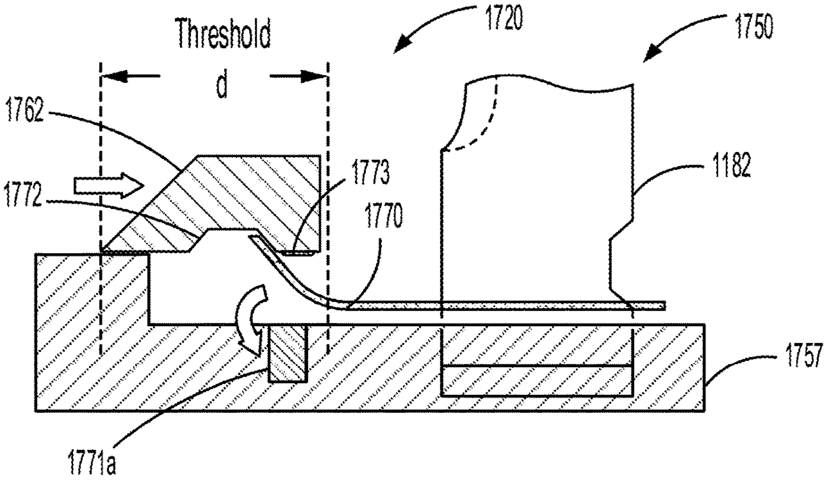
FIG. 26 partially illustrates the staple cartridge assembly of FIG. 25, wherein the staple cartridge is properly seated in the elongated channel.
Figure 27:
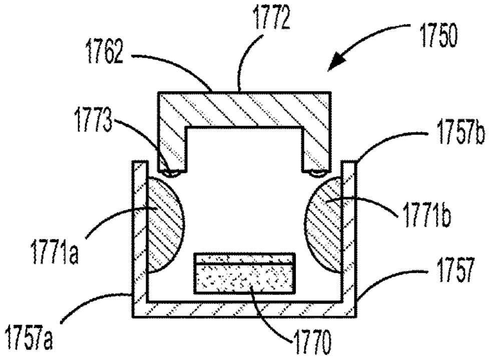
FIG. 27 is a partial transverse cross-sectional view of the staple cartridge assembly of FIG. 25.
Figure 28:
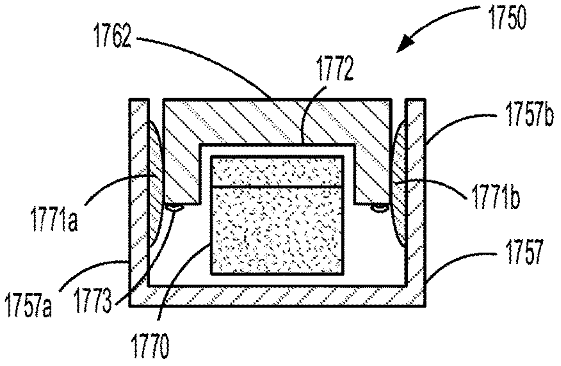
FIG. 28 is a partial transverse cross-sectional view of the staple cartridge assembly of FIG. 26.

FIGS. 22-24 depict an alternative staple cartridge 1620 with a retaining feature 1670 similar in many respects to the staple cartridge 1520 and its retaining features 1570*a*, 1570*b*. For example, the retaining feature 1670 is also in the form of a collapsible leaf spring defined in a cartridge pan 1658 by bending an existing pan sheet metal. However, unlike the retaining features 1570*a*, 1570*b*, the retaining feature 1670 is not collapsed, or flattened, by the insertion of the staple cartridge 1620 into an elongated channel of a loading unit. Instead, a sled 1662 of the staple cartridge 1620 includes a groove, aperture, bore, or detent 1672 configured to receive the retaining feature 1670, as illustrated in FIG. 22.

Like other collapsible retaining features described elsewhere herein, the retaining feature 1670 is configured to maintain the sled 1662 at a first position thereby ensuring an unlocked configuration of the firing lockout assembly 1221 by a sustained engagement between the latch member 1222 and the sled 1662. When a drive force exerted by the drive member 1182 against the sled 1662 exceeds a predetermined threshold, the retaining feature 1670 collapses out of the detent 1672 permitting further advancement of the sled 1662.

In the illustrated example, the retaining feature 1670 includes a first portion 1671, a second portion 1673, and an intermediate bent portion 1675 extending between, and connecting, the portions 1671, 1673. The portion 1671 includes an aperture 1679. During assembly, as illustrated in FIG. 24, a hook member 1681 engages the portion 1671 at the aperture 1679 to temporarily pull the retaining feature 1670 back to permit the sled 1662 to be slidably moved to the first position. The hook member 1681 then releases the portion 1671, which allows the retaining feature 1670 to be received in the detent 1672.

Referring now to FIGS. 25-28, a staple cartridge assembly 1750 is similar in many respects other staple cartridge assemblies described elsewhere herein such as, for example, the staple cartridge assembly 1250. For example, the staple cartridge assembly 1750 includes an elongated channel 1757 dimensioned and designed to receive and releasably retain a staple cartridge 1720 similar in many respects to other staple cartridges described elsewhere herein such as, for example, the staple cartridge 220. 1220. Staples are deployed from the staple cartridge 1720 through a cartridge deck into tissue via staple drivers motivated by the sled 1762 in a similar manner to that described in connection loading units 16, 16', 1100 of FIGS. 1-8. The staples and the staple drivers are stored in a cartridge body of the staple cartridge 1720. During firing, the working end of the drive member 1182 distally advances the sled 1762 from a first position toward a second position within the cartridge body to cause the staple drivers to deploy the staples.

Like the staple cartridge assembly 1250, the staple cartridge assembly 1750 includes a retaining feature 1770 disposed in the elongated channel 1757. In the illustrated example, the retaining feature 1770 is in the form of a leaf spring flattened, or at least partially flattened, in a biased configuration by a hard stop that includes hard stop portions 1771*a*, 1771*b* that are defined in opposing side walls 1757*a*, 1757*b* of the elongated channel 1757. When an unfired staple cartridge 1720 is properly assembled with the elongated channel 1757, the sled 1762 presses the hard stop portions 1771*a*, 1771*b* into the opposing side walls 1757*a*, 1757*b*, respectively, thereby allowing the retaining feature 1770 to be released from the hard stop portions 1771*a*, 1771*b*.

A distal portion of the retaining feature 1770 then engages a corresponding detent 1772 in the sled 1762 pulling and maintaining the sled 1762 at a first position corresponding to an unlocked configuration of the lockout firing assembly 1221. In the illustrated example, the engagement between the retaining feature 1770 and that the detent 1772 permits a slight movement of the sled 1762 within a predefined threshold distance “d” without transitioning the firing lockout assembly 1221 to the locked configuration.

As described in greater detail was other retaining features of the present disclosure, the retaining feature 1770 is configured to resist an advancement of the sled 1762 up to a predetermined force. When the driving force of the drive member 1182 is greater than the predetermined force, the sled 1762 is released from the retaining feature 1770, and is advanced distally beyond the first position. The advancement of the sled 1762 over the retaining feature 1770 resets the retaining feature 1770 into a locking engagement with the hard stop portions 1771*a*, 1771*b*.

The retaining feature 1770 is then maintained in a flattened, or at least partially flattened, configuration by the hard stop portions 1771*a*, 1771*b* until another unfired staple cartridge 1720 is inserted into the elongated channel 1757. In the illustrated example, maintaining the retaining feature 1770 in a flattened, or at least partially flattened, the configuration reduces drag on the drive member 1182 during the remainder of the firing.

In the illustrated example, the sled 1762 include one or more features 1773 designed and dimensioned to engage and depress the hard stop portions 1771*a*, 1771*b* into the opposing side walls 1757*a*, 1757*b*. The hard stop portions 1771*a*, 1771*b* can be spring biased such that they return to a locking engagement with the retaining feature 1770 after disengaging from the one or more features 1773.

In various aspects, one or more of the sled positioning and/or retaining mechanisms described in the present disclosure can be combined position and/or maintain the sled in a staple cartridge prior to and after insertion of the staple cartridge into an elongated channel of the loading unit. For example, a first positioning and/or retaining mechanism can be employed to maintain the sled at a first position within the staple cartridge prior to insertion of the staple cartridge into the elongated channel. Then, second positioning and/or retaining mechanism can be employed to maintain the sled at the first position within the staple cartridge after the insertion of the staple cartridge into the elongated channel.

In the example illustrated in FIGS. 25-28, the one or more features 1773 can be received in corresponding apertures or cutouts of a cartridge pan, as described in connection with the loading unit 1200 of FIGS. 11-13. The features 1773 maintain the sled at the first position within the staple cartridge 1720 prior to insertion of the staple cartridge 1720 into the elongated channel 1757. After the insertion, however, the sled 1762 is maintained at the first position by the retaining feature 1770. Accordingly, a staple cartridge assembly (e.g., staple cartridge assembly 1750) can be configured to maintain the sled at the first position differently before insertion than after insertion into an elongated channel. In other words, the insertion of the staple cartridge into the elongated channel may cause an active retaining feature to deactivated, and cause an inactive retaining feature to be activated.

Figure 30:
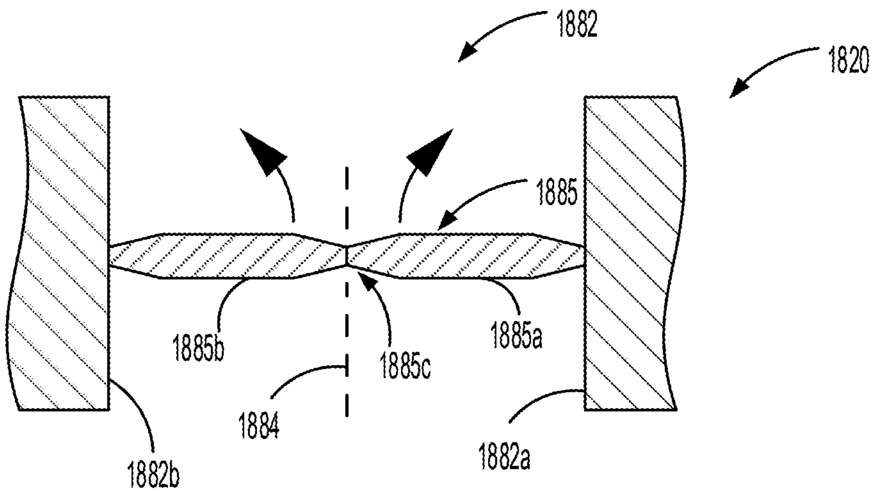
FIG. 30 is a partial cross-sectional view of the staple cartridge of FIG. 29.
Figure 29:
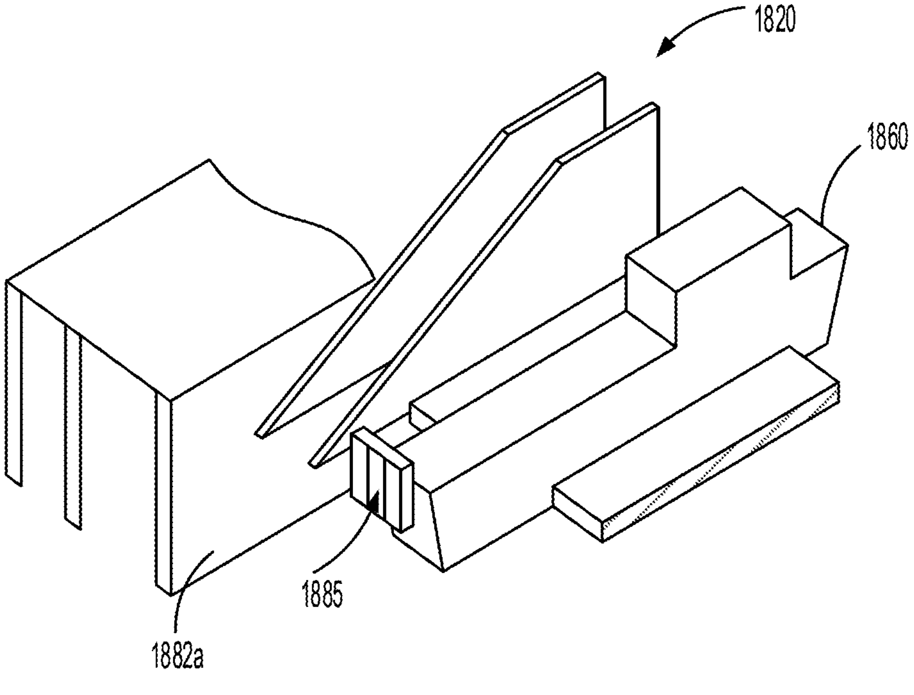
FIG. 29 is a partial perspective of a staple cartridge, in accordance with at least one aspect of the present disclosure.

Referring to FIGS. 29-30, a staple cartridge 1820 is similar respects to other staple cartridges described elsewhere herein such as, for example, the staple cartridge 220. For example, like the staple cartridge 220, the staple cartridge 1820 includes the knife blade 280 (FIG. 5). A central longitudinal slot 1882 is defined in staple cartridge 220 along a central longitudinal plane 1884. The knife blade 280 is generally positioned to translate slightly behind a sled 1860 through the central longitudinal slot 1882 in the staple cartridge 1820 to form an incision between rows of stapled body tissue.

In various aspects, the sled 1860 is maintained at a first, or home, position by a retaining feature 1855 extending across the central longitudinal slot 1882. In the illustrated example, the retaining feature 1855 includes a weakened central portion 1885*c* extending between portions 1885*a*, 1885*b* that defined hinging gates attached at one end thereof to sidewalls 1882*a*, 1882*b*, respectively. In the illustrated example, the central portion 1885*c* includes a perforated breakable body. In other examples, the central portion 1885*c* may comprise a smaller thickness than the portions 1885*a*, 1885*b*.

In any event, the central portion 1885*c* is designed and dimensioned to resist an advancement of the sled 1860 up to a predetermined driving force threshold. Beyond the threshold, the knife blade 280 applies a force to the sled 1860 that breaks through the central portion 1885*c* causing the portions 1885*a*, 1885*b* to fold or swing open allowing the sled 1860 move distally beyond the first, or home, position.

Figure 31:
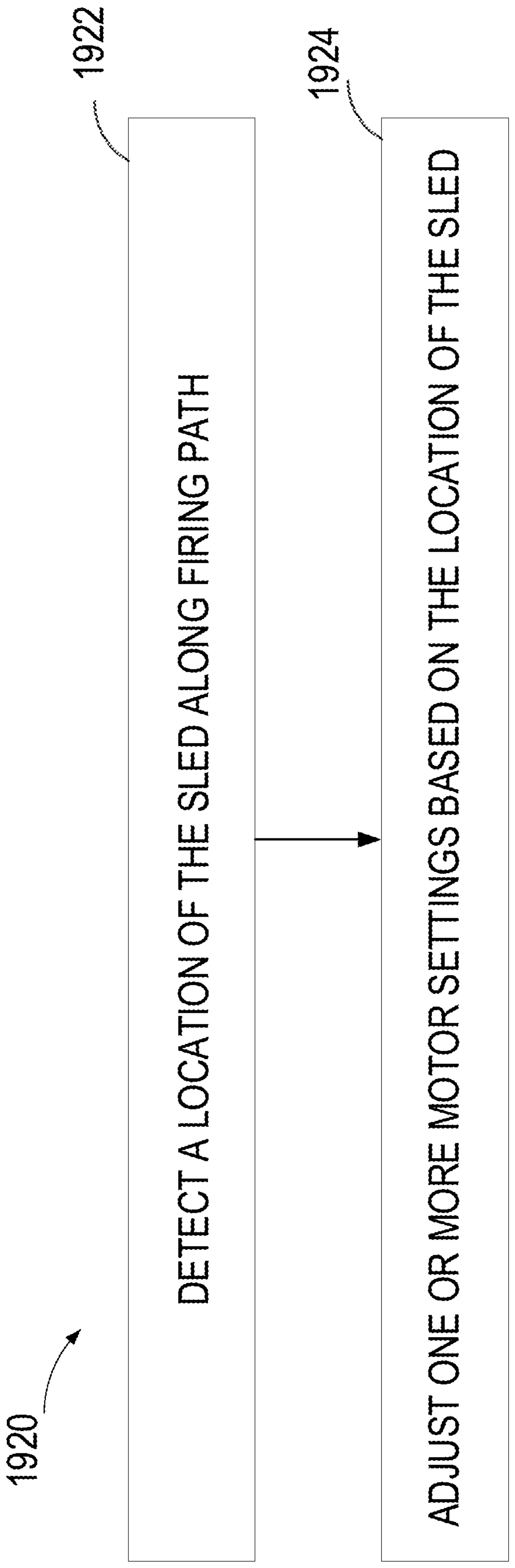
FIG. 31 is a logic flow diagram of a process depicting a control program or a logic configuration, in accordance with at least one aspect of the present disclosure.

As described in greater detail elsewhere herein, an incidental bumping or shaking of the unfired staple cartridge may cause an unintended movement of the sled within the unfired staple cartridge. FIG. 31 illustrates a logic flow diagram of a process 1920 depicting a control program or a logic configuration for detecting 1922 the location of a sled of a powered surgical stapling instrument along a firing path thereof, and adjusting 1924 one or more motor settings, or motor control programs, of the powered surgical stapling instrument based on the location of the sled along the firing path.

Figure 32:
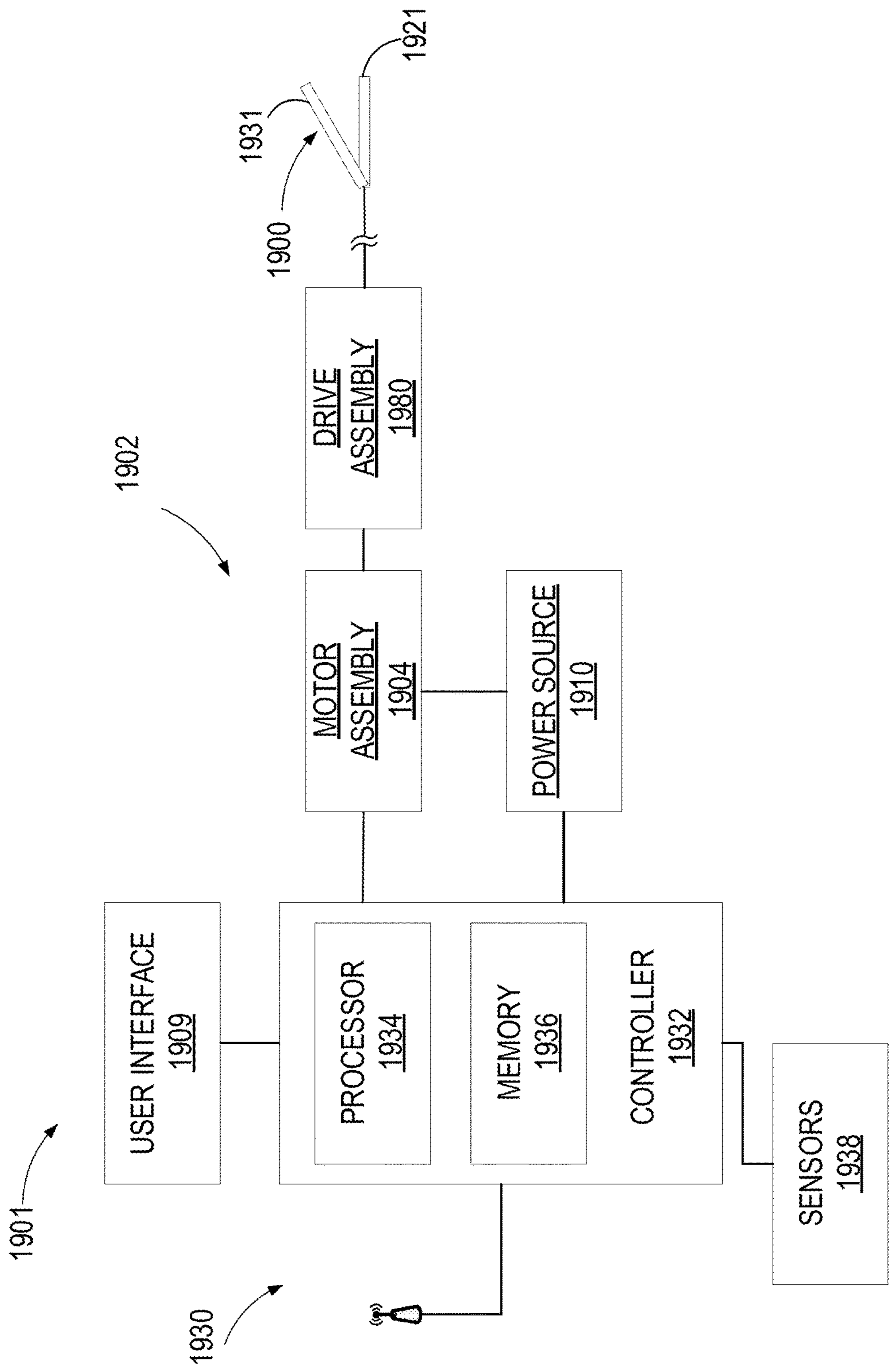
FIG. 32 is a diagram of a surgical stapling instrument including a firing system, in accordance with at least one aspect of the present disclosure.
Figure 34:
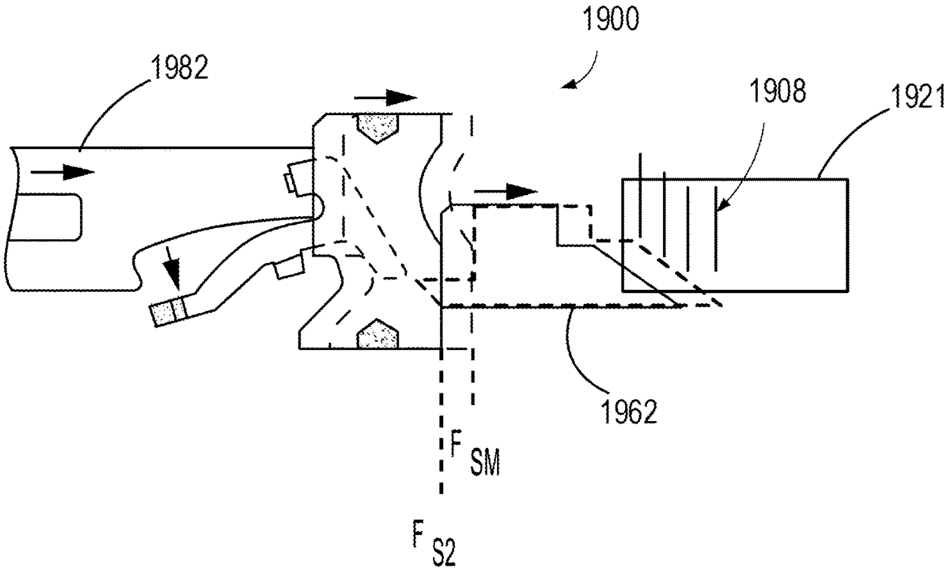
FIG. 34 illustrates the drive member FIG. 32 at two positions along the firing path.
Figure 33:
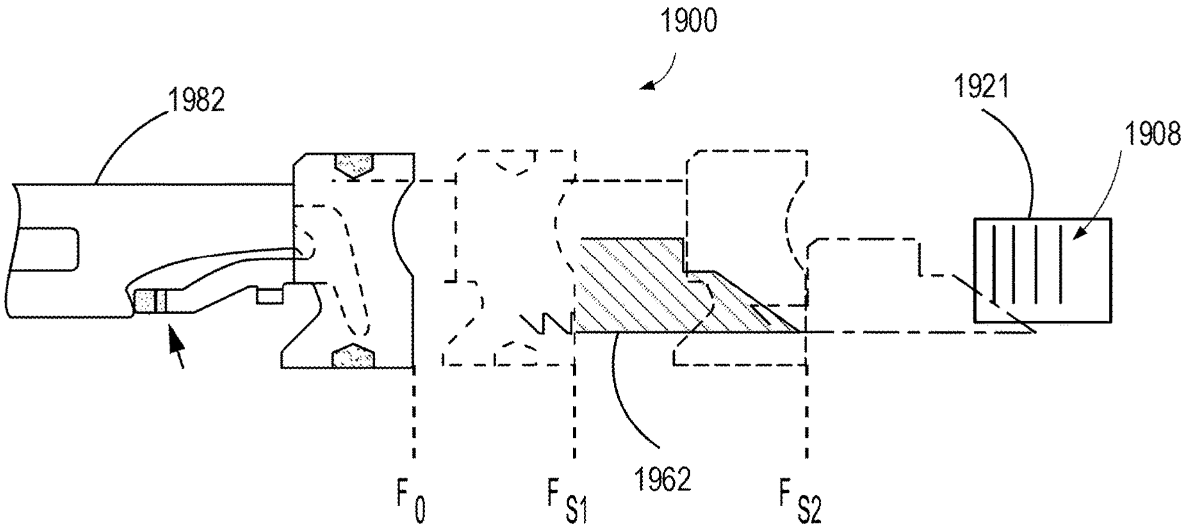
FIG. 33 illustrates a drive member of the surgical stapling instrument of FIG. 32 at three positions along a firing path thereof, and a sled advanceable by the drive member to deploy staples of the surgical stapling instrument of FIG. 32.

FIGS. 32-34 illustrate a powered surgical stapling instrument 1901 that includes a firing system 1902 configured to detect the location of a sled along a firing path thereof, and adjust one or more motor settings, or motor control programs, based on the location of the sled along the firing path, in accordance with the process 1920. The firing system 1902 includes a control circuit 1930 configured to perform the process 1920. In the illustrated example, the control circuit 1930 comprises a controller 1932 that includes a processor 1934 and a memory 1936 storing program instructions, which when executed by the processor 1934, causes the processor 1934 to perform one or more aspects of the process 1920.

The surgical stapling instrument 1901 further includes a loading unit 1900 similar in many respects to other loading units described elsewhere herein such as, for example, the loading units 1100, 1200. For example, like the loading unit 1100, the loading unit 1900 includes a drive assembly 1980 that includes a drive member 1982. A motor assembly 1904 includes a motor configured to move the drive member 1982 along a predefined firing path to advance a sled 1962 distally to deploy staples 1908 from a staple cartridge 1921 into tissue grasped between the staple cartridge 1921 and an anvil assembly 1931. The sled 1962 includes a plurality of cam surfaces which are positioned to engage and lift the pushers within the staple retention slots of the cartridge body of staple cartridge 1921. The pushers are positioned within the staple cartridge 1921 to eject the staples 1908 from the cartridge body when the sled 1962 is advanced by the drive member 1982, as illustrated in FIGS. 33, 34.

Figure 35:
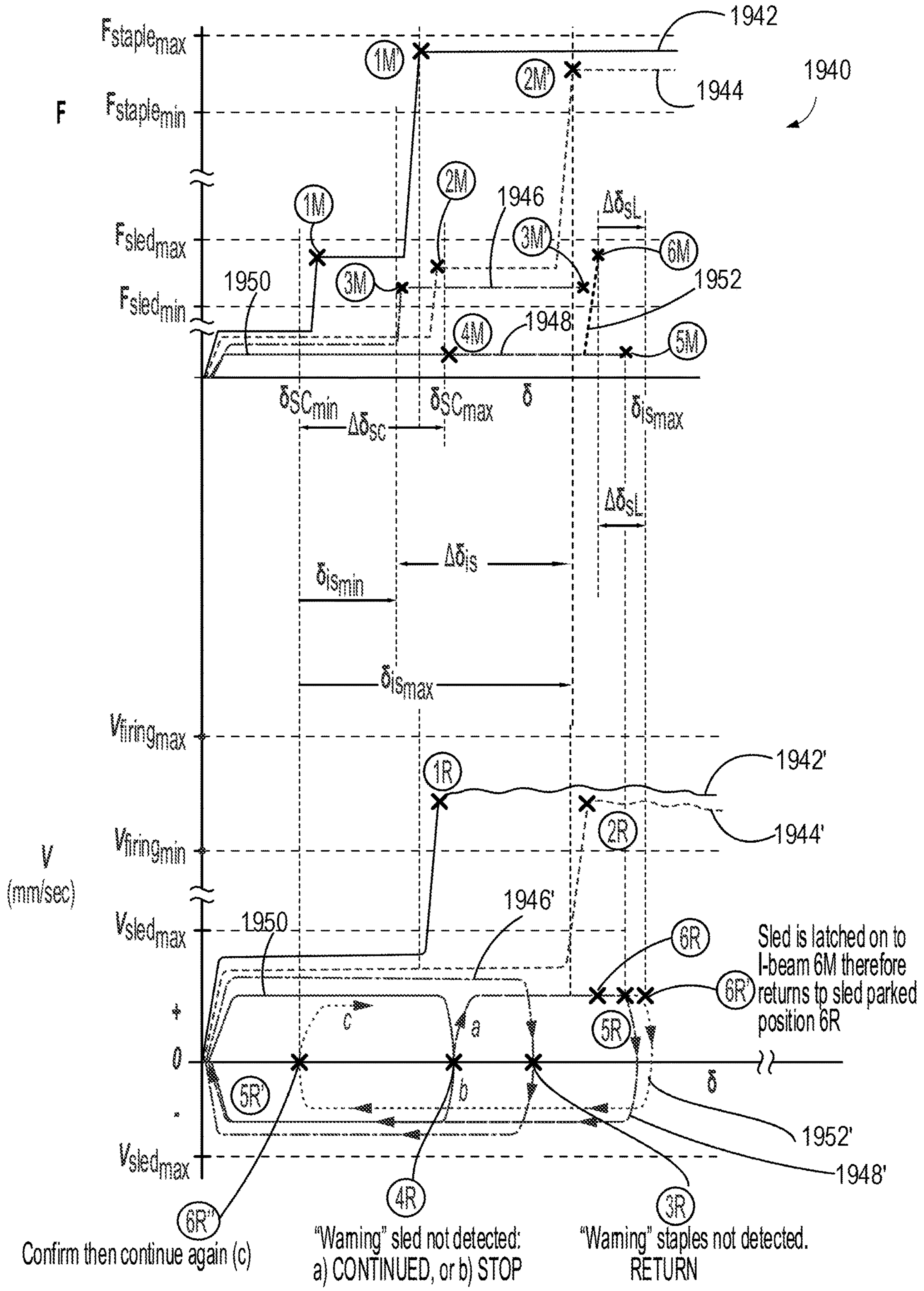
FIG. 35 is a graph depicting, on the x-axis, the distance (δ) traveled by the drive member along the firing path from a starting position, and on the y-axis, the firing speed (V) and corresponding electrical load of the motor during a firing stroke of the powered surgical stapling instrument, in accordance with at least one aspect of the present disclosure.

FIG. 35 is a graph 1940 illustrating, on the x-axis, the distance (δ) traveled by the drive member 1982 along the firing path from a starting position, and on the y-axis, the firing speed (V) and corresponding electrical load of the motor during a firing stroke of the powered surgical stapling instrument 1901 (FIG. 32), which are represented by lines 1942', 1944', 1946', 1948', 1950', 1952', and lines 1942, 1944, 1946, 1948, 1950, 1952, respectively. A segment $\Delta\delta_{SC}$ along the firing path defines acceptable initial sled-contact locations, where the drive member 1982 is configured to first engage (See FIG. 33) the sled 1962 during advancement of the drive member 1982 along the firing path. In addition, a segment $\Delta\delta_{IS}$ along the firing path defines acceptable initial staple-contact locations, where the sled 1962, driven by the drive member 1982, is configured to first engage (See FIG. 33) the pushers of the staples 1908 within the staple cartridge 1921.

In a successful firing, as illustrated by lines 1942, 1944, the drive member 1982 is configured to initially contact (1M, 2M) the sled 1982 within the segment $\Delta\delta_{SC}$, and the sled 1962, driven by the drive member 1982, is configured to initially contact (1M', 2M') the pushers of the staples 1908 within the segment $\Delta\delta_{IS}$.

In various aspects, a rapid increase, or a step-up, in the electric load of the motor to a value ($F_{S1}$, FIG. 33) within a predetermined range (F-$\text{sled}_{min}$ to F-$\text{sled}_{max}$) indicates that an initial contact between the drive member 1982 and the sled 1962 is detected. In various aspects, the control circuit 1930 detects the location of the sled 1962 by monitoring at least one parameter indicative of the electric load of the motor such as, for example, the current draw of the motor.

Likewise, a rapid increase, or a step-up, in the electric load of the motor to a value ($F_{S2}$, FIG. 33) within a predetermined range (F-staple$_{min}$ to F-staple$_{max}$), which is greater than the predetermined range (F-sled$_{min}$ to F-sled$_{max}$), indicates that an initial contact between the sled 1962, driven by the drive member 1982, and the pushers of the staples 1908 is detected. In various aspects, the control circuit 1930 detects the initial contact between the sled 1962 and the staple pushers by monitoring at least one parameter indicative of the electric load of the motor such as, for example, the current draw of the motor.

If the rapid increase in the electric load of the motor is detected within the segment $\Delta\delta_{SC}$, the control circuit 1930 permits the drive member 1982 to continue advancing the sled 1962 along the firing path at a speed less than or equal to a predetermined maximum speed (V-sled$_{max}$) until the sled 1982 engages the pushers of the staple cartridge 1921, which is characterized by another rapid increase in the electric load of the motor to a value ($F_{S2}$, FIG. 33), as discussed above. The detection of the initial contact between the sled 1962 and the staple pusher causes control circuit 1930 to ramp up (1R, 2R) the speed of the of the drive member 1982 to a speed greater than a predetermined minimum speed (V-firing$_{min}$) and less than or equal to a predetermined maximum speed (V-firing$_{max}$).

If, however, the control circuit 1930 fails (4M) to detect the location of the sled 1962 within the segment $\Delta\delta_{SC}$, as illustrated by line 1950, the control circuit 1930 may cause the drive member 1982 to stop (4R) by causing the motor assembly 1904 to stop the motor, for example. The control circuit 1930 may further prompt a user through a user interface 1909 to replace the staple cartridge, as the absence of the sled 1962 can be due to an attachment of a previously fired staple cartridge to the cartridge channel of the loading unit 1900, or the absence of a staple cartridge. If the user approves, the drive member 1982 is returned (b) to the starting position. If, however, the user is confident that an unfired staple cartridge has been attached to the cartridge channel, the sled 1962 may have been moved or misaligned due to an incidental bumping of the staple cartridge.

To resolve the issue, the control circuit 1930 prompts the user for permission to continue (a) advancing the drive member 1982 until a predetermined maximum threshold value $\delta_{max}$ of travel without sled detection is reached (5M, 5R). If the sled 1962 is not detected, and the predetermined maximum threshold value $\delta_{max}$ has been reached, the control circuit 1930 causes the drive member to be returned to its starting position (5R').

If, however, the sled 1962 is detected (6M, 6R) prior to reaching the predetermined threshold value $\delta_{max}$, the control circuit 1930 may permit an additional advancement (6R') of the drive member 1982 in a predetermined segment $\Delta\delta_{SL}$ to couple the drive assembly 1980 to the sled 1962, as described in greater detail below. The predetermined segment $\Delta\delta_{SL}$ defines a functional window of sled travel for ensuring that a coupling between the drive member 1982 and the sled 1962 has occurred.

The control circuit 1980 then causes the motor to retract the drive member 1980 to its starting position, which causes the sled 1962 to return to its home position (6R") within the unfired staple cartridge. The control circuit 1930 may further prompt the user to push down any staples 1908 incidentally lifted above the cartridge deck by the inadvertent advancement of the sled 1962. Once the sled is returned to the home position, the control circuit 1930 may prompt the user to reinitiate (c) the firing stroke.

Further to the above, a successful detection (1M) of the sled 1962 within the segment $\Delta\delta_{SC}$, accompanied by a failure (3M') to detect an initial contact between the sled 1962 and the staple pushers within the segment $\Delta\delta_{IS}$, causes the control circuit 1930 to stop (3R) the advancement of the drive member 1982 at, or about, the end of segment $\Delta\delta_{IS}$. The control circuit 1930 may further cause the drive member 1982 to return to the starting position.

Although the process 1920 is described as being executed by a control circuit 1930, this is merely for brevity, and it should be understood that the process 1920, and other processes described elsewhere herein, can be executed by circuitry that can include a variety of hardware and/or software components and may be located in or associated with various suitable systems described by the present disclosure such as, for example, the combinational logic circuit or the sequential logic circuit.

In various forms, the motor of the motor assembly 1904 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor may be powered by a power source 1910 that, in one form, may comprise a removable power pack. The power source 1910 may comprise, for example, anyone of the various power source arrangements disclosed in further detail in U.S. Patent Application Publication No. 2015/0272575 and entitled SURGICAL INSTRUMENT COMPRISING A SENSOR SYSTEM, the entire disclosure of which is hereby incorporated by reference herein.

In at least one example, the surgical stapling instrument 1901 is implemented as a hand-held surgical instrument similar in many respects to the surgical instrument system 10 of FIG. 1. In another example, the surgical stapling instrument 1901 is implemented as a robotic surgical stapling instrument similar to those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

In various examples, the surgical instrument 1901 includes sensors 1938 that comprise one or more sensors configured to monitor a parameter indicative of the position of the drive member 1982 along the firing path. The sensors 1938 may further include one or more sensors configured to monitor the current draw of the motor. Readings sensors 1938 can aid the control circuit 1930 detect the presence of the drive member 1982 is in the segment $\Delta\delta_{SC}$ or the segment $\Delta\delta_{IS}$, detect an initial contact between the drive member 1982 and the sled 1962, and/or detect an initial contact between the sled 1962, driven by the drive member 1982, and the pushers of the staples 1908, for example.

In various aspects, the sensors 1938 may include various other sensors such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor to perform one or more aspects of the process 1920, for example.

Figure 36:
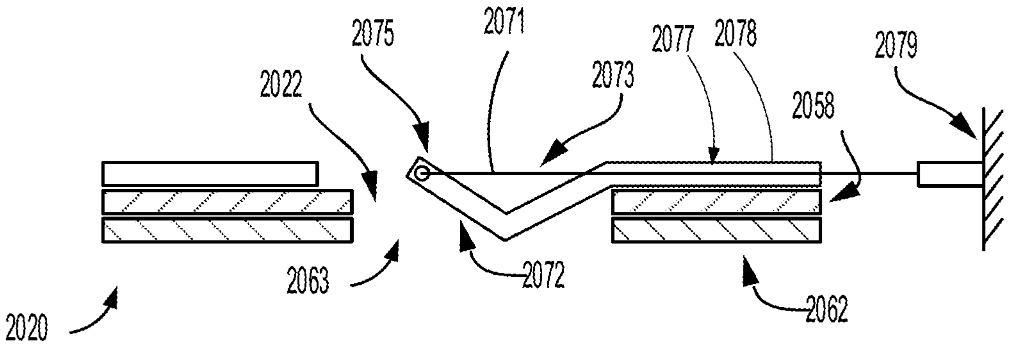
FIG. 36 illustrates a staple cartridge including a retaining feature for maintaining a sled within the staple cartridge at a home position, in accordance with at least one aspect of the present disclosure.
Figure 37:
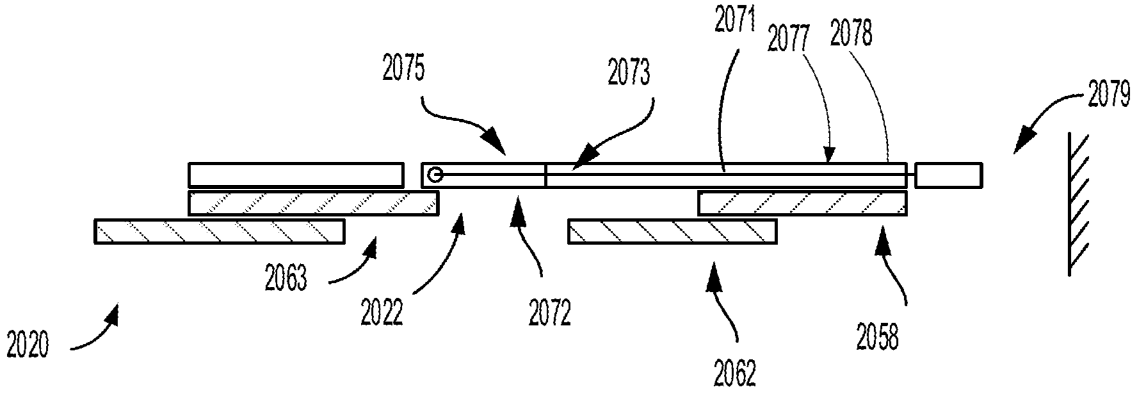
FIG. 37 illustrates the staple cartridge of FIG. 36 where the sled is advanced distally within the staple cartridge beyond the home position.
Figure 38:
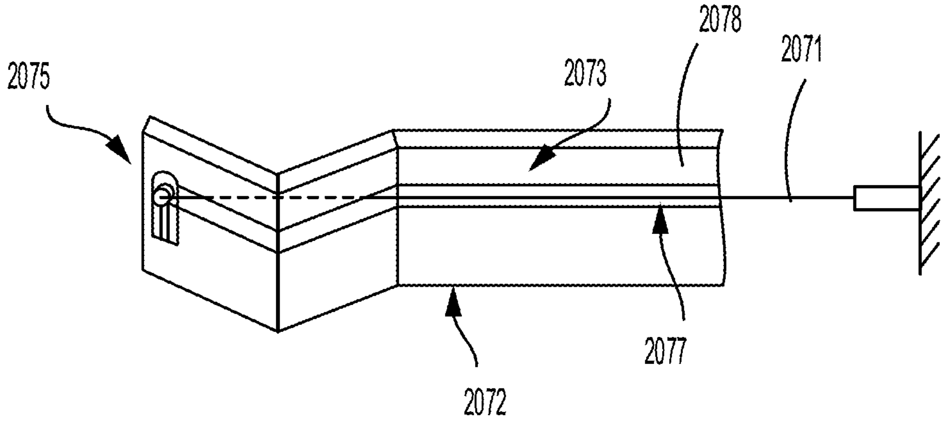
FIG. 38 illustrates the retaining feature of the staple cartridge of FIG. 36.

Referring now to FIGS. 36-38, a staple cartridge 2020 includes a retaining feature 2072 configured to maintain a sled 2062 within the staple cartridge 2020 at a home, or start, position. The staple cartridge 2020 is similar in many respects to other staple cartridges disclosed elsewhere herein such as, for example, the staple cartridges 1520, 1620. To resist a movement of the sled 2062 due to an incidental bumping or shaking of the staple cartridge 2020, a cartridge pan 2058 of the staple cartridge 2020 includes one or more retaining features (e.g., retaining features 2020) configured to matingly engage the sled 2062 and resist a movement of the sled 2062 up to a predetermined force.

In the illustrated example, the retaining feature 2072 is in the form of a leaf spring projecting, or bent, inward. The leaf spring can be stamped or formed in a base proximal portion of the cartridge pan 2058. The retaining feature 2072 includes a base attached to, and protruding from, the base portion of the cartridge pan 2058. An apex portion extends from the base, and is dimensioned to pass through cutouts (e.g., cutout 2022) defined in the cartridge pan 2058, and into the detents defined in sidewalls of the sled 2062 (e.g., detent 2063). The retaining feature 2072 defines a ramp that resists a distal advancement of the sled 2062 up to a predetermined driving force. The retaining feature 2072 is flattened by the advancement of the sled 2072 when a drive member (e.g., drive member 1982) exerts a driving force on the sled 2072 greater than the predetermined driving force.

The staple cartridge 2020 includes a sled detection circuit 2073 configured to determine whether the sled 2062 is outside the home, or starting, position. The sled detection circuit 2073 includes the retaining feature 2072 and a wire, or rod, 2071 extending from a distal portion 2075 of the retaining feature 2072 through a groove 2077 defined in a proximal portion 2078 of the retaining feature 2072. The wire 2071 terminates in an electrical contact 2079 such as for example a pogo pin. The electrical contact 2079 is configured to transition the sled detection circuit 2073 between a closed configuration while the retaining feature 2072 is bent as illustrated in FIG. 36, and an open configuration while the retaining feature 2072 is flattened by the sled 2062, as illustrated in FIG. 37.

Accordingly, a control circuit such as, for example, the control circuit 1930 of the surgical instrument 1901 may employ the sled detection circuit 2073 to determine whether the sled 2062 is outside the home, or starting, position by detecting whether or not the sled detection circuit 2073 has transitioned from the closed configuration to the open configuration. A switch of the sled detection circuit 2073 from the closed configuration to an open configuration signals the control circuit 1930 that the sled 2062 has been distally advanced beyond the home, or starting, position. Further, a return of the sled detection circuit 2073 to the closed configuration signals the control circuit 1930 that the sled detection circuit 2073 has been returned to the home, or starting, position.

Figure 39:
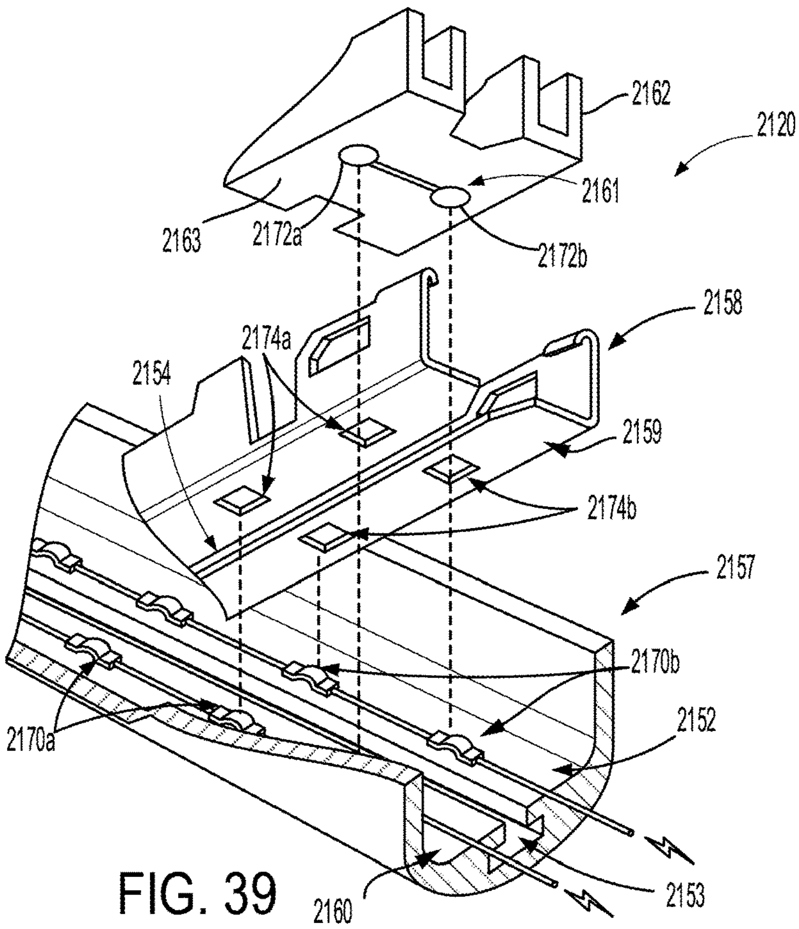
FIG. 39 illustrates a partial exploded view of a surgical stapling assembly, in accordance with at least one aspect of the present disclosure.

Referring now to FIG. 39, a staple cartridge assembly 2150 can be used with a loading unit such as, for example, the loading units 1100, 1200. In the illustrated example, the staple cartridge assembly 2150 includes an elongated channel 2157 dimensioned and designed to receive and releasably retain a staple cartridge 2120 similar in many respects to other staple cartridges described elsewhere herein such as, for example, the staple cartridge 220. For example, staples also are deployed from the staple cartridge 2120 through a cartridge deck into tissue via staple drivers, or pushers, motivated by a sled 2162 in a similar manner to that described in connection loading units 16, 16', 1100 of FIGS. 1-8. The staples and the staple drivers are stored in a cartridge body of the staple cartridge 2120.

A cartridge pan 2158 is attached to the bottom of the cartridge body to prevent the staple drivers from falling out of the staple cartridge 2120. The cartridge pan 2158 includes a pan slot 2154 that is aligned with a cartridge slot defined in the cartridge deck. The pan slot 2154 is also aligned with a channel slot 2153 defined in a base portion 2152 of the elongated channel 2157. During firing, the working end 1184 of the drive member 1182 slidably moves through the cartridge slot, the pan slot 2154, and the channel slot 2153 distally advancing the sled 2162 from a first position toward a second position within the cartridge body to cause the staple drivers to deploy the staples through the cartridge deck.

Figure 41:
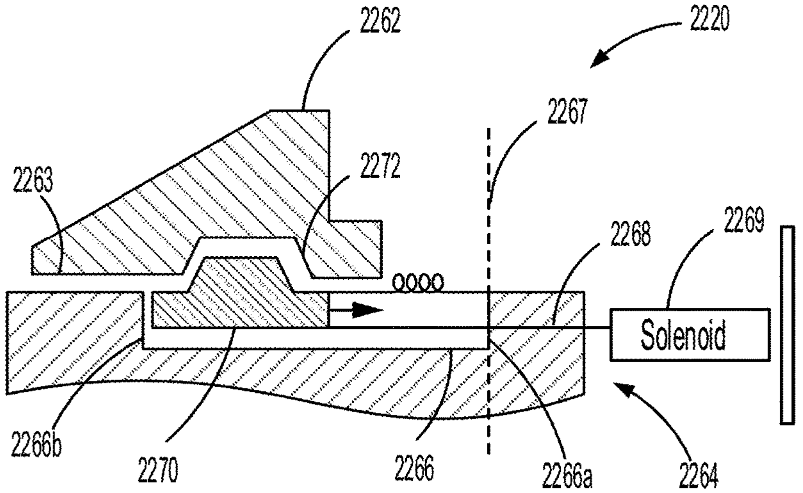
FIG. 41 is a partial cross-sectional view of the staple cartridge including a sled reset circuit, in accordance with at least one aspect of the present disclosure.

As described above in greater detail, a sled such as, for example, the sled 2162 can move from its home, or starting position, due to an incidental bumping or shaking of the staple cartridge 2120. To detect such movement, the staple cartridge assembly 2150 includes a sled detection circuit 2160 configured to detect configured to detect the location of the sled 2162 as the home, or starting position and additional locations distal to the home, or starting position through a series of spaced apart electrical contacts 2170*a*, 2170*b* on opposite sides of the channel slot 2153. When corresponding electrical contacts 2172*a*, 2172*b* of the sled are positioned against a pair of the electrical contacts 2170*a*, 2170*b*, the sled detection circuit 2160 is transitioned into the closed configuration, and a signal unique to such location, as illustrated in FIG. 41, is transmitted to a control circuit such as, for example, the control circuit 1930.

The control circuit 1930 can determine the position of the sled 2162 based on the received signal. For example, the memory 1936 may store an algorithm, an equation, or a lookup table for determining the position of the sled based on one or more parameters of the received signals. The processor 1934 may employ such algorithm, equation, and/or lookup table to determine the position of the sled based on readings of the one or more parameters. In one example, the readings are current or voltage readings indicative of the position of the sled 2162.

In at least one example, the sensors 1938 include a current sensor configured to measure the current passing through the sled detection circuit 2160 in the closed configuration. For a given voltage, the measured current value will change depending on the resistance. FIG. 41 illustrates example resistances associated with different positions of the sled 2162 along the firing path. Each position is designed to yield a unique resistance and, as such, a unique current value associated with the position. Accordingly, the current readings of the current sensor can aid a control circuit (e.g., control circuit 1930) in determining whether the sled 2162 is in the home, or starting, position or in other more distal positions.

Figure 40:
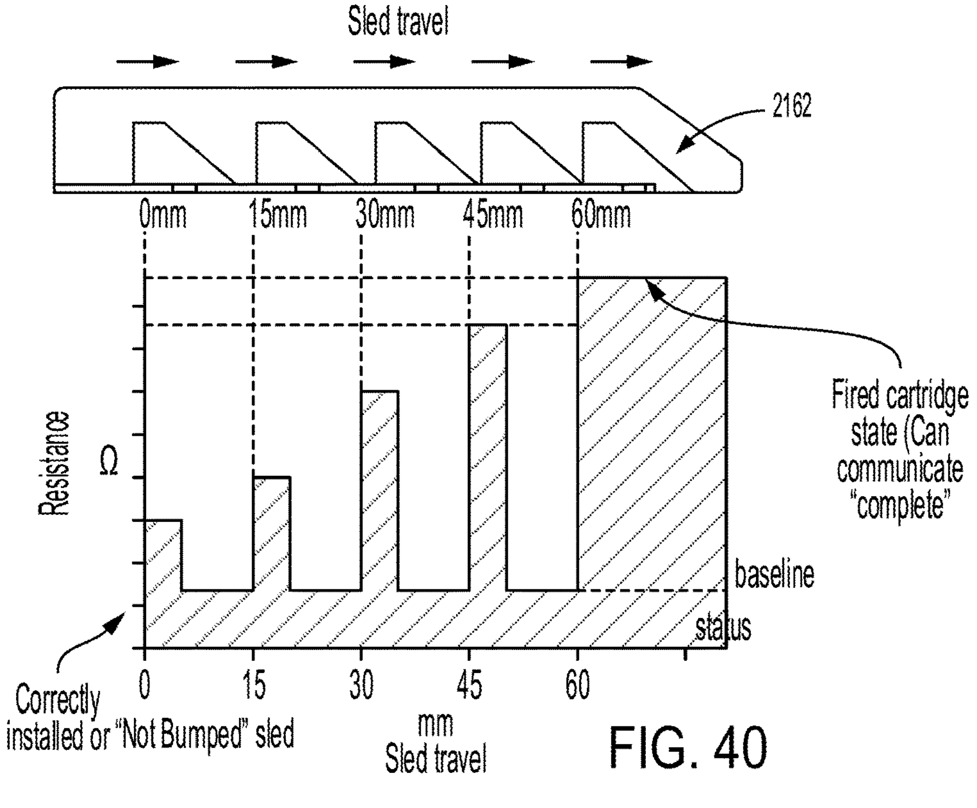
FIG. 40 is a graph illustrating varying resistances, on the y-axis, of a sled detection circuit and corresponding travel distances, on the x-axis, of a sled of the surgical stapling assembly of FIG. 39.

As illustrated in FIG. 40, an inherent baseline resistance exists in the sled detection circuit 2160 leading back to the control circuit 1930. Each time the sled 2162 completes the sled detection circuit 2160, additional resistance inherent to the lines in the channel will increase the total resistance and, as such, yielding unique current readings per each position along the firing path. In various aspects, intentionally high-resistance circuit material and/or actual resistors may be used at each contact-point.

In the illustrated examples, the electrical contacts 2170*a*, 2170*b* are raised above the base portion 2152 of the elongated channel 2157, and define biasing members configured to ensure a good connection with the staple cartridge 2120. The electrical contacts 2170*a*, 2170*b* extend through cutouts 2174*a*, 2174*b* defined in the base portion 2159 of the cartridge pan 2158. In various aspects, the cartridge pan 2158 is coated with a thin film electrical insulator to prevent shorting. Similarly, the internal surface of the base portion 2152 can be coated with a thin film electrical insulator to prevent shorting. The electrical contacts 2170_a_, 2170_b_ extend through the electrical insulator film of the cartridge pan 2158.

In various aspects, signals from the sled detection circuit 2160 indicate the completion of a firing stroke. Electrical contacts 2170_a_, 2170_b_ can be positioned at, or about, the end of the firing path. In the illustrated examples, electrical contacts 2170_a_, 2170_b_ are position at, or about, a distance 60 mm from the home, or starting, position. When the sled 2162 reaches the end of the firing stroke, the electrical contacts 2172_a_, 2172_b_ engage the electrical contacts 2170_a_, 2170_b_ transitioning the sled detection circuit 2160 to a closed configuration, and yielding a unique signal indicative of the completion of the firing stroke.

In the illustrated example, the sled 2162 is insulated except for a conductive portion 2161 that defines the electrical contacts 2172_a_, 2172_b_. In other examples, however, the entire sled 2162 can be comprised of a conductive material. In such instances, the whole sled 2162 becomes part of the sled detection circuit 2160.

Referring now to FIG. 41, a staple cartridge 2220 is depicted. The staple cartridge 2220 is similar in many respects to other staple cartridges disclosed elsewhere herein such as, for example, the staple cartridges 1220', 1220'', 1320, 1620. For example, the staple cartridge 2220 includes a retaining feature 2270 configured to resist incidental movements of a sled to 2262 within the staple cartridge 2220 due to, for example, an incidental bumping of the staple cartridge 2220.

In addition, the staple cartridge 2220 is further equipped with a sled reset circuit 2264 configured to retract the sled 2262 to a home, or starting, position 2267. In the illustrated example, the sled 2262 includes one or more apertures, bores, grooves, or detents (e.g., detent 2272) defined in a sled base 2263. The detent 2272 is aligned with and configured to receive the retaining feature 2270. A driving force greater than a predetermined threshold is needed to separate the retaining feature 2270 from the sled 2262. Accordingly, the retaining feature 2270 is configured to resist an advancement of the sled 2262 up to the predetermined threshold.

Furthermore, the retaining feature 2270 rides in a channel 2266 defined in a cartridge pan 2258 of the staple cartridge 2220. A proximal wall 2266_a_ of the channel 2266 defines a proximal stopping position for the retaining feature 2270, which corresponds to the home, or starting, position 2267 of the sled 2262. A distal wall 2266_b_ of the channel 2266 defines a distal stopping position of the retaining feature 2270 within the channel 2266. Since the retaining feature 2270 is not permitted to move beyond the distal wall 2266_b_, an additional movement of the sled 2262 forces the sled 2262 to decouple from the retaining feature 2270.

Further to the above, the channel 2266 permits incidental movements of the sled 2262 and the retaining feature 2270 without decoupling the sled 2262 from the retaining feature 2270 within a predetermined range defined by the length of the channel 2266, or the distance between the proximal wall 2266_a_ and the distal wall 2266_b_. Prior to firing however the sled reset circuit 2264 is activated to retract the retaining feature 2270 to abut against the proximal wall 2266_a_. The retraction of the retaining feature 2270 causes the sled 2262 to be retracted to the home, or starting, position 2267. In the illustrated example, the sled reset circuit 2264 includes a solenoid 2269 that, when activated, is configured to pull, or retract, a wire or rod 2268 coupled to the retaining feature 2270.

As described elsewhere herein, the sled 2262 of an unfired staple cartridge 2220 prevents the firing lockout assembly 1221 from transitioning to a locked configuration while the sled 2262 is at the home, or starting, position 2267. Accordingly, retraction of the sled 2262 by the sled reset circuit 2264 ensures that an unfired staple cartridge 2220 is not mistaken for a previously fired staple cartridge 2220 due to an incidental advancement of the sled to from the home, or starting, position 2267. Notably, the sled reset circuit 2264 is capable of retracting the sled 2262 only when the retaining feature 2270 is coupled to the sled 2262. Once the sled 2262 is advanced distally by the drive member beyond its coupling engagement was the retaining feature 2270, the staple cartridge 2220 is deemed as fired.

In various aspects, the sled reset circuit 2264 can be incorporated into other staple cartridges disclosed elsewhere herein. In certain aspects, the sled reset circuit 2264 can be coupled to the control circuit 1930, and can be activated by the control circuit 1930, in response to a determination by the control circuit 1930 that the sled 2262 is not at the home, or starting, position 2267. In such aspects, one or more of the sensors 1938 may detect that the sled 2262 is at a position beyond the home, or starting position 2267. In response, the control circuit 1930 may activate the sled reset circuit 2264 to return the sled 2262 to the home, or starting, position 2267 prior to initializing the firing stroke.

Referring now to FIGS. 42-44, an alternative embodiment of a sled reset circuit 2364 is depicted. Like the sled reset circuit 2264, the sled reset circuit 2364 is also configured to retract a sled 2362 to a home, or starting position within a predetermined range of motion of the sled 2362 where a retaining feature 2370 remains movably coupled to the sled 2362. Beyond the predetermined range, a drive member motivates the sled 2362 to decouple from the retaining feature 2370. The retaining feature 2370 is then retracted to a proximal starting position by the sled reset circuit 2364.

Figure 45:
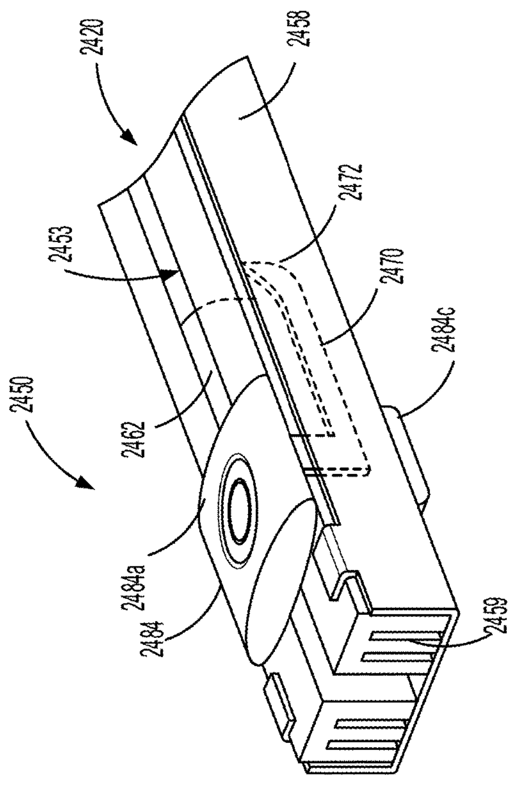
FIG. 45 illustrates a partial perspective view of a staple cartridge including a sled retaining feature, in accordance with at least one aspect of the present disclosure.
Figure 46:
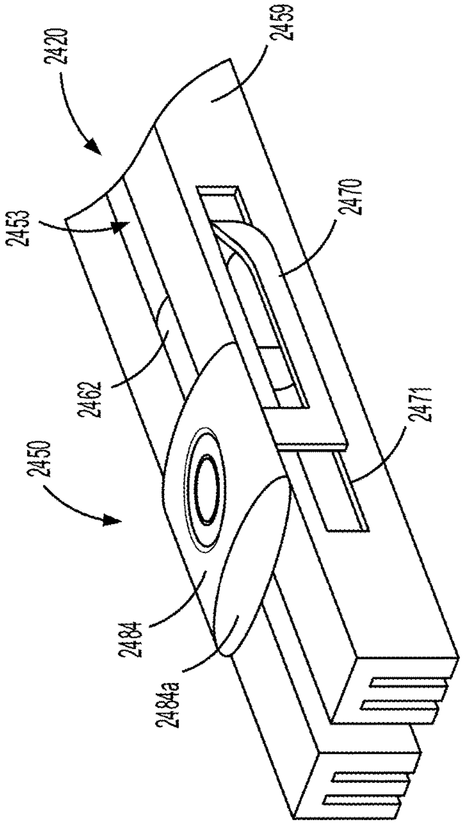
FIG. 46 illustrates the staple cartridge of FIG. 45 with a removed cartridge pan to expose the sled retaining feature.

Referring now to FIGS. 45-46, a surgical stapling assembly 2450 includes a staple cartridge 2420 including a sled 2462. The staple cartridge assembly 2450 is transitionable to a closed configuration to grasp tissue in a similar manner to that described in connection with other staple cartridges assemblies such as, for example, the staple cartridge assemblies 1150, 1250. A working end 2484 of a drive member (e.g., drive member 1182) defines an I-beam configured to effect a firing of the surgical stapling assembly 2450.

The working end 2484 includes a first flange 2484_a_, a second flange, a vertical strut 2484_c_ interconnecting the first flange 2484_a_ and the second flange, and a knife supported on or formed into the vertical strut 2484_c_. The second flange is positioned to be slidably received within a channel of an anvil assembly (e.g., anvil assembly 1130) and the first flange 2484_a_ is positioned to be slidably positioned along an outer surface of surgical stapling assembly 2450. Actuation sled 2462 is disposed within cartridge assembly 2450 at a position distal of the working end 2484.

In various aspects, a flexible arm 2470 extends from the working end 2484 into a channel 2471 defined in a side wall of a cartridge body 2459 of the staple cartridge 2420. In illustrated example, the flexible arm 2470 defines a leaf-spring arm member that passes through the channel 2471 and latches onto a distal portion of the sled 2470. The flexible arm 2470 is configured to retract the sled 2462 to a home, or starting, position.

In the channel 2471, the flexible arm 2470 is flattened such that it is naturally pressing into the side of the sled 2462. In at least one example, a distal end of the flexible arm 2470 passes the distal end of the sled 2462. A tab 2472 extends out from the flexible arm 2470, in the relaxed position, to latch onto the front edge of the sled 2462. The motion of the working end 2484 that occurs prior to driving the knife of the staple cartridge assembly 2450 during a full firing stroke will allow for the flexible arm 2470 to pull the sled 2462 back into the home, or starting, position as long as the sled 2462 is within a threshold defined by the length of the side channel 2471.

FIGS. 47-51 illustrate various aspects of a sled resetting mechanism 2500 for retracting a sled of a staple cartridge (e.g., staple cartridge 2520) to a home position (H) prior to firing a surgical instrument to deploy staples of the staple cartridge 2520. As discussed elsewhere herein, a sled of an unfired staple cartridge can be inadvertently moved if the staple cartridge is bumped or shaken, which may cause the staple cartridge to be mistakenly deemed as fired and/or may cause a firing lockout assembly to be activated. The sled resetting mechanism 2500 is configured to return a sled that was inadvertently moved to its home position (H) within the staple cartridge as long as the sled has not moved beyond a predetermined distance (d1) from the home position (H).

Figure 47:
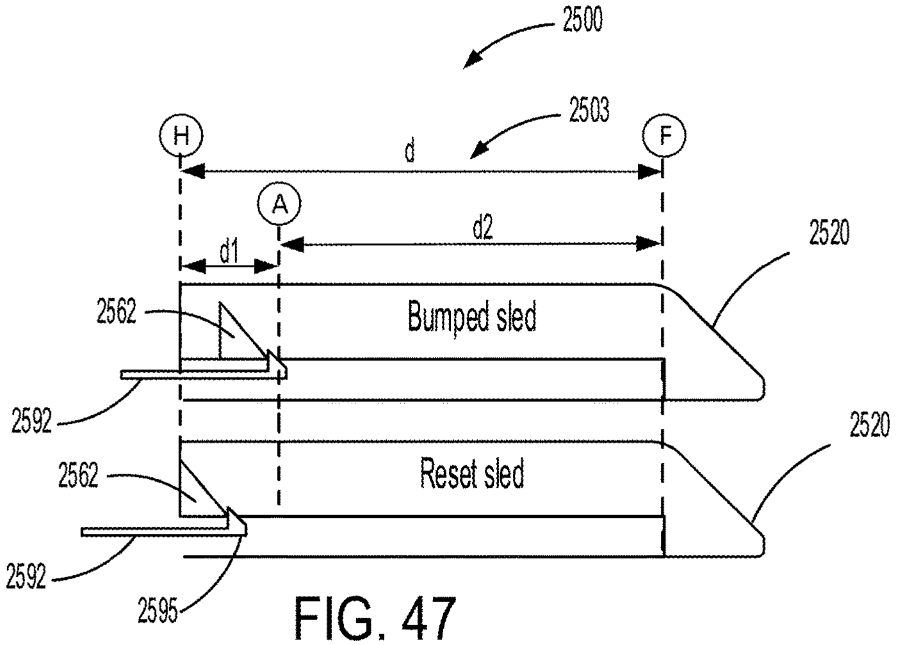
FIG. 47 illustrates a simplified partial cross-sectional view of a staple cartridge assembly with a sled at a home position and at a position different than the home position, in accordance with at least one aspect of the present disclosure.

FIG. 47 illustrates a sled 2562 of the staple cartridge 2520 at a position distal to the home position (H) but proximal to the distal position (A) defined by the predetermined distance (d1). Prior to firing, a sled resetting member 2592 retracts the sled 2562 to the home position (H). The sled resetting member 2592 includes catcher 2595, which can be in the form of a hook or a bent portion, configured to engage a distal portion of the sled 2562 to return the sled 2562 to the home position (H).

Figure 51:
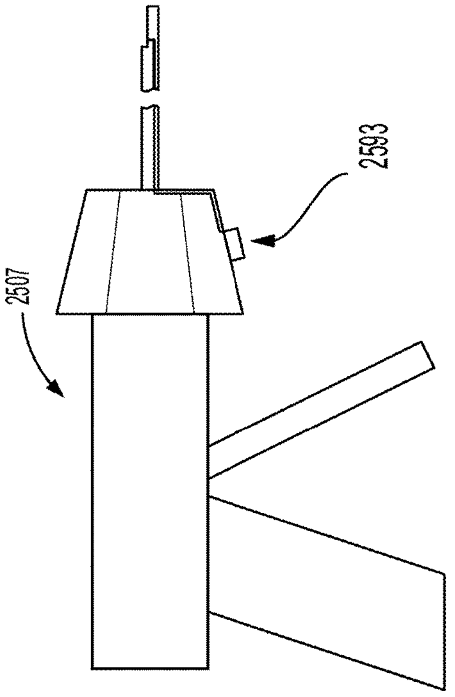
FIG. 51 illustrates a handle of a surgical instrument including a firing trigger and a sled resetting actuator, in accordance with at least one aspect of the present disclosure.

In various aspects, a portion of the sled resetting member 2592 extends, and is slidably movable below the sled 2562 such as, for example, within a channel defined in a cartridge pan of the staple cartridge 2520. In at least one example, as illustrated in FIG. 51, the sled resetting member 2592 is manually operable by an actuation member 2593 defined in a handle 2507. A user can pull the actuation member 2593 proximally to return the sled 2562 to the home position (H) prior to activation of the firing mechanism.

Figure 50:
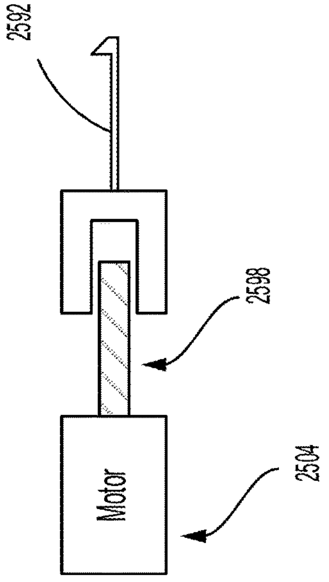
FIG. 50 illustrates a motor assembly operably coupled to a sled resetting member, in accordance with at least one aspect of the present disclosure.
Figure 49:
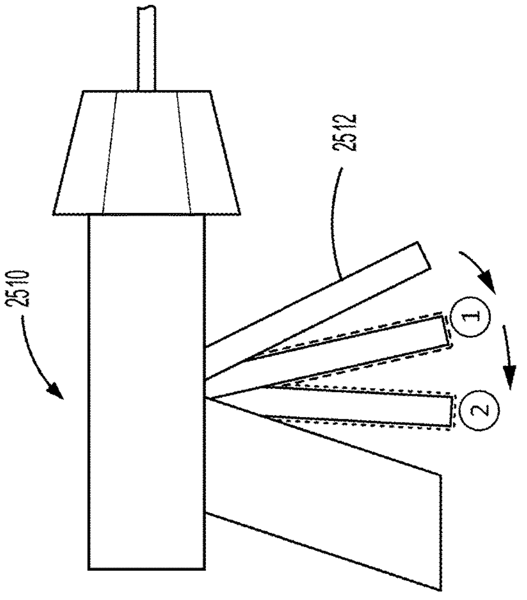
FIG. 49 illustrates a handle of a surgical instrument including a firing trigger movable to a first position and a second position, in accordance with at least one aspect of the present disclosure.
Figure 52:
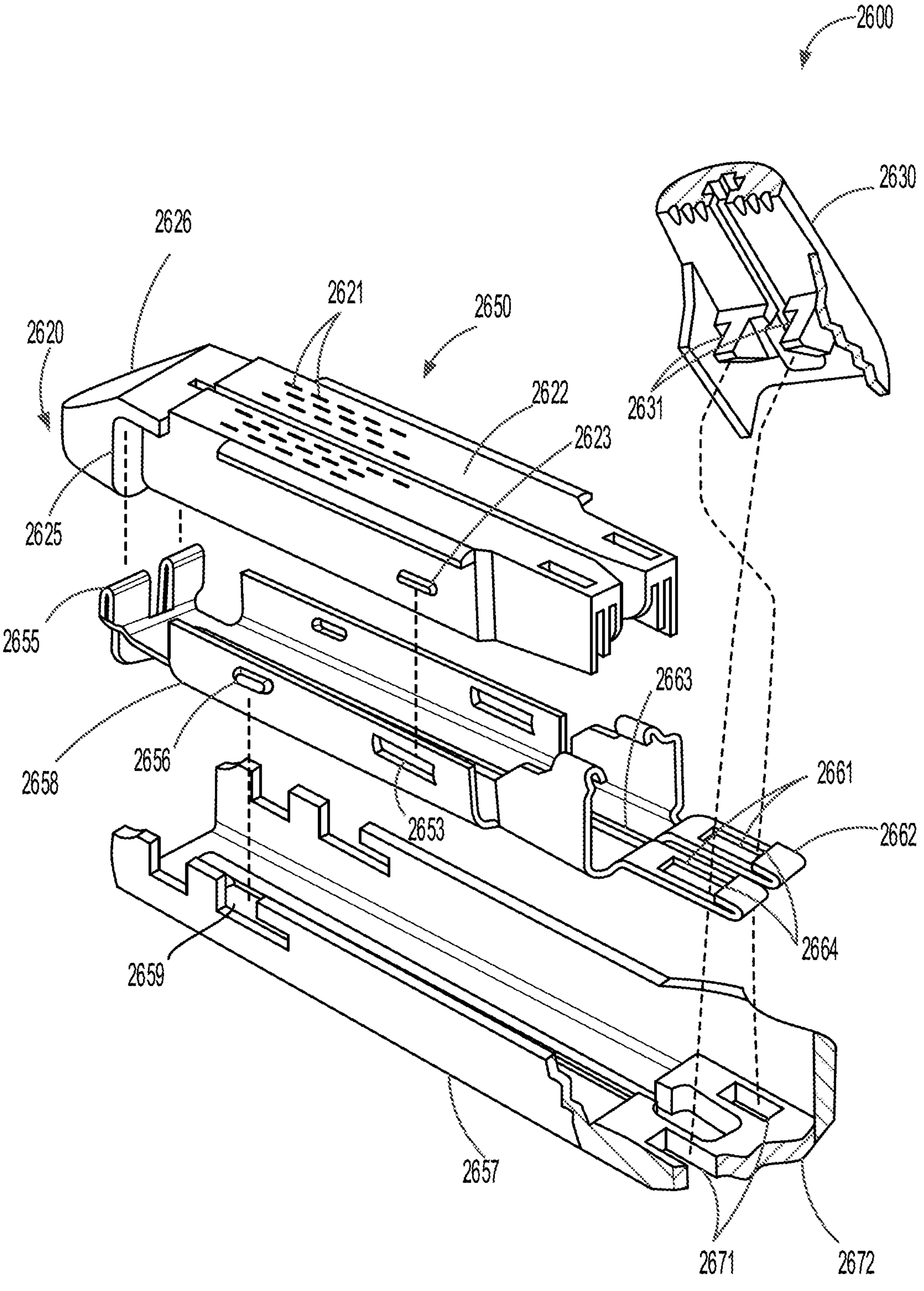
FIG. 52 illustrates a partial exploded view of a loading unit including an anvil and a surgical stapling assembly including a staple cartridge for assembly with an elongated channel, in accordance with at least one aspect of the present disclosure.

In another example, as illustrated in FIGS. 49 and 50, the sled resetting member 2592 is powered by a motor assembly 2504 similar in many respects to the motor drive assembly 1904 of the surgical instrument 1901. In the illustrated example, the motor drive assembly 2504 includes a linear threaded coupler 2598 operably connected to the sled resetting member 2592. In the illustrated example, the motor assembly 2504 is housed in a handle 2510 that includes a trigger member 2512. A movement of the trigger member 2512 to a first position causes the motor assembly 2504 to retract the sled resetting member 2592 thereby returning the sled 2562 to the home position (H). A second movement of the trigger member 2512 from the first position to a second position activates the firing stroke, or firing motion, to deploy staples from the staple cartridge 2520.

The sled resetting mechanism 2500 can be implemented in combination with other suitable embodiments of the present disclosure such as, for example, a sled detection circuit. Further, the sled resetting mechanism 2500 can be implemented in combination with suitable components of the surgical stapling instrument 1901. For example, the control circuit 1930 may determine that the sled is at a position different than the home position based on the sled detection circuit. In response, the control circuit 1930 may cause the motor assembly 2504 to return the sled to the home position, which can be verified by the sled detection circuit, for example.

Figure 48:
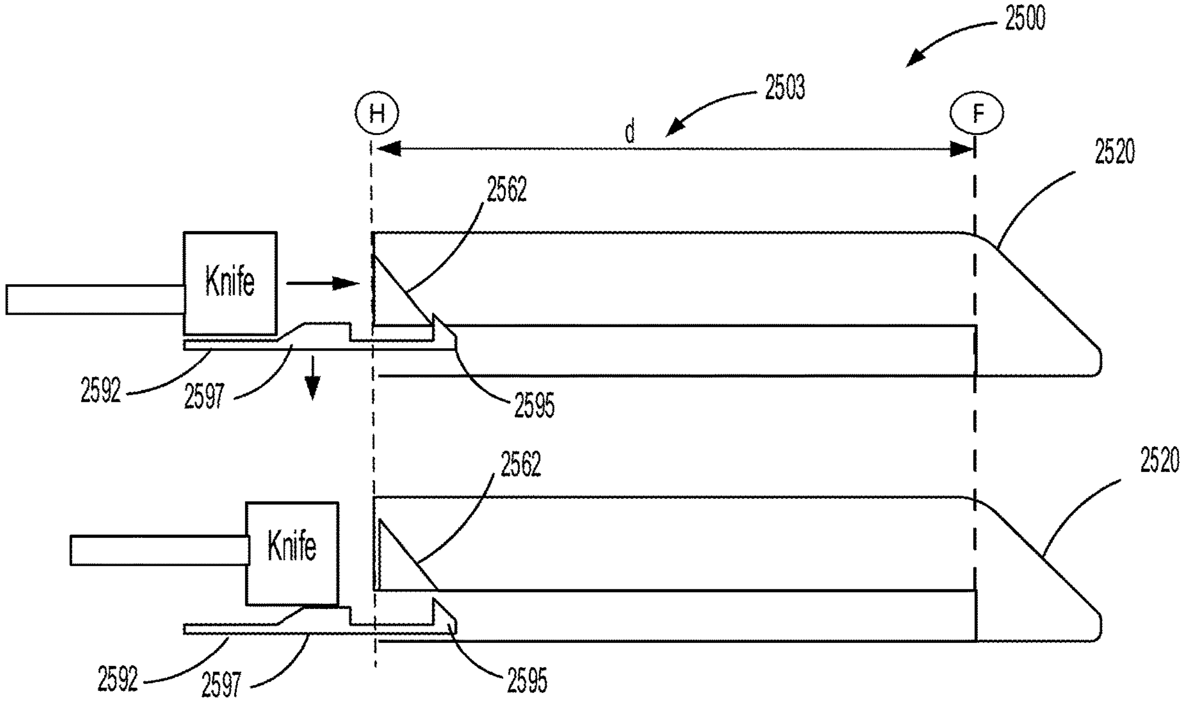
FIG. 48 illustrates a simplified partial cross-sectional view of the staple cartridge assembly of FIG. 47 with a working end of a drive member being advanced to engage a raised portion of a sled resetting member, in accordance with at least one aspect of the present disclosure.

In use, the sled 2562 is returned to the home position (H) by the sled resetting member 2592, as illustrated in FIG. 47. Then, a drive member (e.g. drive member 1182), is configured to advance a working end thereof (e.g. working end 1184) to engage the sled 2562 to advance the sled 2562 to deploy staples from the staple cartridge 2520. In various aspects, as illustrated in FIG. 48, the sled resetting member 2592 includes a raised portion 2597, which can be in the form of a ramp, positioned proximal to the catcher 2595. During advancement of the drive member 2582, the working end 2584 may engage the raised portion 2597 prior to engaging the sled 2562, which causes the catcher 2595 to move out of a firing path 2503 of the sled 2562. In at least one example, the working end 2584 causes the catcher 2595 to drop into the channel defined in the cartridge pan of the staple cartridge 2520, which permits further advancement of the sled 3562.

In various aspects, setting acceptable and/or unacceptable sled positions, or sled distances from the home position, which is also referred to herein as a functional window, along a firing path can depend, at least in part, on staple cartridge size. Accordingly, to accurately set such positions, or distances, surgical cartridge may include identification codes which can be communicated to a control circuit (e.g., control circuit 1930) after attachment of the staple cartridge to the surgical instrument (e.g., surgical instrument 1901). The communication may occur through a wired connection with the staple cartridge, or wirelessly.

In various aspects, the control circuit may select a suitable function window given the expected location of the sled contact based on the communicated identification code of the cartridge. In various aspects, the firing system may further adjust one or more parameters of a predetermined firing program such as, for example, the force/velocity/stroke of both the sensing region based on the identification of the cartridge and/or the actuation region based on the timing/location of the sensed sled relative to its expected location.

Figure 53:
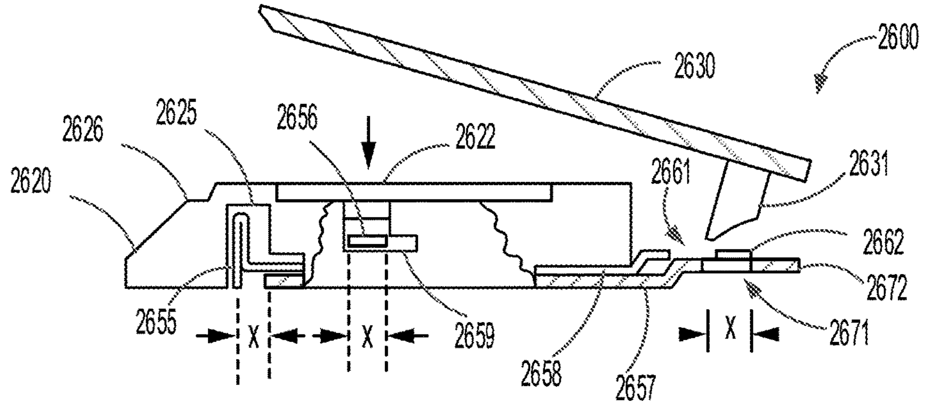
FIG. 53 illustrates a partial cross-sectional view of the loading unit of FIG. 52, showing a staple cartridge assembled with an elongated channel in an unlocked configuration and an anvil in an open configuration with the elongated channel
Figure 54:
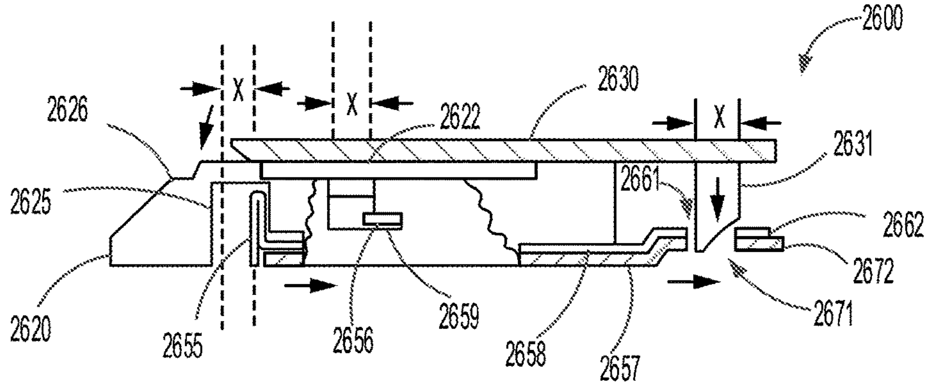
FIG. 54 illustrates a partial cross-sectional view of the loading unit of FIGS. 52 and 53 showing the staple cartridge and the elongated channel in a locked configuration and the anvil in a closed configuration with the elongated channel.

Referring now to FIGS. 52-56, a loading unit 2600 is similar in many respects to other loading units described elsewhere herein such as, for example, the loading units 1100, 1200. For example, the loading unit 2600 includes a staple cartridge assembly 2650 and an anvil assembly 2630. At least one of the anvil assembly 2630 and the staple cartridge assembly 2650 is movable relative to the other from an open configuration, as illustrated in FIG. 53, to a closed configuration, as illustrated in FIG. 54, to grasp tissue. Staples are deployed into the tissue from staple cavities 2621 defined in a cartridge body 2622 of a staple cartridge 2620 of the staple cartridge assembly 2650. The anvil assembly 2630 includes pockets configured to deform the staples.

Further to the above, the staple cartridge 2620 includes a cartridge pan 2658 configured to prevent the staples from falling out of the staple cavities 2621. The cartridge body 2622 is attachable to the cartridge pan 2658 by way projections 2623 receivable in a corresponding cutouts 2653 defined in side walls of the cartridge pan 2658. In various examples, the cutouts 26523 are sized and shaped to receive the corresponding cutouts 2653 to secure the cartridge body 2622 to the cartridge pan 2657.

In use, the staple cartridge 2620 is inserted into the elongated channel 2657 for assembly therewith. In various aspects, the staple cartridge 2620 and the elongated channel 2657 comprise corresponding locking features. In the illustrated example, pan projections 2656, which are defined in side walls of the cartridge pan 2658, are received in L-shaped slots 2659 when the staple cartridge 2620 is inserted into the elongated channel 2657.

The corresponding locking features of the staple cartridge 2620 and the elongated channel 2657 permit a proximal translating motion of the cartridge pan 2658 relative to the elongated channel 2658 to lock the staple cartridge 2620 to the elongated channel 2657, and a distal translating motion of the cartridge pan 2658 relative to the elongated channel 2658 to unlock the staple cartridge 2620 to the elongated channel 2657. In the illustrated example, the L-shaped slots 2659 are sized and shaped to permit the corresponding projections 2656 to translate proximally a distance "X" in the long arm of L-shaped slots 2659 thereby locking the staple cartridge 2620 to the elongated channel 2657, and to translate distally the distance "X" in the long arm of L-shaped slots 2659 thereby unlocking the staple cartridge 2620 from the elongated channel 2657.

In other examples, the projections can be defined in an elongated channel and corresponding L-shaped slots can be defined in a cartridge pan of a staple cartridge. Furthermore, other suitable mating and locking mechanisms can be implemented to produce locked and unlocked configurations of a staple cartridge and an elongated channel. For example, slots with other suitable shapes can replace the L-shaped slot.

Further to the above, the locking mechanism of the staple cartridge 2620 to the elongated channel 2657 is implemented automatically during the transition to a closed configuration of the anvil assembly 2630 and the staple cartridge assembly 2650, as illustrated in FIGS. 53 and 54. In certain examples, the anvil assembly 2630 is configured to cause the cartridge pan 2658 to translate proximally relative to the elongated channel 2657 into the locked configuration. In the illustrated example, the anvil assembly 2630 includes camming members 2631 configured to retract the cartridge pan 2658 to the locked configuration as the loading unit 2600 is transitioned into the closed configuration (FIG. 54).

In the illustrated example, the cartridge pan 2658 includes a proximal tongue portion 2662 bisected by a pan slot 2663. The proximal tongue portion 2662 includes cutouts 2661 on opposite sides of the pan slot 2663. The camming members 2631 are configured to engage proximal edges 2664 of the cutouts 2661 during a closure motion of the loading unit 2600. As the loading unit 2600 is transitioned to the closed configuration, the camming members 2631 exert a camming force against the proximal edges 2664 of the cutouts 2661 thereby causing the cartridge pan 2658 to translate proximally into the locked configuration. Accordingly, the closure motion of the loading unit 2600 automatically transitions the staple cartridge 2620 into a locked configuration with the elongated channel 2657.

In the illustrated example, to ensure a proper engagement with the camming member 2631 the proximal end of the proximal tongue portion 2662 is bent toward the cutouts 2661 thereby forming the edges 2664. The camming members 2631 are configured to engage the edges 2664 as the camming members 2631 pivot with the anvil assembly 2630 towards the staple cartridge 2620. In other example, an anvil assembly including the camming members 2631 can be fixed, and an elongated channel is pivoted towards the anvil assembly to yield a closed configurations. In such examples, the edges 2664 are moved towards the camming members 2631. When the edges 2664 engage the camming members 2641, the camming force causes the cartridge pan 2658 to translate proximally to the locked configuration.

Further to the above, the elongated channel 2657 includes proximal slots or cutouts 2671 defined in a proximal portion of a base 2672 of the elongated channel 2657. The cutouts 2671 are laterally or transversely aligned, or at least partially aligned, with the cutouts 2661. In the unlocked configuration, as illustrated in FIG. 53, the cutouts 2661 are distal to the cutouts 2671. However, in the locked configuration, as illustrated in FIG. 54, the cutouts 2661 are longitudinally aligned with cutouts 2671, or at least are closer to a longitudinal alignment with the cutouts 2671 than in the unlocked configuration. As the camming members 1631 are pivotally moved in the cutouts 2661, 2671, the camming members 2631 are configured to cause the cutouts 2661 to move proximally a distance "X" to be aligned, or at least partially aligned, with the cutouts 2671, as illustrated in FIG. 54.

Figure 55:
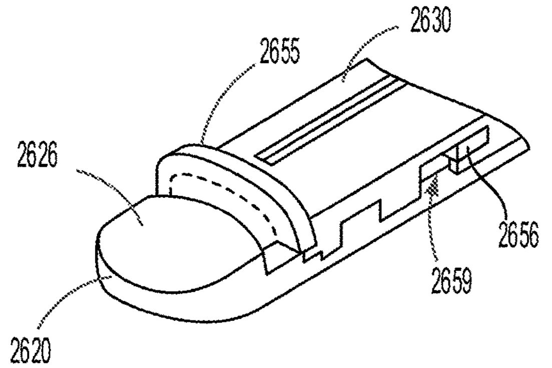
FIG. 55 illustrates a partial perspective view of the surgical stapling assembly of FIG. 52 in the locked configuration.
Figure 56:
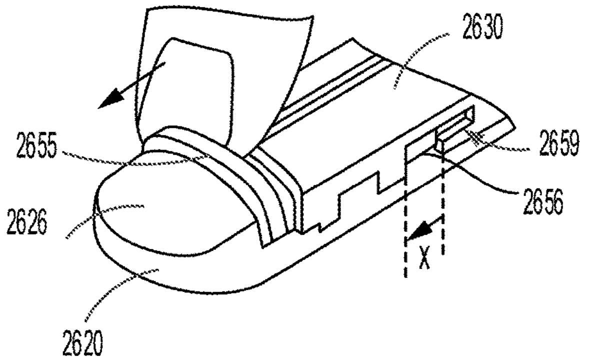
FIG. 56 illustrates a partial perspective view of the surgical stapling assembly of FIG. 52 being transitioned into from the locked configuration to the unlocked configuration.

After completion of the firing stroke, a spent staple cartridge 2620 is removed from the elongated channel 2657 by translating the cartridge pan 2658 to the unlocked configuration. In the illustrated example, the cartridge pan 2658 includes a release feature 2655, which can be in the form of a finger tab. The release feature 2655 is slidably movable distally in a corresponding slot 2620, defined in nose portion 2626 of the cartridge body 2622, to transition the staple cartridge 2620 to the unlocked configuration, as illustrated in FIGS. 55 and 56.

Referring now to FIGS. 57-61, a staple surgical assembly 2750 includes an elongated channel 2757, a staple cartridge 2758, and a retainer 2730. The staple surgical assembly 2750 is similar in many respects to other staple surgical assemblies described elsewhere herein. For example, the staple surgical assembly 2750 can be incorporated into any suitable surgical instrument described elsewhere herein.

Figure 57:
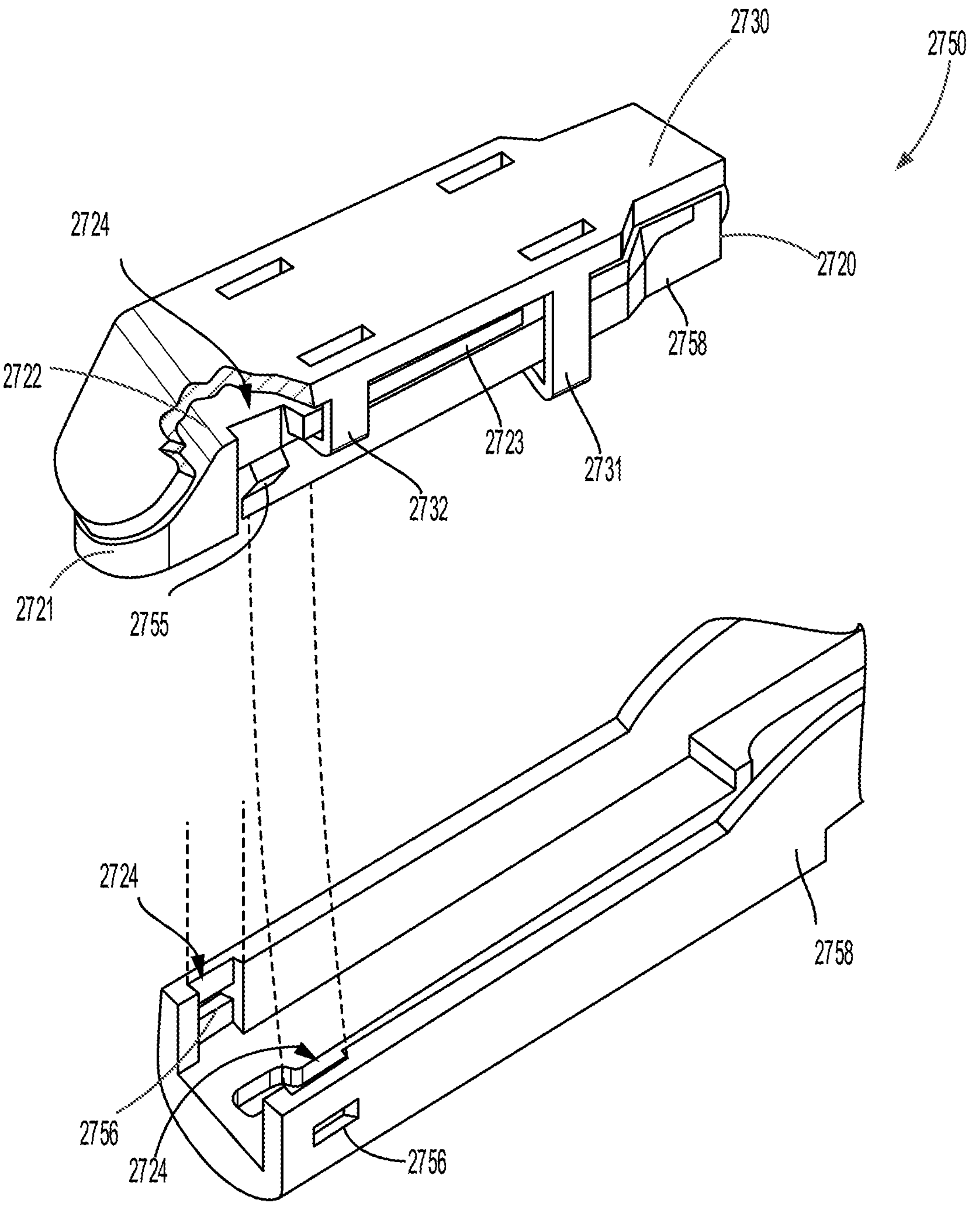
FIG. 57 illustrates a partial perspective view of a surgical stapling assembly including a retainer, a staple cartridge, and an elongated channel, in accordance with at least one aspect of the present disclosure.
Figure 58:
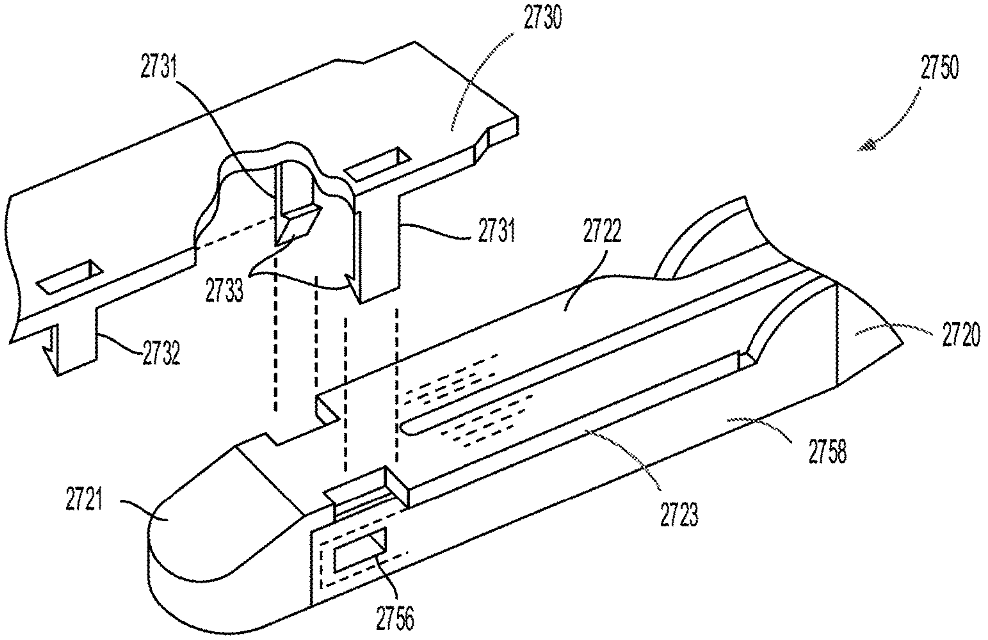
FIGS. 58-61 illustrate a method of utilizing the retainer of FIG. 57 to release the staple cartridge from the elongated channel.

In the example illustrated in FIG. 57, the staple cartridge assembly 2750 is in a first configuration where the retainer 2730 is assembled with the staple cartridge 2720 to prevent staples from inadvertently falling out of staple cavities of the staple cartridge 2720. In the first configuration, long tabs 2731 of the retainer 2730 define retainer arms that engage a cartridge pan 2758 of the staple cartridge 2720, and short tabs 2732 define retainer arms that engage a cartridge body 2721 of the staple cartridge 2720. The tabs 2731, 2732 cooperate to maintain the retainer 2730 pressed against a deck 2722 of the cartridge body 2721 in the first configuration to maintain staples in their staple cavities. In the illustrated example, the cartridge body 2721 includes ledges 2723 extending laterally from the deck 2722. The ledges 2723 are engaged by the short tabs 2732 in the first configuration.

Figure 59:
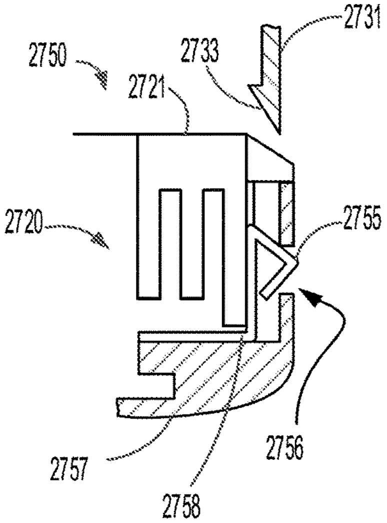
Figure 60:
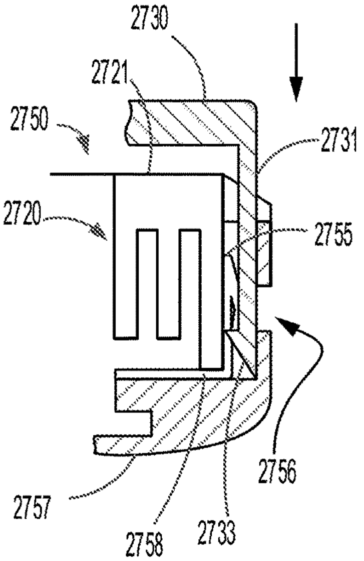
Figure 61:
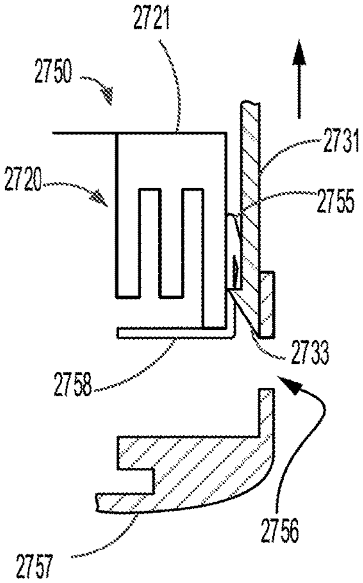

After completion of the firing stroke, a spent staple cartridge 2720 is removed from the elongated channel 2757, as illustrated in FIGS. 58-61, by the retainer 2730. In a second configuration, the long tabs 2731 of the retainer 2730 are inserted through tracks or notches 2724 defined in the cartridge body 2721, as best illustrated in FIG. 60. The tabs 2731 release collapsible members 2755 of the cartridge pan 2558 from corresponding apertures 2756 of the elongated channel 2757 to permit removal of the staple cartridge 2720 from the elongated channel 2757 by the retainer 2730, as illustrated in FIG. 61.

In the illustrated example, the collapsible members 2755 are in the form of leaf springs that can be stamped or formed in the sidewalls of the cartridge pan 2758. The tabs 2731 include hook features 2733 configured to collapse the collapsible members 2755 to release the collapsible members 2755 from the apertures 2756 as the tabs 2731 are advanced in the tracks 2724, and further configured to form a movable locking-engagement with the collapsed collapsible members 2755 in the second configuration, as illustrated in FIG. 60.

The retainer 2730 is then pulled away from the elongated channel 2757 to remove the staple cartridge 2720 from the elongated channel 2757, as illustrated in FIG. 61. As the retainer 2730 is pulled away, the hook features 2733 lift the collapsible members 2755 out of the tracks 2724 thereby releasing the staple cartridge 2720 from the elongated channel 2757.

In the illustrated example, the apertures 2756 are defined in sidewalls of the elongated channel 2757 in the form of cutouts. In other examples, the apertures 2756 can be replaced with recesses or slots defined on inner surfaces of the inner walls of the elongated channel 2757. The recesses or slots are shaped and sized to receive the collapsible members 2755 in their natural state in a similar manner to that illustrated in FIG. 59 with respect to the apertures 2756.

Referring still to FIGS. 59-61, a method of using the retainer 2730 to remove a spent staple cartridge 2720 from the elongated channel 2757 is depicted. The method includes decoupling the retainer 2730 from the staple cartridge assembly 2750. The method further includes inserting the tabs 2731 into the track 2724, releasing the collapsible members 2755 from the apertures 2756 by the hook features 2733 of the tabs 2731, and forming a movable locking-engagement between the collapsed collapsible members 2755 and the hook features 2733 in the tracks 2724. The method further includes pulling the retainer 2730 away from the elongated channel 2757 to remove the spent staple cartridge 2720 from the elongated channel 2757.

Figure 62:
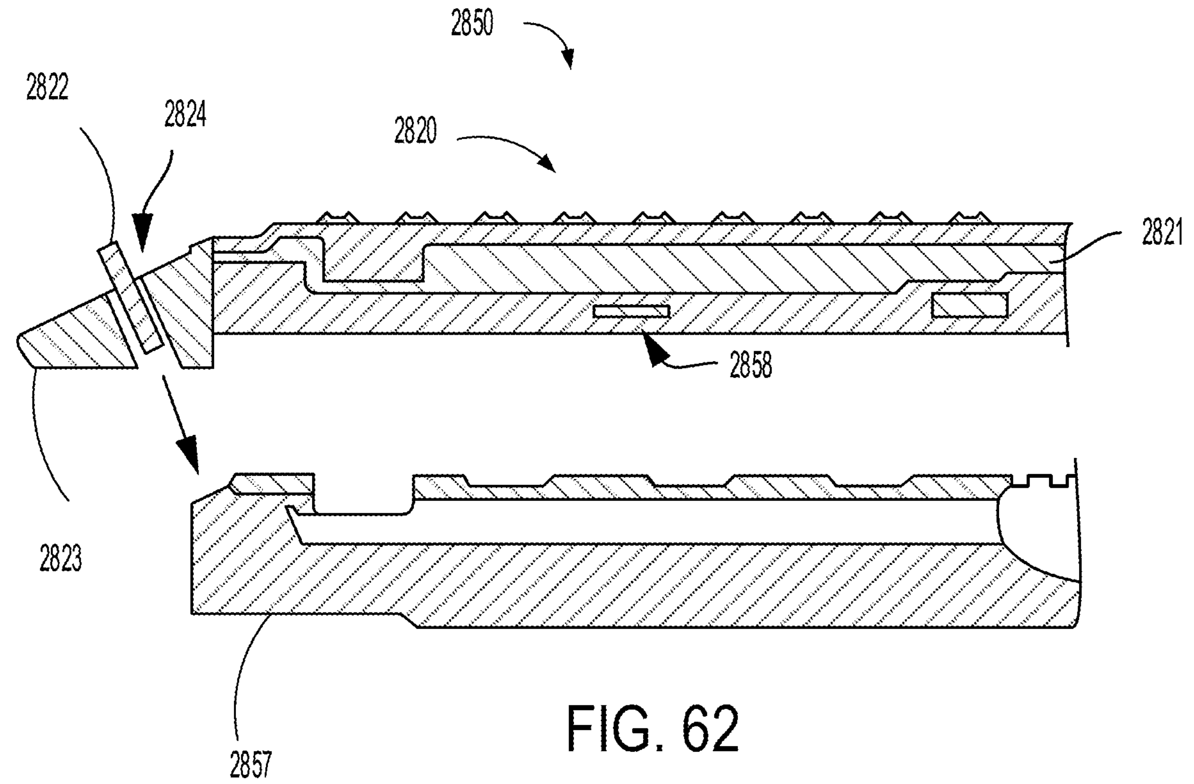
FIG. 62 illustrates a partial cross-sectional view of a staple cartridge assembly, in accordance with at least one aspect of the present disclosure.

Referring now to FIG. 62, a staple surgical assembly 2850 includes a quick-release feature that facilitates removal of a staple cartridge 2820 from an elongated channel 2857 of a surgical instrument. The staple surgical assembly 2850 is similar in many respects to other staple surgical assemblies described elsewhere herein. For example, the staple surgical assembly 2850 can be incorporated into any suitable surgical instrument described elsewhere herein.

The staple cartridge 2820 includes a cartridge body 2821 and a cartridge pan 2858. Furthermore, the staple cartridge 2858 includes a cartridge release member 2822 movably disposed in a nose portion 2823 of the cartridge body 2821. In the illustrated example, the cartridge release member 2822 is linearly movable through a passage 2824 defined in the nose portion 2823 from an unactuated configuration to an actuated configuration. In the unactuated configuration, as illustrated in FIG. 62, the cartridge release member 2822 protrudes from the nose portion 2823 through one end of the passage 2824. When actuated, by applying an external pressure thereto for example, the cartridge release member 2822 moves in the passage 2824, and protrudes through the other end of the passage 2824. The cartridge release member 2822 then presses against the elongated channel 2857 to release the staple cartridge 2820 from the elongated channel 2857. In the illustrated example, the passage 2824 defines a direction of motion for the cartridge release member 2822 that is at an acute angle with the elongated channel 2857.

Figure 63:
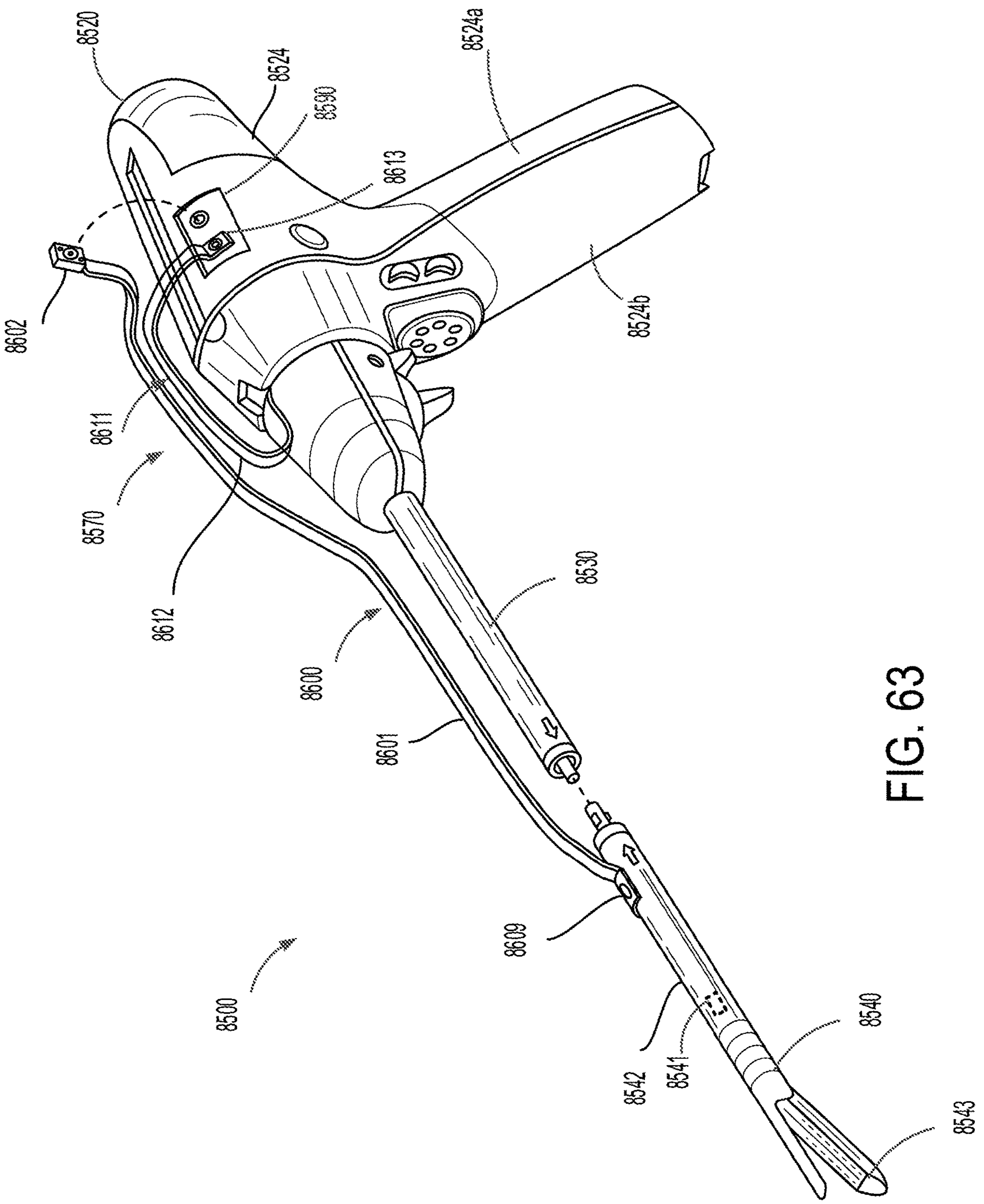
FIG. 63 illustrates a perspective view of a surgical instrument system, in accordance with at least one aspect of the present disclosure.
Figure 64:
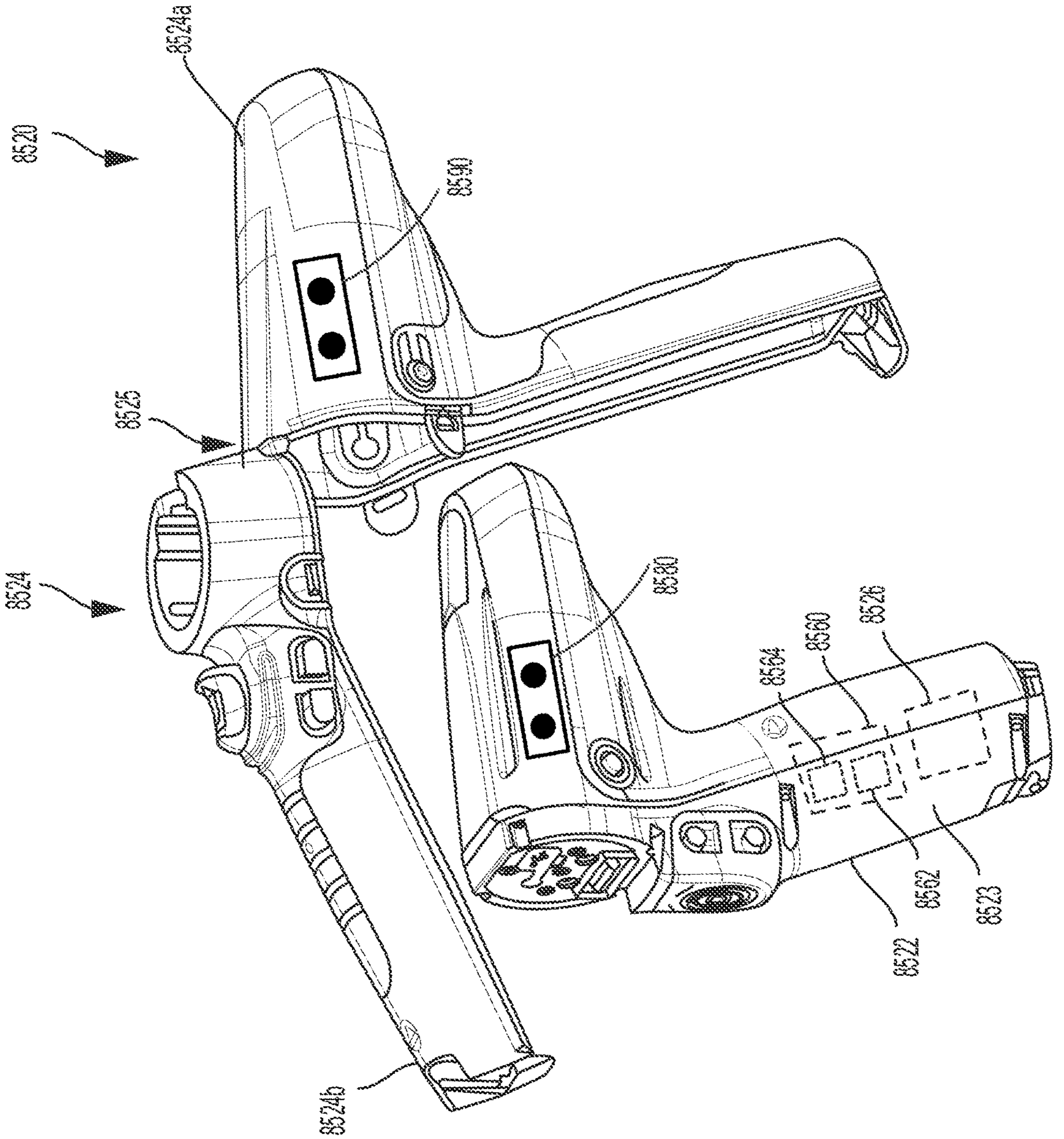
FIG. 64 illustrates a perspective view of handle assembly of the surgical instrument system of FIG. 63 in a disassembled configuration, the handle assembly including an outer disposable housing and an inner core.
Figure 65:
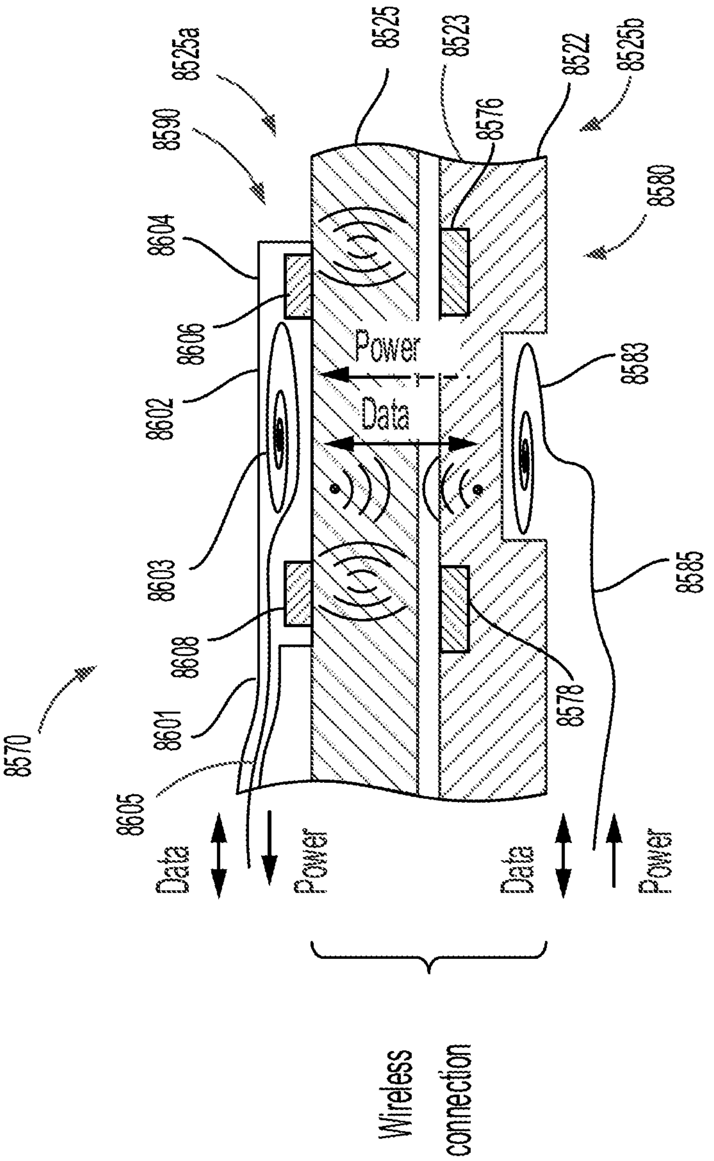
FIG. 65 illustrates a cross-sectional view of an electrical interface for transmitting at least one of power and data between an end effector of the surgical instrument system of FIG. 63 and the inner core of FIG. 64.

With reference to FIGS. 63-65, a surgical instrument system is provided, such as, for example, an electromechanical surgical instrument system 8500. System 8500 includes a handle assembly 8520, a plurality of types of adapter or shaft assemblies such as, for example, shaft assembly 8530, and a plurality of types of loading units or end effectors such as, for example, end effector 8540. Handle assembly 8520 is configured for selective attachment thereto with any one of a number of shaft assemblies, for example, shaft assembly 8530 and, in turn, each unique shaft assembly 8530 is configured for selective connection with any number of surgical loading units or end effectors, such as, for example, end effector 8540. End effector 8540 and shaft assembly 8530 are configured for actuation and manipulation by handle assembly 8520. Upon connecting one shaft assembly 8530, for example, to handle assembly 8520 and one type of end effector such as, for example, end effector 8540 to the selected shaft assembly 8530 a powered, hand-held, electromechanical surgical instrument is formed.

Various suitable loading units or end effectors for use with the surgical instrument system 8500 are discussed in U.S. Pat. No. 5,865,361, entitled SURGICAL STAPLING APPARATUS, and issued Feb. 2, 1999, the disclosure of which is herein incorporated by reference in its entirety. Various handle assemblies for use with the surgical instrument system 8500 are discussed in U.S. Pat. No. 10,426,468, entitled HANDHELD ELECTROMECHANICAL SURGICAL SYSTEM, and issued on Oct. 1, 2019, the disclosure of which is herein incorporated by reference in its entirety.

The handle assembly 8520 includes an inner core 8522 and a disposable outer housing 8524 configured to selectively receive and encase inner core 8522 to establish a sterile barrier 8525 (FIG. 65) around the inner core 8522. Inner core 8522 is motor operable and configured to drive an operation of a plurality of types of end effectors. Inner core 8522 has a plurality of sets of operating parameters (e.g., speed of operation of motors of inner core 8522, an amount of power to be delivered by motors of inner core 8522 to a shaft assembly, selection of motors of inner core 8522 to be actuated, functions of an end effector to be performed by inner core 8522, or the like). Each set of operating parameters of inner core 8522 is designed to drive the actuation of a specific set of functions unique to respective types of end effectors when an end effector is coupled to inner core 8522. For example, inner core 8522 may vary its power output, deactivate or activate certain buttons thereof, and/or actuate different motors thereof depending on the type of end effector that is coupled to inner core 8522.

The inner core 8522 defines an inner housing cavity therein in which a power-pack 8526 is situated. Power-pack 8526 is configured to control the various operations of inner core 8522. Power-pack 8526 includes a plurality of motors operatively engaged thereto. The rotation of motors function to drive shafts and/or gear components of shaft assembly 8530, for example, in order to drive the various operations of end effectors attached thereto, for example, end effector 8540.

When end effector 8540 is coupled to inner core 8522, motors of power-pack 8526 are configured to drive shafts and/or gear components of the shaft assembly 8530 in order to selectively effect a firing motion, a closure motion, and/or an articulation motion at the end effector 8540, for example.

Further to the above, the disposable outer housing 8524 includes two housing portions **8524*a*, 8524*b* releasably attached to one another to permit assembly with the inner core 8522. In the illustrated example, the housing portion 8524*b* is movably coupled to the housing portion 8524*a* by a hinge 8525 located along an upper edge of housing portion 8524*b*. Consequently, the housing portions 8524*a*, 8524*b* are pivotable relative to one another between a closed, fully coupled configuration, as shown in FIG. 63, and an open, partially detached configuration, as shown in FIG. 64. When joined, the housing portions 8524*a*, 8524*b* define a cavity therein in which inner core 8522** may be selectively situated.

In the illustrated example, the inner core 8522 includes a control circuit 8560. In other examples, the control circuit 8560 is disposed on an inner wall of the disposable outer housing 8524, and is releasably couplable to the inner core 8522 such that an electrical connection is established between the inner core 8522 and the control circuit 8560 when the inner core 8522 is assembled with the outer housing 8524. The control circuit 8560 includes a processor 8562 and a storage medium such as, for example, a memory unit 8564. The control circuit 8560 can be powered by the power-pack 8526, for example. The memory unit 8564 may store program instructions, which when executed by the processor 8562, may cause the processor 8562 to adjust/perform various control functions of the surgical instrument system 8500.

In the illustrated example, the control circuit 8560 is releasably couplable to the inner core 8522. When the inner core 8522 is assembled with the outer housing 8524, an electrical connection is established between the inner core 8522 and the control circuit 8560. In other examples, however, the control circuit 8560 is incorporated into the inner core 8522.

In various examples, the memory unit 8564 may be non-volatile memories, such as, for example, electrically erasable programmable read-only memories. The memory unit 8564 may have stored therein discrete operating parameters of inner core 8522 that correspond to the operation of one type of end effector, for example, end effectors such as, for example end effector 8540 and/or one type of adapter assembly such as, for example, shaft assembly 8530. The operating parameter(s) stored in memory 8564 can be at least one of: a speed of operation of motors of inner core 8522; an amount of power to be delivered by motors of inner core 8522 during operation thereof; which motors of inner core 8522 are to be actuated upon operating inner core 8522; types of functions of end effectors to be performed by inner core 8522; or the like.

Referring still to FIGS. 63-65, the surgical instrument system 8500 includes an electrical interface assembly 8570 configured to transmit at least one of data signal and power between the inner core 8522 and the end effector 8540. In the illustrated example, the electrical interface assembly 8570 includes a first interface portion 8580 on a first side 8525*a* of the sterile barrier 8525 and a second interface portion 8590 on a second side 8525*b* of the sterile barrier 8525 opposite the first side. In various aspects, the first interface portion 8580 is configured to form a wireless electrical interface with the second interface portion 8590. The wireless electrical interface facilitates a wireless transmission of at least one of data signal and power between the inner core 8522 and the second interface portion 8590.

Furthermore, the electrical interface assembly 8570 includes an exteriorly-mounted wiring connection 8600. In the illustrated example, the exteriorly-mounted wiring connection 8600 is separately-attachable to the second interface portion 8690 to facilitate a wired transmission of the at least one of data signal and power between the second interface portion 8590 and the end effector 8540.

In various aspects, the first interface portion 8580 and the second interface portion 8590 are configured to cooperatively form a wireless segment of an electrical pathway between the inner core 8522 and the end effector 8540. In addition, the exteriorly-mounted wiring connection 8600 forms a wired segment of the electrical pathway. At least one of data signal and power is transmitted between the inner core 8522 and the end effector 8540 through the electrical pathway.

Referring still to FIGS. 63-65, the exteriorly-mounted wiring connection 8600 includes a wire flex circuit 8601 terminating at an attachment member 8602 releasably couplable to the second interface portion 8590. The wire flex circuit 8601 is of sufficient length to permit the attachment member 8602 to exteriorly reach the second interface portion 8590.

The attachment member 8602 is magnetically couplable to the second interface portion 8590. For example, the attachment member 8602 includes magnetic elements 8606, 8608 disposed in the housing 8604. The first interface portion 8580 includes ferrous elements 8576, 8578 for magnetic attachment and proper alignment of the attachment member 8602 onto the outer housing 8524, as illustrated in FIG. 65.

The ferrous elements 8576, 8578 are disposed on an outer housing 8523 of the inner core 8522 such that the ferrous elements 8576, 8578 and the magnetic elements 8606, 8608 are aligned when the inner core 8522 is properly positioned within the disposable outer housing 8524 and the attachment member 8602 is properly positioned against the second interface portion 8590.

Alternatively, in certain examples, magnetic elements can be disposed on the outer housing 8523 of the inner core 8522, and the ferrous elements can be disposed on the housing 8604 of the attachment member 8602. Alternatively, in certain examples, corresponding magnetic elements can be disposed on both of the housings 8604, 8523.

Further to the above, another exteriorly-mounted wiring connection 8611 connects the shaft assembly 8530 to the second interface portion 8590. The exteriorly-mounted wiring connection 8611 is similar in many respects to the exteriorly-mounted wiring connection 8600. For example, the exteriorly-mounted wiring connection 8611 also includes a wire flex circuit 8612 that terminates in an attachment member 8613 that is similar to the attachment member 8602 of the exteriorly-mounted wiring connection 8600. The attachment member 8613 is also magnetically-couplable to the handle assembly 8520 to exteriorly transmit at least one of data and power between the shaft assembly 8530 and the inner core 8522.

Further to the above, the electrical interface assembly 8570 utilizes inductive elements 8603, 8583 positionable on opposite sides of the sterile barrier 8525. In the illustrated example, the inductive elements 8603, 8583 are in the form of wound wire coils that are components of inductive circuits 8605, 8585, respectively. The wire coils of the inductive elements 8603, 8583 comprise a copper, or copper alloy, wire; however, the wire coils may comprise suitable conductive material, such as aluminum, for example. The wire coils can be wound around a central axis any suitable number of times.

When a proper magnetic attachment is established by the elements 8608, 8606, 8576, 8578, as illustrated in FIG. 65, the wire coils of the inductive elements 8603, 8583 are properly aligned about a central axis extending therethrough. The proper alignment of the wire coils of the inductive elements 8603, 8583 improves the wireless transmission of the at least one of data and power therethrough.

In various examples, the inductive circuit 8585 is electrically coupled to the power-pack 8526 and the control circuit 8560. In the illustrated example, the inductive circuit 8605 is electrically couplable to a transponder 8541 in the end effector 8540. To transmit signals to the transponder 8541 and receive signals therefrom, the inductive element 8603 is inductively coupled to the inductive element 8583. The transponder 8541 may use a portion of the power of the inductive signal received from the inductive element 8603 to passively power the transponder 8541. Once sufficiently powered by the inductive signals, the transponder 8541 may receive and transmit data to the control circuit 8560 in the handle assembly via the inductive coupling between the inductive circuits 8605, 8585.

In various examples, as illustrated in FIG. 63, the transponder 8541 is located in the shaft portion 8542 of the end effector 8540. In other examples, the transponder 8541 can be disposed in the jaws of the end effector 8540. In the illustrated example, the end effector 8540 includes a staple cartridge 8543. In certain instances, the transponder 8541 can be located in the staple cartridge 8543. Internal wiring within the shaft portion 8542 connects the exteriorly-mounted wiring connection 8600 to the transponder 8541. In the illustrated example, the exteriorly-mounted wiring connection 8600 includes an attachment member 8609 configured to connect the wire flex circuit 8601 to the shaft portion 8542. In certain instances, the attachment member 8609 is permanently connected to the shaft portion 8542. In other instances, the attachment member 8609 is releasably coupled to the shaft portion 8542.

To transmit signals to the transponder 8541, the control circuit 8560 may comprise an encoder for encoding the signals and a modulator for modulating the signals according to the modulation scheme. The control circuit 8560 may communicate with the transponder 8541 using any suitable wireless communication protocol and any suitable frequency (e.g., an ISM band).

In various examples, the control circuit 8560 through queries identification devices (e.g., radio frequency identification devices (RFIDs)), or cryptographic identification devices, can determine whether an attached staple cartridge and/or end effector is compatible with the surgical instrument system 8500. An identification chip and/or an interrogation cycle can be utilized to assess the compatibility of an attached staple cartridge and/or end effector. Various identification techniques are described in U.S. Pat. No. 8,672,995, entitled ELECTRICALLY SELF-POWERED SURGICAL INSTRUMENT WITH CRYPTOGRAPHIC IDENTIFICATION OF INTERCHANGEABLE PART, issued Jan. 14, 2014, which is hereby incorporated by reference herein in its entirety.

Figure 66:
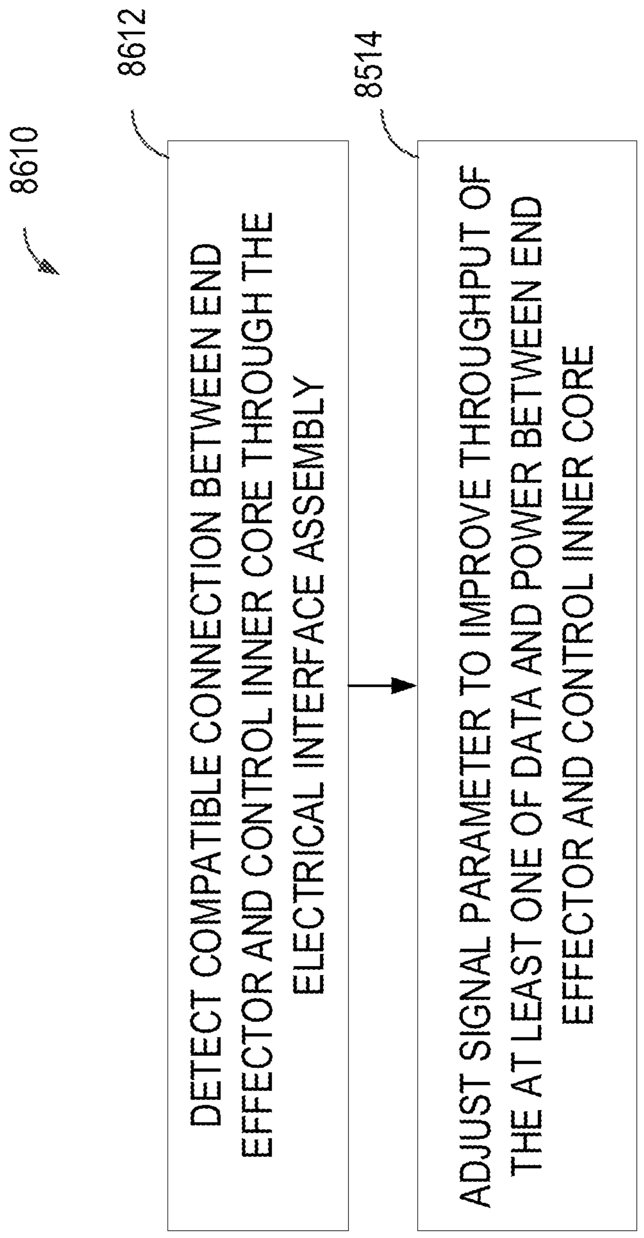
FIG. 66 is a logic flow diagram of a process depicting a control program or a logic configuration for electrically connecting an inner core of a surgical instrument system with a staple cartridge or an end effector, in accordance with at least one aspect of the present disclosure.

FIG. 66 is a logic flow diagram of a process 8610 depicting a control program or a logic configuration electrically connecting an inner core 8522 of a surgical instrument system (e.g. surgical instrument system 8500) with a staple cartridge (e.g. staple cartridge 8543) or an end effector (e.g. end effector 8540). The process 8610 includes detecting 8612 a compatible connection between the end effector 8540 and the inner core 8522, more specifically the control circuit 8560, through the electrical interface assembly 8570. The process 8610 further includes adjusting 8614 a signal parameter of a signal passing through the electrical interface assembly 8570 to improve a throughput of the at least one of data and power between the end effector 8540 and the inner core 8522.

In the illustrated example, the process 8610 is implemented by the control circuit 8560. The memory unit 8564 may store program instructions, which when executed by the processor 8562, may cause the processor 8562 to perform one or more aspects of the process 8610. In other examples, one or more aspects of the process 8610 can be implemented by a connection circuit separate from, but can be in communication with, the control circuit 8560. The connection circuit can incorporated into the disposable outer housing 8524 of the handle assembly 8520, for example.

In various aspects, the end effector 8540 includes a memory unit that stores an identification code. The control circuit 8560 may assess whether a compatible connection exists between the end effector 8540 and the inner core 8522 based on the identification code retrieved from the memory unit through the electrical interface assembly 8570.

In various aspects, the electrical interface assembly 8570 includes one or more sensors configured to detect, measure, and/or monitor aspects of the signal transmitted through the electrical interface assembly 8570. The control circuit 8560 may further adjust one or more aspects of the signal such as, for example, the signal strength, frequency, and/or bandwidth and/or adjust power levels to optimize the throughput of the at least one of data and power between the end effector 8540 and the inner core 8522 through the electrical interface assembly 8570. In various aspects, the control circuit 8560 can determine if the surgical instrument system 8500 is within an environment where one or more components or connections of the electrical interface assembly 8570 are shorted and/or the signal is lost. In response, the control circuit 8560 may adjust the signal frequency, signal strength, and/or signal repeat in order to improve data or power throughput. In at least one example, the control circuit 8560 may respond by turning off one or more connections in order to improve other connections of the electrical interface assembly 8570.

Figure 67:
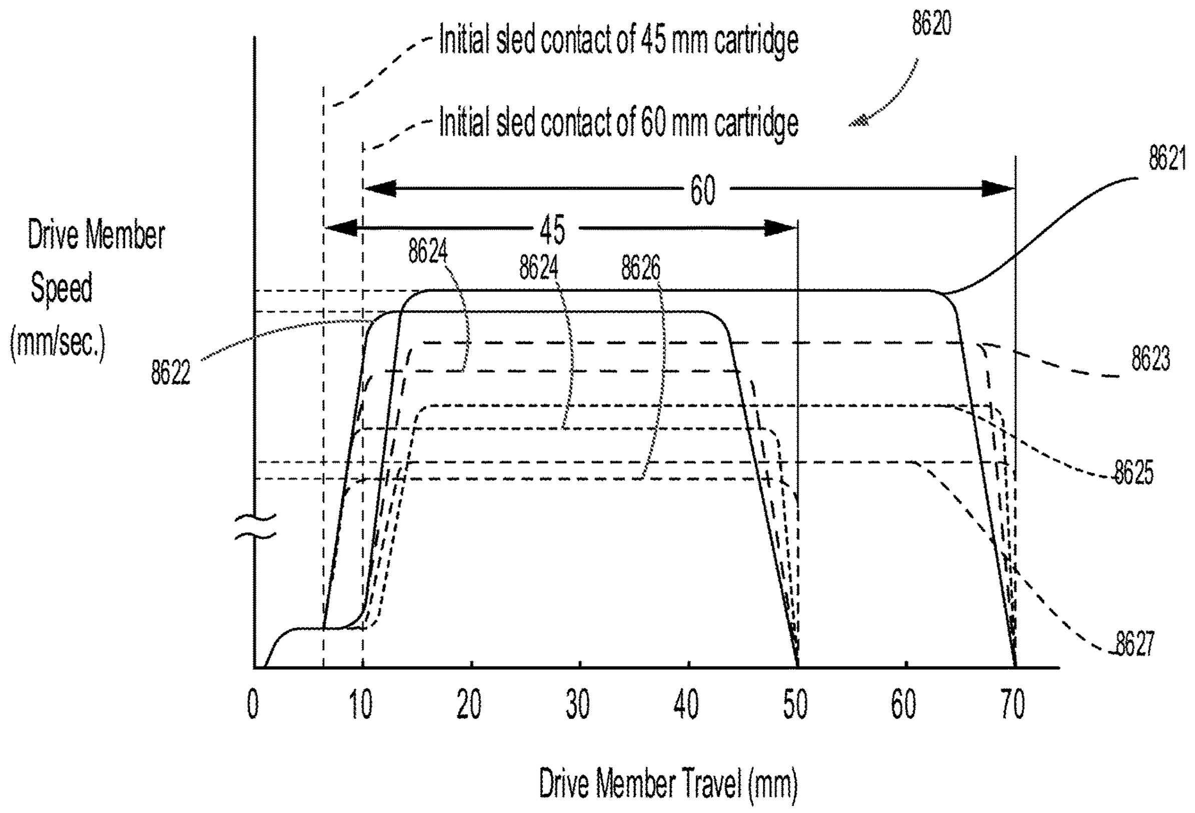
FIG. 67 is a graph illustrating drive member travel on the x-axis and drive member speed on the y-axis, in accordance with at least one aspect of the present disclosure.
Figure 68:
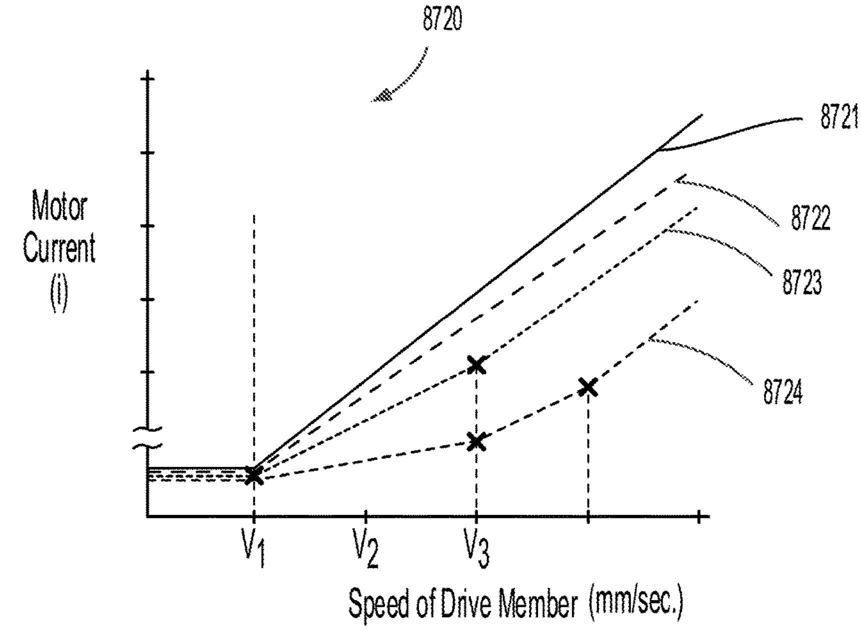
FIG. 68 is a graph illustrating drive member speed on the x-axis and motor current on the y-axis, in accordance with at least one aspect of the present disclosure.

Referring primarily to FIGS. 67 and 68, the control circuit 8560 may set one or more operational parameter of the surgical instrument system 8500 based on an identifier received through the electrical interface assembly 8570. FIG. 67 depicts a graph 8620 that represents several control schemes (e.g. 8621, 8622, 8623, 8624, 8625, 8626, 8627) that can be stored in the memory unit 8564, and can be selected by the processor 8562 based on the identifier received through the electrical interface assembly 8570. The graph 8620 includes an x-axis representing drive member travel distance in millimeters (mm) and a y-axis representing drive member speed in millimeters per second (mm/sec).

The drive member is motivated by the motor(s) of the inner core 8522 to effect a closure and/or firing motion of the end effector 8540. In at least one example, the drive member is motivated by the mortar to advance an I-beam assembly along a predefined firing path to deploy staples from the staple cartridge 8543 into tissue and, optionally, advance a cutting member to cut the stapled tissue in a firing stroke. In such example, the drive member speed of motion and distance traveled from starting position represent the speed of motion of the I-beam assembly and the distance traveled by the I-beam assembly along the predefined firing pathway, respectively.

The example control schemes (8621, 8622, 8623, 8624, 8625, 8626, 8627) represented in the graph 8620 can be stored in the memory unit 8564 in any suitable form such as, for example, tables and/or equations. In various aspects, the control schemes (8621, 8622, 8623, 8624, 8625, 8626, 8627) represent different types and sizes (e.g. 45 mm, 60 mm) of staple cartridges suitable for use with the surgical instrument system 8500 to treat different tissue types with different thicknesses. For example, the control scheme 8621 is for use with a cartridge type suitable for treating thin tissue and, as such, permits relatively faster speeds of motion of the drive member, which yields a higher inertia, which necessitates an earlier slowdown before the end of the firing stroke. Contrarily, the control scheme 8627 is for use with a cartridge type suitable for treating thick tissue and, as such, permits slower speeds of motion of the drive member than the control scheme 8621. Accordingly, the control scheme 8627 yields a lower inertia than the control scheme 8621, which justifies a later slowdown before the end of the firing stroke compared to the control scheme 8621.

FIG. 68 depicts another graph 8720 representing additional control schemes (8721, 8722, 8723, 8724). The graph 8720 illustrates drive member speed on the x-axis and motor current (i) on the y-axis for different cartridge types suitable for different tissue types/thicknesses. The current draw of the motor of the inner core 8522 to achieve a particular speed of the drive member varies depending on the cartridge type. Accordingly, the control circuit 8560 selects from the control schemes (8721, 8722, 8723, 8724) based on the identifier received through the electrical interface assembly 8570 to ensure a current draw by the motor sufficient to achieve a desired speed as determined by the selected control scheme.

Figure 69:
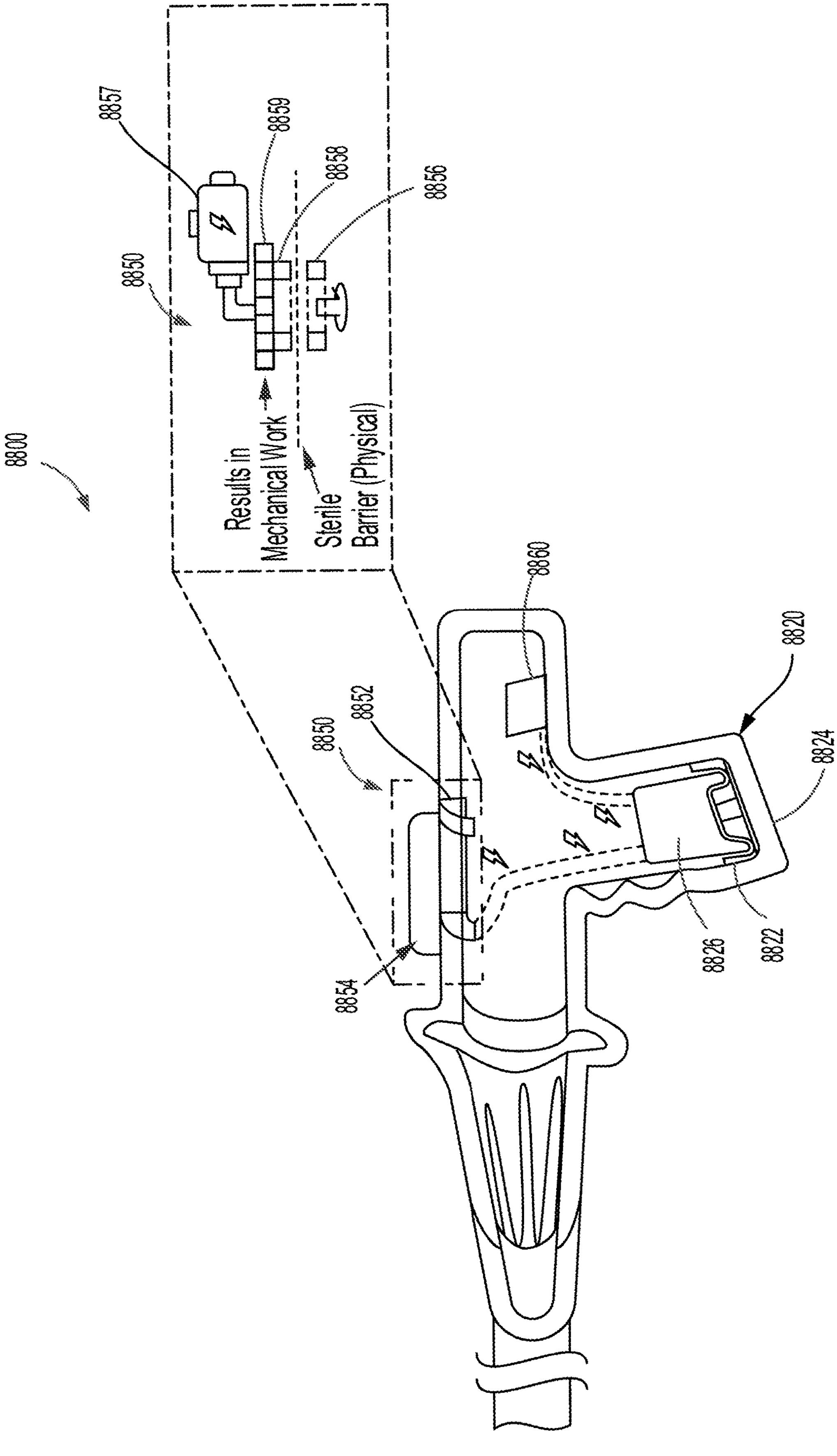
FIG. 69 is a partial elevational view of a surgical instrument system, in accordance with at least one aspect of the present disclosure.

Referring now to FIG. 69, a surgical instrument system 8800 is similar in many respects to the surgical instrument system 8500. For example, the surgical instrument system 8800 also includes a handle assembly 8820 that includes an inner core 8822 which has a motor assembly for motivating a drive member configured to effect a closure motion and/or a firing motion in an end effector 8540. The inner core 8822 further includes an internal power pack 8826 that powers the motor assembly and a control circuit 8860. In various aspects, the power pack 8826 comprises one or more batteries, which can be rechargeable. In certain aspects, the power pack 8826 can be releasably couplable to the inner core 8822.

Similar to the control circuit 8560, the control circuit 8860 includes a memory unit that stores program instructions. The program instructions, when executed by the processor, cause the processor to control the motor assembly, a feedback system, and/or one or more sensors. In various examples, the feedback system can be employed by the control circuit 8860 to perform a predetermined function such as, for example, issuing an alert when one or more predetermined conditions are met. In certain instances, the feedback systems may comprise one or more visual feedback systems such as display screens, backlights, and/or LEDs, for example. In certain instances, the feedback systems may comprise one or more audio feedback systems such as speakers and/or buzzers, for example. In certain instances, the feedback systems may comprise one or more haptic feedback systems, for example. In certain instances, the feedback systems may comprise combinations of visual, audio, and/or haptic feedback systems, for example.

Still referring to FIG. 69, a wireless power transfer system 8850 is utilized to wirelessly transmit power across a sterile barrier created by a disposable outer housing 8824 disposed around the inner core 8822. The disposable outer housing 8824 is similar in many respects to the disposable outer housing 8524. For example, the disposable outer housing 8824 may include two housing portions detachably couplable to one another to permit insertion of the inner core 8822 inside the disposable outer housing 8824. The inner core 8822 is sealed inside the disposable outer housing 8824, thereby creating the sterile barrier around the inner core 8822.

The wireless power transfer system 8850 utilizes magnetic coupling of bearings to drive mechanical work to ultimately be converted to usable electrical energy. The wireless power transfer system 8850 includes an internal power transfer unit 8852 and an external disposable energy receiver/converter 8854. In the illustrated example, the internal power transfer unit 8852 and the external disposable energy receiver/converter 8854 are positioned on opposite sides of the sterile barrier defined by the disposable outer housing 8824.

The internal power transfer unit 8852 is positioned inside the disposable outer housing 8824, and is hardwired to the power pack 8826. In one example, the internal power transfer unit 8852 is attached to an inner wall of the disposable outer housing 8824, and is releasably connected to the power pack 8826. When the inner core 8822 is properly positioned within the disposable outer housing 8824, an external connector thereof is brought into a mating engagement with a corresponding connector of the internal power transfer unit 8852. When the connectors are engaged, the power pack 8826 and the internal power transfer unit 8852 become electrically connected. In other examples, however, the inner core 8822 may include an external wiring that can be manually connected to the internal power transfer unit 8852.

In other examples, the internal power transfer unit 8852 is incorporated into the inner core 8822. In such examples, the internal power transfer unit 8852 is positioned near an external housing of the inner core 8822 in such a manner that brings the internal power transfer unit 8852 into a proper operational alignment with the external disposable energy receiver/converter 8854 when the inner core 8822 is finally positioned within the disposable outer housing 8824.

Further to the above, the internal power transfer unit 8852 includes a magnetic bearing 8856. The control circuit 8860 causes a current to drive the rotation of the magnetic bearing 8856. The mechanical energy is magnetically transmitted across the sterile barrier to the external disposable energy receiver/converter 8854, and is converted again to electrical energy via a linear alternator 8857. The external disposable energy receiver/converter 8854 includes a magnetic bearing 8858 configured to rotate with rotation of the magnetic bearing 8856. In operation, the magnetic bearing 8858 is synchronized to the rotation of the magnetic bearing 8856, which causes mechanical work to be generated externally in an outer power transfer unit 8854. The generated mechanical work is harnessed and converted to electrical energy via the linear alternator 8857 and is then available for utilization with an end effector 8540, for example. In various aspects, a gear assembly 8859 is utilized to transfer the mechanical energy from the magnetic bearing 8858 to the linear alternator 8857.

In various instances, power transfer across the sterile barrier can be achieved via a direct conductive connection is between the internal and external environments. A specific region of the outer disposable housing can be over-molded onto a metal strip that extends the thickness of the sterile barrier when implemented. The over-molding will allow for tight seals to remove the chance of contaminants getting through, and once the outer housing is transitioned to a closed configuration to create the sterile barrier, the metal strip will act as a conductive bridge allowing energy to be transferred directly to the external environment.

Figure 70:
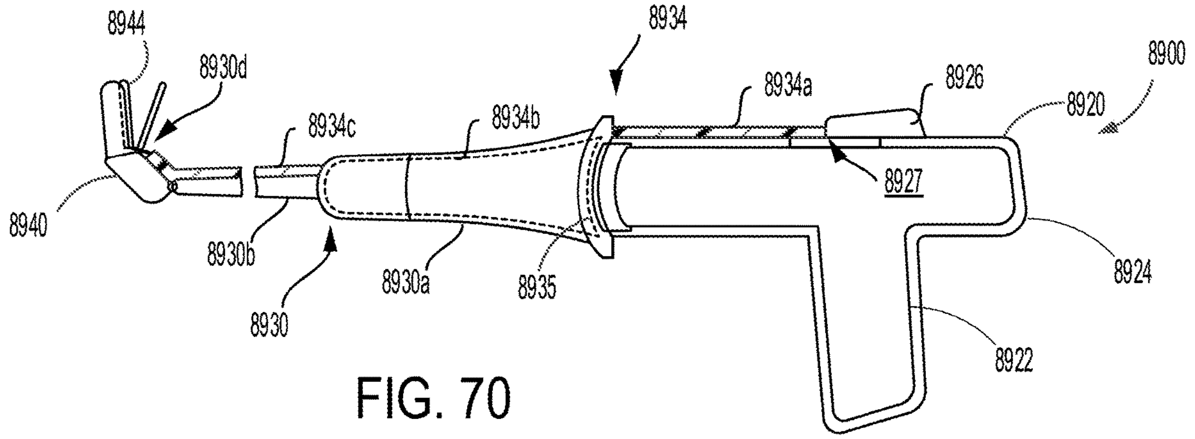
FIG. 70 is a partial elevational view of a surgical instrument system, in accordance with at least one aspect of the present disclosure.
Figure 71:
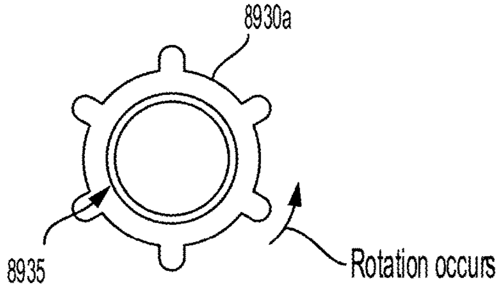
FIG. 71 is a cross-sectional view of a nozzle portion of the surgical instrument system of FIG. 70.

Referring now to FIGS. 70 and 71, a surgical instrument system 8900 is similar in many respects to the surgical instrument systems 8500, 8800. For example, the surgical instrument system 8900 also includes a handle assembly 8920 that includes an inner core 8922 which has a motor assembly for motivating a drive member configured to effect a closure motion and/or a firing motion in an end effector 8940.

In addition, the surgical instrument system 8900 includes a shaft 8930 with a nozzle portion 8930*a* and a shaft portion 8930*b* extending distally from the nozzle portion 8930*a*. The nozzle portion 8930*a* permits rotation of the end effector 8940 relative to the handle assembly 8920. A flex circuit 8934 is configured to transmit power to the end effector 8940 through the nozzle portion 8930*a*. The flex circuit 8934 comprises a proximal flex circuit segment 8934*a* disposed on the handle assembly 8920 and a distal flex circuit segment 8934*c* disposed on the shaft portion 8930*b* and the end effector 8940.

In addition, the flex circuit 8934 includes a conductive metal segment 8934*b* frictionally connected to the proximal flex circuit segment 8934*a* and fixedly connected to the distal flex circuit segment 8934*c*. The conductive metal segment 8934*b* facilitates rotation of the shaft 8930 and the end effector 8940 relative to the handle assembly 8920 while maintaining an electrical connection between the handle assembly 8920 and the end effector 8940. In the illustrated example, the conductive metal segment 8934*b* includes a conductive ring 8935 frictionally attached to the proximal flex circuit segment 8934*a*.

Further to the above, the flex circuit 8934 is configured to transmit power from an external power source 8926 to the end effector 8940. The external power source 8926 is disposed onto the disposable outer housing 8924. A connection between the external power source 8926 and the flex circuit 8934 can be protected from surrounding environment by being partially, or fully, embedded in the disposable outer housing 8924, for example. In the illustrated example, the external power source 8926 includes a connection port 8927 configured to receive a proximal end of the proximal flex circuit segment 8934*a*.

Additionally, the inner core 8922 may include an internal power pack that powers the motor assembly and a control circuit. In various aspects, the power pack electrically coupled to the flex circuit 8934 and/or the external power source 8926 by an electrical interface assembly 8570 in a similar manner to that described in connection with the surgical instrument system 8500. In certain examples, the external power source 8926 is fully replaced by the internal power pack of the inner core 8922. In such examples, power is transmitted to the flex circuit 8934 from the internal power pack through the sterile barrier via the electrical interface assembly 8570.

Further to the above, the flex circuit 8934 may also include an end effector segment 8934*d* configured to connect the distal flex circuit segment 8934*c* to a staple cartridge 8944 releasably coupled to the end effector 8940. The end effector segment 8930*d* comprises sufficient slack to prevent over extension of the end effector segment 8930*d*, which can be caused by end effector motions.

Figure 72:
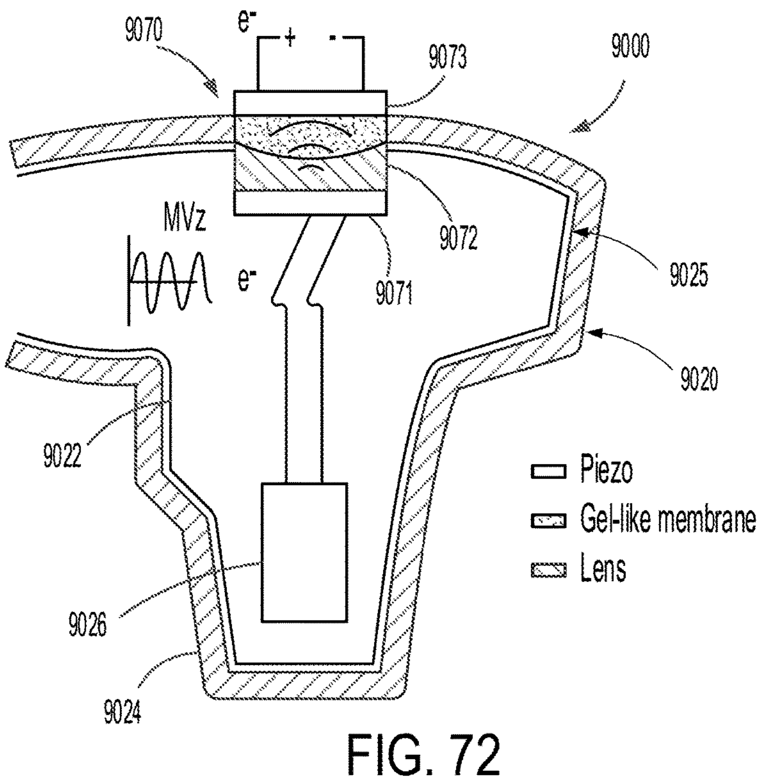
FIG. 72 is a cross-sectional view of a handle assembly of a surgical instrument system, in accordance with at least one aspect of the present disclosure.

Referring now to FIG. 72, a surgical instrument system 9000 is similar in many respects to the surgical instrument system 8500. For example, the surgical instrument system 9000 also includes a handle assembly 9020 that includes an inner core 9022 which has a motor assembly for motivating a drive member configured to effect a closure motion and/or a firing motion in an end effector (e.g. end effector 8540). A disposable outer housing 9024 defines a sterile barrier 9025 around the inner core 9022.

The handle assembly 9020 further includes an electrical interface assembly 9070 configured to transmit at least one of data signal and power between the inner core 8922 and the end effector 8540 through the sterile barrier 9025 defined by the disposable outer housing 9024. The electrical interface assembly 9070 includes an internal piezoelectric transducer 9071 coupled to an internal power pack 9026 configured to energize the internal piezoelectric transducer 9071. The electrical interface assembly 9070 further includes a lens coupled to the internal piezoelectric transducer 9071, and configured to focus ultrasound energy generated by the internal piezoelectric transducer 9071 through a gel-like membrane 9072 into an external piezoelectric transducer 9073. Accordingly, electrical energy provided by the power pack 9026 is converted into ultrasound energy that is transmitted across the sterile barrier 9025 to be received by the external piezoelectric transducer 9073. The ultrasound energy is then transferred to electrical energy by the external piezoelectric transducer 9073. In certain instances, a flex circuit further transmits the electrical energy to an end effector, for example.

Figure 73:
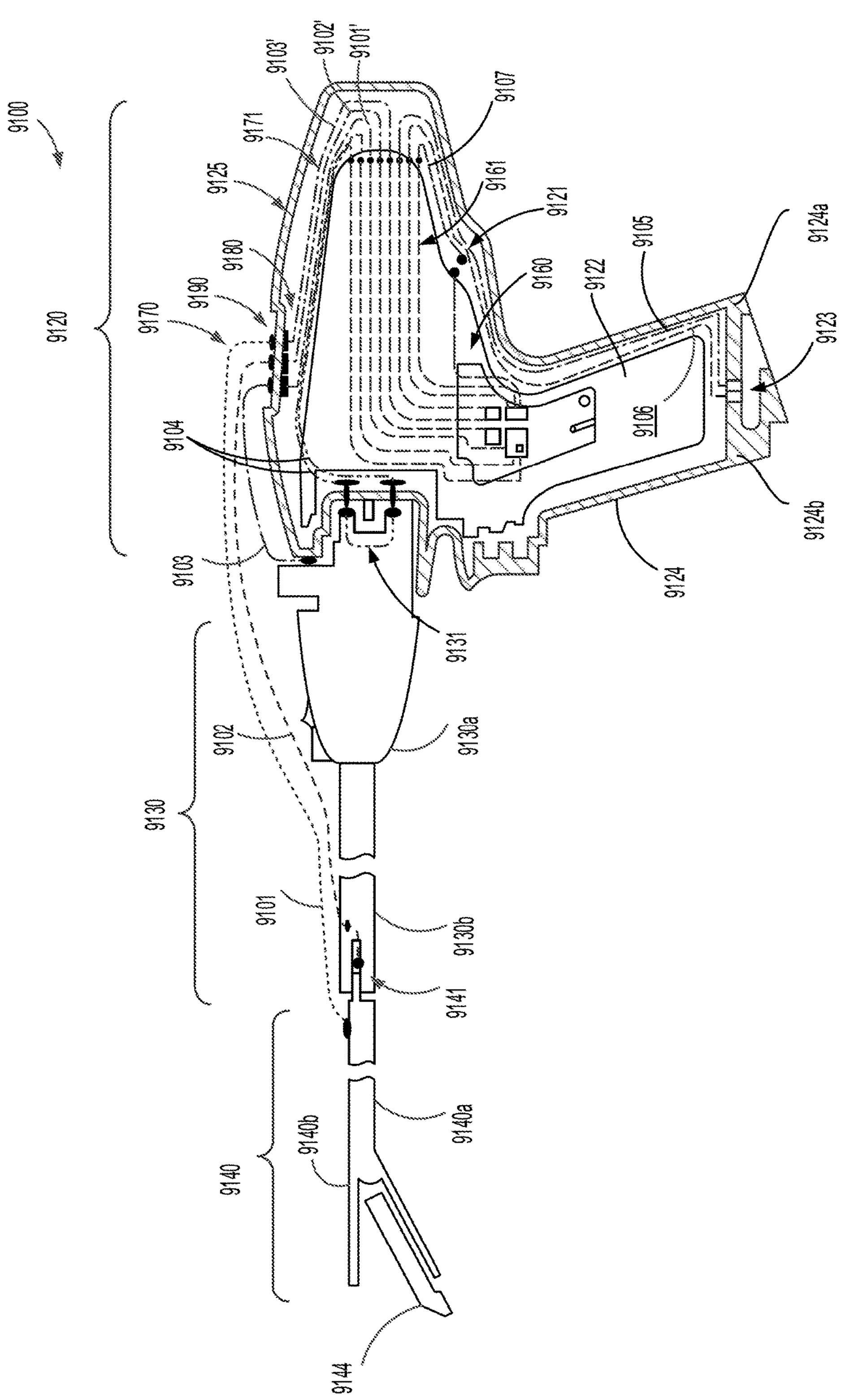
FIG. 73 is a cross-sectional view of a modular configuration of a modular surgical instrument system, in accordance with at least one aspect of the present disclosure.

FIG. 73 depicts a modular surgical instrument system 9100 similar in many respects to the surgical instrument system 8500. For example, the modular surgical instrument system 9100 also includes a handle assembly 9120, a shaft 9130, and a loading unit 9140 including a proximal shaft portion 9140*a* and an end effector 9140*b*. The loading unit 9140 is releasably connectable to a distal shaft portion 9130*b* of the shaft 9130. A nozzle portion 9130*a* of the shaft 9130 is also releasably connectable to the handle assembly 9120. Furthermore, a staple cartridge 9144 is releasably connectable to the end effector 9140*b*. In other instances, the staple cartridge is integrated with the end effector 9140*b*.

Like the handle assembly 8520, the handle assembly 9120 includes an inner core 9122 and a disposable outer housing 9124 configured to selectively receive and encase the inner core 9122 to establish a sterile barrier 9125 around the inner core 9122. Inner core 9122 is motor operable and configured to drive an operation of a plurality of types of end effectors. Inner core 9122 has a plurality of sets of operating parameters (e.g., speed of operation of motors of inner core 9122, an amount of power to be delivered by motors of inner core 9122 to a shaft assembly, selection of motors of inner core 9122 to be actuated, functions of an end effector to be performed by inner core 9122, or the like). Each set of operating parameters of inner core 9122 is designed to drive the actuation of a specific set of functions unique to respective types of end effectors when an end effector is coupled to inner core 9122. For example, inner core 9122 may vary its power output, deactivate or activate certain buttons thereof, and/or actuate different motors thereof depending on the type of end effector that is coupled to inner core 9122.

The inner core 9122 defines an inner housing cavity that accommodates a power pack and one or more motors powered by the power pack. The rotation of motors function to drive shafts and/or gear components of the shaft 9130, for example, in order to drive the various operations of end effectors attached thereto, for example, end effector 9140.

Further to the above, the outer housing 9124 includes two housing portions 9124*a*, 9124*b* releasably attached to one another to permit assembly with the inner core 9122. In the illustrated example, the housing portion 9124*b* is movably coupled to the housing portion 9124*a* by a hinge located along an upper edge of the housing portion 9124*b*. Consequently, the housing portions 9124*a*, 9124*b* are pivotable relative to one another between a closed, fully coupled configuration, as shown in FIG. 73, and an open, partially detached configuration. When joined, the housing portions 9124*a*, 9124*b* define a cavity therein in which inner core 9122 may be selectively situated.

Similar to the control circuit 8560, the control circuit 9160 includes a memory unit that stores program instructions. The program instructions, when executed by a processor, cause the processor to control the motor assembly, a feedback system, and/or one or more sensors, for example. In various examples, the feedback system can be employed by the control circuit 9160 to perform a predetermined function such as, for example, issuing an alert when one or more predetermined conditions are met. In certain instances, the feedback systems may comprise one or more visual feedback systems or a visual interface such as display screens, backlights, and/or LEDs, for example. In certain instances, the feedback systems may comprise one or more audio feedback systems such as speakers and/or buzzers, for example. In certain instances, the feedback systems may comprise one or more haptic feedback systems, for example. In certain instances, the feedback systems may comprise combinations of visual, audio, and/or haptic feedback systems, for example.

In various aspects, one or more sensors can be configured to detect or measure whether the disposable outer housing 9124 in an open configuration or a closed configuration. In the illustrated example, a Hall Effect sensor 9123 detects a transition of the housing portion 9124*a*, 9124*b* to a closed configuration or to an open configuration. The control circuit 9160 may receive an input signal indicative of whether the disposable outer housing 9124 is in the open configuration or closed configuration. In certain examples, other suitable sensors can be employed to detect the closed configuration and/or the open configuration such as, for example, other magnetic sensors, pressure sensors, inductive sensors, and/or optical sensor.

Referring still to FIG. 73, the modular surgical instrument system 9100 includes an electrical interface assembly 9170 configured to transmit at least one of data signal and power across the sterile barrier 9125, outside the sterile barrier 9125, and/or within the sterile barrier 9125. The at least one of data signal and power is transmitted between one or more of the modular components of the modular surgical instrument system 9100. In the illustrated example, the electrical interface assembly 9170 includes a first interface portion 9180 on a first side (inside the disposable outer housing 9124) of the sterile barrier 9125 and a second interface portion 9190 on a second side (outside the disposable outer housing 9124) of the sterile barrier 9125 opposite the first side.

Furthermore, the electrical interface assembly 9170 includes a wiring assembly 9171 that includes exteriorly-mounted wiring connections 9101, 9102, 9103 that electrically couple the second interface portion 9190 to the loading unit 9140, a loading unit-to-shaft connection sensor 9141, and the nozzle portion 9130*a*, respectively, and corresponding internally-mounted wiring connections 9101', 9102', 9103' that couple the first interface portion 9180 to the control circuit 9160. The wiring connections 9101, 9102, 9103, 9101', 9102', 9103' cooperate with the interface portions 9180, 9190 to transmit signals between the control circuit 9160 and the loading unit 9140, the staple cartridge 9144, the loading unit-to-shaft connection sensor 9141, and the nozzle portion 9130*a*, as discussed in greater detail below. In certain instances, a buttress is attached to the staple cartridge 9144. In such instances, the wiring connections 9101, 9101' may facilitation the transmission of signals between the control circuit 9160 and a buttress-attachment sensor configured to detect a buttress unique identifier, for example, as discussed in greater detail below.

In addition, the wiring assembly 9171 further includes internally-mounted wiring connections 9104, 9105, 9106, 9107 configured to electrically couple the control circuit 9160 to a handle assembly-to-shaft connection sensor 9131, the first housing portion 9124*a*, the second housing portion, and an inner core-to-handle assembly connection sensor 9121. In at least one example, one or more of the wiring connections of the wiring assembly 9161 comprise connector ends releasably couplable to corresponding connector ends of corresponding modular components of the modular surgical instrument system 9100.

In certain examples, the handle assembly 9120 may include an electrical interface assembly that facilitates a wired connection through the sterile barrier 9125. Wire portions may be passed through the disposable outer housing 9124. For example, the wire portions can be partially embedded in a handle assembly outer wall. Suitable insulation can be provided to prevent fluid leakage.

Figure 74:
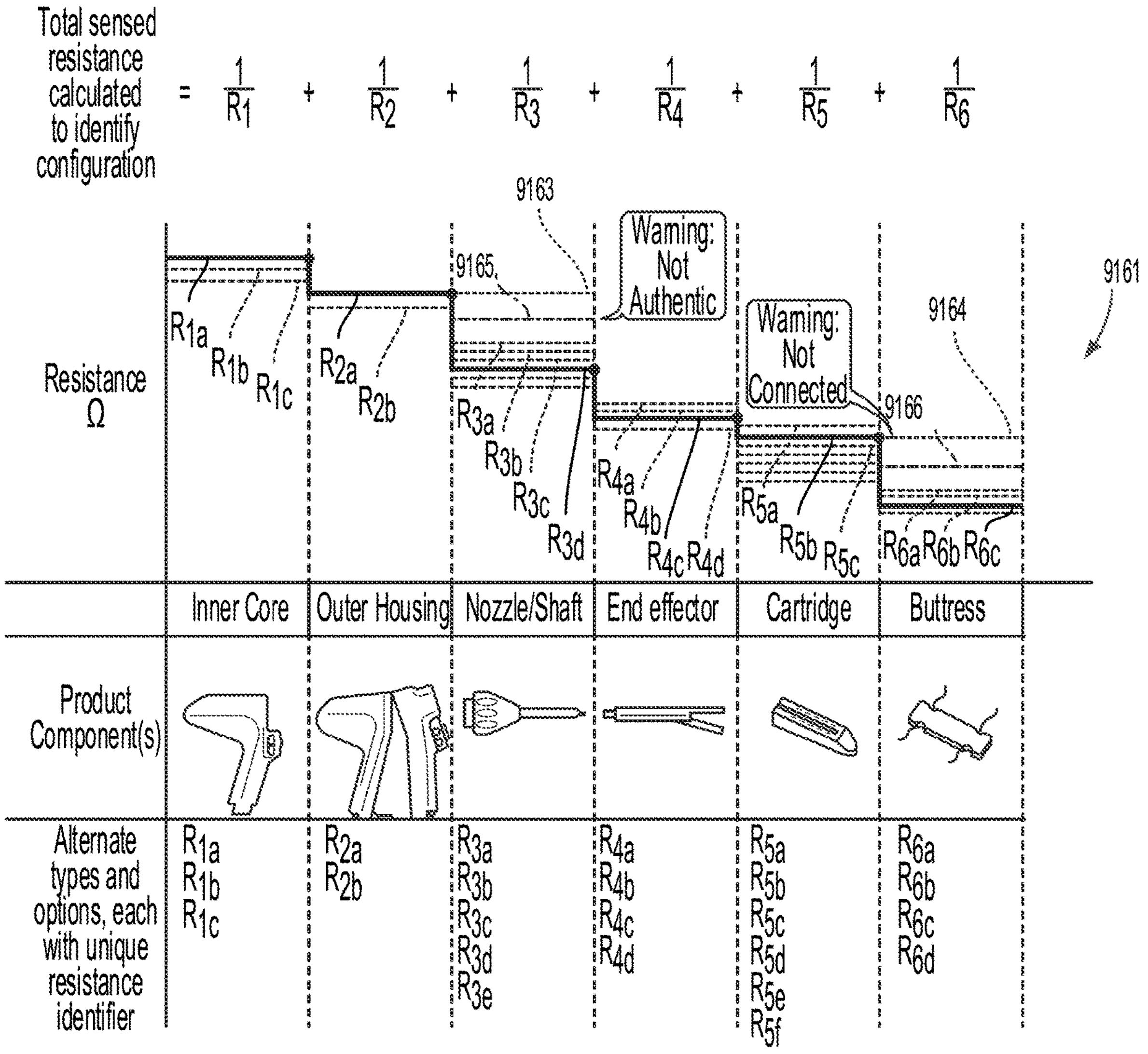
FIG. 74 is a graph illustrating resistance identifiers of various potential modular components of the modular surgical instrument system, in accordance with at least one aspect of the present disclosure.

Referring to FIG. 74, various possible modular components of the modular surgical instrument system 9100 are listed along with unique identifier resistances for each of the listed modular components. The listed modular components may facilitate surgical stapling, surgical ultrasonic energy treatment, surgical radio-frequency (RF) energy treatment, and various combinations thereof.

The modular components include various types of inner cores, handle assemblies, shafts, loading units, staple cartridges with different types and sizes, and/or buttress attachments with different shapes and sizes, which can be assembled in various combinations to form a modular surgical instrument system 9100. Since each modular component comprises a unique identifier resistance, a total sensed resistance can be determined to identify a connected modular configuration based on the unique identifier resistances of its modular components.

In certain aspects, the control circuit 9160 may compare an expected value of the total sensed resistance to a measured value of the total sensed resistance to verify, or confirm, the identity of the modular components in a modular configuration. In at least one example, the control circuit 9160 may receive user input identifying components of modular configuration through a user interface, for example. Additionally, or alternatively, the control circuit 9160 may directly compare expected values of the identifier resistances to corresponding measured values of the identifier resistances to verify, or confirm, the identity of the modular components in a modular configuration, for example.

In other aspects, the control circuit 9160 may compare an expected value of the total sensed resistance to a measured value of the total sensed resistance to assess or detect irregularities in connected modular components of a modular configuration. Additionally, or alternatively, the control circuit 9160 may compare expected values to measured values for each of the modular components to assess or detect irregularities in the connected modular components of a modular configuration.

In the illustrated example, a graph 9161 illustrates expected and measured, or detected, identifier resistance values. Based on a comparison of the expected and measured, or detected, resistant identifier values the control circuit 9160 determines that an inner core, a disposable outer housing, a shaft, an end effector, a cartridge, and a buttress with unique identifier resistances $R_{1a}$, $R_{2a}$, $R_{3d}$, $R_{4c}$, $R_{5b}$, $R_{6c}$, respectively, are connected in a modular configuration.

In the illustrated examples, lines 9163, 9164 illustrate scenarios where an outer housing and a buttress, respectively, are either not connected or are not authentic. Additionally, lines 9165, 9166 illustrate scenarios where an outer housing and a buttress, respectively, are connected, but are not authentic. In such complex configurations, checking authenticity of the modular components ensures that the modular configuration will work properly A deviation between the expected and measured, or detected, resistant identifier values may indicate a not-connected status, a not-authentic status, or other irregularities. The amount of deviation dictates whether the control circuit 9160 determines a not-connected status, a not-authentic status, or a connected authentic status. In certain examples, the control circuit 9160 may calculate the deviation amount and compare the calculated deviation amount to a predetermined threshold to assess whether the deviation represents a not-connected status, a not-authentic status, or an authentic/connected status.

In certain examples, a deviation magnitude selected from a range of greater than 0% to about 10%, a range of greater than 0% to about 20%, a range of greater than 0% to about 30%, a range of greater than 0% to about 40%, or a range of greater than 0% to about 50% indicates a not-authentic status. In certain examples, a deviation indicative of a not-authentic status is less than a deviation indicative of a not-connected status.

Figure 75:
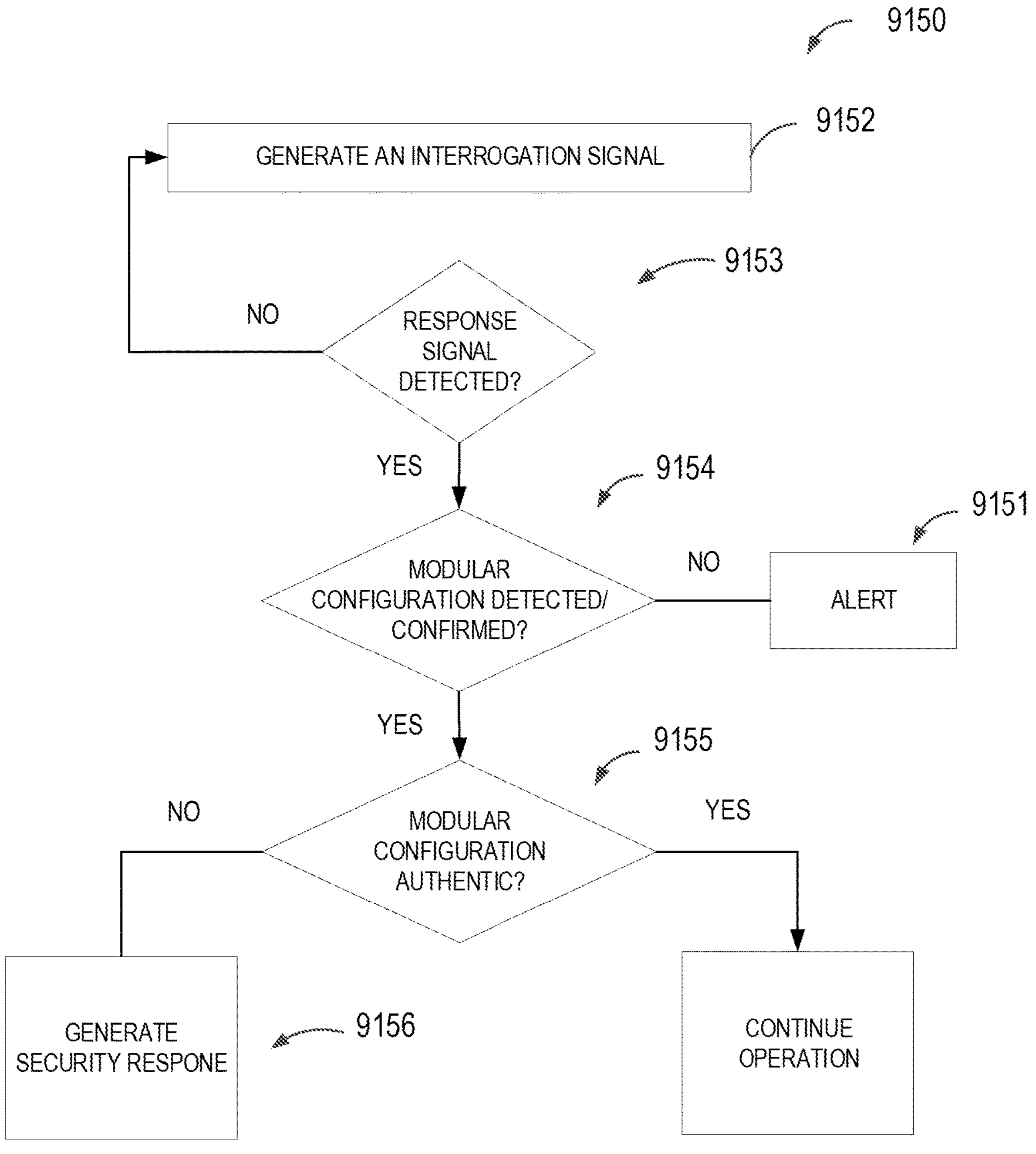
FIG. 75 is a logic flow diagram of a process depicting a control program or a logic configuration for detecting and/or authenticating a modular configuration of a modular surgical instrument system or assembly.

FIG. 75 is a logic flow diagram of a process 9150, depicting a control program or a logic configuration for detecting and/or authenticating a modular configuration of a modular surgical instrument system or assembly. One or more aspects of the process 9150 can be performed by a control circuit such as, for example, the control circuit 9160 of the modular surgical instruments system 9100. In various aspects, the process 9150 includes generating 9152 an interrogation signal to detect, or confirm identity, of modular components of an assembled modular configuration of a modular surgical instruments system 9100. In the event, the identities of the modular components are to be confirmed, the identities could be supplied through a user interface coupled to the control circuit 9160, for example.

In any event, the interrogation signal can be transmitted to the modular components of the modular configuration through the wiring assembly 9171 and/or electrical interface assembly 9170. The interrogation signal may trigger a response signal from the modular components of the modular configuration. The response signal can be detected 9153 and utilized by the control circuit 9160 to detect 9154, or confirm, identity of the modular components in the modular configuration.

As described above in greater detail, each of the modular components available for use with the modular surgical instrument system 9100 includes an identifier resistance unique to the modular component. Accordingly, the control circuit 9160 may utilize the response signal to calculate the identifier resistances of the modular components of the modular configuration. The identities of the modular components of the modular configuration can then be detected 9154, or confirmed, based on the calculated identifier resistances. Confirmation of the identities of the modular components of the modular configuration can be achieved by the control circuit 9160 by comparing the identities entered through the user interface with the identities detected based on the response signal.

In certain aspects, the control circuit 9160 causes a current to pass through the wiring assembly 9171 and the electrical interface assembly 9170 to the modular components of the modular configuration. The return current can then be sampled to calculate a total sensed resistance of the modular configuration. Since each of the individual modular components has a unique identifier resistance, the control circuit 9160 can determine the identities of the individual modular components based on the total sensed resistance of the modular configuration.

In certain aspects, the control circuit 9160 compares an expected value of the total sensed resistance to a determined value of the total sensed resistance to confirm a proper assembly of a modular configuration. In at least one form, the expected value is stored in a memory unit, which is accessed by the control circuit 9160 to perform the comparison.

A deviation between the expected value and the determined value with a magnitude equal to, or at least substantially equal to, the resistance identifier of one or more modular components causes the control circuit 9160 to conclude that the one or more modular components are not connected in the modular configuration. In response, the control circuit 9160 may assign a not-connected status. The control circuit 9160 may also issue an alert 9151 regarding the one or more modular components through the user interface. The control circuit 9160 may further provide instructions for how to properly connect the deemed-unconnected modular components.

In certain instances, the process 9150 may further include assessing 9155 authenticity of the modular configuration based on the response signal. In at least one example, the control circuit 9160 assesses the authenticity of the modular configuration based on a comparison between expected and determined values of the unique identifier resistances of the modular components. The control circuit 9160 may compare the magnitude of a detected deviation between expected and determined values of a unique identifier resistance to a predetermined threshold to assess 9155 authenticity of a detected modular component in a modular configuration.

In at least one example, the predetermined threshold is a threshold range. If the magnitude of the detected deviation is beyond, the predetermined threshold, the control circuit 9160 may select a suitable security response 9156 such as, for example, assigning a non-authentic status to the modular component, issuing an alert through the user interface, and/or temporarily deactivating the surgical instrument system 9100. In various aspects, the threshold range is about ±1%, about ±2%, about ±3%, about ±4%, about ±5%, about ±10%, or about ±20% from the expected value, for example. Other ranges are contemplated by the present disclosure.

Figure 76:
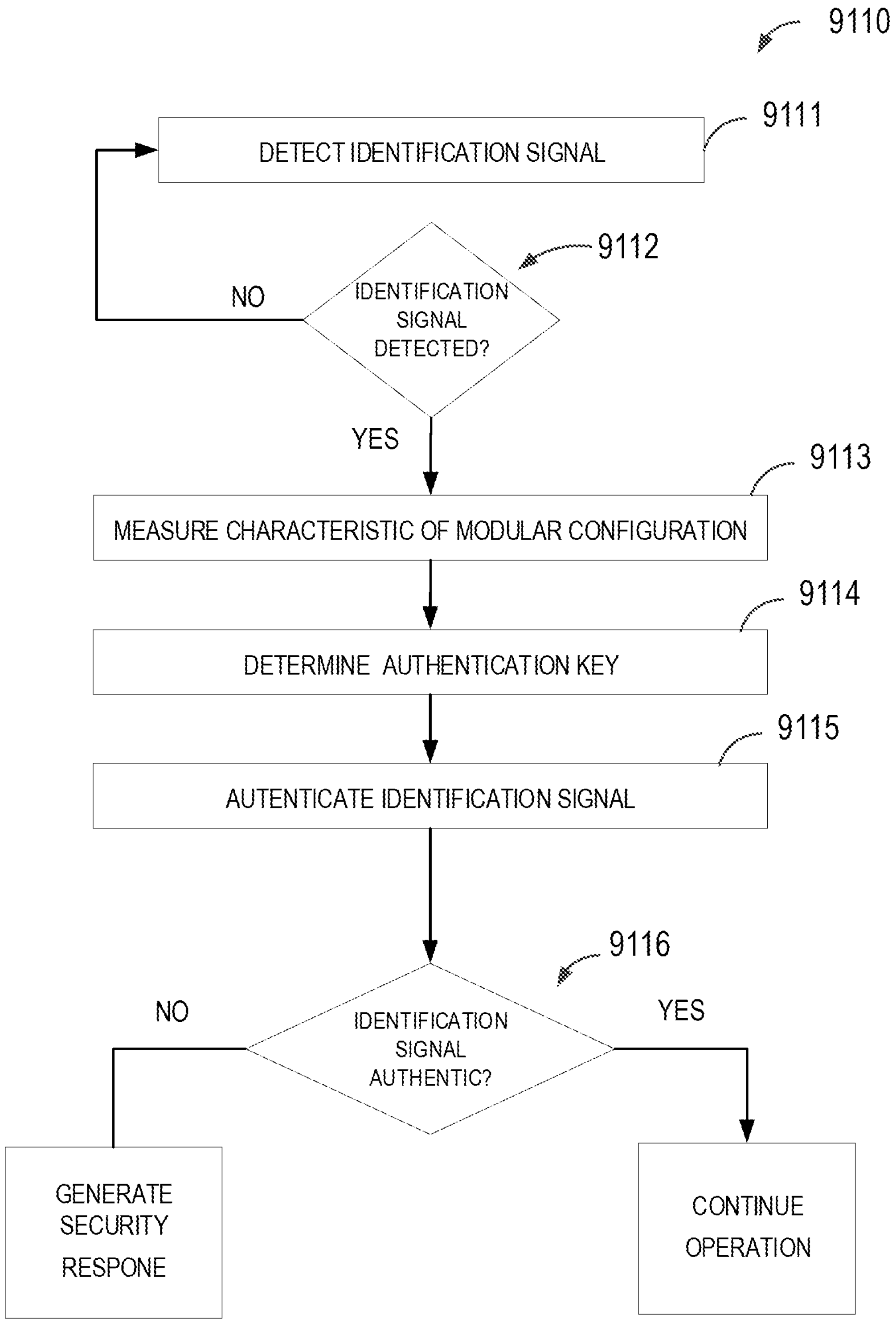
FIG. 76 is a logic flow diagram of a process depicting a control program or a logic configuration for detecting and/or authenticating a modular configuration of a modular surgical instrument system or assembly.

FIG. 76 is a logic flow diagram of a process 9110, depicting a control program or a logic configuration for detecting and/or authenticating a modular configuration of a modular surgical instrument system or assembly. One or more aspects of the process 9110 can be performed by a control circuit such as, for example, the control circuit 9160 of the modular surgical instruments system 9100. In various aspects, the process 9110 includes detecting 9111 an identification signal of an assembled modular configuration of the modular surgical instrument system 9100. In certain examples, the identification signal is a combined response signal transmitted by modular components of the modular configuration in response to an interrogation signal generated by the control circuit 9160.

Furthermore, the control circuit 9160 may assess authenticity of the modular components of the modular configuration. If 9112 the identification signal is detected, the control circuit 9160 measures 9113 a characteristic of the modular configuration, determines 9114 an authentication key based on at least one measurement of the characteristic, and authenticates 9115 the identification signal based on the authentication key. If 9116 the control circuit 9160 determines that the modular configuration is not authentic, the control circuit 9160 may further generate a security response, as described in connection with the process 9150.

In various aspects, the control circuit 9160 is configured to determine the authentication key independently of the identification signal. The authentication key can be based on a characteristic common among individual modular components of the modular configuration. In at least one example, the common characteristic can be an environmental characteristic. In certain examples, the common characteristic can be a location, a radio-frequency (RF) intensity, a sound level, a light level, and/or a magnetic field strength.

In various aspects, a modular component of the modular configuration measures the common characteristic, and generates the authentication key based on at least one measurement of the common characteristic. The modular component may further encode an identification signal based on the generated authentication key, and transmits the encoded identification signal to the control circuit 9160 through the wiring assembly 9171 and/or the electrical interface assembly 9170. The control circuit 9160 may independently measure the common characteristic, and determine the authentication key based on at least one measurement of the common characteristic. The control circuit 9160 may further utilize the authentication key to authenticate and/or decode the identification signal received from the modular component.

In certain examples, the handle assembly 9120 generates a magnetic field with a strength measureable by each of the modular components in a modular configuration. The modular components can utilize the measured magnetic field strength to encode identification signals transmitted to the control circuit 9160 through the wiring assembly 9171 and/or the electrical interface assembly 9170. In addition, the control circuit 9160 separately determines the strength of the magnetic field. In certain instances, the control circuit 9160 sets the strength of the magnetic field. In other instances, the control circuit 9160 measures the strength in a similar manner to modular components.

The control circuit 9160 decodes the encoded identification signals based on an authentication key generated from one or more measurements of the strength of the magnetic field. Measuring the magnetic field can be accomplished by one or more sensors such as, for example, a magnetometer. In other instances, the common characteristic is a radio-frequency (RF) intensity, a sound level, or a light level, the control circuit 9160 employs an RF intensity sensor, an auditory sensor, or a photoelectric sensor, respectively, to measure the common characteristic.

Figure 77:
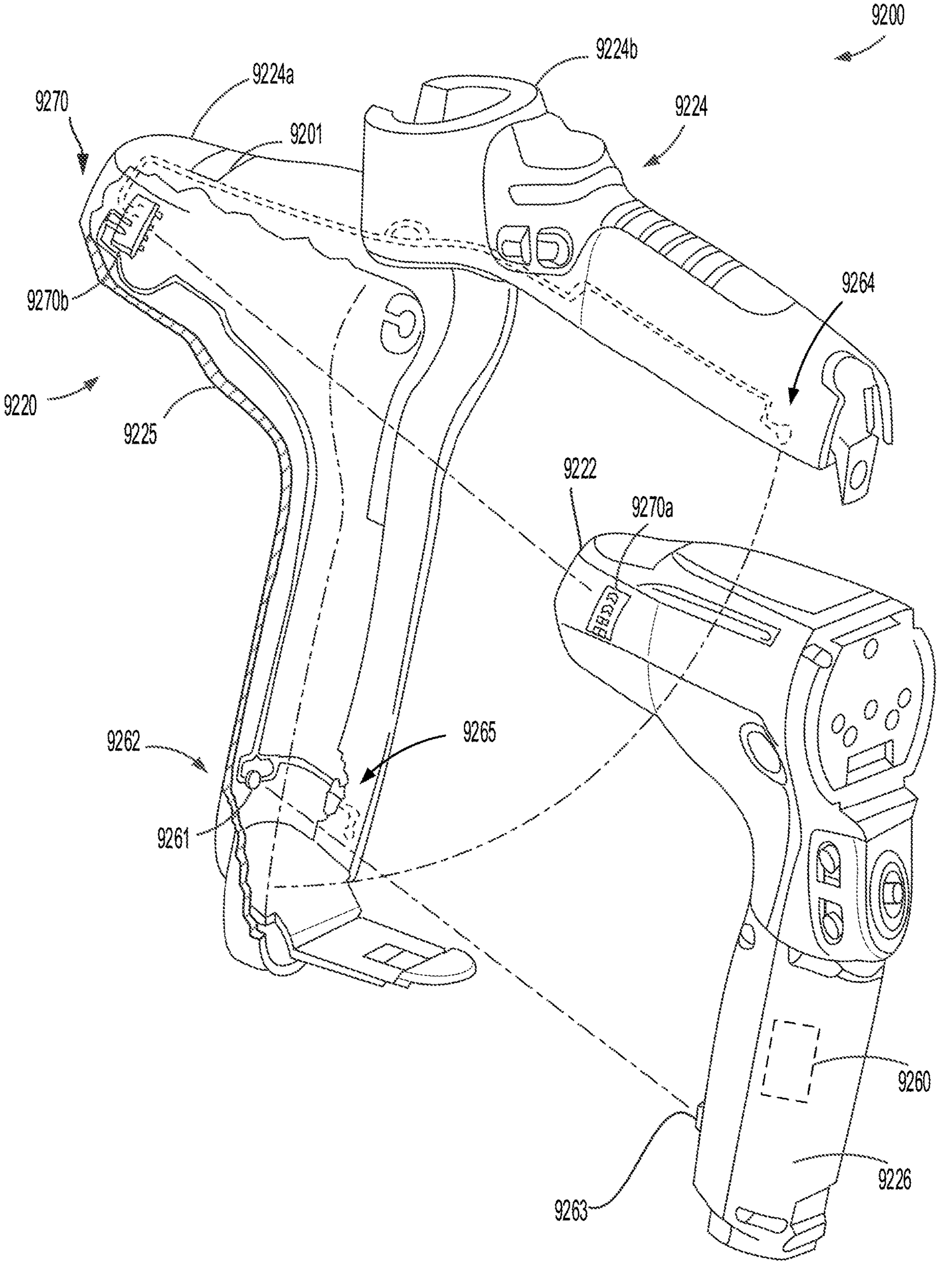
FIG. 77 is a perspective view of a handle assembly of a modular surgical instrument system, the handle assembly including a disposable outer housing and an inner core, in accordance with at least one aspect of the present disclosure.

FIG. 77 illustrates a handle assembly 9220 of a modular surgical instrument 9200 similar in many respects to the modular surgical instruments 8500, 9100, which are not repeated herein in the same level of detail for brevity. For example, the handle assembly 9220 includes an inner core 9222 and a disposable outer housing 9224 configured to selectively receive and encase inner core 9222 to establish a sterile barrier 9225 around the inner core 9222. Inner core 9222 is motor operable and configured to drive an operation of a plurality of types of end effectors. Inner core 9222 has a plurality of sets of operating parameters (e.g., speed of operation of motors of inner core 9222, an amount of power to be delivered by motors of inner core 9222 to a shaft assembly, selection of motors of inner core 9222 to be actuated, functions of an end effector to be performed by inner core 9222, or the like). Each set of operating parameters of inner core 9222 is designed to drive the actuation of a specific set of functions unique to respective types of end effectors when an end effector is operably coupled to inner core 9222. For example, inner core 9222 may vary its power output, deactivate or activate certain buttons thereof, and/or actuate different motors thereof depending on the type of end effector that is operably coupled to inner core 9222.

Further to the above, the outer housing 9224 includes two housing portions 9224*a*, 9224*b* releasably attached to one another to permit assembly with the inner core 9222. In the illustrated example, the housing portions 9224*a*, 9224*b* are movable relative to one another between a closed, fully coupled configuration, and an open, partially detached, or fully detached, configuration. When joined, the housing portions 9224*a*, 9224*b* define a cavity therein in which inner core 9222 may be selectively situated.

Furthermore, the handle assembly 9220 includes a primary interface assembly 9270 configured to transmit at least one of data and power between the inner core 9222 and at least one of modular components of the modular surgical instrument system 9200. The primary interface assembly 9270 includes a first interface portion 9270*a* disposed onto the inner core 9222 and a second interface portion 9270*b* disposed on an inner wall of the disposable outer housing 9224. The interface portions 9270*a*, 9270*b* include corresponding electrical contacts that become electrically connected, or form an electrical connection, when the inner core 9222 is properly assembled with the disposable outer housing 9224. In various aspects, the primary interface assembly 9270 facilitates an electrical connection between a power pack 9226 of the inner core 9222 and an external charging system. The primary interface assembly 9270 also facilitates the detection of a modular configuration of the modular surgical instrument system 9200 by transmitting at least one of power and data therethrough between the inner core 9222 and the modular configuration. In at least one example, the electrical contacts comprise spring contacts such as, for example, leaf-spring contacts.

In various aspects, the handle assembly 9220 includes a secondary interface 9262 including one or more sensors 9261 configured to detect the presence of the inner core 9222 in the disposable outer housing 9224. The control circuit 9260 is configured to confirm a primary connection through the primary interface assembly 9270 based on at least one reading of the sensor 9261. Position and/or sensitivity of a sensor 9261 can be set to detect the inner core 9222 when the inner core 9222 is in the right position and alignment within the disposable outer housing to establish a wired connection between the interface portions 9270*a*, 9270*b*. In certain instances, readings from the sensor 9261 must be greater than, or equal, to a predetermined threshold to cause the control circuit 9260 to detect that the inner core 9222 is correctly inserted into the disposable outer housing 9224. The control circuit 9260 may continuously compare readings of the sensor 9261 to the predetermined threshold to determine whether the inner core 9222 is correctly inserted into the disposable outer housing 9224.

In various aspects, the sensor 9261 comprises a proximity sensor such as, for example, a magnetic sensor, such as a Hall Effect sensor, an inductive sensor, such as an eddy current sensor, a resistive sensor, a capacitive sensor, an optical sensor, and/or any other suitable sensor. In certain examples, the control circuit 9260 is configured to identify/detect an inner core 9222 through the secondary interface 9262 based on a unique identifier 9263 of the inner core 9222 such as, for example, a QR code, a resistance identifier, a voltage identifier, and/or a capacitance identifier.

Referring still to FIG. 77, the control circuit 9260 is further configured to detect a closed configuration of the disposable outer housing 9224 of the handle assembly 9220. The control circuit 9260 may detect the closed configuration based on at least one reading of at least one sensor 9264 within the disposable outer housing 9224. In at least one example, the sensor 9264 is a proximity sensor. In the illustrated example, the sensor 9264 is a Hall Effect sensor. In other instances, the sensor 9264 can be an inductive sensor, such as an eddy current sensor, a resistive sensor, a capacitive sensor, an optical sensor, and/or any other suitable sensor.

Additionally, or alternatively, the control circuit 9260 may detect the closed configuration when an input signal is received from a closed-configuration detection circuit 9265. Electrical contacts of the closed-configuration detection circuit 9265 are disposed on the housing portions 9224*a*, 9224*b* such that the closed-configuration detection circuit 9265 becomes a closed-circuit when the disposable outer housing 9224 is in the closed configuration. The transition to the closed-circuit causes an electrical signal to be transmitted to the control circuit 9260, which causes the control circuit 9260 to detect/confirm the closed configuration.

Figure 78:
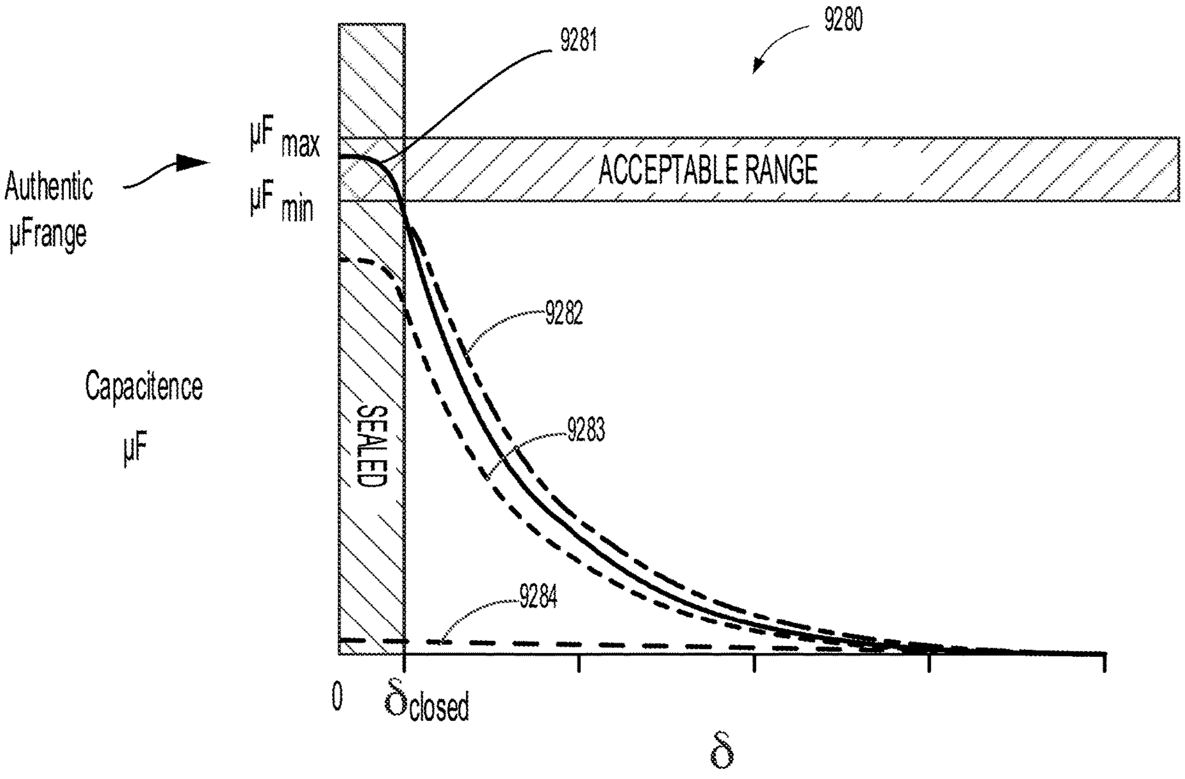
FIG. 78 is a graph for assessing proximity and alignment of the disposable outer housing and the inner core of FIG. 77 in an assembled configuration.
Figure 79:
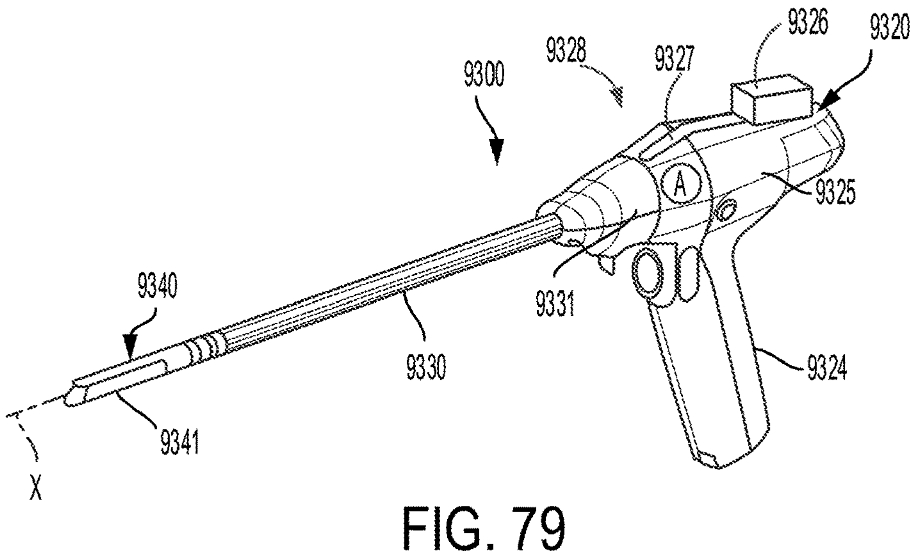
FIG. 79 is a perspective view of a surgical instrument system, in accordance with at least one aspect of the present disclosure.
Figure 80:
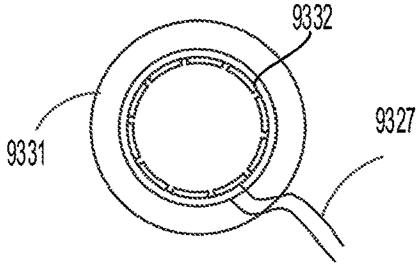
FIG. 80 is a cross-sectional view of a nozzle portion of a shaft assembly of the surgical instrument system of FIG. 79.
Figure 81:
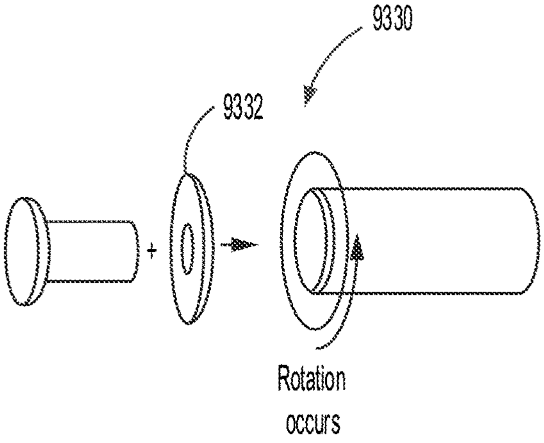
FIG. 81 is a partial exploded view of components of the surgical instrument system of FIG. 79.
Figure 82:
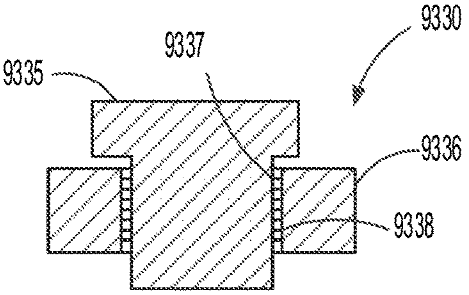
FIG. 82 is a partial cross-sectional view of components of the surgical instrument system of FIG. 79.

Referring to FIG. 78, a graph 9280 is depicted. Distance (δ) between the housing portions 9224*a*, 9224*b* is illustrated on the X-axis, and capacitance measured from the inner core 9222 to the disposable outer housing 9224 is depicted on the Y-axis. In various aspects, the control circuit 9260 is configured to assess a proper assembly of the inner core 9222 with the disposable outer housing 9224 based on the distance between the housing portions 9224*a*, 9224*b*, and based on capacitance measured from the inner core 9222 to the disposable outer housing 9224. Alternatively, the control circuit 9260 can be configured to assess the proper assembly of the inner core 9222 with the disposable outer housing 9224 based on the distance between the inner core 9222 and the disposable outer housing 9224, and based on capacitance measured from the inner core 9222 to the disposable outer housing 9224.

In various aspects, a proper assembly of the inner core 9222 with the disposable outer housing 9224 is detected by the control circuit 9260 when two conditions are met, as represented by curved line 9281 of graph 9280. The first condition is that a detected distance (δ) between a first datum on the first housing-portion 9224*a* and a corresponding second datum on the second housing-portion 9224*b* is less than or equal to a predetermined threshold distance. The second condition is that a detected value of the capacitance measured from the inner core 9222 to the disposable outer housing 9224 is within a predetermined capacitance range ($\mu F_{min}$–$\mu F_{max}$).

In the illustrated example, curved line 9281 represents a properly assembled handle assembly 9220, wherein the inner core 9222 is properly positioned within the disposable outer housing 9224, and wherein the housing portions 9224*a*, 9224*b* are properly sealed in the closed configuration. Conversely, curve lines 9282, 9283, 9284 represent improperly assembled handle assemblies 9220. The curve line 9282 indicates that a closed configuration has not been achieved, and the curve line 9283 indicates that the inner core 9222 is not properly positioned with thin the disposable outer housing 9224.

Capacitance can also be indicative of authenticity of the inner core 9222 and/or the disposable outer housing 9224. In the illustrated example, the predetermined capacitance range ($\mu F_{min}$–$\mu F_{max}$) also represents a capacitance-based authentication range. For example, curved lines 9281, 9282 of graph 9280 represent an authentic inner core 9222 and/or disposable outer housing 9224, while the curved line 9283 on the graph 9280 illustrates non-authentic inner core 9222 and/or disposable outer housing 9224. Additionally, the curved line 9284 indicates the absence of a capacitive identifier from the inner core 9222.

Referring now to FIGS. 79-82, a surgical instrument system 9300 is similar in many respects to other surgical instrument systems described elsewhere herein such as, for example, the surgical instrument systems 8500, 9100, 9200, which are not repeated herein at the same level of detail for brevity. For example, the surgical instrument system 9300 includes a handle assembly 9320, a shaft assembly 9330, and a loading unit including an end effector 9340 that releasably accommodates a staple cartridge 9341. The handle assembly 9320 includes a disposable outer housing 9324 configured to define a sterile barrier 9325. An inner core is positionable within the disposable outer housing 9324. The inner core is configured to drive and/or control various functions of the surgical instrument system 9300, as described elsewhere herein with respect to other similar inner cores.

Further to the above, the surgical instrument system 9300 includes an external power source 9326. In the illustrated example, the external power source 9326 is disposed on to an outer wall of the disposable outer housing 9324. In other examples, the external power source 9326 can be integrated into the disposable outer housing 9324. An electrical interface assembly 9328 is configured to transmit at least one of data and power from the handle assembly 9320 to the end effector 9340. In the illustrated example, the electrical interface assembly 9328 includes a flex circuit 9327 extending between, and coupled to, the external power source 9326 and a data communication band 9332 disposed in a nozzle portion 9331 of the shaft assembly 9330. In the illustrated example, the data communication band 9332 comprises an annular shape that permits rotation of the nozzle portion 9331 and other portions of the shaft assembly 9330 without wire entanglement.

Furthermore, the shaft assembly 9330 includes concentric conductive rings 9337, 9338 that facilitate a transmission of the at least one of power and data therebetween without hindering notation of the shaft assembly 9330. The conductive ring 9337 is disposed on an outer surface of an inner portion 9335, and the conductive ring is disposed on an inner annular surface of an outer portion 9336. In the illustrated example, the inner portion 9335 is concentric with the outer portion 9336.

Figure 83:
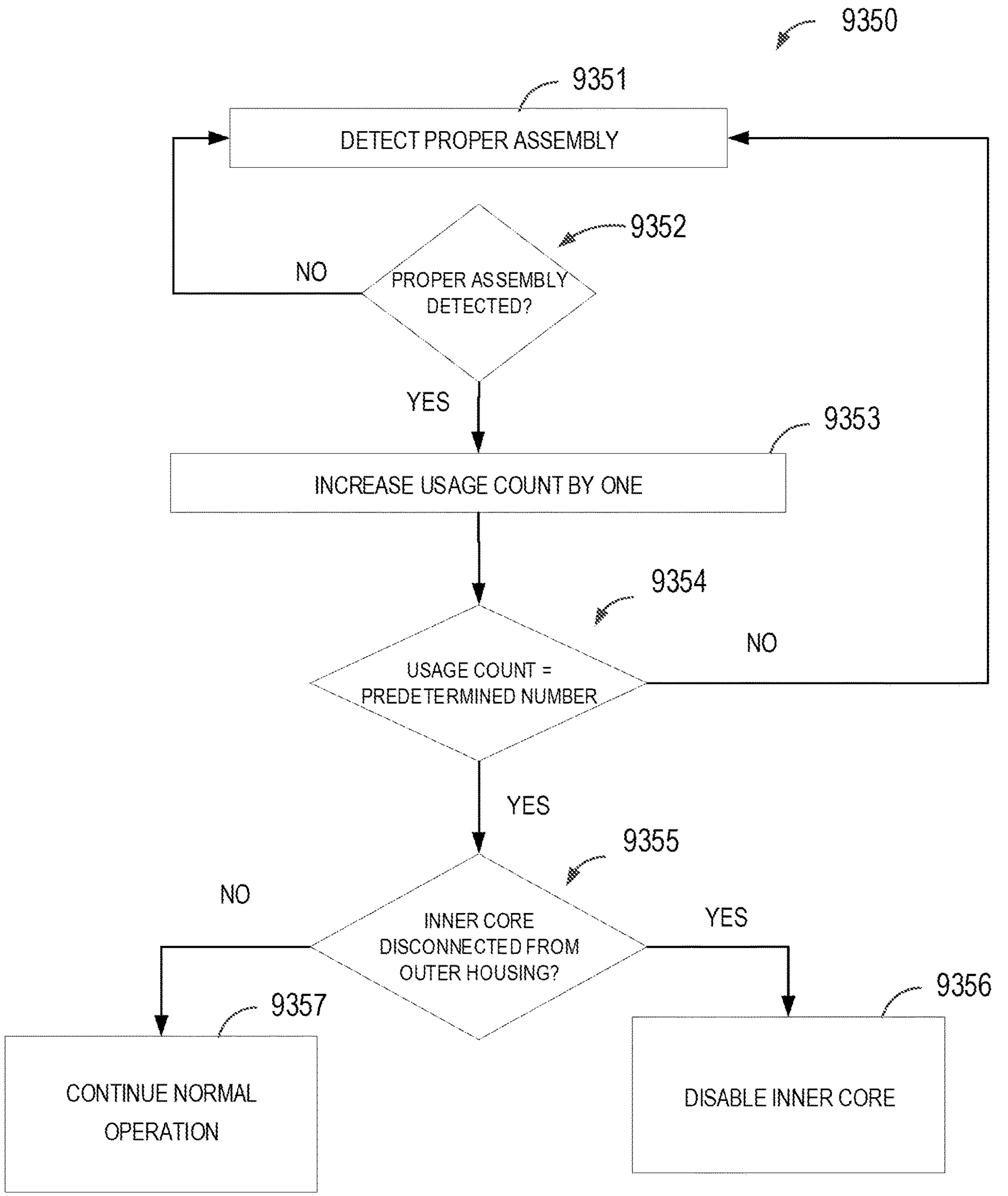
FIG. 83 is a logic flow diagram of a process depicting a control program or a logic configuration for disabling an inner core of a handle assembly of a surgical instrument system at an end-of-life event.

FIG. 83 is a logic flow diagram of a process 9350 depicting a control program or a logic configuration for disabling an inner core of a handle assembly of a surgical instrument system at an end-of-life event. Using the inner core beyond its lifecycle poses a serious risk to the patient. Various circuits and other features of the inner core are carefully designed to ensure a safe operation of the inner core within its lifecycle. Beyond the predetermined lifecycle, however, the inner core may not function properly which, in many events, is not discovered until the handle assembly is actually used in surgery.

In various aspects, the process 9350 can be performed by the handle assembly 9220 of the surgical instrument system 9200, for example. The process 9350 detects 9351 a proper assembly of the inner core 9222 with the disposable outer housing 9224. A control circuit performing one or more aspects of the process 9350 can be configured to detect the proper assembly based on at least one reading of at least one sensor within the outer housing 9224. In at least one example, one or more aspects of the process 9350 can be performed by the control circuit 9260 (FIG. 77). As discussed elsewhere herein in greater detail, the control circuit 9260 can be configured to detect a proper assembly of the inner core 9222 with the disposable outer housing 9224 based on readings from the sensors 9261, 9264, for example.

In any event, if 9352 a proper assembly is detected, a usage count of the inner core 9222 is increased 9353 by one. In at least one example, the control circuit 9260 is in communication with a counter configured to maintain a usage count of the inner core 9222. In certain instances, the control circuit 9260 is configured to store the usage in a memory unit, for example.

Furthermore, if 9354 the usage count becomes equal to a predetermined threshold number, the process 9355 further determines whether the inner core 9222 is disconnected from the disposable outer housing 9224. The disconnection indicates a termination of the usage, or completion of the procedure, that constitutes an end-of-life event based on the usage count. If 9355 it is so, the disconnection triggers a disabling event 9356 of the inner core 9222 to prevent unsafe usage beyond the predetermined end-of-life usage count. Normal operation 9357, however, is continued until the disconnection is detected.

Various suitable mechanisms can be employed to disable the inner core 9222 at an end-of-life event. In at least one example, the control circuit 9260 employees a current limiter to ensure that current within the inner core is maintained below a predetermined threshold during normal operation. To disable the inner core 9222, the control circuit 9260 may remove, disable, or disconnect the current limiter, which causes excessive current to pass through the circuitry of the inner core 9222 thereby disabling the inner core. Disabling the inner core prevents unauthorized use thereof beyond a predetermined lifecycle carefully selected to ensure the safe operation of the handle assembly in surgery.

FIGS. 84-87 illustrate a safety mechanism for disabling a disposable outer housing 9424 of a handle assembly 9420 to protect against unsafe reuse of the disposable outer housing 9424 beyond its design capabilities. The handle assembly 9420 is similar in many respects to other handle assemblies described elsewhere herein, which are not repeated herein for brevity. For example, like the disposable outer housing 9224, the disposable outer housing 9424 is configured to selectively receive and encase inner core 9422 to establish a sterile barrier around the inner core 9422.

Furthermore, the outer housing 9424 includes two housing portions movable relative to one another between a closed, fully coupled configuration, and an open, partially detached, or fully detached, configuration to accommodate insertion of the inner core 9422 therein. When joined, the housing portions define a cavity therein in which inner core 9222 may be selectively situated.

Figure 84:
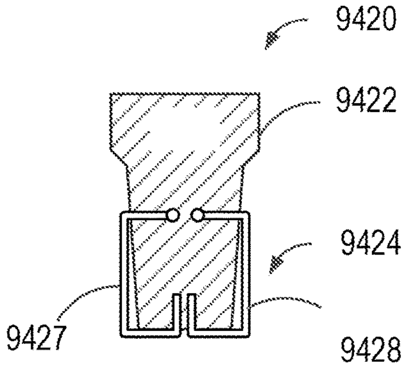
FIGS. 84-87 illustrate safety mechanisms for disabling a disposable outer housing of a handle assembly after usage in a surgical procedure, in accordance with at least one aspect of the present disclosure.
Figure 85:
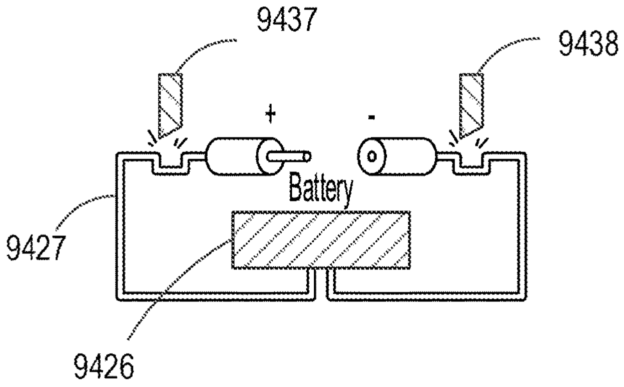
Figure 87:
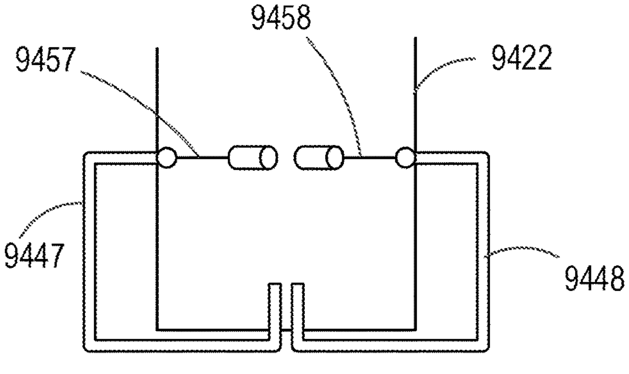
Figure 86:
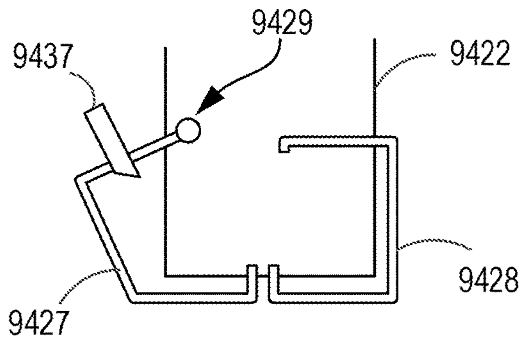

The inner core 9422 includes a power source 9426 that can be in the form of one or more batteries. In an assembled configuration, as illustrated in FIG. 84, connector wires 9427, 9428 electrically connect the inner core 9422 to the disposable outer housing 9424. In various aspects, as illustrated in FIG. 85, the disposable outer housing 9424 includes one or more cutting members 9437, 9438 configured to cut, or several, one or both of the connector wires 9427, 9428 thereby permanently disconnecting a circuit electrically coupling the disposable outer housing 9424 to the inner core 9422, which disables the disposable outer housing 9424, as illustrated in FIG. 86. In an alternative embodiment, as illustrated in FIG. 87, connector wires 9447, 9448, which are similar to the connector wires 9427, 9428, include weekend, or tethering, portions 9457, 9458 that are severed when the housing portions of the disposable outer housing are transitioned to the open configuration.

In certain instances, a connector wire of a disposable outer housing is coupled to an identifier 9429 of the disposable outer housing. In the example illustrated in FIG. 86, the connector wire 9427 is coupled to an RFID chip that is disabled on the connector wire 9427 is cut by the cutting member 9437 during a transition of the disposable outer housing 9424 to an open configuration. Disabling the identifier 9429 prevents an inner core from establishing a successful connection with a used disposable outer housing.

Figure 88:
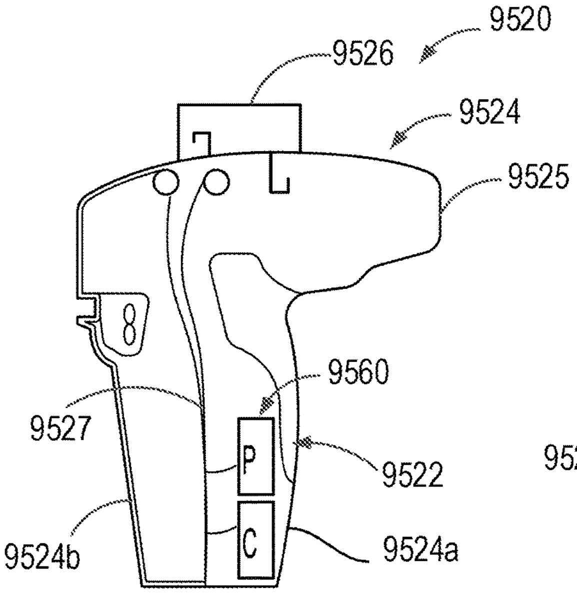
FIGS. 88-91 illustrate safety mechanisms for disabling a disposable outer housing of a handle assembly after usage in a surgical procedure, in accordance with at least one aspect of the present disclosure.
Figure 89:
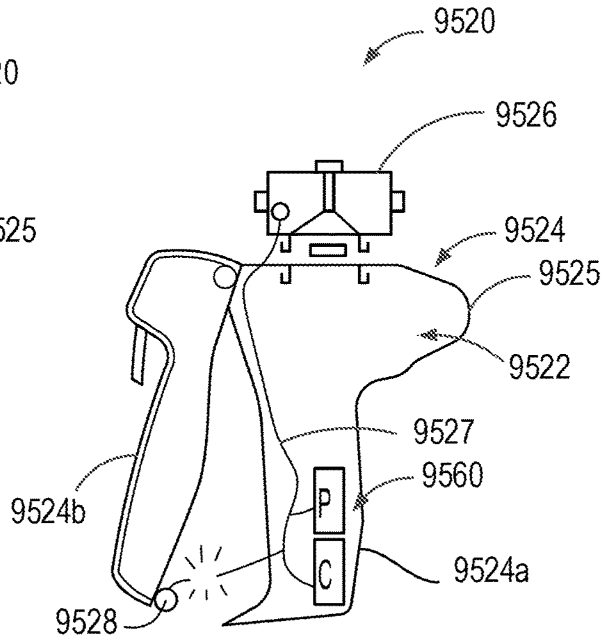

FIGS. 88-89 illustrate additional safety mechanisms for disabling a disposable outer housing 9524 of a handle assembly 9520 to protect against unsafe reuse of the disposable outer housing 9524 beyond its design capabilities. The handle assembly 9520 is similar in many respects to other handle assemblies described elsewhere herein, which are not repeated herein for brevity. For example, like the disposable outer housing 9224, the disposable outer housing 9524 is configured to selectively receive and encase inner core 9522 to establish a sterile barrier 9525 around the inner core 9522.

Furthermore, the outer housing 9524 includes two housing portions **9524*a*, 9524*b* movable relative to one another between a closed, fully coupled configuration (FIG. 88), and an open, partially detached, or fully detached, configuration (FIG. 89) to accommodate insertion of the inner core 9522 therein. The handle assembly 9520 further includes an external power source 9526 connected via a connector wire 9527 extending through the sterile barrier 9525 to a control circuit 9560. In the illustrated example, the external power source 9526 is releasably mounted onto the disposable outer housing 9524, and the connector wire 9527 is severed when the external power source 9526 is released from the disposable outer housing 9524 after completion of the surgical procedure, which disables the disposable outer housing 9524 thereby preventing unsafe reuse thereof. Furthermore, a second wire connector 9528, extending between the housing portion 9524*a*, 9524*b*, can also be severed when the disposable outer handle 9524 is transitioned to the open configuration to prevent unsafe reuse of the disposable outer housing 9524**.

Figure 90:
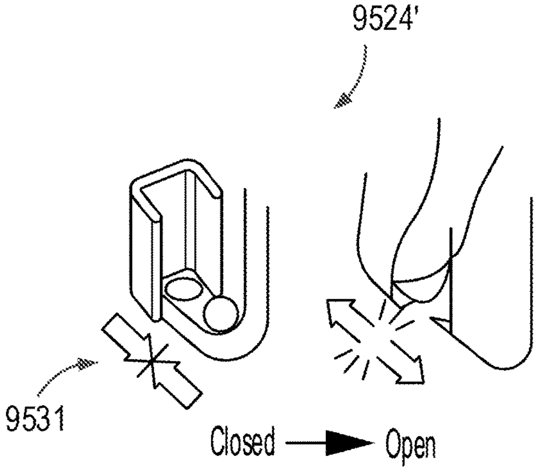
Figure 91:
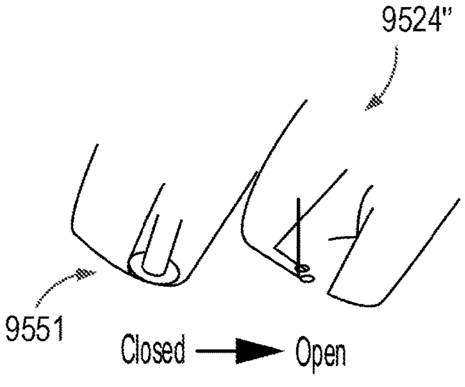
Figure 92:
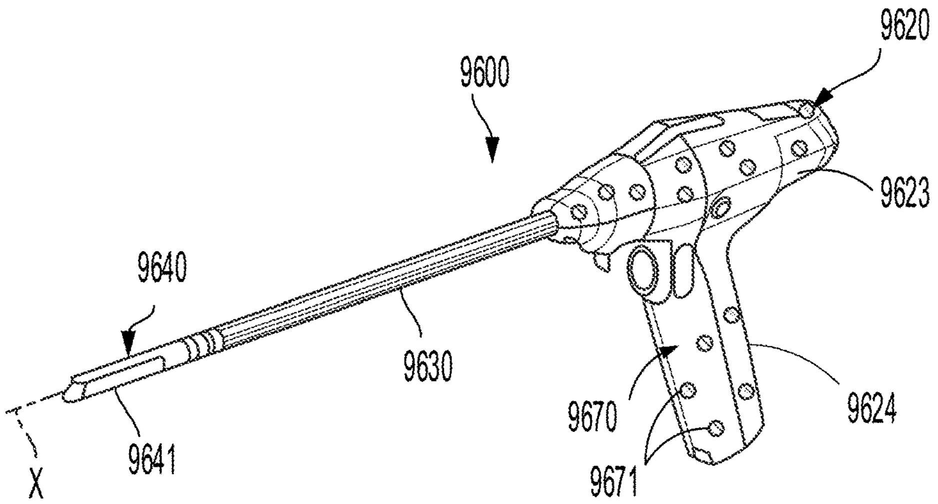
FIG. 92 is a perspective view of a surgical instrument system, in accordance with at least one aspect of the present disclosure.
Figure 93:
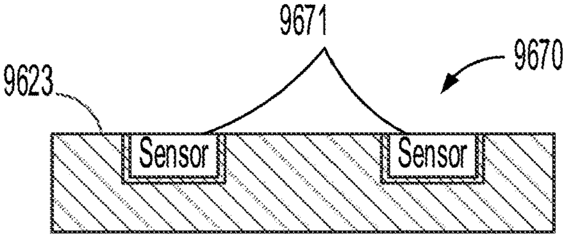
FIG. 93 is a partial cross-sectional view of an outer wall of a handle assembly of the surgical instrument system of FIG. 92.
Figure 94:
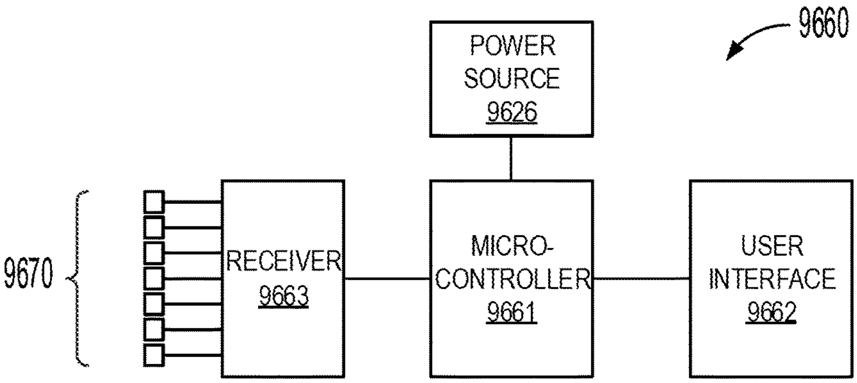
FIG. 94 is a simplified representation of a sterilization-detection circuit of the handle assembly of the surgical instrument system FIG. 92.
Figure 95:
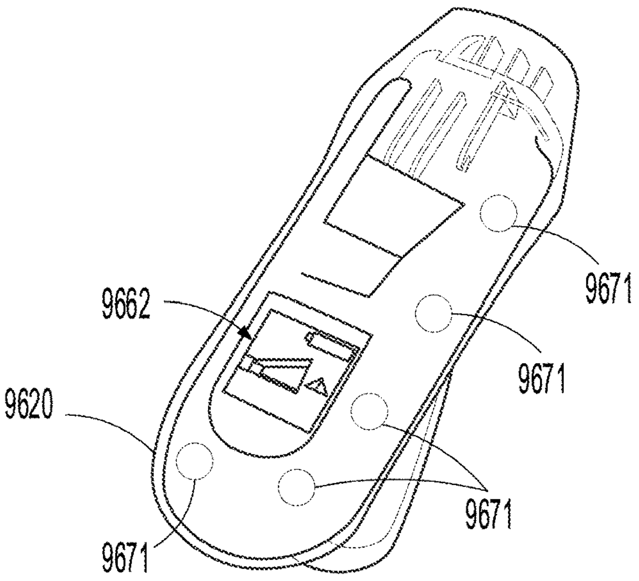
FIG. 95 is a top view of the handle assembly of the surgical instrument system of FIG. 92 showing a light-emitting diode (LED) display thereof.

Further to the above, in various aspects, as illustrated in FIGS. 90-91, one or both of the housing portions **9524*a*, 9524*b* of a disposable outer housing 9524' (FIG. 90), 9524" (FIG. 91) are equipped with a mechanical connector 9531 (FIG. 90), 9551 (FIG. 91) that maintains the housing portions 9524*a*, 9524*b* in a closed configuration, and is severed or broken when the housing portions 9524*a*, 9524*b* are pulled apart after completion of a surgical procedure to recover the inner core 9522**, for example.

Referring now to FIGS. 92-96, a surgical instrument system 9600 is similar in many respects to the surgical instrument systems 8500, 8800. For example, the surgical instrument system 9600 also includes a handle assembly 9620 that includes an inner core which has a motor assembly for motivating one or more drive members configured to effect a closure motion, an articulation motion, and/or a firing motion of an end effector 9640. A shaft assembly 9630 extends between the end effector 9640 and the handle assembly 9620 to transmit drive motion from the inner core to the end effector 9640 to deploy staples from a staple cartridge 9641.

Figure 96:
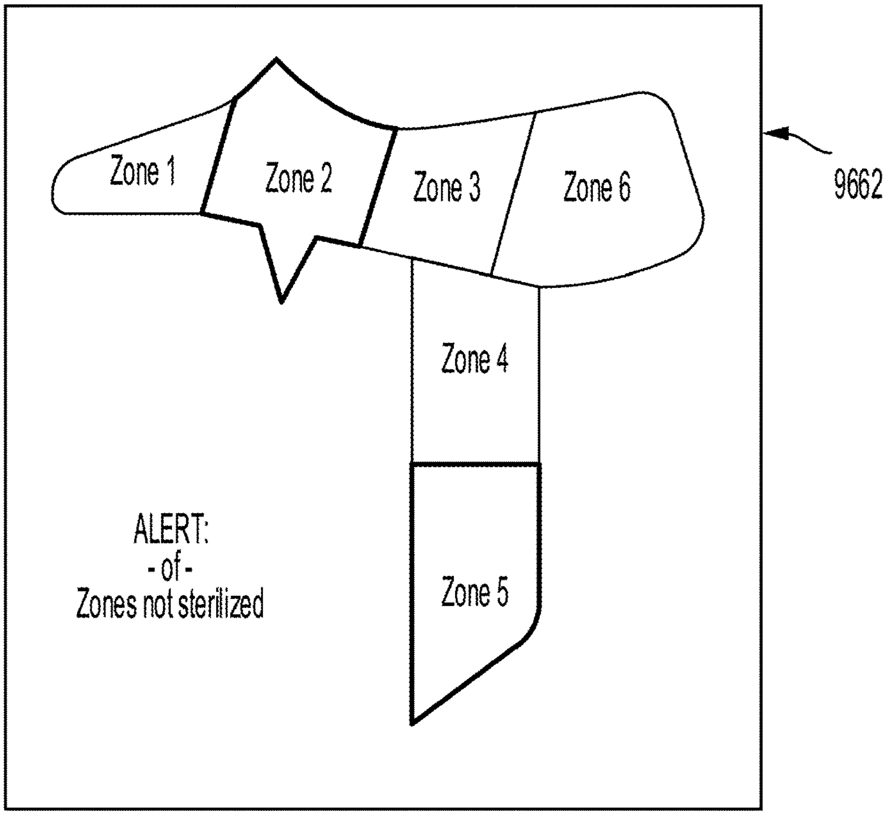
FIG. 96 is an expanded view of the LED display of FIG. 95.

The handle assembly 9620 includes a power source 9626 that can be in the form of one or more batteries. A sterilization-detection circuit 9660 is coupled to the power source 9626 and to a receiver 9663 connected to a sensor array 9670 configured to monitor a sterilization status of the handle assembly 9620. The sensor array 9670 includes a number of sensors 9671 disposed onto an outer surface 9623 of the disposable outer housing 9624. The sensors 9671 are configured to detect the sterilization statuses of various portions, or zones, of the handle assembly 9620, which are then communicated to a microcontroller 9661. The microcontroller 9661 causes a user interface 9662 to present the sterilization statuses, as illustrated in FIG. 96.

In the illustrated example, the user interface 9662 is in the form of an LED display. A representation of the handle assembly 9620 is displayed onto the LED display. Each of the various portions, or zones, of the handle assembly 9620 is shown in one of two different visual indicators representing either an acceptable sterilization status or an unacceptable sterilization status. The microcontroller 9661 assigns one of the two visual indicators to each of the zones based on at least one reading of at least one of the sensors 9671 in such zone. In the illustrated example, zones 2, 5 are assigned an unacceptable sterilization status, while zones 1, 3, 4, 6 are assigned an acceptable sterilization status.

In certain instances, a handle assembly such as, for example, the handle assembly 9620 is re-usable. Accordingly, the handle assembly 9620 is re-sterilized before each use to maintain a sterile surgical field while using the handle assembly 9620 in surgery. In the illustrated example, the handle assembly 9620 is sterilized by exposure to hydrogen peroxide ($H_2O_2$). In at least one example, a clinician may wipe the handle assembly 9620 with hydrogen peroxide wipes to sterilize the handle assembly 9620. In other examples, other means of sterilizing the handle assembly 9620 via hydrogen peroxide can be employed, as described elsewhere in the present disclosure in greater detail.

In certain instances, a handle assembly may include a disposable outer housing and a reusable inner core. In such instances, the sensors 9671 can be disposed onto an outer surface of the inner core to evaluate sterilization statuses of various portions, or zones, of the inner core in a similar manner to that described in connection with the handle assembly 9620.

In the event hydrogen peroxide is employed, the sensors 9671 of the sensor array 9670 are hydrogen peroxide sensors configured to detect the presence of hydrogen peroxide in each of the zones of the handle assembly 9620. Accordingly, the sensor readings of a sensor 9671 can indicate the amount of hydrogen peroxide detected by the sensor 9671 in a portion, or zone, of the handle assembly 9620 where the sensor 9671 resides. As illustrated in graph 9672 of FIG. 97, an acceptable sterilization status corresponds to a reading of the sensor 9671 that is greater than or equal to a predetermined threshold 9673.

Figure 98:
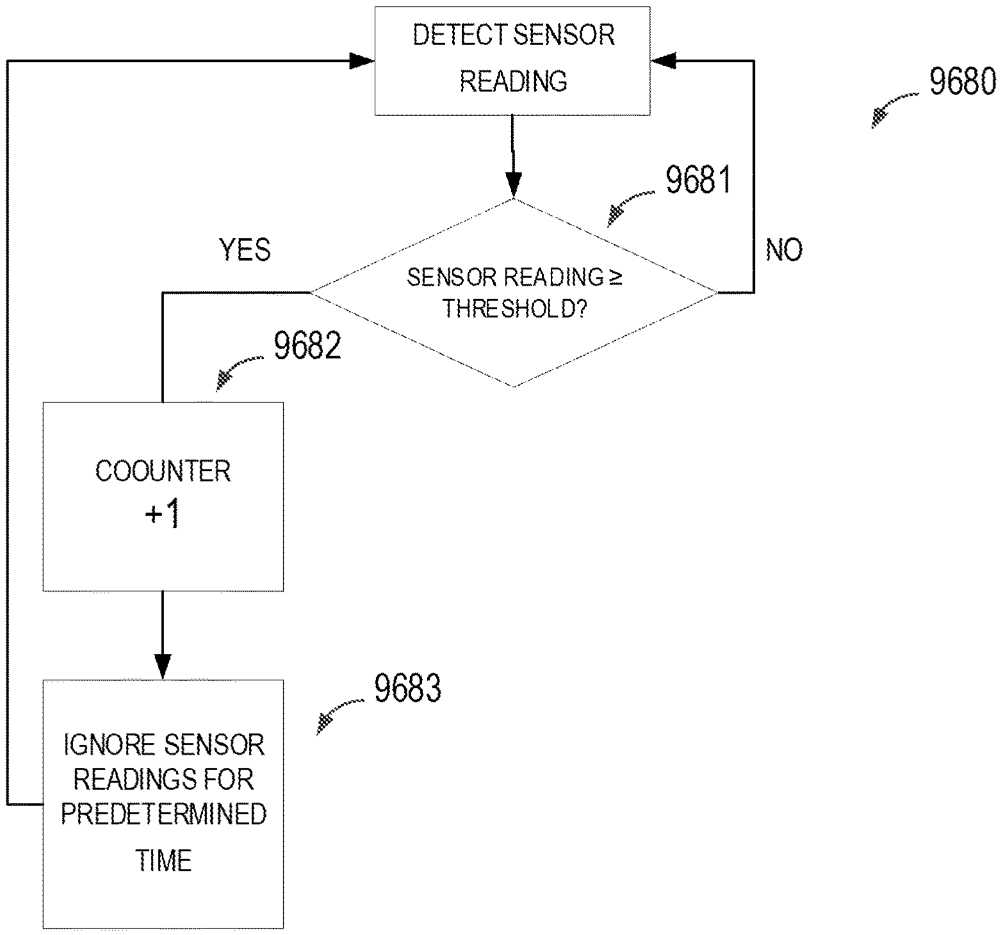
FIG. 98 is a logic flow diagram of a process depicting a control program or a logic configuration for detecting an end of a lifecycle of a re-serializable component of a surgical instrument system, in accordance with at least one aspect of the present disclosure.

Further to the above, FIG. 98 is a logic flow diagram of a process 9680 depicting a control program or a logic configuration for detecting an end of a lifecycle of a reserializable component of a surgical instrument system such, as for example, a handle assembly or an inner core. The process 9680 detects the end of the lifecycle by counting the number of times the component has been re-sterilized.

Figure 97:
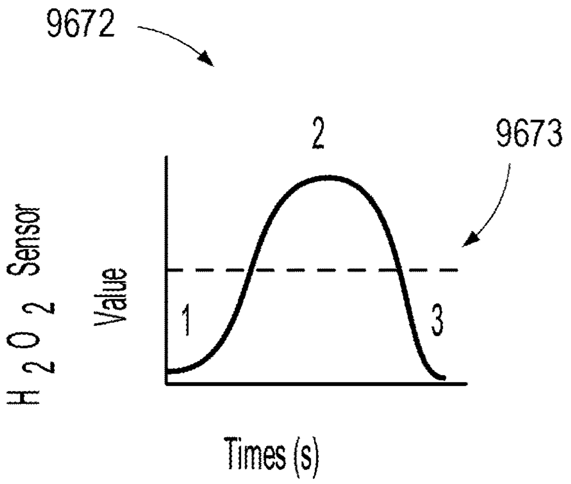
FIG. 97 is a graph illustrating sensor readings of a hydrogen peroxide sensor, in accordance with at least one aspect of the present disclosure.

In at least one example, the process 9680 can be implemented by the sterilization-detection circuit 9660. If 9681 the microcontroller 9661 detects a sensor reading greater than or equal to the predetermined threshold 9673, the microcontroller 9661 increases a count kept by any suitable counter by one. In the event, the re-sterilization is performed by hydrogen peroxide, the sensor reading increases to reach a peak value, then decreases as the hydrogen peroxide begins to evaporate, as illustrated in FIG. 97. To avoid false counts, the microcontroller 9661 is configured to ignore 9683 sensor readings for a predetermined time period.

Figure 99:
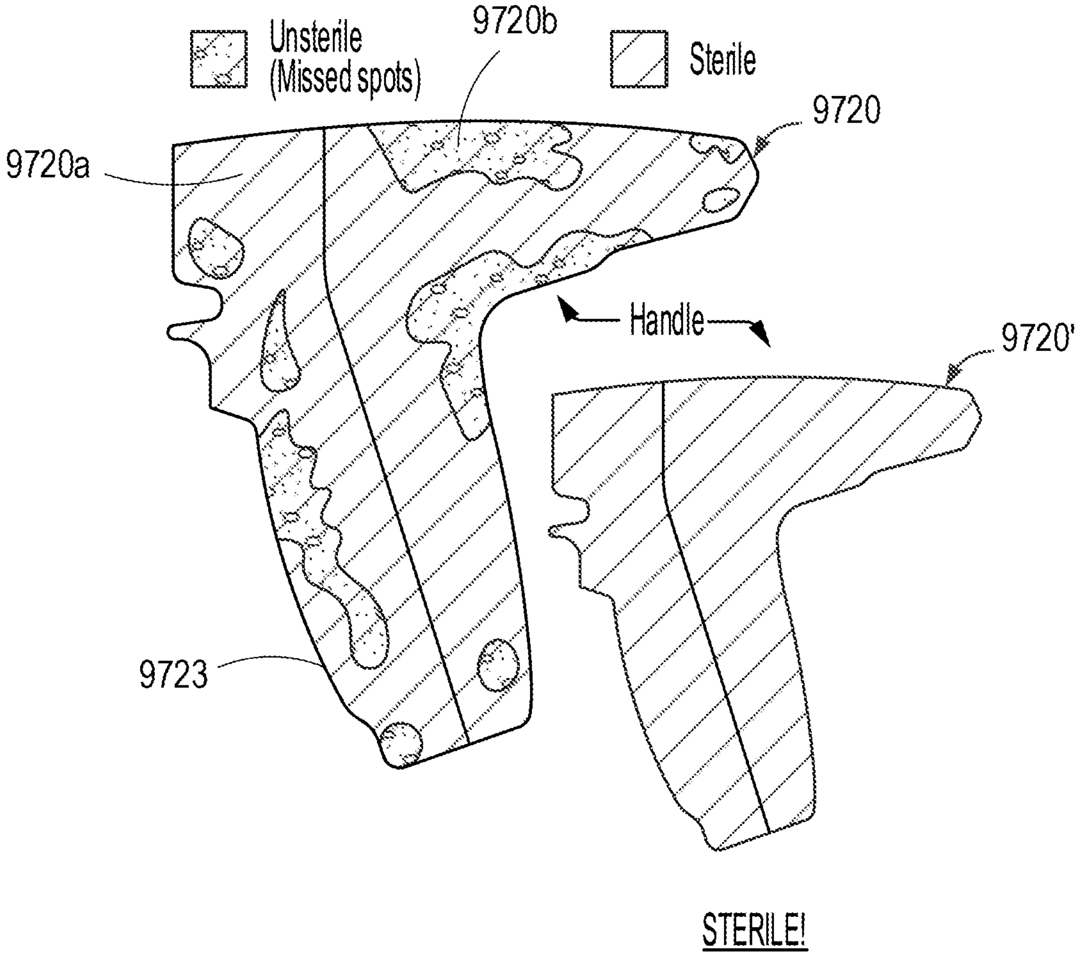
FIG. 99 illustrates a process of re-sterilizing a handle assembly of a surgical instrument system, in accordance with at least one aspect of the present disclosure.

In certain instances, as illustrated in FIG. 99, a component of a surgical instrument system such as, for example, a handle assembly 9720 includes an outer surface 9723 coated with a coating that changes color upon exposure to a sterilization solution such as, for example, hydrogen peroxide. The coating provides a visual indicator of areas 9720*a* of the handle assembly 9720 that have been sufficiently exposed to hydrogen peroxide and areas 9720*b* that have not been sufficiently exposed to hydrogen peroxide. This gives the clinician a chance to ensure application of the sterilization solution to all portions of the handle assembly 9720 with sufficient quantities to yield a properly sterilized handle assembly 9720'.

Figure 100:
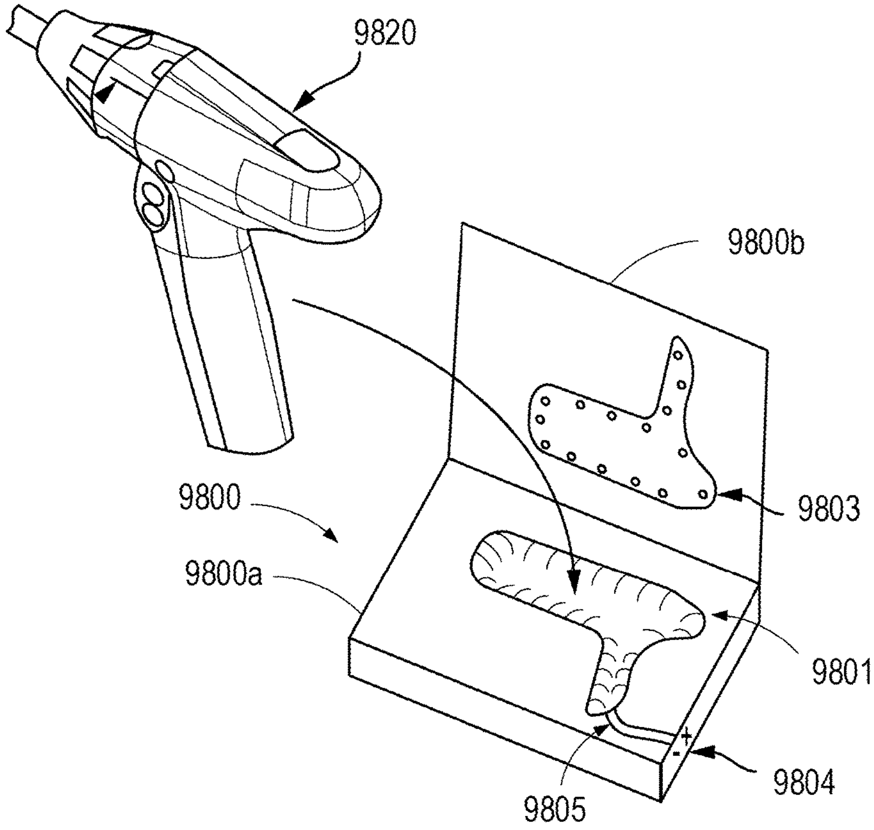
FIG. 100 is a re-serialization system for re-sterilizing a handle assembly of a surgical instrument system, in accordance with at least one aspect of the present disclosure.
Figure 102:
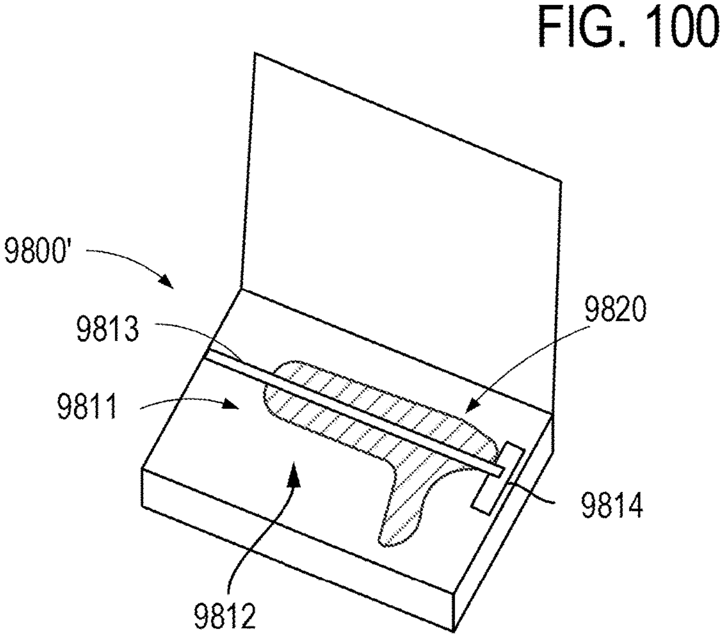
FIG. 102 is a re-serialization system for re-sterilizing a handle assembly of a surgical instrument system, in accordance with at least one aspect of the present disclosure.
Figure 101:
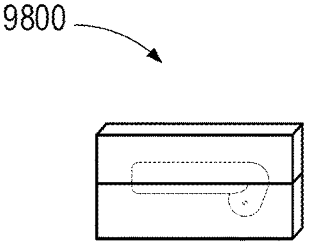
FIG. 101 illustrates the re-serialization system of FIG. 100 in a closed configuration.

Referring now to FIGS. 100-102, a re-sterilization system 9800 is depicted. The re-sterilization system 9800 includes a receiving chamber 9801 configured to accommodate a re-usable handle assembly 9820 of a surgical instrument system. In other instance, however, the re-sterilization system 9800 can be configured to accommodate other components of a surgical instrument system such as, for example, an inner core a handle assembly.

In the illustrated example, the re-sterilization system 9800 includes two portions 9800*a*, 9800*b* movable between an open configuration, FIG. 100, and a closed configuration, FIG. 101, to accommodate the re-usable handle assembly 9820. A receiving chamber 9801 is defined between the portions 9800*a*, 9800*b* of the re-sterilization system 9800. Furthermore, a number of irrigation ports 9806 are defined in the portion 9800*b*. Additionally, or alternatively, irrigation ports can be defined in the portion 9800*a*. Furthermore, the re-sterilization system 9800 includes a charging port 9804 and corresponding connectors 9805 configured to connect the handle assembly 9820 to a charging system while the handle assembly 9820 is in the receiving chamber.

In various aspects, the irrigation ports 9802 are connected to a source of sterilization solution that is delivered through the irrigation ports 9802 into the receiving chamber 9801. A pump can be utilized to inject the sterilization solution through the irrigation ports 9802 and to remove it in a re-sterilization cycle. In an alternative embodiment, as illustrated in FIG. 101, a re-sterilization system 9800' includes a receiving chamber 9811 that includes an absorbent material or cloth 9812 saturated with a sterilization solution. A motor 9814 causes a driver 9813 to repeatedly move the cloth 9812 between a starting position and an end position relative to a handle assembly 9820 to re-sterilize the handle assembly. Alternatively, the motor 9814 may cause the driver 9813 to move the handle assembly 9820 between a starting position and an end position relative to the cloth 9812.

Figure 103:
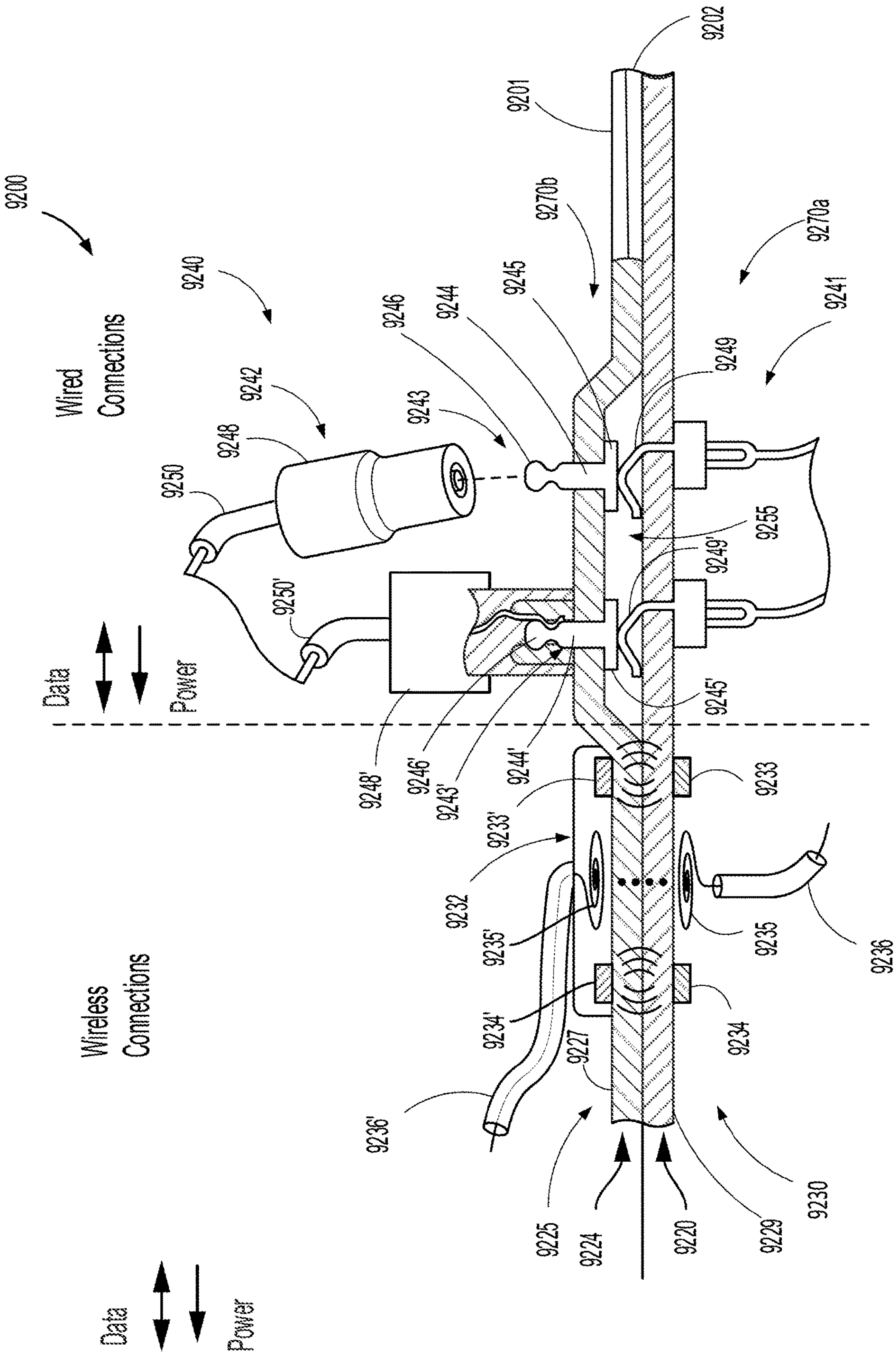
FIG. 103 is a primary electrical interface for use with a surgical instrument system, in accordance with at least one aspect of the present disclosure.

Referring now to FIGS. 77 and 103, in certain instances, the primary interface assembly 9270 includes a wireless electrical interface 9230 and a wired electrical interface 9240. As illustrated in FIG. 103, the wireless electrical interface 9230 and the wired electrical interface 9240 are configured to transmit at least one of data and power through the sterile barrier 9225. The at least one of power and data can be transmitted between the inner core 9222 and an end effector and/or a shaft assembly of the surgical instrument system 9200. In various aspects, the first wireless interface portion 9231 and the second wireless interface portion 9232 are configured to cooperatively form a wireless segment of an electrical pathway between the inner core 9222 and the end effector and/or between the inner core 9222 and the shaft assembly. Additionally, one or more flex circuits can be configured to define one or more segment of the electrical pathway.

In the illustrated example, the wireless electrical interface 9230 includes a first wireless interface portion 9231 housed by the inner core 9222, and a second wireless interface portion 9232 releasably attachable to an outer wall 9227 of the disposable outer housing 9224. In other examples, the second wireless interface portion 9232 is integrated with the outer wall 9227 of the disposable outer housing 9224. In the illustrated example, the first wireless interface portion 9231 is located within an outer wall 9229 of the inner core 9222. In other examples, however, the first wireless interface portion 9231 can be, at least partially, disclosed on an outer surface of the outer wall 9229.

Further to the above, second wireless interface portion 9232 is magnetically couplable to the first wireless interface portion 9231 when the inner core 9222 is properly positioned within the disposable outer housing 9224. In the illustrated example, the second wireless interface portion 9232 includes attachment elements 9233', 9234' therefore magnetically couplable to corresponding attachment elements 9233, 9234 of the first wireless interface portion 9231. In certain instances, the attachment elements 9233', 9234' are magnetic elements, and the corresponding attachment elements 9233, 9234 are ferrous elements. In other instances, the attachment elements 9233', 9234' are ferrous elements, and the corresponding attachment elements 9233, 9234 are magnetic elements. In other instances, the attachment elements 9233', 9234' and the corresponding attachment elements 9233, 9234 are magnetic elements.

The attachment elements 9233, 9234, 9233', 9234' cooperate to ensure a proper alignment between an inductive element 9235 of the first wireless interface portion 9231 and a corresponding inductive element 9235' of the second wireless interface portion 9232, as illustrated in FIG. 103. In the illustrated example, the inductive elements 9235, 9235' are in the form of wound wire coils that are components of inductive circuits 9236, 9236', respectively. The wire coils of the inductive elements 9235, 9235' comprise a copper, or copper alloy, wire; however, the wire coils may comprise suitable conductive material, such as aluminum, for example. The wire coils can be wound around a central axis any suitable number of times.

When a proper magnetic attachment is established by the elements 9233, 9234, 9233', 9234', as illustrated in FIG. 103, the wire coils of the inductive elements 9235, 9235' are properly aligned about a central axis extending therethrough. The proper alignment of the wire coils of the inductive elements 9235, 9235' improves the wireless transmission of the at least one of data and power therethrough.

Further to the above, the wired electrical interface 9240 includes a first wired interface portion 9241 on the first side of the sterile barrier 9225, and a second wired interface portion 9242 on the second side of the sterile barrier 9225. In the example illustrated in FIG. 103, the wired electrical interface 9240 further includes connectors 9243, 9243' configured to cooperate with the first wired interface portion 9241 and second wired interface portion 9242 to facilitate a wired transmission of at least one data and power through the sterile barrier 9225 without contaminating the sterile environment protected by the sterile barrier 9225.

In the illustrated example, the wired electrical interface 9240 defines two wired electrical pathways extending through the sterile barrier 9225. In other examples, however, the wired electrical interface 9240 may define more or less than two wired electrical pathways.

The connectors 9243, 9243' include bodies 9244, 9244' that extend through the outer wall 9227 of the disposable outer housing 9224. The connectors 9243, 9243' further include inner contacts 9245, 9245' that are inside the disposable outer housing 9224, and outer contacts 9246, 9246' that are outside the disposable outer housing 9224. In the illustrated example, the second wired interface portion 9242 includes flex circuits 9250, 9250' terminating at connectors 9247, 9247' configured to form a sealed connection with the outer contacts 9246, 9246'. In the illustrated example, the connectors 9247, 9247' comprise insulative outer housings 9248, 9248' configured to receive and guide the outer contacts 9246, 9246' into an electrical engagement with corresponding electrical contacts of the flex circuit 9250, 9250'.

In various examples, the bodies 9244, 9244' are tightly fitted through the outer wall 9227 of the disposable outer housing 9224 to prevent, or at least resist, fluid contamination. In addition, the insulative outer housings 9248, 9248' comprise flush ends that rest against an outer surface of the outer wall 9227 to prevent, or at least resist, fluid contact with the outer contacts 9246, 9246' in operation.

Furthermore, the inner contacts 9245, 9245' of the connectors 9243, 9243' are configured to engage leaf spring contacts 9249, 9249' when the inner core 9222 is properly assembled with the disposable outer housing 9224. In the illustrated example, the outer walls 9227, 9229 comprise portions that are flush with one another to facilitate the wireless connection between the first wireless interface portion 9231 and the second wireless interface portion 9232. In addition, the outer walls 9227, 9229 also comprise portions that are spaced apart to facilitate the wired connection between the inner contacts 9245, 9245' and the leaf spring contacts 9249, 9249'. In the illustrated example, a portion of the outer wall 9227 is slightly raised, which forms an isolated chamber 9255 between the outer walls 9227, 9229. The isolated chamber 9255 has a predetermined depth that ensures a good electrical contact between the inner contacts 9245, 9245' and the leaf spring contacts 9249, 9249' in the assembled configuration, as illustrated in FIG. 103.

In various aspects, one or more of the surgical instrument systems of the present disclosure include a display for providing feedback to a user, which may include information about one or more characteristics of the tissue being treated and/or one or more parameters of the surgical instrument system. For example, the display may provide the user with information regarding the size of a staple cartridge assembled was the surgical instrument system and/or a measured thickness of the tissue being treated. In various aspects, the display can be a flexible display, for example.

In the example illustrated in FIG. 103, a flexible display 9201 is incorporated into the disposable outer housing 9224. A microcontroller 9202 resides beneath the flexible display 9201. The flexible display 9201 is configured to face the outside of the disposable outer housing 9224, while the microcontroller 9202 is configured to face the inside of the disposable outer housing 9224. The flexible display 9201 can connected through a wireless or a wired electrical interface to a suitable power source. In at least one example, the flexible display 9201 is powered by the power source 9226 of the inner core 9222. In at least one example, the flexible display 9201 is powered by an external power source attachable to the disposable outer housing 9224.

In other examples, the flexible display 9201 can be incorporated into a shaft of a surgical instrument system. In such examples, the flexible display 9201 is bent to conform to, or at least substantially conform to, the cylindrical shape of the shaft. In certain instances, the flexible display 9201 is incorporated into an outer wall of the shaft. In other instances, however, the flexible display 9201 is positioned underneath, or inside, the shaft, and is visible through a clear outer wall of the shaft. Positioning the flexible display 9201 on the disposable outer housing 9224, or within the shaft, helps against fog accumulation on the display which may occur if a display is located with the inner core 9222 inside the disposable outer housing 9224 due to the heat generated by the motor assembly of the inner core 9222.

Figure 104:
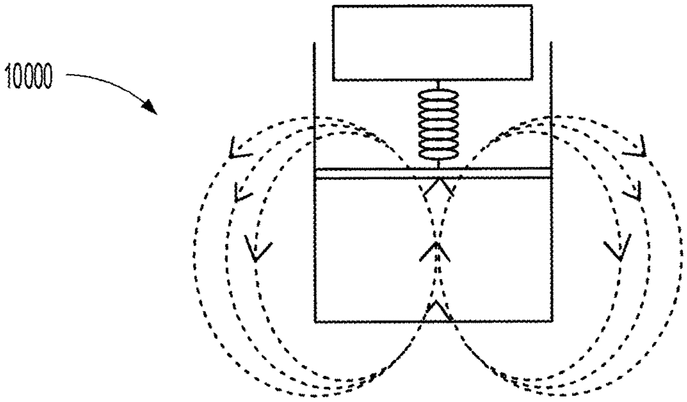
FIG. 104 is an actuator for use with a surgical instrument system, in accordance with at least one aspect of the present disclosure.
Figure 105:
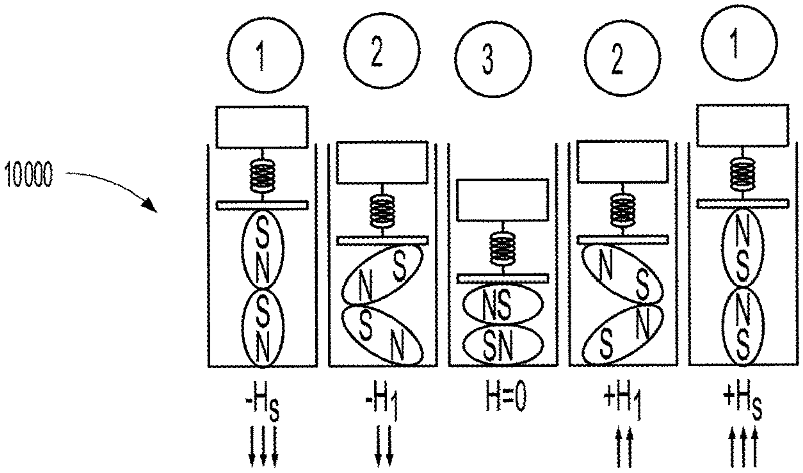
FIG. 105 illustrates the actuator of FIG. 104 in different configurations yielding different closure forces, in accordance with at least one aspect of the present disclosure.
Figure 106:
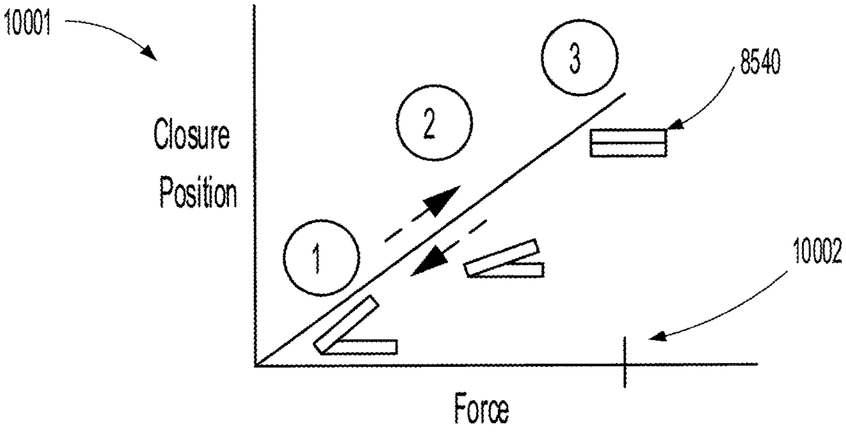
FIG. 106 is a graph illustrating different closure positions of an end effector and corresponding closure forces as determine based on the different configurations of FIG. 105.

Referring now to FIGS. 104-106, an actuator 10000 can be incorporated into a handle assembly of a surgical instrument system such as, for example, the handle assembly 8520 of the surgical instrument system 8500, the handle assembly 9220 of the surgical instrument system 9200, and/or the handle assembly 9120 of the surgical instrument system 9100. The actuator 10000 can be configured to cause an inner core 8522, for example, to produce drive motions to close, fire, and/or articulate the end effector 8540 that are proportional a mechanical pressure applied by a user, as detected by the actuator 10000. In various aspects, the actuator 10000 comprises a magnetostrictive transducer configured to change a magnetic field in response to the amount of force applied thereto. FIG. 105 illustrates different actuation configurations of the actuator 10000, and the amount of strain produced from null magnetization (configuration 1) to full magnetization (configurations 1, 5). The actuator 10000 is divided into discrete mechanical and magnetic attributes that are coupled in their effect on the magnetostrictive core strain and magnetic induction.

Referring still to FIG. 105, where no magnetic field is applied, a change in length will also be null along with the magnetic induction produced. Further, the amount of the magnetic field (H) is increased to its saturation limits (±Hsat) at configurations 1, 5. This causes an increase in the axial strain to a maximum value. Configurations 2, 4 represent an intermediate increase in the value of the magnetization but to a lesser extent (±$H_1$) than the configurations 1, 5. The maximum strain saturation and magnetic induction is obtained at the saturation limits (±Hsat). Flux lines associated with configurations 1, 2 are in the opposite direction to flux lines of configurations 4, 5. These flux fields produced are measured using the principle of Hall Effect or by calculating the voltage produced in a conductor kept in right angle to the flux produced, for example. This value will be proportional to the input strain or force.

Accordingly, a control circuit 8560, for example, may adjust the drive motions produced by the inner core 8522, for example, based on readings of a magnetic sensor configured to measure the flux fields generated by the actuator 10000 in response to an actuation force applied by a user to the actuator 10000. FIG. 106 is a graph 10001 that illustrates changes in closure position (Y-axis) of the jaws of the end effector 8540, for example, in response to actuation force (X-axis) applied by a user, as detected by the actuator 10000. In the illustrated example, a fully closed configuration of the end effector 8540 corresponds to a predetermined actuation force threshold 10002, which corresponds to configuration 5 of the actuator 10000, as illustrated in FIG. 105. If the predetermined actuation force threshold 10002 is detected by the control circuit 8560, based on readings of the magnetic sensor, the control circuit 8560 causes the drive motions to stop by deactivating one or more motors of the inner core 8522, for example. Furthermore, the control circuit 8560 may further reverse the direction of rotation of the motor to transition the end effector 8540 back to the open configuration.

The example illustrated in FIGS. 104-106 illustrate the utilization of the actuator 10000 as an end effector closure actuator. In other examples, the actuator 10000 can be similarly utilized to effect and control a firing motion and/or an articulation motion of the end effector 8540, for example.

Figure 107:
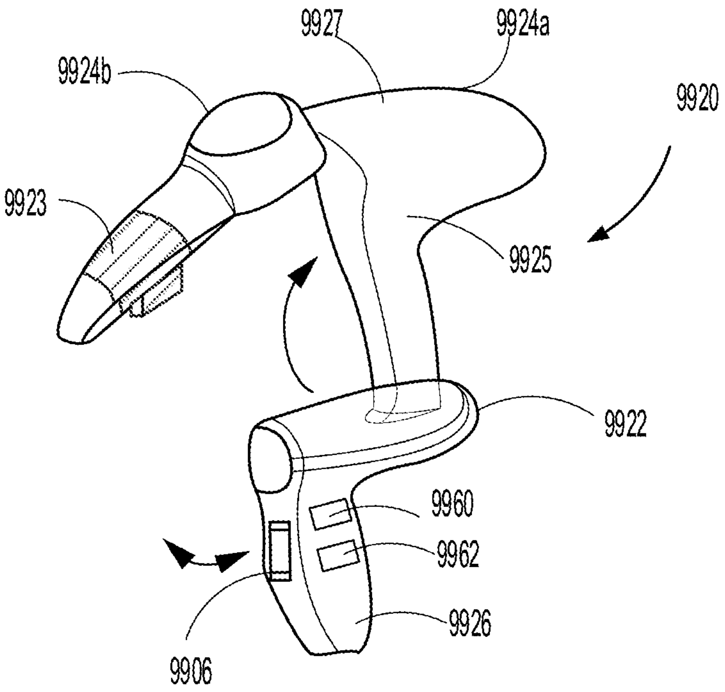
FIG. 107 is a perspective view of a disposable outer housing and an inner core of a handle assembly, in accordance with at least one aspect of the present disclosure.
Figure 108:
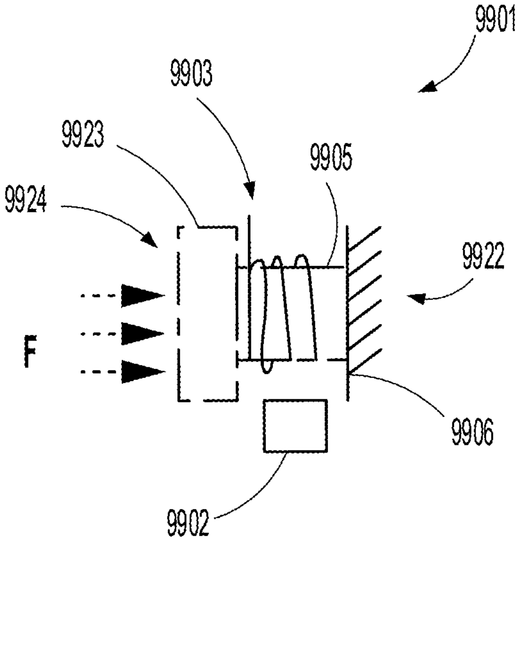
FIG. 108 is a partial cross-sectional view of an actuator of the handle assembly of FIG. 107.

Referring now to FIGS. 107 and 108, a handle assembly 9920 is similar in many respects to other handle assemblies described elsewhere herein such as, for example, the handle assemblies 8520, 9120, 9220, which are not repeated herein for brevity. For example, the handle assembly 9920 also includes an inner core 9922 which has a motor assembly for motivating one or more drive members configured to effect a closure motion, an articulation motion, and/or a firing motion in an end effector (e.g. end effector 8540). The handle assembly 9920 further includes a disposable outer housing 9924 that includes two housing portions **9924*a*, 9924*b* releasably attached to one another to permit assembly with the inner core 9922. When joined, the housing portions 9924*a*, 9924*b* define a cavity therein in which inner core 9922 may be selectively situated within a sterile barrier 9925 defined by an outer wall 9927 of the disposable outer housing 9924**.

Further to the above, the handle assembly 9920 includes an actuator 9901 configured to transform changes in an external actuation force (F) applied by a user to the actuator 9901 into changes in an internal magnetic field detectable by one or more magnetic field sensors 9902 within the handle assembly 9920. The actuator 9901 permits an accurate detection by the inner core 9922 of the changes in the external actuation force (F) without compromising the sterile barrier 9925.

In the illustrated example, the housing portion **9924*b* includes a pressure-sensitive actuation member 9923 configured to detect the changes in the external actuation force (F). A stem 9905 extends from the pressure-sensitive actuation member 9923 inside the disposable outer housing 9924, and is configured to abut against a rigid surface 9906 of the inner core 9922 when the inner core 9922 is properly assembled with the disposable outer housing 9924, as illustrated in FIG. 108. A wire coil 9903 is wound around the stem 9905, and is configured to form a magnetic field when a current is passed therethrough. In at least one example, the wire coil 9903 is a part of a circuit powered by a power source 9926 of the inner core 9922, for example. In a similar manner to that described in connection with the actuator 10000, changes in the external actuation forces (F) applied to the pressure-sensitive actuation member 9923 cause changes in a magnetic field generated by the wire coil 9903**, which correspond to the changes in the external actuation forces (F).

In the illustrated example, the inner core 9922 includes a control circuit 9960 connected to the magnetic field sensor 9902. The control circuit 9960 is also connected to a motor assembly 9962 of the inner core 9922, and is configured to cause the motor assembly 9962 to adjust drive motions generated by the motor assembly 9962 in accordance with changes in the external actuation forces (F) as detected by the control circuit 9960 based on readings of the magnetic field sensor 9902. In various aspects, the drive motions are configured to close, fire, and/or articulate an end effector operably coupled to the hand assembly 9920. In certain aspects, the control circuit 9960 includes a storage medium such as, for example, a memory unit that stores one or more databases, formulas, and/or tables that can be utilized to select one or more parameters of the drive motions based on the readings of the magnetic field sensor 9902.

In various aspects, the wire coil 9903 comprise a copper, or copper alloy, wire; however, the wire coil 9903 may comprise suitable conductive material, such as aluminum, for example. The wire coil 9903 can be wound around the stem 9905 any suitable number of times.

Figure 109:
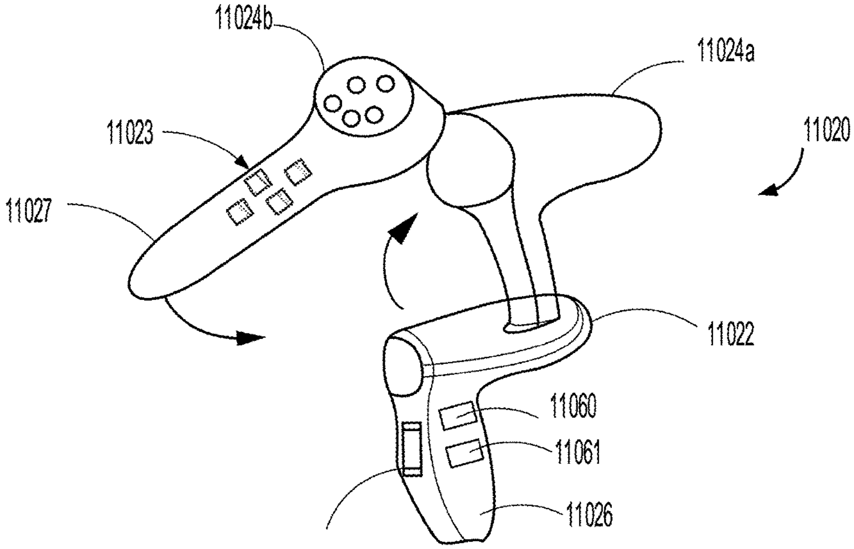
FIG. 109 is a perspective view of a disposable outer housing and an inner core of a handle assembly, in accordance with at least one aspect of the present disclosure.
Figure 110:
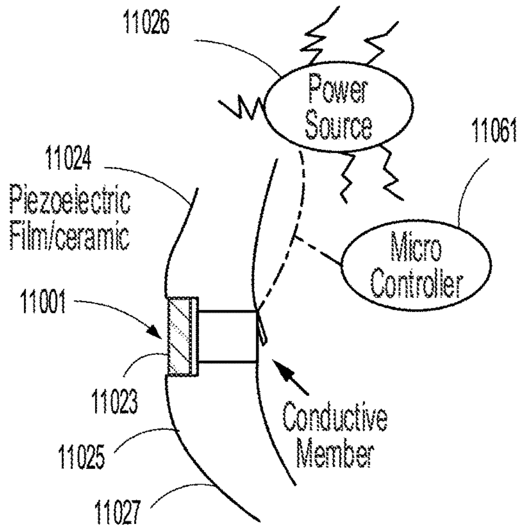
FIG. 110 is a partial cross-sectional view of an actuator of the handle assembly of FIG. 109.

Referring now to FIGS. 109 and 110, a handle assembly 11020 is similar in many respects to other handle assemblies described elsewhere herein such as, for example, the handle assemblies 9920, 8520, 9120, 9220, which are not repeated herein for brevity. For example, the handle assembly 11020 also includes an inner core 11022 which has a motor assembly for motivating one or more drive members configured to effect a closure motion, an articulation motion, and/or a firing motion in an end effector (e.g. end effector 8540). The handle assembly 11020 further includes a disposable outer housing 11024 that includes two housing portions 11024*a*, 11024*b* releasably attached to one another to permit assembly with the inner core 11022. When joined, the housing portions 11024*a*, 11024*b* define a cavity therein in which inner core 11022 may be selectively situated within a sterile barrier 11025 defined by an outer wall 11027 of the disposable outer housing 11024.

Figure 111:
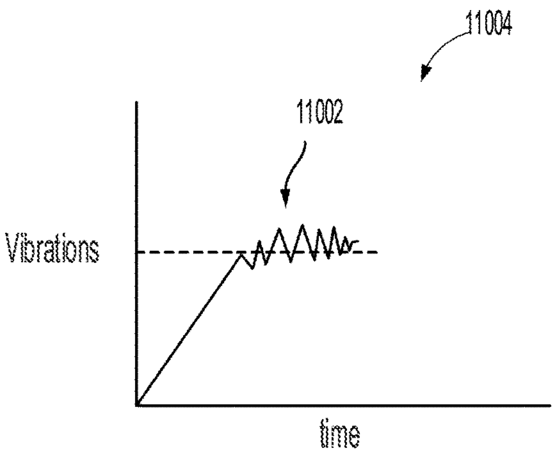
FIG. 111 is a graph vibrations, on the Y-axis, as a function of time on the x-axis.

Further to the above, the handle assembly 11020 includes an actuator 11001 configured to detect an external compression force (F) applied by a user to the actuator 9901 and, in response, cause an electromechanical member 11023 to produce vibrations when the external actuation force (F) is greater than or equal to a predetermined threshold 11002, as illustrated in graph 11004 of FIG. 111. In at least one example, the electromechanical member 11023 is in the form of a piezoelectric film or, alternatively, a ceramic member. The electromechanical member 11023 is coupled to a power source 11026 of the inner core 11022 which supplies power to the electromechanical member 11023 when a conductive member 11003 closes a circuit connecting the electromechanical member 11023 to the power source 11026.

Figure 112:
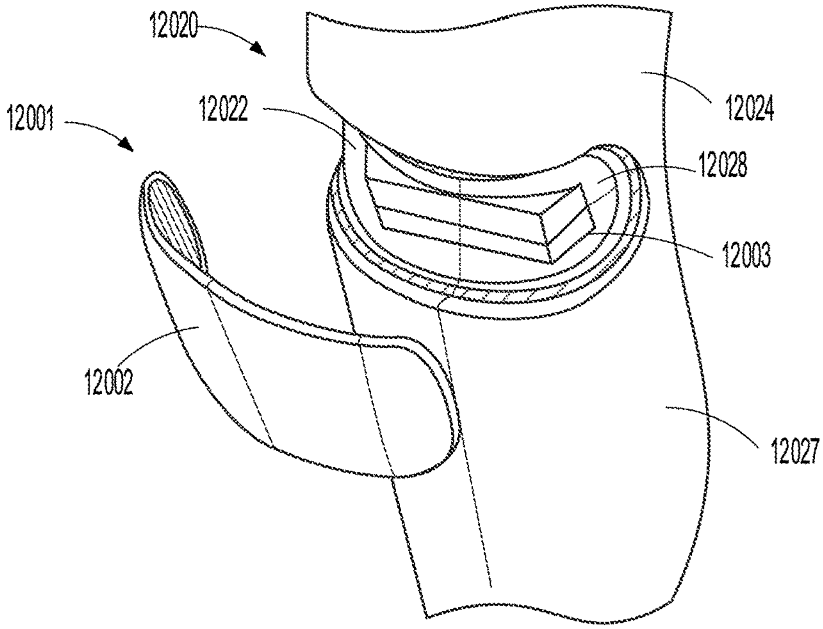
FIG. 112 is a partial exploded view of a handle assembly, in accordance with at least one aspect of the present disclosure.
Figure 113:
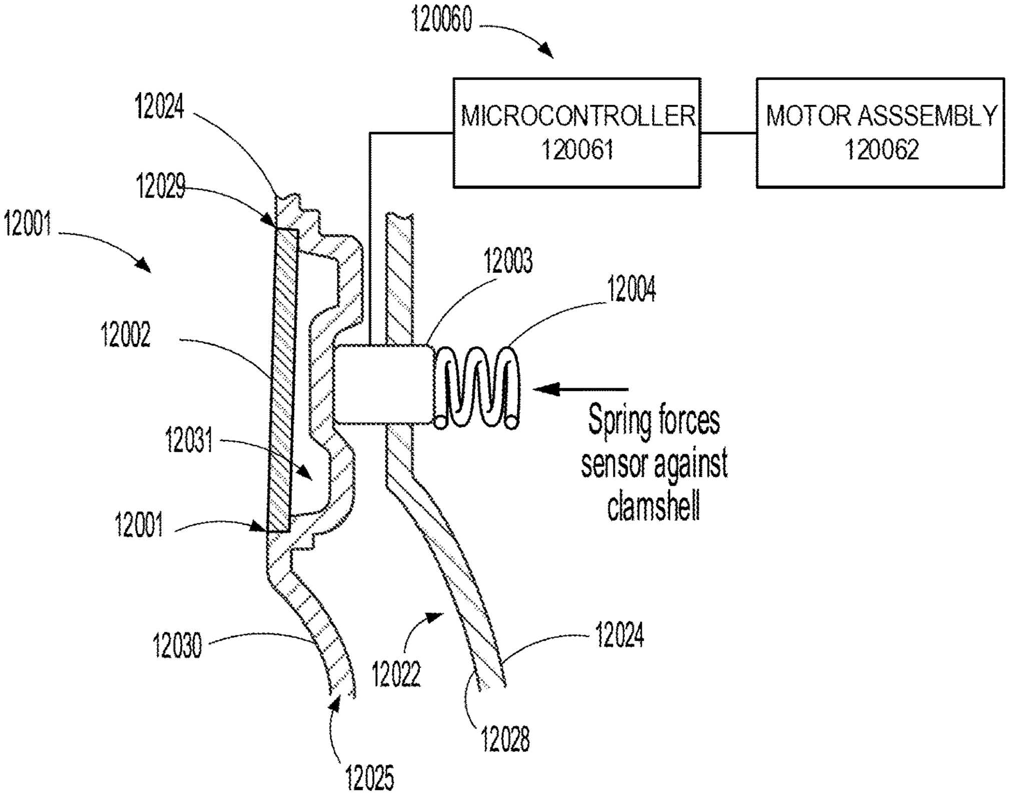
FIG. 113 is a partial cross-sectional view of an actuator of the handle assembly of FIG. 112.

Referring now to FIGS. 112 and 113, a handle assembly 12020 is similar in many respects to other handle assemblies described elsewhere herein such as, for example, the handle assemblies 9920, 8520, 9120, 9220, 11020, which are not repeated herein for brevity. For example, the handle assembly 12020 also includes an inner core 12022 which has a motor assembly for motivating one or more drive members configured to effect a closure motion, an articulation motion, and/or a firing motion in an end effector (e.g. end effector 8540). The handle assembly 12020 further includes a disposable outer housing 12024 that includes two housing portions releasably attached to one another to permit assembly with the inner core 12022. When joined, the housing portions define a cavity therein in which inner core 12022 may be selectively situated within a sterile barrier 12025 defined by an outer wall 12027 of the disposable outer housing 12024.

Further to the above, the handle assembly 12020 includes an actuator 12001 configured to detect an external compression force (F) applied by a user to the actuator 12001. The detection occurs across the sterile barrier 12025. Said another way, the external compression force (F) is applied on a first side of sterile barrier 12025, and is detected on a second side, opposite the first side, of the sterile barrier 12025, without compromising the sterile barrier 12025. In the illustrated example, the actuator 12001 includes components on both sides of the sterile barrier 12025 that are capable of a magnetic interaction across the sterile barrier 12025. A ferromagnetic plate, or film, 12002 is positioned outside the disposable outer housing 12024, and a corresponding magnetic sensor 12003 is positioned inside the disposable outer housing 12024. A movement of the ferromagnetic plate 12002, in response to the external compression force (F), causes a change in the readings of the magnetic sensor 12003 commensurate with the change in position of the ferromagnetic plate 12002 caused by the external compression force (F).

Furthermore, a control circuit 120060 of the handle assembly 12020 may include a microcontroller 120061 configured to adjust drive motions of a motor assembly 120062 in accordance with the readings of the magnetic sensor 12003. The drive motions may effect one or more of a closure motion, a firing motions, and an articulation motion of an end effector, for example.

In the illustrated example, the ferromagnetic plate 12002 extends across a cavity 12031 defined in the outer wall 12027 of the disposable outer housing 12024. Edges of the ferromagnetic plate 12002 or attached to sidewalls of the cavity 12031. In the illustrated example, form-in-place seals 12029, 12030 are configured to attach the edges of the ferromagnetic plate 12002 to the sidewalls of the cavity 12031. However, in other examples, it is envisioned that other attachment mechanisms can be employed. In at least one example, an adhesive can be utilized to attach the edges of the ferromagnetic plate 12002 to the sidewalls of the cavity 12031.

Further to the above, the magnetic sensor 12003 protrudes through an outer wall 12028 of the inner core 12022, and is compressed by a spring 12004 against the outer wall 12027. The spring 12004 ensures that the magnetic sensor 12003 remains in sufficient proximity to the ferromagnetic plate 12002 to detect changes in the position of the ferromagnetic plate 12002 caused by the external compression force (F).

When the inner core 12022 is properly assembled with the disposable outer housing 12024, the magnetic sensor 12003 and the ferromagnetic plate 12002 are aligned with each other on opposite sides of a wall portion of the outer wall 12027 that forms the cavity 12031. The ferromagnetic plate 12002 is configured to move, or bend, toward the magnetic sensor 12003 in response to the external compression force (F). The movement of the ferromagnetic plate 12002 changes the readings of the magnetic sensor 12003 in accordance with the magnitude of the external compression force (F). When the user releases the ferromagnetic plate 12002, or reduces the external compression force (F), the ferromagnetic plate 12002 returns to its natural state, moving away from the magnetic sensor 12003, which changes the readings of the magnetic sensor 12003 in accordance with the reduction in the external compression force (F). As described above, the microcontroller 120061 is in communication with the magnetic sensor 12003. Accordingly, the changes in the readings of the magnetic sensor 12003 are translated into changes and drive motions of the motor assembly 120062.

Figure 114:
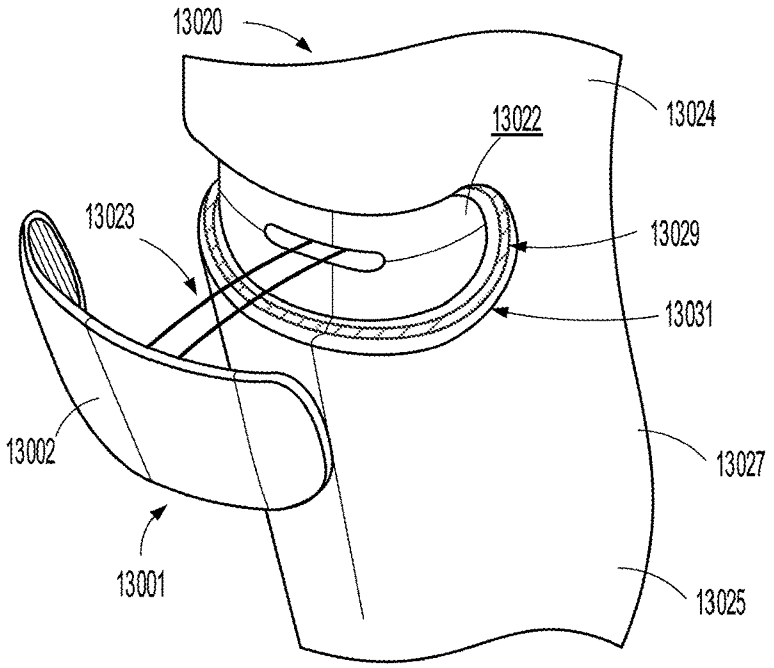
FIG. 114 is a partial exploded view of a handle assembly, in accordance with at least one aspect of the present disclosure.
Figure 115:
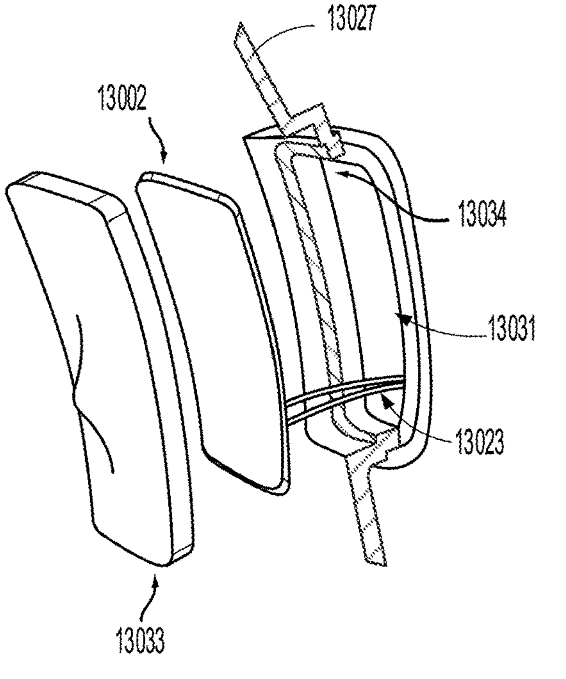
FIG. 115 is a partial exploded view of an actuator of a handle assembly, in accordance with at least one aspect of the present disclosure.
Figure 116:
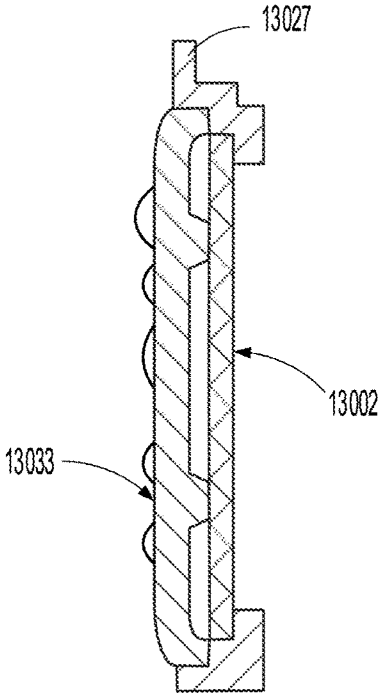
FIG. 116 is a partial cross-sectional view of the actuator of FIG. 115.

Referring now to FIGS. 114-116, alternative actuator embodiments are depicted. FIG. 114 illustrates a handle assembly 13020 similar in many respects to handle assemblies described elsewhere herein such as, for example, the handle assemblies 9920, 8520, 9120, 9220, 11020, 12020, which are not repeated for brevity. For example, the handle assembly 13020 also includes an inner core 13022 which has a motor assembly for motivating one or more drive members configured to effect a closure motion, an articulation motion, and/or a firing motion in an end effector (e.g. end effector 8540). The handle assembly 13020 further includes a disposable outer housing 13024 that includes two housing portions releasably attached to one another to permit assembly with the inner core 13022. When joined, the housing portions define a cavity therein in which inner core 13022 may be selectively situated within a sterile barrier 13025 defined by an outer wall 13027 of the disposable outer housing 13024.

Further to the above, the handle assembly 13020 includes an actuator 13001 similar in many respects to the actuator 12001, which are not repeated for brevity. The actuator 13001 includes a ferromagnetic plate 13002 similar in many respects to the ferromagnetic plate 12002. In addition, the ferromagnetic plate 13002 is connected to the inner core 13022 via wire connectors 13023 that extend through an outer wall of the inner core 13022. Furthermore, an adhesive 13029 is configured to seemingly secure the ferromagnetic plate 13002 to an opening 13031 of the disposable outer housing 13024. In the illustrated example, the ferromagnetic plate 13002 defines a portion of the outer wall 13027.

In the examples illustrated in FIGS. 115 and 116, a flexible rubberized outer cover 13033 is disposed over the ferromagnetic plate 13002 forming a portion of the outer wall 13027. The flexible rubberized outer cover 13033 can be attached to the outer wall 13027 via a form-in-place seal and/or an adhesive 13034. The ferromagnetic plate 13002 and the flexible rubberized outer cover 13033 provide a double seal that ensures the integrity of the sterile barrier 13025.

Figure 117:
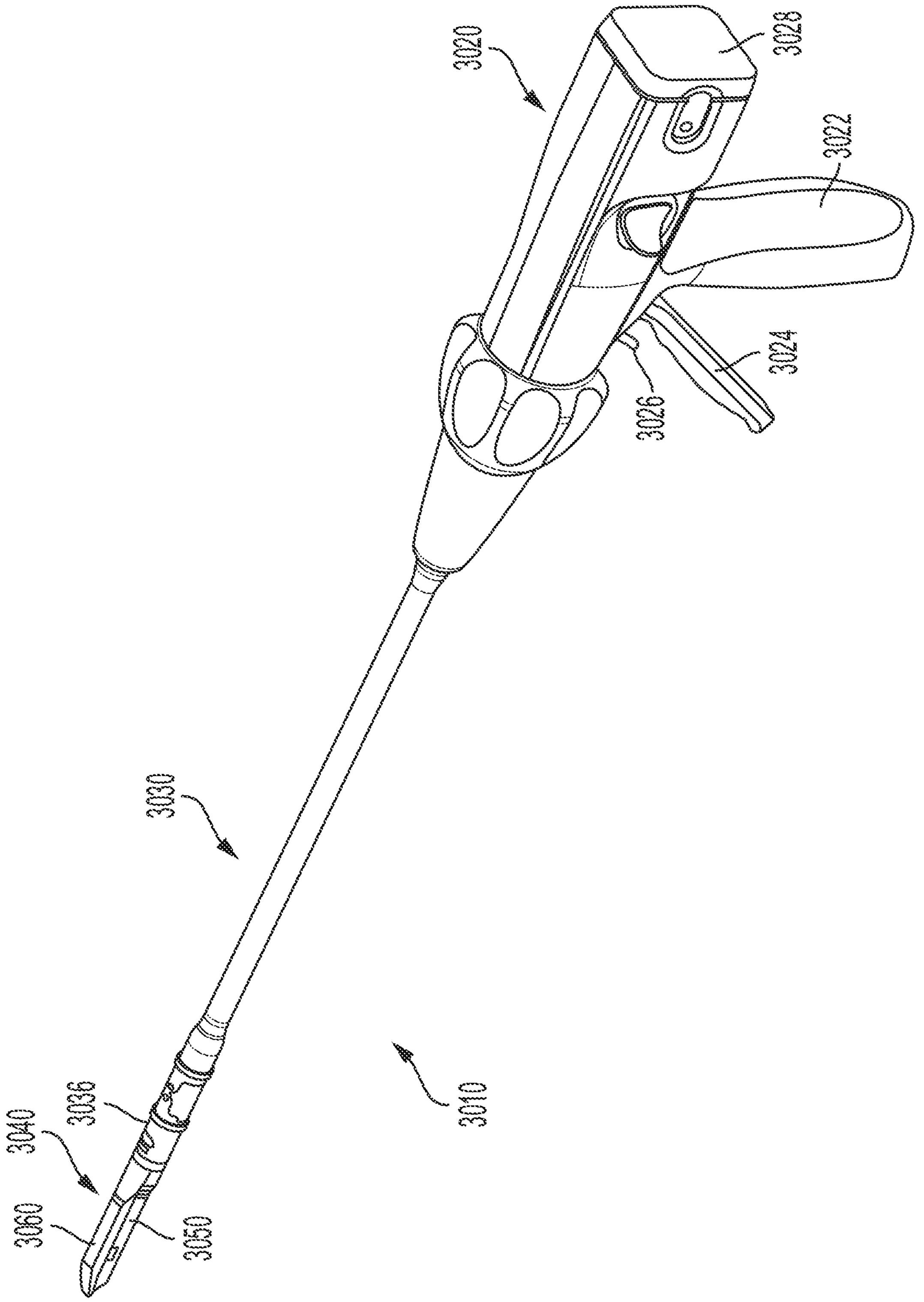
FIG. 117 illustrates a perspective view of an exemplary articulating surgical stapling instrument.

FIG. 117 depicts an exemplary surgical stapling and severing instrument 3010 that includes a handle assembly 3020, a shaft assembly 3030, and an end effector 3040. End effector 3040 and the distal portion of shaft assembly 3030 are sized for insertion, in a nonarticulated state as depicted in FIG. 117, through a trocar cannula to a surgical site in a patient for performing a surgical procedure. By way of example only, such a trocar may be inserted in a patient's abdomen, between two of the patient's ribs, or elsewhere. In some settings, instrument 3010 is used without a trocar. For instance, end effector 3040 and the distal portion of shaft assembly 3030 may be inserted directly through a thoracotomy or other type of incision. It should be understood that terms such as "proximal" and "distal" are used herein with reference to a clinician gripping handle assembly 3020 of instrument 3010. Thus, end effector 3040 is distal with respect to the more proximal handle assembly 3020. It will be further appreciated that for convenience and clarity, spatial terms such as "vertical" and "horizontal" are used herein with respect to the drawings. However, surgical instruments are used in many orientations and positions, and these terms are not intended to be limiting and absolute.

As also shown in FIGS. 117-120, end effector 3040 of the present example includes a lower jaw 3050 and a pivotable anvil 3060. Anvil 3060 includes a pair of integral, outwardly extending pins 3066 that are disposed in corresponding curved slots 3054 of lower jaw 3050. Anvil 3060 is pivotable toward and away from lower jaw 3050 between an open position (shown in FIG. 118) and a closed position (shown in FIG. 117). Use of the term "pivotable" (and similar terms with "pivot" as a base) should not be read as necessarily requiring pivotal movement about a fixed axis. For instance, in the present example, anvil 3060 pivots about an axis that is defined by pins 3066, which slide along curved slots 3054 of lower jaw 3050 as anvil 3060 moves toward lower jaw 3050. In such versions, the pivot axis translates along the path defined by slots 3054 while anvil 3060 simultaneously pivots about that axis. In addition or in the alternative, the pivot axis may slide along slots 3054 first, with anvil 3060 then pivoting about the pivot axis after the pivot axis has slid a certain distance along the slots 3054. It should be understood that such sliding/translating pivotal movement is encompassed within terms such as "pivot," "pivots," "pivotal," "pivotable," "pivoting," and the like. Of course, some versions may provide pivotal movement of anvil 3060 about an axis that remains fixed and does not translate within a slot or channel, etc.

Figure 119:
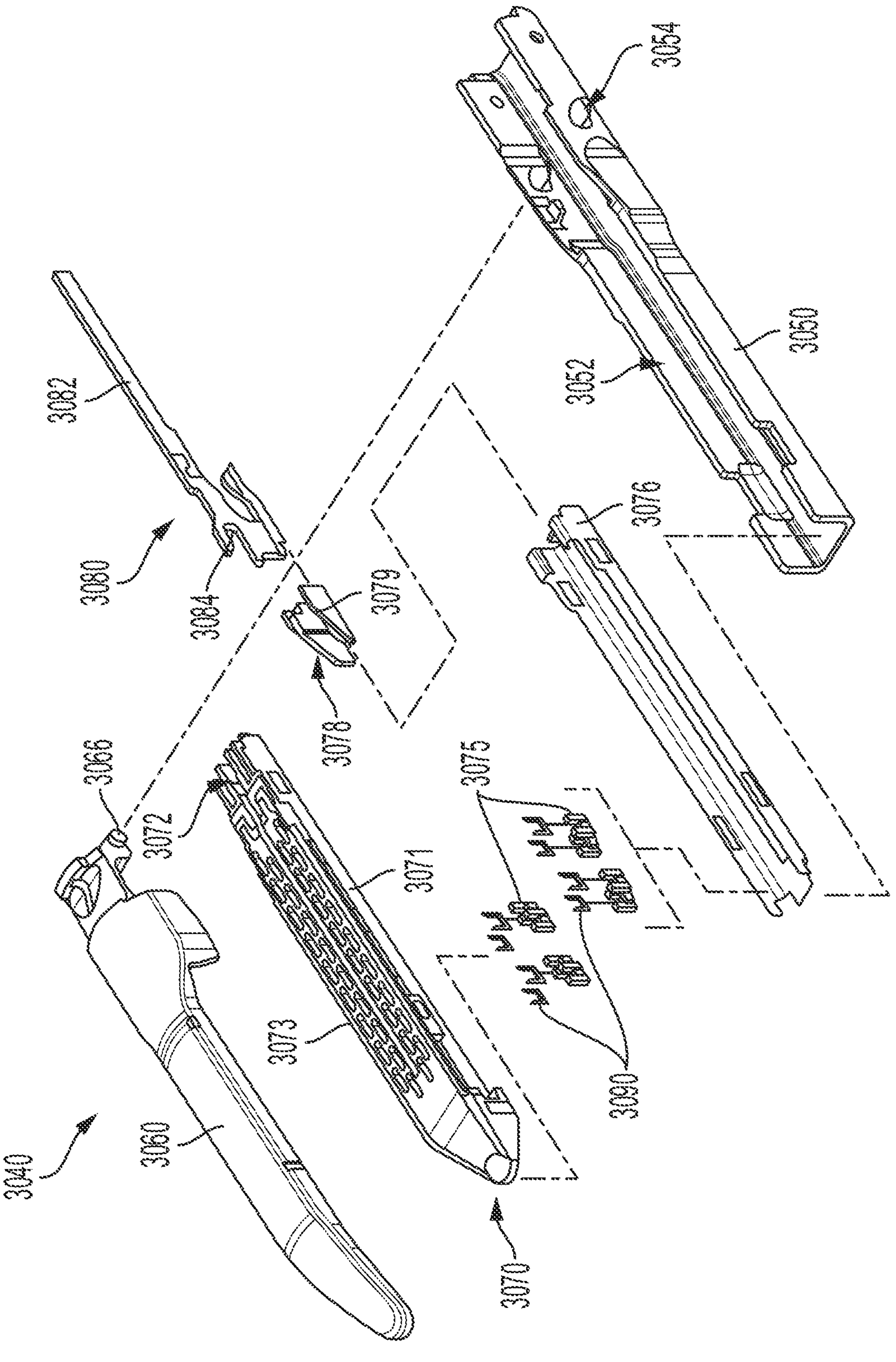
FIG. 119 illustrates an exploded perspective view of the end effector of FIG. 118.

As best seen in FIG. 119, lower jaw 3050 of the present example defines a channel 3052 that is configured to receive a staple cartridge 3070. Staple cartridge 3070 may be inserted into channel 3052, end effector 3040 may be actuated, and then staple cartridge 3070 may be removed and replaced with another staple cartridge 3070. Lower jaw 3050 thus releasably retains staple cartridge 3070 in alignment with anvil 3060 for actuation of end effector 3040. In some versions, lower jaw 3050 is constructed in accordance with at least some of the teachings of U.S. Patent Application Publication No. 2014/0239044, entitled INSTALLATION FEATURES FOR SURGICAL INSTRUMENT END EFFECTOR CARTRIDGE, published Aug. 28, 2014, issued as U.S. Pat. No. 9,808,248 on Nov. 30, 2016, the disclosure of which is incorporated by reference herein. Other suitable forms that lower jaw 3050 may take will be apparent to those of ordinary skill in the art in view of the teachings herein.

Figure 118:
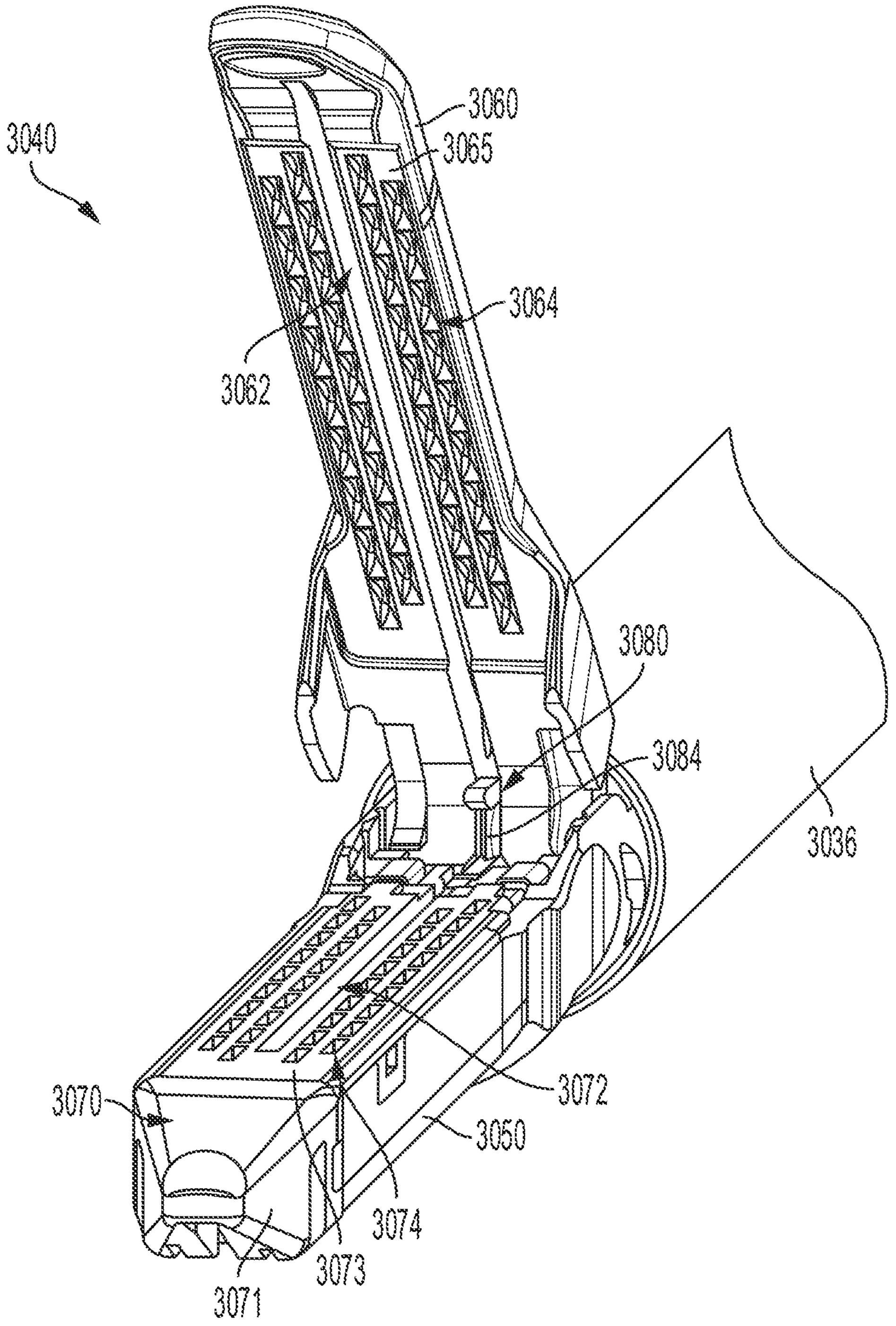
FIG. 118 illustrates a perspective view of an end effector of the instrument of FIG. 117, with the end effector in an open configuration.

As best seen in FIGS. 118 and 119, staple cartridge 3070 of the present example comprises a cartridge body 3071 and a tray 3076 secured to the underside of cartridge body 3071. The upper side of cartridge body 3071 presents a deck 3073, against which tissue may be compressed when anvil 3060 is in a closed position. Cartridge body 3071 further defines a longitudinally extending channel 3072 and a plurality of staple pockets 3074. A staple 3090 is positioned in each staple pocket 3074. A staple driver 3075 is also positioned in each staple pocket 3074, underneath a corresponding staple 3090, and above tray 3076. As will be described in greater detail below, staple drivers 3075 are operable to translate upwardly in staple pockets 3074 to thereby drive staples 3090 upwardly through staple pockets 3074 and into engagement with anvil 3060. Staple drivers 3075 are driven upwardly by a wedge sled 3078, which is captured between cartridge body 3071 and tray 3076, and which translates longitudinally through cartridge body 3071.

Wedge sled 3078 includes a pair of obliquely angled cam surfaces 3079, which are configured to engage staple drivers 3075 and thereby drive staple drivers 3075 upwardly as wedge sled 3078 translates longitudinally through cartridge 3070. For instance, when wedge sled 3078 is in a proximal position, staple drivers 3075 are in downward positions and staples 3090 are located in staple pockets 3074. As wedge sled 3078 is driven to the distal position by a translating knife member 3080, wedge sled 3078 drives staple drivers 3075 upwardly, thereby driving staples 3090 out of staple pockets 3074 and into staple forming pockets 3064 that are formed in the underside 3065 of anvil 3060. Thus, staple drivers 3075 translate along a vertical dimension as wedge sled 3078 translates along a horizontal dimension.

In some versions, staple cartridge 3070 is constructed and operable in accordance with at least some of the teachings of U.S. Patent Application Publication No. 2014/0239042, entitled INTEGRATED TISSUE POSITIONING AND JAW ALIGNMENT FEATURES FOR SURGICAL STAPLER, published Aug. 28, 2014, issued as U.S. Pat. No. 9,517,065 on Dec. 13, 2016, the disclosure of which is incorporated by reference herein. In addition or in the alternative, staple cartridge 3070 may be constructed and operable in accordance with at least some of the teachings of U.S. Patent Application Publication No. 2014/0239044, entitled INSTALLATION FEATURES FOR SURGICAL INSTRUMENT END EFFECTOR CARTRIDGE, published Aug. 28, 2014, issued as U.S. Pat. No. 9,808,248 on Nov. 7, 2017, the disclosure of which is incorporated by reference herein. Other suitable forms that staple cartridge 3070 may take will be apparent to those of ordinary skill in the art in view of the teachings herein.

As best seen in FIG. 118, anvil 3060 of the present example comprises a longitudinally extending channel 3062 and a plurality of staple forming pockets 3064. Channel 3062 is configured to align with channel 3072 of staple cartridge 3070 when anvil 3060 is in a closed position. Each staple forming pocket 3064 is positioned to lie over a corresponding staple pocket 3074 of staple cartridge 3070 when anvil 3060 is in a closed position. Staple forming pockets 3064 are configured to deform the legs of staples 3090 when staples 3090 are driven through tissue and into anvil 3060. In particular, staple forming pockets 3064 are configured to bend the legs of staples 3090 to secure the formed staples 3090 in the tissue. Anvil 3060 may be constructed in accordance with at least some of the teachings of U.S. Patent Application Publication No. 2014/0239042, entitled INTEGRATED TISSUE POSITIONING AND JAW ALIGNMENT FEATURES FOR SURGICAL STAPLER, published Aug. 28, 2014, issued as U.S. Pat. No. 9,517,065 on Dec. 13, 2016; at least some of the teachings of U.S. Patent Application Publication No. 2014/0239036, entitled JAW CLOSURE FEATURE FOR END EFFECTOR OF SURGICAL INSTRUMENT, published Aug. 28, 2014, issued as U.S. Pat. No. 9,839,421 on Dec. 12, 2017; and/or at least some of the teachings of U.S. Patent Application Publication No. 2014/0239037, entitled STAPLE FORMING FEATURES FOR SURGICAL STAPLING INSTRUMENT, published Aug. 28, 2014, issued as U.S. Pat. No. 10,092,292 on Oct. 9, 2018, the disclosure of which is incorporated by reference herein. Other suitable forms that anvil 3060 may take will be apparent to those of ordinary skill in the art in view of the teachings herein.

In the present example, a knife member 3080 is configured to translate through end effector 3040. As best seen in FIG. 119, knife member 3080 is secured to the distal end of a firing beam 3082, which extends through a portion of shaft assembly 3030. As best seen in FIG. 118, knife member 3080 is positioned in channels 3062, 3072 of anvil 3060 and staple cartridge 3070. Knife member 3080 includes a distally presented cutting edge 3084 that is configured to sever tissue that is compressed between anvil 3060 and deck 3073 of staple cartridge 3070 as knife member 3080 translates distally through end effector 3040. As noted above, knife member 3080 also drives wedge sled 3078 distally as knife member 3080 translates distally through end effector 3040, thereby driving staples 3090 through tissue and against anvil 3060 into formation.

In the present example, anvil 3060 is driven toward lower jaw 3050 by advancing closure ring 3036 distally relative to end effector 3040. Closure ring 3036 cooperates with anvil 3060 through a camming action to drive anvil 3060 toward lower jaw 3050 in response to distal translation of closure ring 3036 relative to end effector 3040. Similarly, closure ring 3036 may cooperate with anvil 3060 to open anvil 3060 away from lower jaw 3050 in response to proximal translation of closure ring 3036 relative to end effector 3040. By way of example only, closure ring 3036 and anvil 3060 may interact in accordance with at least some of the teachings of U.S. Patent Application Publication No. 2014/0239036, entitled JAW CLOSURE FEATURE FOR END EFFECTOR OF SURGICAL INSTRUMENT, published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled JAW OPENING FEATURE FOR SURGICAL STAPLER, filed on Jun. 25, 2014, published as U.S. Patent Application Publication No. 2015/0374373 on Dec. 31, 2015, the disclosure of which is incorporated by reference herein.

Handle assembly 3020 includes a pistol grip 3022 and a closure trigger 3024. As noted above, anvil 3060 is closed toward lower jaw 3050 in response to distal advancement of closure ring 3036. In the present example, closure trigger 3024 is pivotable toward pistol grip 3022 to drive closure tube 3032 and closure ring 3036 distally. Various suitable components that may be used to convert pivotal movement of closure trigger 3024 toward pistol grip 3022 into distal translation of closure tube 3032 and closure ring 3036 relative to handle assembly 3020 will be apparent to those of ordinary skill in the art in view of the teachings herein.

Also in the present example, instrument 3010 provides motorized control of firing beam 3082. In particular, instrument 3010 includes motorized components that are configured to drive firing beam 3082 distally in response to pivoting of firing trigger 3026 toward pistol grip 3022. In some versions, a motor (not shown) is contained in pistol grip 3022 and receives power from battery pack 3028. This motor is coupled with a transmission assembly (not shown) that converts rotary motion of a drive shaft of the motor into linear translation of firing beam 3082. By way of example only, the features that are operable to provide motorized actuation of firing beam 3082 may be configured and operable in accordance with at least some of the teachings of U.S. Pat. No. 8,210,411, entitled MOTOR-DRIVEN SURGICAL INSTRUMENT, issued Jul. 3, 2012, the disclosure of which is incorporated by reference herein; U.S. Pat. No. 8,453,914, entitled MOTOR-DRIVEN SURGICAL CUTTING INSTRUMENT WITH ELECTRIC ACTUATOR DIRECTIONAL CONTROL ASSEMBLY, issued Jun. 4, 2013, the disclosure of which is incorporated by reference herein; and/or U.S. patent application Ser. No. 14/226,142, entitled SURGICAL INSTRUMENT COMPRISING A SENSOR SYSTEM, filed Mar. 26, 2014, issued as U.S. Pat. No. 9,913,642 on Mar. 13, 2018, the disclosure of which is incorporated by reference herein.

Additional details regarding the exemplary surgical stapling and severing instrument 3010 can be found in U.S. Pat. No. 10,342,542, which is hereby incorporated by reference in its entirety herein.

In some instances, it may be desirable to equip end effector 3040 with a buttress material to reinforce the mechanical fastening of tissue provided by staples 3090. Such a buttress may prevent the applied staples 3090 from pulling through the tissue and may otherwise reduce a risk of tissue tearing at or near the site of applied staples 3090. In addition to or as an alternative to providing structural support and integrity to a line of staples 3090, a buttress may provide various other kinds of effects such as spacing or gap-filling, administration of therapeutic agents, and/or other effects. In some instances, a buttress may be provided on deck 3073 of staple cartridge 3070. In some other instances, a buttress may be provided on the surface of anvil 3060 that faces staple cartridge 3070. It should also be understood that a first buttress may be provided on deck 3073 of staple cartridge 3070 while a second buttress is provided on anvil 3060 of the same end effector 3040. Various examples of forms that a buttress may take will be described in greater detail below. Various ways in which a buttress may be secured to a staple cartridge 3070 or an anvil 3060 will also be described in greater detail below.

Figure 120:
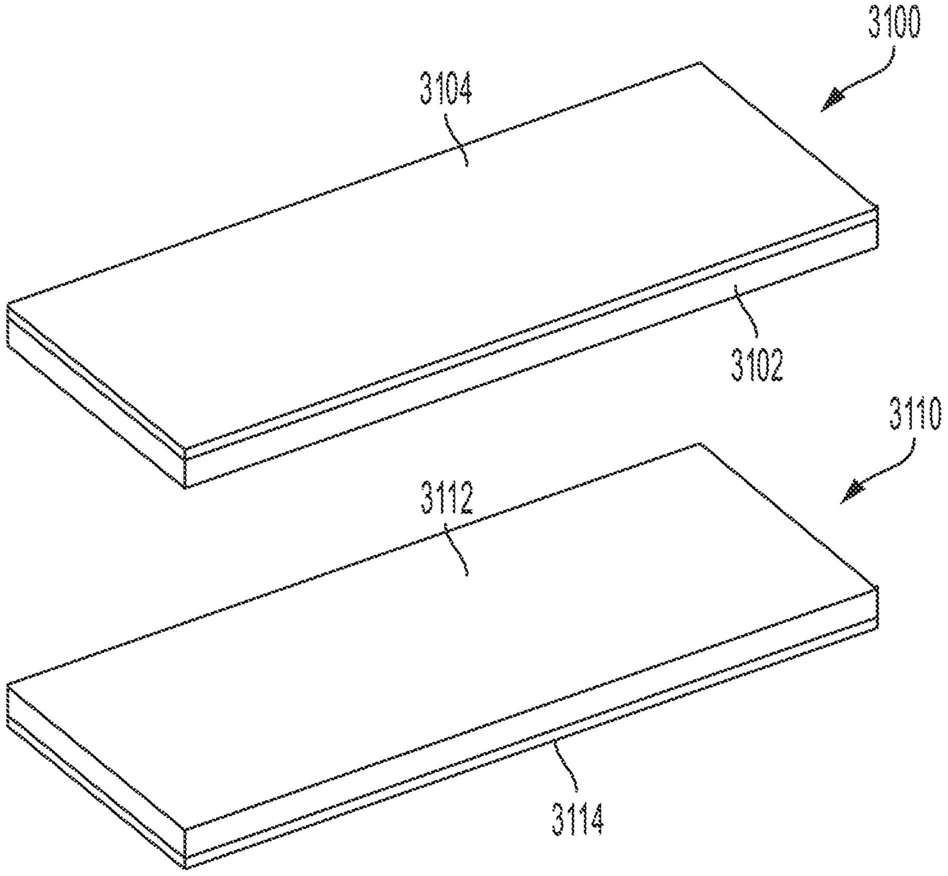
FIG. 120 illustrates a perspective view of an exemplary upper buttress and an exemplary lower buttress, each of which may be applied to the end effector of FIG. 118.

FIG. 120 shows an exemplary pair of buttress assemblies 3100, 3110 with a basic composition. Buttress assembly 3100 of this example comprises a buttress body 3102 and an upper adhesive layer 3104. Similarly, buttress assembly 3110 comprises a buttress body 3112 and a lower adhesive layer 3114. In the present example, each buttress body 3102, 3112 comprises a strong yet flexible material configured to structurally support a line of staples 3090. By way of example only, each buttress body 3102, 3112 may comprise a woven mesh of polyglactin 910 material by Ethicon, Inc.

of Somerville, N.J. Alternatively, any other suitable materials or combinations of materials may be used in addition to or as an alternative to polyglactin 910 material to form each buttress body 3102, 3112. Each buttress body 3102, 3112 may take any other suitable form and may be constructed of any other suitable material(s). By way of further example only, each buttress body 3102, 3112 may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body 3102, 3112 will be apparent to those of ordinary skill in the art in view of the teachings herein.

In addition or in the alternative, each buttress body 3102, 3112 may comprise a material including, for example, a hemostatic agent such as fibrin to assist in coagulating blood and reduce bleeding at the severed and/or stapled surgical site along tissue. As another merely illustrative example, each buttress body 3102, 3112 may comprise other adjuncts or hemostatic agents such as thrombin may be used such that each buttress body 3102, 3112 may assist to coagulate blood and reduce the amount of bleeding at the surgical site. Other adjuncts or reagents that may be incorporated into each buttress body 3102, 3112 may further include but are not limited to medical fluid or matrix components. Merely illustrative examples of materials that may be used to form each buttress body 3102, 3112, as well as materials that may be otherwise incorporated into each buttress body 3102, 3112, are disclosed in U.S. patent application Ser. No. 14/667,842, entitled METHOD OF APPLYING A BUTTRESS TO A SURGICAL STAPLER, filed Mar. 25, 2015, published as U.S. Patent Application Publication No. 2016/0278774 on Sep. 29, 2016, the disclosure of which is incorporated by reference herein. Alternatively, any other suitable materials may be used.

By way of further example only, each buttress body 3102, 3112 may be constructed in accordance with at least some of the teachings of U.S. Patent Application Publication No. 2012/0241493, entitled TISSUE THICKNESS COMPENSATOR COMPRISING CONTROLLED RELEASE AND EXPANSION, published Sep. 27, 2012, issued as U.S. Pat. No. 10,123,798 on Nov. 13, 2018, the disclosure of which is incorporated by reference herein; U.S. Patent Application Publication No. 2013/0068816, entitled SURGICAL INSTRUMENT AND BUTTRESS MATERIAL, published Mar. 21, 2013, now abandoned, the disclosure of which is incorporated by reference herein; U.S. Patent Application Publication No. 2013/0062391, entitled SURGICAL INSTRUMENT WITH FLUID FILLABLE BUTTRESS, published Mar. 14, 2013, issued as U.S. Pat. No. 9,999,408 on Jun. 19, 2018, the disclosure of which is incorporated by reference herein; U.S. Patent Application Publication No. 2013/0068820, entitled FIBRIN PAD MATRIX WITH SUSPENDED HEAT ACTIVATED BEADS OF ADHESIVE, published Mar. 21, 2013, issued as U.S. Pat. No. 8,814,025 on Aug. 26, 2014, the disclosure of which is incorporated by reference herein; U.S. Patent Application Publication No. 2013/0082086, entitled ATTACHMENT OF SURGICAL STAPLE BUTTRESS TO CARTRIDGE, published Apr. 4, 2013, issued as U.S. Pat. No. 8,899,464 on Dec. 2, 2014, the disclosure of which is incorporated by reference herein; U.S. Patent Application Publication No. 2013/0037596, entitled DEVICE FOR APPLYING ADJUNCT IN ENDOSCOPIC PROCEDURE, published Feb. 14, 2013, issued as U.S. Pat. No. 9,492,170 on Nov. 15, 2016, the disclosure of which is incorporated by reference herein; U.S. Patent Application Publication No. 2013/0062393, entitled RESISTIVE HEATED SURGICAL STAPLE CARTRIDGE WITH PHASE CHANGE SEALANT, published Mar. 14, 2013, issued as U.S. Pat. No. 8,998,060 on Apr. 7, 2015, the disclosure of which is incorporated by reference herein; U.S. Patent Application Publication No. 2013/0075446, entitled SURGICAL STAPLE ASSEMBLY WITH HEMOSTATIC FEATURE, published Mar. 28, 2013, issued as U.S. Pat. No. 9,393,018 on Jul. 19, 2016, the disclosure of which is incorporated by reference herein; U.S. Patent Application Publication No. 2013/0062394, entitled SURGICAL STAPLE CARTRIDGE WITH SELF-DISPENSING STAPLE BUTTRESS, published Mar. 14, 2013, issued as U.S. Pat. No. 9,101,359 on Aug. 11, 2015, the disclosure of which is incorporated by reference herein; U.S. Patent Application Publication No. 2013/0075445, entitled ANVIL CARTRIDGE FOR SURGICAL FASTENING DEVICE, published Mar. 28, 2013, issued as U.S. Pat. No. 9,198,644 on Dec. 1, 2015, the disclosure of which is incorporated by reference herein; U.S. Patent Application Publication No. 2013/0075447, entitled ADJUNCT THERAPY FOR APPLYING HEMOSTATIC AGENT, published Mar. 28, 2013, now abandoned, the disclosure of which is incorporated by reference herein; U.S. Patent Application Publication No. 2013/0256367, entitled TISSUE THICKNESS COMPENSATOR COMPRISING A PLURALITY OF MEDICAMENTS, published Oct. 3, 2013, issued as U.S. Pat. No. 9,211,120 on Dec. 15, 2015, the disclosure of which is incorporated by reference herein; U.S. patent application Ser. No. 14/300,954, entitled ADJUNCT MATERIALS AND METHODS OF USING SAME IN SURGICAL METHODS FOR TISSUE SEALING, filed Jun. 10, 2014, issued as U.S. Pat. No. 10,172,611 on Jan. 8, 2019, the disclosure of which is incorporated by reference herein; U.S. patent application Ser. No. 14/827,856, entitled IMPLANTABLE LAYERS FOR A SURGICAL INSTRUMENT, filed Aug. 17, 2015, published as U.S. Patent Application Publication No. 2017/0049444 on Feb. 23, 2017, the disclosure of which is incorporated by reference herein; U.S. patent application Ser. No. 14/840,613, entitled DRUG ELUTING ADJUNCTS AND METHODS OF USING DRUG ELUTING ADJUNCTS, filed Aug. 31, 2015, published as U.S. Patent Application Publication No. 2017/0055986 on Mar. 2, 2017, the disclosure of which is incorporated by reference herein; U.S. patent application Ser. No. 14/871,071, entitled COMPRESSIBLE ADJUNCT WITH CROSSING SPACER FIBERS, filed Sep. 30, 2015, published as U.S. Patent Application Publication No. 2017/0086837 on Mar. 30, 2017, the disclosure of which is incorporated by reference herein; and/or U.S. patent application Ser. No. 14/871,131, entitled METHOD FOR APPLYING AN IMPLANTABLE LAYER TO A FASTENER CARTRIDGE, filed Sep. 30, 2015, published as U.S. Patent Application Publication No. 2017/0086842 on Mar. 30, 2017, the disclosure of which is incorporated by reference herein.

In the present example, adhesive layer 3104 is provided on buttress body 3102 in order to adhere buttress body 3102 to underside 3065 of anvil 3060. Similarly, adhesive layer 3114 is provided on buttress body 3112 in order to adhere buttress body 3112 to deck 3073 of staple cartridge 3070. Adherence of the buttress body 3102 to underside 3065 of anvil 3060 or to deck 3073 of staple cartridge 3070 can occur through a variety of mechanisms including but not limited to a pressure sensitive adhesive. In some versions, each adhesive layer 3104, 3114 comprise a pressure sensitive adhesive material. Examples of various suitable materials that may be used to form adhesive layers 3104, 3114 are disclosed in U.S. patent application Ser. No. 14/667,842, entitled METHOD OF APPLYING A BUTTRESS TO A SURGICAL STAPLER, filed Mar. 25, 2015, published as U.S. Patent Application Publication No. 2016/0278774 on Sep. 29, 2016, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers 3104, 3114 will be apparent to those of ordinary skill in the art in view of the teachings herein.

As noted above, buttress assembly 3100 may be applied to the underside 3065 of anvil 3060, and buttress 3110 may be applied to deck 3073 of staple cartridge 3070, before tissue is positioned in end effector 3040, and before end effector 3040 is actuated. Because end effector 3040 may be actuated many times during use of instrument 3010 in a single surgical procedure, it may be desirable to enable an operator to repeatedly and easily load buttress assemblies 3100 on underside 3065 of anvil 3060 during that single surgical procedure. In other words, because end effector 3040 may be actuated many times during use of instrument 3010 in a single surgical procedure, it may be insufficient to simply provide anvil 3060 pre-loaded with a buttress assembly 3100 without facilitating the re-loading of anvil 3060 with additional buttress assemblies 3100 after end effector 3040 has been actuated.

Similarly, those of ordinary skill in the art will recognize that staple cartridge 3070 will need to be replaced each time end effector 3040 is actuated. When end effector 3040 is actuated several times during use of instrument 3010 in a single surgical procedure, several staple cartridges 3070 may thus be used during that surgical procedure. It may seem that each of these staple cartridges 3070 may be provided with buttress assembly 3110 pre-loaded on deck 3073. However, there are some reasons why it may be undesirable to provide a staple cartridge 3070 with buttress assembly 3110 pre-loaded on deck 3073. In other words, it may be desirable to provide loading of buttress assembly 3110 on deck 3073 immediately prior to usage of staple cartridge in the surgical procedure, rather than loading buttress assembly 3110 on deck 3073 a substantial time prior to the surgical procedure. For instance, buttress assembly 3110 may not be compatible with the same sterilization techniques as staple cartridge 3070, such that it may present processing difficulties to package staple cartridge 3070 with buttress assembly 3110 pre-loaded on deck 3073. In addition, the material forming buttress assembly 3110 may have certain environmental sensitivities that staple cartridge 3070 does not have, such that it may be beneficial to enable buttress assembly 3110 and staple cartridge 3070 to be stored separately before use. Moreover, buttress assembly 3110 may not be warranted or otherwise desired in some surgical procedures, such that it may be desirable to enable a physician to easily choose whether staple cartridge 3070 should be loaded with buttress assembly 3110 before that staple cartridge 3070 is used in the surgical procedure.

In view of the foregoing, it may be desirable to enable an operator to repeatedly and easily load buttress assemblies 3100, 3110 on end effector 3040 on an ad hoc basis during a given surgical procedure. It may also be desirable to provide a device that provides support and protection to buttress assemblies 3100, 3110 before buttress assemblies 3100, 3110 are loaded on end effector 3040, in addition to that same device also enabling buttress assemblies 3100, 3110 to be easily loaded on end effector. The examples described below relate to various cartridge assemblies that provide such support, protection, and loading of buttress assemblies 3100, 3110. It should be understood that the following examples are merely illustrative. Numerous variations will be apparent to those of ordinary skill in the art in view of the teachings herein.

Figure 121:
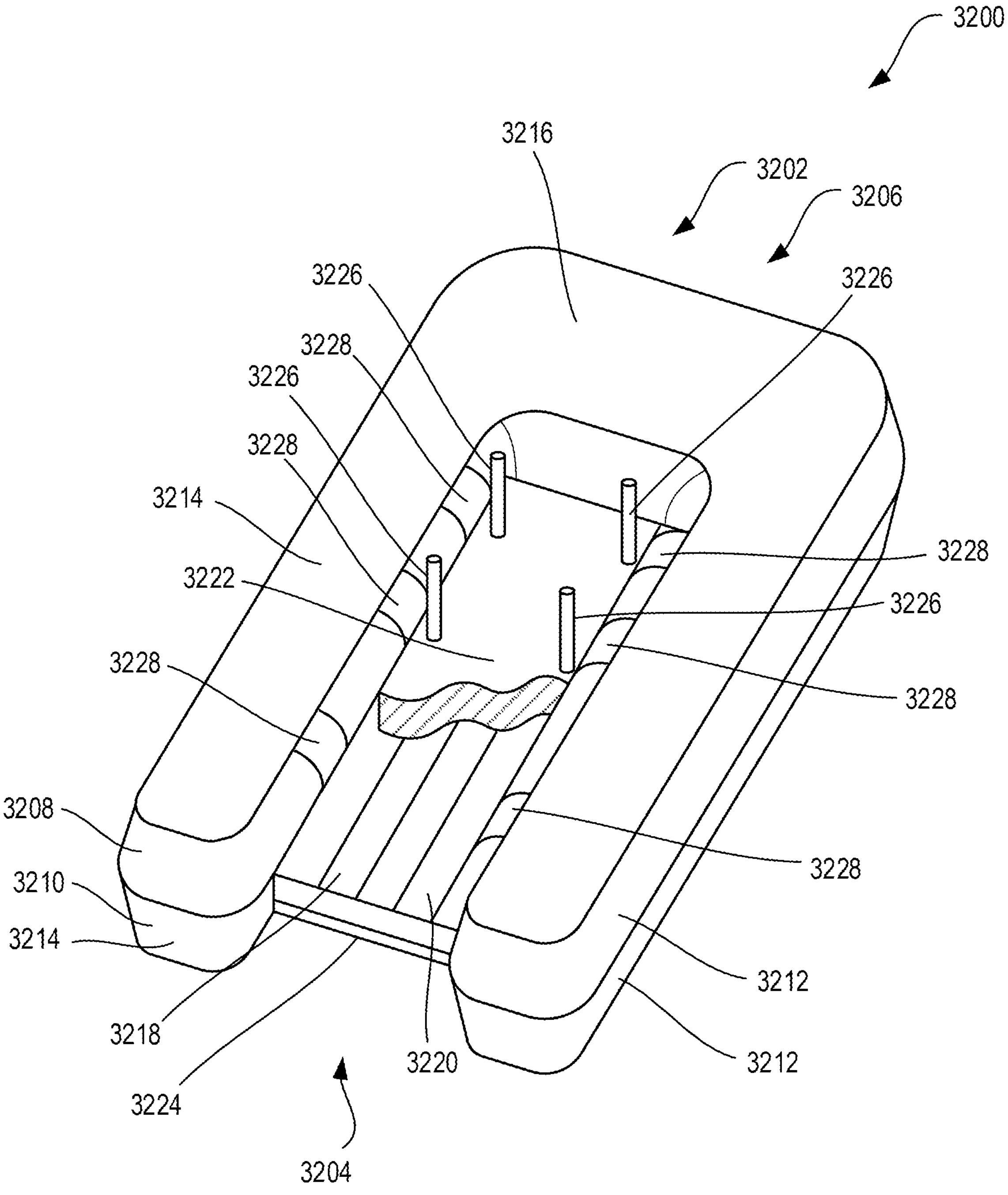
FIG. 121 illustrates a buttress applier cartridge, according to at least one aspect of the present disclosure.

FIG. 121 illustrates a buttress applier cartridge 3200, according to at least one aspect of the present disclosure. The buttress applier cartridge 3200 can include a generally U-shaped housing assembly 3202 that defines an open end 3204 and a closed end 3206. In various embodiments, the housing assembly 3202 can include a top housing portion 3208 and a bottom housing portion 3210 that are coupleable together to form an outer shell of the housing assembly 3202. The top housing portion 3208 and the bottom housing portion 3210 each include a first leg 3212, a second leg 3214, and a connecting portion 3216 that connects the first leg 3212 to the second leg 3214 at the closed end 3206. The top housing portion 3208 and the bottom housing portion 3210 can be coupled with any suitable coupling mechanism, such as with snap-fit, latches, or press-fit, as examples. In one example embodiment, the housing assembly 3202 can include various internal components, such as those described in U.S. Pat. No. 10,342,542, the disclosure of which is hereby incorporated by reference in its entirety herein.

The buttress applier cartridge 3200 can further include a support platform 3218 positioned between the first legs 3212 and second legs 3214 and that generally extends from the connecting portion 3216 of the housing assembly 3202 towards the open end 3204. In one aspect, the support platform 3218 can be manufactured out of any suitable, compressible material such that the support platform 3218 is compressible when force is applied thereto. In various other embodiments, the support platform 3218 can be rigid as opposed to compressible. In various embodiments, the support platform 3218 can be supported by the housing assembly 3202. In one example embodiment, the support platform 3218 can include a lip around the perimeter thereof that is captured between the top housing portion 3208 and the bottom housing portion 3210 when the top housing portion 3208 and bottom housing portion 3210 are coupled together. In other embodiments, the support platform 3218 can be coupled to the housing assembly 3202 in any suitable manner such that the support platform 3218 is substantially supported relative to the housing assembly 3202 when a force is applied thereto.

In various embodiments, the support platform 3218 can include a substantially planar top surface 3220 that can support a first buttress layer 3222 and a substantially planar bottom surface that can support a second buttress layer 3224. The first and second buttress layers 3222, 3224 can be removably coupled to the support platform 3218 by any suitable means, such as an adhesive, such that the first and second buttress layers 3222, 3224 are supported on their support platforms until the first and second buttress layers 3222, 3224 interface with an end effector of a surgical instrument, as will be described in more detail below.

In various aspects, the buttress applier cartridge 3200 can further include a plurality of suture legs 3226. In one example embodiment, as is shown in FIG. 121, the suture legs 3226 can extent from the first buttress layer 3222. The suture legs 3226 can be coupled to the first buttress layer 3222 in any suitable manner such that the suture legs 3226 can support the first buttress layer 3222 and, in various embodiments, such that movements of the suture legs 3226 causes movement of the first buttress layer 3222. In one example embodiment, two laterally offset suture legs 3226 form a continuous suture that is threaded through the first buttress layer 3222. In another example embodiment, two laterally offset suture legs 3226 form a continuous suture that supports a bottom surface of the first buttress layer 3222. Stated another way, the continuous suture extends underneath the first buttress layer and is positioned between the bottom surface of the first buttress layer 3222 and the top planar surface 3220 of the support platform 3218. In another example embodiment, each suture leg 3226 is coupled to the first buttress layer 3222 at discrete locations, such as by adhesive or embedded in the first buttress layer 3222, or any other suitable coupling mechanism.

Figure 123:
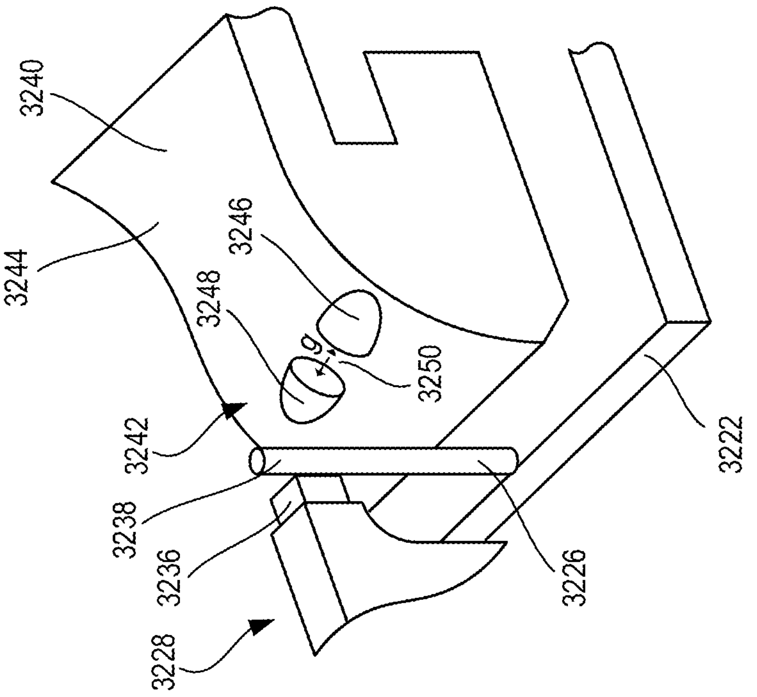
FIG. 123 illustrates an anvil prior to receiving a suture from a buttress applier cartridge, according to at least one aspect of the present disclosure.
Figure 122:
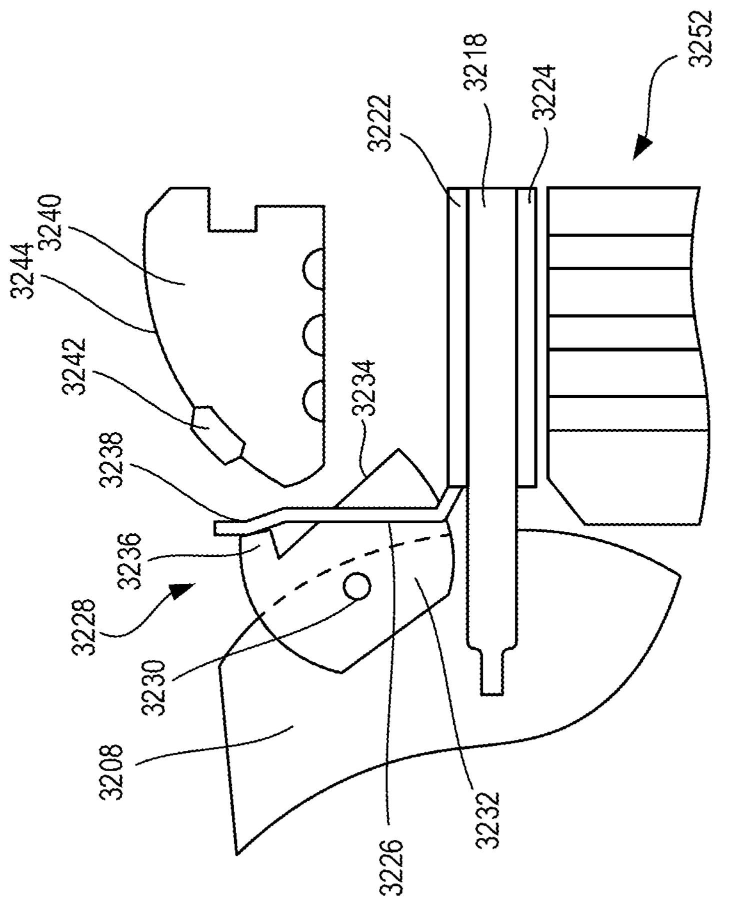
FIG. 122 illustrates the buttress applier cartridge of FIG. 117 receiving an end effector, according to at least one aspect of the present disclosure.
Figure 124:
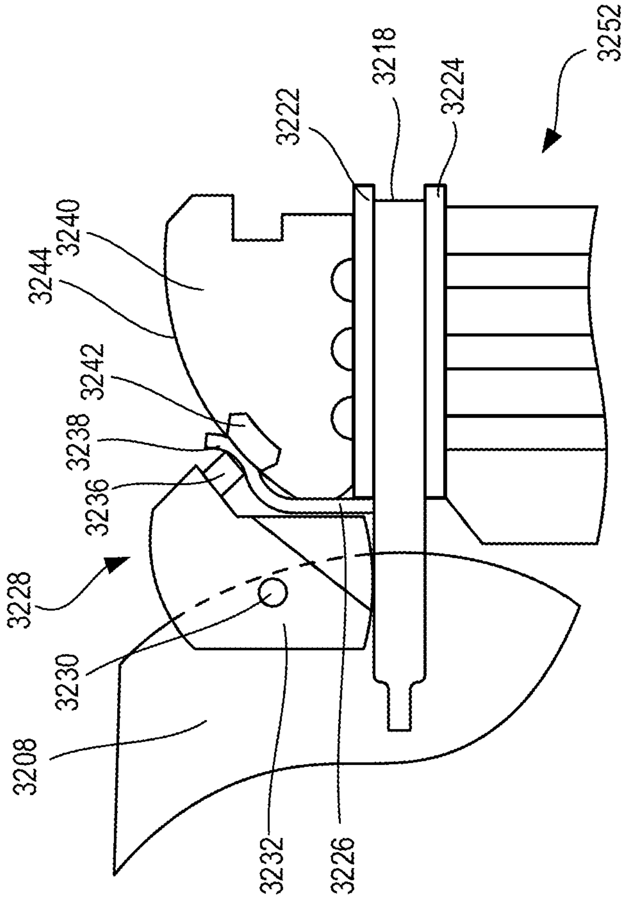
FIG. 124 illustrates the buttress applier cartridge of FIG. 117 interfacing with an end effector, according to at least one aspect of the present disclosure.

In one aspect, the buttress applier cartridge 3200 can further include a plurality of suture appliers 3228 (FIG. 121 shows the general position of the suture appliers 3228, while FIGS. 122-125 show an example embodiment of the structure of the suture appliers 3228). In various embodiments, each suture applier 3228 can be rotatably coupled to the buttress applier cartridge 3200. In one example embodiment, as seen in FIGS. 122 and 124, the suture appliers 3228 can be rotatable coupled to the top housing portion 3208 by pins 3230. The suture appliers 3228 can include a body portion 3232, a camming surface 3234, and an arm 3236 extending from the body portion 3232. Ends 3238 of each suture leg 3226 extending from the first buttress layer 3222 can removably couple to a corresponding arm 3236 of a suture applier 3228, such as with an adhesive, as an example.

Figure 125:
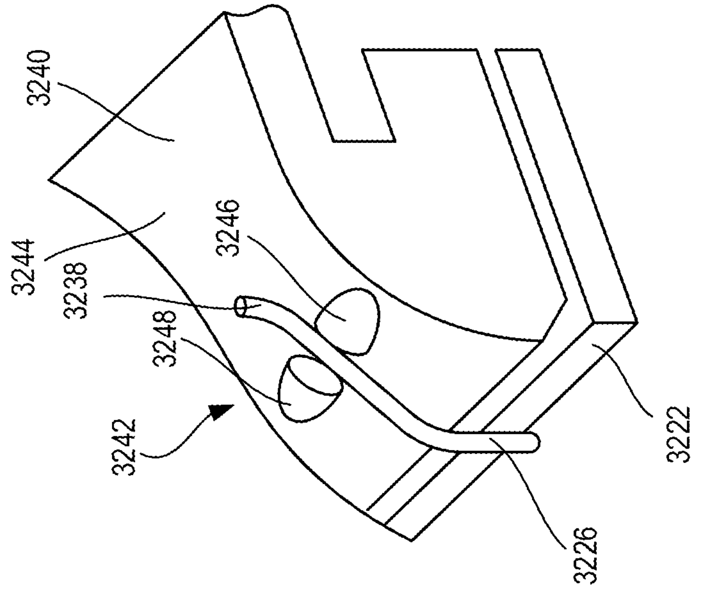
FIG. 125 illustrates an anvil after receiving a suture from a buttress applier cartridge, according to at least one aspect of the present disclosure.

As is shown in FIGS. 122-124, an anvil 3240 of an end effector can interface with the buttress applier cartridge 3200. The anvil 3240 can include a plurality of suture grabbers 3242 positioned on an outer, top surface 3244 thereof. As shown in FIGS. 123 and 125, the suture grabbers 3242 can include a first arm 3246 and a second arm 3248 spaced apart from the first arm 3246 such that a gap 'g' is defined therebetween. In one aspect, the gap 'g' is defined such that the ends 3238 of the suture legs 3226 can be received between the first arm 3246 and the second arm 3248 and would be press-fit and held by the suture grabber 3242. In various embodiments, the suture grabber 3242 can include an adhesive positioned between the first arm 3246 and the second arm 3248 on a receiving surface 3250 of the suture grabber 3242 such that, when an end 3238 of a suture leg 3226 is pressed between the first arm 3246 and the second arm 3248 (as is shown in FIG. 125), the end 3238 would at least be partially adhered to the anvil 3240, as well as being press-fit between the first arm 3246 and the second arm 3248, thus increasing the suture grabbers 3242 ability to hold the suture legs 3226.

In operation, as is shown in FIGS. 122-125, the anvil 3240 can be moved toward the first buttress layer 3222. Outer edges of anvil 3240 can contact and ride along camming surfaces 3234 of suture appliers 3228. In one example embodiment, the suture appliers 3228 are spaced along the buttress applier cartridge 3200 such that the suture appliers 3228 collectively cause the anvil 3240 to longitudinally align with the buttress applier cartridge 3200. In other embodiments, the buttress applier cartridge 3200 includes an alignment feature that allows the anvil 3240 to be positioned within the buttress applier cartridge 3200 such that each of the suture grabbers 3242 of the anvil 3240 is aligned with a corresponding suture applier 3228. In one example embodiment, the anvil 3240 is sized such that the anvil 3240 can abut against the connecting portion 3216 of the housing assembly 3202, causing the suture grabbers 3242 of the anvil 3240 to align with a corresponding suture applier 3228.

Continuing from above, outer edges of anvil 3240 can contact and ride along camming surfaces 3234 of suture appliers 3228. The force on the camming surfaces 3234 can cause the suture appliers 3228 to rotate about their pins 3230, causing the arms 3236, and thus, the ends 3238 of the suture legs 3226, to rotate towards the anvil 3240. Continued rotation of the suture applier 3228 can cause the suture appliers 3228 to force the ends 3238 of the suture legs 3226 into the gap 'g' between the first arms 3246 and the second arms 3248 of the suture grabbers 3242. As the anvil 3240 contacts first buttress layer 3222, the suture appliers 3228 can reach a completed rotated position, as is shown in FIG. 124 and the suture appliers 3228 completely force ends 3238 of suture legs 3226 into the suture grabbers 3242. Once the ends 3238 of the suture legs 3226 have been pressed into the suture grabbers 3242, the anvil 3240 can be moved away from the buttress applier cartridge 3200. In one example embodiment, the suture appliers 3228 can include a torsional spring such that, as the anvil 3240 is moved away from the support platform 3218, the arms 3236 of the suture appliers 3228 can be biased away from the anvil 3240 towards a non-rotated position, as is shown in FIG. 122. As the arms 3236 of the suture appliers 3228 rotate away from the anvil 3240, the suture grabbers 3242 can hold the ends 3238 of the suture legs 3226, causing the ends 3238 to release from arms 3236 of the suture appliers 3228. The suture legs 3226 and the suture grabbers 3242 collectively function to retain the first buttress layer 3222 against the anvil 3240.

Other than just the suture legs 3226 and the suture grabbers 3242, other suitable means for coupling the first buttress layer 3222 to the anvil 3240 can be used in combination with the suture legs 3226 and suture grabbers 3242. In one example embodiment, the first buttress layer 3222 can include an adhesive on a surface thereof such that, when the anvil 3240 is brought into contact with the first buttress layer 3222 (as is shown in FIG. 124), a tissue contacting surface of the anvil 3240 and the first buttress layer 3222 can be at least partially adhered together. Other means of coupling the anvil 3240 to the first buttress layer 3222 are described throughout the present application and can be used in connection with the buttress applier cartridge 3200.

While the figures and the above-provided description describe using suture appliers 3228 to couple a buttress layer 3222 to an anvil 3240, it should be understood that other embodiments are envisioned where the buttress applier cartridge 3200 can include suture appliers 3228 on the bottom surface on the buttress applier cartridge 3220 such that a buttress layer can be coupled to a staple cartridge positioned within an elongate channel of an end effector. In one example embodiment, similar to the anvil 3240, an elongate channel of the end effector can include suture grabbers positioned on an outside surface thereof. The bottom surface of the buttress applier cartridge 3200 can include suture appliers 3228 and suture legs 3226 that support the second buttress layer 3224. In one example embodiment, as the elongate channel and staple cartridge are brought toward the second buttress layer, the suture appliers 3228 on the bottom surface of the buttress applier cartridge 3200 can force suture legs 3226 into suture grabbers on the elongate channel, similar to what was described above in regards to the anvil 3240. In other example embodiments, as shown in FIGS. 122-124, the bottom surface of the buttress applier cartridge 3220 may not include suture appliers 3228; rather just a buttress layer 3224 that can interface with the staple cartridge 3252. Other example embodiments are envisioned where other suitable means can be included on the bottom surface of the buttress applier cartridge 3200 to assist in coupling the second buttress layer 3224 to the staple cartridge 3252.

As described above, the support platform 3218 can be manufactured out of a compressible material. In operation, while the anvil 3240 is brought towards the first buttress layer 3222, staple cartridge 3252 positioned in the elongate channel of the end effector can be brought towards the second buttress layer 3224 of the buttress applier cartridge 3200, as shown in FIGS. 122 and 124. The anvil 3240 and the staple cartridge 3252 collectively compress against buttress layers 3222, 3224 towards the support platform 3218, helping maintain the position of the buttress applier cartridge 3200 and providing additional support in adhering the buttress layers 3222, 3224 to anvil 3240 and staple cartridge 3252, respectively.

After the buttress layers 3222, 3224 have been applied to the anvil 3240 and staple cartridge 3252, respectively, in one example embodiment, new buttress layers can be positioned on the planar surfaces of the support platform 3218 and the buttress applier cartridge 3200 can be utilized again. In another example embodiment, the support platform 3218 can be removed and replaced with another support platform 3218 that already includes new buttress layers 3222, 3224 positioned thereon. Other example embodiments are envisioned where the buttress applier cartridge 3200 is disposable after a single use.

Figure 126:
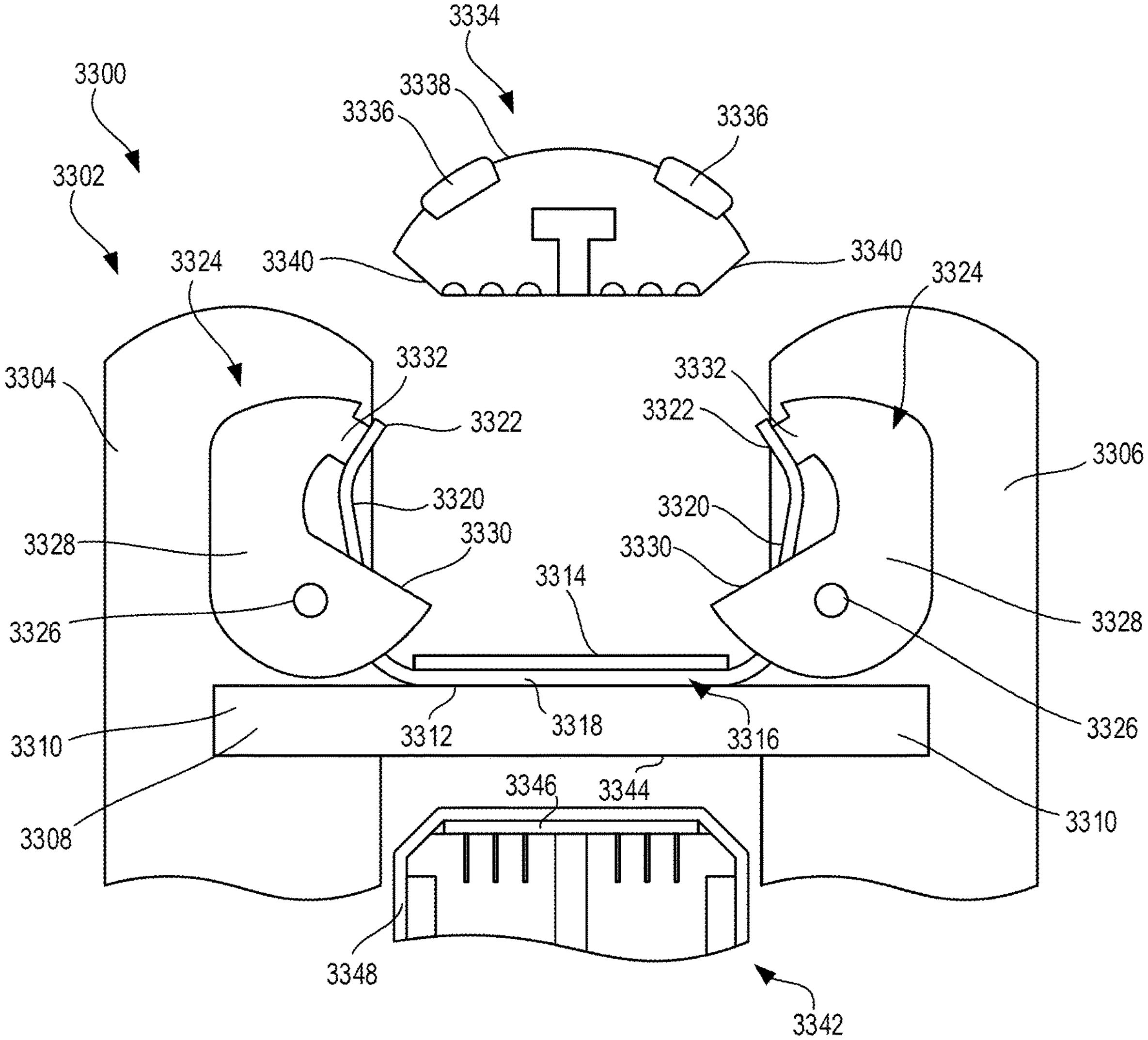
FIG. 126 illustrates a buttress applier cartridge, according to at least one aspect of the present disclosure

Referring now to FIG. 126, another buttress applier cartridge 3300 is provided, according to at least one aspect of the present disclosure. The buttress applier cartridge 3300 can include a housing assembly 3302 that can include a first leg 3304 and a second leg 3306. In one example embodiment, the housing assembly 3302 can be of unitary construction; however, other example embodiments are envisioned where the housing assembly 3302 is not of unitary construction. In one example embodiment, the housing assembly 3302 can include a top housing portion and a bottom housing portion that are coupleable together to form an outer shell of the housing assembly 3302, similar to housing assembly 3202. In various embodiments, the constructions of the buttress applier cartridge 3300 can be substantially similar to buttress applier cartridge 3200 apart from the difference referenced below.

The buttress applier cartridge 3300 can further include a support platform 3308 positioned between the first leg 3304 and second leg 3306. The support platform 3308 can be manufactured out of any suitable material such that the support platform 3308 is compressible when force is applied thereto. In various other embodiments, the support platform 3308 could be rigid as opposed to compressible. In various embodiments, the support platform 3308 can be supported by the housing assembly 3302. In one example embodiment, the support platform 3308 could include a lip 3310 around the perimeter thereof that is captured and held by the housing assembly 3302. In one embodiment where the housing assembly 3302 isn't of unitary construction, the lip 3310 can be positioned between a top housing portion and a bottom housing portion when the top housing portion and bottom housing portion are coupled together. In other embodiments, the support platform 3308 can be coupled to the housing assembly 3302 in any suitable manner such that the support platform 3308 is substantially supported relative to the housing assembly 3302 when a force is applied thereto.

The support platform 3308 can include a substantially planar top surface 3312 that can support a first buttress layer 3314. The first buttress layer 3314 can be removably coupled to the support platform 3218 by any suitable means, such as an adhesive, such that the first buttress layer 3314 is supported on their support platform 3308 until the first buttress layer 3314 interface with an end effector of a surgical instrument, as will be described in more detail below.

The buttress applier cartridge 3300 can further include a suture 3316 that includes a suture base 3318 and suture legs 3320 extending from the suture base 3318. In one example embodiment, as is shown in FIG. 126, the suture base 3318 can be positioned between the first buttress layer 3314 and the top surface 3312 of the support platform 3308 such that the suture 3316 supports the first buttress layer 3314. While one suture 3316 is shown and described, it should be understood that a plurality of sutures 3316 can be utilized to support the first buttress layer 3314.

The buttress applier cartridge 3300 can further include a plurality of suture appliers 3324. Each suture applier 3324 can be rotatably coupled to the buttress applier cartridge 3300. In one example embodiment, as seen in FIG. 126, the suture appliers 3324 can be rotatable coupled to the legs 3304, 3306 by pins 3326. The suture appliers 3324 can include a body portion 3328, a camming surface 3330, and an arm 3332. Ends 3322 of each suture leg 3320 can removable couple to a corresponding arm 3332 of a suture applier 3324, such as with an adhesive, as an example.

Similar to what was described for FIGS. 122-124, an anvil 3334 of an end effector of a surgical instrument can interface with the buttress applier cartridge 3300. The anvil 3334 can include a plurality of suture grabbers 3336 positioned on an outer, top surface 3338 thereof. In one example embodiment, the suture grabbers 3336 can be similar to suture grabbers 3242 described herein above. In various other embodiments, the suture grabbers 3242 can be similar to the suture grabbers described in more detail elsewhere in the present application.

In operation, the anvil 3334 is moved toward the first buttress layer 3314. Outer edges of anvil 3340 can contact and ride along camming surfaces 3330 of suture appliers 3324. In one example embodiment, the suture appliers 3324 are spaced along the buttress applier cartridge 3300 such that the suture appliers 3324 collectively cause the anvil 3334 to longitudinally align with the buttress applier cartridge 3300. The camming force on the camming surfaces 3330 causes the suture appliers 3324 to rotate about their pins 3326, causing the arms 3332, and thus, the ends 3322 of the suture legs 3320 to rotate towards the anvil 3334.

Continued rotation of the suture applier 3324 causes the suture appliers 3324 to force the ends 3322 of the suture legs 3320 into the suture grabbers 3336. As the anvil 3334 contacts first buttress layer 3314, the suture appliers 3324 can reach a complete rotated position and the suture appliers 3324 completely force ends 3322 of suture legs 3320 into the suture grabbers 3336. Once the ends 3322 of the suture legs 3320 have been pressed into the suture grabbers 3336, the anvil 3334 can be moved away from the buttress applier cartridge 3300. In one example embodiment, the suture appliers 3324 can include a torsional spring such that, as the anvil 3334 is moved away from the support surface 3308, the arms 3332 of the suture appliers 3324 can be biased away from the anvil 3334 towards a non-rotated position, as is shown in FIG. 126. As the arms 3332 of the suture appliers 3324 rotate away from the anvil 3334, the suture grabbers 3336 can hold the ends 3322 of the suture legs 3320, causing the ends 3322 to release from arms 3332 of the suture appliers 3324. As the anvil is moved away from the buttress appliers cartridge 3300, the base 3318 of the suture can support the bottom surface of the first buttress layer 3314, while the ends 3322 of the suture legs 3320 are held by the anvil, thereby retaining the first buttress layer 3314 against the tissue contacting surface of the anvil 3334.

As described above, the support platform 3308 can be manufactured out of a compressible material. In operation, while the anvil 3334 can be brought towards the first buttress layer 3314, a staple cartridge 3342 positioned in the elongate channel of the end effector can be brought towards the bottom surface 3344 of the support platform 3308. In one example embodiment, as is shown in FIG. 126, the staple cartridge 3342 can already be supplied with a buttress layer 3346 that is supported by a suture 3348. In other example embodiments, the bottom of the buttress applier cartridge 3300 can include suture appliers 3324 such that the staple cartridge 3342 can receive a buttress layer at the same time as the anvil 3334 receiving a buttress layer. In operation, as the anvil 3334 and the staple cartridge 3342 can collectively compress the support platform 3308, helping maintain the position of the buttress applier cartridge 3300 and providing additional support in adhering the buttress layer 3314 to anvil 3334.

As described above, the anvil and/or elongate channel of an end effector can be modified to include suture grabbers, such as suture grabbers 3242, 3336, that can receive and hold sutures in tension to hold a buttress against the anvil and/or elongate channel prior to firing the surgical instrument. As the surgical instrument is fired, a knife traveling within the end effector can cut through the buttress and the suture. When the surgical device is removed from the trocar, a free end of the suture can be removed from the suture grabber and another buttress can be applied to the surgical device using a buttress applier cartridge. In one example embodiment, as described above, the anvil can include a suture grabber 3242 that includes first arm 3246 and a second arm 3248 spaced from the first arm 3246 and that can releasably hold a suture therein.

Figure 128:
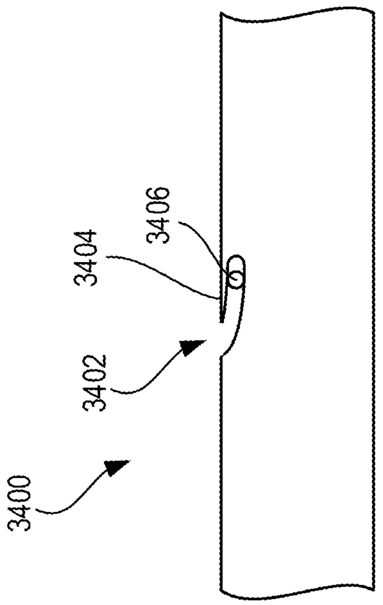
FIG. 128 illustrates a side view of the suture grabber of FIG. 127, according to at least one aspect of the present disclosure.
Figure 127:
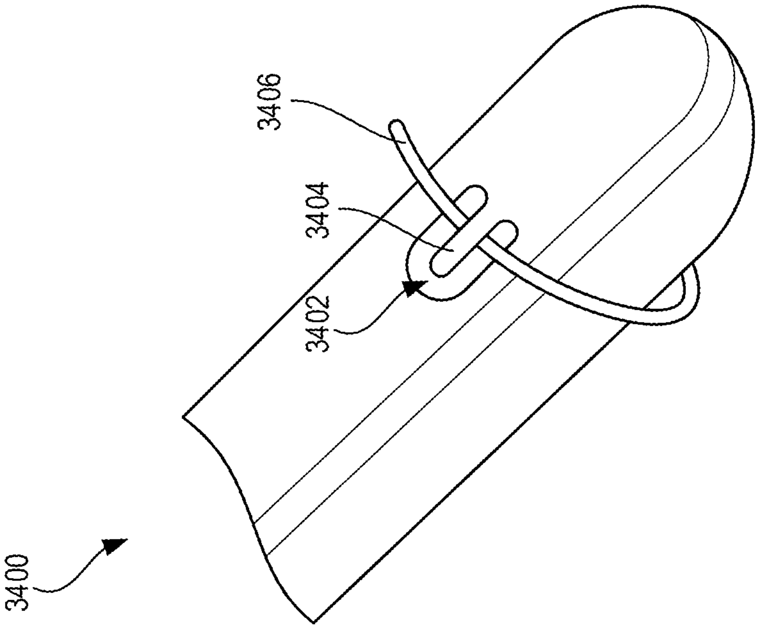
FIG. 127 illustrates a suture grabber, according to at least one aspect of the present disclosure.

Another example embodiment of a suture grabber is shown in FIGS. 127 and 128, which illustrates an anvil 3400 that includes a cutout 3402 defined therein and a flap 3404 extending over the cutout 3402. The cutout 3402 and flap 3404 function in manner similar to that of a dental floss contain. In operation, a suture 3406 can be pulled through the cutout 3402 and wedged beneath the flap 3404 (shown most clearly in FIG. 128). The flap 3404 can be dimensioned such that the suture is retained within the cutout 3402, allowing the suture 3406 to be tensioned and held in place. The cutout 3402 and flap 3404 allows the suture 3406 to hold a buttress against the anvil 3400. In another embodiment, the cutout 3402 and flap 3404 can be included on an elongate channel of the end effector so as to allow a suture (or a plurality of sutures) to retain a buttress against a staple cartridge. While one cutout 3402 and flap 3404 is shown and described, it should be understood that the anvil (or elongate channel) can include a plurality of cutouts 3402 and flaps 3404 to allow a plurality of sutures to retain a buttress against the anvil (or elongate channel).

Figure 129:
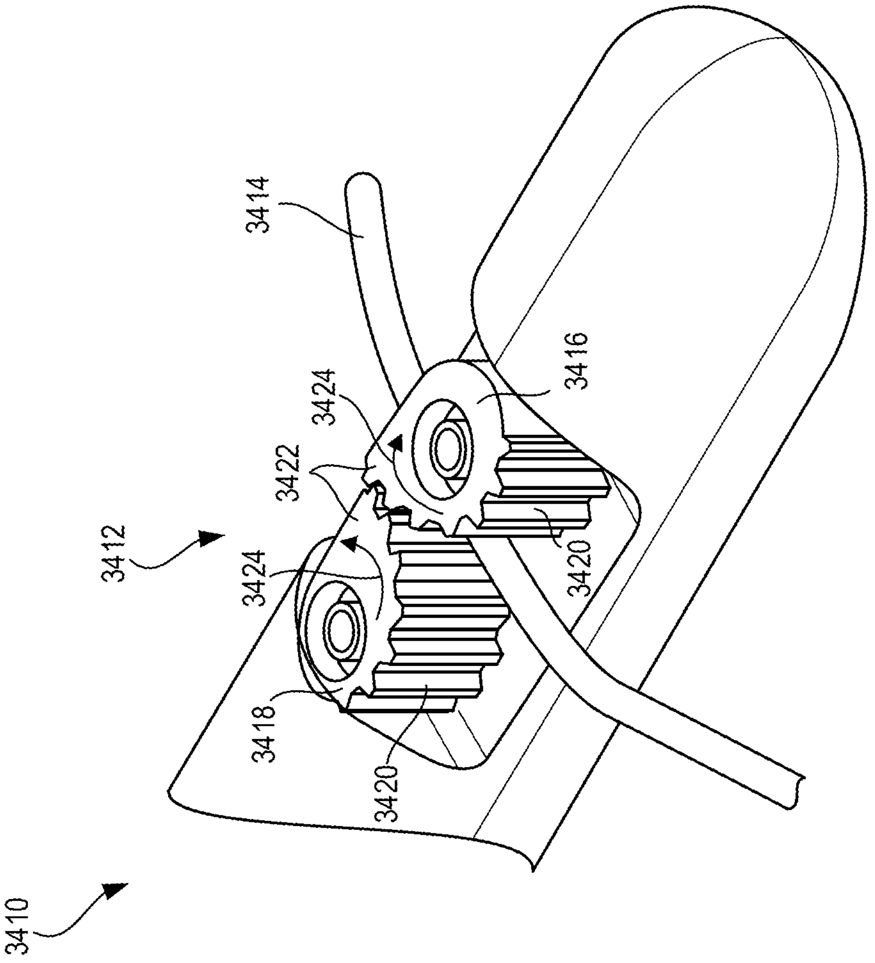
FIG. 129 illustrates a suture grabber, according to at least one aspect of the present disclosure.

Another example embodiment of a suture grabber is shown in FIG. 129, which illustrates an anvil 3410 that includes a cam-cleat style lock 3412 that can hold a suture 3414 in tension. The cam-cleat lock 3412 can include a first cleat 3416 and a second cleat 3418, each of which includes a plurality of teeth 3420 and an arm 3422. The first cleat 3416 and second cleat 3418 can be rotatably coupled to the anvil 3410 and can be rotatable relative to each other between a captured configuration, where the arms 3422 of the first 3416 and second cleats 3418 contact each other (as is shown in FIG. 129), and an uncaptured configuration, where the arms 3422 of the first 3416 and second cleats 3418 are rotated away from each other. In the uncaptured configuration, a gap can be defined between the first 3416 and second cleats 3418 such that the suture 3414 can be threaded between the cleats 3416, 3418. Each of the cleats 3416, 3418 can further include a biasing mechanism, such as a torsional spring, such that each of the cleats 3416, 3418 can be biased towards the captured configuration.

In operation, each of the cleats 3416, 3418 can be moved toward the uncaptured configuration (as indicated by arrows 3424). A suture 3414 can be threaded between the cleats 3416, 3418 in the gap that is defined between the cleats 3416, 3418 when the cleats 3416, 3418 are in the uncaptured configuration. Once the suture 3414 has been pulled through the cleats and a sufficient amount of tension has been achieved in the suture 3414, the cleats 3416, 3418 can be released such that the cleats 3416, 3418 are biased towards the captured configuration. The arms 3422 of the cleats engage the suture 3414 (as is shown in FIG. 129) therebetween and maintain the suture 3414 in tension.

Figure 131:
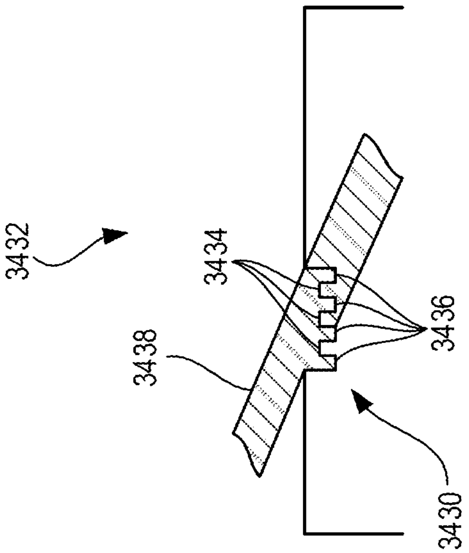
FIG. 131 illustrates a side view of the suture grabber of FIG. 131, according to at least one aspect of the present disclosure.
Figure 130:
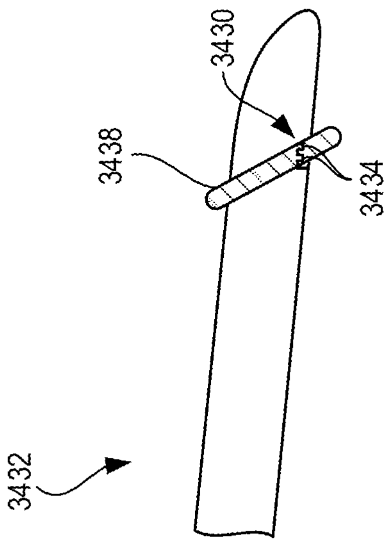
FIG. 130 illustrates a suture grabber, according to at least one aspect of the present disclosure.

Another example embodiment of a suture grabber is shown in FIGS. 130 and 131, which illustrate a small cutout 3430 defined in an anvil 3432. The cutout 3430 can include a plurality of alternating teeth 3434 and grooves 3436 (shown most clearly in FIG. 131) such that, when a suture 3438 is tensioned and pulled through the cutout 3430, the strands of the suture 3438 are intermeshed and captured by the teeth 3434 and grooves 3436. The teeth 3434 and grooves 3436 can hold and restrict movement of the suture 3438 when the strands are captured, thus allowing the suture 3438 to maintain tension and hold a buttress against the anvil 3432.

Figure 132:
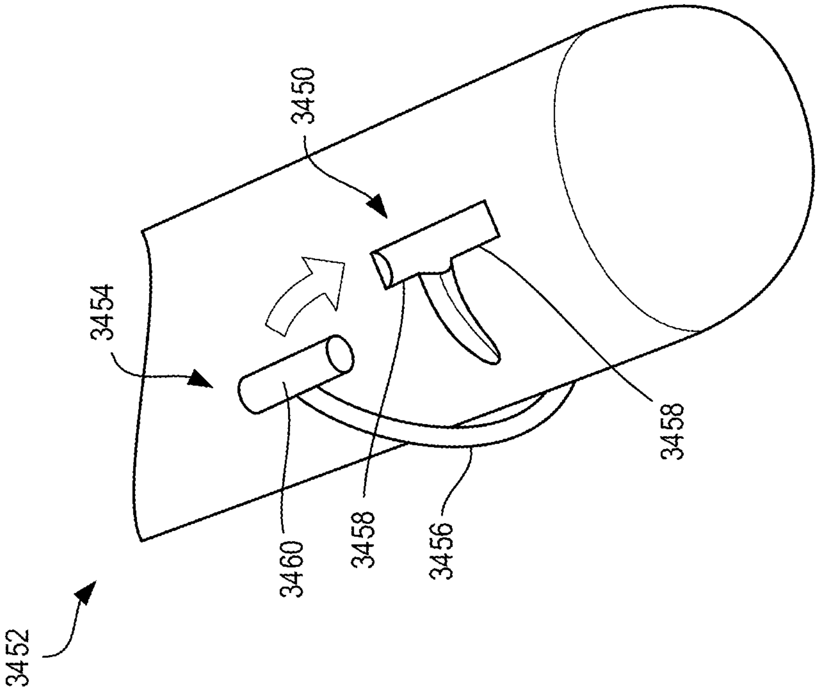

Another example embodiment of a suture grabber is shown in FIG. 132, which illustrates a shaped groove 3450 defined in an anvil 3452. The groove 3450 can be shaped to receive a correspondingly-shaped T-tag 3454 at an end of a suture leg 3456. In one example embodiment, the suture leg 3456 can be tensioned and stretched such that the T-tag 3454 is pulled over the groove 3450. Once sufficiently tensioned, the T-tag 3454 of the suture leg 3456 can be released such that the T-tag 3454 is dropped into and captured by the groove 3450. Walls 3458 of groove 3450 can contact and hold the transverse portion 3460 of the T-tag 3454 within the groove 3450, keeping the suture leg 3456 in tension and maintaining the T-tag 3454 in place during the surgical procedure. In another example embodiment, the T-tag 3454 and corresponding groove can have similar geometries with tight tolerances such that the T-tag 3454 can be press-fit into the groove 3450 to maintain tension in the suture leg 3456, but loose enough so that the T-tag 3454 can be released from the anvil 3452 after completion of the surgical stapling procedure. While a T-tag is shown and described, any suitable geometry and shape of tag and groove can be used at the end of the suture leg 3456, such as a square shape or star shape, as example.

Figure 133:
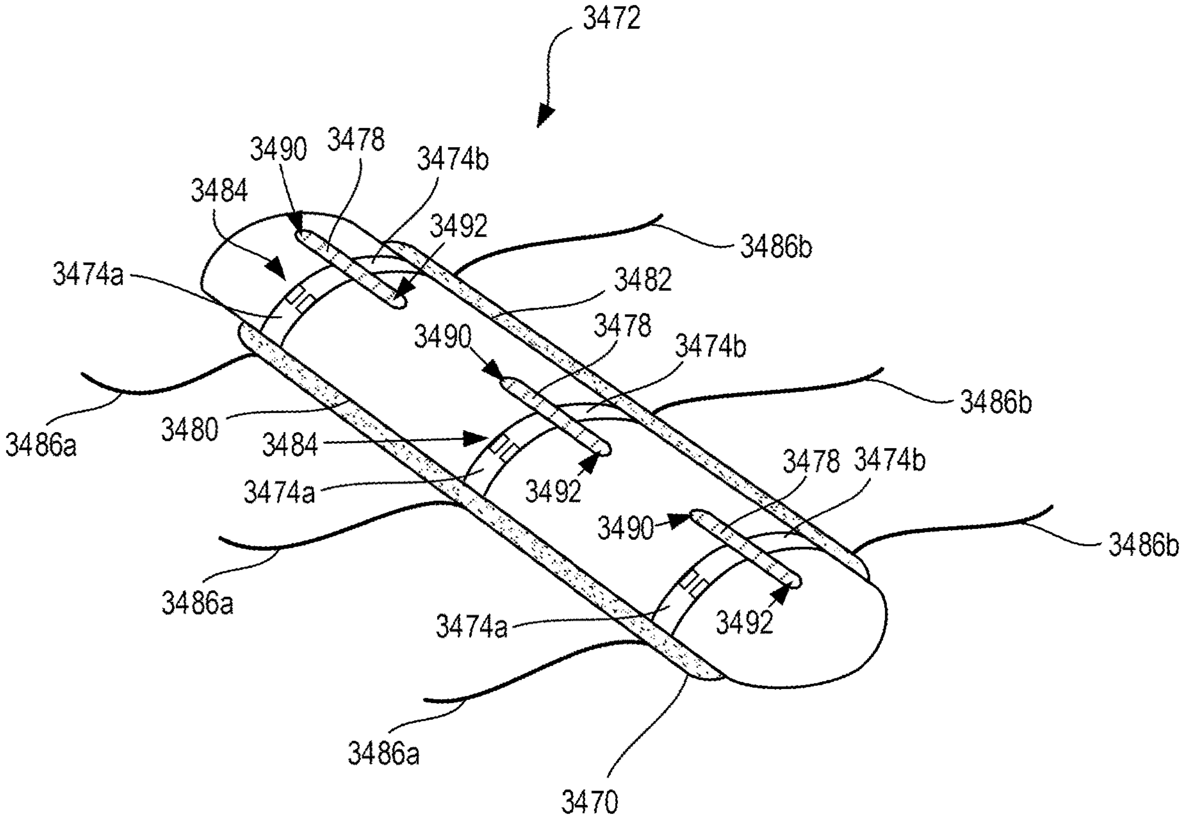

Another example embodiment for securing a buttress 3470 to an anvil 3472 is shown in FIG. 133. As shown in FIG. 133, the anvil 3472 can include a plurality of grooves 3474*a*, 3474*b* longitudinally spaced along an outside, top surface of the anvil. The first grooves 3474*a* and second grooves 3474*b* can extend towards a suture knife pocket 3478 from a first lateral side 3480 of the anvil 3472 and a second lateral side 3482 of the anvil 3472, respectively. Each of the grooves 3474*a*, 3474*b* can include suture pinch feature 3484, which can capture and hold suture legs, as will be explained in more detail below.

In various embodiments, the buttress 3470 can include a plurality of suture legs 3486*a*, 3486*b* extending therefrom. The suture legs 3486*a*, 3486*b* can be coupled to or support the buttress 3470 in any suitable manner such that the suture legs 3486*a*, 3486*b* are able to maintain the buttress 3470 against the anvil 3472. In various embodiments, each suture leg 3486*a*, 3486*b* can be positioned within an adjacent groove 3474*a*, 3474*b* and be held by the suture pinch feature 3484 within the grooves 3474*a*, 3474*b*. In one aspect, suture legs 3486*a*, 3486*b* in laterally offset grooves 3474*a*, 3474*b* can be tensioned and coupled together in any suitable manner, such as by tying the ends of the suture legs 3486*a*, 3486*b* together in a knot. Once tied, the coupled suture legs 3486*a*, 3486*b* form a continuous suture that extends from a first side of the buttress 3470, through a groove 3474*a*, the suture knife pocket 3478, and a groove 3474*b* to a second side of the buttress 3470.

Figure 134:
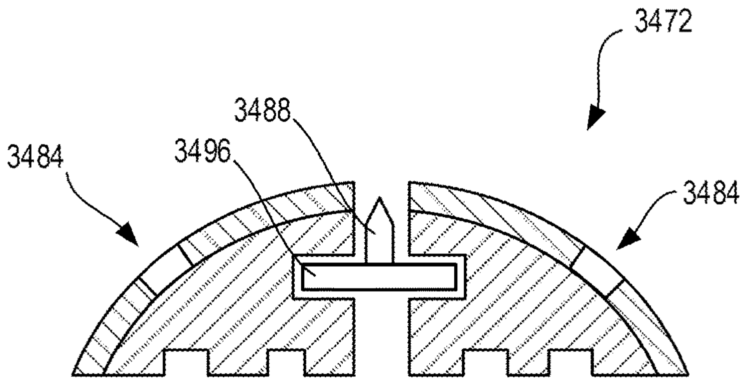

As shown in FIG. 134, each suture knife pocket 3478 can include a suture knife 3488. Each suture knife 3488 is movable within and through the suture knife pocket 3478 between a proximal position 3490 and a distal position 3492. In one example embodiment, as the suture knife 3488 moves between the proximal position 3490 and the distal position 3492, the suture knife 3488 severs the coupled suture legs 3486*a*, 3486*b* that extend over the suture knife pocket 3478. In various embodiments, the suture knife 3488 can move from the proximal position 3490 toward the distal position 3492 based on movement of a firing member, such as firing beam 3082, within the end effector. In one example, embodiment the firing member can abut a base portion 3496 of the suture knife 3488 as the firing member moves within the end effector to cut and staple tissue positioned therein. In other embodiments, the suture knives 3488 can be positioned at the distal positions 3492 of the suture knife pockets 3478 such that, as the firing member is retracted after the cutting and stapling procedure, the firing member can abut the base portions 3496 and move the suture knives 3488 proximally, severing the coupled suture legs 3486*a*, 3486*b*. The above-described embodiments allow for the progressive release of the buttress 3470 from the anvil 3472.

As described above, the buttress applier cartridge 3200 may be utilized to apply buttress layers to an anvil and a deck of a staple cartridge before tissue is positioned in an end effector and before end effector is actuated. Because end effector may be actuated many times during use of instrument and multiple staple cartridges may be used, it may be desirable to enable an operator to repeatedly and easily load buttress assemblies onto an anvil, while simultaneously loading the elongate channel of the end effector with a new staple cartridge that includes a buttress layer. In other words, because end effector may be actuated many times during use of instrument in a single surgical procedure, it may be desirable to include a buttress applier cartridge that is a 'one stop shop' for both reloading the end effector with a new staple cartridge that already includes a buttress layer and applying a buttress layer to an anvil.

Figure 135:
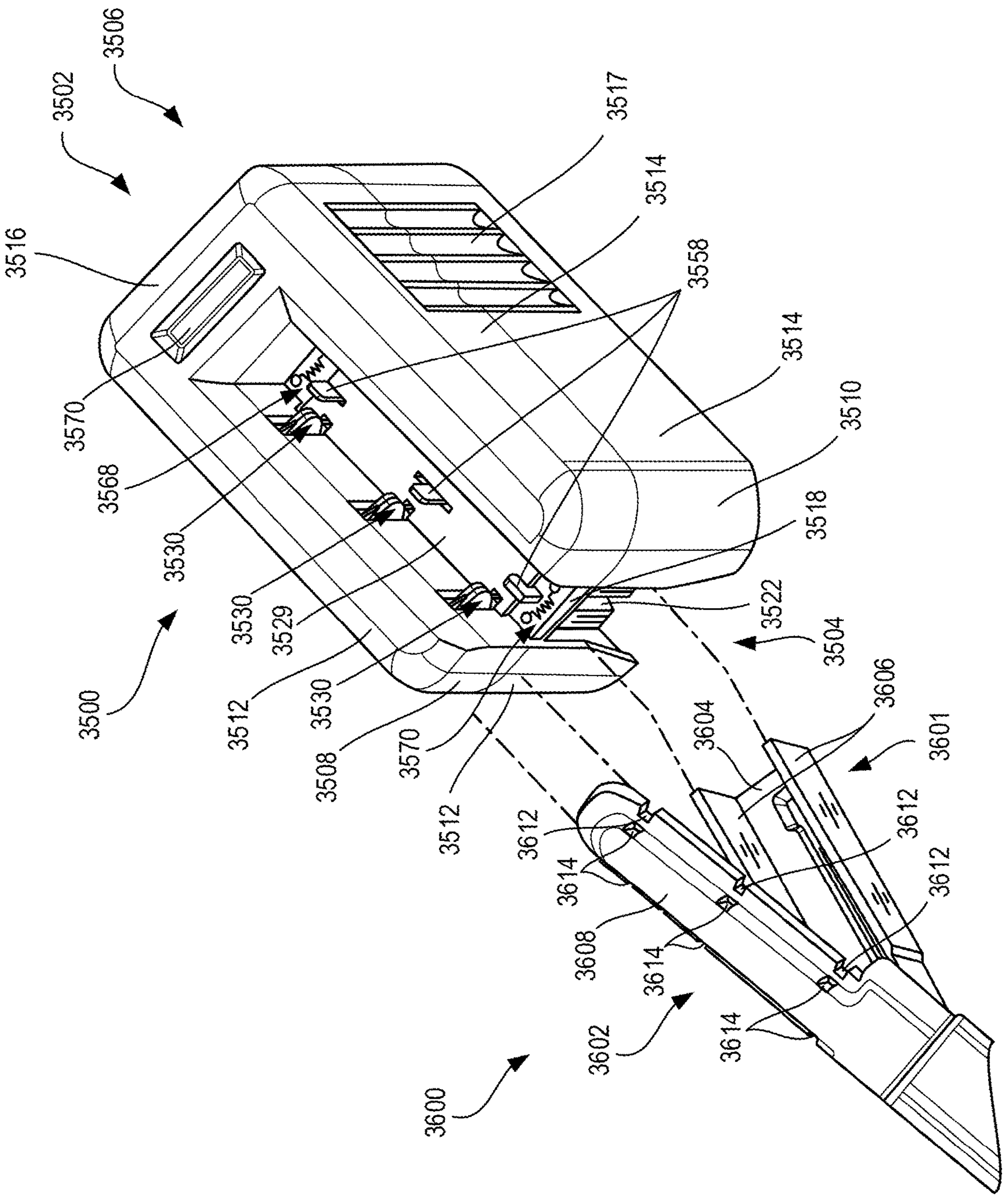

In one example embodiment, referring to FIG. 135, an end effector 3600 is provided that includes an elongate channel 3601 and an anvil 3602. The elongate channel 3601 includes a base 3604 and sidewalls 3606 extending upwardly from the base. The elongate channel 3601 is sized and configured to receive a staple cartridge therein that can be removably replaceable over the course of a surgical procedure. The anvil 3602 can include an outer surface 3608 and a tissue contacting surface 3610 (seen in FIG. 136). The outer surface 3608 of the anvil 3602 can include a plurality of notches 3612 and recessed pockets 3614, as will be discussed in more detail below. The end effector 3600 can interface with a buttress applier cartridge 3500, as will be discussed in more detail below, such that a buttress layer can be applied to the tissue contacting surface 3610 while a staple cartridge including a buttress layer is positioned within the elongate channel.

Continuing to refer to FIG. 135, a buttress applier cartridge 3500 accordingly to at least one aspect of the current disclosure is shown. The buttress applier cartridge 3500 can include a generally U-shaped housing assembly 3502 that defines an open end 3504 and a closed end 3506. The housing assembly 3502 includes a top housing portion 3508 and a bottom housing portion 3510 that are coupleable together to form an outer shell of the housing assembly 3502. The top housing portion 3508 and the bottom housing portion 3510 each include a first leg 3512, a second leg 3514, and a connecting portion 3516 that connects the first leg 3512 to the second leg 3514 at the closed end 3506. The top housing portion 3508 and the bottom housing portion 3510 can be coupled with any suitable coupling mechanism, such as with snap fit, latches, press-fit, as examples. In one example embodiment, the housing assembly 3502 can include various internal components, such as those described in U.S. Pat. No. 10,342,542, the disclosure of which is hereby incorporated by reference in its entirety herein. In other example embodiments, the housing assembly 3502 can be of unitary construction as opposed to being separable into a top housing portion and a bottom housing portion. In various embodiments, the buttress applier cartridge 3500 can include grip features 3517 on each of the legs 3512, 3514 (grip feature only shown on second legs 3514) that allows a user to grip and position the buttress applier cartridge 3500.

The buttress applier cartridge 3500 can further include a support platform 3518 positioned between the first legs 3512 and second legs 3514 and that generally extends from the connecting portion 3516 of the housing assembly 3502 towards the open end 3504. The support platform 3518 can be manufactured out of any suitable material such that the support platform 3518 is compressible when force is applied thereto. In various other embodiments, the support platform 3518 could be rigid as opposed to compressible. In various embodiments, the support platform 3518 can be supported by the housing assembly 3502. In one example embodiment, the support platform 3518 could include a lip around the perimeter thereof that is captured between the top housing portion 3508 and the bottom housing portion 3510 when the top housing portion 3508 and bottom housing portion 3510 are coupled together. In other embodiments, the support platform 3518 can be coupled to the housing assembly 3502 in any suitable manner such that the support platform 3518 is substantially supported relative to the housing assembly 3502 when a force is applied thereto. In one example embodiment, the support platform 3518 can be integrally coupled to the housing assembly 3502. In various embodiments, the buttress applier cartridge 3500 can have similar construction attributes to the buttress applier cartridges described herein, such as buttress applier cartridges 3200, 3300.

The support platform 3218 can include a substantially planar top surface that can support a first buttress layer 3520 and a substantially planar bottom surface that interfaces with a buttress layer 3524 positioned on the deck on a staple cartridge 3522. In various embodiments, the first buttress layer 3520 and the second buttress layer 3524 can be removably coupled to the support platform 3218 by any suitable means, such as an adhesive, such that the first buttress layer 3520 and the second buttress layer 3524 are supported on the support platform 3518 until the first buttress layer 3520 and the staple cartridge 3522 interface with the end effector 3600 of a surgical instrument, as will be described in more detail below. In other example embodiments, only the first buttress layer 3520 is adhered to the support platform 3218, while the second buttress layer 3524 is merely supported by the staple cartridge 3522, such as by an adhesive or a suture. Other example embodiments of coupling the first buttress layer 3520 and the staple cartridge 3524/second buttress layer 3524 to the buttress applier cartridge 3500 will be described below.

The buttress applier cartridge 3500 can further include a first loading region, or zone 3529 that can include a loading assembly for securing an absorbable layer to an anvil as the anvil approaches the absorbable layer. In various embodiments, the loading assembly can include a plurality of suture applying assemblies 3530 (shown most clearly in FIG. 136). Each suture applying assembly 3530 can include a suture applier 3532 that includes a suture applier body 3534, a camming surface 3536, an arm 3538, a plug 3540 extending from the arm 3538, and a knife 3542 extending from the arm 3538. Each suture applier body 3532 is rotatably coupled to one of the legs 3512, 3514 of the housing assembly 3502 about a pin 3544. The suture appliers 3532 are rotatable between a resting position (shown in the BEFORE side of FIG. 136) and an actuated position (shown in the AFTER side of FIG. 136). In various embodiments, a biasing mechanism, such as a torsion spring 3546, can be utilized to bias the suture appliers 3532 to the rested position. The suture appliers 3532 can be rotated toward the actuated position based on outer edges 3616 of the anvil 3602 riding along the camming surface 3536, as will be described in more detail below.

Figure 136:
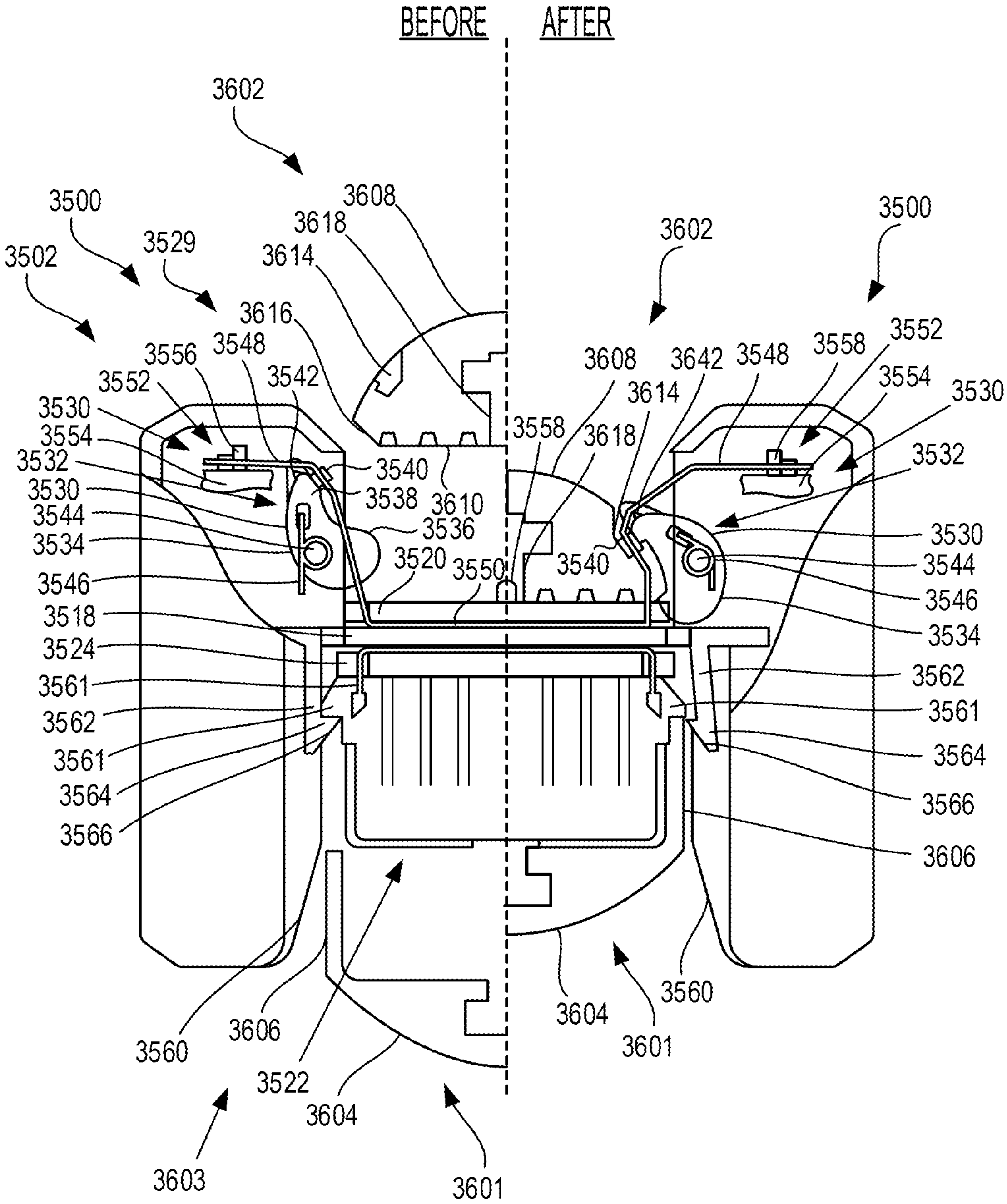

Each of the suture applying assemblies 3530 can further include a suture leg 3548. As is shown in FIG. 136, laterally offset suture applying assemblies 3530 each include a suture leg 3548 of one common, continuous suture 3550. The suture legs 3548 can be coupled to the plugs 3540 of the suture appliers 3532 such that movement of the plug 3540 causes movement in the suture legs 3548. In one aspect, the sutures 3550 can support the first buttress layer 3520 such that movement of the suture legs 3548 can move the first buttress layer 3520. In one example embodiment, as shown in FIG. 136, the suture 3550 extends from one suture applier assembly 3530, under a bottom surface of the first buttress layer 3520 and to a laterally offset suture applying assembly 3530.

Each of the suture applying assemblies 3530 can further include a suture anchor 3552. The suture anchors 3552 are fixably coupled to the housing assembly 3502 and include a base 3554 and an attachment portion 3556. In various embodiments, the suture legs 3548 can extend toward and couple to the attachment portions 3556 such that, as the suture leg 3548 are moved by the suture appliers 3532 toward the anvil 3602, as will be described in further detail below, the suture anchors hold the ends of the suture legs 3548, generating tension in the sutures 3550.

In addition, as reference above, the buttress applier cartridge 3500 can further include a second loading region, or zone 3603 that includes staple cartridge 3522 that can include a second buttress layer 3524. In various embodiments, the second buttress layer 3524 can be coupled to the staple cartridge 3522 such as by an adhesive or a suture 3561 applied to the staple cartridge 3522 prior to inserting the staple cartridge into the buttress applier cartridge 3500. In various other embodiments, the second loading region 3603 of the buttress applier cartridge can include suture appliers such that a staple cartridge can be loaded into the buttress applier cartridge and a buttress layer can be added to the staple cartridge therein.

In one aspect, the staple cartridge 3522 can include laterally extending fins 3561 that are held and supported by latches 3562 extending from the buttress applier cartridge 3500. The latches 3562 include arms 3564 that can hold the staple cartridge 3522 within the buttress applier cartridge 3500. The latches 3562 can further include camming surfaces 3566 that interface with the sidewalls 3606 of the elongate channel 3601 to release the staple cartridge 3522, as will be described in more detail below.

In operation, the anvil 3602 and the elongate channel 3601 of the end effector 3600 are brought toward the first loading region 3529 of the buttress applier cartridge 3500, as is shown in the BEFORE side of FIG. 136. The anvil 3602 can be moved toward the first buttress layer 3520 such that that outer edges 3616 of anvil 3602 can engage and ride along camming surfaces 3536 of the suture appliers 3532. As the outer edges 3616 of the anvil 3602 ride along the camming surfaces 3536, the anvil 3602 is brought into longitudinal alignment with the buttress applier cartridge 3500 due to the lateral spacing of the suture appliers 3632. Stated another way, the suture appliers 3532 are laterally positioned on the buttress applier cartridge 3500 such that the suture appliers 3532 collectively align the anvil 3602 with the support platform 3518 of the buttress applier cartridge 3500, ensuring that the anvil 3602 is properly aligned as the anvil 3602 approaches the first buttress layer 3520.

In one aspect, continued movement of the outer edges 3616 of the anvil 3602 along the camming surfaces 3536 causes suture appliers 3532 to rotate toward the actuated position, as described above. As the anvil 3602 is brought toward the first buttress layer 3520, the suture appliers 3532 can rotate and force the suture legs 3548 through the anvil notches 3612 and further forces the suture plugs 3540 into the recessed pockets 3614 defined in the anvil 3602. The suture plugs 3540 can be press-fit into the recessed pockets 3614 such that the suture plugs 3540, and thus, the suture legs 3548, are coupled to the anvil 3602. Further, as the suture plugs 3540 are forced into recessed pockets 3614, the suture anchors 3552 resist motion of the suture legs 3548 toward the recessed pockets 3614, causing tension to develop in the suture 3550, allowing the suture 3550 to securely press the first buttress layer 3520 against the tissue contacting surface 3610 of the anvil. As the suture appliers 3532 reach the actuated position, the knives 3542 on the suture appliers 3532 can contact and sever the suture legs 3548, releasing the sutures 3550 from the buttress applier cartridge 3500.

In addition to the above, in various embodiments, the buttress applier cartridge 3500 can further include anvil centering features 3558 that further assist in properly aligning the anvil 3602 with the first buttress layer 3520. The anvil centering features 3558 can extend from the support platform 3518 through the first buttress layer 3520 and can be received within the elongate channel 3618 of the anvil 3602. The anvil centering features 3558 are sized such that the anvil centering features 3558 force the anvil 3602 into proper alignment with the first buttress layer 3520.

At substantially the same time as the first buttress layer 3520 is being applied to the anvil 3602, the elongate channel 3601 of the end effector 3600 can be moved towards the second loading region 3603, as is shown in the BEFORE side of FIG. 136. The housing assembly 3502 of the buttress applier cartridge 3500 can include guide walls 3560 that are sized and positioned to abut the sidewalls 3606 of the elongate channel 3601 as the elongate channel 3601 is brought toward the staple cartridge 3522. The guide walls 3560 are sloped toward the base of the staple cartridge such that, if the sidewalls 3606 were to engage the guide walls 3560, the sidewalls 3606 would ride along the guide walls 3560 to become properly aligned with the camming surfaces 3566 of the latches 3562.

As the base 3604 of the elongate channel 3601 is brought toward the base of the staple cartridge 3522, the sidewalls 3606 can travel along the sidewalls of the staple cartridge 3522 and engage the camming surfaces 3566 of the latches 3562, as is shown in the AFTER side of FIG. 136. The sidewalls 3606 and latches 3562 are made of any suitable material of thickness such that, as the sidewalls 3606 engage the camming surfaces 3566, the arms 3564 of the latches 3562 can flex away from the fins 3561, releasing the staple cartridge 3522 from the buttress applier cartridge 3500. As the latches 3562 disengage the fins 3561, the base 3604 of the elongate channel 3601 can engage the base of the staple cartridge 3522 and the sidewalls 3606 engage the fins 3561 of the staple cartridge 3522, thus removably coupling the staple cartridge 3522 with the elongate channel 3601.

It should be understood that the anvil 3602 and elongate channel 3601 can be brought toward the buttress applier cartridge in the manner described above at substantially the same time such that, as the anvil 3602 engages the first buttress layer 3520 and the elongate channel 3601 engages the staple cartridge 3522, the anvil 3602 and the elongate channel 3601 can apply a sufficient force to the support platform 3518 such that a user ensures that enough force is generated to attach the suture legs 3548 to the anvil and removably seat the staple cartridge 3522 within the elongate channel 3601.

In addition, the buttress applier cartridge 3500 can further include a plurality of sensors that can sense or detector proper alignment of the end effector 3600 with the buttress applier cartridge 3500. In one example embodiment, the support platform 3518 can include a first sensor 3568 positioned near the closed end 3506 of the buttress applier cartridge 3500 and a second sensor 3570 positioned near the open end 3504 of the buttress applier cartridge 3500. As the tissue contacting surface 3610 of the anvil 3602 is brought into contact with the first buttress layer 3520, the first and second sensors 3568, 3570 can detect the alignment of the anvil 3602 relative to the support platform 3518 to determine if the anvil 3602 is properly aligned.

In one example embodiment, the first and second sensors 3568, 3570 can comprise resistors that form a circuit when the anvil 3602 is brought into properly alignment with the buttress applier cartridge. In another example embodiment, the first and second sensors 3568, 3570 can comprise Hall-effect sensors that detect magnets coupled to the anvil 3602. In various other embodiments, the first and second sensors 3568, 3570 can sense a position of the anvil 3602 prior to the tissue contacting surface 3610 reaching the first buttress layer 3520 or prior to the outer edges 3616 of the anvil 3602 engaging the camming surfaces 3536 of the suture appliers 3532, thus allowing a user to know if the anvil 3602 is properly longitudinally and laterally aligned within the buttress applier cartridge 3500 prior to moving the anvil 3602 toward the first buttress layer, ensuring that the suture appliers 3532 are not inadvertently actuated before the anvil 3602 is properly aligned. While the sensors described above were discussed regarding proper alignment of the anvil, various other embodiments are contemplated where sensors are utilized to ensure proper lateral and longitudinal alignment of the elongate channel 3601 within the buttress applier cartridge 3500.

In various embodiments, the buttress applier cartridge 3500 can further include a display 3572 in electrical communicate with the first and second sensors 3568, 3570. The display 3572 can provide a user with audible or visual feedback regarding information sensed by the first and second sensors 3568, 3570, such as whether or not the anvil 3602 and/or the elongate channel 3601 is properly aligned within the buttress applier cartridge. Various other embodiments are envisioned where the display 3572 can also provide additional information to the user regarding the buttress applier cartridge 3500, such as the size of the cartridge 3522 positioned therein, status information, or error messages if the buttress applier cartridge 3500 has damaged, or the like.

Figure 137:
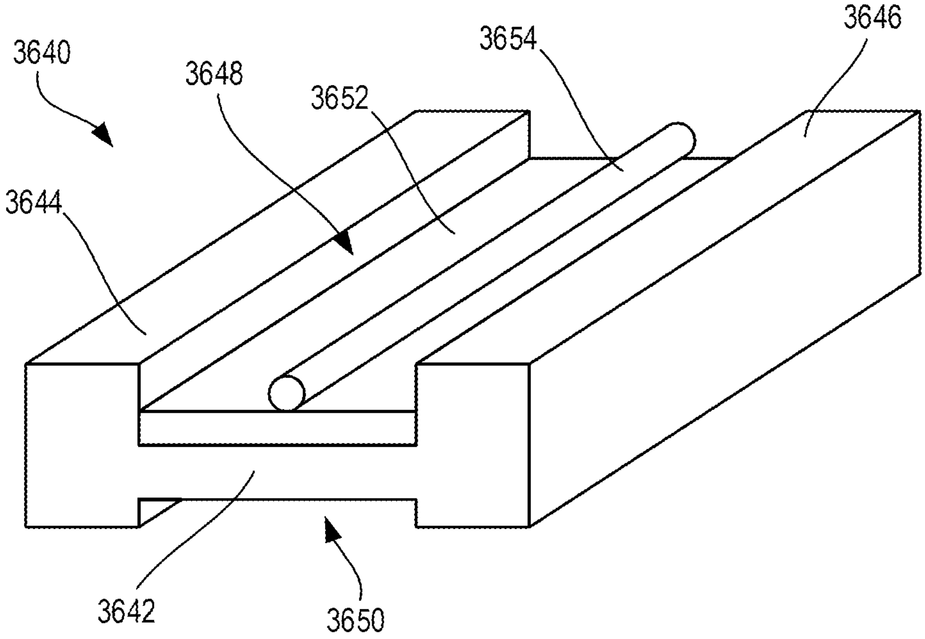
Figure 138:
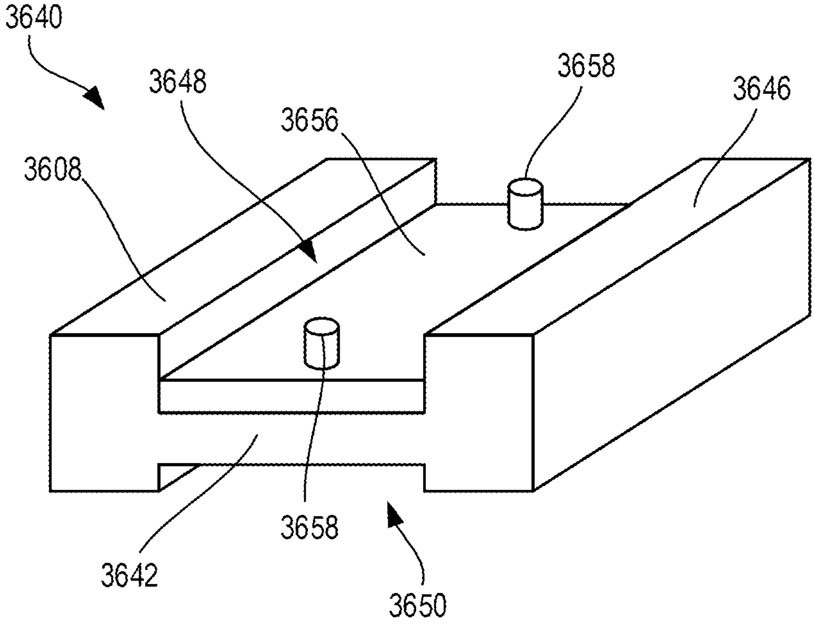

Referring now to FIGS. 137 and 138, another buttress applier cartridge 3640 is provided, in accordance with at least one aspect of the present disclosure. The buttress applier cartridge 3640 includes a support platform 3642, a first sidewall 3644, and a second sidewall 3646. The sidewalls 3644, 3646 extend in directions away from the support platform 3642 so as to define recessed areas 3648, 3650 on a top and bottom side of the buttress applier cartridge 3640.

Referring to FIG. 137, a first embodiment is provided where the first recessed area 3648 can include a buttress layer 3652 positioned on the planar support platform 3642. The buttress layer 3652 can include an elongate support 3654 extending from a surface of the buttress layer 3652. The elongate support 3654 is sized and manufactured such that the elongate support 3654 can be received within an elongate channel of an anvil, such as elongate channel 3618, as an example. As the anvil is brought toward buttress layer 3652, the elongate support 3654 can deform and be press-fit into the elongate channel so as to releasably couple the buttress layer 3652 to the anvil.

Referring to FIG. 138, a second embodiment is provided where the first recessed area 3648 can include a buttress layer 3656 positioned on the planar support platform 3642. The buttress layer 3656 can include a plurality of pins 3658 extending from a surface of the buttress layer 3652. The pins 3658 is sized and manufactured such that the pins 3658 can be received within the elongate channel of an anvil, such as elongate channel 3618, as an example. As the anvil is brought toward buttress layer 3656, the pins 3658 can deform and be press-fit into the elongate channel so as to releasably couple the buttress layer 3656 to the anvil. In various other embodiments, the pins can be laterally aligned as opposed to longitudinally aligned. In such embodiments, an anvil can include apertures defined in the tissue contacting surface such that the pins could be press-fit in the apertures. In this way, the buttress applier cartridge can be coupled to the anvil by way of pins, but the pins are positioned away from the elongate channel.

While the above-provided buttress applier cartridges were shown and described as having buttress layers positioned within the first recessed areas 3648, it should be understood that buttress layers can also be positioned against the support platform 3642 in the second recess area 3650. It should also be understood that the buttress layers 3652, 3656 can be utilized in a variety of buttress applier cartridges, such as buttress applier cartridges 3200, 3500 and any other buttress applier cartridges described herein.

Figure 139:
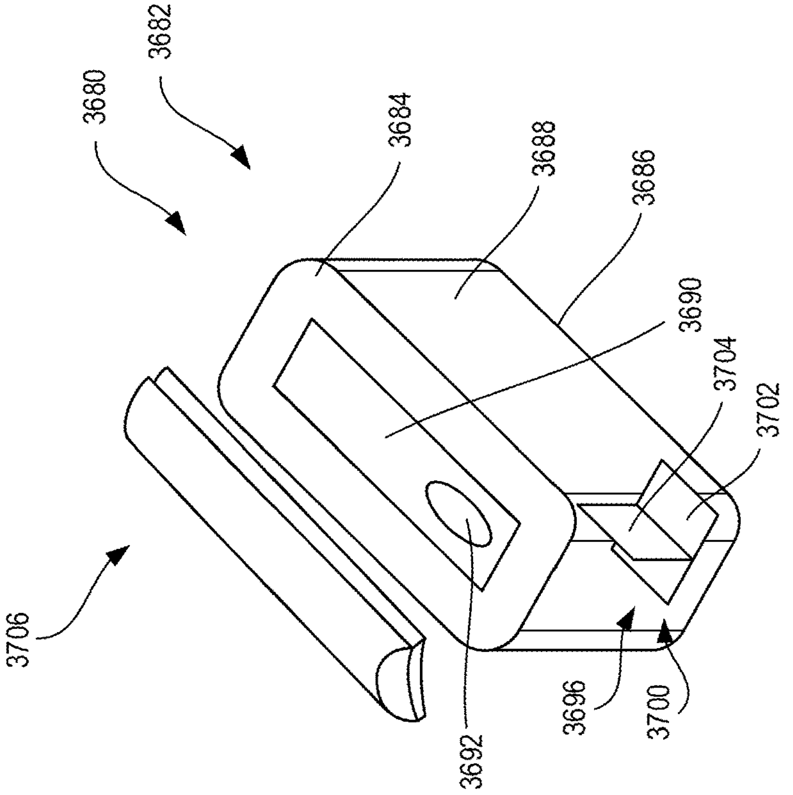

Referring now to FIG. 139, another buttress applier cartridge 3680 for attaching a buttress layer to an anvil is provided, in accordance with at least one aspect of the present disclosure. The buttress applier cartridge 3680 can include a housing assembly 3682 that includes a support platform 3684, a base 3686, and walls 3688 connecting the support platform 3684 to the base 3686. In various embodiments, the support platform 3684 is sized to support a buttress layer 3690 thereon. In various embodiments, both the support platform 3684 and the buttress layer 3690 can include a slot 3692 defined therein such that, when the buttress layer 3690 is properly aligned on the support platform 3684, the slots 3692 can align such that an opening is defined through the support platform 3684 into the interior 3694 of the housing assembly 3682. In various other embodiments, only the support platform 3684 may include a slot 3692, as will be described in more detail below.

Figure 140:
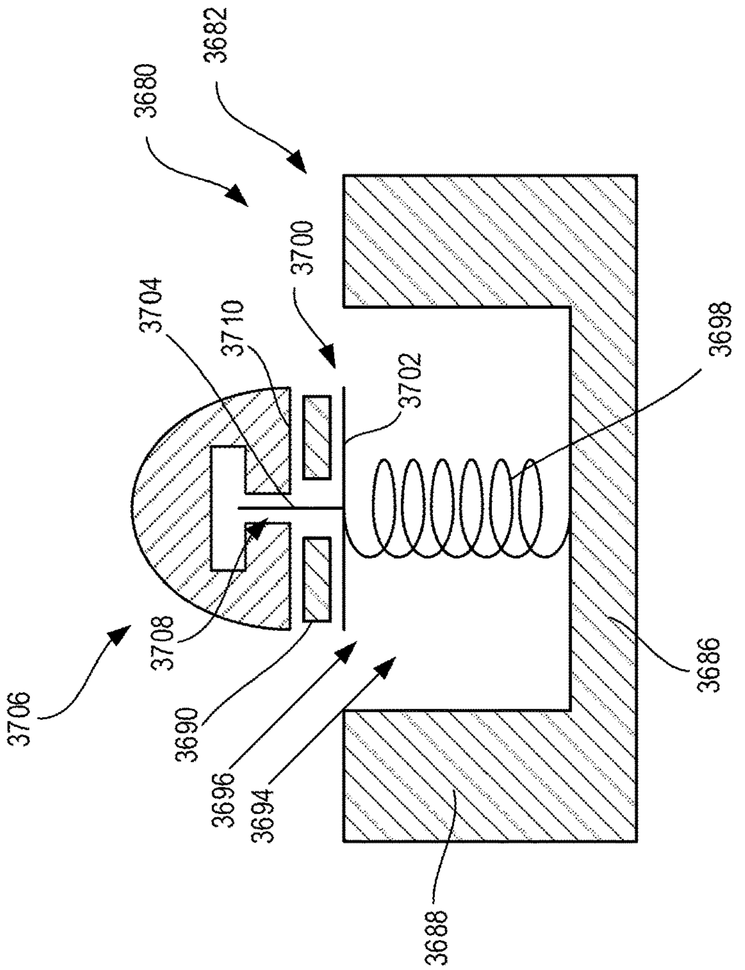

Referring now to FIGS. 139 and 140, the housing assembly 3682 can further include a spring-loaded key assembly 3696 position within the interior 3694 of the housing assembly 3682. The spring-loaded key assembly 3696 can include a spring 3698 and a key 3700 coupled to the spring 3698. In various embodiment, the key 3700 can include a base 3702 and an alignment feature 3704 extending from the base 3702. The spring-loaded key assembly 3696 can be movable between a rested position (shown in FIG. 139), wherein the spring 3698 is compressed and the key 3700 is positioned within the housing assembly 3682, and an actuated position (shown in FIG. 140), where the spring is expanded and the key 3700 extends through the slots 3692 of the support platform 3684 and the buttress layer 3690. In embodiments where only the support platform 3684 includes a slot 3692, as referenced above, the alignment feature 3704 can include a blade such that, as the alignment feature 3704 moves toward the actuated position, the knife can move through the slot 3692 of the support platform 3684 and pierce through the buttress layer 3690.

As referenced above, the buttress applier cartridge 3680 can attach a buttress layer, such as buttress layer 3690, to an anvil 3706. In various embodiments, the anvil 3706 can include an elongate channel 3708 defined therein that can receive the alignment feature 3704 of the key 3700. In operation, the tissue contacting surface 3710 of the anvil 3706 can be pressed down onto the buttress layer 3690 positioned on the support platform 3684. Based on the pressure applied to the buttress layer 3690 and the buttress applier cartridge 3680, the spring-loaded key assembly 3696 can be actuated such that the spring-loaded key assembly 3696 moves from the resting position to the actuated position, as described above. In various embodiments, the support platform 3684 can include a pressure sensor that can sense the pressure the anvil 3706 applies to the housing assembly 3682. Once a threshold pressure is reached or exceeded by the anvil 3706, the spring-loaded key assembly 3696 can be actuated and moved to the actuated position. Various other embodiments are envisioned that can actuate the spring-loaded key assembly 3696 when sufficient force is provided by the anvil 3706.

In one aspect, when the spring-loaded key assembly 3696 is actuated, the alignment feature 3704 can extend from the housing assembly 3682 via the slots 3692 and into the elongate channel 3708 of the anvil 3706. The alignment feature 3704 can ensure that the buttress layer 3690 cannot be misaligned from its proper position on the tissue contacting surface 3710 of the anvil 3706 during the process of attaching the buttress layer 3690 to the anvil 3706. In various aspects, with the location of the slot 3692 in the buttress layer 3690 and the alignment feature 3704 within the buttress applier cartridge 3680, it can be ensured that misalignment of the buttress layer 3690 in translation along the major axis of the anvil 3706, in translation along the minor axis of the anvil 3706, or in rotation about the vertical axis through the anvil 3706 can be maintained. In various other embodiments, the slot 3692 of the buttress applier cartridge 3680 can be sized to be larger than the slot 3692 of the buttress layer 3690 such that the base 3702 of the key 3700 can extend from the housing assembly 3682 and abut the bottom surface of the buttress layer 3690, forcing the buttress layer 3690 against the tissue contacting surface 3710 of the anvil 3706, helping ensure the buttress layer 3690 doesn't move relative to the anvil 3706 during the alignment process.

Once the buttress layer 3690 has been properly aligned and affixed to the tissue contacting surface 3710 of the anvil 3706, such as with an adhesive, as an example, the anvil 3706 can be moved away from the buttress applier cartridge 3680, which can cause the spring-loaded key assembly 3696 to retract back to the resting position. In one example embodiment, the pressure sensor can continuously sense the pressure the anvil 3706 applies to the buttress applier cartridge 3680. When the applied pressure drops before a threshold level, such as the threshold level that activated the spring-loaded key assembly 3696, described above, a mechanism can retract the spring-loaded key assembly 3696 back to the resting position. In various embodiment, the threshold level to retract the spring-loaded key assembly 3696 can be less than the original threshold level that moved the spring-loaded key assembly 3696 to the actuated position, such that the level of pressure required to actuate the spring-loaded key assembly 3696 does not need to be maintained during the alignment process of the buttress layer 3690. In various embodiments, the threshold level to retract the spring-loaded key assembly 3696 could be the pressure sensor sensing zero force, thus indicating the anvil 3706 has been completed moved away from the buttress applier cartridge 3680.

Figure 141:
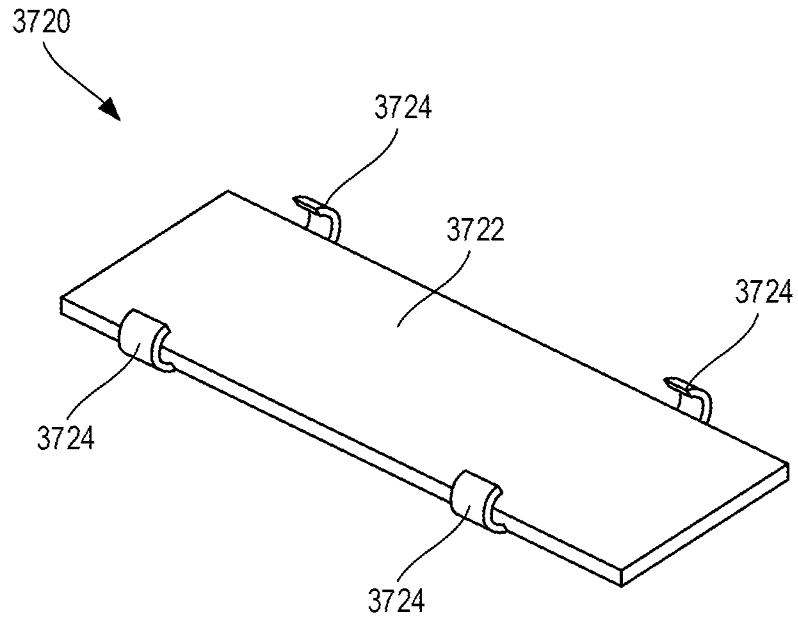

Referring now to FIG. 141, a buttress assembly 3720 is provided in accordance with at least one aspect of the present disclosure. The buttress assembly 3720 includes a buttress layer 3722 and a plurality of brackets 3724 extending from the buttress layer 3722. The brackets 3724 can be coupled to the buttress layer 3722 in an suitable manner, such as with an adhesive, such that, when a threshold force is applied to the brackets 3724, the brackets 3724 snap off of and release the buttress layer 3722, as will be described in more detail.

Figure 142:
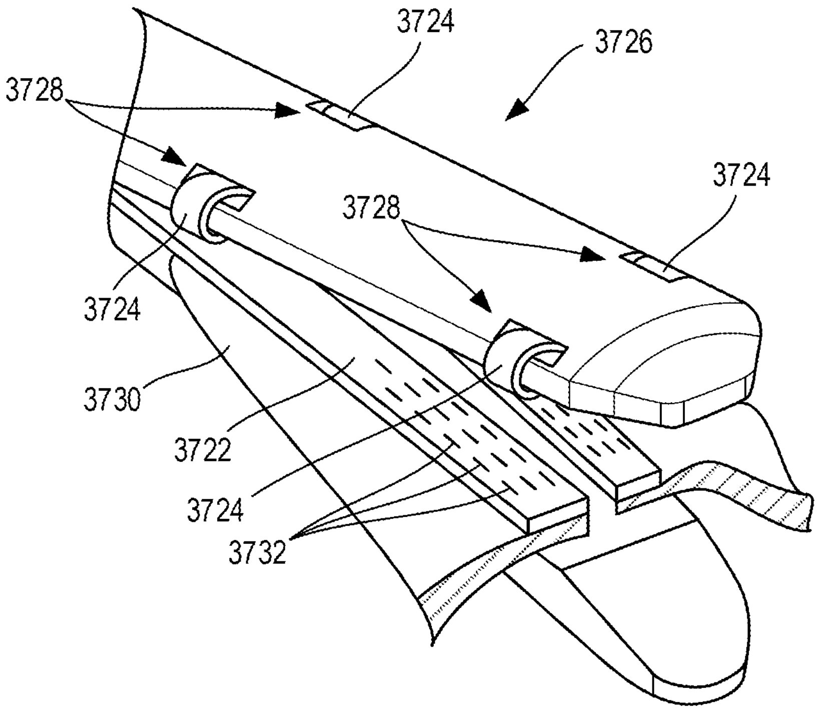

In various embodiments, referring to FIG. 142, the buttress assembly 3720 can be coupled to an anvil 3726 that includes a plurality of notches 3728 defined around a perimeter thereof. In one example embodiment, each bracket 3724 of the buttress assembly 3720 can align with a notch 3728 in the anvil 3726 such that, when each of the brackets 3724 are snapped into and captured by a corresponding notch 3728, the buttress layer 3722 can be brought into proper lateral and longitudinal alignment with the anvil 3726.

In one aspect, once the buttress assembly 3720 is coupled to the anvil 3726, by way of brackets 3724 and notches 3728, the anvil 3726 can be utilized in a surgical stapling procedure. After completion of a cutting and firing stroke, the buttress layer 3722 can be severed and stapled to tissue 3730, as is shown in FIG. 142. With the buttress layer 3722 held to the tissue 3730 by way of staples 3732 (three pointed to in FIG. 142), the anvil 3726 can be pulled away from the tissue 3730. In various embodiments, as the anvil 3726 is moved away from the tissue 3730, the brackets 3724 can be sufficiently stiff such that the brackets 3724 are held in notches 3728, causing the brackets 3724 to release from the buttress layer 3722. Once the brackets 3724 have been separated from the buttress layer 3722, a clinician can remove the brackets 3724 from the notches 3728 and reload the anvil 3726 with a new buttress assembly 3720. While brackets were shown and described that can couple the buttress layer 3722 to the anvil 3726, various embodiments are envisioned where the brackets 3724 are replaced or utilized in connection with other structures to couple the buttress layer 3722 to the anvil 3726. In various embodiments, these other structures could comprise pins, magnets, or slot mechanisms.

Referring now to FIG. 143, a buttress assembly 3750 is provided in accordance with at least one aspect of the present disclosure. The buttress assembly 3750 can include a buttress layer 3752, a coupling member 3754 and a bracket 3756. In one aspect, the coupling member 3754 and the bracket 3756 can be longitudinally aligned and laterally spaced along a central buttress axis 3758 such that, when the buttress layer 3752 is coupled to an anvil 3780, as will be described in more detail below, the buttress layer 3752 can cover the plurality of staple forming pockets 3782 on the tissue contacting surface 3784 of the anvil 3780.

In various embodiments, the coupling member 3754 can include a base 3760 extending from the buttress layer 3752 and a head 3762 extending from the base 3760. The base 3760 can be coupled to the buttress layer 3752 in any suitable manner, such as with an adhesive. In other embodiments, the coupling member 3754 can of unitary construction with the buttress layer 3752 and comprise the same material as the buttress layer 3752. In various embodiment, the head 3762 can include any suitable shape such that the head 3762 can be press-fit into an elongate channel 3786 of the anvil 3780 and thereby retain the buttress layer 3752 to the anvil 3780. In one example embodiment, as is shown in FIG. 143, the head 3762 can include a triangular shape such that the coupling member 3754 forms an arrow-like shape. The triangular head 3762 can be pressed into the elongate channel 3786 such that the head 3762 can abut an inner contact surface 3770 of the anvil 3780 (shown in FIG. 144) and hold the coupling member 3754, and therefore, the buttress layer 3752, against the anvil 3780. Various other shapes are contemplated by the present disclosure that can be used as opposed to a triangular shaped head, such as a rectangular shaped head such that the coupling member 3754 forms a ‘T’ shape. While one coupling member 3754 is shown and described, a plurality of coupling members 3754 can be utilized to support the buttress layer 3752 and retain the buttress layer 3752 against the tissue contacting surface 3784.

In various embodiments, the bracket 3756 can include a base 3764 releasably coupled the buttress layer 3752 and a head 3766 extending from the base 3760. The base 3764 can be releasably coupled to the buttress layer 3752 in any suitable fashion, such as with an adhesive, such that when a threshold force is applied to the bracket 3756, the base 3764 can be released from the buttress layer 3752, as will be described in more detail below. In various embodiments, the bracket 3756 can comprise a material that is different than the buttress layer 3752. In one example embodiment, the bracket 3756 can be comprised of plastic. Other embodiments are envisioned where the bracket 3756 and the buttress layer 3752 comprise the same material.

In one aspect, the head 3766 can be received with an aperture 3768 at a distal end of the elongate channel 3786 of the anvil 3780 (illustrated by the dashed line in FIG. 143). Once inserted into the aperture 3768, the buttress assembly 3750 can be moved proximally (away from the tip of the anvil 3780) such that the head 3766 is positioned within the elongate channel 3786 of the anvil 3780 (as is shown in FIG. 144). The head 3766 can be sized such that the head 3766 abuts the contacting surface 3770 of the elongate channel 3786, thereby coupling the bracket 3756, and thus, the buttress layer 3752, to the anvil 3780. In various example embodiments, as the head 3766 is being received within the aperture 3768, the head 3762 of the coupling member 3754 can also being inserted into the elongate channel 3786, as described above. Once the head 3762 of the coupling member 3754 has been inserted into the elongate channel 3786 and the head 3766 of the bracket 3756 has been positioned within the aperture 3768, the buttress assembly 3750 can be pulled proximally such that the head 3762 of the coupling member 3754 and the head 3766 of the bracket 3756 are engaging the contact surface 3770 of the elongate channel 3786, thereby retaining the buttress layer 3752 to the anvil 3780.

Once the buttress layer 3752 is coupled to the anvil 3780, by way of the coupling member 3754 and the bracket 3756), the anvil 3780 can be used in a surgical stapling procedure, as described elsewhere herein. In one aspect, as shown in FIG. 143, a knife member 3790 can traverse the anvil toward the distal tip of the anvil 3780 during the surgical stapling procedure. In one example embodiment, the knife member 3790 can be similar to knife member 3080. The knife member 3790 can include an abutment surface that can engage the contact surface 3770 of anvil 3780 as the knife member 3790 traverses the elongate channel 3786. The knife member 3790 can also include a tissue cutting blade 3794 for cutting tissue and the buttress layer 3752 as the knife member traverses the elongate channel 3786.

In operation, the knife member 3790 can traverse distally through the elongate channel 3786 of the anvil 3780, severing the buttress layer 3752 and tissue positioned against the buttress layer 3752 with the blade 3794. When the blade 3794 encounters the coupling member 3754, the blade 3794 can severe the coupling member 3754, releasing the portion of the buttress layer 3752 to which the coupling member 3754 was coupled. In other example embodiments, the knife member 3790 abuts the coupling member 3754 such that the head 3762 of the coupling member 3754 is forced out of the elongate channel 3786 and is also severed by the blade 3794. In one aspect, the knife member 3790 is designed such that little to no remnants of the coupling member 3754 remain within the elongate channel 3786 after the knife member 3790 releases the coupling member 3754 from the anvil 3780.

Continuing from above, the knife member 3790 can continue to traverse distally through the elongate channel 3786 of the anvil 3780 and approach the bracket 3756, as is shown in FIG. 144. In various embodiments, the abutment surface 3792 can abut the head 3766 of the bracket 3756 and apply a sufficient force so as to release the bracket 3756 from the buttress layer 3752 (shown in FIG. 145). The abutment surface 3792 can force the bracket 3756 distally and force the head 3766 into a receiving area 3796 of the anvil 3780. After the knife member 3790 has positioned the bracket within the receiving area 3796, the knife member 3790 can be retracted proximally, leaving the bracket 3756 positioned within the receiving area 3796. At this point, a user of the surgical instrument can remove the anvil from the surgical site, manually remove the bracket 3756 from the receiving area 3796 of the anvil 3780 through the aperture 3768, and attached a new buttress assembly 3750 to the anvil 3780.

Referring now to FIG. 146, an anvil 3800 is provided in accordance with at least one aspect of the present disclose. The anvil 3800 can include a plurality of levers 3802 rotatably coupled to the anvil 3800 about pins 3804. In various embodiments, the levers 3802 are friction clamps, meaning that the levers 3802 can retain their position about the pins 3804 until a sufficient force is applied to the levers 3802 to rotate them about the pins 3804. In one aspect, the levers 3802 can include a body 3806 and an arm 3808 extending from the body 3806.

In various embodiments, the anvil 3800 can further include a plurality of suture receivers 3810 (shown in more detail in FIG. 147). In various embodiments, the suture receives 3810 can include a first arm 3812 and a second arm 3814 spaced from the first arm 3812 to define a gap therebetween. In use, the suture receives 3810 can receive a suture leg 3816 between the first arm 3812 and the second arm 3814, as will be described in more detail below. In various embodiments, the first arm 3812 and the second arm 3814 are spaced apart such that the suture leg 3816 can be press fit and held between the first arm 3812 and the second arm 3814.

In one aspect, a buttress layer 3820 can interface with a tissue contacting surface 3822 of the anvil 3800, as shown in FIG. 146. In various embodiments, the buttress layer 3820 can include a plurality of suture legs 3816 extending therefrom. The suture legs 3816 can be coupled to the buttress layer 3820 in any suitable manner, such as manners described elsewhere herein, such that the suture legs 3816 can support the buttress layer 3820 against the tissue contacting surface 3822 of the anvil 3800.

As shown in FIG. 146 and described above, the buttress layer 3820 can interface with the tissue contacting surface 3822 of the anvil 3800. In one aspect, as the buttress layer 3820 is interfacing with the tissue contacting surface, the suture legs 3816 can wrap about an outer surface of the anvil 3800 and extend toward the suture receivers 3810. In one example embodiment, the suture legs 3816 can be press fit within first and second arms 3812, 3814 of a corresponding suture receiver 3810. Once the suture legs 3816 are positioned within a suture receiver 3810, the levers 3802 can be rotated above pins 3804 such that arms 3808 of the levers 3802 engage the suture legs 3816, as is shown in FIG. 148, thereby releasably retaining the suture legs 3816, and therefore, the buttress layer 3820, to the anvil 3800. Once the buttress layer 3820 has be coupled to the anvil 3800, the anvil 3800 can be utilized in a surgical procedure as described elsewhere herein.

In one example embodiment, after the surgical instrument to which the anvil 3800 is being utilized with has been utilized in a stapling operation, the suture legs 3816 can be cut from the buttress layer 3820 in any suitable manner, such as with surgical scissors, as an example, and the anvil 3800 can be removed from the patient. In one aspect, as shown in FIG. 149, once the anvil 3800 has been removed from the patient, the arms 3808 of the levers 3802 can be rotated away from the anvil 3800 and the suture legs 3816 can be removed from the suture receivers 3810. After the suture legs have been removed from the suture receivers 3810, a new buttress layer 3820 including suture legs 3816 can be coupled to the anvil 3800 in the same manner as described above.

Referring now to FIGS. 150 through 152, a lockout mechanism 3824 is provided in accordance with at least one aspect of the present disclosure. In various embodiments, the lockout mechanism 3824 can be positioned within an anvil of an end effector. In various embodiments, the lockout mechanism 3824 can be positioned within the elongate channel and/or a staple cartridge of the end effector. In various embodiments, as will be discussed in more detail below, the lockout mechanism 3824 can interface with the elongate slot of the end effector such that the lockout mechanism can engage and prevent progress of a firing member through the elongate channel of the end effector. In one aspect, the lockout mechanism 3824 can interface with the I-beam slot of the end effector.

In various embodiments, the lockout mechanism 3824 can include a leaf spring 3826. In one aspect, the leaf spring 3826 can comprise a single, unitary structure. In other aspect, the leaf spring 3826 can comprise a grouping of like-structures grouped together to form the leaf spring 3826. In various embodiments, the leaf spring 3826 can be transitionable between a contracted configuration (shown in FIG. 151) and an expanded configuration (as shown in FIG. 152). While one leaf spring 3826 is shown and described, various other embodiments are envisioned where more than one leaf spring 3826 is utilized. In one aspect, the leaf spring 3826 can include a central body 3828, a first arm 3830 extending from the central body 3828 and a second arm 3832 extending from the central body 3828. The first and second arms 3830, 3832 can be rotatable relative to the central body 3828 to transition the leaf spring 3826 between the contracted configuration and the expanded configuration.

As shown in FIGS. 150-152, the lockout mechanism 3824 can include a first window 3834 and a second window 3836. The first window 3834 is sized to receive the first arm 3830 of the leaf spring 3826 and the second window 3836 is sized to receive the second arm 3832 of the leaf spring 3826. In various embodiments, the leaf spring 3826 can be movable relative to the windows 3834, 3836 between an unlocked position (as shown in FIG. 151) and a lockout position (as shown in FIG. 152). In one aspect, as the leaf spring 3826 moves to the lockout position, the first arm 3830 can rotate into the first window 3834 and the second arm 3832 can rotate into the second window 3836. When the leaf spring 3826 is in the lockout position, the first arm 3830 can engage the first window 3834 and the second arm 3832 can engage the second window 3836, thereby preventing the leaf spring 3826 from moving back toward the unlocked position. In various embodiments, once the leaf spring 3826 is in the lockout position, the leaf spring 3826 is permanently locked in the lockout position. In various other embodiments, the leaf spring 3826 is capable of being reset to the unlocked position. In one example embodiment, a user can use their fingers to press the first arm 3830 and the second arm 3832 toward the central body 3828 through the first window 3834 and second window 3836, respectively, thereby allowing the leaf spring 3826 to move back to the unlocked position.

In various embodiments, the lockout mechanism 3824 can include a piston head 3838. The piston head 3838 can be movable to detect if a buttress layer 3840 is present within the end effector. In one example embodiment, as is shown in FIG. 151, in an instance where a buttress layer 3840 is present, the piston head 3838 can contact the buttress layer 3840. In another example embodiment, as is shown in FIG. 152, in an instance where a buttress layer in not present, the piston head 3838 can move beyond the position of where the buttress layer 3840 would be positioned. In such an instance, the piston head 3838 moving beyond the buttress layer 3840 location can cause the leaf spring 3826 to actuate and transition to the expanded configuration, thereby causing a lock-out situation, as will be described in more detail below. In various embodiments, when the lockout mechanism 3824 is in the lock-out situation, the firing member of the surgical instrument is prevented from performing a firing stroke.

Continuing to refer to FIGS. 151 and 152, the lockout mechanism 3824 can include a piston rod shaft 3842 and a piston rod cylinder 3844. In various embodiment, the piston rod shaft 3842 can be coupled to, or affixed, to the piston head 3838, with the distal end 3843 of the piston rod shaft 3842 terminating at the piston head 3838. In various embodiments, the piston rod cylinder 3844 can be coupled to, or affixed, to the leaf spring 3826, with the distal end 3845 of the piston rod cylinder 3844 terminating at the leaf spring 3826. In one aspect, the piston rod cylinder 3844 can be hollow and include an inside diameter that is greater than the outside diameter of the piston rod shaft 3842. In such an aspect, the piston rod shaft 3842 can be freely slidable within the piston cylinder 3844. In various embodiment, a spring 3846, such as a coil spring, can be coupled to the leaf spring 3826 and the piston head 3838, which can cause the piston rod shaft 3842 to be biased away from the piston rod cylinder 3844.

In one example operation when a buttress layer 3840 is present, as shown in FIG. 151, the piston head 3838 is pushed toward the buttress layer 3840 by way of the coil spring 3846. In one example embodiment, the piston head 3838 can be held in place prior to operation of the surgical instrument. Once the surgical instrument is actuated and a firing member is caused to begin moving within the end effector, the piston head 3838 can be released, initiating the lockout mechanism 3824. In one aspect, the coil spring 3846 is partially compressed such that, when the lockout mechanism 3838 is activated, the coil spring 3846 can force the piston head 3838 toward the position of the buttress layer 3840. In various embodiments, the spring leaf 3826 is held at least substantially in place, such as by friction fit or by the piston rod cylinder 3844, as examples, such that the leaf spring 3826 is prevented from moving upward and away from the position of the buttress layer 3840.

Continuing to refer to FIG. 151, as a buttress layer 3840 is present, the piston head 3838 abuts a surface of the buttress layer 3840 and halts further motion of the piston head 3838. Owing to the displacement of the piston head 3838 toward the buttress layer 3840, tension can be developed within the spring 3846, causing the coil spring 3846 to impart a force onto the leaf spring 3826, pulling the leaf spring 3826 toward the piston head 3838. As the leaf spring 3826 moves toward the buttress layer 3840, the coil spring 3846 begins to compress, owing to the piston head 3838 being held in place by the buttress layer 3840. As the coil spring 3846 compresses, the coil spring 3846 resistance force builds up and stops travel of the leaf spring 3826 before the first arm 3830 and the second arm 3832 are able to reach the first window 3834 and the second window 3836, respectively, preventing a lock-out situation. In one aspect, preventing the lock-out situation allows the firing member to freely to travel unobstructed through the end effector.

In another example operation when a buttress layer is absent, as shown in FIG. 152 the piston head 3838 is pushed toward the buttress layer 3840 by the coil spring 3846. In one aspect, the coil spring 3846 is partially compressed such that, when the lockout mechanism 3838 is activated, the coil spring 3846 can force the piston head 3838 toward the intended position of the buttress layer 3840, In various embodiments, the spring leaf 3826 is held at least substantially in place, such as by friction fit or by the piston rod cylinder 3844, as examples, such that the spring leaf 3826 is prevented from moving upward and away from the intended position of the buttress layer 3840.

Continuing to refer to FIG. 152, as a buttress layer is absent, the piston head 3838 moves beyond the intended position of where the buttress layer 3840 would be located. Owing to the displacement of the piston head 3838 toward the intended position of the buttress layer 3840, tension can be developed in the spring 3846, which causes the coil spring 3846 to impart a force onto the leaf spring 3826, pulling the leaf spring 3826 toward the piston head 3838. As the buttress layer 3840 is absent and the piston head 3838 is allowed to continue moving beyond the intended position of the buttress layer 3840, the coil spring 3846 does not compress at the same rate as if a buttress layer 3840 were present. As the coil spring 3846 is unable to generate enough coil resistance force to deter movement of the leaf spring 3826, the first arm 3830 and the second arm 3832 of the leaf spring 3826 are able to reach the first window 3834 and the second window 3836, respectively, and are therefore actuated to the expanded position, initiating a lock-out situation. In various embodiments, a lock-out situation can include preventing distal translation of a firing member through the end effector.

In various embodiments, the lockout mechanism 3824 can be made primarily out of plastic to enable elastic deformation to control the lockout. In various embodiments, the piston rod shaft 3842 and the piston rod cylinder 3844 can be comprised of metal to enhance rigidity, thereby allowing the lockout mechanism 3824 to resist side loading of the firing member and for connection to portions of the end effector, such as the anvil or channel body, as examples. The lockout mechanism 3824 can be placed in conjunction with other mechanisms to enable detection of proper buttress positioning throughout the entire area of the anvil or cartridge body. In one aspect, the lockout mechanism 3824 can be positioned to lockout motion of the firing that would lead to initial tissue clamping. In other aspects, the lockout mechanism 3824 can be positioned to lockout motion of the firing that would lead to firing of the staple cartridge within the end effector.

Referring now to FIG. 153, a suture applier 3900 is illustrated in accordance with at least one aspect of the present disclosure. The suture applier 3900 can include a housing assembly 3902 that includes a first housing half 3904 and a second housing half 3906 pivotably coupled to the first housing half 3904 about a pivot 3908. The first housing half 3904 can be rotatable relative to the second housing half 3906 between an open position (see FIG. 154) and a closed position (see FIG. 156) to capture an anvil 3910 of an end effector 3912 therebetween. Each of the first housing half 3904 and the second housing half 3906 can include a first leg 3914, a second leg 3916, a connector 3918 connecting the first leg 3914 to the second leg 3916, and surfaces 3920 (all shown most clearly in FIG. 155).

In various embodiments, the suture applier 3900 can include a plurality of plungers 3922 extending from the surface 3920 first housing half 3904. Referring to FIG. 158, each of the plungers 3922 can include a base 3924, a needle 3926, and a cam arm 3928 as will be described in more detail below.

In operation, the first housing half 3904 can be moved to the open position, as is shown in FIG. 154. The anvil 3910 can then be placed within the second housing half 3906 such that, when the first housing half 3904 is rotated to the closed positon, as is shown in FIG. 156, the anvil 3910 can be captured between the first housing half 3904 and the second housing half 3906. In various embodiments, the first leg 3914, the second leg 3916, and the connector 3918 of the second housing half 3906 are sized to guide the anvil 3910 such that, when a tissue contacting surface of the anvil 3910 abuts the surface 3920 of the second housing half 3906, apertures 3930 and cam members 3932 on the surface of the anvil 3910, which will be discussed in more detail below, are aligned with the needles 3926 and cam arms 3928 of the plungers 3922, respectively, when the first housing half 3904 is rotated to the closed position.

As shown in FIG. 155 and most clearly in FIG. 158, the anvil 3910 can include a plurality of apertures 3930 and cam members 3932 (FIG. 158 only illustrates one aperture 3930 and cam member 3932, but this is merely for illustrative purposes and it should be understood that the anvil 3910 can include a plurality of apertures 3930 and cam members 3932, each pair corresponding to a plunger 3922 in the first housing half 3904, as will be described in more detail below).

In various aspects, the apertures 3930 are sized to receive the needles 3926 of the plungers 3922 as the first housing half 3904 is rotated toward the closed position. The needles 3926 can travel through the apertures 3930 and extend into the second housing half 3906 as the first housing half 3904 is brought to the closed position. In the second housing half 3906, each of the needles 3926 can interface and capture a suture leg 3934. In one aspect, the second housing half 3906 can include a plurality of spools 3936 of suture material such that, when the needles 3926 extend into the second housing half 3906, the needles 3926 can interface and capture the free suture leg 3934 extending from spool 3936. Once the needle 3926 has coupled to and captured the suture leg 3934, the first housing half 3904 can be rotated toward the open position, causing the needles 3926 to pull the suture legs 3934 through the apertures 3930 of the anvil 3910 (shown in FIG. 157). In various embodiments, the suture legs 3634 can be coupled to a buttress layer such, as the suture legs 3934 are pulled through the apertures 3930, the buttress layer can be compressed against a tissue contacting surface of the anvil 3910.

As reference above, the anvil 3910 can include a plurality of cam members 3932. The cam members 3932 can be rotatably coupled to the anvil 3910 and can be rotatable between an engaged position and a disengaged position (disengaged position shown in FIG. 158). In various aspects, as the first housing half 3904 is rotated toward the closed position, the cam arms 3928 of the plungers 3922 can engage the cam member 3932 and rotate the cam member 3932 toward the disengaged position prior to the needle 3926 entering the aperture 3930. In one aspect, this can be accomplished by having the cam arm 3928 extend further from the base 3924 than the needle 3926, as is shown clearly in FIG. 158. As the needle 3926 traverses the aperture 3930 to interface with the suture legs 3934 in the second housing half 3906, as described above, the cam arm 3928 can ride along cam members 3932 to maintain the cam members 3932 in the disengaged position. In one example embodiment, the cam member 3932 can be sized such that the cam member 3932 can slide between the needle 3926 and the cam arm 3928 in the gap 3938 as the needle 3926 moves through the aperture 3930. As the cam member 3932 slides within the gap 3938, the cam member 3932 can abut the cam arm 3928, keeping the cam member 3932 in the disengaged position.

As the first housing half 3904 is rotated to the open position and the needles 3926 brings the suture legs 3934 through the apertures 3930, the cam arms 3928 can disengage the cam members 3932. In various embodiments, a biasing mechanism, such as a spring, can bias the cam member 3932 toward the engaged position such that, as the cam arms 3928 disengages the cam members 3932, the cam members 3932 can rotate towards the engaged position and engage the suture legs 3934 pulled through the apertures 3930 of the anvil 3910. In one aspect, the cam members 3932 can engage and hold the suture legs 3934, maintaining tension of the suture legs 3934 through the apertures 3930 of the anvil 3910.

Further to the above, as the first housing half 3904 rotates to the open position and the cam members 3932 engages the suture legs 3934, a knife member can sever the suture legs 3934 from the plungers 3922, leaving the suture legs 3934 engaged by the cam members 3932, and thus maintaining tension in the suture legs 3934 through the apertures 3930 of the anvil 3910. In one example embodiment, the knife can sever the suture legs 3934 as the first housing half 3904 approaches the open position. In one example embodiment, the first housing 3902 half can include an actuation feature 3940 extending from a pivot side thereof. As best shown in FIG. 157, as the first housing half 3904 moves to the open position, the actuation feature 3940 can rotate towards the second housing half 3906 and engage a knife positioned in the second housing half 3906. In one example embodiment, the second housing half 3906 can include an aperture defined in the connector 3918 of the second housing half 3906 such that the actuation feature 3940 can extend through the second housing half 3906 and engage the knife as the first housing half 3904 is rotated toward the open position. In one aspect, the actuation feature 3940 can engage and actuate the knife, causing the knife to sever each of the suture legs 3934 to release the suture legs 3914 from the plungers 3922, but still maintain the tension in the suture legs 3934 with the cam members 3932. In one example embodiment, the knife can progressively sever the suture legs 3934 are the first housing half 3904 is rotated toward the open position.

Referring now to FIG. 159, an anvil 3940 is provided in accordance with at least one aspect of the present disclosure. In various embodiments, the anvil 3940 can include a first track 3942 on a first lateral side 3944 of the anvil 3940 and a second track 3946 on a second lateral side 3948 of the anvil 3940. Each of the tracks 3942, 3944 are sized to allow for a suture assembly to pass from one side of the anvil, such as an outer, top surface 3950 of the anvil 3940, to another side of the anvil, such as the tissue contacting surface 3952 of the anvil 3940, as will be described in more detail below. In one aspect, the first track 3942 can include an entrance aperture 3954 defined in the outer surface 3950 of the anvil 3940 and an exit aperture 3956 defined in the tissue contacting surface 3952 of the anvil 3940. Similarly, the second track 3946 can include an entrance aperture 3958 defined in the tissue contacting surface 3952 of the anvil 3940 and an exit aperture 3960 defined in the outer surface 3950 of the anvil 3940.

In various embodiments, the anvil 3940 can further include a first cam lock 3962 and a second cam lock 3964.

Referring to FIG. 164, a detailed view of cam lock 3962 is provided, however, it should be understood that the second cam lock 3964 is of similar construction. As shown in FIG. 164, each of the cam locks 3962, 3964 can include a body portion 3966, an engagement surface 3968 extending from the body portion 3966, and a cam arm 3970 extending from the body portion 3966. In one aspect, the body portions 3966 of the cam locks 3962, 3964 can be rotatable coupled to the outer surface 3950 of the anvil 3940 by pins. In one aspect, the first cam lock 3962 can be rotatably coupled to the anvil 3940 near the entrance aperture 3954 of the first track 3942 and the second cam lock 3964 can be rotatable coupled to the anvil 3940 near the exit aperture 3960 of the second track 3946.

In one aspect, the cam locks 3962, 3964 can be rotatable relative to the anvil 3940 between a locked position and an unlocked position. In various embodiments, when the first and second cam locks 3962, 3964 are in the unlocked positions, the engagement surfaces 3968 of the cam locks 3962, 3964 are rotated away from their respective apertures 3954, 3960 defined in the outer surface 3950 of the anvil 3940, therefore allowing a suture assembly to pass through the respective first track 3942 and the second track 3946 uninterrupted. In addition, when the first and second cam locks 3962, 3964 are in the locked positions, the engagement surfaces 3968 of the cam locks 3962, 3964 can at least partially extend over their respective apertures 3954, 3960 defined in the outer surface 3950 of the anvil 3940 such that a suture extending through the respective aperture can be held in place by the engagement surfaces 3968 of the cam locks 3962, 3964. In various embodiments, the cam locks 3962, 3964 can be coupled to a biasing member, such as a torsional spring, such that the cam locks 3962, 3964 can be biased to the locked position. In one example embodiment, in order to rotate the cam locks 3962, 3964 to the unlocked position, a force can be applied to the cam arms 3970, causing the cam locks 3962, 3964 to rotate about pins to the unlocked positon.

In various embodiments, referring to FIGS. 159 and 160, a suture assembly 3972 can be usable with the anvil 3940 to attach a buttress layer to the tissue contacting surface 3952 of the anvil 3940. In various embodiments, the suture assembly 3972 can include a semi-rigid, flexible needle 3974, a suture 3976 removably coupled to and extending from the needle 3974, and a hard stop ball 3978 coupled to and extending from the suture 3976. The needle 3974 can be made of any suitable material, such as plastic, such that the needle 3974 is rigid enough to be threaded through the first and second tracks 3942, 3946 of the anvil 3940, while also being flexible enough to navigate any twists or turns in the tracks. In one example embodiment, the needle 3974 can include a sharp tip such that the needle 3974 can be threaded through a buttress layer, therefore coupling the suture assembly 3972 to the buttress layer. In another example embodiments, the needle 3974 can include a blunt tip in instances where the needle 3974 is intended to be wrapped around and support a bottom surface of the buttress layer, as opposed to piercing the buttress layer itself. In various embodiments, referring to FIG. 163, the needle can comprise a hooked shaped needle 3990 that can be utilized to facilitate passage of the needle 3990 through the first track 3942 and the second track 3946. In various embodiments, the hooked shaped needle can include a coupling portion 3992 that can couple to the suture 3976 of the suture assembly 3972.

In one example operation, the anvil 3940 can be placed in a buttress cartridge 3980, illustrated in FIG. 161, to apply a buttress layer 3982 to the anvil 3940. The buttress cartridge 3980 can include a base 3984 including a buttress layer 3982 positioned thereon, a first sidewall 3985 extending from the base 3984 and a second sidewall 3987 extending from the base 3984. The sidewalls 3985, 3987 can be sized such that, when the tissue contacting surface 3952 is brought towards the base 3984 of the buttress cartridge 3980, the sidewalls 3985, 3987 can force the anvil 3940 into proper lateral alignment with the base 3984 to avoid the buttress layer 3982 being mispositioned on the tissue contacting surface 3952.

In various embodiments, the buttress cartridge 3980 can further include a first arm 3986 extending from the first sidewall 3985 and a second arm 3988 extending from the second sidewall 3987. The first and second arms 3986, 3988 can be sized that, as the tissue contacting surface 3952 is moved towards the buttress layer 3982 in the buttress cartridge 3980, the first and second arms 3986, 3988 can contact the first and second cam arms 3970 of the first and second cam locks 3962, 3964, respectively, causing the first and second cam locks 3962, 3964 to rotate to the unlocked positions. An example of this procedure is illustrated in FIG. 162. In one aspect, the first and second arms 3986, 3988 can hold the cam locks 3962, 3964 in the unlocked positions until the anvil 3940 is moved out of the buttress cartridge 3980, at which point the biasing members can rotate the cam members 3962, 3964 back to their locked positions.

In one example embodiment, the tissue contacting surface 3952 can be moved into the buttress cartridge 3980 and into contact the buttress layer 3982 on the base 3984. In various embodiments, buttress layer 3982 can include an adhesive that can at least partially adhere the buttress layer 3982 to the tissue contacting surface 3982. As the tissue contacting surface 3952 of the anvil 3940 is brought into contact with the buttress layer 3982, the first and second arms 3986, 3988 can move and hold the cam locks 3962, 3964 in the unlocked position. In various embodiments, the suture assembly 3972 can then be utilized to further couple the buttress layer 3982 to the anvil 3970 in a manner as was described above. In one example embodiment, while the cam locks 3962, 3964 are held in the unlocked position, the needle 3974 can be threaded from the entrance aperture 3954 to the exit aperture 3964 of the first track 3942, coupled to the buttress layer 3982 in any suitable manner (such as the manners described above), and then threaded from the entrance aperture 3958 to the exit aperture 3960 of the second track 3946. In one example embodiment, the base 3984 can include a track defined therein that includes entrance and exit apertures that correspond to the exit aperture 3956 and the entrance aperture 3958, respectively, such that the needle 3974 can travel through the first track 3942, through (or around) the buttress layer 3982, through the track in the base 3984, back through (or around) the buttress layer 3982 and through the second track 3946.

In various embodiments, as the needle 3970 is pulled through the exit aperture 3956 of the second track 3946, the hard stop ball 3978 can abut the outer surface 3950 of the anvil 3940. In one aspect, the hard stop ball 3978 can be sized such that the hard stop ball 3978 is prevented from entering the entrance aperture 3954 of the first track 3942, therefore preventing the suture assembly 3972 from being pulled completely through the first track 3942. In various embodiments, the suture 3976 can have a sufficient length so as to allow the needle 3974 to be pulled through the exit aperture 3960 prior to the hard stop ball 3978 contacting the entrance aperture 3954, therefore allowing a user to pull the needle 3974 and tension the suture 3976, causing the buttress layer 3982 to be securely pulled against the tissue contacting surface 3952 of the anvil 3940. In various embodiments, the above-described threading procedure can clear old suture material that is still held in the tracks 3942, 3946 of the anvil 3940 from previous uses of the anvil 3940.

In one aspect, once the buttress layer 3982 is coupled to the anvil 3940 by way of the suture assembly 3972 and the suture 3976 has been sufficiently tensioned by way of the needle 3974 and the hard stop ball 3978, the anvil 3940 can be moved out of the buttress cartridge 3980. Movement of the anvil 3940 away from the buttress cartridge 3940 can cause the cam locks 3962, 3964 to rotate towards their locked positions, therefore causing the engagement surfaces 3968 of the cam locks 3962, 3964 to engage portions of the suture 3976 extending from the outer surface 3950 of the anvil 3940 (at the entrance aperture 3954 of the first track 3942 and the exit aperture 3960 of the second track 3946), holding the suture assembly 3972 in place and maintaining tension in the suture 3976. In various embodiments, once the cam locks 3962, 3964 have been rotated to the locked positions, the needle 3974 of the suture assembly 3972 can be decoupled from the suture 3976, allowing the needle to be used with a different suture assembly 3972.

Referring now to FIG. 165, a buttress applier cartridge 4000 is provided in accordance with at least one aspect of the present disclosure. The buttress applier cartridge 4000 can include a generally U-shaped housing assembly 4002 that includes a first leg 4004, a second leg 4006, and a connector 4007 connecting the first leg 4004 and the second leg 4006. The housing assembly 4002 can further include a support platform 4008 that can support a buttress assembly 4010 thereon. In various embodiments, the housing assembly 4002 can be of similar constriction to other buttress applier cartridges described herein, such as buttress applier cartridges 3200, 3300, as examples.

In one aspect, the buttress applier cartridge 4000 can be utilized to apply the buttress assembly 4010 to an anvil of an end effector. In various embodiments, referring to FIG. 167, the buttress assembly 4010 can include a buttress layer 4012 and a plurality of suture loops 4014 extending from the buttress layer 4012. In various embodiments, as shown in FIG. 168, the suture loops 4014 can be embedded in the buttress layer 4012 between a top surface 4016 of the buttress layer 4012 and a bottom surface 4017 of the buttress layer 4012. In other embodiments, the suture loops 4014 can be coupled to the buttress layer 4012 in any suitable manner such that the suture loops 4014 can support the buttress layer 4012 as the buttress layer 4012 is applied to an anvil. In one such embodiment, the suture loops 4014 are not continuous loops as is shown in FIG. 168, rather, the legs of the suture loops 4014 are attached the buttress layer 4012 at discrete locations, as described elsewhere herein. In various other embodiments, the suture loops 4014 are not embedded between a single buttress layer 4012, rather, a portion of the suture loop 4014 is capture between two pieces of buttress layer 4012 adhered together.

As shown in FIG. 165, the buttress assembly 4010 can be positioned within the buttress applier cartridge 4000 and can be supported by the support platform 4008. In one aspect, the buttress applier cartridge 4000 can include a plurality of wedge shaped suture clamps 4020 extending from the first leg 4004 and the second leg 4006 of the buttress applier cartridge 4000. In various embodiments, referring to FIG. 170, the suture clamps 4020 can include a first arm 4022 and a second arm 4024 spaced from the first arm 4022 so as to define a gap 4026 therebetween such that, when the buttress assembly 4010 is properly seated on the support platform 4008, the legs of the suture loops 4014 can be held in a recess 4028 by the first arm 4022 and the second arm 4024. In other embodiments, the legs of the suture loops 4014 can be positioned in the recesses 4028 of the suture clamps when the suture clamps 4020 are in a resting state, as will be described in more detail below.

In various embodiments, the suture clamps 4020 can be transitionable between a resting state, where the suture clamps 4020 can hold the legs of the suture loops 4014 within the recesses 4028, and an actuated state, where the suture clamps 4020 can allow the legs of the suture loops 4014 to escape the suture clamps 4020. In one embodiment, a portion of the suture clamps 4020 can move toward the connector 4007 while another portion of the suture clamps 4020 can remain stationary. In such an embodiment, the relative movement between the portions of the suture clamps 4020 can transition the suture clamps 4020 between the resting state and the actuated state. As the suture clamps 4020 move to the actuated state, as described above, the legs of the suture loops 4014 can be released and allowed to move out of the suture clamps 4020. In various other embodiments, one or both of the first arm 4022 and the second arm 4024 of the suture clamps 4020 can be moveable relative to the other to increase the gap size 4026 therebetween. In various embodiments, the relative movement of the first arm 4022 and the second arm 4024 can transition the suture clamps 4020 between the resting state and the actuated state.

In operation, a user can slide an anvil 4018 from the open end of the buttress applier cartridge 4000 (the end opposite of the connector 4007) along the buttress assembly 4010 toward the connector 4007. In one aspect, as shown in FIG. 169, as the anvil 4018 moves under the proximal-most suture loop 4014, the anvil 4018 can abut a camming surface 4021 of the proximal-most suture clamps 4020, causing the suture clamps 4020 to slightly elevate, causing the suture loop 4014 held by the suture clamp 4020 to expand in tension. The anvil 4018 can continue to progress along the buttress applier cartridge 4000 and through the suture loops 4014 and contact the camming surfaces 4021, causing the suture clamps 4020 to slightly elevate and develop tension in all of the suture loops 4014. In various embodiments, the connector 4007 of the housing assembly 4002 can include a release button 4030 operably coupled to the suture clamps 4020. In one aspect, after the anvil 4018 has progressed through all of the suture loops 4014 and reached the connector 4007, the anvil 4018 can engage the release button 4030, causing the suture clamps 4020 to transition to the actuated state, releasing the suture loops 4014 from the suture clamps 4020, as described above. As the suture loops 4014 were tensioned as the anvil 4018 moved along the buttress assembly 4010 towards the release button 4030 (owing to the elevation of the suture clamps 4020 by way of camming surfaces 4021), the suture loops 4014 can be released from the suture clamps 4020 and tighten around the anvil 4018, coupling the buttress assembly 4010 to the anvil 4018, and more specifically, coupling the buttress layer 4012 to a tissue contacting surface of the anvil 4018.

In various embodiments, as shown in FIG. 171, an anvil 4032 is provided that can be utilized with the buttress applier cartridge 4000. The anvil 4032 includes a plurality of detents 4034 along the length thereof that can receive the suture loops 4014 when the buttress assembly 4010 is coupled to the anvil 4032. The detents 4034 can be sized to receive and hold the suture loops 4014 such that the chance of the suture loops 4014 sliding along the anvil 4032 is minimized. In various other embodiments, the anvil 4032 can include a plurality of grooves 4036 extending between laterally offset detents 4034 that can further be utilized to maintain the suture loops 4014 on the anvil 4032.

Referring now to FIG. 172, an anvil 4050 is provided in accordance with at least one aspect of the present disclosure. The anvil 4050 can include a set of tracks 4052 defined in both lateral sides of the anvil 4050 that extend along the length thereof from a receiving location 4054 to an ending location 4056. The tracks 4052 can include a narrow track 4058 and an expanded receiving aperture 4060 that can be larger in size than the narrow track 4058. In one aspect, the aperture 4060 can correspond to the receiving location 4054 and an end of the narrow track 4058 can correspond to the ending location 4056.

In various embodiments, the anvil 4050 can interface with a buttress assembly 4062. Referring to FIGS. 172 and 173, the buttress assembly 4062 can include a buttress layer 4064, arms 4066 extending from the buttress layer 4064, and a stop 4068 extending from each arm 4066. The stops 4068 are sized to be received within the receiving apertures 4060, while the arms 4066 are sized such that a portion thereof can be slidably received within the narrow tracks 4058. In one aspect, the buttress assembly 4062 can be coupled to the anvil 4050 by sliding the stops 4068 and the arms 4066 within the receiving aperture 4060 and the narrow tracks 4058, respectively. Once coupled, the size of the stops 4068 can prevent the stops 4068 from escaping laterally through the narrow tracks 4058, maintaining the buttress assembly 4062 coupled to the anvil 4050. In various embodiments, the arms 4066 and the stops 4068 are manufactured of a semi-rigid material to prevent the arms 4066 and stops 4068 from releasing from the anvil 4050 through the narrow tracks 4058. In various embodiments, only the stops 4068 are manufactured of a semi-rigid material so as to prevent the stops 4068 from escaping through the narrow tracks 4058.

In operation, the anvil 4050 can be coupled to the buttress assembly 4062 in the manner described above. Once coupled, the anvil 4050 has been utilized in a stapling procedure as described elsewhere here, resulting in the buttress layer 4064 being stapled to tissue. To remove the stapled buttress assembly 4062 from the anvil 4050, the anvil 4050 can be pulled proximally so that the stops 4068 and the arms 4066 of the buttress assembly 4062 can slide through the tracks 4052 and be released from the anvil 4050 through the receiving apertures 4060 and the narrow tracks 4058, respectively. As substantially all of the buttress assembly 4062 is left at the stapling site, there are no post-firing steps regarding the buttress assembly 4062, and therefore, a new buttress assembly can be coupled to the anvil 4050 in the same manner as described above. The above-provided design eliminates the need for another other type of buttress applicator/system and eliminates the need for sutures.

Referring now to FIGS. 174 and 175, an anvil 4100 is provided in accordance with at least aspect of the present disclosure. The anvil 4100 can include a tissue contacting surface 4102 and an outer surface 4104 on an opposite to the tissue contacting surface 4102. The tissue contacting surface 4102 can include an elongate slot 4106 and a plurality of staple pockets 4108 (only three are pointed to). The outer surface 4104 can include a suture lock 4120 extending therefrom. In various embodiments, as shown best in FIG. 176, the suture lock 4120 can include a base 4122 coupled to the outer surface 4104, a receiving area 4124 extending from the base 4122, and a cap 4126 extending from the receiving area 4124. In various embodiments, the cap 4126 can have a larger diameter than the receiving area 4124 such that the cap 4126 and the receiving area 4124 define a 'mushroom-like' shape, as shown in FIG. 176. In various embodiments, as shown in FIGS. 176 and 177, the cap 4126 can include a plurality of detents 4128 defined therein that can receive and hold suture legs (one such example shown in FIG. 176), as will be described in more detail below. In one embodiment, as is shown in FIGS. 176 and 177, the cap 4126 can include a pair of opposing detents 4128.

In various embodiments, the anvil 4100 can interface with a buttress later 4130 including a plurality of suture legs 4132. In one embodiment, as is shown in FIG. 178, the buttress layer 4130 can include four suture legs 4132 extending from the four corners of the buttress layer 4130. In one aspect, a pair of suture legs 4132 can be part of one continuous suture 4134 that threads through one corner of the buttress layer 4130 and out of another corner of the buttress layer 4130. In various other embodiments, the suture legs 4132 can be discretely coupled to corners of the buttress layer 4130. Other embodiments are envisioned where the suture legs 4132 extend from the buttress layer at other locations other than the corners of the buttress layer 4130, such as the sides of the buttress layer 4130.

As shown in FIG. 179, the buttress layer 4130 can interface with the tissue contacting surface 4102 of the anvil 4100 such that the suture legs 4132 are laterally positioned away from the anvil 4100. In one aspect, as shown in FIG. 180, a first pair of suture legs can be pulled 4136 around the receiving area 4124 of the suture lock 4120 and held by a first detent 4128 defined in the cap 4126 of the suture lock 4120. In addition, as shown in FIG. 181, a second pair of suture legs 4132 can be pulled 4138 around the receiving area 4124 of the suture lock 4120 and held by a second detent 4128 defined in the cap 4126 of the suture lock 4120. The pairs of suture legs 4132 can be held by the suture lock 4120, thus coupling the buttress layer 4130 to the anvil 4100, allowing the anvil 4100 to be used in a stapling procedure as described elsewhere herein.

After the completion of the stapling procedure, the free ends of the suture legs 4132 extending from the cap 4126 of the suture lock 4120 can be pulled 4140, as shown by arrows in FIG. 182. The detents 4128 of the cap 4126 can include a sharp edge such that, as the free ends of the suture legs 4132 are pulled 4140, the detents 4128 can sever the suture legs 4132, releasing the buttress layer 4130 from the anvil 4100.

FIG. 183 depicts an exemplary surgical device 20000 that can include a handle assembly 20001 that can be selectively connectable with an adapter 20002, and, in turn, the adapter 20002 can be selectively connectable with end effectors or single use loading units ("SULU's") 20004. In other embodiments, the adapter 20002 can be selectively connectable with multi-use use loading units ("MULU's"). The handle assembly 20001 can include an outer shell housing 20006 that is sized to selectively receive and substantially encase a power-pack 20008, illustrated in FIG. 184, therein that can drive various functions of the surgical device 20000, as explained below. The outer shell housing 20006 can include a distal half-section 20010*a* and a proximal half-section 20010*b* pivotably connected to distal half-section 20010*a* by a hinge 20012 located along an upper edge of distal half-section 20010*a* and proximal half-section 20010*b*. When joined, distal and proximal half-sections 20010*a*, 20010*b* define a shell cavity therein in which power-pack 20008 is selectively situated. In various embodiments, the adapter 20002 can include an adapter housing 20003 that can mechanically and electrically couple to the outer shell housing 20006 and the power pack 20008, respectively, and a shaft assembly 20005 extending distally from the adapter housing 20003. In one aspect, the shaft assembly 20005 can mechanically and electrically couple to the end effector 20004.

In one aspect, the power pack 20008 can include a plurality of motors disposed therein for selectively driving various functions of the end effector 20004 when the surgical device is properly prepared for use. For example, rotation of motor shafts by respective motors function to drive shafts and/or gear components of the adapter 20002 in order to perform the various operations of surgical device 20000. In particular, motors of power-pack core assembly 20008 can drive shafts and/or gear components of adapter 20002 in order to selectively control functions of the end effector 20004. For example, motors can articulation the jaws of the end effector 20004 about an articulation joint, rotate the end effector 20004 about a longitudinal axis "X" extending through the adapter 20002, move a cartridge assembly of the end effector 20004 and an anvil assembly of end effector 20004 between an open position and a closed position to capture tissue therebetween, and/or to fire staples from within cartridge assembly of the end effector 20004, as examples. In various other embodiments, the end effector 20004 could include a radiofrequency (RF) or ultrasonic end effector where the motors can drive various functions of the RF or ultrasonic end effector. Additional functions of the motors are described in U.S. Pat. No. 10,603,128, which is hereby incorporated by reference in its entirety herein.

In various embodiments, the power pack 20008 can include a control system that can perform various operational functions of the surgical device 20000. For example, the control system can receive input signals from a user via input buttons or switches positioned on the outer shell housing 20006 to control various functions of the surgical device 20000, such as driving the motors, transmitting electrical communication signals to the end effector 20004, transmitting RF or ultrasonic drive signals to the end effector 20004, etc. In various embodiments, the control system can include a control circuit 20014 in electrical communication with various electrical components disposed throughout the surgical device 20000. In various embodiments, the control circuit 20014 can be in electrical communication with electrical components of the adapter 20002 and the SULU 20004 when the adapter 20002 is properly coupled to the outer shell housing 20006 and power pack 20008 and the end effector 20004 is properly coupled to the adapter 20002. For example, in various embodiments, the power pack 20008 can include an electrical output portion 20020 and the adapter 20002 can include an electrical input portion. When the adapter 20002 is properly coupled to the outer shell housing 20006 and the power pack 20008, the electrical output portion 20020 and electrical input portion can be in electrical communication such that the control system can transmit electrical signals to the adapter 20002 and the end effector 20004. In some embodiments, the control system can include a processor 20016 and a memory 20018 in communication with the processor. The memory 20018 can store instructions that can be executable by the processor 20016 to perform various operational functions of the surgical device 20000.

In various embodiments, the control system can be in electrical communication with a display such that the control system can provide feedback to a user of the surgical device 20000. For example, the control system can provide visual indicators to the user about various functional parameters of the end effector 20004 coupled to the surgical device 20000. As another example, the display can provide visual feedback to the user about various interconnections between the surgical device 20000, such as the connection between the power pack 20008 and the housing assembly 20006 with the adapter 20002, or the adapter 20002 and the end effector 20004. In various embodiments, the control system can further provide other forms of feedback to the user of the surgical device 20000 other than visual feedback, such as audible feedback, haptic feedback, or the like.

Currently, when a user attempts to connect the various components of the surgical device 20000 together, such as the outer shell housing 20006, the adapter 20002, the power pack 20008, the end effector 20004 as referenced above, the connections therebetween may be incomplete without the user knowing. In other instances, the connections therebetween may be complete, but the user has no way of knowing for sure whether or not this is the case. In such situations, attempting to operate the surgical device 20000 could raise safety concerns as the surgical device may fail to properly operate as intended due to the incomplete connection. For example, the motors of the power pack 20008 may be improperly coupled to the components of the adapter 20002 that are intended to be driven by the motors, or the electrical output portion 20020 may be improperly coupled to the electrical input portion of the adapter 20002. In other instances, the end effector 20004 may be improperly coupled to the adapter 20002 such that the adapter 20002 is unable to transmit electrical and mechanical signals from the power pack 20008 to the end effector 20004. It would therefore be desirable to ensure that components of a surgical device 20000 are properly connected and complete before utilizing the surgical device 20000 in a surgical procedure.

Referring now to FIG. 185, a housing assembly 21000 and adapter 21002 are provided, in accordance with at least one aspect of the present disclosure. The housing assembly 21000 can include an outer shell housing 21004 and a power pack 21006 disposed within the outer shell housing 21004. In various embodiments, the outer shell housing 21004 and the power pack 21006 can be similar to outer shell housing 20006 and power pack 20008, respectively. In various embodiments, the adapter 21002 can be similar to adapter 20002. The housing assembly 21000 can further include a recessed receiving area 21008 that is sized to receive a correspondingly shaped drive coupling assembly 21010 extending proximally from the adapter 21002. The housing assembly 21000 can further include a plurality of rotatable drive shafts 21012*a*, 21012*b*, 21012*c* extending from the receiving area 21008 of the housing assembly 21000. In various embodiments, the power pack 21006 can include a plurality of motors operably coupled to the rotatable drive shafts 21012*a*, 21012*b*, 21012*c* that can drive the rotatable drive shafts 21012*a*, 21012*b*, 21012*c*.

In various embodiments, the rotatable drive shafts 21012*a*, 21012*b*, 21012*c* can be sized such that, when the drive coupling assembly 21010 of the adapter 21002 is properly positioned within the receiving area 21008 of the housing assembly 21000, the drive shafts 21012*a*, 21012*b*, 21012*c* can be operably disposed within connecting sleeves 21014*a*, 21014*b*, 21014*c* of the drive coupling assembly 21010. More specifically, when the drive coupling assembly 21010 of the adapter 21002 is properly positioned within the receiving area 21008 of the housing assembly 21000, the first drive shaft 21012*a* can drivingly engage the first coupling sleeve 21014*a*, the second drive shaft 21012*b* can drivingly engage the second coupling sleeve 21014*b*, and the third drive shaft 21012*c* can drivingly engage the third coupling sleeve 21014*c*. When the drive shafts 21012*a*, 21012*b*, 21012*c* are in driving engagement with the coupling sleeves 21014*a*, 21014*b*, 21014*c*, rotation of the drive shafts 21012*a*, 21012*b*, 21012*c* can drive end effector functions of the surgical instrument. In various embodiments, the end effector functions can be similar to those discussed elsewhere herein, such as moving jaws of an end effector between an open and closed position, translating a firing member proximally or distally within an end effector to cause stapling and severing of tissue positioned between the jaws of the end effector, or articulating the end effector about an articulation joint positioned proximal to the end effector, as examples. The drive shafts 21012*a*, 21012*b*, 21012*c* could also effect end effector functions of non-surgical stapling end effectors, such as RF or ultrasonic end effectors.

Continuing to refer to FIG. 185, the drive coupling assembly 21010 can further include a first shaft 21016*a* extending from a first channel 21018*a* defined in the drive coupling assembly 21010 and a second shaft 21016*b* extending from a second channel 21018*b* defined in the drive coupling assembly 21010. The first and second shafts 21016*a*, 21016*b* can be movably coupled to the drive coupling assembly 21010 such that the first and second shafts 21016*a*, 21016*b* can be movable between an extended position, illustrated in FIG. 185, wherein the shafts 21016*a*, 21016*b* are extending out of the channels 21018*a*, 21018*b*, and a depressed position, wherein the shafts 21016*a*, 21016*b* are at least partially depressed into the channels 21018*a*, 21018*b*. Each channel 21018*a*, 21018*b* can include a spring disposed therein such that the shafts 21016*a*, 21016*b* are 'pogo-stick' like shafts in that they are depressable toward the depressed position, but are biased toward the extended position when no force is applied thereto. In various embodiments, as will be described in more detail below, the depressed positions of the shafts 21016*a*, 21016*b* can correspond to the adapter 21002 being completely and fully coupled to the housing assembly 21000.

In various embodiments, the shafts 21016*a*, 21016*b* can be constructed of an electrically conductive material. In one aspect, the first and second shaft 21016*a*, 21016*b* can be in electrical communication with one another when both the first and second shaft 21016*a*, 21016*b* are in the depressed position, therefore signifying that the adapter 21002 is completely and fully coupled to the housing assembly 21000. In one example embodiment, an electrically conductive plate can be positioned at the distal end of both of the channels 21018*a*, 21018*b* such that, when the first and second shafts 21016*a*, 21016*b* are both in the depressed positions, a current can flow through the first shaft 21016*a*, through the conductive plate and then through the second shaft 21016*b*. In this way, a circuit can be formed between the first shaft 21016*a* and the second shaft 21016*b* when both the shafts 21016*a*, 21016*b* are in the depressed positions. While a conductive plate is described as being used to complete a circuit between the first and second shafts 21016*a*, 21016*b* when in the depressed positions, it should be understood that any suitable mechanism can be utilized to complete a circuit between the first and second shafts 21016*a*, 21016*b* when the first and second shafts 21016*a*, 21016*b* are in the depressed positions, such as a wire, a circuit board, or any suitable electrically conductive component positioned within the adapter 20002, as examples.

In various embodiments, the housing assembly 21000 can further include a first contact 21020*a* and a second contact 21020*b*. The first and second contacts 21020*a*, 21020*b* are spaced such that, when the drive coupling assembly 21010 is properly positioned within the receiving area 21008, the first shaft 21016*a* can abut and be depressed by the first contact 21020*a* and the second shaft 21016*b* can abut and be depressed by the second contact 21020*b*. In one aspect, the contacts 21020*a*, 21020*b* can be comprised of an electrically conductive material and be in electrical communication with a control circuit positioned within the housing assembly 21000, such as control circuit 20014, as an example, such that an electrical potential can be generated between the two contacts 21020*a*, 21020*b*. In various embodiments, when the drive coupling assembly 21010 is properly positioned within the receiving area 21008, the first contact 21020*a* can depress the first shaft 21016*a* to the depressed position and the second contact 21020*b* can depress the second shaft 21016*b* to the depressed position. When the shafts 21016*a*, 21016*b* are in the depressed positons, the control circuit can generate an electrical signal that can traverse through the first contact 21020*a*, the first shaft 21016*a*, the second shaft 21016*b* and the second contact 21020*b*, therefore signifying that the adapter 21002 is properly coupled to the housing assembly 21000. With such a system, when an electrical potential is generated at the contacts 21020*a*, 21020*b* and a circuit is unable to be completed, a user can know that the adapter 21002 is not properly coupled to the housing assembly 21000 and that appropriate action is required. The above-referenced system therefore provides a user with a mechanism for verifying if the adapter 21002 is properly coupled to the housing assembly 21000. In various embodiments, the control circuit can provide feedback to a user, such as via a display, haptic feedback, or audible feedback, when the control circuit determines that the adapter 21002 is properly coupled to the housing 21000, as described above.

In one aspect, the drive coupling assembly 21010 can further include a plurality of flange features 21022*a-e* extending around the perimeter thereof. In various embodiments, the flange features 21022*a-e* can be comprised of a substantially rigid material, such as a hard plastic, as an example. In addition, the housing assembly 21000 can include a plurality of flange features 21024*a-e* disposed about the receiving area 21008 that can correspond to the positions of the flange features 21022*a-e* of the drive coupling assembly 21010. In various embodiments, the flange features 21024-*e* can be comprised of an elastomeric material such that the flange features 21024*a-e* can at least partially, elastically deform when a force is applied thereto, but can return to an undeformed state when the force is removed. In one aspect, a minimum threshold amount of force can be required to elastically deform the flange features 21024*a-e* to a deformed state.

In operation, when the drive coupling assembly 21010 of the adapter 21002 is moved toward the receiving area 21008 of housing assembly 21000, each of the plurality of flange features 21022*a-e* of the drive coupling assembly 21010 can abut the corresponding positioned flange features 21024*a-e* of the housing assembly 21010. Stated another way, flange feature 21022*a* can abut flange feature 21024*a*, flange feature 21022*b* can abut flange feature 21024*b*, flange feature 21022*c* can abut flange feature 21024*c*, flange feature 21022*d* can abut flange feature 21024*d*, and flange feature 21022*e* can abut flange feature 21024*e*. In order to properly seat the drive coupling assembly 21010 within the receiving area 21008 of the housing assembly 21000, once the flange features 21022*a-e* are abutting the corresponding positioned flange features 21024*a-e*, a user can apply a force to the adapter 21002 such that the flange features 21022*a-e* can cause the correspondingly positioned flange features 21024*a-e* to elastically deform, therefore allowing the flange features 21022*a-e* to pass the flange features 21024*a-e*.

In one aspect, the force applied by the user to the adapter 21002 can be large enough such that the flange features

21022*a-e* can apply a force to the correspondingly positioned flange features 21024*a-e* that meets or exceeds the minimum threshold amount of force to cause the flange features 21024*a-e* to elastically deform. Once the flange features 21022*a-e* pass the flange features 21024*a-e*, the flange features 21024*a-e* can return to their undeformed state, holding the flange features 21022*a-d* within the receiving area 21008, thereby holding the adapter 21002 to the housing assembly 21000. In various embodiments, the flange features 21022*a-e* and flange features 21024*a-e* can be shaped such that, when the adapter 21002 is coupled to the housing assembly 21000, as described above, the flange features 21024*a-e* can releasably hold the flange features 21022*a-e* therein. In some example embodiments, the flange features 21022*a-e*, 21024*a-e* can comprise ramp-like shapes, cylindrical shapes, or any suitable shape.

The use of the correspondingly positioned flange features 21022*a-e*, 21024*a-e* between the adapter 21002 and the housing assembly 21000 provides a mechanical means for a user to ensure that the adapter 21002 is properly seated and coupled with the housing assembly 21000 and that the adapter 21002 and housing assembly 21000 are properly rotatably aligned, owing to the positioning of the flange features 21022*a-e*, 21024*a-e*. In addition, the use of the correspondingly positioned flange features 21022*a-e*, 21024*a-e* between the adapter 21002 and the housing assembly 21000 can ensure that the adapter 21002 is maintained coupled to the housing assembly 21000 until a minimum threshold force is applied to the adapter 21002 to cause the flange features 21024*a-e* to elastically deform, thereby allowing the flange features 21022*a-e* to pass the flange features 21024*a-e* and exit the receiving area 21008.

In addition, the flange features 21022*a-e*, 21024*a-e* can be positioned to ensure that the first and second shafts 21016*a*, 21016*b* properly align with the contacts 21020*a*, 21020*b*, which, as described above, can be used as another level of security in ensuring that the adapter 21002 is both completely and properly coupled to the housing assembly 21000, thereby ensuring that operation of the housing assembly 21000, such as operation of the rotatable shafts 21012*a-c*, properly transmits forces and signals to the adapter 21002, such as to the coupling sleeves 21014*a-c*.

In various embodiments, the housing assembly 21000 can further includes an electrical output connector 21026 coupled to the control circuit in the housing assembly 21000 and the adapter 21002 can include an electrical input connector 21028 sized to operably electrically couple to the electrical connector 21024 of the housing assembly 21000. In operation, when the electrical input connector 21026 is electrically, operably coupled to the electrical output connector 21028, the control circuit can transmit electrical signals, such as control signals or drive signals, such as RF or ultrasonic drive signals, from the housing assembly 21000 to the adapter 21002. In one aspect, a user can attempt to operate the surgical device utilizing the electrical connectors 21026, 21028 and the motors 21012*a-c* as a primary means of the determining if the housing assembly 21000 is properly coupled to the adapter 21002. A user can also use the above-described flange features 21022*a-e*, 21024*a-e*, shafts 21016*a*, 21016*b* and contacts 21020*a*, 21020*b* as a secondary means of ensuring that the electrical and mechanical connections between the housing assembly 21000 and the adapter 21002 are properly aligned and properly coupled to each other before operation of the surgical device.

Referring now to FIG. 186, a mechanism for determining if a loading unit, such as a SULU or a MULU, is properly coupled and completely installed with a handle assembly is provided, according to at least one aspect of the present disclosure. In various embodiments, a handle assembly 21100 can include a handle portion 21102 and a shaft assembly 21104 extending distally from the handle portion 21102. In various embodiments, the handle assembly 21100 can be similar to handle assembly 20001 or housing assembly 21000. In various embodiments, the shaft assembly 21104 could be similar to shaft assembly 20005. The handle portion 21102 can include a stationary handle 21106, a closure trigger 21108 and a firing trigger 21110. The closure trigger 21108 can be rotatable toward the stationary handle 21106 to transmit, for example, a closing motion to an end effector 21112 of a loading unit 21114 when the loading unit 21114 is properly attached to the shaft assembly 21104. The closing motion can cause a first jaw 21116 and a second jaw 21118 of the end effector 21112 to transition between an open configuration, wherein the first jaw 21116 and second jaw 21118 are spaced apart from one another, as shown in FIG. 186, and a closed configuration, wherein the first jaw 21116 and second jaw 21118 are spaced near each other to capture tissue therebetween. Similarly, the firing trigger 21110 can be rotatable toward the stationary handle 21106 to transmit, for example, a firing motion to the end effector 21112 when the loading unit 21114 properly attached to the shaft assembly 21104. The firing motion can cause staples to be deployed from the end effector 21112 into the tissue positioned between the first jaw 21116 and second jaw 21118, as well as cause a knife to sever the stapled tissue. In various embodiments, the first jaw 21116 can include an anvil and the second jaw 21118 can include a cartridge try with a staple cartridge removably positioned in the cartridge tray.

In various embodiments, as is shown in FIG. 187, the distal end 21120 of the shaft assembly 21104 can include a drive shaft 21122 that can transmit actuation motions from the handle assembly 21100 to the loading unit 21114 when the loading unit 21114 is properly coupled and completely installed with the shaft assembly 21104. In one aspect, the drive shaft 21122 can be insertable into an aperture 21124 defined in the proximal end 21126 of the loading unit 21114. The loading unit 21114 can include a drive assembly sized to receive the drive shaft 21122 through the aperture 21124 such that, when the drive shaft 21122 is inserted into the aperture 21124, the drive assembly can operably couple to the drive shaft 21122. When coupled, actuation motions from the drive shaft 21122 can be transmitted to the drive assembly, allowing actuation motions from the handle assembly 21100 to be transferred to the end effector 21112 to effect end effector functions, such as closing motions, firing motions, articulation motions, etc., as described above. In various embodiments, when the loading unit 21114 is properly coupled to the distal end 21120 of the shaft assembly 21104, the handle assembly 21100 can transmit electrical signals, such as communication or drive signals, to the loading unit 21114.

In various embodiments, the loading unit 21114 can be properly coupled and completely installed with the shaft assembly 21104 by initially positioning the drive shaft 21122 into the aperture 21124. This can be accomplished, for example, by moving the aperture 21124 toward the drive shaft 21122 in an installation direction 21128 along an installation axis. In one aspect, the installation direction 21128 can be substantially parallel to a longitudinal axis defined through the shaft assembly 21104.

Once the drive shaft 21122 is inserted into the aperture 21124, the loading unit 21114 can be rotated relative to the shaft assembly 21104 about the longitudinal axis defined by the shaft assembly 21104. In various embodiments, the loading unit 21114 can be rotatable relative to the shaft assembly 21104 between an unlocked position, where the loading unit 21114 can be moved away from the shaft assembly 21104 along the installation axis, and a locked position, wherein the loading unit 21114 is locked to the shaft assembly 21104, resulting in a loading unit 21114 that is properly coupled and completely installed with the shaft assembly 21104. Once the loading unit 21114 has rotated to the locked position, a locking mechanism can lock the loading unit 21114 to the shaft assembly 21104, thereby completely coupling and completely installing the loading unit with the shaft assembly. Once the loading unit 21114 is locked to the shaft assembly 21104, actuation motions and electrical signals from the handle assembly 21100 can be safety transmitted to the loading unit 21114 to effect end effector functions.

In various embodiments, a user may desire to know if the loading unit 21114 is properly coupled to the shaft assembly 21104 prior to actuating the closure trigger 21108, actuating the firing trigger 21110, or attempting to transmit electrical signals to the loading unit 21114. For example, in instances where the loading unit 21114 wasn't completed rotated relative to the shaft assembly 21104 to the locked position and, therefore, wasn't completed locked into place, actuation motions or electrical signals from the handle assembly 21100, as an example, may not properly transfer to the loading unit 21114, and/or the loading unit 21114 may inadvertently decouple from the shaft assembly 21104 during the surgical procedure.

In addition, in various embodiments, the shaft assembly 21104 can comprise a first electrical contact and the loading unit 21114 can comprise a second electrical contact. In some embodiments, when the loading unit 21114 is properly coupled to the shaft assembly 21104, the first and second electrical contact can be in electrical communication with other another such that electrical signals, such as RF or communication signals, can be transmitted between the shaft assembly 21104 and the loading unit 21114. In some embodiments, these contacts can be in electrical communication with a control circuit that can utilize these contacts to determine if the loading unit 21114 is properly coupled to the shaft assembly 21104, such as by determining if a signal can be transmitted from the shaft assembly 21104 to the loading unit 21114. However, in some instances, these contacts may not properly detect that the loading unit 21114 is coupled to the shaft assembly 21104. It is therefore desirable to provide secondary means for determining if the loading unit 21114 is properly coupled to the shaft assembly 21104. It should be understood that the secondary means disclosed herein can be utilized as means for determining if any two components are coupled together, such as determining if a loading unit is properly coupled to an elongate shaft of a shaft assembly or determining if an adapter is properly coupled to a housing assembly, as examples.

In order to remedy the aforementioned problems, in various embodiments, the shaft assembly 21104 can include a first capacitor 21130 mounted to the distal end 21120 of the shaft assembly 21104. Similarly, the loading unit 21114 can include a second capacitor 21132 mounted to the proximal end 21126 of the loading unit 21114. In some embodiments, the first capacitor 21130 can be in electrical communication with a control circuit positioned in the handle assembly 21100, such as control circuit 20014, as an example. The capacitors 21130, 21132 can be positioned on the shaft assembly 21104 and the loading unit 21114, respectively, such that the control circuit can monitor a capacitance between the capacitors 21130, 21132 as the loading unit 21114 is coupled to the shaft assembly 21104, thereby allowing the control circuit to determine the location of the loading unit 21114 relative to the shaft assembly 21104, and therefore, determine if the loading unit 21114 is in the locked position.

For example, referring now to FIG. 188, a graphical representation 21140 of capacitance detected by the control circuit over time is provided. In some embodiments, prior to the drive shaft 21122 being inserted into the aperture 21124 of the loading unit 21114 ($t_0$), the control circuit can detect no capacitance between the first capacitor 21130 and the second capacitor 21132. As the drive shaft 21122 is inserted into the aperture 21124, the control circuit can detect an increase 21142 in capacitance. For example, at $t_1$, a first capacitance $C_1$ can be detected by the control circuit between the first capacitor 21130 and the second capacitor 21132 as the loading unit 21114 is placed in the unlocked position relative to the shaft assembly 21104. In various embodiments, the first capacitance $C_1$ detected by the control circuit can be a predetermined capacitance level corresponding to the drive shaft 21122 being properly inserted into the aperture 21114 and being placed in the unlocked position. In various embodiments, the first capacitance level $C_1$ can correspond to the first capacitor 21130 and the second capacitor 21132 being angularly spaced apart from one another a first angle. In one aspect, when the control circuit detects a capacitance that is less than the first capacitance $C_1$, the control circuit can provide feedback, such as through a display coupled to the control circuit, haptic feedback, audible feedback, etc., indicating that the drive shaft 21122 isn't properly inserted into the aperture 21114, indicating to a user that a corrective action is required prior to rotating the loading unit 21114 to the locked position.

As described above, to completely couple the loading unit 21114 to the shaft assembly 21104, the loading unit 21114 can be rotated relative to the shaft assembly 21104 to the locked position to lock and completely couple and install the loading unit 21114 to the shaft assembly 21104. As illustrated in FIG. 188, as the drive shaft 21122 is rotated relative to the shaft assembly 21104, the control circuit can detect an increase 21144 in capacitance between the first capacitor 21130 and the second capacitor 21132 as the second capacitor 21132 slides relative to the first capacitor 21130. For example, at $t_2$, a second capacitance $C_2$ can be detected by the control circuit between the first capacitor 21130 and the second capacitor 21132. In various embodiments, the second capacitance $C_2$ detected by the control circuit can be a capacitance level that is less than a predetermined maximum capacitance $C_{max}$, where $C_{max}$ corresponds to the loading unit 21114 not being completely rotated relative to the shaft assembly 211104 to the locked position, therefore signifying that the loading unit 21114 is not properly coupled to the shaft assembly 21104. At $t_2$, as the control circuit detects a capacitance level $C_2$ that is less than the predetermined maximum capacitance $C_{max}$, the control circuit can alert a user, via the display, haptic feedback, audible feedback, etc., that the loading unit 21114 is not properly coupled to the shaft assembly 21104 and that further rotation toward the locked position is required.

As further illustrated in FIG. 188, as the loading unit 21114 continues to rotate relative to the shaft assembly 21104, the control circuit can continue to detect an increase 21144 in capacitance between the first capacitor 21130 and the second capacitor 21132 as the second capacitor 21132 slides relative to the first capacitor 21130. For example, at $t_3$, a capacitance detected by the control circuit between the first capacitor 21130 and the second capacitor 21132 can meet or exceed the predetermined maximum capacitance $C_{max}$. As the control circuit detects a capacitance level that is substantially equal to or greater than the predetermined maximum capacitance $O_{max}$, the control circuit can alert a user, via the display, haptic feedback, audible feedback, etc., that the loading unit 21114 is properly coupled to the shaft assembly 21104 and that no further rotation is required.

In various embodiments, in addition to the above-described capacitance assembly, the loading unit 21114 can be provided with a dielectric thereon that is able to be read and interpreted by the control circuit. In one aspect, the control circuit can interpret the dielectric to determine a type of loading unit 21114 that is coupled to the shaft assembly 21104. In various embodiments, the control circuit can interpret the dielectric to determine any number of parameters associated with the loading unit 21114, such as the length of the loading unit, the type of loading unit (RF, ultrasonic, stapling, etc.), the height of the staples positioned in the staple cartridge of a stapling end effector, the orientation of the staples in the staple cartridge, the length of the staples, the length of the anvil coupled to the loading unit 21114, as examples.

Referring now to FIGS. 189-191, another mechanism for determining if a loading unit, such as a SULU or a MULU, is properly coupled and completely installed with a handle assembly is provided, according to at least one aspect of the present disclosure. In various embodiments, a shaft assembly 21200 and a loading unit 21202 are provided. In some embodiments, the shaft assembly 21200 can be similar to shaft assembly 20005 and/or shaft assembly 21104 and the loading unit 21202 can be similar to loading unit 21114 and/or loading unit 20004. The shaft assembly 21200 can extend from a housing assembly, such as the housing assemblies 20001, 21000, 21100, as examples, and can facilitate transmission of actuation motions from the housing assembly to the loading unit 21202 when the loading unit 21202 is properly coupled and completely installed therewith.

In various embodiments, the loading unit 21202 can be properly coupled and completely installed with the shaft assembly 21200 by initially positioning a proximal end 21204 of the loading unit 21202 into an aperture 21206 defined at a distal end 21208 of the shaft assembly 21200. This can be accomplished, as an example, referring to FIG. 192, by moving the proximal end 21204 of the loading unit 21202 toward the aperture 21206 in an installation direction 21210 along an installation axis. The installation direction 21128 can be substantially parallel to a longitudinal axis defined through the shaft assembly 21200. Once the proximal end 21204 of the loading unit 21202 is inserted into the aperture 21206, the loading unit 21202 can be rotated relative to the shaft assembly 21200 about the longitudinal axis defined by the shaft assembly 21200. In various embodiments, the loading unit 21202 can be rotatable relative to the shaft assembly 21200 between an unlocked position, where the loading unit 21202 can be moved away from the shaft assembly 21200 along the installation axis, and a locked position, wherein the loading unit 21202 is locked to the shaft assembly 21200. Once the loading unit 21202 has rotated to the locked position, a locking mechanism can lock the loading unit 21200 to the shaft assembly 21200, thereby completely coupling and completely installing the loading unit 21202 with the shaft assembly 21200. Once the loading unit 21202 is locked to the shaft assembly 21200, actuation motions and electrical signals from the handle assembly can be safety transmitted from the shaft assembly 21200 to the loading unit 21202 to effect end effector functions.

In one aspect, a user may desire to know if the loading unit 21202 is properly coupled to the shaft assembly 21200 prior to transmitting actuation motions and electrical signals to the loading unit 21202 through the shaft assembly 21200. For example, in instances where the loading unit 21202 wasn't completed rotated relative to the shaft assembly 21200 to the locked position and, therefore, wasn't completed locked into place, actuation motions and electrical signals from the handle assembly may not properly transfer to the loading unit 21202, or the loading unit 21202 may inadvertently decouple from the shaft assembly 21200 during the surgical procedure.

In various embodiments, the loading unit 21202 can include a first magnet 21220 and a second magnet 21222. The first magnet 21220 can include a first polarity and the second magnet 21222 can include a second polarity that is different that the first polarity. In one example embodiment, the second polarity can be opposite of the first polarity. The first magnet 21220 and the second magnet 21222 can be coupled to the proximal end 21204 of the loading unit 21202. In addition, in various embodiments, the shaft assembly 21200 can include a sensor assembly 21226 coupled to the distal end 21208 of the shaft assembly 21200. In some embodiments, the sensor assembly 21226 can be in electrical communication with a control circuit positioned in the handle assembly, such as control circuit 20014, as an example. In various embodiments, the sensor assembly 21226 can comprise a Hall-effect sensor that can sense a polarity of the first magnet 21220 and the second magnet 21222 to determine a position of the loading unit 21202 relative to the shaft assembly 21200 when the loading unit 21202 is coupled to the shaft assembly 21200. In various embodiments, referring to FIGS. 190 and 191, the magnets 21222, 21220 and the sensor assembly 21226 can be integral to the loading unit 21202 and the shaft assembly 21200.

In one aspect, when the loading unit 21202 is coupled to the shaft assembly 21200, the sensor assembly 21226 can sense a polarity of the first magnet 21220 and the second magnet 21222 and transmit a signal to the control circuit indicative of the sensed polarity. The control circuit can interpret the detected polarity to determine a position of the loading unit 21202 relative to the shaft assembly 21200. In some embodiments, when the loading unit 21220 is initially moved to the unlocked position along the installation axis 21210, as is shown in FIGS. 192 and 193, the sensor assembly 21226 can detect first polarity of the first magnet 21220. The control circuit can interpret this first polarity and determine that the first magnet 21220 is positioned at least substantially adjacent to the sensor assembly 21226, indicating that the loading unit 21202 is in the unlocked position and not yet completely installed or coupled to the shaft assembly 21200. In various embodiments, the control circuit can provide feedback, such as visual through a display, audible, or haptic, as examples, of the control circuit determining that the loading unit 21202 is in the unlocked position.

As discussed above, in the unlocked position, the loading unit 21202 can be rotated relative to the shaft assembly 21200 about a longitudinal axis defined by the shaft assembly 21200. As the loading unit 21202 rotates toward the locked position, the first magnet 21220 can move away from the sensor assembly 21226 and the second magnet 21222 can move toward the sensor assembly 21226. The control circuit can, through the sensor assembly 21226, determine that the second magnet 21222 is moving toward the sensor assembly 21226 by sensing the polarity shift of the first magnet 21220 to the second magnet 21222, thereby allowing the control circuit to monitor the rotation of the loading unit 21202. The second magnet 21222 can continue to be rotated toward the sensor assembly 21226 until the second magnet 21226 is adjacently positioned to the sensor assembly 21226, as is shown in FIG. 194. In various embodiments, the second magnet 21222 being adjacently positioned to the sensor assembly 212260 can be indicative of the loading unit 21202 being in the locked and fully coupled orientation with the shaft assembly 21200. Once the second magnet 21222 reaches the adjacent relationship with the sensor assembly 21226, thereby indicating that the loading unit 21202 is in the locked and fully coupled orientation with the shaft assembly 21200, the control circuit can provide feedback to the user, via visual, audible, haptic, or the like, indicating that the loading unit 21202 is properly coupled to the shaft assembly 21200, and is therefore safe to use.

In various aspects, the control circuit can determine that the loading unit 21202 is in the locked position by monitoring the sensor assembly 21226 and comparing a sensed value of the sensor assembly 21226 to a predetermined threshold. As one example, when the control circuit interrogates the sensor assembly 21226 and determines that the value sensed by the sensor assembly 21226 has reached or exceeded the predetermined threshold, the control circuit can conclude that the loading unit 21202 is in the locked position. As another example, when the control circuit interrogates the sensor assembly 21226 and determines that the value sensed by the sensor assembly 21226 has not yet reached the predetermined threshold, the control circuit can conclude that the loading unit 21202 is not in the locked position and further rotation is required.

Referring now to FIG. 195, a mechanism for ensuring that a loading unit, such as a SULU or a MULU, is properly coupled to a shaft assembly is provided, according to at least one aspect of the present disclosure. In various embodiments, a shaft assembly 21300 and a loading unit 21302 are provided. In some embodiments, the shaft assembly 21300 can be similar to shaft assembly 21200, shaft assembly 20005 and/or shaft assembly 21104 and the loading unit 21302 can be similar to loading unit loading unit 21202, loading unit 21114, and/or loading unit 20004. The shaft assembly 21300 can extend from a housing assembly, such as the housing assemblies 20001, 21000, 21100, as examples, and can facilitate transmission of actuation motions and electrical signals from the handle assembly to the loading unit 21302 when the loading unit 21302 is properly coupled and completely installed therewith.

In various embodiments, the loading unit 21302 can be properly coupled and completely installed with the shaft assembly 21300 by initially positioning a proximal end 21304 of the loading unit 21302 into an aperture 21306 defined at a distal end 21308 of the shaft assembly 21300. This can be accomplished, as an example, by moving the proximal end 21304 of the loading unit 21302 toward the aperture 21306 in an installation direction, similar to installation direction 21128 or installation direction 21210, along an installation axis. The installation direction can be substantially parallel to a longitudinal axis defined through the shaft assembly 21300.

Once the proximal end 21304 of the loading unit 21302 is inserted into the aperture 21306, the loading unit 21302 can be rotated relative to the shaft assembly 21300 about the longitudinal axis defined by the shaft assembly 21300. In various embodiments, the loading unit 21302 can be rotatable relative to the shaft assembly 21300 between an unlocked position, where the loading unit 21302 can be moved away from the shaft assembly 21300 along the installation axis, and a locked position, wherein the loading unit 21302 is locked to the shaft assembly 21300. Once the loading unit 21302 has rotated to the locked position, a locking mechanism can lock the loading unit 21300 to the shaft assembly 21300, thereby completely coupling and completely installing the loading unit 21302 with the shaft assembly 21300. Once the loading unit 21302 is locked to the shaft assembly 21300, actuation motions and electrical signals from the handle assembly can be safety transmitted to the loading unit 21302 through the shaft assembly 21300 to effect end effector functions.

In one aspect, a user may desire to know if the loading unit 21302 is properly coupled to the shaft assembly 21300 prior to transmitting actuation motions and electrical signals to the loading unit 21302. For example, in instances where the loading unit 21302 wasn't completed rotated relative to the shaft assembly 21300 to the locked position and, therefore, wasn't completed locked into place, actuation motions and electrical signals from the handle assembly may not properly transfer to the loading unit 21302, or the loading unit 21302 may inadvertently decouple from the shaft assembly 21300 during the surgical procedure.

In various embodiments, the loading unit 21302 can include a first lug or flange 21310 extending a first lateral direction from the proximal end 21304 of the loading unit 21302 and a second lug or flange 21312 extending from a second lateral direction from the proximal end 21304 of the loading unit 21302. In some embodiments, the first lateral direction can be opposite the first lateral direction, as is shown in FIGS. 195-197. In some embodiments, the first lateral direction can be perpendicular to the second lateral direction. In some embodiments, any suitable angle can be defined between the first lateral direction and the second lateral direction such that the first lateral direction is different than the first lateral direction. In various embodiments, while two lugs 21310, 21312 are shown and described, it should be understood that fewer or more than two lugs can be utilized without diverting from the scope of the disclosure that will be described below.

In addition, the shaft assembly 21300 can include a spring assembly 21314 extending from an inner wall 21315 of the shaft assembly 21300. In various embodiments, the spring assembly 21314 can include a base 21317 mounted to the inner wall 21315 and a spring 21319 extending from the base, as shown best in FIG. 197. In one aspect, the spring 21319 can comprise a linear spring or a torsional spring, as examples, such that the spring assembly 21314 is able to provide a biasing force against one of the first lug 21310 or second lug 21312 when a force is applied to the spring assembly 21314 by the same, as will be described in more detail below.

Similar to other loading units and shaft assemblies disclosed herein, to completely couple the loading unit 21302 to the shaft assembly 21300, the loading unit 21302 can first be brought into an unlocked position with the shaft assembly 21300, as described above. As the loading unit 21302 is moved toward the unlocked position, the first lug 21310 and the second lug 21312 can move through the aperture 21306 and be positioned within the shaft assembly 21300 such that the first lug 21310 and the second lug 21312 are radially aligned with the spring assembly 21314, as is shown in FIG. 197. To bring the loading unit 21302 to the locked position, as was described above, the loading unit 21302 can be rotated relative to the shaft assembly 21300 toward the locked position. Once the loading unit 21302 has rotated to the locked position, a locking mechanism can lock the loading unit 21300 to the shaft assembly 21300, as referenced above, thereby completely coupling and completely installing the loading unit 21302 with the shaft assembly 21300.

In various embodiments, the shaft assembly 21300 could include a switch, such as an on-off switch, that can be in electrical communication with a control circuit in the housing assembly, such as control circuit 20014. In some embodiments, one of the lugs can abut the on-off switch when the loading unit 21302 reaches the locked position. The control circuit can identify that the on-off switch has been actuated and provide feedback, such as visual with a display, audible, or haptic, as examples, to a user indicating that the loading unit 21302 has been placed in the locked position.

In one aspect, as the loading unit 21302 is rotated toward the locked position, the first lug 21310 can abut the spring 21319 of the spring assembly 21314. The spring 21319 can resist rotation of the first lug 21310 as the loading unit 21310 moves toward the locked position. In various embodiments, in order to completely couple the loading unit 21302 with the shaft assembly 21300, the loading unit 21302 can be rotated toward the locked position with such a force so as the first lug 21310 can impart a sufficient amount of force to overcome the spring bias of the spring 21319 and enter into the locked position. In instances where the loading unit 21302 is only partially rotated to the locked position, the spring assembly 21314 can bias the loading unit 21302 toward the unlocked position by applying a resistive force to the first lug 21310. Thus, the spring assembly 21314 is configured to give haptic feedback to a user attempting to rotate the loading unit 21302 toward the locked position in the form of the resistive force. In the locked position, the user no longer feels the resistive force. Additionally, in certain instances, entering the locked position yields audible feedback in the forming of a clicking sound, for example.

As described above, the spring assembly 21314 provides a mechanism to ensure that the loading unit 21302 is completely placed in the locked position prior to the shaft assembly 21300 and loading unit 21302 being used in a surgical procedure. If the loading unit 21302 is not rotated to the completely to the locked position, the spring 21319 can bias the loading unit 21302 to the unlocked position, allowing a user to identify that the loading unit 21302 has not been properly attached and that corrective action is required. In various embodiments, the spring assembly 21314 prevents the loading unit 21302 from entering the locked configuration unless a threshold amount of force is applied to the spring assembly 21314 by the first flange 21310 so as to overcome the spring bias of the spring assembly 21314.

In various embodiments, the shaft assembly 21300 can further include a stop member 21316 extending from the inner wall 21315 of the shaft assembly 21300. The stop member 21316 can be sized and positioned such that, should the loading unit 21302 be rotated to the unlocked position by the spring 21314, the stop member 21316 both prevents the loading unit from rotating beyond the unlocked position, as well as prevents the spring bias of the spring 21319 from forcing the loading unit 21302 out of the aperture 21306 of the shaft assembly 21300. In various embodiments, the stop member 21316 can be sized and positioned such that, as the spring 21319 forces the loading unit to the unlocked position, the stop member 21316 can abut one of the lugs 21310, 21312 in the unlocked position to prevent the spring bias force of the spring 21319 from forcing the loading unit 21302 out of the aperture 21306. The stop member 21316 can therefore require that the loading unit 21302 be removed from the aperture 21306 along the linear, installation axis. In various embodiments, the stop member 21316 can be positioned slightly offset the unlocked position such that, in the unlocked position, the loading unit 21302 can be rotated slightly toward the locked position to disengage the stop member 21316 from one of the lugs 21310, 21312 and then moved along the installation axis to remove the loading unit 21302 from the aperture. The above described stop member 21316 can be utilized in any embodiments described herein that require one component to rotate relative to another component to move between a locked and unlocked position. While one stop member 21316 was described, it should be understood that more than one stop member 21316 can be used. For example, there can be a 1:1 ratio of lugs to stop members 21316.

In various other embodiments, the shaft assembly 21300 can further include a second spring assembly positioned on an opposite side of the shaft assembly 21300 such that the first spring assembly 21314 can resist rotation of the first flange 21310 and the second spring assembly can resist rotation of the second flange 21312. The use of a second spring assembly can further increase the threshold force required for the loading unit 21302 to enter the locked position. Various other embodiments are envisioned where the loading unit 21302 includes a 1:1 ration of flanges to spring assemblies.

Referring now to FIGS. 198 and 199, a mechanism for determining if a staple cartridge is properly seated in a cartridge channel of an end effector and a type of staple cartridge that is seated in the cartridge channel is provided, according to at least one aspect of the present disclosure. In various embodiments, a staple cartridge can include a resistor assembly 21400 operably coupled thereto. In one aspect, the resistor assembly 21400 can include a housing 21402, an attachment feature 21404 extending from the housing 21402 to removably attach the resistor assembly 21400 to the cartridge, a circuit 21406 disposed within the housing 21402, a first arm 21408 and a second arm 21410. In various embodiments, the first arm 21408 can include a first contact arm 21409 disposed therein and the second arm 21410 can include a second contact arm 21411 disposed therein. In various other embodiments, the first contact arm 21409 and the second contact arm 21411 extent from the housing 21408 and are not disposed within the first arm 21408 and the second arm 21410. Stated another way, the resistor assembly 21400, in various embodiments, does not employ the first arm 21408 and the second arm 21410.

In various embodiments, the circuit 21406 can be tuned with a predetermined resistance value that corresponds to a type of cartridge to which the resistor assembly 21400 is coupled thereto. In one example embodiment, a circuit 21406 with a resistance R1 can correspond to a staple cartridge that includes staples with a staple height H1. In another embodiment, a circuit 21406 with a resistance R2 can correspond to a staple cartridge that includes staples with a staple height H2, where H2 is different than H1. In another embodiment, a circuit 21406 with a resistance R3 can correspond to a staple cartridge that includes a cartridge length of L3. In another embodiment, a circuit 21406 with a resistance R4 can correspond to a staple cartridge that includes a cartridge length of L4, where L4 is different than L3. Any number of resistance values of the circuit 21406 can correspond to any number of staple cartridge parameters, such as staple size, staple height, cartridge length, or the like.

In various embodiments, a unique resistance value of the circuit 21406 can correspond to more than one parameter of the staple cartridge. In one example embodiment, a circuit with a resistance of R1 can correspond to a staple cartridge that includes staples having a staple height H1 and a cartridge with a length L1, as an example. Various other embodiments are envisioned where the resistor assembly 21400 can be coupled to cartridges other than staple cartridges, such as RF cartridges, where the resistance value of the circuit 21406 can correspond to various parameters associated with the cartridges.

In various embodiments, an end effector of a surgical instrument can include a cartridge channel that is sized to receive a staple cartridge therein. In some situations, it would be desirable to ensure that the staple cartridge is properly seated in the cartridge channel prior to the staple cartridge being utilized in a surgical procedure. In various embodiments, the cartridge channel can be provided with a receptacle assembly 21420 that includes housing 21422, a first window 21424, a second window 21426, a circuit 21428, a first contact arm 21430 extending from the circuit 21428 and positioned in the first window 21424 and a second contact arm 21432 extending from the circuit 21428 and positioned in the second window 21426. Various other embodiments are envisioned where the receptacle assembly 21420 does not include the housing 21420, the first window 21424, or the second window 21426 and instead merely includes the circuit 21428, the first contact arm 21430 and the second contact arm 21432.

In certain instances, the housing 21422, or at least a portion thereof, is comprised of an insulative material such as a polymer, more specifically a polyimide, polyester, fluorocarbon, or any polymeric material, or any combinations thereof. In certain instances, the contact arms 21430, 21432 are comprised of an electrically conductive materials such as, for example, a metal.

In one aspect, the circuit 21428 can be in electrical communication with a control circuit positioned within a housing assembly, such as control circuit 20014, as an example, that is operably coupled with the cartridge channel of the end effector. In various embodiments, the first window 41424 and second window 21426 are sized such that, when a staple cartridge including a resistor assembly 21400 is properly seated within the cartridge channel, the first arm 21408 of the resistor assembly 21400 is inserted into the first window 21424 and the second arm 21410 is inserted into the second window 21426. When the first arm 21408 is positioned in the first window 21424 and the second arm 21410 is positioned in the second window, the circuit 21428 can electrically communicate with the circuit 21406. More specifically, when the first arm 21408 is positioned in the first window 21424, the first contact arm 21409 can electrically communicate with the first contact arm 21430 and the second contact arm 21411 can electrically communicate with the second contact arm 21432, thereby completing the circuit from the circuit 21428 to the circuit 21406. In various other embodiments, when a staple cartridge including a resistor assembly 21400 is properly seated within the cartridge channel, a user can determine that the staple cartridge is properly positioned in the cartridge channel if the first contact arm 21430 and the second contact arm 21432 are able to electrically communicate with the first contact arm 21409 and the second contact arm 21411, as will be discussed in more detail below.

In one aspect, when the circuit 21428 is in operable electrical communication with the circuit 21406, the control circuit of the housing assembly can transmit an electrical signal through the circuit 21428 to the circuit 21406 of the resistor assembly 21400, therefore verifying that the staple cartridge is properly positioned in the cartridge channel. In a scenario where a user attempts to verify if the staple cartridge is properly positioned in the cartridge channel and a complete circuit is not able to be made, as described above, a user is able to determine that the staple cartridge is not properly positioned in the cartridge channel and that appropriate action is required.

In addition to being able to determine if the staple cartridge is properly positioned in the cartridge channel, the receptacle assembly 21420 and the resistor assembly 21400 provides the added benefit of being able to determine the type of cartridge that is positioned in the cartridge channel, as referenced above. In various embodiments, once the control circuit is able to verify that the cartridge is properly positioned in the cartridge channel, by way of circuit 21428 and circuit 21406, an electrical signal can be transmitted to the circuit 21406 to determine a resistance of the resistor assembly 21400. As shown in FIGS. 200 and 201, in various embodiments, a resistance determined from the resistor assembly can correspond to the color of the cartridge positioned within the cartridge channel, where the color of the cartridge can correspond to a variety of parameters of the staple cartridge, such as staple size, staple height, cartridge length, etc.

In one example embodiment, continuing to refer to FIGS. 200 and 201, when cartridge 21540 is positioned in cartridge channel, the control circuit can interrogate resistor assembly 21452 and sense that the resistance of the circuit therein is 10 kΩ and determine that the cartridge is a tan staple cartridge that includes a plurality of staple cartridge parameters, such as cartridge length L1, staple height H1, etc. In another example embodiment, when cartridge 21544 is positioned in cartridge channel, the control circuit can interrogate resistor assembly 21456 and sense that the resistance of the circuit therein is 20 kΩ and determine that the cartridge is a purple staple cartridge that includes a plurality of staple cartridge parameters, such as cartridge length L2, staple height H2, etc. In another example embodiment, when cartridge 21548 is positioned in cartridge channel, the control circuit can interrogate resistor assembly 21460 and sense that the resistance of the circuit therein is 30 kΩ and determine that the corresponding staple cartridge is a black staple cartridge that includes a plurality of staple cartridge parameters, such as cartridge length L3, staple height H3, etc. While the above-provided discussion has been provided in the context of surgical stapling cartridges and staple cartridge parameters, it should be understood that the resistor assembly could be utilized in a plurality of other cartridge applications, such as RF cartridges, to determine the type of cartridge being attached to the surgical instrument.

In various embodiments, the control circuit can be in electrical communicate with a display, such as other displays referenced herein, such that the control circuit can communicate information to a user of the surgical instrument. In one aspect, when the control circuit is able to verify that the cartridge is properly positioned in the cartridge channel, as described above with the circuits 21406, 21428, the control circuit can provide a visual indication that the cartridge properly coupled to the cartridge channel and is ready for use. In various other embodiments, the control circuit can cause audible or haptic feedback based on the cartridge properly coupled to the cartridge channel. In various embodiments, after the control circuit identifies the type of cartridge positioned in the cartridge channel, the control circuit can display information about the cartridge onto the display, such as the color of the cartridge, the parameters of the cartridge, etc. In addition, after the control circuit identifies the type of cartridge positioned in the cartridge channel, the control circuit can modify parameters of the surgical instrument according to the parameters determined from the cartridge. For example, in instances where the control circuit identifies a cartridge with cartridge length L1, the cartridge can adjust a firing bar that traverses the cartridge to a suitable length for firing all of the staples from the cartridge, but not exceeding the length L1.

Referring now to FIGS. 202 and 203, a mechanism for determining if a staple cartridge is properly seated in a cartridge channel is provided, according to at least one aspect of the present disclosure. In various embodiments, a staple cartridge can include a sled 21500 that can translate through the staple cartridge during a staple firing motion to deploy staples removably stored in the staple cartridge. In one aspect, the sled 21500 can include a plurality of ramps, such as an inner ramp 21502 and an outer ramp 51204 on a first lateral side of the staple cartridge, which are shaped to cam and deploy the staples from the staple cartridge during the firing stroke. In various embodiments, the outer ramp 21504 of the sled 21500 can include an electrically printed circuit 21506 printed on an outer wall thereof. The circuit 21506 can include a first contact 21508 and a second contact 21510 in electrical communication with the first contact 21508.

In various embodiments, the staple cartridge can further include a cartridge pan 21520 and an outer cartridge wall 21530. The cartridge pan 21520 can be sized to house the sled 21500 therein and can include a first window 21522 aligned with the first contact 21508 of the circuit 21506 and a second window 21524 aligned with the second contact 21510 of the circuit 21506. As shown in FIG. 203, the outer cartridge wall 21530 can at least partially abut the cartridge pan at an engagement region 21532 such that a gap ‘g’ can be defined between the cartridge wall 21530 and the cartridge pan 21520 in a connector receiving region 21534.

In some embodiments, the connector receiving region 21534 and the gap ‘g’ are sized to receive a connector assembly 21540 therein. In various embodiments, the connector assembly 21540 can include a housing 21542, a connector portion 21544 extending from the housing 21542, a first window 21546, a second window 21548, and a circuit 21550 that can include a first contact arm 21552 that can extend proximally from the connector assembly 21540 and at least partially out of the first window 21546 and a second contact arm 21554 that can extend proximally from the connector assembly 21540 and at least partially out of the second window 21548. In various embodiments, the proximal portions of the first contact arm 21552 and the second contact arm 21554 can be similar to the first contact arm 21409 and the second contact arm 21411, respectively, in that they are designed to electrically couple to a control circuit, such as control circuit 20014, as an example, located in the surgical instrument. For example, the surgical instrument can include circuit 21560, illustrated in FIG. 203, that can be in electrical communication with control circuit in the surgical instrument such that the control circuit can verify if the staple cartridge is properly positioned in the cartridge channel. Similarly, the connector assembly 21540 could include a circuit, similar to circuit 21406 in electrical communication with the first contact arm 21552 and the second contact arm 21554 such that the control circuit in the surgical instrument could determine a type of cartridge that the connector assembly 21540 is coupled to.

As shown in FIG. 203, when the connector assembly 21540 is properly positioned within the connector receiving region 21532 of the staple cartridge, the first circuit arm 21552 can extend through the first window 21546 of the connector assembly 21540, through the first window 21522 of the cartridge pan 21520, and can abut the first contact 21508 of the circuit 21506. Similarly, when the connector assembly 21540 is properly positioned within the connector receiving region 21532 of the staple cartridge, the second contact arm 21554 can extend through the second window 21548 of the connector assembly 21540, through the second window 21524 of the cartridge pan 21520, and can abut the second contact 21510 of the circuit 21506.

In various embodiments, in operation, a user can determine if the connector assembly 21540 is properly coupled to the surgical instrument, by way of the proximal portions of the first contact arm 21552 and the second contact arm 21554 being electrically coupled with the circuit 21560, and if staple cartridge is properly seated within the cartridge channel, by way of the portions of the first contact arm 21552 and the second contact arm 21554 extending out of the first window 21546 and second window 21548, respectively, and electrically contacting the first contact 21508 and the second contact 21510. In one example embodiment, the control circuit can determine if the staple cartridge is properly coupled to the surgical instrument by generating an electrical signal that can transmit from the control circuit, through the circuit 21560, the first contact arm 21552, the circuit 21506, the second contact arm 21554 arm, the circuit 21560, and back to the control circuit. If the control circuit is unable to transmit an electrical signal from the control circuit as described above, a user will be able to determine that the connector assembly 21540 or the staple cartridge is improperly positioned and that corrective action is required.

In various embodiments, the control circuit can be in electrical communication with a display, such as other displays referenced herein, such that the control circuit can communicate information to a user of the surgical instrument. In one aspect, when the control circuit is able to verify that the connector assembly 21540 and the staple cartridge are properly coupled to the surgical instrument, as described above, the control circuit can provide a visual indication verifying the same. In various other embodiments, the control circuit can cause audible or haptic feedback based on the control circuit verifying that the connector assembly 21540 and the staple cartridge are properly coupled to the surgical instrument.

Referring now to FIGS. 204-211, a mechanism for ensuring that loading units are properly coupled to a surgical instrument is disclosed, according to at least one aspect of the present disclosure. As shown in FIG. 204, a shaft assembly 21600 can extend from a surgical housing assembly, such as a handle assembly or housing assembly. In various embodiments, the shaft assembly 21600 can also be similar to other shaft assemblies described herein, such as shaft assembly 20005, shaft assembly 21104, shaft assembly 21200, and/or shaft assembly 21300, as non-limiting examples. In various embodiments, the housing assembly can be similar to any other housing assemblies described herein, such as housing assembly 20001, housing assembly 21000, and/or housing assembly 21100, as non-limiting examples.

In various embodiments, the shaft assembly 21600 can include a J-shaped passage 21602 defined therein. The J-shaped passage 21602 can include a first passage portion 21604, a second passage portion 21606 extending laterally away from the first passage portion 21602, and a third passage portion 21608 extending longitudinally away from the second passage portion 21606.

Referring primarily to FIG. 205, the shaft assembly 21600 can further include a closed-end tunnel 21610 positioned adjacent to the second passage portion 21606 and extending between the first passage portion 21604 and the second passage portion 21608. The closed-end tunnel 21610 can be sized to include a magnet 21612 therein that can be movable between a first position, as is shown in FIG. 205, where the magnet 21612 is positioned on a first end of the closed-end tunnel 21610 that is adjacent to the third passage portion 21608, and a second position, as is shown in FIG. 208, where the magnet 21612 is positioned on a second end of the closed-end tunnel 21610 that is adjacent to the first passage portion 21604. The shaft assembly 21600 can further include a window 21615 defined therein that allows a user to view the magnet 21612 when the magnet 21612 is in the second position.

In various embodiments, as is shown in FIG. 205, the magnet 21612 can include a first magnet portion 21616 that includes a first polarity and a second magnet portion 21618 that includes a second polarity that is different than the first polarity. As an example, as shown in FIG. 205, the first magnet portion 21614 can include a south, negative polarity and the second magnet portion 21616 can include a north, positive polarity.

As referenced above, the above-provided mechanism can ensure that loading units, such as SULUs and/or MULUs, are properly coupled the shaft assembly 21600. In various embodiments, referring to FIGS. 206-208, the loading unit can include a magnet 21620 coupled thereto. The magnet 21620 can include a first magnet portion 21622 that includes a first polarity, such as a south, negative polarity, and a second magnet portion 21624 that includes a second polarity that is different than the first polarity, such as a north, positive polarity. In various embodiments, the first polarities of the magnets 216212, 21620 can be the same and the second polarities of the magnets 216212, 21620 can be the same. In some embodiments, the loading unit can include a flange extending therefrom that includes the magnet coupled thereto. The flange can be sized to traverse through the J-shaped passage 21602 from the first passage portion 21604 to the third passage portion 21608. In various embodiments, in order to lock the loading unit to the shaft assembly 21600, the magnet 21620 can move through the J-shaped passage 21602 and be positioned in the third passage portion 21608, as shown in FIGS. 208 and 211, as will be described in more detail below. In one aspect, the magnet 21620 being positioned in the third passage portion 21608 can correspond to the loading unit being locked to the shaft assembly 21600, therefore, allowing the user to know that the loading unit and the shaft assembly 21600 are safe for use with the surgical instrument.

In operation, as an example, the magnet 21620 of the loading unit can enter the first passage portion 21604 through an open-end 21630 of the J-shaped passage 21602 at a distal end of the shaft assembly 21600. The loading unit can be moved relative to the shaft assembly 21600 such that the magnet 21620 can be moved along the first passage portion 21604 toward the second passage portion 21606, as shown in FIG. 206. In one aspect, the magnet 21620 can be oriented such that the, as the magnet 21620 approaches the second passage portion 21620, the second polarities of the magnets 21612, 21620 can laterally align, as is shown in FIG. 206, causing the magnet 21612 to move to the first end of the closed-end tunnel 21640. In one aspect, when the magnet 21612 is on the first end of the closed-end tunnel 21610, the user is not able to view the magnet 21612 through the window 21615, therefore signifying that the loading unit is not yet coupled completely to the shaft assembly 21600.

Once the magnet 21620 has traversed the first passage portion 21604 and has reached the second passage portion 21606, the user can rotate the loading unit relative to the shaft assembly 21600 to traverse the magnet 21620 through the second passage portion 21606 toward the third passage portion 21608. As the magnet 21620 traverses the second passage portion 21606, the magnet 21620 can begin to longitudinally align with the magnet 21612 in the closed-end tunnel 21610, as is shown in FIG. 207. In one aspect, when the magnet 21620 begins to longitudinally align with magnet 21612, the first polarities of the magnets 21612, 21620 can begin to longitudinally align with the second polarities of the magnets 21612, 21620. The magnetic coupling force induced by the attraction between the polarities can cause the loading unit to experience resistance as the magnet 21620 is moved toward the third passage portion 21608. In some embodiments, this magnetic arrangement can be utilized to reject immature attachments if the loading unit is incompletely attached to the shaft assembly 21600. With the magnets 21612, 21620 longitudinally aligned, a threshold force can be applied by the user to the loading unit to overcome the magnetic attractive forces between the magnets 21612, 21620 such that the magnet 21620 can continue to traverse the second passage portion 21606 toward the third passage portion 21608.

Once the magnet 21620 has reached the third passage portion 21608, the magnet 21602 can be moved to an end 21632 of the third passage portion 21608 that is adjacent to the first end of the closed-end passage 21610. In various embodiments, as is shown in FIGS. 209-211, a spring assembly 21640 can be positioned at a transition point between the second passage portion 21606 and the third passage portion 21608. In some embodiments, the spring assembly 21640 can include a spring 21642 coupled to the shaft assembly 21600 and a pusher plate 21644 coupled to the spring 21642. The spring 21642 can be transitionable between a compressed position, as shown in FIG. 210, where the pusher plate 21644 at least substantially is pushed out of the J-shaped passage 21602 and the spring 21642 is compressed, and an extended position, as shown in FIG. 211, where the pusher plate 21644 extends through the third passage portion 21608. The pusher plate 21644 can include a cam surface 21646 that can be engaged by the magnet 21620 as the magnet 21620 moves toward the third passage portion 21608 to transition the spring assembly 21640 toward the compressed position. As the magnet 21620 aligns with the third passage portion 21608, the user can release the loading unit, causing the spring assembly 21640 to transition toward the extended position, which can cause the pusher plate 21644 to force the magnet 21620 toward the end 21632 of the third passage portion 21608, as is shown in FIG. 211. In various embodiments, the spring assembly 21640 can be designed such that, in the expanded position, the pusher plate 21644 can hold the magnet 21620 at the end 21632 of the third passage portion 21608 to maintain the loading unit locked and coupled to the shaft assembly 21600.

In one aspect, after the magnet 21620 overcomes the magnetic force experienced due to the magnet 21612, the second polarities of the magnets 21612, 21620 begin to approach one another, as is shown in FIG. 208, as an example, therefore causing the magnet 21612 to resist the magnet 21620. For example, as the magnet 21620 is moved toward the end 21632 of the third passage portion 21608, which can correspond to the loading unit being placed in the locked and coupled position with the shaft assembly 21600, magnetic resistance between the second polarities of the magnets 21612, 21620 can cause the magnet 21612 to move toward the second end of the closed-end channel 21610, as is shown in FIG. 208. As referenced above, when the magnet 21612 is in the second position at the second end of the closed-end channel 21610, a user is able to view the magnet 21612 through the window 21615, therefore signifying to the user that the magnet 21620 has reached the end 21632 of the third passage portion 21608 and that the loading unit is properly attached and coupled to the shaft assembly 21600.

Referring now to FIG. 212, a graphical representation 21650 of the resistive force provided by the magnet 21612 as the magnet 21620 traverses the J-shaped passage 21602 is provided, according to at least one aspect of the present disclosure. In various embodiments, a sensor assembly can be provided in the shaft assembly 21600 to measure magnetic forces between the magnets 21612, 21620 as the magnet 21620 traverses the J-shapes passage 21602. In various embodiments, a control circuit located within the housing assembly, such as control circuit 20014, can be in electrical communication with the sensor assembly to monitor the magnetic forces between the magnets 21612, 21620 to provide feedback to a user indicative of the position of the magnet 21620 in the J-shapes passage 21602. In various embodiments, the surgical instrument can include a display and the control circuit provide information to the user indicative of the magnetic force sensed by the sensor assembly via the display.

Initially, the magnet 21612 enters the open end 21630 of the J-shaped passage 21602 and traverses the first passage portion 21604 toward the second passage portion 21606. As the magnet 21620 traverses the first passage portion 21604 toward the second passage portion 21606, the circumferential outward force by the magnet 21620 can begin to increase until an inflection point 21652 is reached, where the magnet 21620 is laterally aligned with the magnet 21612, as is shown in FIG. 206, as an example.

After the magnet 21620 has laterally aligned with the magnet 21612, the magnet 21620 can continue to traverse the first passage portion 21604 toward the second passage portion 21606. As the magnetic moves toward the corner between first passage portion 21604 and the second passage portion 21606, the circumferential outward force by the magnet 21620 can diminish and reach inflection point 21654 when the magnet 21620 reaches the corner between the first passage portion 21606 and the second passage portion 21606.

After the magnet 21620 has reached the corner between the first passage portion 21606 and the second passage portion 21606, the magnet 21620 can traverse the second passage portion 21606 toward the third passage portion 21608. As the magnet 21620 traverses the second passage portion 21606 toward the third passage portion 21608, the circumferential outward force by the magnet 21612 begins to increase until an inflection point 21656 is reached, where the magnet 21620 is longitudinally aligned with the magnet 21612, as is shown in FIG. 207, as an example. As shown in FIG. 212, the inflection point 21565 force can be greater than the inflection point 21562.

After the magnet 21620 has longitudinally aligned with the magnet 21612, the magnet 21620 can continue to traverse the second passage portion 21606 toward the third passage portion 21608. As the magnet 21620 moves toward the corner between the second passage portion 21606 and the third passage portion 21608, the circumferential outward force by the magnet 21612 can shift as the phase change between the repulsion forces of the magnets 21612, 21620 changes from repulsive forces between the second polarities of the magnets 21612, 21620 (the north, positive polarities, as an example) to the first polarities of the magnets 21612, 21620 (the south, negative polarities, as an example). As the magnet 21620 moves toward the second corner between the second passage portion 21606 and the third passage portion 21608, the magnetic force between the magnets 21612, 21620, causes the magnet 21612 to translate toward the second end of the closed-end tunnel 21610, as is shown in FIG. 208, as an example.

As the magnet 21612 translates toward the second end of the closed-end tunnel 21610, the magnetic force can reach an inflection point 21658 and then can increase to inflection point 21660 as the magnet 21620 reaches the corner between the second passage portion 21606 and the third passage portion 21608. As the magnet 21620 then translates toward the end 21632 of the third passage portion 21608, the force can fluctuate as shown in FIG. 212 until the magnet 21620 reaches the end 21632 of the third passage portion 21608, where the loading unit is then locked to the shaft assembly 21600.

Referring now to FIGS. 213-215, a mechanism for determining if a nozzle assembly is properly coupled and completely installed with a handle assembly is provided, according to at least one aspect of the present disclosure. In various embodiments, a handle assembly 21700 can include a housing portion 21702 and handle portion 21704. The handle portion 21704 can include a stationary handle 21706 and a trigger 21708 rotatable relative to the stationary handle 21706. The trigger 21708 can be rotatable toward the stationary handle 21706 to transmit actuation motions to an end effector of a loading unit, similar to as was described elsewhere herein. In one aspect, the trigger 21706 can transmit a closing motion that can cause a first jaw and a second jaw of the end effector to transition between an open configuration, wherein the first jaw and second jaw are spaced apart from one another, and a closed configuration, wherein the first jaw and second jaw are spaced near each other to capture tissue therebetween. In another aspect, the trigger 21708 can transmit a firing motion to the end effector to cause staples to be deployed from the end effector into the tissue positioned between the first jaw and second jaw, as well as cause a knife to sever the stapled tissue. In various embodiments, the handle assembly can include more than one trigger than each effect different end effector functions of the end effector, such as closing motion and firing motions, as an example. In various embodiments, the handle assembly 21700 can further include a control circuit, such as control circuit 21766, as an example, that can transmit electrical signals to various other components within the surgical instrument, such as to an end effector of a loading unit or a nozzle assembly 21710, as will be described in more detail below. In various embodiments, the nozzle assembly 21710 can be similar to adapter assemblies described elsewhere herein, such as adapter 20002 and/or adapter 21002, as examples. In various embodiments, the handle assembly 21700 can be similar to any other housing assemblies described herein, such as housing assembly 20001, housing assembly 21000 and/or housing assembly 21100, as non-limiting examples.

In various embodiments, a nozzle assembly 21710 can include a nozzle housing 21712 that can be removably coupled to the handle housing 21702 and a shaft assembly 21714 extending distally from the nozzle housing 21712. In various embodiments, the shaft assembly 21714 can be similar to other shaft assemblies described herein, such as shaft assembly 20005, shaft assembly 21104, shaft assembly 21200, shaft assembly 21300, and/or shaft assembly 21600, as non-limiting examples.

As shown in FIGS. 213-215, the nozzle assembly 21710 can include a nozzle latch 21716 extending proximally from the nozzle housing 21712. The nozzle latch 21716 can include a first seating platform or portion 21718 extending proximally from the nozzle housing 21712 and a first ramped portion 21720 extending proximally from the first seating portion 21718. Similarly, the nozzle latch 21716 can include a second seating platform or portion 21722 extending proximally from the nozzle housing 21712 and a second ramped portion 21724 extending proximally from the second seating portion 21722.

In some embodiments, the handle assembly 21700 can include handle latch 21730 that includes a base portion 21732 and a pair of fingers 21734, 21736 extending transversely therefrom. In one aspect, to properly couple the nozzle assembly 21710 to the handle assembly 21700, the fingers 21734, 21736 can be positioned on correspondingly positioned seating portions 21718, 21722 to latch the nozzle assembly 21710 to the handle assembly 21700. Stated another way, to properly couple the nozzle assembly 21710 to the handle assembly 21700, finger 21734 can be seated on seating portion 21718 and finger 21736 can be seated on seating portion 21722.

In various embodiments, in order to properly couple the nozzle assembly 21710 to the handle assembly 21700, the handle assembly 21700 can be brought towards the handle assembly 21700 in an installation direction 21738. As the nozzle assembly 21710 is brought towards the handle assembly 21700 in the installation direction 21738, finger 21734 can engage ramped portion 21720 and finger 21736 can engage ramped portion 21724 of the nozzle latch 21716. The fingers 21734, 21736 can slide along and cam the ramped portions 21720, 21724 downwardly away from the base portion 21732 of the handle latch 21730. As the fingers 21734, 21736 reach the apexes of the ramped portions 21720, 21724, the fingers 21724, 21736 can move distally and seat onto the seating portions 21718, 21722 of the nozzle latch 21716, respectively. As the fingers 21734, 21736 reach the seating portions 21718, 21722 of the nozzle latch 21716, the ramped portions 21720, 21724 can be biased such that the ramped portions 21720, 21724 return to their original, unbiased positions, as shown in FIG. 215, as an example. With the ramped portions 21720, 21724 in their original, unbiased positions and the fingers 21724, 21736 seated on the seating portions 21718, 21722, the distal surfaces 21721, 21725 of the ramped portions 21720, 21724 can engage the proximal surfaces 21735, 21737 of the fingers 21734, 21376, respectively, retaining the nozzle assembly 21710 to the handle assembly 21700, thereby properly coupling the nozzle assembly 21710 to the handle assembly 21700.

When the nozzle assembly 21710 is properly coupled to the handle assembly 21700, the handle assembly 21700 is capable of transmitting actuation motions and electrical signals through the nozzle assembly 21710 to an end effector at a distal end of the shaft assembly 21714, such as the aforementioned closure motions or firing motions, as an example. In situations where the nozzle assembly 21710 isn't properly coupled to the handle assembly 217100, the handle assembly 217100 may not be able to properly or safely transmit actuation motions or electrical signals to the end effector. In addition, in situations where the nozzle assembly 21700 isn't properly coupled to the handle assembly 21700, the nozzle assembly 21700 may decouple from the handle assembly 21700 during a surgical procedure, such as when the user attempts to transmit actuation motions to the end effector.

In various embodiments, in order to ensure that the nozzle assembly 21710 is properly coupled to the handle assembly 21700, the nozzle latch 21716 can include a contact arrangement 21750 that includes a first latch contact 21752 positioned on the first seating portion 21718 and a second latch contact 21754 positioned on the second seating portion 21722. The first latch contact 21752 and the second latch contact 21754 can be in electrical communication by way of a wire 21756 that extends from the first latch contact 21752, along a distal, inner wall of the latch assembly 21716 and to the second latch contact 21756, as shown best in FIG. 215. In addition, the handle latch 21730 can include a contact arrangement 21760 that includes a first finger contact 21762 positioned on a bottom surface of the first finger 21734 and a second finger contact 21764 positioned on a bottom surface of the second finger 21736. The first finger contact 21762 and the second finger contact 21764 can be in electrical communication with the control circuit 21766 that is positioned in the handle assembly 21700.

In operation, when the nozzle assembly 21710 is coupled to the handle assembly 21700, as described above, the first finger contact 21762 can engage the first latch contact 21752 and the second finger contact 21764 can engage the second latch contact 21754. In order to verify if the nozzle assembly 21710 is properly coupled to the handle assembly 21700, the control circuit 21766 can attempt transmit an electrical signal through the contact arrangement 21760. In one aspect, if the control circuit 21766 is able to successfully transmit an electrical signal through the contact arrangement 21760, the control circuit 21766 can determine that the contact arrangement 21766 is in electrical communication with the contact arrangement 21750, signifying that the nozzle assembly 21710 is properly coupled to the handle assembly 21700. If the control circuit 21766 is unable to transmit an electrical signal through the contact arrangement 21760, the control circuit 21766 can determine that the nozzle assembly 21710 is improperly coupled to the handle assembly 21700 and that corrective action is required.

In various alternative embodiments, referring now to FIG. 216, the latch assembly 21716 may not include the contact arrangement 21750 and the latch assembly 21730 may include a first on-off switch 21770 and a second on-off switch 21772 on the first finger 21734 and the second finger 21736, respectively, in lieu of the first latch contact 21762 and the second contact 21764. The first on-off switch 21770 and the second on-off switch 21772 may be in electrical communication with a control circuit, such as control circuit 21766, which can determine an actuation state of the on-off switches 21770, 21772. In various embodiments, the on-off switches 21770, 21772 can be transitionable between a resting position, as is shown in FIG. 216, which can signify to the control circuit that the fingers 21734, 21736 are not engaged with the seating portions 21718, 21722 of the latch assembly 21716, and an actuated position, which can signify to the control circuit that the fingers 21734, 21736 are engaged with the seating portions 21718, 21722 of the latch assembly 21716. The on-off switches 21770, 21772 can transition to the actuated position when the on-off switches 21770, 21772 are depressed toward the fingers 21734, 21736.

In operation, when the nozzle assembly 21710 is coupled to the handle assembly 21700, as described above, the first on-off switch 21770 can engage the first seating portion 21718 and the second on-off switch 21772 can engage the second seating portion 21722. In order to verify if the nozzle assembly 21710 is properly coupled to the handle assembly 21700, the contact circuit can monitor a voltage of the first on-off switch 21770 and the second on-off switch 21772. For example, referring to the graph 21774 in FIG. 217 that illustrates voltage sensed by the control circuit over time, when the nozzle assembly 21710 is not coupled to the handle assembly 21700, as is shown in FIG. 216, the on-off switches 21770, 21772 can be in the resting positions. The control circuit can sense that the on-off switches 21770, 21772 are in the resting position by measuring the voltage of the on-off switches to determine the position of the on-off switches 21770, 21772. As shown in FIG. 217, the control circuit senses a voltage of zero, therefore signifying to the control circuit that the nozzle assembly 21710 is not coupled to the handle assembly 21700. When the nozzle assembly 21710 is properly coupled to the handle assembly 21700, as described above, the control circuit can detect a voltage $V_1$ by the on-off switches 21770, 21772, thereby signifying that the nozzle assembly 21710 is properly coupled to the handle assembly 21700. If the nozzle assembly 21710 appears to be coupled to the handle assembly 21700, but the control circuit continues to detect a zero voltage, a user can determine that the nozzle assembly 21710 is not properly coupled to the handle assembly 21700 and that corrective action is required. In some embodiments, the control circuit could detect a voltage that is greater than 0, but less than $V_1$. In such a scenario, the control circuit could determine that the first on-off switch 21770, as an example, is properly seated in the seating portion 21718, but on-off switch 21772 is not properly seated in the seating portion 21722, therefore resulting in a voltage detected by the control circuit that is less than $V_1$.

Referring now to FIG. 218, a mechanism for ensuring that an adapter is properly coupled and completely installed with a handle assembly is provided, according to at least one aspect of the present disclosure. In various embodiments, a handle assembly 21800 can include a housing portion 21802 and handle portion 21804. The handle portion 21804 can be similar to other housing portions described herein, such as housing assembly 20001, housing assembly 21000, housing assembly 21100 and/or housing assembly 21700, as non-limiting examples.

In one aspect, the handle portion 21804 could include a stationary handle and one or more triggers that are rotatable relative to the stationary handle to effect end effector functions of a shaft assembly when the shaft assembly is properly coupled thereto. For example, when the shaft assembly is properly coupled to the handle assembly 21800, actuation of the triggers can cause the handle assembly 21800 to transmit actuation motions to the end effector of the shaft assembly, similar to what was described elsewhere herein. In some embodiments, actuation of one of the triggers could cause a closing motion that can cause a first jaw and a second jaw of the end effector to transition between an open configuration, wherein the first jaw and second jaw are spaced apart from one another, and a closed configuration, wherein the first jaw and second jaw are spaced near each other to capture tissue therebetween. In other embodiments, actuation of one of the triggers could cause a firing motion to the end effector to cause staples to be deployed from the end effector into the tissue positioned between the first jaw and second jaw, as well as cause a knife to sever the stapled tissue.

In various embodiments, the handle assembly 21800 can further include receiving area 21806 defined at a distal end 21808 thereof. The receiving area 21806 can be sized to receive a proximal end of an adapter assembly therein such that the handle assembly 21800 can transmit actuation motions and electrical signals through the adapter assembly. In one aspect, the receiving area can be similar to receiving area 21008 and adapter assembly can be similar to adapter assemblies described elsewhere herein, such as adapter 20002 and/or adapter 21002, as examples.

In various embodiments, the receiving area 21806 can include a spring assembly that includes a first spring 21810 positioned on a first lateral side of a distal wall 21814 of the receiving area 21806 and a second spring 21812 positioned on a second lateral side of the distal wall 21816 of the receiving area 21806. In various embodiments, the spring assembly could include only a single spring positioned at any suitable location of the receiving area 21806, such as in the center of the receiving area 21806. In various embodiments, the spring assembly can include more than two springs positioned at any suitable locations of the receiving area 21806, such as around the perimeter of the distal wall 21814 of the receiving area 21806, as an example. In various embodiments, the springs 21810, 21812 can be movable between an extended position, as shown in FIG. 218, and a compressed position, where the springs 21810, 21812 are compressed towards the distal wall 21814. In one aspect, the spring 21810, 21812 are linear springs and can be biased outwardly toward the extended position when no force is applied thereto. In various other embodiments, the springs 21810, 21812 can comprise torsional springs.

In one aspect, in order to properly and completely couple the adapter assembly to the handle assembly 21800, the proximal end of the adapter assembly can be moved into the receiving area 21806 to latch the adapter assembly to the housing assembly 21800. As one example, the adapter assembly can be latched to the handle assembly 21800 by way of flange features 21022*a-e* extending around the proximal end of the adapter assembly and flange features 21024*a-e* extending around the receiving area 21806, as described elsewhere herein. In various embodiments, as the adapter assembly is moved into the receiving area 21806 to latch the shaft assembly to the handle housing 21802, the springs 21810, 21812 can abut the proximal end of the adapter assembly and apply a resistive force thereto. The springs 21810, 21812 can apply a resistive force to the adapter assembly such that the adapter assembly is biased away from the receiving area 21806 until the adapter assembly is latched to the handle assembly 21800.

The springs 21810, 21812 can provide a means of ensuring that the adapter assembly is properly coupled to the handle housing 21802 before the adapter assembly is utilizing in a surgical procedure. For example, should the flange features 21024*a-e* not completely or properly couple to the flange features 21022*a-e*, therefore signifying that the adapter assembly is properly coupled to the handle assembly 21800, the springs 21810, 21812 can force the adapter assembly away from the receiving area 21806. The springs 21810, 21812 therefore require that both a threshold force be applied to the adapter assembly to overcome the spring bias of the springs 21810, 21812, as well as also requires that the adapter assembly be properly coupled to the handle assembly 21800, otherwise the springs 21810, 21812 will force the adapter assembly away from the handle assembly 21800.

Referring now to FIG. 219, an alternative embodiment is illustrated where springs 21820, 21822 can extend around a receiving area 21824 to bias a adapter assembly away from the receiving area 21826 unless the adapter assembly is properly coupled to a handle assembly 21826. In one aspect, spring 21822 can include a first platform 21830 coupled to spring 21822 and spring 21824 can include a second platform 21832 coupled to spring 21824. The platforms 21830, 21832 can increase the surface area to which the springs 21820, 21822 can apply the resistive force to the adapter assembly as the adapter assembly is brought into the receiving area 21824 of the handle assembly 21826.

Referring now to FIGS. 220 and 221, another mechanism for ensuring that an adapter assembly is properly coupled and completely installed with a handle assembly is provided, according to at least one aspect of the present disclosure. In various embodiments, an adapter assembly 21850 can include an adapter housing 21852 and a shaft 21854 extending distally therefrom. In one aspect, the adapter 21850 can be similar to adapter assembly 20002 and/or 21002, as examples. Similar to the above, the adapter assembly 21850 can be coupleable with a handle assembly by moving the proximal end 21856 of the adapter assembly 21850 into a receiving area of the handle assembly. Once the proximal end 21856 of the adapter assembly 21850 is properly positioned in the receiving area, a latch assembly, such as flange features 21022*a-e* and flange features 21024*a-e*, can lock the adapter assembly 21850 to the handle assembly.

Similar to the above, the adapter assembly 21850 can include a spring assembly that can include a first spring 21860 positioned on a first lateral side of the proximal end 21856 of the adapter assembly 21850 and a second spring 21862 positioned on a second lateral side of the proximal end 21856 of the adapter assembly 21850. In various embodiments, the spring assembly can include more than two springs positioned at any suitable locations of the proximal end 21856 of the adapter assembly 21850, such as around the perimeter of the proximal end 21856 of the adapter assembly 21850, as an example. In various embodiments, the springs 21860, 21862 can be movable between an extended position, as shown in FIG. 220, and a compressed position, as is shown in FIG. 221, where the spring 21860, 21862 are compressed towards the shaft 21854 of the adapter assembly 21850. In one aspect, the springs 21860, 21862 area linear springs and can be biased outwardly toward the extended position when no force is applied thereto.

In various embodiments, as shown in FIGS. 220 and 221, the shaft assembly 21850 can further include a mounting plate 21864 that is coupled to the spring assembly. The mounting plate 21864 can be sized to be received within the receiving area of the housing assembly so as to align the adapter assembly 21850 with the handle assembly as the adapter assembly 21850 is coupled to the handle assembly. In addition, in various embodiments, the adapter assembly 21850 can include an alignment shaft 21866 extending from the proximal end 21856 of the adapter assembly 21850 and through the mounting plate 21864. The alignment shaft 21864 can be sized to be received with an alignment aperture defined in the receiving area to assist in properly aligning the adapter assembly 21850 with the handle assembly as the adapter assembly 21850 is coupled to the handle assembly. In various embodiments, the tip of the alignment shaft 21864 can be flush with the surface of the mounting plate 21864, as is shown in FIG. 220. As the mounting plate 21864 is pressed into the receiving area, the mounting plate 21864 can move toward the adapter assembly 21850 by way of the springs 21860, 21862 being compressed. As the mounting plate 21864 moves toward the shaft 21854, the alignment shaft 21864 can become exposed, as shown in FIG. 221, which can then move into the alignment aperture defined in the receiving area of the housing assembly to align the adapter assembly 21850 with the housing assembly.

As referenced above, as the adapter assembly 21850 is brought toward the handle assembly, the mounting plate 21864 and the alignment shaft 21866 can enter into the receiving area to assist in coupling the adapter assembly 21850 to the handle assembly. As the mounting plate 21864 is seated within the handle assembly, the springs 21860, 21862 can be compressed toward the compressed positions, as shown in FIG. 221. Similar to the above, the springs 21860, 21862 can apply a resistive force to bias the adapter assembly 21850 away from the mounting plate 21864. The springs 21860, 21862 can apply a resistive force to the adapter assembly 21850 such that the adapter assembly 21850 is biased away of the receiving area until the adapter assembly 21850 is latched to the handle assembly. In various embodiments, the adapter assembly 21850 can be latched to the handle assembly when a portion of the adapter housing 21852 enters into the receiving area. For example, the adapter housing 21852 can include the plurality of flange features 21024*a-e* around the perimeter thereof such that, as the adapter housing 21852 enters the receiving area, the flange features 21024*a-e* can engage flange features 21024*a-e* of the receiving area of the housing assembly. Until flange features 21024*a-e* engage flange features 21024*a-e* to latch the adapter assembly 21850 to the housing assembly, the springs 21860, 21862 can bias the adapter assembly 21850 away from the receiving area.

The springs 21860, 21862 therefore provide a mechanism of ensuring that the adapter assembly 21850 is properly coupled to the handle housing before the adapter assembly 21850 is utilized in a surgical procedure. For example, should the flange features 21024*a-e* not completely or properly couple to the flange features 21022*a-e*, therefore signifying that the shaft assembly 21850 is not properly coupled to the handle assembly, the springs 21860, 21862 can force the shaft assembly 21850 away of the receiving area. The springs 21860, 21862 therefore require that both a threshold force be applied to the adapter assembly 21850 to overcome the spring bias of the springs 21860, 21862, as well as also requires that the adapter assembly 21850 be properly coupled to the handle assembly, otherwise the springs 21860, 21862 will force the adapter assembly 21850 away from the handle assembly.

Referring now to FIG. 222, a housing 29000 and adapter 29002 are provided, in accordance with at least one aspect of the present disclosure. In various embodiments, the housing 29000 and the adapter 29002 can substantially similar to housing assembly 21000 and adapter 21000 where like numbers are utilized to denote like features.

In various embodiments, the recessed receiving area 21008 of the housing assembly 29000 can include a compliant material 29010 disposed therein. In some embodiments, the compliant material 29010 can be positioned within the recessed receiving area 21008 such that the compliant material 29010 does not longitudinally overlap components of the housing assembly 29000 that interface with components of the adapter 29002, such as the contacts 21020*a*, 21020*b*, the electrical output connector 21026, the rotatable drive shafts 21012*a*, 21012*b*, 21012*c*, etc. Stated another way, the compliant material 29010 can occupy free space within the receiving area 21008 so as to take up any much surface area as possible without interfering in the adapters 29002 ability to properly couple to the housing 29000 and properly function.

In various embodiments, the compliant material 29010 can comprise a compliant foam. In some embodiments, the compliant material 29010 can comprise a compliant rubber. In some embodiments, the compliant material 29010 can comprise a compliant lattice frame material. In one aspect, the compliant material 29010 is positioned within the receiving area 21008 such that, as the drive coupling assembly 21010 is moved into the receiving area 21008 to couple the adapter 29002 to the housing 29000, as described elsewhere herein, the compliant material 29010 can be deformed and resist the drive coupling assembly 21010 from moving proximally toward the latched orientation with the housing 29000.

For example, referring to FIG. 223, as the drive coupling assembly 21010 is moved toward the receiving area 21008 to latch the adapter 29002 to the housing 29000, the compliant material 29010 can be depressed by the drive coupling assembly 21010 and apply a resistive force to the drive coupling assembly 21010. The compliant material 29010 can be compressed by the drive coupling assembly 21010 as the flanges 21022*a-e* are moved towards the flanges 21024*a-e*, for example. In instances where the drive coupling assembly 21010 is not moved a sufficient amount relative to the housing such that the flanges 21022*a-e* engage flanges 21024*a-e* to couple the adapter 29002 to the housing 29000, the compliant material 29010 can expand and bias the drive coupling assembly 21010 away from the housing 29000. In one aspect, a user can need to apply a threshold force to the adapter 29002 so as to overcome the resistive force of the compliant material 29010 and compress the compliant material 29010 a sufficient amount, such as is shown in FIG. 224, in order to bring the flanges 21022*a-e* into operative engagement with the flanges 21204*a-e* to couple the adapter 29002 to the housing 29000. With the flanges 21022*a-e* in operative engagement with the flanges 21204*a-e*, the compliant material 29010 can be held compressed by the drive coupling assembly 21010, as shown in FIG. 223.

The above-provided compliant material 29010 can provide a means of ensuring that the adapter 29002 is properly coupled to the housing 29000 before the adapter 29002 is utilized in a surgical procedure. For example, should the flange features 21024*a-e* not completely or properly couple to the flange features 21022*a-e*, therefore signifying that the adapter 29002 is not properly coupled to the housing 29000, the compliant material 29010 can force the adapter 29002 away from the housing 29000. The compliant material 29010 therefore requires that a threshold force be applied to the adapter 29002 to overcome the compliant material 29010 resistive bias, otherwise the compliant material will force the adapter 29002 away from housing 29000.

It should be understood any of the foregoing embodiments can be utilized in connection with one another so that a user would be capable of detecting irregularities and incomplete connections at various positions throughout the surgical instrument. For example, a surgical instrument could include a detector assembly of determining if an adapter is properly coupled to a handle assembly, a detector assembly for determining if a shaft assembly is properly connected to a loading unit, and a detector assembly for determining if an end effector and/or cartridge is properly coupled to the surgical instrument. Each of the detection assemblies can include their own dedicated electrical arrangement and be coupled to the control circuit positioned within the handle assembly such that the control circuit can identify the position of the incomplete connection within the surgical instrument. In an instance where the control circuit identifies an incomplete connection within the surgical instrument using any of the foregoing mechanisms disclosed herein, the control circuit can provide feedback to user indicative of the location of the incomplete connection. For example, the control circuit can cause a display to display a location of the incomplete connection detected by any of the foregoing mechanisms disclosed herein.

According to some non-limiting aspects of the present disclosure, surgical instruments can include handle assemblies that are configured to accommodate a variety of interchangeable tools, such as end effectors and/or single-use loading units (SLUs), among others. As such, the surgical instruments disclosed herein can provide increased versatility and, thus, value for implementing clinicians. However, not all surgical instruments and end effectors are configured to operate in the same way. For example, according to one non-limiting aspect of the present disclosure, a surgical instrument can employ a rotational transmission of power and an interchangeable tool (e.g., an end effector) can be configured for linear actuation. The surgical instrument configured to employ a rotational transmission of power would thus be incompatible with the linear driven end effector and, thus, its versatility and value would be diminished.

Certain surgical instruments are known to address the aforementioned incompatibilities, such as the surgical instrument described in U.S. Pat. No. 10,603,128, entitled HANDHELD ELECTROMECHANICAL SURGICAL SYSTEM, granted Mar. 31, 2020, the disclosure of which is hereby incorporated by reference in its entirety. Such surgical instruments utilize a specifically configured outer shell housing, which includes one or more interfacing components configured to selectively transfer rotational forces from motors of the surgical instrument to an adaptor of a connected end effector. Although the outer shell houses the aforementioned components, it must inherently encompass the surgical instrument to effectively interface the surgical instrument with any interchangeable tool, thereby facilitating the enhanced versatility of the surgical instrument. The outer shell housing is of increased importance due to the sterilization requirements of operating rooms that the surgical instruments are typically used in.

It is axiomatic that strict sterilization of the operating room and surgical equipment is required during any surgery. The strict hygiene and sterilization conditions required in an operating room necessitate the highest possible sterility of all medical devices and equipment. Part of that sterilization process is the need to sterilize anything that comes in contact with the patient or penetrates the sterile field, such as the surgical instrument, including its end effector, adapter assembly, and requisite components. Aside from the aforementioned adapter assemblies being configured to transfer rotational forces from motors of the surgical instrument to an adaptor of a connected end effector, the outer shell of such adapter assemblies can be configured to prevent contaminants from adversely effecting the sterile barrier.

However, the handheld devices encased in the outer housing often include a power pack, a motor assembly, and/or a control assembly among other electromechanical subassemblies. Each of these subassemblies can generate energy (e.g., thermal, vibrational, acoustic) that can adversely effect the environment the surgical instrument is expected to function in. These environments are contained when the handheld surgical device is encased within the outer housing, especially since the outer housing is typically configured to create a sterile barrier between the operating room and the handheld surgical device. Thus, although encasing a handheld surgical device can enhance versatility and sterility, it can also result in instrument failure, decreased life, and/or hazardous operating conditions. Accordingly, the surgical instruments disclosed herein are specifically configured to accommodate adaptors of a wide variety of interchangeable tools while responsibly managing the environmental conditions in which the surgical instrument is expected to function. As such, the disclosed surgical instruments are versatile, longer lasting, and more reliable than existing surgical instruments.

Referring now to FIG. 225, a perspective view of a surgical instrument 6000 that includes an adapter assembly 6001 configured to create a sterile barrier around a handheld surgical device with energy management components 6010, 6012, 6014 is depicted in accordance with at least one non-limiting aspect of the present disclosure. According to the non-limiting aspect of FIG. 225, the adapter assembly 6001 can include a proximal portion 6002 and a distal portion 6004 connected in a clamshell configuration via a hinge 6007. Collectively, the proximal portion 6002 and the distal portion 6004 can constitute an outer shell or housing that defines an internal cavity configured to encase a handheld device that can generate energy when the surgical instrument is in use. Accordingly, the adapter assembly 6001 is configured to transition from an open configuration, wherein the hinge 6007 is open and the sterile barrier is disrupted, to a closed configuration, as seen in FIG. 232, wherein the hinge 6206 is closed and the sterile barrier is established. The proximal portion 6202 can include a handle portion 6203 configured for the ergonomic handling of the surgical instrument when the handheld device is installed within the adapter assembly 6200. As also can be seen in FIG. 232, the proximal portion 6202 and distal portion 6204 of the adapter assembly 6200 can each include energy management components 6210, 6212 configured to effectively manage energy created by a handheld device when installed within an internal cavity 6209 of the adapter assembly 6200.

Still referring to FIG. 225, the adapter assembly 6001 of the surgical instrument 6000 can be configured to accommodate a variety of interchangeable shaft assemblies 6006 and end effectors 6008. In other words, the surgical instrument 6000 is configured for selective attachment thereto of a plurality of different end effectors 6008 that are each configured for actuation and manipulation by the powered handheld electromechanical surgical instrument 6000. As such, the adapter assembly 6001 can include a drive assembly configured to engage with a drive assembly of a handheld device encased within the internal cavity of the adapter assembly 6001. Likewise, the adapter assembly 6001 can include external buttons 6009 configured to engage with buttons of the handheld device encased within, while preserving the sterile barrier. Additionally, the drive assembly can be mechanically configured to translate forces generated by the drive assembly of the handheld assembly to the drive assembly of the interchangeable shaft and/or end effector. The drive assembly of the handheld device can include one or more motors that can generate energy (e.g., thermal, vibrational, and acoustic) when the surgical instrument 6000 is in use. However, because the adapter assembly 6001 is also configured to establish a sterile barrier around the handheld device, the dissipated energy can be trapped. Accordingly, the energy management components 6010, 6012, 6014 can assist in the effective management and dissipation of energy dissipated by the handheld device.

Referring now to FIG. 226, a sectioned perspective view of a handheld device 6016 configured to be encased within the adapter assembly 6001 of the surgical instrument 6000 of FIG. 225 is depicted in accordance with at least one aspect of the present disclosure. According to the non-limiting aspect of FIG. 226, the handheld device can further include energy management components 6018, 6019, 6020, 6022, 6024. Additionally, FIG. 226 a plurality of interface components 6026 of the drive assembly of the handheld device 6016 can be dispositioned on a forward-facing surface of the handheld device 6016. The interface components 6026 can mechanically engage corresponding interface components of the adapter assembly 6001 (FIG. 225) such that activation of the drive assembly of the handheld device 6016 can translate forces to the interchangeable shaft assembly 6006 (FIG. 225) and end effector 6008 (FIG. 225). It shall be appreciated that, through the use of the adapter assembly 6001 and the plurality of interface components 6026, the handheld device 6016 can be reused with versatility. Additionally, the handheld device 6016 can include a plurality of function buttons 6028, which can be configured to engage the external buttons 6009 (FIG. 225) of the adapter assembly 6001 (FIG. 225), such that a user can activate them without disrupting the sterile barrier.

Referring now to FIGS. 227 and 228, perspective views of the adapter assembly 6001 and handheld device 6016 of the surgical instrument 6000 of FIG. 225 are depicted in accordance with at least one aspect of the present disclosure. According to the non-limiting aspect of FIG. 227, the relative size of the handheld device 6016 can be specifically configured such that it can be encased within an internal cavity of the adapter assembly 6001. It shall be appreciated that geometrical energy management components 6012, 6038, 6040, 6042 of the adapter assembly 6001 can mechanically engage corresponding energy management components 6018, 6019, 6022, 6024 of the handheld device 6016 when the handheld device 6016 is properly installed within the internal cavity of the adapter assembly 6001. Accordingly, energy dissipated by the handheld device 6016 can be effectively managed by the mechanical engagement of the energy management components 6012, 6038, 6040, 6042 of the adapter assembly 6001 and the corresponding energy management components 6018, 6019, 6022, 6024 of the handheld device 6016. In the non-limiting aspect of FIG. 227, the hinge 6007 of the adapter assembly 6001 can be positioned in a closed configuration, thereby establishing a sterile barrier between the ambient environment of the operating room in which it is used and an internal cavity configured to encase the handheld device 6016.

According to the non-limiting aspect of FIG. 228, the hinge 6007 of the adapter assembly 6001 can be positioned in an open configuration, exposing the internal cavity 6011 such that the handheld device 6016 can be properly installed. Additional features such as corresponding male 6034 and female 6036 components of a clasping lock can be included to enhance the sterile barrier, thereby fortifying the adapter assembly 6001 from being inadvertently opened and exposed to the non-sterile environment. Once again, it is evident how the energy management components 6012, 6038, 6040, 6042 (FIG. 227) of the adapter assembly 6001 can be configured to engage the corresponding energy management components 6018, 6019 (FIG. 226), 6022 (FIG. 226), 6024 (FIG. 226) of the handheld device 6016 upon proper installation. The energy management systems and components will be further discussed in detail. However, it shall be appreciated that the non-limiting aspect of FIGS. 225-228 are only presented for illustrative purposes. Accordingly, other non-limiting aspects contemplated by the present disclosure include any number of the following energy management components and systems in any combination, to accomplish a desired means of energy management when the surgical instrument is in use.

Referring now to FIG. 229, a perspective front view of the adapter assembly 6100 of FIG. 229 is depicted in accordance with at least one non-limiting aspect of the present disclosure. According to the non-limiting aspect of FIG. 229, the adapter assembly 6100 can include a proximal portion 6102 and a distal portion 6104 connected in a clamshell configuration via a hinge 6106. Collectively, the proximal portion 6102 and the distal portion 6104 can constitute an outer shell or housing configured to encase a handheld device including one or more motors 6112. The proximal portion 6102 can include a handle portion 6103 configured for ergonomic handling of the surgical instrument when the handheld device is installed within the adapter assembly 6100. As can be seen in FIG. 229, the proximal portion 6102 and distal portion 6104 of the adapter assembly 6100 can each include energy management components 6108, 6114 configured to effectively manage energy created by a handheld device when installed within an internal cavity 6109 of the adapter assembly 6100.

In further reference to FIG. 229, the proximal portion 6102 of the adapter assembly 6100 can be dimensionally configured to accommodate one or more motors 6112 of the handheld device. As previously discussed, the adapter assembly 6100 can be configured as a sterile barrier that can protect the handheld device from the non-sterile environment of the operating room. Thus, the adapter assembly 6100 of FIG. 229 can be structurally sealed, thereby capable of preventing contaminants from the operating environment from accessing an internal cavity 6109 of the adaptor assembly 6100 and, thus, preventing the reuse of the handheld device stored within. However, the one or more motors 6112 of the handheld device can produce energy (e.g., thermal, vibration, acoustical) when the surgical instrument is in use. Because the adapter assembly 6100 of FIG. 229 can be structurally sealed, it not only prevents contaminants from accessing the internal cavity 6109, but it also prevents energy (e.g., thermal, vibration, acoustical) that is generated during use from escaping the internal cavity 6109. Accordingly, the adapter assembly 6100 can include several energy management components 6108, 6114 to assist the release of energy (e.g., thermal, vibration, acoustical) from the internal cavity 6109.

Still referring to FIG. 229, the adapter assembly 6100 can include a first heat sink 6108 on the distal portion 6104. The first heat sink 6108 can be configured to remove thermal energy dissipated by the one or more motors 6112 from the internal cavity 6109 of the adapter assembly 6100. The first heat sink 6108 can be configured to mechanically contact thermally conductive channels 6114, which include a surface area within the internal cavity 6109. For example, the first heat sink 6108 can be configured to mechanically engage a thermally conductive channel 6114 when the distal portion 6104 engages the proximal portion 6102 of the adapter assembly 6100, thereby creating a sterile barrier. However, because the first heat sink 6108 remains in thermal communication with the internal cavity 6109 via the thermally conductive channel 6114, the first heat sink 6108 can still remove dissipated thermal energy dissipated in the internal cavity 6109 of the adapter assembly 6100. Thus, even though contaminants cannot enter the internal cavity 6109 of the adapter assembly 6100, thermal energy can escape the internal cavity 6109 of the adapter assembly 6100. In the non-limiting aspect of FIG. 229, the thermally conductive channel 6114 can include an external heat sink, which supplements the heat transfer capabilities of the first heat sink 6108.

In some non-limiting aspects, the adapter assembly 6100 of FIG. 229 can include thermally conductive channels 6114 that can be placed in mechanical contact with the 6112 motors themselves, thereby improving the thermally conductive path from the energy source and enhancing the efficiency of the thermally conductive channel 6114. According to such aspects, the thermally conductive channel 6114 can eliminate the radiative means of heat transfer and can provide a more efficient, conductive path to the first heat sink 6108. Alternatively and/or additionally, the thermally conductive channel 6114 can be placed in mechanical contact with a specifically configured surface area within the internal cavity 6109. For example, a portion of an inner wall of the internal cavity 6109 can be configured as part of the thermally conductive channel 6114. Since the efficiency of the thermally conductive channel 6114 can improve as the surface area increases, this can enhance the removal of thermal energy from the internal cavity 6109. Accordingly, the radiative means of heat transfer can be inherently more efficient due to the increased surface area. Although the non-limiting aspect of FIG. 229 includes a first and second heat sink 6108, 6110 (FIG. 225), it shall be appreciated that the present disclosure contemplates other non-limiting aspects wherein any number of heat sinks, channels, and baffles are used to establish similar paths by which generated thermal energy can escape the internal cavity 6109.

Referring now to FIG. 230, a perspective view of the back of the adapter assembly 6100 of FIG. 229 is depicted in accordance with at least one non-limiting aspect of the present disclosure. According to the non-limiting aspect of FIG. 230, the adapter assembly 6100 can further include a second heat sink 6110 coupled to the proximal portion 6102, in close proximity to the one or more motors 6112. The second heat sink 6110 can also be coupled to a thermally conductive channel, thereby enabling it to remove thermal energy produced by the one or more motors 6112 from the internal cavity 6109 without disturbing the sterile barrier created by adapter assembly 6100. In other non-limiting aspects, the second heat sink 6110 can be directly coupled to the one or more motors 6112, which can provide a more efficient, conductive path to the second heat sink 6110. Although the non-limiting aspect of FIGS. 229 and 230 depict a first heat sink 6108 and a second sink 6110 that are passive and include a plurality of integrally formed fins, the present disclosure contemplates other non-limiting aspects wherein any number of heat sink configurations can be implemented to enhance energy management within the adapter assembly 6100. For example, the adapter assembly 6100 can include active heat sinks, stamped heat sinks, bonded-formed heat sinks, and/or the like.

Referring now to FIGS. 231A and 231B, a sectioned front view of a handheld surgical device installed in the adapter assembly of FIGS. 229 and 230 is depicted in accordance with at least one non-limiting aspect of the present disclosure. According to the non-limiting aspect of FIG. 231A, the adapter assembly 6100 of FIGS. 229 and 230 is shown in more detail. Specifically, the thermally conductive channels 6114 are clearly depicted as defining a thermal path from the internal cavity 6109 to the exterior of the adapter assembly 6100. Accordingly, the thermally conductive channels 6114 enable the adapter assembly 6100 to preserve the sterile barrier, thereby protecting the contents of its internal cavity 6109 from external contamination. FIG. 231A also depicts the handheld device 6116, including three motors 6112, although other non-limiting aspects include handheld devices 6116 with any number of motors. Two conductive contacts 6118 are also depicted as configured to mechanically contact each of the three motors 6112. The conductive contacts 6118 are likewise configured to mechanically contact the thermally conductive channels 6114 when the handheld device 6116 is properly installed within the internal cavity 6109 of the adapter assembly 6100.

According to the non-limiting aspect of FIG. 231B, the handheld device 6116 has been properly installed within the internal cavity 6109 of the adapter assembly 6100. The conductive contacts 6118 of the handheld device 6116 can be in mechanical contact with the thermally conductive channels 6114, establishing a direct conductive path from the motors 6112 to an exterior of the adapter assembly 6100. When the surgical instrument is in use and the motors 6112 are generating thermal energy, the resulting thermal energy can travel through the conductive contacts 6118 into the thermally conductive channels 6114 and into the fins of the external heat sinks, where it can be safely convected away from the surgical instrument and into the operating room. Accordingly, generated thermal energy will not remain within the internal cavity 6109 of the adapter assembly 6100, and the surgical instrument will be at less of a risk of overheating, and thus, the damage and/or dangers associated with overheating.

Referring now to FIG. 232, a sectioned side view of an adapter assembly 6200 that includes energy management components 6210, 6212 is depicted in accordance with at least one non-limiting aspect of the present disclosure. According to the non-limiting aspect of FIG. 232, the adapter assembly 6200 can include a proximal portion 6202 and a distal portion 6204 connected in a clamshell configuration via a hinge 6206. Collectively, the proximal portion 6202 and the distal portion 6204 can constitute an outer shell or housing that defines an internal cavity 6209 configured to encase a handheld device that can generate energy when the surgical instrument is in use. Accordingly, the adapter assembly 6200 is configured to transition from an open configuration, wherein the hinge 6206 is open and the sterile barrier is disrupted, to a closed configuration, wherein the hinge 6206 is closed and the sterile barrier is established. The proximal portion 6202 can include a handle portion 6203 configured for the ergonomic handling of the surgical instrument when the handheld device is installed within the adapter assembly 6200. As can be seen in FIG. 232, the proximal portion 6202 and distal portion 6204 of the adapter assembly 6200 can each include energy management components 6210, 6212 configured to effectively manage energy created by a handheld device when installed within an internal cavity 6209 of the adapter assembly 6200.

Still referring to FIG. 232, the adapter assembly 6200 can include a pivoting contact 6210 on the proximal portion 6202. The pivoting contact 6210 can be configured to mechanically contact a thermally conductive surface area 6212 dispositioned on the distal portion 6204 of the adapter assembly 6200 when the clamshell outer housing is closed. Accordingly, the pivoting contact 6210 and thermally conductive surface area 6212 can establish a thermally conductive path when the clamshell outer housing is closed, wherein the thermally conductive path is configured to remove thermal energy generated from the internal cavity 6209 of the adapter assembly 6200. The pivoting contact 6210 can be pivotally coupled to the proximal portion 6202 of the adapter assembly 6200 and therefore, configured to optimize mechanical contact with the thermally conductive surface area 6212. For example, the thermally conductive path can be improved based on the degree of contact established between the pivoting contact 6210 and the thermally conductive surface area 6212. As previously discussed, the hinge 6206 facilitates motion between the proximal portion 6202 and distal portion 6204 as the adapter assembly 6200 transitions from the open configuration to the closed configuration. The pivoting contact 6210 can be pivotally coupled to the proximal portion 6202 such that it can accommodate for mechanical perturbations and misalignments when the adapter assembly 6200 is in a closed configuration. Therefore, the pivoting contact 6210 can ensure that proper mechanical contact is established with the thermally conductive surface area 6212 when the adapter assembly 6200 is closed and the sterile barrier is established. Because the pivoting contact 6210 can remain in thermal communication with the thermally conductive surface area 6212, a thermal path is established by which thermal energy can be removed from the internal cavity 6209 of the adapter assembly 6200. Thus, even though contaminants cannot enter the internal cavity 6209 of the adapter assembly 6200, thermal energy can escape the internal cavity 6209 of the adapter assembly 6200 via the pivoting contact of 6210.

According to the non-limiting aspect of FIG. 232, the thermally conductive surface area 6212 can facilitate a convection of the thermal energy from the internal cavity 6209 to the environment of the operating room. Thus, thermal energy can be convected out of the internal cavity 6209 and away from the adapter assembly 6200. Although the non-limiting aspect of FIG. 232 depicts a pivoting contact 6210 with a flat surface area, it shall be appreciated that in other non-limiting aspects, the thermally conductive surface area 6212 can include any number of additional geometric components configured to enhance the amount of heat convected off and away from the adapter assembly 6200. For example, according to some non-limiting aspects, the thermally conductive surface area 6212 further includes a heat sink. Additionally and/or alternatively, the adapter assembly 6200 can include additional heat mitigation channels, baffles, etc., to supplement the removal of thermal energy from the internal cavity 6209.

Referring now to FIG. 233 a sectioned side view of a surgical instrument 6300 that includes energy management components 6308, 6310 is depicted in accordance with at least one non-limiting aspect of the present disclosure. According to the non-limiting aspect of FIG. 233, the surgical instrument 6300 can include an adapter assembly 6302 configured to encase a handheld device 6304. The handheld device 6304 can include a motor 6306, which, when in operation, can produce energy. For example, the motor 6306 can produce thermal energy, which can heat up an internal cavity of the adapter assembly 6302. Accordingly, the surgical instrument 6300 can further include a control circuit 6309 coupled to energy management components 6308, 6310 configured to manage the thermal energy produced by the motor 6306.

In further reference to FIG. 233, the surgical device 6300 can include a temperature sensor 6308 configured to generate a signal associated with a temperature of the handheld device 6304 and an piezoelectric oscillating fan 6310. As previously discussed, temperature detection is part of preventative reliability. For example, the surgical instrument could risk overheating since the handheld device 6304—and specifically, the motor 6306—are encased within the sterile barrier established by the adapter assembly 6302. Although this risk can arise from specific external factors, such as a harsh operating environment, the non-limiting aspect of FIG. 233 is configured to monitor the self-heating of electronics within the adapter assembly 6302. By detecting when overheating occurs, the surgical instrument 6300—or an operating clinician—can take preventative action. Accordingly, the temperature sensor 6308 can be specifically configured to function over the expected operating temperature range for the surgical instrument, including a conservative factor of safety.

Still referring to FIG. 233, the temperature sensor 6308 (e.g., a thermocouple, a thermistor, a resistance temperature detector, a semiconductor-based sensor) can generate a signal associated with a temperature of the handheld device 6304. The surgical instrument can further include a control circuit 6309 coupled to the temperature sensor 6308 and configured to receive the signal and determine a temperature of the handheld device 6304 based, at least in part, on the signal generated by the temperature sensor 6308. The control circuit 6309 can also be coupled to a power source 6311 and the piezoelectric oscillating fan 6310. According to some non-limiting aspects, the control circuit 6309 can be positioned within the surgical instrument 6300 itself. Alternatively, the control circuit 6309 can be positioned within the adapter assembly 6302 or a hub to which the surgical instrument 6300 is connected. Regardless of the specific configuration, it shall be appreciated that the temperature sensor 6308 can be implemented with the control circuit 6309 to monitor the temperature of the motor 6306, the handheld device 6304, the adapter assembly 6302, or any other aspect of the surgical instrument 6300 depicted in FIG. 233.

The surgical instrument 6300 of FIG. 233 further includes a piezoelectric oscillating fan 6310 coupled to the control circuit 6309, wherein the piezoelectric oscillating fan 6310 is configured to alter the temperature within the handheld device 6304. For example, if the control circuit 6309 receives a signal from the temperature sensor 6308 and determines that the temperature within the handheld device 6304 has exceeded a predetermined threshold, the control circuit can direct power from the power source 6311 to the piezoelectric oscillating fan 6310, which is configured to lower the temperature within the handheld device 6304 when powered on. Alternatively, the control circuit 6309 can be configured to automatically activate the piezoelectric oscillating fan 6310 whenever the motor 6306 is activated, and to attenuate an operating mode of the piezoelectric oscillating fan 6310 when the temperature exceeds a predetermined threshold. Although the non-limiting aspect of FIG. 233 depicts a piezoelectric oscillating fan 6310, the present disclosure contemplates other non-limiting aspects wherein the surgical instrument utilizes any number of components configured to alter the temperature within the adapter assembly 6302 (e.g., electric fans, cooling plates, heat pipes, synthetic jet air components, electrostatic fluid accelerators). Regardless of the specific combination or method of operation, it shall be appreciated that the combination of the temperature sensor 6308, the control circuit 6309, the power source 6311, and the piezoelectric oscillating fan 6310 can be implemented to manage energy within the adapter assembly 6302, as it is produced by the motor 6306 of the handheld device 6304.

Referring now to FIGS. 234A and 234B, sectioned top views of the surgical instrument 6300 of FIG. 233 are depicted in accordance with at least one non-limiting aspect of the present disclosure. According to the non-limiting aspect of FIGS. 234A and 234B, the adapter assembly 6302 of the surgical device 6300 can include two piezoelectric oscillating fans 6310, which are specifically oriented to be inserted into two corresponding electrical contacts 6312 of the handheld device 6304. When the handheld device 6304 is installed into the adapter assembly 6302, as is depicted in FIG. 234B, the piezoelectric oscillating fans 6310 are received by the electrical contacts 6312 of the handheld device 6304, as is depicted in FIG. 234B. Accordingly, the piezoelectric oscillating fans 6310 are placed in electrical contact with the power source 6311 and/or the control circuit 6309, as depicted in FIG. 233. When the handheld device 6304 is installed in the adapter assembly 6302, the piezoelectric oscillating fans 6310 are further positioned within an inner housing of the handheld device 6304 and thus, can cool the motors 6306 and, generally, the entire interior cavity of the handheld device 6304. As such, the piezoelectric oscillating fans 6310 of FIG. 234B can be activated, receive signals from the temperature sensor 6308 (FIG. 233) and, subsequently, alter an operating temperature of the handheld device 6304 and its components.

Referring now to FIGS. 235A and 235B, top views of an energy management component 6310 of the adapter assembly 6302 of FIGS. 233 and 234 are depicted in accordance with at least one aspect of the present disclosure. According to the non-limiting aspect of FIGS. 235A and 235B, the piezoelectric oscillating fans 6310 can include electrical contacts 6314 that correspond to the electrical contacts 6312 of the handheld device 6304. In the non-limiting aspect of FIG. 235A, the piezoelectric oscillating fans 6310 are deactivated. In other words, the electrical contacts 6314 of the piezoelectric oscillating fans 6310 do not have access to the power source 6311 (FIG. 233). The power source 6311 (FIG. 233) is either turned off or the handheld device 6304 is not properly installed within the adaptor assembly 6302, as is depicted in FIG. 234A. However, in the non-limiting aspect of FIG. 235B, electrical contacts 6314 are energized and the piezoelectric oscillating fans 6310 are oscillating and, therefore, cooling the handheld device 6304 and its internal components (e.g., motors 6306, power source 6311, temperature sensor 6308, and/or control circuit 6309, depicted in FIG. 233). The configuration of FIG. 235B provides an example of the piezoelectric oscillating fans 6310 depicted in FIG. 234B.

Referring now to FIG. 236, a chart depicting a variable rate of energy management implemented by the surgical instrument 6300 of FIGS. 233-235 is depicted, in accordance with at least one non-limiting aspect of the present disclosure. According to the non-limiting aspect of FIG. 233, the piezoelectric oscillating fans 6310 (FIGS. 233-235) can be configured to oscillate at a variable rate, depending on the temperature detected by the temperature sensor 6308 (FIG. 233). For example, the control circuit 6309 (FIG. 233) can activate a first piezoelectric oscillating fan 6310 when the temperature sensor 6308 (FIG. 233) detects an operating temperature of the handheld device 6304 (FIGS. 233 and 234) has exceeded a first temperature threshold $T_{hot}$. However, if the temperature does not decrease and instead, continues to exceed a second temperature threshold $T_{max}$, the control circuit 6309 (FIG. 233) can activate a second piezoelectric oscillating fan 6310. According to the non-limiting aspect of FIG. 236, the activation of the second piezoelectric oscillating fan 6310 begins to reduce the operating temperature of the handheld device 6304 (FIGS. 233 and 234). Accordingly, the chart of FIG. 236 illustrates a step function indicating a step that correlates to the activation of each piezoelectric oscillating fan 6310, as well as a steady increase and subsequent decrease in the operating temperature of the handheld device 6304 (FIGS. 233 and 234) from $T_{hot}$ to $T_{max}$ and down once again. The reserve of resources based on the sensed operating temperature of the handheld device 6304 (FIGS. 233 and 234) can result in a more efficient surgical instrument that conserves power and thus, provides an extended life while retaining the energy management benefits discussed in association with FIGS. 233-235.

Referring now to FIG. 237, a sectioned side view of a surgical instrument including a handheld surgical device 6404 and an adapter assembly 6400 that includes energy management components 6408, 6410, 6414 is depicted in accordance with at least one non-limiting aspect of the present disclosure. According to the non-limiting aspect of FIG. 237, the adapter assembly 6400 can include proximal portion 6402 and a distal portion 6403 connected in a clamshell configuration via a hinge 6406. Collectively, the proximal portion 6402 and the distal portion 6403 can constitute an outer shell or housing that defines an internal cavity 6409 configured to encase a handheld device 6404 with a motor 6412 that can generate energy when the surgical instrument is in use. Accordingly, the adapter assembly 6400 can be configured to transition from an open configuration—wherein the hinge 6206 is open and the sterile barrier is disrupted—to a closed configuration, wherein the hinge 6406 is closed and the sterile barrier is established. Collectively, the proximal portion 6402 and the distal portion 6403 can define a handle portion configured for the ergonomic handling of the surgical instrument when the handheld device 6404 is installed within the adapter assembly 6400. As can be seen in FIG. 237, the proximal portion 6402 and the distal portion 6403 of the adapter assembly 6400 can each include energy management components 6408, 6410, 6414 configured to effectively manage energy created by a the motor 6412 when the handheld device 6404 is installed within an internal cavity 6409 of the adapter assembly 6400.

Still referring to FIG. 237, the adapter assembly 6400 can include a heat sink assembly including an external heat sink 6408 and an internal heat sink 6410 positioned within the internal cavity 6409 of the adapter assembly 6400. According to the non-limiting aspect of FIG. 237, the external heat sink 6408 is positioned on an external surface of the distal portion 6403 of the adapter assembly 6400 and is configured to convect thermal energy produced by the motor 6412 away from the adapter assembly 6400. In some non-limiting aspect, the external heat sink can include a plurality of fins configured to expand the surface area off of which thermal energy can be convected. The internal heat sink 6410 can be positioned within the proximal portion 6402 of the adapter assembly 6400 and configured to mechanically contact a motor 6412 of the handheld device 6404, thereby creating a conductive thermal path for thermal energy to be routed off of—and away from—the motor 6412. A second internal heat sink 6414 can be positioned within the distal portion 6403 of the adapter assembly 6400 and configured to mechanically contact the external heat sink 6408 while preserving the sterile barrier formed by the adapter assembly 6400. According to the non-limiting aspect of FIG. 237, the external heat sink 6408 can include an internal portion 6414 configured to traverse inside the internal cavity 6409 of the adapter assembly 6400 while maintaining the sterile barrier when the adapter assembly 6400 is in its closed configuration. The internal portion 6414 of the external heat sink 6408 can be further configured to mechanically contact a compressible, conductive material 6416. The compressible, conductive material 6416 can be configured to interface the internal heat sink 6410 and the internal portion 6414 of the external heat sink 6408 when the hinge 6406 is closed, thereby extending the thermally conductive path from the motor 6412 to the external heat sink 6408, where it can be convected away from the surgical instrument. Accordingly, when the hinge 6406 is closed and the surgical instrument is being used by a clinician, the heat sink assembly can transfer thermal energy generated by the motor 6412 away from the internal cavity 6409.

Referring now to FIG. 238, the compressible, conductive material 6416 of FIG. 237 is depicted in accordance with at least one non-limiting aspect of the present disclosure. According to the non-limiting aspect of FIG. 238, the compressible, conductive material 6416 can be configured to compress, thereby establishing an interference fit between the internal heat sink 6410 and the internal portion 6414 of the external heat sink 6408. According to the non-limiting aspect of FIG. 237, the compressible, conductive material 6416 can improve the conductive efficiency between the internal heat sink 6410 and the internal portion 6414 of the external heat sink 6408. For example, the compressible, conductive material 6416 can include a metal mesh (e.g., scouring, sponge, type material) or a thermally conductive elastomer, among others. The compressible, conductive material 6416 of FIG. 238 can be configured to compress around imperfections, thereby filling discontinuities in the collective, conductive thermal path established by the internal heat sink 6410 and the internal portion 6414 of the external heat sink 6408. Accordingly, the compressible, conductive material 6416 can account for thermal and dimensional tolerances.

Referring now to FIG. 239, a sectioned side view of a surgical instrument including a handheld surgical device 6504 and an adapter assembly 6500 that includes energy management components 6508, 6510, 6514, 6516 is depicted in accordance with at least one non-limiting aspect of the present disclosure. According to the non-limiting aspect of FIG. 239, the adapter assembly 6500 can include proximal portion 6502 and a distal portion 6503 connected in a clamshell configuration via a hinge 6506. Collectively, the proximal portion 6502 and the distal portion 6503 can constitute an outer shell or housing that defines an internal cavity 6509 configured to encase a handheld device 6504 that can generate energy when the surgical instrument is in use. Accordingly, the adapter assembly 6500 is configured to transition from an open configuration, wherein the hinge 6206 is open and the sterile barrier is disrupted, to a closed configuration, wherein the hinge 6506 is closed and the sterile barrier is established. Collectively, the proximal portion 6502 and the distal portion 6503 can define a handle portion configured for the ergonomic handling of the surgical instrument when the handheld device 6504 is installed within the adapter assembly 6500. As can be seen in FIG. 239, the proximal portion 6502 and distal portion 6503 of the adapter assembly 6500 can each include energy management components 6508, 6510, 6514, 6516 configured to effectively manage energy created by a handheld device when installed within an internal cavity 6509 of the adapter assembly 6500.

Still referring to FIG. 239, the adapter assembly 6500 can include a heat sink assembly including an external heat sink 6508 and several internal heat sinks 6510, 6514 positioned within the internal cavity 6509 of the adapter assembly 6500. According to the non-limiting aspect of FIG. 239, the external heat sink 6508 is positioned on an external surface of the distal portion 6503 of the adapter assembly 6500 and is configured to convect thermal energy produced by the motor 6512 away from the surgical instrument 6500. In some non-limiting aspect, the external heat sink can include a plurality of fins configured to expand the surface area off of which thermal energy can be convected. A first internal heat sink 6510 can be positioned within the proximal portion 6502 of the adapter assembly 6500 and configured to mechanically contact a motor 6512 of the handheld device 6504, thereby creating a conductive thermal path for thermal energy to be routed off of—and away from—the motor 6512. A second internal heat sink 6514 can be positioned within the distal portion 6503 of the adapter assembly 6500 and configured to mechanically contact the external heat sink 6508 while preserving the sterile barrier formed by the adapter assembly 6500. The second internal heat sink 6514 can be further configured to mechanically contact with the first heat sink 6510 when the hinge 6506 is closed, thereby extending the thermally conductive path from the motor 6512 to the external heat sink 6508. Accordingly, when the hinge 6506 is closed and the surgical instrument is being used by a clinician, the heat sink assembly can transfer thermal energy generated by the motor 6512 away from the internal cavity 6509. The non-limiting aspect of FIG. 239 is notably depicted in an open configuration, and thus, the second heat sink 6514 is not depicted in mechanical contact with the first heat sink 6510.

In further reference to FIG. 239, the heat sink assembly can further include a thermal paste 6516 (e.g., thermal compound, grease) configured to interface the first internal heat sink 6510 and the second internal heat sink 6514. According to the non-limiting aspect of FIG. 239, the thermal paste 6516 can improve the conductive efficiency between the first internal heat sink 6510 and the second internal heat sink 6514 and, thus, the external heat sink 6508. Additionally, the thermal paste 6516 can be configured to alleviate hot spots that typically develop between coupled heat sinks by filling discontinuities in the collective, conductive thermal path established by the first internal heat sink 6510 and second internal heat sink 6514 and accounting for thermal and dimensional tolerances. The thermal paste 6516 of FIG. 239 can be similar to those used in integrated circuit electronics, as are typically applied between computer processing units and corresponding heat sinks. For example, although the thermal paste 6516 can be thermally conductive, it may not be electrically conductive, thereby reducing the potential for shocks and/or short circuits. The thermal paste 6516 can be pre-applied to the adapter assembly 6500 and re-applied to the handheld device 6504 when the adapter assembly 6500—and sterile barrier—needs to be replaced. The thermal paste 6516 can offer several advantages over graphite pads and/or thermally conductive pads, which can break down over time and, thus, become less efficient. Additionally, the thermal paste 6516 contemplated by the present disclosure is less expensive than comparable graphite and/or thermally conductive pads.

Referring now to FIG. 240, a sectioned side view of a surgical instrument including a handheld surgical device 6604 and an adapter assembly 6600 that includes energy management components 6608, 6610, 6614, 6616 is depicted in accordance with at least one non-limiting aspect of the present disclosure. According to the non-limiting aspect of FIG. 240, the adapter assembly 6600 can include a proximal portion 6602 and a distal portion 6603 connected in a clamshell configuration via a hinge 6606. Collectively, the proximal portion 6602 and the distal portion 6603 can constitute an outer shell or housing that defines an internal cavity 6609 configured to encase a handheld device 6604 that can generate energy when the surgical instrument is in use. Accordingly, the adapter assembly 6600 is configured to transition from an open configuration, wherein the hinge 6606 is open and the sterile barrier is disrupted, to a closed configuration, wherein the hinge 6606 is closed and the sterile barrier is established. Collectively, the proximal portion 6602 and the distal portion 6603 can define a handle portion configured for the ergonomic handling of the surgical instrument when the handheld device 6604 is installed within the adapter assembly 6600. As can be seen in FIG. 240, the proximal portion 6602 and distal portion 6603 of the adapter assembly 6600 can each include energy management components 6608, 6610, 6614, 6616 configured to effectively manage energy created by a handheld device when installed within an internal cavity 6609 of the adapter assembly 6600.

Still referring to FIG. 240, the adapter assembly 6600 can include a heat sink assembly including an external heat sink 6608 and several internal heat sinks 6610, 6614, 6616 positioned within the internal cavity 6609 of the adapter assembly 6600. According to the non-limiting aspect of FIG. 240, the external heat sink 6608 is positioned on an external surface of the distal portion 6603 of the adapter assembly 6600 and is configured to convect thermal energy produced by the motor 6612 away from the surgical instrument 6600. In some non-limiting aspect, the external heat sink 6608 can include a plurality of fins configured to expand the surface area off of which thermal energy can be convected. An internal heat sink 6610 can be positioned within the proximal portion 6602 of the adapter assembly 6600 and configured to mechanically contact a motor 6612 of the handheld device 6604, thereby creating a conductive thermal path for thermal energy to be routed off of—and away from—the motor 6612. The internal heat sink 6610 can terminate in a wedge-shaped, thermally conductive surface area 6614. The thermally conductive surface area 6614 can be configured to mechanically contact a translating conductor 6616 positioned within the distal portion 6603 of the adapter assembly 6600. The translating conductor 6616 can be further configured to move between a first position and a second position within the distal portion 6603 of the adapter assembly 6600. For example, when the adapter assembly 6600 is in the closed configuration, the translating conductor 6616 makes mechanical contact with the thermally conductive surface area 6614, which is moved from the first position to the second position based, at least in part, on the wedge-shaped configuration of the thermally conductive surface area 6614. In the second position, the translating conductor 6616 is in mechanical contact with the external heat sink 6608, thereby extending the thermally conductive path from the motor 6612 to the external heat sink 6608 while preserving the sterile barrier formed by the adapter assembly 6600.

Referring now to FIG. 241, a sectioned side view of the energy management components 6608, 6610, 6614, 6616 of FIG. 240 is depicted in accordance with at least one non-limiting aspect of the present disclosure. According to the non-limiting aspect of FIG. 241, the internal heat sink 6610 can mechanically contact the motor 6612 of the handheld device 6604 (FIG. 240) and can terminate in a wedge-shaped, thermally conductive surface area 6614. The translating conductor 6616 is further illustrated as configured with a corresponding geometry to the wedge shape of the thermally conductive surface area 6414. As is depicted in FIG. 241, as the proximal portion 6602 of the adapter assembly 6600 (FIG. 240) moves towards the distal portion 6603 of the adapter assembly 6600, the wedge-shaped, thermally conductive surface area 6614 forces the translating conductor 6616 up towards the external heat sink 6608. The non-limiting aspect of FIG. 241 further includes a spring 6617, which can be configured to movably couple the translating conductor 6616 to an interior wall of the internal cavity 6609 (FIG. 240) or in some aspects, to the external heat sink 6608 itself. Although the non-limiting aspect of FIG. 241 includes a wedge-shaped geometry, it shall be appreciated that any corresponding geometry capable of engaging the thermally conductive surface area 6614 and thus, moving the translating conductor 6616 into mechanical contact with the external heat sink 6608 can be employed to extend the thermally conductive path from the motor 6612.

Referring now to FIGS. 242 and 243, the adapter assembly 6600 of FIG. 240 is depicted in accordance with another non-limiting aspect of the present disclosure. According to the non-limiting aspect of FIGS. 242 and 243, the spring 6617 of FIG. 241 includes a wave spring 6618 geometry that is dispositioned within the distal portion 6603 between the translating conductor 6616 and the wedge-shaped, thermally conductive surface area 6614. The wave spring 6618 can include any compressible and/or elastic material that is thermally conductive, rendering it suitable for efficiently transferring thermal energy from the translating conductor 6616 to the external heat sink 6608. As is depicted in FIG. 243, the wave spring 6618 can include a plurality of internal pockets 6620 that provide the spring 6617 with an increased surface area. When compressed, the pockets 6620 can compress, causing the interior walls of the pockets 6620 to contact one another. Accordingly, the wave spring 6618—and more specifically, the pockets 6620—can increase the conductive surface area of the thermal path, thereby creating a more efficient removal of thermal energy from the internal cavity 6609 of the adapter assembly 6000. Although the wave spring 6618 of FIGS. 242 and 243 include a specific geometry, it shall be appreciated that any geometry configured to enable the movement of the translating conductor 6616 relative to the external heat sink 6608 while increasing the conductivity of the thermal path to the motor 6612 can be implemented to achieve an improved efficiency of heat transfer.

Referring now to FIG. 244, a sectioned perspective view of a surgical instrument 6700 including a handheld surgical device 6702 and a distal portion 6704 of an adapter assembly with energy management components 6708, 6710 (FIG. 246), 6712 is depicted in accordance with at least one non-limiting aspect of the present disclosure. According to the non-limiting aspect of FIG. 244, the distal portion 6704 of the adapter assembly includes an external heat sink 6712. In some non-limiting aspects, the distal portion 6704 can be connected to a proximal portion of the adapter assembly in a clamshell configuration via a hinge. Regardless, the distal portion 6704 of the adapter assembly partially defines an outer shell that includes an internal cavity 6709 configured to encase a handheld device 6702. Similar to other disclosed aspects, a motor 6706 of the handheld device 6702 can generate energy when the surgical instrument 6700 is in use. Accordingly, the distal portion 6704 can be configured to mechanically couple to the handheld device 6702, thereby establishing a sterile barrier. As can be seen in FIG. 244, the distal portion 6704 of the adapter assembly and the handheld device 6702 can collectively include energy management components 6708, 6710 (FIG. 246), 6712 configured to effectively manage energy created by a handheld device 6702 when installed within an internal cavity 6709 of the adapter assembly.

In further reference to FIG. 244, the surgical instrument 6700 can include an external heat sink 6712 and several internal heat sinks 6708, 6710 (FIG. 246), 6711 positioned within the internal cavity 6709 of the adapter assembly. According to the non-limiting aspect of FIG. 244, the external heat sink 6712 can be positioned on an external surface of the distal portion 6704 of the adapter assembly and is configured to convect thermal energy produced by the motor 6706 away from the surgical instrument 6700. In some non-limiting aspects, the external heat sink 6712 can include a plurality of fins configured to expand the surface area off of which thermal energy can be convected. An internal heat sink 6708 can be positioned within the internal cavity 6709 of the adapter assembly and configured to mechanically contact the a motor 6706 of the handheld device 6702, thereby creating a conductive thermal path for thermal energy to be routed off of—and away from—the motor 6706. The internal heat sink 6708 can terminate in thermally conductive surface area 6710 positioned proximal to a distal end of the handheld device 6702. The thermally conductive surface area 6710 can be configured to mechanically contact a leaf spring 6711 coupled to an internal surface of the external heat sink 6712 when the handheld device 6702 is properly installed within the internal cavity 6709 and arranged within the distal portion 6704 of the adapter assembly.

Referring now to FIG. 245, a sectioned perspective view of the energy management components 6710 (FIG. 246), 6711, 6712 of FIG. 244 is depicted in accordance with at least one non-limiting aspect of the present disclosure. According to the non-limiting aspect of FIGS. 244 and 245, the leaf spring 6711 is coupled to an internal surface 6713 of the external heat sink 6712. Specifically, the mechanical nature of the leaf spring 6711 is depicted in FIG. 245. For example, it shall be appreciated that the leaf spring 6711 can include a specific elastic nature, enabling it to apply an inward force when compressed. Accordingly, when the handheld device 6702 (FIG. 244) is properly installed within the internal cavity 6709 (FIG. 244) and arranged within the distal portion 6704 of the adapter assembly, the leaf spring 6711 applies an inward force on the thermally conductive surface area 6710 (FIG. 246). This ensures that the leaf spring 6711 remains in mechanical engagement with the thermally conductive surface area 6710, thereby establishing a conductive path capable of efficiently removing thermal energy from the motor 6706 of the surgical instrument 6700. The leaf spring 6711 can be either integrally formed with the thermally conductive surface area 6710 or attached separately. In other non-limiting aspects, the leaf spring 6711 can be mechanically coupled to the thermally conductive surface area 6710 and configured to mechanically contact an internal surface of the external heat sink 6712 when the handheld device 6702 is properly installed within the internal cavity 6709 and arranged within the distal portion 6704 of the adapter assembly.

Referring now to FIG. 246, various views of the energy management components 6710, 6711, 6712 of FIGS. 244 and 245 are depicted in accordance with at least one non-limiting aspect of the present disclosure. According to the non-limiting aspect of FIG. 246, the leaf spring 6711 can be positioned between the thermally conductive surface area 6710 of the handheld device 6702 (FIG. 244) and compressed when the handheld device 6702 is properly installed within the internal cavity 6709 (FIG. 244) and arranged within the distal portion 6704 of the adapter assembly. Due to the corresponding frustoconical structure of the thermally conductive surface area 6710 and distal portion 6704 of the adapter assembly, the leaf spring 6711 can compress more and more as the handheld device 6702 is installed. Due to the elastic nature of the leaf spring 6711, the inward force applied by the leaf spring 6711 gradually increases, thereby increasing the surface area by which the thermally conductive surface area 6710, the leaf spring 6711, and the external heat sink 6712 are in thermally conductive contact. It shall be appreciated that conductive efficiency improves as the conductive surface area increases. Therefore, the energy management components 6710, 6711, 6712 of FIGS. 244 and 245 can be implemented to effectively remove thermal energy generated by the motor 7606 (FIG. 244) from the internal cavity 6709 (FIG. 244) of the surgical instrument 6700 (FIG. 244).

Referring now to FIG. 247, a sectioned side view of a surgical instrument 6800 including a handheld surgical device 6804 and an adapter assembly 6801 that includes energy management system 6610, 6614, 6616 is depicted in accordance with at least one non-limiting aspect of the present disclosure. According to the non-limiting aspect of FIG. 247, the surgical instrument 6800 can include a proximal portion 6802 and a distal portion 6803 connected in a clamshell configuration via a hinge 6806. Collectively, the proximal portion 6802 and the distal portion 6803 can constitute an outer shell or housing that defines an internal cavity 6809 configured to encase the handheld device 6804 configured to generate energy when the surgical instrument is in use. Accordingly, the adapter assembly 6801 can be configured to transition from an open configuration, wherein the hinge 6806 is open and the sterile barrier is disrupted, to a closed configuration, wherein the hinge 6806 is closed and the sterile barrier is established. Collectively, the proximal portion 6802 and the distal portion 6603 can further define a handle portion 6805 configured for the ergonomic handling of the surgical instrument 6800 when the handheld device 6804 is installed within the adapter assembly 6801. As can be seen in FIG. 247, the proximal portion 6802 and distal portion 6803 of the adapter assembly 6800 can each include energy management components 6812, 6814, 6813, 6816 configured to effectively manage energy created by a handheld device 6804 when installed within an internal cavity 6809 of the adapter assembly 6801.

Still referring to FIG. 247, the surgical instrument 6800 can include an energy storage and removal assembly 6812, 6814, 6813, 6816 including a removable thermal energy storage device 6816 configured to be installed within a dedicated compartment 6813 within the internal cavity 6809 of the adapter assembly 6801. According to the non-limiting aspect of FIG. 247, one or more internal heat sinks 6812 can be configured to mechanically contact a motor 6810 of the handheld device 6804, thereby creating a conductive thermal path for thermal energy to be routed off of—and away from—the motor 6810. The one or more internal heat sinks 6812 can terminate in one or more conductive contacts 6814 positioned within the dedicated compartment 6813 of the internal cavity 6809. When properly installed within the dedicated compartment 6813, the removable thermal energy storage device 6816 can be configured to mechanically contact the one or more contacts 6814, thereby extending the thermally conductive path into the removable thermal energy storage device 6816.

In further reference to FIG. 247, rather than utilizing an external heat sink configured to convect and/or radiate heat away from the handheld device 6804, the surgical instrument 6800 can route thermal energy away from the motor 6810 and store it within the thermal energy storage device 6816. For example, the thermal energy storage device 6816 can include a material including a high specific heat configured to dissipate heat throughout the storage device 6816 and strategically retard any rise in internal temperature. The removable storage device 6816 can include one or more conductive contacts 6824 configured to engage the conductive contacts 6814 positioned within the dedicated compartment when the storage device 6816 is properly installed within the adapter assembly 6801. Accordingly, the removable storage device 6816 of FIG. 247 can be configured to charge—that is, receive and store thermal energy generated by the motor 6810—as the surgical device 6800 is in use. Specifically, the material with the high specific heat can absorb and dissipate thermal energy it receives from the motor 6810 throughout the storage device 6816. For example, the material can include a solid ingot or a liquid such as water. Of course, other non-limiting aspects contemplated by the present disclosure contemplate any number of suitable materials for the removable storage device 6816. When the storage device 6816 achieves a critical temperature, it can be removed from the dedicated compartment and replaced with a similarly configured—albeit cooler—storage device 6816. The replacement can either be ambient temperature or pre-cooled below an ambient temperature to further delay the time it takes to achieve a critical temperature.

Referring now to FIG. 248, a sectioned perspective view of the energy management components 6824, 6826, 6828 of the energy management system 6816 of FIG. 247 is depicted in accordance with at least one aspect of the present disclosure. According to the non-limiting aspect of FIG. 248, either the dedicated compartment 6813, the storage device 6816, or both can include a temperature sensor 6822 (e.g., a thermocouple, a thermistor, a resistance temperature detector, a semiconductor-based sensor) configured to generate a signal associated with an operating temperature of the removable storage device 6816. The surgical instrument 6800 can further include a control circuit 6826 coupled to the temperature sensor 6822 and configured to receive the signal and determine a temperature of the removable storage device 6816 based, at least in part, on the signal generated by the temperature sensor 6822. Accordingly, the control circuit can determine that the temperature of the removable storage device 6816 has exceeded a predetermined threshold and, thus, notify a clinician via alert.

Still referring to FIG. 248, the energy management system can further include a light emitting diode indicator 6828 coupled to the control circuit 6826 that can be configured to indicate the determined operating temperature of the removable storage device 6816 to a clinician. According to the non-limiting aspect of FIG. 248, the indicator 6828 can illuminate a specific color associated with the operating temperature of the removable storage device 6816. For example, the indicator can illuminate a first color 6830 to indicate that the storage device 6816 is of a cool temperature, a second color 6832 to indicate that the storage device 6816 is of a warm temperature, and a third color 6834 to indicate that the storage device 6816 is of a hot temperature. When the indicator is illuminated the third color 6834, the operating clinician can remove and/or replace the removable storage device 6816. Although the non-limiting aspect of FIG. 248 illustrates a light emitting diode indicator 6828, the present disclosure contemplates other non-limiting aspects featuring a variety of different alerts, including audible, haptic, and/or visual alerts. Likewise, the surgical instrument 6800 of FIG. 247 can be alerted to include any number of user interface components, including screens, speakers, motors, lights, and/or the like. As previously discussed, the storage device 6816 can include a solid ingot. Alternatively, the storage device 6816 can include a hollow cavity and/or bladder comprising a fluid, such as water. Additionally and/or alternatively, the adapter assembly 6801 can include insulation 6836 positioned between an interior wall of the dedicated compartment 6813 to further manage and/or contain any thermal energy generated by the motor 6810 that is not stored within the storage device 6816. Accordingly, the indicator 6828 and removable storage device 6816 of FIGS. 247 and 248 can be utilized to effectively manage energy dissipated by the handheld device 6804, thereby facilitating a safe and continued use of the surgical instrument 6800.

Referring now to FIG. 249, a sectioned perspective view of an energy management system 7000 of a surgical instrument is depicted in accordance with at least one non-limiting aspect of the present disclosure. According to the non-limiting aspect of FIG. 249, the energy management system 7000 can include a thermoelectric cooling configuration, including a Peltier module 7002 configured to assist in the management of thermal energy generated by the motor 7010. The Peltier module 7002 can be configured to utilize a thermoelectric effect, which utilizes an electric current configured to flow between two material junctions, which can cause cooling. In the non-limiting aspect of FIG. 249, the Peltier module 7002 can include a matrix of P/N junctions dispositioned between a plurality of P nodes 7004 and a plurality of N nodes 7006. The plurality of P nodes 7004 and the plurality of N nodes 7006 collectively constitute a matrix of joined electrical conductors 7004, 7006 that can be connected to a power source 7012 via a pair of leads 7008*a*, 7008*b*. The power source 7012 can thus apply a voltage across the matrix of joined conductors 7004, 7006 to create an electric current. When the current flows through the junctions of the two conductors 7004, 7006, thermal energy can be removed from a first side 7014 of the matrix of the two conductors 7004, 7006 and deposited on a second side 7016 of the matrix of the two conductors 7004, 7006. The first side 7014 can be configured to abut the motor 7010, and the second side 7016 can be positioned away from motor 7010 such that thermal energy is pulled away from the motor 7010 to prevent overheating. According to some non-limiting aspects, the energy management system 7000 of FIG. 249 can further include a heat sink to assist in dispelling the thermal energy that is pulled away from the motor 7010 via the Peltier module 7002.

Although the non-limiting aspects of FIGS. 229-249 depict energy management systems configured to manage the generation of thermal energy, it shall be appreciated that similar systems can be implemented to effectively manage the generation of a wide variety of energies produced by the motor, handheld device, or surgical instrument as a whole. For example, the following aspects can be implemented to assist with the management of vibrational and/or acoustic energy generated by the motor of a handheld device when the surgical instrument is in use. As is the case with thermal energy, the inclusion of an adapter assembly that establishes a sterile barrier around the handheld device can complicate the dissipation of vibrational and/or acoustic energy. Without a proper means of managing this energy, the surgical instrument can suffer from reduced accuracy and/or an accelerated degradation of components and can become difficult for a clinician to handle. Accordingly, there is a need for energy management systems that can be configured to manage and mitigate the generation of vibrational and/or acoustic energy.

Referring now to FIG. 250, a sectioned perspective view of a surgical instrument 7500 including a handheld surgical device and an adapter assembly 7502 that includes an energy management system 7504 is depicted in accordance with at least one non-limiting aspect of the present disclosure. According to the non-limiting aspect of FIG. 250, the surgical instrument 7500 can include an adapter assembly 7502 with an outer shell housing that defines an internal cavity 7509. A handheld device can be installed within the internal cavity 7509, including its requisite components. For example, the non-limiting aspect of FIG. 250 includes a motor 7506, a power source 7508, a sensor 7510, and a control circuit 7512 within the internal cavity 7509. The motor 7506, specifically, can produce vibrational energy when the surgical instrument 7500 is in operation, as is depicted in FIG. 250.

In further reference to FIG. 250, the surgical instrument can include an energy management system 7504 dispositioned within the internal cavity 7509 of the adapter assembly 7502. According to the non-limiting aspect of FIG. 250, the surgical instrument 7500 can include composites 7504, which are strategically situated throughout the internal cavity 7509, wherein the composites 7504 are configured to manage the vibrational energy generated by the motor 7506. For example, the composites 7504 can include piezoelectric characteristics that are configured to dampen the vibrational energy by producing a counterforce to the generated vibrational energy when activated. In some non-limiting aspects, the composites can be configured to automatically produce the aforementioned counterforces as soon as the motor 7506 is activated. As will be discussed, the counterforces can be specifically configured to mitigate and/or substantially eliminate the vibrational energy generated by the motor 7506. For example, the composites 7504 can produce counterforces that are equal, albeit opposite, to the vibrational energy generated by the motor 7506.

According to other non-limiting aspect of FIG. 250, the sensor 7510 can detect the vibrational energy generated by the motor 7506 when the surgical instrument 7500 is in use. The sensor 7510 can generate a signal associated with the detected vibrational energy. The control circuit 7512 can be configured to receive the signal from the sensor 7510 and determine an operational level of the vibrational energy produced by the motor 7506 when the surgical instrument 7500 is in use. Upon determining that the operational level of the vibrational energy produced by the motor 7506 exceeds a predetermined threshold, the control circuit 7512 can route energy from the power source 7508 to the piezoelectric composites 7504. Upon activation, the piezoelectric composites 7504 can be configured to generate the counterforce, thereby dampening the vibrational energy generated by the motor 7506 when the surgical instrument 7500 is in use. Accordingly, the surgical instrument 7500 of FIG. 250 can be configured self-stabilize, making it easier for an operating clinician to use.

Referring now to FIG. 251, a chart depicting an energy response 7516 of the energy management system 7504 of FIG. 250 is depicted in accordance with at least one non-limiting aspect of the present disclosure. As was previously discussed, the counterforces 7516 produced by the composites 7504 of FIG. 250 can be specifically configured to mitigate and/or substantially eliminate the vibrational energy 7514 generated by the motor 7506 (FIG. 250). According to the non-limiting aspect of FIG. 251, the composites 7504 of FIG. 250 can produce counterforces 7516 that are equal—albeit opposite—to the vibrational energy 7514 generated by the motor 7506. As such, the composites of FIG. 250 can reduce the vibrational energy 7514 generated by the motor 7506 (FIG. 250), improving the stability of the surgical instrument 7500 and, therefore, the accuracy with which an operating clinician can use the surgical instrument 7500. Although the non-limiting aspect of FIG. 251 depicts an energy response 7516 configured to match the vibrational energy generated by the motor 7506 (FIG. 250), it shall be appreciated that the energy management system 7504 contemplated by the present disclosure can be specifically configured to produce any desired level of energy response 7516, in accordance with user preference and/or intended application. This can be done via a user interface communicably coupled to the control circuit 7512 (FIG. 250).

Referring now to FIG. 252, illustrating a sectioned perspective view of an adapter assembly 7602 of a surgical instrument 7600 that includes an energy management component 7604 is depicted in accordance with at least one non-limiting aspect of the present disclosure. The adapter assembly 7602 can define an internal cavity 7609 configured to accommodate a handheld device and its requisite components, such as motor 7606. According to the non-limiting aspect of FIG. 252, the surgical instrument 7600 can include a material layer 7604 strategically situated throughout the internal cavity 7609, wherein the material layer 7604 is specifically configured to manage the vibrational energy generated by the motor 7606. For example, the material layer 7604 can include a butyl rubber configured to absorb vibrational energy generated by the motor 7606 when the surgical instrument 7600 is in use.

In further reference to FIG. 252, the material layer 7604 can generally include any vibration-reducing material with a sufficiently high damping coefficient and an ability to maintain performance without degradation. Accordingly, when the surgical instrument 7600 is used, the material layer 7604 can absorb shock energy and reduce the vibrations generated by the motor 7606. Additionally and/or alternatively, the material layer 7604 can include sound-deadening properties to reduce the vibrational energy impact on the surgical instrument 7600. For example, the material layer 7604 can include a material configured to absorb acoustic energy, thereby reducing the energy of sound waves generated by the motor 7606. The material layer 7604 can also be configured to absorb shock over a wide range of frequencies and temperatures. Although the non-limiting aspect of FIG. 252 includes a material layer 7604 of butyl rubber, other non-limiting aspects of the present disclosure contemplate a wide variety of material layers 7604 that possess the aforementioned properties.

Still referring to FIG. 252, the present disclosure contemplates material layers 7604 composed of any natural or synthetic materials, including visco-elastic polymers, latex, and cork, among others. Likewise, the material layer 7604 can include various mechanical components, such as springs, to assist the material layer 7604 in managing vibrational energy produced by the motor 7606. Although the non-limiting aspect of FIG. 252 includes a material layer 7604 configured to line the internal cavity 7609, still other non-limiting aspects include the material layer 7606 dispositioned within the walk of the adapter assembly 7602 itself. Accordingly, it shah be appreciated that the material layer 7604 can be intentionally dispositioned throughout the structure of the surgical instrument 7600 to accomplish a desired degree of energy management.

Referring now to FIG. 253A, a sectioned profile view of an alternate energy management component 7604*a* of the adapter assembly of FIG. 251 is depicted in accordance with at least one non-limiting aspect of the present disclosure. According to the non-limiting aspect of FIG. 253A, the surgical instrument 7600 can include a material layer 7604*a* configured to manage the acoustic energy of sound waves produced by the motor 7606. For example, the material layer 7604*a* of FIG. 253A can include a plurality of pyramid absorbers, similar to those found in anechoic chambers. The anechoic geometry of the material layer 7604*a* of FIG. 253A is specifically configured to absorb and suppress the reflection of acoustic energy generated by the motor 7606 when the surgical instrument 7600 is in use. Acoustic waves emitted by the motor 7606 reflect off the angled walls of each pyramid, which prevent the energy from reflecting off the wall and back into the internal cavity 7609 (FIG. 252). In other words, the anechoic geometry prevents reverberation, which can exacerbate the vibration of the surgical instrument 7600. Accordingly, the material layer 7604*a* can be used to supplement and/or enhance the management of energy, thereby reducing the ensuing vibration and/or degradation of the surgical instrument 7600.

Referring now to FIG. 253B, a sectioned profile view of an alternate energy management component 7604*b* of the adapter assembly of FIG. 251 is depicted in accordance with at least one non-limiting aspect of the present disclosure. According to the non-limiting aspect of FIG. 253B, the surgical instrument 7600 can include a material layer 7604*a* with a similar anechoic geometry depicted in FIG. 253A. The material layer 7604*b* manages the acoustic energy emitted by the motor 7606 similar to the material layer 7604*a* of FIG. 253A. However, the material layer 7604*a* of FIG. 253A can inadvertently insulate the adapter assembly 7602 (FIG. 252), which can be detrimental to the management of thermal energy generated by the motor 7606. Accordingly, the material layer 7604*b* of FIG. 253B can further include a plurality of air chambers 7610 between the material layer 7604*b* and an interior wall of the internal cavity 7609 of the adapter assembly 7602. As such, thermal energy can still escape the internal cavity 7609 (FIG. 252) through the plurality of air chambers 7610. Additionally and/or alternatively, the material layer 7604*b* to be combined with the thermally conductive channels, baffles, and heat sinks, as previously discussed. Accordingly, the material layer 7604*b* of FIG. 253B can be implemented to effectively manage thermal, acoustic, and vibrational energy generated by the surgical instrument 7600.

Referring now to FIG. 254A, an energy management system 7700 of a surgical instrument is depicted in accordance with at least one non-limiting aspect of the present disclosure. According to the non-limiting aspect of FIG. 254A, the energy management system 7700 can include a counterweight 7708*a* configured to be coupled to the driveshaft 7702 of a motor 7706 of a surgical instrument. The driveshaft 7702 of the motor 7706 traverses along a driveshaft axis A. The driveshaft axis A defines a first side 7710 and a second side 7712 of the motor 7706. In the non-limiting aspect of FIG. 254A, both the counterweight 7708*a* and the drive member 7704 that engages the drive shaft 7702 are both positioned on the first side 7710 of the motor 7706. Accordingly, the counterweight 7708*a* of the energy management system 7700 is configured to rotate in an opposite direction of the driveshaft, thereby producing a counterforce configured to dampen vibrational energy generated by the motor 7706 when the surgical instrument is in use.

Referring now to FIG. 254B, a chart depicting an energy response 7716 of the energy management system 7700 of FIG. 254A is depicted in accordance with at least one non-limiting aspect of the present disclosure. As was previously discussed, the counterforces 7716 produced by the energy management system 7700 of FIG. 254A can be specifically configured to mitigate the vibrational energy 7714 generated by the motor 7706 (FIG. 254A). The rotation of the counterweight 7708*a* of FIG. 254B in an opposite direction to the driveshaft 7702 can produce counterforces 7716 that are similar in magnitude—albeit opposite—to the vibrational energy 7714 generated by the motor 7706. As is depicted in FIG. 254B, the delta in magnitude between the vibrational energy 7714 generated by the motor 7706 (FIG. 254A) and the dampening energy 7716 generated by the counterweight 7708*a* can produce a resulting energy 7718 that can be felt by an operating clinician but is substantially lower in magnitude than the unmitigated vibrational energy 7714 generated by the motor 7706 (FIG. 254A).

Referring now to FIG. 254C, an energy management system 7700 of a surgical instrument is depicted in accordance with at least one non-limiting aspect of the present disclosure. According to the non-limiting aspect of FIG. 254C, the energy management system 7700 can include a counterweight 7708*b* configured to be coupled to the driveshaft 7702 of a motor 7706, similar to the non-limiting aspect of FIG. 254A. Once again, the driveshaft 7702 of the motor 7706 traverses along a driveshaft axis A, which defines a first side 7710 and a second side 7712 of the motor 7706. However, in the non-limiting aspect of FIG. 254C, the counterweight 7708*b* is positioned on the first side 7710 of the motor 7706 and the drive member 7704 that engages the drive shaft 7702 is positioned on the second side 7712 of the motor 7706. Accordingly, the counterweight 7708*b* of the energy management system 7700 is configured to rotate in the same direction of the driveshaft, thereby producing a counterforce configured to dampen vibrational energy generated by the motor 7706 when the surgical instrument is in use. This is exhibited in FIG. 254C via the imbalance vectors, which are oriented in an opposite direction as the force vectors produced by the counterweight 7708*b* dampers. Thus, the counterweight 7708*b* can produce a similar energy response to the energy response 7716 depicted in FIG. 254B, which is shown to substantially mitigate the vibrational energy 7714 (FIG. 254B) generated by the motor 7706.

Referring now to FIG. 255, a perspective view of an energy management system 7800 of a surgical instrument is depicted in accordance with at least one non-limiting aspect of the present disclosure. According to the non-limiting aspect of FIG. 255, the surgical instrument can include a motor 7806, which can include a proximal pin 7804 configured to couple to a bushing 7810 positioned within a proximal handle 7802 of the surgical instrument. The bushing 7810 can be positioned among ball bearings 7808, which enable the bushing 7810 to freely spin within the proximal handle 7802. The bushing 7810 can further include a weight 7812 configured to produce forces when the busing 7810 spins. Because the proximal pin 7804 can mechanically couple the bushing 7810 to a drive shaft of the motor 7806, the weight 7812 can be tuned to produce an energy response specifically configured to counterbalance vibrational energy generated by the motor 7806. Additionally, because the bushing 7810 can anchor the motor 7806 to the proximal handle 7802 of the surgical instrument, the motor 7806 can be inhibited from moving relative to the proximal handle 7802 of the surgical instrument. Accordingly, the bushing 7810 can produce a similar energy response to the energy response 7716 depicted in FIG. 254B, which is shown to substantially mitigate the vibrational energy 7714 (FIG. 254B) dissipated by the motor 7706.

Referring now to FIG. 256, a sectioned perspective view of an energy management system 7900 of a surgical instrument is depicted in accordance with at least one non-limiting aspect of the present disclosure. According to the non-limiting aspect of FIG. 256, the energy management system 7900 can include a motor housing 7904 surrounding a motor 7903 of the handheld device 7902. According to the non-limiting aspect of FIG. 256, the motor housing 7904 can include a piezoelectric sheath 7908 that is coupled to a control circuit 7910, which is further coupled to a power source 7912. A sensor 7906 can be mechanically coupled to the motor and configured to detect the vibrational energy generated by the motor 7503 when the surgical instrument 7500 is in use.

In further reference to FIG. 256, the sensor 7906 can be further configured to generate a signal associated with the detected vibrational energy of the motor 7903. A control circuit 7910 can be coupled to the sensor 7906 and configured to receive the signal from the sensor 7906 and determine an operating level of the vibrational energy produced by the motor 7506 when the surgical instrument 7500 is in use. The control circuit 7910 can be further coupled to a power source 7912. Upon determining that the operational level of the vibrational energy produced by the motor 7903 exceeds a predetermined threshold, the control circuit 7910 can route energy from the power source 7912 to the piezoelectric sheath 7908. Upon activation, the piezoelectric sheath 7908 can be configured to generate the counterforce, thereby dampening the vibrational energy generated by the motor 7903 when the surgical instrument is in use. Accordingly, the energy management system 7900 of FIG. 256 can be configured to self-stabilize the handheld device 7902 of the surgical instrument, making it easier for an operating clinician to use.

Referring now to FIG. 257, a sectioned front view of the energy management system 7900 of FIG. 256 is depicted in accordance with at least one non-limiting aspect of the present disclosure. According to the non-limiting aspect of FIG. 257, the energy management system 7900 can include a motor housing 7904 configured as a chassis that surrounds, supports, and suspends a motor 7903 assembly of the handheld device 7902 from a piezoelectric sheath 7908. As previously discussed, a sensor 7906 coupled to a control circuit 7910 (FIG. 256) and a power source 7912 (FIG. 256) is dispositioned at a predetermined location on the motor housing 7904. As can be seen in the non-limiting aspect of FIG. 257, the piezoelectric sheath 7908 can include a circumferential perimeter around the chassis specifically configured to translate a piezoelectric force uniformly throughout the chassis 7904 to mitigate—and potentially eliminate—any mechanical reactions to the vibrational energy created by the motor 7903 assembly when the surgical assembly is in use. It shall be appreciated that the chassis 7904 configuration of FIG. 257 can be attenuated depending on the number of motors and the desired reaction to the piezoelectric stimulation provided by the sheath 7908. Accordingly, any geometrical configuration can be implemented to fine-tune the performance of the energy management system 7900 in accordance with user preference and/or intended application.

Referring now to FIG. 258, a schematic of a control circuit 8000 configured to manage energy dissipated by a surgical instrument is depicted in accordance with at least one aspect of the present disclosure. For example, the control circuit 8000 can be configured to implement the various energy management processes described herein. According to the non-limiting aspect of FIG. 258, the control circuit 8000 can include a microcontroller comprising one or more processors 8002 (e.g., microprocessor, microcontroller) coupled to at least one memory circuit 8008. The memory circuit 8008 can be configured to store machine-executable instructions that, when executed by the processor 8002, can cause the processor 8002 to execute machine instructions to implement the various processes described herein. The processor 8002 can be any one of a number of single-core or multicore processors known in the art. Alternatively and/or additionally, the microcontroller can include a logic board, such as a Field Programmable Gate Array, for example. The memory circuit 8008 can comprise volatile and non-volatile storage media. The processor 8002 may include an instruction processing unit 8004 and an arithmetic unit 8006. The instruction processing unit 8004 can be configured to receive instructions from the memory circuit 8008 of this disclosure.

FIG. 259 illustrates a schematic diagram of a surgical instrument 750 configured to deliver a surgical treatment to a tissue to seal and/or cut the tissue. The surgical treatment includes at least two phases. In the first phase, a therapeutic electrical energy is employed to seal the tissue. In at least one example, the therapeutic electrical energy is an RF energy. In the second phase, staples are deployed into the tissue and, optionally, a cutting member 721 (FIG. 260) cuts the tissue.

The surgical instrument 750 includes an end effector 752 with jaws 753. At least one of the jaws 753 is movable relative to the other from an open configuration to a closed configuration to grasp tissue therebetween. As illustrated in FIG. 260, the end effector 752 includes at least one electrode 796 configured to deliver the therapeutic electrical energy to the tissue in the first phase of the surgical treatment. The end effector 752 further includes an anvil 766 and a staple cartridge 767 configured to cooperate to form staples 742 (FIG. 261) deployable from the staple cartridge 767 into the tissue in the second phase of the surgical treatment. The staples 742 are formed by anvil pockets 747*a*, 747*b* (FIG. 262).

One of the jaws 753 of the end effector 752 includes a channel 744 configured to slidably receive the staple cartridge 767. In the illustrated example, the staple cartridge 767 is inserted into the channel 744 through a distal opening 755. The channel 744 and the staple cartridge 767 include corresponding locking features 763, 768 that cooperate to reversibly lock the staple cartridge 767 and the channel in a locked configuration. In the illustrated example, the locking features 763, 768 are in the form of a ramp and a corresponding groove. In other examples, the locking features 763, 768 can be in the form of protrusions, nubs, bulges, dimples, or any suitable projections, and corresponding valleys, holes, or any suitable depressions. In certain instances, the projections can be in the form of biasing or spring members.

In the illustrated example, the staple cartridge 767 includes two staple cavity rows 757*a*, 757*b* on opposite sides of a longitudinal slot 759 configured to accommodate a sliding movement of a cutting member 721. The cutting member 721 is slidably advanced through the longitudinal slot 759 to cut tissue grasped between the jaws 753. In other examples, more or less than two rows of staple cavities can be longitudinally disposed alongside the longitudinal slot 759.

Further to the above, the channel 744 includes a ceiling or cover 740 that includes a longitudinal opening 741 configured to at least partially accommodate the staple cavity rows 757*a*, 757*b* when the staple cartridge 767 is assembled with the channel 744. In the illustrated example, the staple cartridge 767 includes a stepped deck 730 that raises the staple cavity rows 757*a*, 757*b*. Side walls 744*a*, 744*b* of the channel 744 include narrowed portions configured to snuggly receive the stepped deck 730 to ensure a proper alignment of the staple cavity rows 757*a*, 757*b* with the longitudinal opening 741 defined in the ceiling or cover 740.

In the illustrated example, the at least one electrode 796 includes electrode segments 796*a*, 796*b*, 796*c* that define a partial perimeter around the longitudinal opening 741. In the assembled configuration, as illustrated in FIG. 262, the raised staple cavity rows 757*a*, 757*b* of the stepped deck 730 extend longitudinally in parallel, or substantially in parallel, with the electrode segments 796*a*, 796*b*, 796*c* cooperatively defining a tissue contacting surface. FIG. 261 illustrates a tissue T including a tissue portion T1 fastened by a staple 742 from the staple cavity row 757*a*, and a tissue portion T2 sealed by RF energy from the electrode segment 796*b*. The tissue T is cut, in the second phase, along a plane P (perpendicular to the page) by a cutting member 721 driven by an I-beam 720, for example, through the longitudinal slot 759, for example.

In the illustrated example, the electrode segments 796*a*, 796*b*, 796*c* are disposed onto, or are partially embedded, in corresponding insulative segments 797*a*, 797*b*, 797*c* of an insulative layer 797. Furthermore, the anvil 766 includes electrodes 731, 732, which are disposed onto, or are partially embedded, in corresponding insulative segments 733, 734. RF energy may flow from the at least one electrode 796 to the electrodes 731, 732 through tissue grasped between the jaws 753.

To avoid unintentionally forming a short circuit, the electrodes 731, 732 are offset from the electrode segments 797*a*, 797*c*, as illustrated in FIG. 262. In other words, the electrodes 731, 732 remain spaced apart from the electrode segments 797*a*, 797*c*, respectively, in a closed configuration of the end effector without tissue. In the illustrated example, the channel 744 is grounded, and the at least one electrode 796 is an integral part of the channel 744 with no moving parts. In at least one example, the at least one electrode 796 is hard-wired into channel 744 so electrical connections are not exposed to fluids that may cause a short. In the illustrated example, the electrodes 731, 732 are separated from the anvil 766 by the insulative segments 733, 734, respectively. In other examples, the electrodes 731, 732 are integral with the anvil 766. In such examples, the anvil 766 is a part of the return path of the RF energy.

In the illustrated example, the RF energy is configured to flow from the at least one electrode 796 toward the electrodes 731, 732. In other examples, however, the end effector 752 can be configured to cause the RF energy to flow from the electrodes 731, 732 toward the at least one electrode 796.

When the staple cartridge 767 is assembled with the channel 744, a nose portion 769 of the staple cartridge 767 extend beyond the distal opening 755, while the remainder of the staple cartridge 767 is received within the channel 744. Furthermore, the staple cartridge 767 comprises a cartridge release latch 765 configured to unlock the locking engagement of the locking features 763, 768 to permit removal of the staple cartridge 767 from the channel 744.

FIGS. 263 and 264 illustrate an end effector 852 similar in many respects to the end effector 752. The end effector 852 can be utilized with the surgical instrument 750 in lieu of the end effector 752. Like the end effector 752, the end effector 852 includes jaws configured to grasp tissue to deliver a surgical treatment to the tissue in first and second treatment phases.

Furthermore, the end effector 852 includes an anvil 866 and a channel 844 configured to releasably retain a staple cartridge 867. An RF overlay 890 is pivotally coupled to the channel 844. FIGS. 265-267 illustrates a process and mechanisms for attaching and detaching the RF overlay 890 to the staple cartridge 867 while the staple cartridge 867 is retained in the channel 844.

In certain examples, the staple cartridge 867, similar to the staple cartridge 767, includes a stepped deck 830 with raised staple cavity rows 857*a*, 857*b* and an insulative depressed region 831 configured to releasably retain the RF overlay 890, as best illustrated in FIG. 264. In an assembled configuration, as illustrated in FIG. 264, the staple cavity rows 857*a*, 857*b* and at least one electrode 896 of the RF overlay 890 cooperatively define a tissue contacting surface.

Furthermore, the staple cavity rows 857*a*, 857*b* and electrode segments 896*a*, 896*b* of the at least one electrode 896 extend longitudinally in parallel, or at least substantially in parallel, on opposite sides of a longitudinal slot 859 cooperatively defined by the RF overlay 890 and the staple cartridge 867 while the staple cartridge 867 is retained in the channel 844. In the illustrated example, the drive member 751 terminates in an I-beam 720 that includes a cutting member 721 movable through the longitudinal slot 859 to cut tissue grasped between the jaws of the end effector 852 in a similar manner described in connection with the end effector 752.

In the illustrated example, the RF overlay 890 comprises a U-shape, and includes two body portions 897*a*, 897*c* extending longitudinally in parallel, or at least substantially in parallel. The body portions 897*a*, 897*c* are separated by a longitudinal opening 841 defined in the RF overlay 890. A distal arcuate portion 897*b* connects the body portions 897*a*, 897*c*. The longitudinal opening 841 facilitates translation of the cutting member 721 relative to the RF overlay 890. The at least one electrode 896 also comprises a U-shape, and is disposed onto, or is at least partially embedded into, the portions 897*a*, 897*b*, 897*c*. In certain instances, the at least one electrode 896 includes 896*a*, 896*b*, 896*c* that can be connected to the RF energy source 762. Other electrode shapes and configurations for the RF overlay 890 are contemplated by the present disclosure.

In the illustrated examples, the overlay 890 includes pivots 891 extending laterally from a proximal portion of the RF overlay 890. The pivots 893 are received in corresponding pivot holes 843 defined in sidewalls of the channel 844. The overlay 890 is rotatable between an unlocked configuration (FIG. 265) and a locked configuration (FIG. 266) about an axis extending through the pivot holes 891. In the illustrated example, the anvil 866 pivots the RF overlay 890 toward the staple cartridge 867. The anvil 866 may cause the staple cartridge 867 to snap into the channel 844, and the RF overlay 890 to snap into the staple cartridge 867.

Furthermore, the staple cartridge 867 includes a latch mechanism 860 including a latch member 861 and a biasing member 862 configured to maintain the latch member 861 at a first position, as illustrated in FIG. 266. In the illustrated example, the RF overlay includes a distal projection 898 configured to be caught by the latch member 861 in the locked configuration.

Further to the above, as illustrated in FIG. 267, a sled 863 can be motivated by the drive member 751 to disengage the latch member 861 from the distal projection 898. In the illustrated example, the sled 863, toward the end of a sled-firing-stroke, pushes the latch member 861 distally, which compresses the biasing member 862, and releases the distal projection 898 from the latch member 861. The spent staple cartridge 867 can then be pulled out of the channel 844, and replaced with an unspent staple cartridge 867. The RF overlay 890 can then be motivated by the anvil 866 into a locking engagement with the unspent staple cartridge 867.

Referring primarily to FIG. 259, a control circuit 760 may be programmed to control one or more functions of the surgical instrument 750 such as, for example, closure of the end effector 752, activation of the at least one electrode, and/or firing the staple cartridge. The control circuit 760, in some examples, may comprise one or more microcontrollers, microprocessors, or other suitable processors for executing instructions that cause the processor or processors to control the one or more functions of the surgical instrument 750. In one aspect, a timer/counter 781 provides an output signal, such as the elapsed time or a digital count, to the control circuit 760. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the drive member 751 via a transmission 756. The transmission 756 may include one or more gears or other linkage components to couple the motor 754 to a drive member 751.

Further to the above, an RF energy source 762 is coupled to an end effector (e.g., end effectors 752 (FIG. 260), 852 (FIG. 263)), and is applied to an RF electrode of the end effector (e.g., electrodes 796 (FIG. 260), 896 (FIG. 263)) or the RF electrode. In at least one example, the anvil 766 is at least partial made of electrically conductive metal and may be employed as the return path for electrosurgical RF current. The control circuit 760 controls the delivery of the RF energy to the RF electrode 796, or the RF electrode 896.

Additional details are disclosed in U.S. patent application Ser. No. 15/636,096, entitled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752.

In one aspect, sensors 788 may be implemented as a limit switch, electromechanical device, solid-state switches, Hall-effect devices, MR devices, GMR devices, magnetometers, among others. In other implementations, the sensors 788 may be solid-state switches that operate under the influence of light, such as optical sensors, IR sensors, ultraviolet sensors, among others. Still, the switches may be solid-state devices such as transistors (e.g., FET, junction FET, MOS- FET, bipolar, and the like). In other implementations, the sensors 788 may include electrical conductorless switches, ultrasonic switches, accelerometers, and inertial sensors, among others. The sensors 788 may include one or more sensors.

The control circuit 760 can be configured to simulate the response of the actual system of the instrument in the software of a controller. The drive member 751 can move one or more elements in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

As described above in greater detail, various example aspects are directed to a surgical instrument 750 comprising an end effector 752, or an end effector 852, with motor-driven surgical sealing and cutting implements. In various examples, the surgical instrument 750 may comprise a control circuit 760 programmed to control the distal translation of the drive member 751 based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the drive member 751. Different control programs may be selected to better treat different tissue conditions. For example, when thicker tissue is present, the control circuit 760 may be programmed to translate the drive member 751 at a lower velocity and/or with lower power. When thinner tissue is present, the control circuit 760 may be programmed to translate the drive member 751 at a higher velocity and/or with higher power.

FIG. 268 is a logic flow diagram of a process 900 depicting a control program or a logic configuration for effecting a surgical treatment of a tissue. In certain instances, the process 900 is implemented using the surgical instrument 750, for example. In certain instances the process 900 is implemented, or at least partially implemented, using the control circuit 760, for example. In the illustrated example, the process 900 includes applying 901 a first phase of a surgical treatment to the tissue grasped by the surgical instrument 750. In certain instances, the process 901 includes switching 903 from the first phase of the surgical treatment to the second phase of the surgical treatment based on at least one of a predetermined threshold of the tissue property and a predetermined threshold time of the first phase.

In the illustrated example, if 902 a property of the tissue being treated becomes equal to or greater than a predetermined threshold, the process 901 switches 903 to a second phase of the surgical treatment. The process 904 also switches 903 to the second phase of the surgical treatment if 904 a threshold application time of the first phase is reached prior to the property of the tissue being treated reaching the predetermined threshold. Accordingly, the process 900 may switch from the first phase of the surgical treatment to the second phase of the surgical treatment if at least one of two conditions is met. The first condition is triggered by reaching or exceeding a predetermined threshold of the first tissue property, and the second condition is triggered by reaching or exceeding a predetermined threshold time of the first phase.

In certain instances, the tissue property determined in the first phase is a tissue impedance. Various mechanisms for monitoring tissue impedance are disclosed in U.S. Patent Application Publication No. 2017/0000553, entitled SURGICAL SYSTEM WITH USER ADAPTABLE TECHNIQUES EMPLOYING MULTIPLE ENERGY MODALITIES BASED ON TISSUE PARAMETERS, filed Jun. 9, 2016, which is hereby incorporated by reference herein in its entirety. In at least one example, the tissue impedance is determined based on a current passed through the tissue by the RF energy source 762. A current sensor may measure the current passed through the tissue based on a preset voltage value. Alternatively, voltage sensor may measure the voltage between the electrode 796, or alternatively the electrode 896, and a return electrode based on a preset current values. Tissue impedance can be determined based on the current and voltage values.

Further to the above, the first phase and the second phase are different. In at least one example, the first phase comprises an electrical sealing of the tissue, while the second phase comprises a mechanical sealing of the tissue and, optionally, a mechanical cutting of the tissue. In at least one example, the first phase comprises applying a therapeutic RF energy to the tissue, while the second phase comprises stapling the tissue via staples from a staple cartridge. In certain instances, the second phase is applied after completion of the first phase. In other instances, the second phase is set to begin before completion of the first phase. In other instances, the second phase and the first phase are separated by a predetermined wait-time. In certain instances, the wait-time is based on a characteristic of the tissue determined during the first phase.

Further to the above, the process 900 includes setting 905 a parameter of the second phase based on at least one measurement of the tissue property determined in the first phase. In certain examples, the at least one measurement is taken at a beginning of the first phase of the surgical treatment or an end of the first phase of the surgical treatment. In other examples, the at least one measurement comprises multiple measurements of the first tissue property taken during the first phase of the surgical treatment. In one example, the parameter of the second phase is set based on an average of multiple measurements of the first tissue property taken during the first phase of the surgical treatment.

In various aspects, the parameter of the second phase is a drive velocity of the motor controller 758, for example. In certain aspects, the parameter of the second phase is a velocity of the drive member 751, for example. The drive velocity can be an initial drive velocity. In certain instances, the drive velocity is a velocity in a predetermined initial zone of a firing path of the I-beam 720, for example.

The process 900 may further include monitoring 906 a second tissue property, different from the first tissue property, in the second phase of the surgical treatment. In certain instances, the second tissue property is a tissue compression. The sensors 788 may be configured to measure forces exerted on the jaws by a drive member 751 of a drive system 761 of the surgical instrument 750. The forces exerted on the jaws can be representative of the tissue compression experienced by the tissue section grasped by the jaws. The one or more sensors 788 can be positioned at various interaction points along the drive system 761 to detect the closure and/or firing forces applied to the end effector (e.g., end effectors 752, 852) by the drive system 761 (FIG. 259). The one or more sensors 788 may be sampled in real time during the surgical treatment involving a closure/firing operation by the control circuit 760. The control circuit 760 receives real-time sample measurements to provide and analyze time-based information and assess, in real time, closure/firing forces applied to the end effector 752 in the surgical treatment.

In one form, the one or more sensors 788 include a strain gauge sensor that can be used to measure the force applied to the tissue by the end effector, for example. A strain gauge can be coupled to the end effector to measure the force on the tissue being treated by the end effector. In at least one example, the strain gauge sensor is a micro-strain gauge configured to measure one or more parameters of the end effector. In one aspect, the strain gauge sensor can measure the amplitude or magnitude of the strain exerted on a jaw member of an end effector during a surgical treatment, which can be indicative of the tissue compression. The measured strain is converted to a digital signal and provided to the control circuit 760. In certain instances, sensors 788 may comprise a load sensor configured to detect a load generated by the presence of compressed tissue between the jaws of the end effector.

In certain instances, a current sensor 786 can be employed to measure the current drawn by the motor 754. The force required to advance the drive member 751 corresponds to the current drawn by the motor 754. The force is converted to a digital signal and provided to the control circuit 760. The current drawn by the motor 754 can represent tissue compression.

FIG. 269 is a graph 500 representing an example implementation of the surgical treatment of the process 900 to two tissues with different tissue compressibility. A less-compressible tissue is represented by dashed lines, while a more-compressible tissue is represented by solid lines. Graph 500 tracks tissue impedance (Z), I-beam force (F), and I-beam travel distance (δ) against time (t). As RF energy is applied to the tissues, in the first phase of the surgical treatment, the tissue impedance (Z) generally decreases to a minimum value ($Z_0$ at $t_0$, $Z_{0'}$ at $t_{0'}$), which depends, in part, on the compressibility of the tissue. With further application of the RF energy, the minimum tissue impedance is maintained. At $t_{1'}$, $t_1$, the tissue impedance begins to rise toward a predetermined maximum threshold of the tissue impedance (Zmax).

The rise of the tissue impedance is faster in the more-compressible tissue than the less-compressible tissue. In the illustrated example, the end of the first phase is determined by reaching, at $t_{2'}$, a predetermined maximum threshold of the tissue impedance (Zmax) in the case of the more-compressible tissue. However, in the less-compressible tissue, the end of the first phase is determined by reaching, at time $t_2$, a maximum time threshold (Δt'max) of the first phase. Accordingly, the switch 903 from the first phase to the second phase occurs earlier for the more-compressible tissue, at $t_{2'}$, than the less-compressible tissue, at $t_2$.

In the illustrated example, reaching the end of the first phase triggers activation of the motor 754, which begins the second phase of the surgical treatment. The second phase of the surgical treatment involves activating the motor 754 to effect firing a staple cartridge (e.g., staple cartridges 767, 867) by deploying staples from the staple cavity rows into the tissue. The staples are formed against anvil pockets of the anvil (e.g., anvil 766, 866). In the instance of the more-compressible tissue, activation of the motor 754 is triggered by reaching the predetermined maximum threshold of the tissue impedance (Zmax) in the first phase. However, in the instance of the less-compressible tissue, activation of the motor 754 is triggered by reaching the maximum time threshold (Δt'max) of the first phase at time $t_2$.

Further to the above, different initial I-beam or motor drive velocities V0', V0 (slopes of lines 501, 511) are selected for the second phase based on the tissue impedance readings determined at the ends ($t_{2'}$, $t_2$) of the first phase, as determined by reaching the predetermined maximum threshold of the tissue impedance (Zmax), or by reaching the maximum time threshold (Δt'max). In other examples, the initial I-beam or motor drive velocities V0', V0 (slopes of lines 501, 511) of the second phase can be determined based on tissue impedance readings at the beginnings (Z1', Z1) of the first phase. In yet other examples, the initial I-beam or motor drive velocities V0', V0 (slopes of lines 501, 511) of the second phase can be determined based on multiple tissue impedance readings at various points of the first phase. For example, and average of multiple tissue impedance readings at various points of the first phase can be used to determine an initial I-beam or motor drive velocity of the second phase.

In various instances, the control circuit 760 includes a microcontroller with a storage medium and a processor. The storage medium may be in the form of a memory unit storing a database, an equation, or a lookup table that can be utilized by the processor to determine an initial I-beam or motor drive velocity for the second phase based on tissue impedance readings of the first phase. In certain instances, the initial I-beam or motor drive velocity is an initial steady state velocity after an initial ramping segment to reach the initial steady state velocity. In certain instances, the initial I-beam or motor drive velocity is a target initial velocity set by the processor based on the tissue impedance readings of the first phase.

Referring still to FIG. 269, as described above in greater detail, the process 900 may include monitoring 906 tissue compression during the second phase, and making adjustments to the I-beam or motor drive velocity based on the detected tissue compression. In the illustrated example, the control circuit 760 is configured to maintain the I-beam force within a predetermined force threshold range (Fmin-Fmax). The I-beam force in the instance of the less-compressible tissue reaches 521 the predetermined maximum I-beam force (Fmax) at $t_3$, which triggers the control circuit 760 to adjust the drive velocity of the I-beam or motor. In the illustrated example, the control circuit 760 adjusts the drive velocity from the initial drive velocity $V_0$ (slope of the line 511) to a drive velocity $V_1$ (slope of the line 512) less than the initial drive velocity $V_0$. The reduction in drive velocity at $t_3$ causes the I-beam force to decrease to a level below the predetermined maximum I-beam force (Fmax).

Conversely, at $t_4$, the I-beam force in the instance of the less-compressible tissue, reaches 522 the predetermined minimum I-beam force (Fmin), which triggers the control circuit 760 to adjust the drive velocity of the I-beam or motor. In the illustrated example, the control circuit 760 adjusts the drive velocity from the drive velocity $V_1$ (slope of the line 512) to a drive velocity $V_2$ (slope of the line 513) greater than the drive velocity $V_1$. The increase in drive velocity at $t_4$ causes the I-beam force to increase to a level above the predetermined minimum I-beam force (Fmin), and remain within the predetermined force threshold range (Fmin-Fmax).

In addition to making adjustments to the drive velocity based on the I-beam force, the control circuit 760 may also make adjustments to the drive velocity based on the tissue impedance readings determined within the second phase. In certain instances, the tissue impedance is monitored in the second phase by driving a non-therapeutic, or therapeutic, current through the tissue, and measuring the tissue impedance based on the non-therapeutic, or therapeutic, current. In certain instances, the adjustments to the drive velocity based on the tissue impedance readings within the second phase are performed while the I-beam force is maintained within the predetermined force threshold range (Fmin-Fmax). Accordingly, in such instances, the control circuit 760 is configured to make first adjustments to the drive velocity based on the tissue compression, and second adjustments to the drive velocity based on the tissue impedance.

In certain instances, the adjustments to the drive velocity during the second phase can be based on the rate of change of the tissue impedance. As the I-beam is advanced distally, the tissue compression causes changes in tissue impedance over time. In the illustrated example, the control circuit 760 determines the rate of change of tissue impedance ($\Delta Z_1/\Delta t_1$), e.g., slope of the line 531, by monitoring changes in tissue impedance over time, e.g., time period $t_{2'}$–$t_{3'}$.

If the control circuit 760 determines that the rate of change of the tissue impedance is beyond a predetermined threshold range, the control circuit 760 may adjust the drive velocity to return the rate of change of the tissue impedance to a value within the predetermined threshold range. For example, the drive velocity may be adjusted from the initial drive velocity V0', slope of the line 501, to a drive velocity V1', slope of the line 502, which causes the rate of change of the tissue impedance to be adjusted from ($\Delta Z_1/\Delta t_1$), slope of the line 531, to ($\Delta Z_2/\Delta t_2$), slope of the line 532.

In certain instances, the rate of change of the tissue impedance in the second phase is utilized as a feedback indicator for drive velocity adjustments. The adjustments in the drive velocity can yield changes in the rate of change of the tissue impedance. In the illustrated examples, slopes of the lines 541, 542, 543 correspond to the slopes of the lines 511, 512, 513, for example. Accordingly, a control circuit 760 can be configured to confirm changes made to the drive velocity settings by monitoring the rate of change of the tissue impedance, for example.

Further to the above, still referring to FIG. 269, the second phase of the surgical treatment involves firing a staple cartridge (e.g., staple cartridges 767, 867) by deploying staples from the staple cavity rows into the tissue. The staples are formed against anvil pockets of the anvil (e.g., anvil 766, 866). As the staples are gradually deployed and formed, the I-beam force fluctuates within the predetermined force threshold range (Fmin-Fmax). As described above, the control circuit 760 is configured to maintain the I-beam force within the predetermined force threshold range (Fmin-Fmax) by making adjustments to the drive velocity. Toward the end of the second phase, after the staple deployment and forming is completed, the I-beam force rapidly decreases to a minimum value, which coincides with a rapid increase in the tissue impedance curve (e.g., at $t_5$, $t_{5'}$), which can be detected by the control circuit 760 based on tissue impedance readings. In response, the control circuit 760 further adjusts the drive velocity (e.g., slopes of lines 503, 514) to terminate the second phase.

Referring now to FIG. 270, a top view of a cartridge deck 630 is represented. The cartridge deck 630 is similar in many respects to other cartridge decks disclosed elsewhere herein such as, for example, the cartridge decks 730, 830. For example, the cartridge deck 630 includes two staple cavity rows 657*a*, 657*b* on opposite sides of a longitudinal slot 659. Furthermore, the cartridge deck 630 also includes electrode segments 696*a*, 696*c*, 696*e* and electrode segments 696*b*, 696*d*, 696*f* on opposite sides of the longitudinal slot 659.

In the illustrated example, the staple cavity rows 657*a*, 657*b* are closer to the longitudinal slot 659 than the electrode segments 696*a*-696*f*. In other arrangements, however, the staple cavity rows 657*a*, 657*b* can be further away from the longitudinal slot 659 than the electrode segments 696*a*-696*f*. In various instances, a cartridge deck 630 may include more, or less, than two staple cavity rows and/or more, or less, than six electrode segments.

In certain instances, the cartridge deck 630 can be implemented using an end effector similar in many respects to the end effector 752 (FIG. 260). In such instances, the electrode segments 696*a*-696*f* can be integrated with a channel 744 (FIG. 260), for example. The cartridge deck 630 can be formed by insertion of a staple cartridge including the staple cavity rows 657*a*, 657*b* into a distal end of the channel 744.

In other instances, the cartridge deck 630 can be implemented using an end effector similar in many respects to the end effector 852 (FIG. 263). In such instances, the electrode segments 696*a*-696*f* can be integrated into an RF overlay, similar in many respects to the RF overlay 890. Further, the cartridge deck 630 can be formed by insertion of a staple cartridge including the staple cavity rows 657*a*, 657*b* into a channel 844, and pivoting the RF overlay that includes the electrode segments 696*a*-696*f* toward the channel 844, and into a locking engagement with the staple cartridge, as detailed by the assembly process described in connection with FIGS. 265-267.

Further to the above, the cartridge deck 630 may form a tissue contacting surface 631 for grasping tissue in cooperation with an anvil 766, for example, and in response to drive motions generated by the motor 754 of the surgical instrument 750, for example. Furthermore, the electrode segments 696*a*-696*f* can be electrically coupled to the RF energy source 762, which can selectively transmit RF energy to the tissue grasped between the tissue contacting surface 631 of the cartridge deck 630 and the anvil 766. The control circuit 760 may cause the RF energy source 762 to selectively energize and de-energize, or activate and deactivate, the electrode segments 696*a*-696*f* in a predetermined sequence to deliver a therapeutic RF energy to the grasped tissue.

In the illustrated example, the electrode segments 696*a*-696*f* are arranged in two rows on opposite sides of the longitudinal slot 659. The electrode segments in each row are separately residing in consecutive treatment zones: a proximal zone (Zone 1), an intermediate zone (Zone 2), and a distal zone (Zone 3), for example. In other examples, more or less than three consecutive treatment zones are contemplated such as, for example, two, four, five, and/or size treatment zones.

In the illustrated example, the electrode segments 696*a*-696*f* are arranged are arranged in pairs in each of the consecutive treatment zones. The electrode segments of a pair (e.g., electrode segments 695*a*, 696*b*) are positioned on opposite sides of the longitudinal slot 659. In other examples, electrode segments in the consecutive treatment zones can be arranged on one side of the longitudinal slot 659. In other examples, electrode segments in the consecutive treatment zones could alternate where a first electrode segment resides in a first treatment zone on one side of the longitudinal slot 659, while a second electrode segment resides in a second treatment zone, distal, or proximal, to the first treatment zone, on the other side of the longitudinal slot 659.

In the illustrated example, the electrode segments 696*a*-696*f* are different in size. Specifically, the electrode segments 696*c*, 696*d* of the intermediate zone are smaller in size than the electrode segments 696*a*, 696*b*, 696*e*, 696*f* in the proximal and distal zones. In other examples, electrode segments with different, or the same, sizes are contemplated. In one example, electrode segments arranged in a row may comprise sizes increasing gradually in a proximal direction or a distal direction.

In the illustrated example, the electrode segments of different treatment zones are spaced apart and can be separately activated, or deactivated, in a predetermined sequence. In at least one example, each electrode segment, or pair of electrode segments, in a treatment zone is separately coupled to the RF energy source thereby allowing the RF energy source 762 to selectively energize and de-energize, or activate and deactivate, the electrode segments 696*a*-696*f* in a predetermined sequence to selectively deliver a therapeutic RF energy to the grasped tissue in a predetermined zone-treatment order, as discussed in greater detail below.

In addition to the RF energy, staples from the staple cavity rows 657*a*, 657*b* are deployed into the tissue. The staples are formed against anvil pockets of the anvil (e.g., anvil 766, 866). The staples are sequentially deployed by a sled driven by the I-beam 720 and advanced from a proximal end 632 toward a distal end 634 of the cartridge deck 630. The sled advancement by the I-beam 720 is motivated by drive motions generated by the motor 754 and transmitted to the I-beam 720 by the drive member 751, for example.

FIGS. 272 and 273 are logic flow diagrams of processes 600, 650 depicting control programs or logic configurations for effecting surgical treatments of tissue. In one form, the processes 600, 650 are implemented by the surgical instrument 750 while equipped with an end effector including the cartridge deck 630 (FIG. 270), for example. The tissue is grasped between the tissue contacting surface 631 of the cartridge deck 630 of a staple cartridge 667 and an anvil 766 (FIG. 259), for example.

The processes 600, 650 include simultaneously delivering 601 a therapeutic energy to the tissue in all the consecutive treatment zones. The processes 600, 650 further include causing 602 the motor 754 to drive staple deployment from the staple cartridge 667 sequentially in the consecutive treatment zones residing between the proximal end 632 and the distal end 634 of the cartridge deck 630.

The process 600 includes detecting 609 a parameter indicative of progress of the staple deployment from the staple cartridge in the consecutive treatment zones, and sequentially deactivating electrode segments 696*a*-696*f* to sequentially seize 610 the delivery of the therapeutic energy to the tissue in the consecutive treatment zones based on the progress of the staple deployment from the staple cartridge.

In at least one example, as illustrated in FIG. 273, and as illustrated in a graph 680 of FIG. 271, the process 650 continues to deliver the therapeutic RF energy to Zone1, Zone2, and Zone 3 until certain conditions are met. If 603 it is detected that the staple deployment in Zone 1 is completed, the process 650 stops 604 delivery of the therapeutic RF energy to Zone 1, while continuing to deliver the therapeutic RF energy to Zone 2 and Zone 3. Then, if 605 it is detected that the staple deployment in Zone 2 is completed, the process 650 stops 606 delivery of the therapeutic RF energy to Zone 2, while continuing to deliver the therapeutic RF energy to Zone 3. Finally, if 607 it is detected that the staple deployment in Zone 3 is completed, the process 650 stops 608 delivery of the therapeutic RF energy to Zone 3.

In certain instances, the parameter indicative of the progress of the staple deployment is a distance-based parameter or a position-based parameter. In such instances, the control circuit 760 is configured to implement a predetermined deactivation sequence of the electrode segments 696*a*-696*f* based on the progress of the staple deployment, as detected based on distance and/or position readings received from one or more sensors 788.

The distance can be a distance travelled by the drive member 751 or the I-beam 720 to advance a sled, for example, through the consecutive treatment zones. Likewise, the position can be a position of the I-beam 720, or a sled driven by the I-beam 720, with respect to the consecutive treatment zones. In certain instances, detecting that the I-beam 720 has transitioned from a proximal zone to a distal zone triggers the control circuit 760 to seize the delivery of the therapeutic RF energy to the proximal zone.

In various aspects, the one or more sensors 788 may include a position sensor configured to sense a position of the drive member 751 and/or I-beam 720, for example. The position sensor may be or include any type of sensor that is capable of generating position data that indicate a position of the drive member 751 and/or I-beam 720. In some examples, the position sensor may include an encoder configured to provide a series of pulses to the control circuit 760 as the drive member 751 and/or I-beam 720 translates distally and proximally. The control circuit 760 may track the pulses to determine the position of the drive member 751 and/or I-beam 720. Other suitable position sensors may be used, including, for example, a proximity sensor. Other types of position sensors may provide other signals indicating motion of the drive member 751 and/or I-beam 720.

In certain instances, where the motor 754 is a stepper motor, the control circuit 760 may track the position of the drive member 751 by aggregating the number and direction of steps that the motor 754 has been instructed to execute. Accordingly, in such instances, the parameter indicative of the progress of the staple deployment can be based on the number and direction of steps that the motor 754 has been instructed to execute.

The position sensor may be located in the end effector 752 or at any other portion of the instrument. Further, a detailed description of an absolute positioning system, for use with the surgical instrument 750, is described in U.S. Patent Application Publication No. 2017/0296213, entitled SYSTEMS AND METHODS FOR CONTROLLING A SURGICAL STAPLING AND CUTTING INSTRUMENT, which published on Oct. 19, 2017, which is herein incorporated by reference in its entirety.

In certain instances, the parameter indicative of the progress of the staple deployment is a time-based parameter. The control circuit 760 may employ the timer/counter 781 to assess the staple deployment progress, for example. The control circuit 760 may start the timer/counter 781 and activate the motor 754 (FIG. 259) simultaneously. The control circuit 760 utilizes the time spent after activation of the motor 754, as detected by the timer/counter 781, to assess the staple deployment progress based on a technique, an equation, a formula, a database, and/or a lookup table stored in a memory unit, for example.

In certain instances, the parameter indicative of the progress of the staple deployment is a tissue impedance-based parameter or a force-based parameter. In certain instances, the parameter indicative of the progress of the staple deployment is based on tissue thickness, for example.

Measurements of the tissue compression, the tissue impedance, the tissue thickness, and/or the force required to close the end effector on the tissue, as measured by the sensors 788, can be used by a microcontroller of the control circuit 760 to assess the staple deployment progress, for example. In one instance, the microcontroller may include a memory that stores a technique, an equation, a formula, a database, and/or a lookup table, which can be employed by the microcontroller to assess the staple deployment progress based on readings from the sensors 788.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRUMENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELEMENT AND DUAL DISTAL PULLEYS, U.S. Patent Application Publication No. 2017/0265865, filed Feb. 15, 2017, entitled STAPLER WITH CABLE-DRIVEN ADVANCEABLE CLAMPING ELEMENT AND DISTAL PULLEY, and U.S. Patent Publication No. 2017/0290586, entitled STAPLING CARTRIDGE, filed on Mar. 29, 2017, are incorporated herein by reference in their entireties.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Examples

Various aspects of the subject matter described herein are set out in the following numbered examples.

Example 1—A method for treating tissue using a surgical instrument including at least one electrode and a staple cartridge, the method comprising causing the at least one electrode to deliver a therapeutic energy to the tissue in a first phase of a surgical treatment by the surgical instrument, deploying staples from the staple cartridge into the tissue in a second phase of the surgical treatment, monitoring a first tissue property in the first phase of the surgical treatment, switching from the first phase of the surgical treatment to the second phase of the surgical treatment if at least one of two conditions is met, setting a parameter of the second phase of the surgical treatment based on at least one measurement of the first tissue property determined in the first phase of the surgical treatment, and monitoring a second tissue property, different from the first tissue property, in the second phase of the surgical treatment. A first of the two conditions is triggered by reaching or exceeding a predetermined threshold of the first tissue property. A second of the two conditions is triggered by reaching or exceeding a predetermined threshold time of the first phase.

Example 2—The method of Example 1, wherein the parameter of the second phase is a drive velocity of a motor assembly of the surgical instrument, the motor assembly operable to deploy the staples.

Example 3—The method of Examples 1 or 2, wherein the first tissue property is a tissue impedance.

Example 4—The method of any one of Examples 1-3, wherein the at least one measurement is taken at a beginning of the first phase of the surgical treatment or an end of the first phase of the surgical treatment.

Example 5—The method of any one of Examples 1-3, wherein the at least one measurement comprises multiple measurements of the first tissue property taken during the first phase of the surgical treatment.

Example 6—The method of any one of Examples 1-5, further comprising adjusting a level of the therapeutic energy delivered through the at least one electrode based on the first tissue property.

Example 7—A method for treating tissue using a surgical instrument including at least one electrode and a staple cartridge, the method comprising causing the at least one electrode to deliver a therapeutic energy to the tissue in a first phase of a surgical treatment, deploying staples from the staple cartridge into the tissue in a second phase of the surgical treatment, monitoring a tissue property in the first phase of the surgical treatment, switching from the first phase of the surgical treatment to the second phase of the surgical treatment based on at least one of a predetermined threshold of the tissue property and a predetermined threshold time of the first phase, and setting a parameter of the second phase of the surgical treatment based on at least one measurement of the tissue property determined in the first phase of the surgical treatment.

Example 8—The method of Example 7, wherein the parameter of the second phase is a drive velocity of a motor assembly of the surgical instrument, the motor assembly operable to deploy the staples.

Example 9—The method of Examples 7 or 8, wherein the tissue property is a tissue impedance.

Example 10—The method of any one of Examples 7-9, wherein the at least one measurement is taken at a beginning of the first phase of the surgical treatment or an end of the first phase of the surgical treatment.

Example 11—The method of any one of Examples 7-9, wherein the at least one measurement comprises multiple measurements of the tissue property taken during the first phase of the surgical treatment.

Example 12—The method of any one of Examples 7-11, further comprising adjusting a level of the therapeutic energy delivered through the at least one electrode based on the tissue property.

Example 13—A method for treating tissue using a surgical instrument including at least one electrode and a staple cartridge, the method comprising delivering a therapeutic energy to the tissue in consecutive treatment zones, deploying staples from the staple cartridge into the tissue, detecting a parameter indicative of a progress of the staple deployment from the staple cartridge in the consecutive treatment zones, and sequentially deactivating electrodes to sequentially seize the delivery of the therapeutic energy to the tissue in the consecutive treatment zones based on the progress of staple deployment from the staple cartridge.

Example 14—The method of Example 13, wherein a deactivation of a delivery of the therapeutic energy in a proximal treatment zone of the consecutive treatment zones is performed prior to a deactivation of a delivery of the therapeutic energy in a distal treatment zone of the consecutive treatment zones.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for treating tissue using a surgical instrument including at least one electrode, a staple cartridge, and a control circuit including a processor, the method comprising:

causing, by the processor, the at least one electrode to deliver a therapeutic energy to the tissue in a first phase of a surgical treatment by the surgical instrument;

causing, by the processor, staples to be deployed from the staple cartridge into the tissue in a second phase of the surgical treatment;

monitoring, by the processor, a first tissue property in the first phase of the surgical treatment, wherein the first tissue property is a tissue impedance;

switching, by the processor, from delivering the therapeutic energy in the first phase of the surgical treatment to deploying the staples in the second phase of the surgical treatment when a predetermined threshold of the tissue impedance is met, wherein the predetermined threshold of the tissue impedance is configured to be met before completion of the first phase, such that the second phase is operable to begin before completion of the first phase;

setting, by the processor, a parameter of the second phase of the surgical treatment based on at least one measurement of the first tissue property determined in the first phase of the surgical treatment; and monitoring, by the processor, a second tissue property, different from the first tissue property, in the second phase of the surgical treatment.

2. The method of claim 1, wherein the parameter of the second phase is a drive velocity of a motor assembly of the surgical instrument, the motor assembly operable to deploy the staples.

3. The method of claim 2, further comprising switching from delivering the therapeutic energy in the first phase to deploying the staples in the second phase when a predetermined threshold time of the first phase is met before the predetermined threshold of the tissue impedance is met.

4. The method of claim 3, wherein the at least one measurement is taken at a beginning of the first phase of the surgical treatment or an end of the first phase of the surgical treatment.

5. The method of claim 3, wherein the at least one measurement comprises multiple measurements of the first tissue property taken during the first phase of the surgical treatment.

6. The method of claim 1, further comprising adjusting, by the processor, a level of the therapeutic energy delivered through the at least one electrode based on the first tissue property.

7. A method for treating tissue using a surgical instrument including at least one electrode and a staple cartridge, the method comprising:

causing the at least one electrode to deliver a therapeutic energy to the tissue in a first phase of a surgical treatment;

deploying staples from the staple cartridge into the tissue in a second phase of the surgical treatment;

monitoring a tissue property in the first phase of the surgical treatment, wherein the tissue property is a tissue impedance;

automatically switching from delivering the therapeutic energy in the first phase of the surgical treatment to deploying the staples in the second phase of the surgical treatment when a predetermined threshold of the tissue impedance is met, wherein the predetermined threshold of the tissue impedance is configured to be met before completion of the first phase, such that the second phase is operable to begin before completion of the first phase; and setting a parameter of the second phase of the surgical treatment based on at least one measurement of the tissue property determined in the first phase of the surgical treatment.

8. The method of claim 7, wherein the parameter of the second phase is a drive velocity of a motor assembly of the surgical instrument, the motor assembly operable to deploy the staples.

9. The method of claim 8, further comprising automatically switching from delivering the therapeutic energy in the first phase of the surgical treatment to deploying the staples in the second phase of the surgical treatment when a predetermined threshold time of the first phase is met before the predetermined threshold of the tissue impedance is met.

10. The method of claim 9, wherein the at least one measurement is taken at a beginning of the first phase of the surgical treatment or an end of the first phase of the surgical treatment.

11. The method of claim 9, wherein the at least one measurement comprises multiple measurements of the tissue property taken during the first phase of the surgical treatment.

12. The method of claim 11, further comprising adjusting a level of the therapeutic energy delivered through the at least one electrode based on the tissue property.

* * * * *